(12) United States Patent
Takahashi et al.

(10) Patent No.: US 10,858,314 B2
(45) Date of Patent: Dec. 8, 2020

(54) UREA DERIVATIVE OR PHARMACOLOGICALLY ACCEPTABLE SALT THEREOF

(71) Applicant: KYORIN PHARMACEUTICAL CO., LTD., Tokyo (JP)

(72) Inventors: Hiroyasu Takahashi, Miyagi (JP); Hiroyuki Watanabe, Tochigi (JP); Kiyoshi Fujii, Tochigi (JP); Mitsuhito Shibasaki, Tochigi (JP); Mikako Kawashima, Tochigi (JP); Megumi Kamiya, Tochigi (JP); Kohei Ohata, Tochigi (JP)

(73) Assignee: Kyorin Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 15/576,345

(22) PCT Filed: May 26, 2016

(86) PCT No.: PCT/JP2016/002559
§ 371 (c)(1),
(2) Date: Nov. 22, 2017

(87) PCT Pub. No.: WO2016/189877
PCT Pub. Date: Dec. 1, 2016

(65) Prior Publication Data
US 2018/0208552 A1  Jul. 26, 2018

(30) Foreign Application Priority Data
May 27, 2015 (JP) .................. 2015-107597

(51) Int. Cl.
C07C 275/30 (2006.01)
C07C 275/42 (2006.01)
(Continued)

(52) U.S. Cl.
CPC ............ *C07C 275/30* (2013.01); *A61P 29/00* (2018.01); *A61P 31/18* (2018.01); *A61P 35/00* (2018.01); *C07C 275/42* (2013.01); *C07C 275/50* (2013.01); *C07C 311/51* (2013.01); *C07C 317/32* (2013.01); *C07C 317/40* (2013.01); *C07D 213/61* (2013.01); *C07D 231/12* (2013.01); *C07D 239/36* (2013.01); *C07D 249/04* (2013.01); *C07D 249/08* (2013.01); *C07D 249/12* (2013.01); *C07D 257/04* (2013.01); *C07D 261/08* (2013.01); *C07D 263/32* (2013.01); *C07D 263/34* (2013.01); *C07D 271/06* (2013.01); *C07D 271/07* (2013.01); *C07D 271/10* (2013.01); *C07D 271/113* (2013.01); *C07D 273/04* (2013.01); *C07D 277/28* (2013.01); *C07D 285/08* (2013.01); *C07D 285/12* (2013.01); *C07D 285/135* (2013.01); *C07D 307/79* (2013.01); *C07D 311/58* (2013.01); *C07D 333/16* (2013.01); *C07D 333/28* (2013.01); (Continued)

(58) Field of Classification Search
CPC .................................................. C07C 275/30
USPC ........................................................ 514/596
See application file for complete search history.

(56) References Cited

U.S. PATENT DOCUMENTS 6,365,617 B1 * 4/2002 McComsey ......... C07D 209/14
514/403
6,525,059 B1 2/2003 Anantanarayan et al.
(Continued)

FOREIGN PATENT DOCUMENTS

WO    99/64401     12/1999
WO    2004/007459   1/2004
(Continued)

OTHER PUBLICATIONS

Higgins et al. Journal of Medicinal Chemistry (1996), 39(5), 1013-15.*
(Continued)

*Primary Examiner* — Kahsay Habte
(74) *Attorney, Agent, or Firm* — BakerHostetler

(57) ABSTRACT

The present invention provides a urea compound or a pharmacologically acceptable salt thereof that has a formyl peptide receptor like 1 (hereinafter may be abbreviated as FPRL1) agonist effect, a pharmaceutical composition containing the urea compound or the pharmacologically acceptable salt thereof and a pharmaceutical use thereof. It has been found that a urea derivative represented by the general formula (I) below or a pharmacologically acceptable salt thereof has a superior FPRL1 agonist effect. Compound (I) or a pharmacologically acceptable salt thereof is highly useful for treatment, prevention, or suppression of inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

(I)

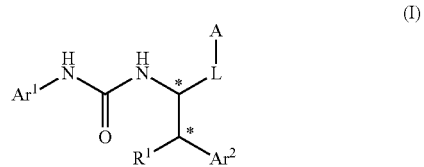

10 Claims, No Drawings
Specification includes a Sequence Listing.

(51) Int. Cl.

| | |
|---|---|
| C07C 275/50 | (2006.01) |
| C07D 231/12 | (2006.01) |
| C07D 239/36 | (2006.01) |
| C07D 271/07 | (2006.01) |
| C07D 271/113 | (2006.01) |
| C07D 285/08 | (2006.01) |
| C07D 285/135 | (2006.01) |
| C07D 413/04 | (2006.01) |
| C07D 333/16 | (2006.01) |
| C07D 333/28 | (2006.01) |
| C07D 263/34 | (2006.01) |
| C07D 271/06 | (2006.01) |
| C07D 213/61 | (2006.01) |
| C07D 261/08 | (2006.01) |
| C07D 307/79 | (2006.01) |
| C07D 285/12 | (2006.01) |
| C07C 317/32 | (2006.01) |
| C07C 317/40 | (2006.01) |
| C07D 263/32 | (2006.01) |
| C07C 311/51 | (2006.01) |
| C07D 257/04 | (2006.01) |
| C07D 273/04 | (2006.01) |
| C07D 277/28 | (2006.01) |
| C07D 271/10 | (2006.01) |
| C07D 249/08 | (2006.01) |
| C07D 311/58 | (2006.01) |
| C07D 249/04 | (2006.01) |
| C07D 417/12 | (2006.01) |
| C07D 413/12 | (2006.01) |
| C07D 249/12 | (2006.01) |
| A61P 31/18 | (2006.01) |
| A61P 29/00 | (2006.01) |
| A61P 35/00 | (2006.01) |

(52) U.S. Cl.
CPC ......... *C07D 413/04* (2013.01); *C07D 413/12* (2013.01); *C07D 417/12* (2013.01); *C07B 2200/07* (2013.01); *C07C 2601/02* (2017.05)

(56) References Cited

U.S. PATENT DOCUMENTS

| | | |
|---|---|---|
| 2013/0018067 A1 | 1/2013 | Beard et al. |
| 2014/0256684 A1 | 9/2014 | Beard et al. |

FOREIGN PATENT DOCUMENTS

| | | | |
|---|---|---|---|
| WO | 2004/064730 A2 | 8/2004 | |
| WO | 2005/047899 A2 | 5/2005 | |
| WO | 2007/076055 | 7/2007 | |
| WO | 2008/002570 | 1/2008 | |
| WO | 2009/077954 A1 | 6/2009 | |
| WO | 2009/077990 A1 | 6/2009 | |
| WO | 2010/143158 A1 | 12/2010 | |
| WO | 2011/163502 A1 | 12/2011 | |
| WO | 2012/066488 A2 | 5/2012 | |
| WO | 2012/074785 A1 | 6/2012 | |
| WO | 2012/077049 A1 | 6/2012 | |
| WO | 2012/077051 A1 | 6/2012 | |
| WO | 2012/109544 A1 | 8/2012 | |
| WO | 2012/125305 A1 | 9/2012 | |
| WO | 2013/062947 A1 | 5/2013 | |
| WO | 2013/070600 A1 | 5/2013 | |
| WO | 2013/071203 A1 | 5/2013 | |
| WO | WO-2013062947 A1 * | 5/2013 | ........... C07C 275/30 |
| WO | 2013/171687 A1 | 11/2013 | |
| WO | 2013/171694 A1 | 11/2013 | |
| WO | 2014/206966 A1 | 12/2014 | |
| WO | 2015/005305 A1 | 1/2015 | |
| WO | 2015/007830 A1 | 1/2015 | |
| WO | 2015/009545 A1 | 1/2015 | |
| WO | 2015/019325 A1 | 2/2015 | |
| WO | 2015/035051 | 3/2015 | |
| WO | 2015/171995 A1 | 11/2015 | |

OTHER PUBLICATIONS

Tae et al, Airway activation of formyl peptide receptors inhibits Th1 and Th17 cell responses via inhibition of mediator release from immune and inflammatory cells and maturation of dendritic cells. The Journal of Immunology. Feb. 15, 2012;188(4):1799-1808.
Summers et al, Singh N, Peters AM, Chilvers ER. Neutrophil kinetics in health and disease. Trends in immunology. Aug. 1, 2010;31(8):318-324.
Sogawa et al, Inhibition of neutrophil migration in mice by mouse formyl peptide receptors 1 and 2 dual agonist: indication of cross-desensitization in vivo. Immunology. Mar. 1, 2011;132(3):441-450.
Schepetkin et al, Gastrin-releasing peptide/neuromedin B receptor antagonists PD176252, PD168368, and related analogs are potent agonists of human formyl-peptide receptors. Molecular pharmacology. Jan. 1, 2011 ;79(1 ):77-90.
Ozensoy et al., Carbonic anhydrase inhibitors: Inhibition of the tumor-associated isozymes IX and XII with a library of aromatic and heteroaromatic sulfonamides, Bioorganic & Medicinal Chemistry Letters, Pergamon, Amsterdam, NL, vol. 15, No. 21, Nov. 1, 2005, pp. 4862-4866.
Nanamori et al, A novel nonpeptide ligand for formyl peptide receptor-like 1. Molecular pharmacology. Nov. 1, 2004;66(5):1213-1222.
Murphy et al, A structural homologue of the N-formyl peptide receptor. Characterization and chromosome mapping of a peptide chemoattractant receptor family. Journal of Biological Chemistry. Apr. 15, 1992;267(11):7637-7643.
Mcmanus J M et al: "tetrazole analogs of amino acids", The Journal of Organic Chemistry, American Chemical Society , US, vol. 24, Jan. 1, 1959, pp. 1643-1649.
Li et al, The synthetic peptide WKYMVm attenuates the function of the chemokine receptors CCR5 and CXCR4 through activation of formyl peptide receptor-like 1. Blood. May 15, 2001;97(10):2941-2947.
Le Y, Murphy PM, Wang JM. Formyl-peptide receptors revisited. Trends in immunology. Nov. 1, 2002;23(11):541-548.
Krishnamoorthy et al, Resolvin D1 binds human phagocytes with evidence for proresolving receptors. Proceedings of the National Academy of Sciences. Jan. 26, 2010;107(4):1660-1665.
Kirpotina et al, Identification of novel small-molecule agonists for human formyl peptide receptors and pharmacophore models of their recognition. Molecular pharmacology. Jan. 1, 2009:mol-109.
Kim S. D, et al., A WKYMVm-containing Combination Elicits Potent anti-Tumor Activity in Heterotopic Cancer Animal Model, PLoS One, vol. 7, No. 1: e30522, Jan. 2012, 10 pages.
Kim S. D, et al., The Immune-stimulating peptide WKYMVm has therapeutic effects against ulcerative colitis, Experimental & Molecular Medicine, 45: e40, Sep. 2013, 6 pages.
Kim et al, The agonists of formyl peptide receptors prevent development of severe sepsis after microbial infection. The Journal of Immunology. Oct. 1, 2010;185(7):4302-4310.
He et al, Characterization of Quin-C1 for its anti-inflammatory property in a mouse model of bleomycin-induced lung injury. Acta Pharmacologica Sinica. May 2011;32(5):601-610.
Gavins, Are formyl peptide receptors novel targets for therapeutic intervention in ischaemia-reperfusion injury?. Trends in pharmacological sciences. Jun. 1, 2010;31(6):266-276.
Frohn et al, New 'chemical probes' to examine the role of the hFPRL1 (or ALXR) receptor in inflammation. Bioorganic & medicinal chemistry letters. Dec. 1, 2007;17(23):6633-6637.
Dufton et al, Anti-inflammatory role of the murine formyl-peptide receptor 2: ligand-specific effects on leukocyte responses and experimental inflammation. The Journal of Immunology. Mar. 1, 2010;184(5):2611-2619.

(56) References Cited

OTHER PUBLICATIONS

Database Registry [Online] Chemical Abstracts Service, Columbus, Ohio, US; Sep. 4, 2011, XP002762125, Database accession No. 1327895-99-7 abstract.

Database Registry [Online] Chemical Abstracts Service, Columbus, Ohio, US; Sep. 5, 2011, XP002762127, Database accession No. 1328412-07-2 abstract.

Database Registry [Online] Chemical Abstracts Service, Columbus, Ohio, US; Sep. 6, 2011, XP002762126, Database accession No. 1328901-17-2 abstract.

Cilibrizzi et al, C. 6-methyl-2, 4-disubstituted pyridazin-3 (2H)-ones: a novel class of small-molecule agonists for formyl peptide receptors. Journal of medicinal chemistry. Jul. 29, 2009;52(16):5044-5057.

Cattaneo et al, Distinct signaling cascades elicited by different formyl peptide receptor 2 (FPR2) agonists. International journal of molecular sciences. Apr. 2, 2013;14(4):7193-7230.

Bürli et al, Potent hFPRL1 (ALXR) agonists as potential anti-inflammatory agents. Bioorganic & medicinal chemistry letters, 16(14), pp. 3713-3718, 2006.

* cited by examiner

SEQUENCE LISTING

<160> NUMBER OF SEQ ID NOS: 6

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic
      5' primer

<400> SEQUENCE: 1
cgaagcttca ccatggaaac caacttctcc actcctctga atg                         43

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      3' primer

<400> SEQUENCE: 2
cgctcgagtc atattgcctt tatttcaatg tcttcagg                               38

<210> SEQ ID NO 3
<211> LENGTH: 1056
<212> TYPE: DNA
<213> ORGANISM: Homo sapiens

<400> SEQUENCE: 3
atggaaacca acttctccac tcctctgaat gaatatgaag aagtgtccta tgagtctgct        60
ggctacactg ttctgcggat cctcccattg gtggtgcttg ggtcacctt tgtcctcggg       120 gtcctgggca atgggcttgt gatctgggtg gctggattcc ggatgacacg cacagtcacc      180
accatctgtt acctgaacct ggccctggct gacttttctt tcacggccac attaccattc      240
ctcattgtct ccatggccat gggagaaaaa tggcctttg gctggttcct gtgtaagtta       300
attcacatcg tggtggacat caacctcttt ggaagtgtct tcttgattgg tttcattgca      360
ctggaccgct gcatttgtgt cctgcatcca gtctgggccc agaaccaccg cactgtgagt      420
ctggccatga aggtgatcgt cggaccttgg attcttgctc tagtccttac cttgccagtt      480
ttcctctttt tgactacagt aactattcca atgggggaca catactgtac tttcaacttt      540
gcatcctggg gtggcacccc tgaggagagg ctgaaggtgg ccattaccat gctgacagcc      600
agagggatta tccggtttgt cattggcttt agcttgccga tgtccattgt tgccatctgc      660
tatgggctca ttgcagccaa gatccacaaa aagggcatga ttaaatccag ccgtcccta       720 cgggtcctca ctgctgtggt ggcttctttc ttcatctgtt ggtttccctt tcaactggtt      780
gcccttctgg gcaccgtctg gctcaaagag atgttgttct atggcaagta caaaatcatt      840
gacatcctgg ttaacccaac gagctccctg gccttcttca cagctgcct caaccccatg      900 ctttacgtct ttgtgggcca agacttccga gagagactga tccactccct gcccaccagt      960
ctggagaggg ccctgtctga ggactcagcc ccaactaatg acacggctgc caattctgct     1020
tcacctcctg cagagactga gttacaggca atgtga                              1056

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic 5' primer

<400> SEQUENCE: 4
cgaagcttca ccatggcccg ctcgctgac                                    29

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgctcgagtc acagcaggtt gatctcgtcc                                   30

<210> SEQ ID NO 6
<211> LENGTH: 1125
<212> TYPE: DNA
<213> ORGANISM: Homo sapiens

<400> SEQUENCE: 6
atggcccgct cgctgacctg gcgctgctgc ccctggtgcc tgacggagga tgagaaggcc    60
gccgcccggg tggaccagga gatcaacagg atcctcttgg agcagaagaa gcaggaccgc   120
ggggagctga agctgctgct tttgggccca ggcgagagcg ggaagagcac cttcatcaag   180
cagatgcgga tcatccacgg cgccggctac tcggaggagg agcgcaaggg cttccggccc   240
ctggtctacc agaacatctt cgtgtccatg cgggccatga tcgaggccat ggagcggctg   300
cagattccat tcagcaggcc cgagagcaag caccacgcta gcctggtcat gagccaggac   360
ccctataaag tgaccacgtt tgagaagcgc tacgctgcgg ccatgcagtg gctgtggagg   420
gatgccggca tccgggccta ctatgagcgt cggcgggaat tccacctgct cgattcagcc   480
gtgtactacc tgtcccacct ggagcgcatc accgaggagg gctacgtccc acagctcag   540 gacgtgctcc gcagccgcat gcccaccact ggcatcaacg agtactgctt ctccgtgcag   600
aaaaccaacc tgcggatcgt ggacgtcggg gccagaagt cagagcgtaa gaaatggatc   660
cattgtttcg agaacgtgat cgccctcatc tacctggcct cactgagtga atacgaccag   720
tgcctggagg agaacaacca ggagaaccgc atgaaggaga gcctcgcatt gtttgggact   780
atcctggaac taccctggtt caaaagcaca tccgtcatcc tctttctcaa caaaaccgac   840
atcctggagg agaaaatccc cacctcccac ctggctacct atttccccag tttccagggc   900
cctaagcagg atgctgaggc agccaagagg ttcatcctgg acatgtacac gaggatgtac   960
accgggtgcg tggacggccc cgagggcagc aagaagggcg cacgatcccg acgcctcttc  1020
agccactaca catgtgccac agacacacag aacatccgca aggtcttcaa ggacgtgcgg  1080
gactcggtgc tcgcccgcta cctggacgag atcaacctgc tgtga              1125

UREA DERIVATIVE OR PHARMACOLOGICALLY ACCEPTABLE SALT THEREOF

CROSS-REFERENCE TO RELATED APPLICATIONS

This application is the National Stage of International Patent Application No. PCT/JP2016/002559 filed May 26, 2016, which claims priority from Japanese Patent Application No. 2015-107597 filed May 27, 2015, the disclosures of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 3, 2017, is named 082867_000152_SL.txt and is 4,256 bytes in size.

TECHNICAL FIELD

The present invention relates to a urea derivative or a pharmacologically acceptable salt thereof that are useful as pharmaceuticals and have a formyl peptide receptor like 1 (hereinafter may be abbreviated as FPRL1) agonist effect, a pharmaceutical composition containing the urea derivative or the pharmacologically acceptable salt thereof, and a pharmaceutical use thereof.

BACKGROUND ART

FPRL1 (formyl peptide receptor like 1, also known as Lipoxin A4 Receptor, ALXR, and FPR2) is a G protein-coupled receptor cloned as a subtype of N-formyl peptide receptors (FPRs) by Murphy et al. (Non-Patent Literature 1). The FPRL1 was discovered as a receptor that mediates calcium mobilization in response to high concentration of fMLF (formyl methionine leucyl phenylalanine peptide).

Expression of FPRL1 has been found in neutrophils, monocytes, T-lymphocytes, dendritic cells, etc. (Non-Patent Literature 2), but the role of FPRL1 in a living body is complicated and has therefore not been elucidated sufficiently (Non-Patent Literature 3). However, in a paw edema model and an arthritis model using FPRL1 deficient mice, it has been recognized that the reactions become worse (Non-Patent Literature 4). Therefore, it is considered that FPRL1 contributes to the resolution of the inflammation.

Endogenous lipid mediators such as Lipoxin A4 (LXA4) and Resolvin D1 (RvD1) and peptides such as WKYMVm have been reported as agonists that bind to FPRL1 (Non-Patent Literatures 5 and 6).

Such FPRL1 agonists can reduce neutrophil chemotaxis in vitro (Non-Patent Literatures 7 and 8). Although neutrophils perform host defense, they cause vascular injury, result in an increase in vascular permeability and edema, followed by release of chemotactic factors, and thereby contribute to inflammation (Non-Patent Literature 9). Therefore, it is considered that the FPRL1 agonists exhibit an anti-inflammatory effect.

For example, it has been confirmed that peptide agonists exhibit an inhibitory effect on intestinal inflammation (Non-Patent Literature 10), an inhibitory effect on airway inflammation (Non-Patent Literature 11), an inhibitory effect on septicemia (Non-Patent Literature 12), and an inhibitory effect on a cancer model (Non-Patent Literature 13). It has also been recognized that QuinC1, a non-peptide low-molecular weight compound, inhibits bleomycin-induced lung inflammation (Non-Patent Literature 14).

Therefore, FPRL1 can be considered as a target of various diseases such as inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders. Therefore, the FPRL1 agonists can be promising therapeutic agent for these diseases.

Known examples of the non-peptide low-molecular weight compound exhibiting FPRL1 agonist activity include quinazolinones (Non-Patent Literature 15), pyrazolones (Non-Patent Literature 16), benzimidazoles (Non-Patent Literature 17), aminoazoles (Patent Literatures 1, 2, 3, 4, and 5), spiro[2,4]heptanes (Patent Literature 6, 7, 8, 9, and 10), pyridazinones (Non-Patent Literature 18), cycloalkyl and cycloalkenyl-1,2-dicarboxylic acids (Patent Literature 11), dihydronaphthalenes (Patent Literature 12), pyrrolidine-2,5-diones (Patent Literature 13), thiazoles (Patent Literature 14), and urea derivatives (Patent Literatures 15, 16, 17, 18, 19, 20, 21, and 22) (Non-Patent Literatures 19 and 20).

However, the basic chemical structures of these compounds are different from those of the compounds of the present invention. It is obvious that the above compounds are not included in the claims of the present application.

CITATION LIST

Non-Patent Literature

[NPL 1] Murphy P. M., et al., "The Journal of Biological Chemistry," 1992, vol. 267, pp. 7637-7643
[NPL 2] Gavins F. N. E, et al., "Trends in Pharmacological Sciences," 2010, vol. 31, pp. 266-276
[NPL 3] Cattaneo F., et al., "International Journal of Molecular Sciences," 2013, vol. 14, No. 4, pp. 7193-7230
[NPL 4] Dufton N, et al., "The Journal of Immunology," 2010, vol. 184, pp. 2611-2619
[NPL 5] Le Y, et al., "Trends in immunology," 2002, vol. 23, No. 11, pp. 541-548
[NPL 6] Krishnamoorthy S, "Proceedings of the National Academy of Sciences," 2010, vol. 107, No. 4, pp. 1660-1665
[NPL 7] Li B. Q, et al., "Blood," 2001, vol. 97, pp. 2941-2947
[NPL 8] Sogawa Y, et al., "Immunology," 2011, vol. 132, pp. 441-450
[NPL 9] Summers C, et al., "Trends in Immunology," 2010, vol. 31, pp. 318-324
[NPL 10] Kim S. D, et al., "Experimental & Molecular Medicine," 2013, vol. 13, No. 45: e40.
[NPL 11] Tae Y. M, et al., "The Journal of Immunology," 2012, vol. 188, pp. 1799-1808
[NPL 12] Kim S. D, et al., "The Journal of Immunology," 2010, vol. 185, pp. 4302-4310
[NPL 13] Kim S. D, et al., "PLoS ONE," vol. 7, No. 1: e30522.
[NPL 14] Min H. E, et al., "Acta Pharmacologica Sinica" 2011, vol. 32, pp. 601-610
[NPL 15] Nanamori M, et al., "Molecular Pharmacology," 2004, vol. 66, pp. 1213-1222
[NPL 16] Burli R. W, et al., "Bioorganic & Medicinal Chemistry Letters," 2006, vol. 16, pp. 3713-3718
[NPL 17] Frohn M, et al., "Bioorganic & Medicinal Chemistry Letters," 2007, vol. 17, pp. 6633-6637

[NPL 18] Cilibrizzi A, et al., "Journal of Medicinal Chemistry," 2009, vol. 52, pp. 5044-5057
[NPL 19] Kirpotina L. N, et al., "Molecular Pharmacology," 2010, vol. 77, pp. 159-170
[NPL 20] Schepetkin I. A, et al., "Molecular Pharmacology," 2011, vol. 79, pp. 77-90

PATENT LITERATURE

[PL 1] WO2009/077990
[PL 2] WO2009/077954
[PL 3] WO2010/143158
[PL 4] WO2012/077049
[PL 5] WO2012/077051
[PL 6] WO2012/066488
[PL 7] WO2013/171687
[PL 8] WO2013/171694
[PL 9] WO2014/206966
[PL 10] WO2015/007830
[PL 11] WO2011/163502
[PL 12] WO2012/125305
[PL 13] U.S. Ser. No. 13/001,8067
[PL 14] WO2015/005305
[PL 15] WO2005/047899
[PL 16] WO2012/074785
[PL 17] WO2012/109544
[PL 18] WO2013/062947
[PL 19] WO2013/070600
[PL 20] WO2013/071203
[PL 21] WO2015/009545
[PL 22] WO2015/019325

SUMMARY OF INVENTION

Technical Problem

At present, no compound has been found which has a superior FPRL1 agonist effect as a prophylactic or therapeutic agent for various disease states described above and can be used as a sufficiently satisfactory pharmaceutical.

It is an object of the present invention to provide a compound having an FPRL1 agonist effect.

Solution to Problem

The present inventors have conducted extensive studies and found that a urea compound represented by the general formula (I) below (this compound may be referred to as a compound (I)) or a pharmacologically acceptable salt thereof has a superior FPRL1 agonist effect and is sufficiently satisfactory as a pharmaceutical, and thus the present invention has been completed.

Accordingly, the present invention is as follows.

[1] A compound represented by the general formula (I) or a pharmacologically acceptable salt thereof:

[Chem. 1]

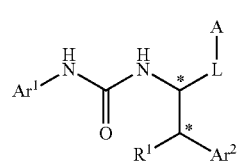

(I)

wherein in the formula (I), $Ar^1$ is a phenyl group optionally having substituent(s), a monocyclic aromatic heterocyclyl group optionally having substituent(s), or a bicyclic aromatic heterocyclyl group having 9 or 10 atoms and optionally having substituent(s);

$Ar^2$ is a phenyl group optionally having substituent(s), a monocyclic aromatic heterocyclyl group optionally having substituent(s), or a bicyclic aromatic heterocyclyl group having 9 or 10 atoms and optionally having substituent(s);

$R^1$ is a hydrogen atom, a $C_1$ to $C_3$ alkyl group, or —CONXY;

X and Y are independently a hydrogen atom or a $C_1$ to $C_3$ alkyl group;

A is a hydrogen atom, a cyano group, a hydroxy group, a $C_1$ to $C_6$ alkyloxycarbonyl group optionally having substituent(s), a 5-membered aromatic heterocyclyl group optionally having substituent(s), a 5-membered non-aromatic heterocyclyl group optionally having substituent(s), a 6-membered aromatic heterocyclyl group optionally having substituent(s), a 6-membered non-aromatic heterocyclyl group optionally having substituent(s), —CONHZ, —C(=NH)—NHZ, or —C(NH$_2$)=NZ wherein Z is a hydrogen atom, a hydroxy group, a tetrazolyl group, a hydroxy $C_1$ to $C_6$ alkyl group optionally having substituent(s), a $C_1$ to $C_6$ acyl group optionally having substituent(s), a $C_1$ to $C_6$ alkyloxy group optionally having substituent(s), a carboxy $C_1$ to $C_6$ alkyl group optionally having substituent(s), an aminocarbonyl group optionally having substituent(s), or a $C_1$ to $C_6$ alkylsulfonyl group optionally having substituent(s);

L is a single bond or a $C_1$ to $C_3$ alkylene; and each carbon atom marked with an asterisk is an asymmetric carbon atom when the carbon is a tertiary carbon atom.

[2] The compound according to [1] or a pharmacologically acceptable salt thereof, wherein in the formula (I), A is a group selected from the group consisting of a cyano group, a hydroxy group, or the following A1), A2), A3), A4), A5), A6), A7), A8), A9), A10), and A11):

[Chem.2]

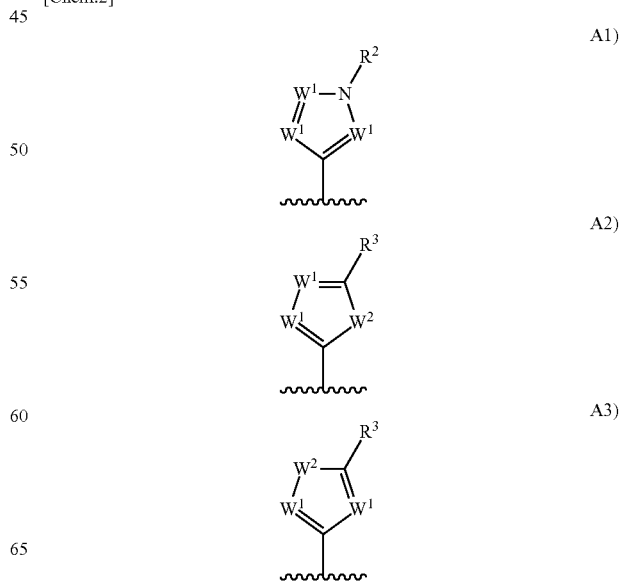

-continued

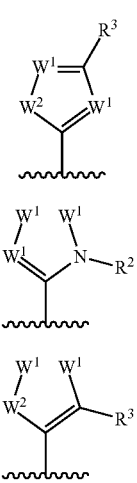

A4)

A5)

A6)

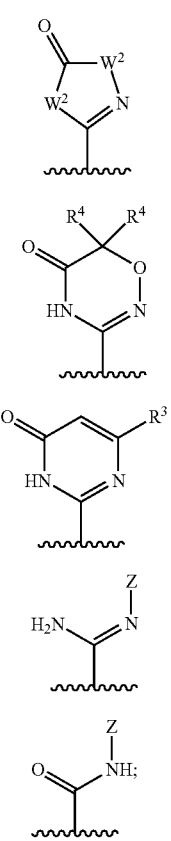

A7)

A8)

A9)

A10)

A11)

wherein $R^2$ is a hydrogen atom or a $C_1$ to $C_6$ alkyl group optionally having substituent(s);

$R^3$ is a hydrogen atom, a halogen atom, a hydroxy group, a cyano group, a carboxyl group, a $C_1$ to $C_6$ alkyl group optionally having substituent(s), a $C_1$ to $C_6$ alkyloxy group optionally having substituent(s), a $C_1$ to $C_6$ alkyloxycarbonyl group, a $C_1$ to $C_6$ acyl group optionally having substituent(s), a $C_1$ to $C_6$ alkylsulfanyl group optionally having substituent(s), a $C_1$ to $C_6$ alkylsulfinyl group optionally having substituent(s), a $C_1$ to $C_6$ alkylsulfonyl group optionally having substituent(s), a heterocyclyl group optionally having substituent(s), —$CONR^5R^6$, or —$NR^5R^6$, wherein when $R^3$ is —$CONR^5R^6$ or —$NR^5R^6$, then $R^5$ is a hydrogen atom, a $C_1$ to $C_6$ alkyl group optionally having substituent(s), a $C_1$ to $C_6$ acyl group optionally having substituent(s), or a $C_1$ to $C_6$ alkylsulfonyl group optionally having substituent(s), and $R^6$ is a hydrogen atom or a $C_1$ to $C_6$ alkyl group optionally having substituent(s), or $R^5$ and $R^6$ may together form a 3- to 10-membered heterocycloalkyl group;

Z is a hydrogen atom, a hydroxy group, a $C_1$ to $C_6$ alkyl group optionally having substituent(s), a $C_1$ to $C_6$ acyl group optionally having substituent(s), a $C_1$ to $C_6$ alkyloxy group optionally having substituent(s), a carboxy $C_1$ to $C_6$ alkyl group optionally having substituent(s), or a $C_1$ to $C_6$ alkylsulfonyl group optionally having substituent(s);

$R^4$ is a $C_1$ to $C_3$ alkyl group optionally having substituent(s);

$W^1$ is C—$R^7$ or a nitrogen atom;

$R^7$ is a hydrogen atom or a $C_1$ to $C_6$ alkyl group optionally having substituent(s); and $W^2$ is an oxygen atom, a sulfur atom, or N—$R^2$.

[3] The compound according to [2] or a pharmacologically acceptable salt thereof, wherein in the formula (I), A is a hydroxy group, or a group selected from the group consisting of the following A1a), A1b), A1c), A1d), A1e), A1f), A2a), A2b), A2c), A2aa), A3a), A3b), A3ba), A3bb), A4a), A4b), A4c), A5a), A6a), A7a), A7b), A7c), A8a), A9a), A10a), and A11a):

[Chem.3]

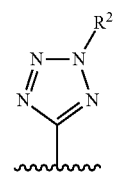

A1a)

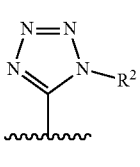

A5a)

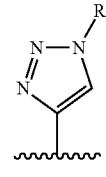

A1b)

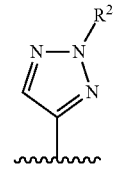

A1c)

A1d)

-continued
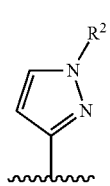
A1e)
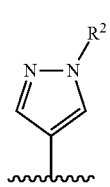
A1f)
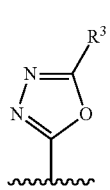
A2a)
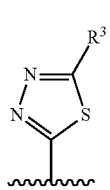
A2b)
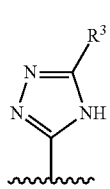
A2c)
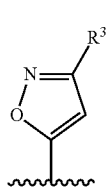
A4a)
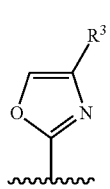
A4b)
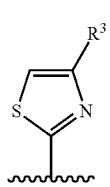
A4c)
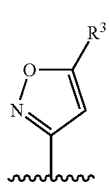
A3a)
-continued
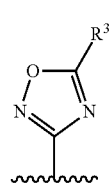
A3b)
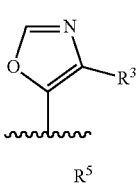
A6a)
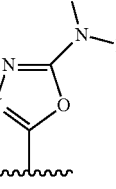
A2aa)
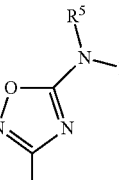
A3ba)
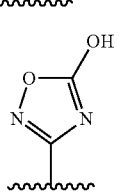
A3bb)
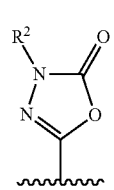
A7a)
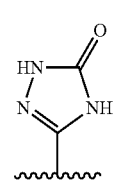
A7b)
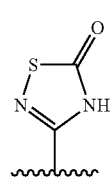
A7c)
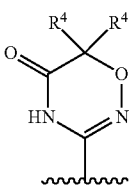
A8a)

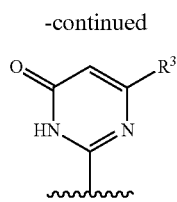
A9a)

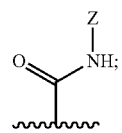
A10a)

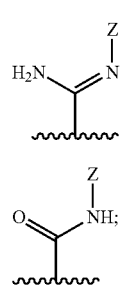
A11a)

wherein when A is A1a), A1b), A1c), A1d), A1e), A1f), A5a) or A7a), $R^2$ is a hydrogen atom, or a $C_1$ to $C_6$ alkyl group optionally substituted with a group selected from the group consisting of a halogen atom, a hydroxy group, a $C_1$ to $C_3$ alkyloxy group, a carboxyl group, a $C_1$ to $C_3$ alkyloxycarbonyl group, a $C_1$ to $C_3$ alkylsulfinyl group, a $C_1$ to $C_3$ alkylsulfonyl group, an amino group, a $C_1$ to $C_3$ alkylamino group, a $C_1$ to $C_3$ alkylsulfonylamino group, a $C_1$ to $C_3$ acylamino group, a $C_1$ to $C_3$ alkylaminocarbonyl group, and a heterocyclyl group;

when A is A2a), A2b), A2c), A4a), A4b), A4c), A3a), A3b), A6a) or A9a), $R^3$ is a group selected from the group consisting of the following i) to ix):

i) a hydrogen atom,
ii) a halogen atom,
iii) a cyano group,
iv) a carboxyl group,
v) a $C_1$ to $C_6$ alkyloxycarbonyl group,
vi) a carbamoyl group optionally substituted with a $C_1$ to $C_3$ alkyl group,
vii) a $C_1$ to $C_6$ alkyl group optionally substituted with a group selected from the group consisting of a halogen atom, a hydroxy group, a $C_1$ to $C_3$ alkyloxy group, a $C_1$ to $C_3$ acyloxy group, a carboxyl group, a $C_1$ to $C_3$ alkyloxycarbonyl group, a $C_1$ to $C_3$ alkylsulfonyl group, an amino group, a $C_1$ to $C_3$ alkylamino group, a $C_1$ to $C_3$ alkylsulfonylamino group, a $C_1$ to $C_3$ acylamino group, a $C_1$ to $C_3$ alkylaminocarbonyl group, and a heterocyclyl group,
viii) —$CONR^5R^6$ wherein $R^5$ is a hydrogen atom, a $C_1$ to $C_6$ alkyl group, a $C_1$ to $C_6$ acyl group, or a $C_1$ to $C_6$ alkylsulfonyl group, and $R^6$ is a hydrogen atom or a $C_1$ to $C_6$ alkyl group, or $R^5$ and $R^6$ may together form a 3- to 10-membered heterocycloalkyl group,
ix) a heterocyclyl group optionally having substituent(s);

when A is A2aa) or A3ba), $R^5$ is a hydrogen atom, a $C_1$ to $C_6$ alkyl group, a $C_3$ to $C_6$ cycloalkyl group, a halo-$C_1$ to $C_6$ alkyl group, a $C_1$ to $C_6$ acyl group, a hydroxy $C_1$ to $C_6$ acyl group, or a $C_1$ to $C_6$ alkylsulfonyl group, and $R^6$ is a hydrogen atom or a $C_1$ to $C_6$ alkyl group, or $R^5$ and $R^6$ may together form 3- to 10-membered heterocycloalkyl group;

when A is A8a), $R^4$ is a $C_1$ to $C_3$ alkyl group;

when A is A10a), Z is a hydroxy $C_1$ to $C_6$ alkyloxy group, a hydroxy $C_1$ to $C_6$ acyl group, a carboxy $C_1$ to $C_6$ alkyloxy group, a $C_1$ to $C_3$ alkylaminocarbonyl group, a $C_1$ to $C_6$ alkylsulfonyl $C_1$ to $C_6$ acyl group, or a $C_1$ to $C_6$ alkylsulfonyl group; and when A is A11a), Z is a hydrogen atom, a hydroxy group, a $C_1$ to $C_6$ alkyl group, a hydroxy $C_1$ to $C_6$ alkyl group, a $C_1$ to $C_6$ acyl group, a $C_1$ to $C_6$ alkyloxy group, a carboxy $C_1$ to $C_6$ alkyl group, or a $C_1$ to $C_6$ alkylsulfonyl group.

[4] The urea compound according to any one of [1] to [3] or a pharmacologically acceptable salt thereof, wherein in the formula (I), $Ar^2$ is a group selected from the group consisting of the following B1), B2), B3), and B4):

[Chem. 4]

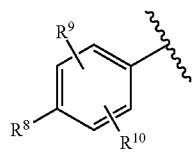
B1)

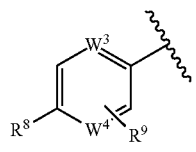
B2)

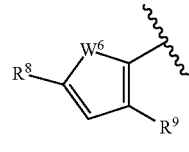
B3)

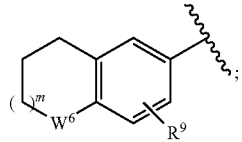
B4)

one of $W^3$ and $W^4$ is a nitrogen atom, and the other one is CH or a nitrogen atom;

$W^5$ is an oxygen atom, a sulfur atom, or N—$R^2$;

$W^6$ is C=O, $CH_2$, $CF_2$, CHOH, N—$R^2$, an oxygen atom, or a sulfur atom;

when $Ar^2$ is B3) or B4), and $W^5$ and $W^6$ are N—$R^2$, then $R^2$ is a hydrogen atom or a $C_1$ to $C_6$ alkyl group;

$R^8$ is a hydrogen atom, a halogen atom, a hydroxy group, a cyano group, a $C_1$ to $C_3$ alkyl group, a $C_2$ to $C_3$ alkenyl group, a $C_3$ to $C_6$ cycloalkyl group, a halo-$C_1$ to $C_3$ alkyl group, a hydroxy $C_1$ to $C_4$ alkyl group, a $C_1$ to $C_3$ alkyloxy group, a halo-$C_1$ to $C_3$ alkyloxy group, a $C_1$ to $C_3$ acyl group, a $C_1$ to $C_3$ alkylsulfanyl group, a $C_1$ to $C_3$ alkylsulfinyl group, a $C_1$ to $C_3$ alkylsulfonyl group, a halo-$C_1$ to $C_3$ alkylsulfonyl group, —$CONR^5R^6$, or —$NR^5R^6$, wherein when $R^8$ is —$CONR^5R^6$ or —$NR^5R^6$, $R^5$ is a hydrogen atom, a $C_1$ to $C_6$ alkyl group, a $C_1$ to $C_6$ acyl group, or a $C_1$ to $C_6$ alkylsulfonyl group, and $R^6$ is a hydrogen atom or a $C_1$ to $C_6$ alkyl group, or $R^5$ and $R^6$ may together form a 3- to 10-membered heterocycloalkyl group;

$R^9$ is a hydrogen atom, a halogen atom, a hydroxy group, cyano group, a $C_1$ to $C_3$ alkyl group, a halo-$C_1$ to $C_3$ alkyl group, a $C_1$ to $C_3$ alkyloxy group, a halo-$C_1$ to $C_6$ alkyloxy group, or —$CONR^5R^6$ wherein $R^5$ is a hydrogen atom or a $C_1$ to $C_6$ alkyl group, and $R^6$ is a hydrogen atom or a $C_1$ to $C_6$ alkyl group, or $R^5$ and $R^6$ may together form a 3- to 10-membered heterocycloalkyl group;

$R^{10}$ is a hydrogen atom, a halogen atom, or a $C_1$ to $C_3$ alkyl group; and m is 0 or 1.

[5] The compound according to any one of [1] to [4] or a pharmacologically acceptable salt thereof, wherein in the formula (I), $Ar^1$ is a group selected from the group consisting of the following C1), C2), and C3):

[Chem. 5]

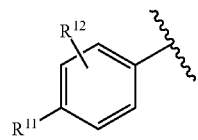
C1)

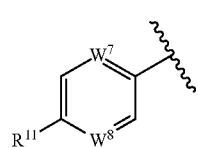
C2)

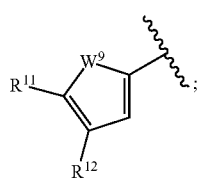
C3)

one of $W^7$ and $W^8$ is a nitrogen atom, and the other one is CH or a nitrogen atom;

$W^9$ is an oxygen atom, a sulfur atom, or $N-R^2$;

when $W^9$ is $N-R^2$, $R^2$ is a hydrogen atom or a $C_1$ to $C_6$ alkyl group;

$R^{11}$ is a hydrogen atom, a halogen atom, a cyano group, a $C_1$ to $C_3$ alkyl group, a halo-$C_1$ to $C_3$ alkyl group, a hydroxy $C_1$ to $C_4$ alkyl group, a $C_2$ to $C_3$ alkenyl group, a $C_2$ to $C_3$ alkynyl group, a $C_3$ to $C_6$ cycloalkyl group, a $C_1$ to $C_3$ alkyloxy group, a halo-$C_1$ to $C_3$ alkyloxy group, a $C_3$ to $C_6$ cycloalkoxy group, a $C_1$ to $C_6$ acyl group, a $C_1$ to $C_3$ alkyloxycarbonyl group, a $C_1$ to $C_3$ alkylsulfanyl group, a $C_1$ to $C_3$ alkylsulfinyl group, a $C_1$ to $C_3$ alkylsulfonyl group, an aryl group, an aryloxy group, a heterocyclyl group substituted with a $C_1$ to $C_3$ alkyl group, —$CONR^5R^6$, or —$NR^3R^6$, wherein when $R^{11}$ is —$CONR^5R^6$ or —$NR^5R^6$, $R^5$ is a hydrogen atom, a $C_1$ to $C_3$ alkyl group, a $C_1$ to $C_3$ acyl group, or a $C_1$ to $C_3$ alkylsulfonyl group, and $R^6$ is a hydrogen atom or a $C_1$ to $C_3$ alkyl group, or $R^5$ and $R^6$ may together form a 3- to 10-membered heterocycloalkyl group; and $R^{12}$ is a hydrogen atom, a halogen atom, a hydroxy group, or a $C_1$ to $C_3$ alkyl group.

[6] The compound according to any one of [1] to [5] or a pharmacologically acceptable salt thereof, wherein in the formula (I), A is a group selected from the group consisting of the following A1a), A2a), A3b), A2e) and A10ab):

[Chem. 6]

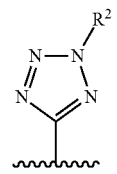
A1a)

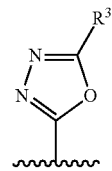
A2a)

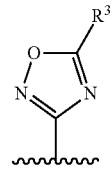
A3b)

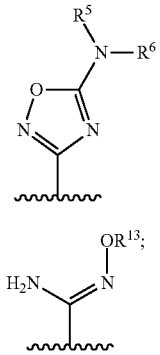
A2e)

A10ab)

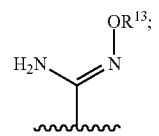

when A is A1a), $R^2$ is a hydrogen atom, a $C_1$ to $C_3$ alkyl group, or a hydroxy $C_1$ to $C_4$ alkyl group;

when A is A2a) or A3b), $R^3$ is a hydrogen atom, a hydroxy group, a $C_1$ to $C_3$ alkyl group, or a hydroxy $C_1$ to $C_4$ alkyl group;

when A is A2e), $R^5$ is a hydrogen atom, a $C_1$ to $C_3$ alkyl group, or a hydroxy $C_1$ to $C_4$ alkyl group, and $R^6$ is a hydrogen atom or a $C_1$ to $C_6$ alkyl group optionally having substituent(s), or $R^5$ and $R^6$ may together form a 3- to 10-membered heterocycloalkyl group; and when A is A10ab), $R^{13}$ is a hydrogen atom, a $C_1$ to $C_3$ alkyl group, or a hydroxy $C_1$ to $C_4$ alkyl group.

[7] The compound according to any one of [1] to [6] or a pharmacologically acceptable salt thereof, wherein in the formula (I), $Ar^2$ is a group selected from the group consisting of B1a) and B4a):

[Chem. 7]

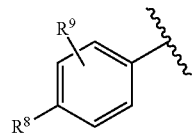
B1a)

-continued

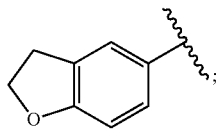

B4a)

when Ar² is B1a), R⁸ is a fluorine atom, a chlorine atom, a cyano group, a $C_1$ to $C_3$ alkyl group, a $C_1$ to $C_3$ alkyloxy group, a $C_1$ to $C_3$ acyl group, or a hydroxy $C_1$ to $C_4$ alkyl group; and R⁹ is a hydrogen atom, a halogen atom, a hydroxy group, a cyano group, or a $C_1$ to $C_3$ alkyl group.

[8] The compound according to any one of [1] to [7] or a pharmacologically acceptable salt thereof, wherein
in the formula (I), Ar¹ is C1a):

[Chem. 8]

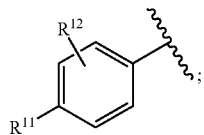

C1a)

$R^{11}$ is a hydrogen atom, a halogen atom, a cyano group, a trifluoromethyl group, or a $C_1$ to $C_3$ alkyl group; and
$R^{12}$ is a hydrogen atom or a halogen atom.

[9] The urea compound according to [8] or a pharmacologically acceptable salt thereof, wherein
in the formula (I), Ar² is B1aa):

[Chem. 9]

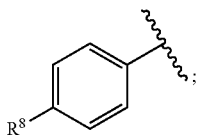

B1aa)

and

R⁸ is a cyano group, an ethyl group, an acetyl group, or a $C_1$ to $C_3$ alkyloxy group.

[10] The compound according to [1] or a pharmacologically acceptable salt thereof, wherein
the compound represented by the formula (I) is
(−)-(S)-1-(4-chlorophenyl)-3-{1-[2-(2-hydroxyethyl)-2H-tetrazol-5-yl]-2-(4-methoxyphenyl)ethyl}urea,
(S)-1-(4-fluorophenyl)-3-{1-[2-(2-hydroxyethyl)-2H-tetrazol-5-yl]-2-(4-methoxyphenyl)ethyl}urea,
(S)-1-(4-cyanophenyl)-3-{1-[2-(2-hydroxyethyl)-2H-tetrazol-5-yl]-2-(4-methoxyphenyl)ethyl}urea,
(S)-1-(4-chlorophenyl)-3-{2-(4-cyanophenyl)-1-[2-(2-hydroxyethyl)-2H-tetrazol-5-yl]ethyl}urea,
(S)-1-(4-chlorophenyl)-3-{2-(2,3-dihydrobenzofuran-5-yl)-1-[2-(2-hydroxyethyl)-2H-tetrazol-5-yl]ethyl}urea,
(S)-1-(4-chlorophenyl)-3-{2-(4-ethylphenyl)-1-[2-(2-hydroxyethyl)-2H-tetrazol-5-yl]ethyl}urea,
(−)-(S)-1-(4-cyanophenyl)-3-{2-(2,3-dihydrobenzofuran-5-yl)-1-[2-(2-hydroxyethyl)-1H-tetrazol-5-yl]ethyl}urea,
1-(4-chlorophenyl)-3-{(1S,2R)-1-[2-(2-hydroxyethyl)-2H-tetrazol-5-yl]-2-(4-methoxyphenyl)propyl)urea,
1-(4-chlorophenyl)-3-{(1S,2S)-1-[2-(2-hydroxyethyl)-2H-tetrazol-5-yl]-2-(4-methoxyphenyl)propyl)urea,
(S)-1-(4-chlorophenyl)-3-(2-(4-ethylphenyl)-1-{5-[(2-hydroxyethyl)(methyl)amino]-1,2,4-oxadiazol-3-yl}ethyl) urea,
(+)-(S)-1-(4-chlorophenyl)-3-{1-[2-(3-hydroxypropyl)-2H-tetrazol-5-yl]-2-(4-methoxyphenyl)ethyl}urea,
(+)-(S)-1-(4-chlorophenyl)-3-(1-(2-(3-hydroxybutyl)-2H-tetrazol-5-yl)-2-(4-methoxyphenyl)ethyl)urea,
(S)-1-(4-fluorophenyl)-3-{1-[5-(2-hydroxyethyl)-1,3,4-thiadiazol-2-yl]-2-(4-methoxyphenyl)ethyl}urea,
(S)-1-(4-chlorophenyl)-3-{1-[5-(2-hydroxyethyl)-1,3,4-oxadiazol-2-yl]-2-(4-methoxyphenyl)ethyl}urea,
(S)-1-(4-fluorophenyl)-3-{1-[5-(2-hydroxyethyl)-1,3,4-oxadiazol-2-yl]-2-(4-methoxyphenyl)ethyl}urea,
(S)-1-(4-cyanophenyl)-3-{1-[5-(2-hydroxyethyl)-1,3,4-oxadiazol-2-yl]-2-(4-methoxyphenyl)ethyl}urea,
(S)-2-(5-{1-[3-(4-chlorophenyl)ureido]-2-(4-methoxyphenyl)ethyl}-1,3,4-oxadiazol-2-yl)-N-methylacetamide,
(S)-2-(5-{1-[3-(4-fluorophenyl)ureido]-2-(4-methoxyphenyl)ethyl}-1,3,4-oxadiazol-2-yl)-N-methylacetamide,
(S)-1-(4-chlorophenyl)-3-{1-[4-(2-hydroxypropan-2-yl)oxazol-5-yl]-2-(4-methoxyphenyl)ethyl}urea,
(S)—N-(5-{1-[3-(4-chlorophenyl)ureido]-2-(4-ethylphenyl)ethyl}-1,3,4-oxadiazol-2-yl)acetamide,
(S)-1-(2-(4-chlorophenyl)-1-{5-[(methylsulfonyl)methyl]-1,2,4-oxadiazol-3-yl}ethyl)-3-(4-fluorophenyl)urea,
1-(4-chlorophenyl)-3-{2-(4-methoxyphenyl)-1-[5-(1-methylpiperazin-4-yl)-1,2,4-oxadiazol-3-yl]ethyl}urea,
(S)-1-(1-(5-amino-1,2,4-oxadiazol-3-yl)-2-(4-methoxyphenyl)ethyl)-3-(4-fluorophenyl)urea,
(S)-1-(1-(5-amino-1,2,4-oxadiazol-3-yl)-2-(4-methoxyphenyl)ethyl)-3-(4-cyanophenyl)urea,
(S)-1-(4-chlorophenyl)-3-(2-(4-methoxyphenyl)-1-(5-(methylamino)-1,2,4-oxadiazol-3-yl)ethyl)urea,
(S)-1-(4-chlorophenyl)-3-(1-(5-(dimethylamino)-1,2,4-oxadiazol-3-yl)-2-(4-methoxyphenyl)ethyl)urea,
(S)-1-(4-chlorophenyl)-3-(1-(5-(3-hydroxyazetidin-1-yl)-1,2,4-oxadiazol-3-yl)-2-(4-methoxyphenyl)ethyl)urea,
(S)-1-(4-chlorophenyl)-3-(1-(1-(2-hydroxyethyl)-1H-pyrazol-3-yl)-2-(4-methoxyphenyl)ethyl)urea,
(S)-1-(4-chlorophenyl)-3-(1-(3-(2-hydroxyethyl)isoxazol-5-yl)-2-(4-methoxyphenyl)ethyl)urea,
(S)-1-(4-chlorophenyl)-3-(1-(5-(2-hydroxyethyl)isoxazol-3-yl)-2-(4-methoxyphenyl)ethyl)urea,
(S)-1-(4-chlorophenyl)-3-(1-(2-(2-hydroxyethyl)-2H-1,2,4-triazol-4-yl)-2-(4-methoxyphenyl)ethyl)urea,
(S)-1-(4-chlorophenyl)-3-(1-(1-(2-hydroxyethyl)-1H-1,2,3-triazol-4-yl)-2-(4-methoxyphenyl)ethyl)urea,
(S)-1-(4-chlorophenyl)-3-(1-(1-(2-hydroxyethyl)-1H-pyrazol-4-yl)-2-(4-methoxyphenyl)ethyl)urea,
(−)-(S)-1-(4-chlorophenyl)-3-(2-(4-methoxyphenyl)-1-(2-((methylsulfonyl)methyl)-2H-tetrazol-5-yl)ethyl)urea,
(−)-(S)-1-(4-chlorophenyl)-3-(2-(4-methoxyphenyl)-1-(2-(2-(methylsulfonyl)methyl)-2H-tetrazol-5-yl)ethyl)urea,
(−)-(S)—N-(2-(5-(2-(4-chlorophenyl)-1-(3-(4-chloro-phenyl)ureido)ethyl)-2H-tetrazol-2-yl)ethyl)methanesulfonamide,
(−)-(S)—N-(2-(5-(2-(4-chlorophenyl)-1-(3-(4-fluorophenyl)ureido)ethyl)-2H-tetrazol-2-yl)ethyl)methanesulfonamide,
(−)-1-(4-chlorophenyl)-3-((1S)-2-(4-methoxyphenyl)-1-(2-((methylsulfinyl)methyl)-2H-tetrazol-5-yl)ethyl)urea,
(−)-(S)—N-((5-(2-(4-chlorophenyl)-1-(3-(4-chlorophenyl)ureido)ethyl)-1,3,4-oxadiazol-2-yl)methyl)acetamide,
(S)-1-(4-chlorophenyl)-3-(2-(4-chlorophenyl)-1-(5-(2-hydroxypropan-2-yl)-1,3,4-oxadiazol-2-yl)ethyl)urea, (S)—N-((5-(3-(4-chlorophenyl)ureido)-2-(4-ethylphenyl)ethyl)-1,3,4-oxadiazol-2-yl)methyl)acetamide,
(−)-(S)-1-(4-chlorophenyl)-3-(2-(4-ethylphenyl)-1-(5-(3-hydroxyethyl)-1,3,4-oxadiazol-2-yl)ethyl)urea,
2-(3-(4-chlorophenyl)ureido-N'-hydroxy-3-(4-methoxyphenyl)propanimidamide,
(S)-1-[1-(5-amino-1,3,4-thiadiazol-2-yl)-2-(4-methoxyphenyl)ethyl]-3-(4-chlorophenyl)urea,
5-(1-(3-(4-chlorophenyl)ureido)-2-(4-methoxyphenyl)ethyl)oxazole-4-carboxylic acid,
(S)-5-(1-(3-(4-chlorophenyl)ureido)-2-(4-methoxyphenyl)ethyl)oxazole-4-carboxylic acid,
(−)-(S)-2-(5-(1-(3-(4-chlorophenyl)ureido)-2-(4-methoxyphenyl)ethyl)-2-oxo-1,3,4-oxadiazol-3(2H)-yl)acetic acid,
1-(4-chlorophenyl)-3-(1-(5-(hydroxymethyl)-1,3,4-oxadiazol-2-yl)-2-(4-methoxyphenyl)ethyl)urea,
1-(4-chlorophenyl)-3-(1-(5-(hydroxymethyl)-1,2,4-oxadiazol-3-yl)-2-(4-methoxyphenyl)ethyl)urea,
(S)-1-(4-chlorophenyl)-3-(1-(5-(2-hydroxyethyl)-1,3,4-thiadiazol-2-yl)-2-(4-methoxyphenyl)ethyl)urea,
(S)-1-(4-chlorophenyl)-3-(1-(5-(2-hydroxyethyl)-4H-1,2,4-triazol-3-yl)-2-(4-methoxyphenyl)ethyl)urea,
(+)-(S)-2-(5-{1-[3-(4-chlorophenyl)ureido]-2-(4-methoxyphenyl)ethyl}-2H-tetrazol-2-yl)acetamide,
(S)-5-(1-(3-(4-chlorophenyl)ureido)-2-(4-methoxyphenyl)ethyl)oxazole-4-carboxamide,
(S)-5-(1-(3-(4-chlorophenyl)ureido)-2-(4-methoxyphenyl)ethyl)-N-methyloxazole-4-carboxamide,
(S)-5-(1-(3-(4-chlorophenyl)ureido)-2-(4-methoxyphenyl)ethyl)-N,N-dimethyloxazole-4-carboxamide,
(S)-2-(5-(1-(3-(4-chlorophenyl)ureido)-2-(4-methoxyphenyl)ethyl)-2H-tetrazol-2-yl)-N-methylacetamide,
(S)-1-(4-chlorophenyl)-3-(2-(4-methoxyphenyl)-1-(2-(2-morpholino-2-oxoethyl)-2H-tetrazol-5-yl)ethyl)urea,
(−)-(S)-1-(1-(2-(azetidin-3-yl)-2H-tetrazol-5-yl)-2-(4-methoxyphenyl)ethyl)-3-(4-chlorophenyl)urea,
(−)-(S)—N-(2-(5-(1-(3-(4-chlorophenyl)ureido)-2-(4-methoxyphenyl)ethyl)-2H-tetrazol-2-yl)ethyl)acetamide,
(−)-(S)—N-(2-(5-(1-(3-(4-chlorophenyl)ureido)-2-(4-methoxyphenyl)ethyl)-2H-tetrazol-2-yl)ethyl)methanesulfonamide,
1-(1-(5-amino-1,2,4-oxadiazol-3-yl)-2-(4-methoxyphenyl)ethyl)-3-(4-chlorophenyl)urea,
(S)-1-(1-(5-amino-1,2,4-oxadiazol-3-yl)-2-(4-chlorophenyl)ethyl)-3-(4-chlorophenyl)urea,
(+)-(S)-1-(4-chlorophenyl)-3-(2-(4-chlorophenyl)-1-(5-(methylamino)-1,2,4-oxadiazol-3-yl)ethyl)urea,
(S)-1-(4-chlorophenyl)-3-(2-(4-chlorophenyl)-1-(5-((2-hydroxyethyl)(methyl)amino)-1,2,4-oxadiazol-3-yl)ethyl)urea,
(S)-1-(4-chlorophenyl)-3-(2-(4-chlorophenyl)-1-(5-(3-hydroxyazetidin-1-yl)-1,2,4-oxadiazol-3-yl)ethyl)urea,
(S)-1-(4-chlorophenyl)-3-(2-(4-chlorophenyl)-1-(5-((1-hydroxy-2-methylpropan-2-yl)amino)-1,2,4-oxadiazol-3-yl)ethyl)urea,
(−)-(S)-1-(2-(4-chlorophenyl)-1-(5-((2-hydroxyethyl)amino)-1,2,4-oxadiazol-3-yl)ethyl)-3-(4-fluorophenyl)urea,
(−)-(S)-1-(4-chlorophenyl)-3-(2-(4-chlorophenyl)-1-(5-((1,3-dihydroxypropan-2-yl)amino)-1,2,4-oxadiazol-3-yl)ethyl)urea,
(−)-(S)-1-(4-chlorophenyl)-3-(1-(5-((1,3-dihydroxypropan-2-yl)amino)-1,2,4-oxadiazol-3-yl)-2-(4-methoxyphenyl)ethyl)urea,
(+)-(S,Z)-2-[3-(4-chlorophenyl)ureido]-3-(4-ethylphenyl)-N'-(2-hydroxyethoxy)propanimidamide,
(S,Z)-2-[3-(4-chlorophenyl)ureido]-N'-(2-hydroxyethoxy)-3-(4-methylthiophenyl)propanimidamide,
(+)-(S,Z)-2-[3-(4-chlorophenyl)ureido]-N'-(2-hydroxyethoxy)-3-(4-methoxyphenyl)propanimidamide,
(S)—N-{2-[3-(4-fluorophenyl)ureido]-1-imino-3-(4-methoxyphenyl)propyl}-3-hydroxypropanamide,
(S)—N-{2-[3-(4-chlorophenyl)ureido]-1-imino-3-(4-methoxyphenyl)propyl}-3-hydroxypropanamide,
(S,Z)—N-{1-amino-3-(4-chlorophenyl)-2-[3-(4-chlorophenyl)ureido]propylidene}-3-hydroxy-2,2-dimethylpropanamide,
(S)-1-{2-(4-chlorophenyl)-1-[5-(1-hydroxy-2-methylpropan-2-yl)-1,2,4-oxadiazol-3-yl]ethyl}-3-(4-fluorophenyl)urea,
(S)-1-(4-chlorophenyl)-3-(2-(4-chlorophenyl)-1-{5-[1-(hydroxymethyl)cyclopropyl]-1,2,4-oxadiazol-3-yl}ethyl)urea,
(S)-1-(2-(4-chlorophenyl)-1-{5-[1-(hydroxymethyl)cyclopropyl]-1,2,4-oxadiazol-3-yl}ethyl)-3-(4-fluorophenyl)urea,
(S)—N-{3-(4-chlorophenyl)-2-[3-(4-fluorophenyl)ureido]-1-iminopropyl}-2-(methanesulfonyl)acetamide,
(S)—N-{4-(4-chlorophenyl)-3-[3-(4-chlorophenyl)ureido]-1-iminobutyl}-2-hydroxyacetamide,
(−)-(S)-1-(4-chlorophenyl)-3-(1-(4-(2-hydroxyethyl)-5-oxo-4,5-dihydro-1,3,4-oxadiazol-2-yl)-2-(4-methoyphenyl)ethyl)urea,
(+)-(R)-1-(4-chlorophenyl)-3-[1-hydroxy-3-(4-methoxyphenyl)propan-2-yl]urea, or
4-[2-[3-(4-chlorophenyl)ureido]-3-hydroxypropyl]-N,N-dimethylbenzamide.

[11] A pharmaceutical comprising, as an active ingredient, the compound according to any one of [1] to [10] or a pharmacologically acceptable salt thereof.

[12] An FPRL1 agonist comprising, as an active ingredient, the compound according to any one of [1] to [10] or a pharmacologically acceptable salt thereof.

[13] A method of treatment or prevention of inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders, comprising administering the compound according to any one of [1] to [10] or a pharmacologically acceptable salt thereof.

[14] Use of the compound according to any one of [1] to [10] or a pharmacologically acceptable salt thereof to produce a pharmaceutical for treatment or prevention of inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders.

[15] A pharmaceutical composition containing the compound according to any one of [1] to [10] or a pharmacologically acceptable salt thereof and a pharmaceutically acceptable carrier, used for prevention or treatment of inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders.

Advantageous Effects of Invention

The compound (I) or a pharmacologically acceptable salt thereof exhibited superior agonist activity in, for example, a test of calcium influx into FPRL1-overexpressing cells. The compound (I) and salts thereof strongly suppressed lipopolysaccharide-induced neutrophilic infiltration into the lungs of mice. In addition, the compound (I) and salts thereof have low toxicity and are therefore safe. Therefore, the compound (I) according to the present invention or a pharmacologically acceptable salt thereof is useful as a therapeutic or prophylactic agent for inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

In addition, the compound (I) according to the present invention or a pharmacologically acceptable salt thereof is highly useful for treatment, prevention, or suppression of various disease states associated with the FPRL1 (such as Behcet's disease, Sweet disease, systemic lupus erythematosus (SLE), Wegener's granulomatosis, virus infection, diabetes, amputations, cancers, bacterial infection, physical external injuries, physical disorders including exposure to radiation, vasoconstriction, anaphylactic reactions, allergic reactions, rhinitis, shocks (endotoxic, hemorrhagic, traumatic, splanchnic ischemia, and circulatory shocks), rheumatoid arthritis, gout, psoriasis, benign prostatic hyperplasia, myocardial ischemia, myocardial infarction, brain injuries, pulmonary diseases, COPD, COAD, COLD, acute lung injury, acute respiratory distress syndrome, chronic bronchitis, pulmonary emphysema, asthma (allergic asthma and non-allergic asthma), cystic pulmonary fibrosis, nephropathy, renal glomerular diseases, ulcerative colitis, IBD, Crohn's disease, periodontitis, pains, Alzheimer's disease, AIDS, uveitic glaucoma, conjunctivitis, Sjoegren's syndrome, and rhinitis).

DESCRIPTION OF EMBODIMENTS

Terms in the present description will be described.

The term "halogen atom" as used herein means a fluorine atom, a chlorine atom, a bromine atom, or an iodine atom. Preferably, the halogen atom is a fluorine atom or a chlorine atom.

The monocyclic aromatic heterocyclyl group in the term "monocyclic aromatic heterocyclyl group optionally having substituent(s)" as used herein means a 5- or 6-membered aromatic heterocyclyl group containing, in its ring, 1 to 4 atoms selected from sulfur, oxygen, and nitrogen atoms. Examples of the monocyclic aromatic heterocyclyl group may include a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyridyl group, a pyridazinyl group, a pyrimidinyl group, a pyrazinyl group and the like.

The bicyclic aromatic heterocyclyl group having 9 or 10 atoms in the term "bicyclic aromatic heterocyclyl group having 9 or 10 atoms and optionally having substituent(s)" as used herein means a bicyclic aromatic heterocyclyl group having 9 or 10 atoms containing 1 to 4 atoms selected from sulfur, oxygen, and nitrogen atoms. Examples of the bicyclic aromatic heterocyclyl group having 9 or 10 atoms may include a benzofuranyl group, an isobenzofuranyl group, a benzoxazolyl group, a benzisoxazolyl group, a benzothiazolyl group, a benzisothiazolyl group, a benzimidazolyl group, a benzothiophenyl group, an indolyl group, an isoindolyl group, an indazolyl group, a thiazolopyridyl group, an oxazolopyrazinyl group, a purinyl group, a quinolizinyl group, an isoquinolyl group, a quinolyl group, a phthalazinyl group, a naphthyridinyl group, a quinoxalinyl group, a quinazolinyl group and the like.

The $C_1$ to $C_6$ alkyloxy group in the terms "$C_1$ to $C_6$ alkyloxy group optionally having substituent(s)" and "$C_1$ to $C_6$ alkyloxy group" as used herein means a linear or branched alkyloxy group having 1 to 6 carbon atoms. Examples of the $C_1$ to $C_6$ alkyloxy group may include a methoxy group, an ethoxy group, a propoxy group, an isopropoxy group, an isobutoxy group, a butoxy group, a sec-butoxy group, a tert-butoxy group, a pentyloxy group, a hexyloxy group and the like. Preferred examples may include a methoxy group and an ethoxy group.

The $C_1$ to $C_6$ alkyl group in the terms "$C_1$ to $C_6$ alkyl group optionally having substituent(s)" and "$C_1$ to $C_6$ alkyl group" as used herein means a linear or branched alkyl group having 1 to 6 carbon atoms and optionally having substituent(s). Examples of the $C_1$ to $C_6$ alkyl group may include a methyl group, an ethyl group, a propyl group, an isopropyl group, a butyl group, an isobutyl group, a sec-butyl group, a tert-butyl group, a pentyl group, an isopentyl group, a neopentyl group, a 1-methylbutyl group, a 2-methylbutyl group, a 1,2-dimethylpropyl group, a hexyl group, an isohexyl group and the like.

The $C_1$ to $C_6$ acyl group in the terms "$C_1$ to $C_6$ acyl group optionally having substituent(s)" and "$C_1$ to $C_6$ acyl group" as used herein means an acyl group derived from a linear or branched aliphatic carboxylic acid having 1 to 6 carbon atoms. Examples of the $C_1$ to $C_6$ acyl group may include a formyl group, an acetyl group, a propanoyl group, a butanoyl group, a pentanoyl group, a hexanoyl group and the like.

The $C_1$ to $C_6$ alkylsulfanyl group in the terms "$C_1$ to $C_6$ alkylsulfanyl group optionally having substituent(s)" and "$C_1$ to $C_6$ alkylsulfanyl group" as used herein means a linear or branched alkylsulfanyl group having 1 to 6 carbon atoms or a cyclic alkylsulfanyl group having 3 to 6 carbon atoms. Examples of the $C_1$ to $C_6$ alkylsulfanyl group may include a methylsulfanyl group, an ethylsulfanyl group, a propylsulfanyl group, an isopropylsulfanyl group, a butylsulfanyl group, an isobutylsulfanyl group, a sec-butylsulfanyl group, a tert-butylsulfanyl group, a cyclopropylsulfanyl group, a cyclobutylsulfanyl group, a cyclopentylsulfanyl group and the like.

The $C_1$ to $C_6$ alkylsulfinyl group in the terms "$C_1$ to $C_6$ alkylsulfinyl group optionally having substituent(s)" and "$C_1$ to $C_6$ alkylsulfinyl group" as used herein means a linear or branched alkylsulfinyl group having 1 to 6 carbon atoms or a cyclic alkylsulfinyl group having 3 to 6 carbon atoms. Examples of the $C_1$ to $C_6$ alkylsulfinyl group may include a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a cyclopropylsulfinyl group, a cyclobutylsulfinyl group, a cyclopentylsulfinyl group and the like.

The $C_1$ to $C_6$ alkylsulfonyl group in the terms "$C_1$ to $C_6$ alkylsulfonyl group optionally having substituent(s)" and "$C_1$ to $C_6$ alkylsulfonyl group" as used herein means a linear or branched alkylsulfonyl group having 1 to 6 carbon atoms or a cyclic alkylsulfonyl group having 3 to 6 carbon atoms. Examples of the $C_1$ to $C_6$ alkylsulfonyl group may include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a cyclopropylsulfonyl group, a cyclobutylsulfonyl group, a cyclopentylsulfonyl group and the like.

The heterocyclyl group in the term "heterocyclyl group optionally having substituent (s)", "heterocyclyl group having $C_1$ to $C_3$ alkyl group", and "heterocyclyl group" as used herein means a 5- to 7-membered heterocyclyl group containing 1 to 4 atoms selected from sulfur, oxygen, and nitrogen atoms. Examples of the heterocyclyl group may include: aromatic heterocyclyl groups such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyranyl group, a pyridyl group, a pyridazinyl group, a pyrimidinyl group, and a pyrazinyl group; unsaturated heterocyclyl groups such as a pyrrolinyl group, an imidazolinyl group, a pyrazolinyl group, a dihydropyranyl group, a dihydrothiopyranyl group, and a dihydropyridyl group; and saturated heterocyclyl groups such as a morpholinyl group, a thiomorpholinyl group, a pyrrolidinyl group, an imidazolidinyl group, an imidazolinyl group, a pyrazolidinyl group, a pyrazolinyl group, a piperidinyl group, a piperazinyl group, a tetrahydrofuranyl group and the like.

The above "heterocyclyl group" may be condensed with another cyclic group. Examples of the heterocyclyl group condensed with another cyclic group may include an isobenzofuranyl group, a benzoxazolyl group, a benzisoxazolyl group, a benzothiazolyl group, a benzisothiazolyl group, a chromenyl group, a chromanonyl group, a xanthenyl group, a phenoxathiinyl group, an indolizinyl group, an isoindolizinyl group, an indolyl group, an indazolyl group, a purinyl group, a quinolizinyl group, an isoquinolyl group, a quinolyl group, a phthalazinyl group, a naphthyridinyl group, a quinoxalinyl group, a quinazolinyl group, a carbazolyl group, a carbolinyl group, an acridinyl group, an isoindolinyl group and the like.

The term "3- to 10-membered heterocycloalkyl group" as used herein means a monocyclic, bicyclic, or tricyclic non-aromatic heterocycloalkyl group which is a 3- to 10-membered heterocycloalkyl group containing at least one nitrogen atom, oxygen atom, or sulfur atom. Examples of the 3- to 10-membered heterocycloalkyl group may include an azetidinyl group, a pyrrolidinyl group, a piperidyl group, a piperazinyl group, a morpholinyl group and the like.

The $C_3$ to $C_6$ cycloalkyl group in the term "$C_3$ to $C_6$ cycloalkyl group" as used herein means a monocyclic saturated alicyclic hydrocarbon group having 3 to 6 carbon atoms. Examples of the $C_3$ to $C_6$ cycloalkyl group may include a cyclopropyl group, a cyclobutyl group, a cyclopentyl group, a cyclohexyl group and the like.

The $C_2$ to $C_3$ alkenyl group as used herein means a linear or branched unsaturated hydrocarbon group having 2 to 3 carbon atoms and having at least one double bond. Examples of the $C_2$ to $C_3$ alkenyl group may include a vinyl group, a 2-propenyl group, a 1-propenyl group, a 3-propenyl group and the like.

The "$C_2$ to $C_3$ alkynyl group" as used herein means a linear unsaturated hydrocarbon group having 2 to 3 carbon atoms and having at least one triple bond. Examples of the $C_2$ to $C_3$ alkynyl group may include an ethynyl group, a 1-propynyl group, a 2-propynyl group and the like.

The "$C_1$ to $C_6$ alkylsulfonylamino group" as used herein means a linear or branched alkylsulfonylamino group having 1 to 6 carbon atoms, or a cyclic alkylsulfonylamino group having 3 to 6 carbon atoms. Examples of the $C_1$ to $C_6$ alkylsulfonylamino group may include a methylsulfonylamino group, an ethylsulfonylamino group, a propylsulfonylamino group, an isopropylsulfonylamino group, a butylsulfonylamino group, an isobutylsulfonylamino group, a sec-butylsulfonylamino group, a tert-butylsulfonylamino group, a cyclopropylsulfonylamino group, a cyclobutylsulfonylamino group, cyclopentylsulfonylamino group and the like.

The "$C_1$ to $C_6$ alkyloxycarbonyl group" as used herein means a linear or branched alkyloxycarbonyl group having 1 to 6 carbon atoms. Examples of the $C_1$ to $C_6$ alkyloxycarbonyl group may include a methoxycarbonyl group, an ethoxycarbonyl group, a propoxycarbonyl group, an isopropoxycarbonyl group, an isobutoxycarbonyl group, a butoxycarbonyl group, a sec-butoxycarbonyl group, a tert-butoxycarbonyl group, a pentyloxycarbonyl group, a hexyloxycarbonyl group and the like. Preferred examples thereof may include a methoxycarbonyl group and a tert-butoxycarbonyl group.

The "hydroxy $C_1$ to $C_6$ alkyl group" as used herein means a linear or branched $C_1$ to $C_6$ alkyl group substituted with one or two hydroxy groups. Examples of the hydroxy $C_1$ to $C_6$ alkyl group may include a hydroxymethyl group, a 2-hydroxyethyl group, a 3-hydroxy-1,1-dimethyl-1-ethyl group, a 3-hydroxy-1-propyl group, a 4-hydroxy-1-butyl group, a 6-hydroxy-1-hexyl group, a 1,3-dihydroxy-2-propyl group, a 1-hydroxymethyl-1-cyclopropyl group and the like.

The "hydroxy $C_1$ to $C_6$ alkyloxy group" as used herein means a linear or branched $C_1$ to $C_6$ alkyloxy group substituted with one or two hydroxy groups. Examples of the hydroxy $C_1$ to $C_6$ alkyloxy group may include a hydroxymethyloxy group, a 2-hydroxyethyloxy group, a 3-hydroxy-1,1-dimethyl-1-ethyl group, a 3-hydroxy-1-propyloxy group, a 4-hydroxy-1-butyloxy group, a 6-hydroxy-1-hexyloxy group, a 1,3-dihydroxy-2-propyloxy group, a 1-hydroxymethyl-1-cyclopropyloxy group and the like.

The "$C_1$ to $C_6$ alkylsulfonyl $C_1$ to $C_6$ alkyloxy group" as used herein means a linear or branched $C_1$ to $C_6$ alkyloxy group substituted with a $C_1$ to $C_6$ alkylsulfonyl. Examples of the $C_1$ to $C_6$ alkylsulfonyl $C_1$ to $C_6$ alkyloxy group may include a methanesulfonylmethyloxy group, a 2-methanesulfonylethyloxy group, a 3-ethylsulfonyl-1-propyloxy group, a 4-propylsulfonyl-1-butyloxy group, a 6-methanesulfonyl-1-hexyloxy group and the like.

The "hydroxy $C_1$ to $C_6$ acyl group" as used herein means an acyl group derived from a linear or branched $C_1$ to $C_6$ aliphatic carboxylic acid substituted with a hydroxy group. Examples of the hydroxy $C_1$ to $C_6$ acyl group may include a hydroxyacetyl group, a 2-hydroxypropanoyl group, a 3-hydroxybutanoyl group, a 4-hydroxy-1-butanoyl group, a 4-hydroxy-1-pentanoyl group, a 5-hydroxy-1-pentanoyl group and the like.

The term "carboxy $C_1$ to $C_6$ alkyl group" as used herein means a $C_1$ to $C_6$ alkyl group substituted with a carboxylic acid. Examples of the carboxy $C_1$ to $C_6$ alkyl group may include a carboxymethyl group, a 2-carboxyethyl group, a 2-carboxypropyl group, a 3-carboxypropyl group, a 4-carboxybutyl group, a 5-carboxypentyl group, a 6-carboxyhexyl group and the like.

The "carboxy $C_1$ to $C_6$ alkyloxy group" as used herein means a $C_1$ to $C_6$ alkyloxy group substituted with a carboxylic acid. Examples of the carboxy $C_1$ to $C_6$ alkyloxy group may include a carboxymethyloxy group, a 2-carboxyethyloxy group, a 2-carboxypropyloxy group, a 3-carboxypropyloxy group, a 4-carboxybutyloxy group, a 5-carboxypentyloxy group, a 6-carboxyhexyloxy group and the like.

The term "halo-$C_1$ to $C_6$ alkyloxy group" as used herein means a $C_1$ to $C_6$ alkyloxy group substituted with 1 to 5 halogen atoms of the same kind or different kinds. Examples of the halo-$C_1$ to $C_6$ alkyloxy group may include a fluoromethoxy group, a difluoromethoxy group, a trifluoromethoxy group, a 2-fluoroethoxy group, a 2-chloroethoxy group, a 2,2-difluoroethoxy group, a 1,1-difluoroethoxy group, a 1,2-difluoroethoxy group, a 2,2,2-trifluoroethoxy group, a 1,1,2,2,2-pentafluoroethoxy group, a 2,2,2-trichloroethoxy group, a 3-fluoropropoxy group, a 2-fluoropropoxy group, a 1-fluoropropoxy group, a 3,3-difluoropropoxy group, a 2,2-difluoropropoxy group, a 1,1-difluoropropoxy group, a 4-fluorobutoxy group, a 5-fluoropentoxy group, a 6-fluorohexyloxy group and the like.

The term "halo-$C_1$ to $C_3$ alkyloxy group" as used herein means a $C_1$ to $C_3$ alkyloxy group substituted with 1 to 5 halogen atoms of the same type or different types. Examples of the halo-$C_1$ to $C_3$ alkyloxy group may include a fluoromethoxy group, a difluoromethoxy group, a trifluoromethoxy group, a 2-fluoroethoxy group, a 2-chloroethoxy group, a 2,2-difluoroethoxy group, a 1,1-difluoroethoxy group, a 1,2-difluoroethoxy group, a 2,2,2-trifluoroethoxy group, a 1,1,2,2,2-pentafluoroethoxy group, a 2,2,2-trichloroethoxy group, a 3-fluoropropoxy group, a 2-fluoropropoxy group, a 1-fluoropropoxy group, a 3,3-difluoropropoxy group, a 2,2-difluoropropoxy group, a 1,1-difluoropropoxy group and the like.

The term "hydroxy $C_1$ to $C_4$ alkyl group" as used herein means a linear or branched alkyl group substituted with one or two hydroxy groups. Examples of the hydroxy $C_1$ to $C_4$ alkyl group may include a hydroxymethyl group, a 2-hydroxyethyl group, 3-hydroxy-1,1-dimethyl-1-ethyl group, 3-hydroxy-1-propyl group, 4-hydroxy-1-butyl group, 1,3-dihydroxy-2-propyl group, 1-hydroxymethyl-1-cyclopropyl group and the like.

The term "$C_1$ to $C_3$ alkylene group" as used herein means a divalent linear or branched saturated hydrocarbon chain having 1 to 3 carbon atoms. Examples of the $C_1$ to $C_3$ alkylene group may include —CH$_2$—, —(CH$_2$)$_2$—, —(CH$_2$)$_3$—, —CH(CH$_3$)CH$_2$—, —CH$_2$CH(CH$_3$)— and the like.

The "aryl group" as used herein means an aromatic hydrocarbon group having 6 to 14 carbon atoms. Examples of the aryl group may include phenyl group, indenyl group, naphthyl group, phenanthrenyl group, anthracenyl group and the like.

The "aryloxy group" as used herein means an aromatic hydrocarbon alkyloxy group having 6 to 14 carbon atoms. Examples of the aryloxy group may include a phenyloxy group, an indenyloxy group, a naphthyloxy group, a phenanthrenyloxy group, an anthracenyloxy group and the like.

The term "$C_1$ to $C_3$ alkylamino group" as used herein means an amino group in which one or two hydrogen atoms in the amino group are substituted with linear or branched alkyl groups having 1 to 3 carbon atoms. Examples of the $C_1$ to $C_3$ alkylamino group may include a methylamino group, an ethylamino group, a propylamino group, an isopropylamino group, a dimethylamino group, a diethylamino group, an N-ethyl-N-methylamino group, an N-ethyl-N-propylamino group and the like.

The term "$C_1$ to $C_3$ acylamino group" as used herein means an amino group substituted with $C_1$ to $C_3$ acyl. Examples of the $C_1$ to $C_3$ acylamino group may include a formylamino group, an acetylamino group, a propanoylamino group and the like.

The "$C_1$ to $C_3$ acyloxy group" as used herein means a hydroxy group substituted with an $C_1$ to $C_3$ acyl. Examples of the $C_1$ to $C_3$ acyloxy group may include a formyloxy group, an acetyloxy group, a propanoyloxy group and the like.

The term "$C_1$ to $C_3$ alkyl group" as used herein means a linear or branched alkyl group having 1 to 3 carbon atoms. Examples of the $C_1$ to $C_3$ alkyl group may include a methyl group, an ethyl group, a propyl group, and an isopropyl group.

The term "$C_1$ to $C_3$ alkyloxy group" as used herein means a linear or branched alkyloxy group having 1 to 3 carbon atoms. Examples of the $C_1$ to $C_3$ alkyloxy group may include a methoxy group, an ethoxy group, a propoxy group, and an isopropoxy group.

The "$C_1$ to $C_3$ alkyloxycarbonyl group" as used herein means a linear or branched alkyloxycarbonyl group having 1 to 3 carbon atoms. Examples of the $C_1$ to $C_3$ alkyloxycarbonyl group may include methoxycarbonyl group, ethoxycarbonyl group, propoxycarbonyl group, isopropoxycarbonyl group and the like.

The "$C_1$ to $C_3$ alkylaminocarbonyl group" as used herein means an aminocarbonyl group in which one or two hydrogen atoms in the amino group are substituted with linear or branched alkyl groups having 1 to 3 carbon atoms. Examples of the $C_1$ to $C_3$ alkylaminocarbonyl group may include a methylaminocarbonyl group, an ethylaminocarbonyl group, a dimethylaminocarbonyl group, an isopropylaminocarbonyl group, an ethylmethylaminocarbonyl group and the like.

The "$C_1$ to $C_3$ alkylsulfonyl group" as used herein means a linear or branched alkylsulfonyl group having 1 to 3 carbon atoms. Examples of the $C_1$ to $C_3$ alkylsulfonyl group may include a methanesulfonyl group, an ethylsulfonyl group, a propylsulfonyl group and the like.

The "$C_1$ to $C_3$ alkylsulfonylamino group" as used herein means an amino group substituted with a linear or branched alkylsulfonyl group having 1 to 3 carbon atoms. Examples of the $C_1$ to $C_3$ alkylsulfonylamino group may include a methanesulfonylamino group, an ethylsulfonylamino group, a propylsulfonylamino group and the like.

Examples of an "aromatic hydrocarbon cyclic group" as used herein may include a phenyl group, an indenyl group, a 1-naphthyl group, a 2-naphthyl group, an azulenyl group, a heptalenyl group, a biphenyl group, an indacenyl group, an acenaphthyl group, a fluorenyl group, a phenalenyl group, a phenanthrenyl group, an anthracenyl group, a benzocyclooctenyl group and the like.

No particular limitation is imposed on the groups acceptable as the "substituent(s)" in the "phenyl group optionally having substituent(s)," the "monocyclic aromatic heterocyclyl group optionally having substituent(s)," "bicyclic aromatic heterocyclyl group having 9 or 10 atoms and optionally having substituent(s)," the "heterocycle optionally having substituent(s)," and the "heterocyclyl group optionally having substituent(s)," so long as the substituent(s) are generally known substituent(s). Examples of these substituent(s) may include halogen atoms, an amino group, a hydroxy group, a cyano group, a nitro group, a carboxy group, $C_1$ to $C_6$ alkyloxycarbonyl groups, a formyl group, $C_1$ to $C_6$ acyl groups, $C_1$ to $C_6$ alkyl groups, $C_1$ to $C_6$ alkylamino groups, $C_1$ to $C_6$ alkyloxy groups, $C_1$ to $C_6$ alkylsulfanyl groups, $C_3$ to $C_6$ cycloalkyl groups, 3- to 10-membered heterocycloalkyl groups, aromatic hydrocarbon cyclic groups optionally having a halogen atom, heterocyclyl groups, $C_1$ to $C_6$ acylamino groups, $C_3$ to $C_6$ cycloalkylcarbonylamino groups, 3- to 10-membered heterocycloalkylcarbonylamino groups, aromatic hydrocarbon cyclic carbonylamino groups, heterocyclyl carbonylamino groups and the like.

No particular limitation is imposed on the groups acceptable as the "substituent(s)" in the "$C_1$ to $C_8$ alkyl group optionally having substituent(s)," the "$C_1$ to $C_3$ alkyl group optionally having substituent(s)," the "$C_1$ to $C_6$ alkylsulfanyl group optionally having substituent(s)," the "$C_1$ to $C_6$ alkylsulfinyl group optionally having substituent(s)," the "$C_1$ to $C_6$ alkylsulfonyl group optionally having substituent(s)," the "hydroxy $C_1$ to $C_6$ alkyl group optionally having substituent(s)," the "$C_1$ to $C_6$ acyl group optionally having substituent(s)," the "$C_1$ to $C_6$ alkyloxy group optionally having substituent(s)," the "aminocarbonyl group optionally having substituent(s)," the "$C_1$ to $C_6$ alkyloxycarbonyl group optionally having substituent(s)," the "heterocyclyl group optionally having substituent(s)," and the "carboxy $C_1$ to $C_6$ alkyl group optionally having substituent(s)," so long as the substituent(s) are generally known substituent(s). Examples of these substituent(s) may include halogen atoms, an amino group, a hydroxy group, a cyano group, a nitro group, a carboxy group, $C_1$ to $C_6$ alkyloxycarbonyl groups, $C_1$ to $C_6$ acyl groups, $C_1$ to $C_6$ alkyl groups, $C_1$ to $C_6$ alkylamino groups, $C_1$ to $C_6$ alkyloxy groups, $C_1$ to $C_6$ alkylsulfanyl groups, $C_3$ to $C_6$ cycloalkyl groups, 3- to 10-membered heterocycloalkyl groups, aromatic hydrocarbon cyclic groups optionally having a halogen atom, heterocyclyl groups, $C_1$ to $C_6$ acylamino groups, $C_3$ to $C_6$ cycloalkylcarbonylamino groups, 3- to 10-membered heterocycloalkylcarbonylamino groups, aromatic hydrocarbon cyclic carbonylamino groups, heterocyclyl carbonylamino groups and the like.

Hereinafter, the present embodiment will be described in more detail.

In the following, descriptions of the definitions of functional groups included in general formulas may be omitted, and the definitions already described may be quoted instead. The definitions quoted refer to definitions in the description of the following embodiment.

As for the definitions of functional groups included in the general formulas, the definition of a symbol is common to general formulas containing this symbol, unless otherwise mentioned.

The present embodiment relates to a urea compound represented by the following general formula (I) or a pharmacologically acceptable salt thereof.

A compound represented by the general formula (I) or a pharmacologically acceptable salt thereof:

[Chem. 10]

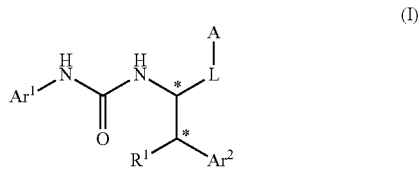

(I)

wherein in the formula (I), $Ar^1$ is a phenyl group optionally having substituent(s), a monocyclic aromatic heterocyclyl group optionally having substituent(s), or a bicyclic aromatic heterocyclyl group having 9 or 10 atoms and optionally having substituent(s);

$Ar^2$ is a phenyl group optionally having substituent(s), a monocyclic aromatic heterocyclyl group optionally having substituent(s), or a bicyclic aromatic heterocyclyl group having 9 or 10 atoms and optionally having substituent(s);

$R^1$ is a hydrogen atom, a $C_1$ to $C_3$ alkyl group, or —CONXY;

X and Y are independently a hydrogen atom or a $C_1$ to $C_3$ alkyl group;

A is a hydrogen atom, a cyano group, a hydroxy group, a $C_1$ to $C_6$ alkyloxycarbonyl group optionally having substituent(s), a 5-membered aromatic heterocyclyl group optionally having substituent(s), a 5-membered non-aromatic heterocyclyl group optionally having substituent(s), a 6-membered aromatic heterocyclyl group optionally having substituent(s), a 6-membered non-aromatic heterocyclyl group optionally having substituent(s), —CONHZ, or —C(NH$_2$)=NZ wherein Z is a hydrogen atom, a hydroxy group, a tetrazolyl group, a hydroxy $C_1$ to $C_6$ alkyl group optionally having substituent(s), a $C_1$ to $C_6$ acyl group optionally having substituent(s), a $C_1$ to $C_6$ alkyloxy group optionally having substituent(s), a carboxy $C_1$ to $C_6$ alkyl group optionally having substituent(s), an aminocarbonyl group optionally having substituent(s), or a $C_1$ to $C_6$ alkylsulfonyl group optionally having substituent(s);

L is a single bond or a $C_1$ to $C_3$ alkylene; and each carbon atom marked with an asterisk is an asymmetric carbon atom when the carbon is a tertiary carbon atom.

In the compound (I) of the present embodiment or a pharmacologically acceptable salt thereof, preferred substituents are as follows.

A is a group selected from the group consisting of a cyano group, a hydroxy group, or the following A1), A2), A3), A4), A5), A6), A7), A8), A9), A10), and A11).

[Chem.11]

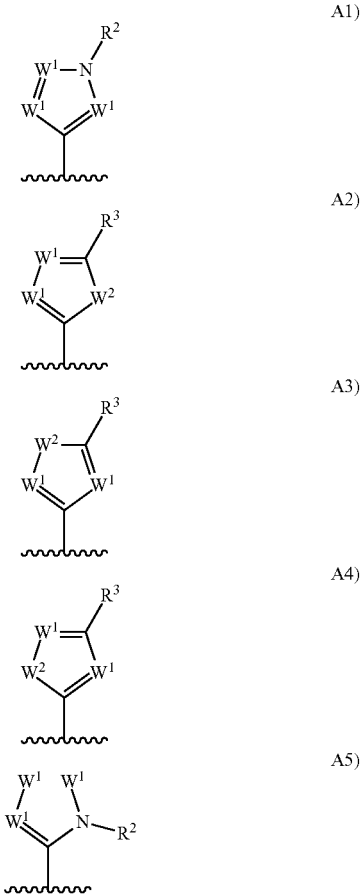

-continued
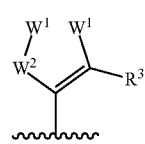
A6)
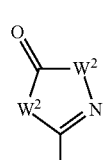
A7)
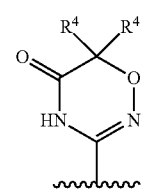
A8)
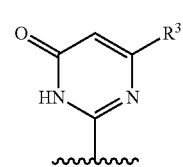
A9)
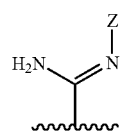
A10)
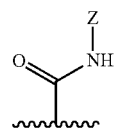
A11)
Preferably, A is a group selected from the group consisting of hydroxy group, or the following A1a), A1b), A1c), A1d), A1e), A1f), A2a), A2b), A2c), A2aa), A3a), A3b), A3ba), A3bb), A4a), A4b), A4c), A5a), A6a), A7a), A7b), A7c), A8a), A9a), A10a), and A11a).
[Chem.12]
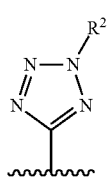
A1a)
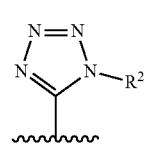
A5a)
-continued
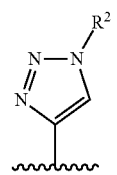
A1b)
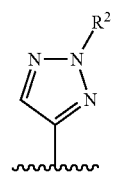
A1c)
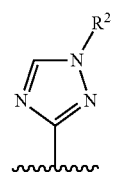
A1d)
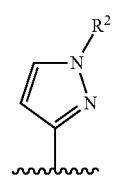
A1e)
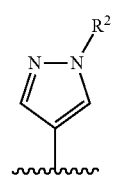
A1f)
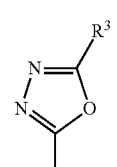
A2a)
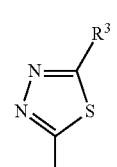
A2b)
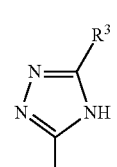
A2c)
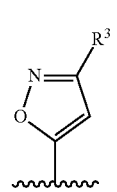
A4a)

A4b) 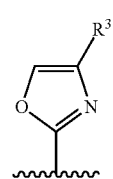
A4c) 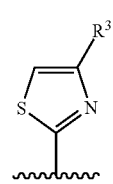
A3a) 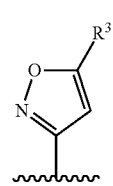
A3b) 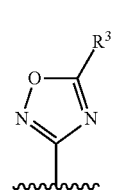
A6a) 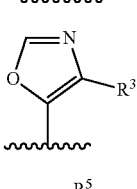
A2aa) 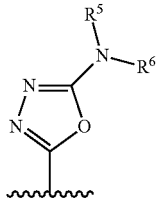
A3ba) 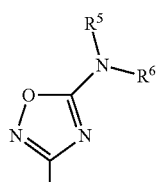
A3bb) 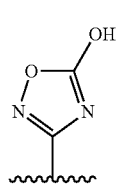
A7a) 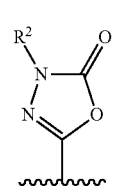
A7b) 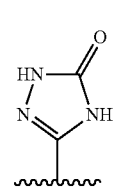
A7c) 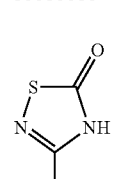
A8a) 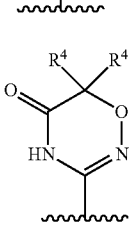
A9a) 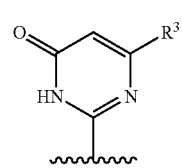
A10a) 
A11a) 
More preferably, A is a group selected from the group consisting of the following A1a), A2a), A3b), A2e), and A10ab).
[Chem. 13]
A1a) 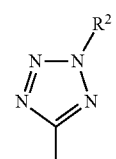
A2a) 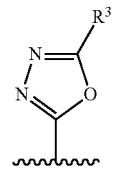

-continued

A3b)

A2e)

A10ab)

$R^2$ is a hydrogen atom or a $C_1$ to $C_6$ alkyl group optionally having substituent(s).

Preferably, $R^2$ is a hydrogen atom, or a $C_1$ to $C_6$ alkyl group optionally substituted with a group selected from the group consisting of a halogen atom, a hydroxy group, a $C_1$ to $C_3$ alkyloxy group, a carboxyl group, a $C_1$ to $C_3$ alkyloxycarbonyl group, a $C_1$ to $C_3$ alkylsulfinyl group, a $C_1$ to $C_3$ alkylsulfonyl group, an amino group, a $C_1$ to $C_3$ alkylamino group, a $C_1$ to $C_3$ alkylsulfonylamino group, a $C_1$ to $C_3$ acylamino group, a $C_1$ to $C_3$ alkylaminocarbonyl group, and a heterocyclyl group.

More preferably, $R^2$ is a hydrogen atom, a $C_1$ to $C_3$ alkyl group, or a hydroxy $C_1$ to $C_4$ alkyl group.

$R^3$ is a hydrogen atom, a halogen atom, a hydroxy group, a cyano group, a carboxyl group, a $C_1$ to $C_6$ alkyl group optionally having substituent(s), a $C_1$ to $C_6$ alkyloxy group optionally having substituent(s), a $C_1$ to $C_6$ alkyloxycarbonyl group, a $C_1$ to $C_6$ acyl group optionally having substituent(s), a $C_1$ to $C_6$ alkylsulfanyl group optionally having substituent(s), a $C_1$ to $C_6$ alkylsulfinyl group optionally having substituent(s), a $C_1$ to $C_6$ alkylsulfonyl group optionally having substituent(s), a heterocyclyl group optionally having substituent(s), —CONR$^5$R$^6$, or —NR$^5$R$^6$, wherein when $R^3$ is —CONR$^5$R$^6$ or —NR$^5$R$^6$, then $R^5$ is a hydrogen atom, a $C_1$ to $C_6$ alkyl group optionally having substituent(s), a $C_1$ to $C_6$ acyl group optionally having substituent(s), or a $C_1$ to $C_6$ alkylsulfonyl group optionally having substituent(s), and $R^6$ is a hydrogen atom or a $C_1$ to $C_6$ alkyl group optionally having substituent(s), or $R^5$ and $R^6$ may together form a 3- to 10-membered heterocycloalkyl group.

Preferably, $R^3$ is a group selected from the group consisting of the following i) to ix):
i) a hydrogen atom,
ii) a halogen atom,
iii) a cyano group,
iv) a carboxyl group,
v) a $C_1$ to $C_6$ alkyloxycarbonyl group,
vi) a carbamoyl group optionally substituted with a $C_1$ to $C_3$ alkyl group,
vii) a $C_1$ to $C_6$ alkyl group optionally substituted with a group selected from the group consisting of a halogen atom, a hydroxy group, a $C_1$ to $C_3$ alkyloxy group, a $C_1$ to $C_3$ acyloxy group, a carboxyl group, a $C_1$ to $C_3$ alkyloxycarbonyl group, a $C_1$ to $C_3$ alkylsulfonyl group, an amino group, a $C_1$ to $C_3$ alkylamino group, a $C_1$ to $C_3$ alkylsulfonylamino group, a $C_1$ to $C_3$ acylamino group, a $C_1$ to $C_3$ alkylaminocarbonyl group, and a heterocyclyl group,
viii) —CONR$^5$R$^6$ wherein preferably $R^5$ is a hydrogen atom, a $C_1$ to $C_6$ alkyl group, a $C_1$ to $C_6$ acyl group, or a $C_1$ to $C_6$ alkylsulfonyl group, and preferably $R^6$ is a hydrogen atom or a $C_1$ to $C_6$ alkyl group, or $R^5$ and $R^6$ may together form a 3- to 10-membered heterocycloalkyl group,
ix) a heterocyclyl group optionally having substituent(s).

More preferably, $R^3$ is a hydrogen atom, a hydroxy group, a $C_1$ to $C_3$ alkyl group, or a hydroxy $C_1$ to $C_4$ alkyl group.

More preferably, $R^5$ is a hydrogen atom, a $C_1$ to $C_3$ alkyl group, or a hydroxy $C_1$ to $C_4$ alkyl group, and more preferably $R^6$ is a hydrogen atom or a $C_1$ to $C_6$ alkyl group optionally having substituent(s), or $R^5$ and $R^6$ may together form a 3- to 10-membered heterocycloalkyl group.

Z is a hydrogen atom, a hydroxy group, a $C_1$ to $C_6$ alkyl group optionally having substituent(s), a $C_1$ to $C_6$ acyl group optionally having substituent(s), a $C_1$ to $C_6$ alkyloxy group optionally having substituent(s), a carboxy $C_1$ to $C_6$ alkyl group optionally having substituent(s), or a $C_1$ to $C_6$ alkylsulfonyl group optionally having substituent (s).

When A is A10a), preferably Z is a hydroxy $C_1$ to $C_6$ alkyloxy group, a hydroxy $C_1$ to $C_6$ acyl group, a carboxy $C_1$ to $C_6$ alkyloxy group, a $C_1$ to $C_3$ alkylaminocarbonyl group, a $C_1$ to $C_6$ alkylsulfonyl $C_1$ to $C_6$ acyl group, or a $C_1$ to $C_6$ alkylsulfonyl group.

When A is A11a), preferably Z is a hydrogen atom, a hydroxy group, a $C_1$ to $C_6$ alkyl group, a hydroxy $C_1$ to $C_6$ alkyl group, a $C_1$ to $C_6$ acyl group, a $C_1$ to $C_6$ alkyloxy group, a carboxy $C_1$ to $C_6$ alkyl group, or a $C_1$ to $C_6$ alkylsulfonyl group.

$R^4$ is a $C_1$ to $C_3$ alkyl group optionally having substituent(s).

Preferably, $R^4$ is a $C_1$ to $C_3$ alkyl group optionally having substituent(s).

$W^1$ is C—R$^7$ or a nitrogen atom.

$R^7$ is a hydrogen atom or a $C_1$ to $C_6$ alkyl group optionally having substituent(s).

$W^2$ is an oxygen atom, a sulfur atom, or N—R$^2$.

More preferably, $R^{13}$ is a hydrogen atom, a $C_1$ to $C_3$ alkyl group, or a hydroxy $C_1$ to $C_4$ alkyl group.

$Ar^2$ is a group selected from the group consisting of the following B1), B2), B3), and B4).

[Chem. 14]

B1)

B2)

B3)

-continued

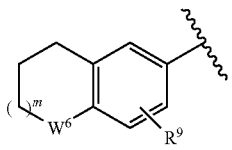
B4)

Preferably, Ar² is B1a) or B4a).

[Chem. 15]

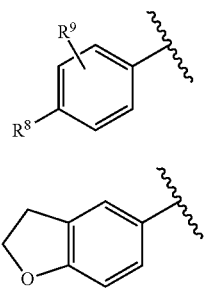
B1a)

B4a)

More preferably, Ar² is B1aa).

[Chem. 16]

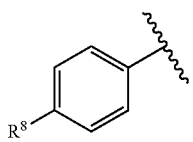
B1aa)

One of $W^3$ and $W^4$ is a nitrogen atom, and the other one is CH or a nitrogen atom.

$W^5$ is an oxygen atom, a sulfur atom, or N—$R^2$.

$W^6$ is C=O, CH—, CF$_2$, CHOH, N—$R^2$, an oxygen atom, or a sulfur atom.

When $W^5$ and $W^6$ are N—$R^2$, $R^2$ is a hydrogen atom or a $C_1$ to $C_6$ alkyl group.

$R^8$ is a hydrogen atom, a halogen atom, a hydroxy group, a cyano group, a $C_1$ to $C_3$ alkyl group, a $C_2$ to $C_3$ alkenyl group, a $C_3$ to $C_6$ cycloalkyl group, a halo-$C_1$ to $C_3$ alkyl group, a hydroxy $C_1$ to $C_4$ alkyl group, a $C_1$ to $C_3$ alkyloxy group, a halo-$C_1$ to $C_3$ alkyloxy group, a $C_1$ to $C_3$ acyl group, a $C_1$ to $C_3$ alkylsulfanyl group, a $C_1$ to $C_3$ alkylsulfinyl group, a $C_1$ to $C_3$ alkylsulfonyl group, a halo-$C_1$ to $C_3$ alkylsulfonyl group, —CONR$^5$R$^6$, or —NR$^5$R$^6$, wherein when $R^8$ is —CONR$^5$R$^6$ or —NR$^5$R$^6$, $R^5$ is a hydrogen atom, a $C_1$ to $C_6$ alkyl group, a $C_1$ to $C_6$ acyl group, or a $C_1$ to $C_6$ alkylsulfonyl group, and $R^6$ is a hydrogen atom or a $C_1$ to $C_6$ alkyl group, or $R^5$ and $R^6$ together form a $C_2$ to $C_9$ heterocycloalkyl group.

Preferably, $R^8$ is a fluorine atom, a chlorine atom, a cyano group, a $C_1$ to $C_3$ alkyl group, a $C_1$ to $C_3$ alkyloxy group, a $C_1$ to $C_3$ acyl group, or a hydroxy $C_1$ to $C_4$ alkyl group.

More preferably, $R^8$ is a cyano group, an ethyl group, an acetyl group, or a $C_1$ to $C_3$ alkyloxy group.

$R^9$ is a hydrogen atom, a halogen atom, a hydroxy group, a cyano group, a $C_1$ to $C_3$ alkyl group, a halo-$C_1$ to $C_3$ alkyl group, a $C_1$ to $C_3$ alkyloxy group, a halo-$C_1$ to $C_6$ alkyloxy group, or —CONR$^5$R$^6$, wherein $R^5$ is a hydrogen atom or a $C_1$ to $C_6$ alkyl group, and $R^6$ is a hydrogen atom or a $C_1$ to $C_6$ alkyl group, or $R^5$ and $R^6$ may together form a 3- to 10-membered heterocycloalkyl group.

Preferably, $R^9$ is a hydrogen atom, a halogen atom, a hydroxy group, a cyano group, or a $C_1$ to $C_3$ alkyl group.

$R^{10}$ is a hydrogen atom, a halogen atom, or a $C_1$ to $C_3$ alkyl group.

m is 0 or 1.

Ar¹ is a group selected from the group consisting of the following C1), C2), and C3).

[Chem. 17]

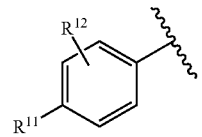
C1)

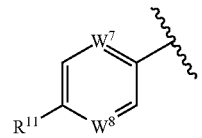
C2)

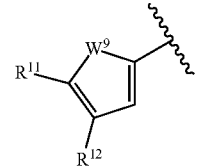
C3)

Preferably, Ar¹ is C1a).

[Chem. 18]

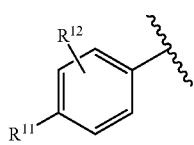
C1a)

One of $W^7$ and $W^8$ is a nitrogen atom, and the other one is CH or a nitrogen atom.

$W^9$ is an oxygen atom, a sulfur atom, or N—$R^2$.

When $W^9$ is N—$R^2$, $R^2$ is a hydrogen atom or a $C_1$ to $C_6$ alkyl group.

$R^{11}$ is a hydrogen atom, a halogen atom, a cyano group, a $C_1$ to $C_3$ alkyl group, a halo-$C_1$ to $C_3$ alkyl group, a hydroxy $C_1$ to $C_4$ alkyl group, a $C_2$ to $C_3$ alkenyl group, a $C_2$ to $C_3$ alkynyl group, a $C_3$ to $C_6$ cycloalkyl group, a $C_1$ to $C_3$ alkyloxy group, a halo-$C_1$ to $C_3$ alkyloxy group, a $C_3$ to $C_6$ cycloalkoxy group, a $C_1$ to $C_6$ acyl group, a $C_1$ to $C_3$ alkyloxycarbonyl group, a $C_1$ to $C_3$ alkylsulfanyl group, a $C_1$ to $C_3$ alkylsulfinyl group, a $C_1$ to $C_3$ alkylsulfonyl group, an aryl group, an aryloxy group, a heterocyclyl group substituted with a $C_1$ to $C_3$ alkyl group, —CONR$^5$R$^6$, or —NR$^5$R$^6$, wherein when $R^{11}$ is —CONR$^5$R$^6$, or —NR$^5$R$^6$, $R^5$ is a hydrogen atom, a $C_1$ to $C_3$ alkyl group, a $C_1$ to $C_3$ acyl group, or a $C_1$ to $C_3$ alkylsulfonyl group, and $R^6$ is a hydrogen atom or a $C_1$ to $C_3$ alkyl group, or $R^5$ and $R^6$ may together form a $C_2$ to $C_9$ heterocycloalkyl group.

Preferably $R^{11}$ is a hydrogen atom, a halogen atom, a cyano group, a trifluoromethyl group, or a $C_1$ to $C_3$ alkyl group.

$R^{12}$ is a hydrogen atom, a halogen atom, a hydroxy group, or a $C_1$ to $C_3$ alkyl group.

Preferably, $R^{12}$ is a hydrogen atom or a halogen atom.

Preferred examples of the compound of the present embodiment may include the following compounds:

(−)-(S)-1-(4-chlorophenyl)-3-{1-[2-(2-hydroxyethyl)-2H-tetrazol-5-yl]-2-(4-methoxyphenyl)ethyl}urea,
(S)-1-(4-fluorophenyl)-3-{1-[2-(2-hydroxyethyl)-2H-tetrazol-5-yl]-2-(4-methoxyphenyl)ethyl}urea,
(S)-1-(4-cyanophenyl)-3-{1-[2-(2-hydroxyethyl)-2H-tetrazol-5-yl]-2-(4-methoxyphenyl)ethyl}urea,
(S)-1-(4-chlorophenyl)-3-{2-(4-cyanophenyl)-1-[2-(2-hydroxyethyl)-2H-tetrazol-5-yl]ethyl}urea,
(S)-1-(4-chlorophenyl)-3-{2-(2,3-dihydrobenzofuran-5-yl)-1-[2-(2-hydroxyethyl)-2H-tetrazol-5-yl]ethyl}urea,
(S)-1-(4-chlorophenyl)-3-{2-(4-ethylphenyl)-1-[2-(2-hydroxyethyl)-2H-tetrazol-5-yl]ethyl}urea,
(−)-(S)-1-(4-cyanophenyl)-3-{2-(2,3-dihydrobenzofuran-5-yl)-1-[2-(2-hydroxyethyl)-2H-tetrazol-5-yl]ethyl}urea,
1-(4-chlorophenyl)-3-{(1S,2R)-1-[2-(2-hydroxyethyl)-2H-tetrazol-5-yl]-2-(4-methoxyphenyl)propyl}urea,
1-(4-chlorophenyl)-3-((1S,2S)-1-[2-(2-hydroxyethyl)-2H-tetrazol-5-yl]-2-(4-methoxyphenyl)propyl)urea,
(S)-1-(4-chlorophenyl)-3-(2-(4-ethylphenyl)-1-{5-[(2-hydroxyethyl)(methyl)amino]-1,2,4-oxadiazol-3-yl}ethyl)urea,
(+)-(S)-1-(4-chlorophenyl)-3-{1-[2-(3-hydroxypropyl)-2H-tetrazol-5-yl]-2-(4-methoxyphenyl)ethyl}urea,
(+)-(S)-1-(4-chlorophenyl)-3-(1-(2-(3-hydroxybutyl)-2H-tetrazol-5-yl)-2-(4-methoxyphenyl)ethyl)urea,
(S)-1-(4-fluorophenyl)-3-{1-[5-(2-hydroxyethyl)-1,3,4-thiadiazol-2-yl]-2-(4-methoxyphenyl)ethyl}urea,
(S)-1-(4-chlorophenyl)-3-{1-[5-(2-hydroxyethyl)-1,3,4-oxadiazol-2-yl]-2-(4-methoxyphenyl)ethyl}urea,
(S)-1-(4-fluorophenyl)-3-{1-[5-(2-hydroxyethyl)-1,3,4-oxadiazol-2-yl]-2-(4-methoxyphenyl)ethyl)urea,
(S)-1-(4-cyanophenyl)-3-{1-[5-(2-hydroxyethyl)-1,3,4-oxadiazol-2-yl]-2-(4-methoxyphenyl)ethyl}urea,
(S)-2-(5-{1-[3-(4-chlorophenyl)ureido]-2-(4-methoxyphenyl)ethyl}-1,3,4-oxadiazol-2-yl)-N-methylacetamide,
(S)-2-(5-{1-[3-(4-fluorophenyl)ureido]-2-(4-methoxyphenyl)ethyl}-1,3,4-oxadiazol-2-yl)-N-methylacetamide,
(S)-1-(4-chlorophenyl)-3-{1-[4-(2-hydroxypropan-2-yl)oxazol-5-yl]-2-(4-methoxyphenyl)ethyl}urea,
(S)—N-(5-{1-[3-(4-chlorophenyl)ureido]-2-(4-ethylphenyl)ethyl}-1,3,4-oxadiazol-2-yl)acetamide,
(S)-1-(2-(4-chlorophenyl)-1-{5-[(methylsulfonyl)methyl]-1,2,4-oxadiazol-3-yl}ethyl)-3-(4-fluorophenyl)urea,
1-(4-chlorophenyl)-3-{2-(4-methoxyphenyl)-1-[5-(1-methylpiperazin-4-yl)-1,2,4-oxadiazol-3-yl]ethyl}urea,
(S)-1-(1-(5-amino-1,2,4-oxadiazol-3-yl)-2-(4-methoxyphenyl)ethyl)-3-(4-fluorophenyl)urea,
(S)-1-(1-(5-amino-1,2,4-oxadiazol-3-yl)-2-(4-methoxyphenyl)ethyl)-3-(4-cyanophenyl)urea,
(S)-1-(4-chlorophenyl)-3-(2-(4-methoxyphenyl)-1-(5-(methylamino)-1,2,4-oxadiazol-3-yl)ethyl)urea,
(S)-1-(4-chlorophenyl)-3-(1-(5-(dimethylamino)-1,2,4-oxadiazol-3-yl)-2-(4-methoxyphenyl)ethyl)urea,
(S)-1-(4-chlorophenyl)-3-(1-(5-(3-hydroxyazetidin-1-yl)-1,2,4-oxadiazol-3-yl)-2-(4-methoxyphenyl)ethyl)urea,
(S)-1-(4-chlorophenyl)-3-(1-(1-(2-hydroxyethyl)-1H-pyrazol-3-yl)-2-(4-methoxyphenyl)ethyl)urea,
(S)-1-(4-chlorophenyl)-3-(1-(3-(2-hydroxyethyl)isoxazol-5-yl)-2-(4-methoxyphenyl)ethyl)urea,
(S)-1-(4-chlorophenyl)-3-(1-(5-(2-hydroxyethyl)isoxazol-3-yl)-2-(4-methoxyphenyl)ethyl)urea,
(S)-1-(4-chlorophenyl)-3-(1-(2-(2-hydroxyethyl)-2H-1,2,4-triazol-4-yl)-2-(4-methoxyphenyl)ethyl)urea,
(S)-1-(4-chlorophenyl)-3-(1-(1-(2-hydroxyethyl)-1H-1,2,3-triazol-4-yl)-2-(4-methoxyphenyl)ethyl)urea,
(S)-1-(4-chlorophenyl)-3-(1-(1-(2-hydroxyethyl)-1H-pyrazol-4-yl)-2-(4-methoxyphenyl)ethyl)urea,
(−)-(S)-1-(4-chlorophenyl)-3-(2-(4-methoxyphenyl)-1-(2-((methylsulfonyl)methyl)-2H-tetrazol-5-yl)ethyl)urea,
(−)-(S)-1-(4-chlorophenyl)-3-(2-(4-methoxyphenyl)-1-(2-(2-(methylsulfonyl)methyl)-2H-tetrazol-5-yl)ethyl)urea,
(−)-(S)—N-(2-(5-(2-(4-chlorophenyl)-1-(3-(4-chlorophenyl)ureido)ethyl)-2H-tetrazol-2-yl)ethyl)methanesulfonamide,
(−)-(S)—N-(2-(5-(2-(4-chlorophenyl)-1-(3-(4-fluorophenyl)ureido)ethyl)-2H-tetrazol-2-yl)ethyl)methanesulfonamide,
(−)-1-(4-chlorophenyl)-3-((1S)-2-(4-methoxyphenyl)-1-(2-((methylsulfinyl)methyl)-2H-tetrazol-5-yl)ethyl)urea,
(−)-(S)—N-((5-(2-(4-chlorophenyl)-1-(3-(4-chlorophenyl)ureido)ethyl)-1,3,4-oxadiazol-2-yl)methyl)acetamide,
(S)-1-(4-chlorophenyl)-3-(2-(4-chlorophenyl)-1-(5-(2-hydroxypropan-2-yl)-1,3,4-oxadiazol-2-yl)ethyl)urea,
(S)—N-((5-(3-(4-chlorophenyl)ureido)-2-(4-ethylphenyl)ethyl)-1,3,4-oxadiazol-2-yl)methyl)acetamide,
(−)-(S)-1-(4-chlorophenyl)-3-(2-(4-ethylphenyl)-1-(5-(3-hydroxyethyl)-1,3,4-oxadiazol-2-yl)ethyl)urea,
2-(3-(4-chlorophenyl)ureido-N'-hydroxy-3-(4-methoxyphenyl)propanimidamide,
(S)-1-[1-(5-amino-1,3,4-thiadiazol-2-yl)-2-(4-methoxyphenyl)ethyl]-3-(4-chlorophenyl)urea,
5-(1-(3-(4-chlorophenyl)ureido)-2-(4-methoxyphenyl)ethyl)oxazole-4-carboxylic acid,
(S)-5-(1-(3-(4-chlorophenyl)ureido)-2-(4-methoxyphenyl)ethyl)oxazole-4-carboxylic acid,
(−)-(S)-2-(5-(1-(3-(4-chlorophenyl)ureido)-2-(4-methoxyphenyl)ethyl)-2-oxo-1,3,4-oxadiazol-3(2H)-yl)acetic acid,
1-(4-chlorophenyl)-3-(1-(5-(hydroxymethyl)-1,3,4-oxadiazol-2-yl)-2-(4-methoxyphenyl)ethyl)urea,
1-(4-chlorophenyl)-3-(1-(5-(hydroxymethyl)-1,2,4-oxadiazol-3-yl)-2-(4-methoxyphenyl)ethyl)urea,
(S)-1-(4-chlorophenyl)-3-(1-(5-(2-hydroxyethyl)-1,3,4-thiadiazol-2-yl)-2-(4-methoxyphenyl)ethyl)urea,
(S)-1-(4-chlorophenyl)-3-(1-(5-(2-hydroxyethyl)-4H-1,2,4-triazol-3-yl)-2-(4-methoxyphenyl)ethyl)urea,
(+)-(S)-2-(5-{1-[3-(4-chlorophenyl)ureido]-2-(4-methoxyphenyl)ethyl}-2H-tetrazol-2-yl)acetamide,
(S)-5-(1-(3-(4-chlorophenyl)ureido)-2-(4-methoxyphenyl)ethyl)oxazole-4-carboxamide,
(S)-5-(1-(3-(4-chlorophenyl)ureido)-2-(4-methoxyphenyl)ethyl)-N-methyloxazole-4-carboxamide,
(S)-5-(1-(3-(4-chlorophenyl)ureido)-2-(4-methoxyphenyl)ethyl)-N,N-dimethyloxazole-4-carboxamide,
(S)-2-(5-(1-(3-(4-chlorophenyl)ureido)-2-(4-methoxyphenyl)ethyl)-2H-tetrazol-2-yl)-N-methylacetamide,
(S)-1-(4-chlorophenyl)-3-(2-(4-methoxyphenyl)-1-(2-(2-morpholino-2-oxoethyl)-2H-tetrazol-5-yl)ethyl)urea,
(−)-(S)-1-(1-(2-(azetidin-3-yl)-2H-tetrazol-5-yl)-2-(4-methoxyphenyl)ethyl)-3-(4-chlorophenyl)urea,
(−)-(S)—N-(2-(5-(1-(3-(4-chlorophenyl)ureido)-2-(4-methoxyphenyl)ethyl)-2H-tetrazol-2-yl)ethyl)acetamide,
(−)-(S)—N-(2-(5-(1-(3-(4-chlorophenyl)ureido)-2-(4-methoxyphenyl)ethyl)-2H-tetrazol-2-yl)ethyl)methanesulfonamide, 1-(1-(5-amino-1,2,4-oxadiazol-3-yl)-2-(4-methoxyphenyl)ethyl)-3-(4-chlorophenyl)urea,
(S)-1-(1-(5-amino-1,2,4-oxadiazol-3-yl)-2-(4-chlorophenyl)ethyl)-3-(4-chlorophenyl)urea,
(+)-(S)-1-(4-chlorophenyl)-3-(2-(4-chlorophenyl)-1-(5-(methylamino)-1,2,4-oxadiazol-3-yl)ethyl)urea,
(S)-1-(4-chlorophenyl)-3-(2-(4-chlorophenyl)-1-(5-((2-hydroxyethyl)(methyl)amino)-1,2,4-oxadiazol-3-yl)ethyl)urea,
(S)-1-(4-chlorophenyl)-3-(2-(4-chlorophenyl)-1-(5-(3-hydroxyazetidin-1-yl)-1,2,4-oxadiazol-3-yl)ethyl)urea,
(S)-1-(4-chlorophenyl)-3-(2-(4-chlorophenyl)-1-(5-((1-hydroxy-2-methylpropan-2-yl)amino)-1,2,4-oxadiazol-3-yl)ethyl)urea,
(−)-(S)-1-(2-(4-chlorophenyl)-1-(5-((2-hydroxyethyl)amino)-1,2,4-oxadiazol-3-yl)ethyl)-3-(4-fluorophenyl)urea,
(−)-(S)-1-(4-chlorophenyl)-3-(2-(4-chlorophenyl)-1-(5-((1,3-dihydroxypropan-2-yl)amino)-1,2,4-oxadiazol-3-yl)ethyl)urea,
(−)-(S)-1-(4-chlorophenyl)-3-(1-(5-((1,3-dihydroxypropan-2-yl)amino)-1,2,4-oxadiazol-3-yl)-2-(4-methoxyphenyl)ethyl)urea,
(+)-(S,Z)-2-[3-(4-chlorophenyl)ureido]-3-(4-ethylphenyl)-N'-(2-hydroxyethoxy)propanimidamide,
(S,Z)-2-[3-(4-chlorophenyl)ureido]-N'-(2-hydroxyethoxy)-3-(4-methylthiophenyl)propanimidamide,
(+)-(S,Z)-2-[3-(4-chlorophenyl)ureido]-N'-(2-hydroxyethoxy)-3-(4-methoxyphenyl)propanimidamide,
(S)—N-{2-[3-(4-fluorophenyl)ureido]-1-imino-3-(4-methoxyphenyl)propyl}-3-hydroxypropanamide,
(S)—N-{2-[3-(4-chlorophenyl)ureido]-1-imino-3-(4-methoxyphenyl)propyl}-3-hydroxypropanamide,
(S,Z)—N-{1-amino-3-(4-chlorophenyl)-2-[3-(4-chlorophenyl)ureido]propylidene}-3-hydroxy-2,2-dimethylpropanamide,
(S)-1-{2-(4-chlorophenyl)-1-[5-(1-hydroxy-2-methylpropan-2-yl)-1,2,4-oxadiazol-3-yl]ethyl}-3-(4-fluorophenyl)urea,
(S)-1-(4-chlorophenyl)-3-(2-(4-chlorophenyl)-1-{5-[1-(hydroxymethyl)cyclopropyl]-1,2,4-oxadiazol-3-yl}ethyl)urea,
(S)-1-(2-(4-chlorophenyl)-1-{5-[1-(hydroxymethyl)cyclopropyl]-1,2,4-oxadiazol-3-yl}ethyl)-3-(4-fluorophenyl)urea,
(S)—N-{3-(4-chlorophenyl)-2-[3-(4-fluorophenyl)ureido]-1-iminopropyl}-2-(methanesulfonyl)acetamide,
(S)—N-{4-(4-chlorophenyl)-3-[3-(4-chlorophenyl)ureido]-1-iminobutyl}-2-hydroxyacetamide,
(−)-(S)-1-(4-chlorophenyl)-3-(1-(4-(2-hydroxyethyl)-5-oxo-4,5-dihydro-1,3,4-oxadiazol-2-yl)-2-(4-methoxyphenyl)ethyl)urea,
(+)—(R)-1-(4-chlorophenyl)-3-[1-hydroxy-3-(4-methoxyphenyl)propan-2-yl]urea, or
4-[2-[3-(4-chlorophenyl)ureido]-3-hydroxypropyl]-N,N-dimethylbenzamide.

If necessary, the compound (I) of the present embodiment can be converted to a pharmacologically acceptable salt according to a usual method. The pharmacologically acceptable salt means a salt with a pharmacologically acceptable nontoxic base or acid (for example, an inorganic or organic base or an inorganic or organic acid).

Examples of the salt derived from a pharmacologically acceptable nontoxic base may include: salts with inorganic bases such as sodium salts, potassium salts, calcium salts, magnesium salts and the like; and salts with organic bases such as piperidine, morpholine, pyrrolidine, arginine, lysine and the like.

Examples of the salt derived from a pharmacologically acceptable nontoxic acid may include: acid addition salts with mineral acids such as hydrochloric acid, hydrobromic acid, sulfuric acid, nitric acid and the like; and acid addition salts with organic acids such as formic acid, acetic acid, maleic acid, fumaric acid, succinic acid, lactic acid, malic acid, tartaric acid, citric acid, methanesulfonic acid, p-toluenesulfonic acid, salicylic acid, stearic acid, palmitic acid and the like.

The compound (I) of the present embodiment or a pharmacologically acceptable salt thereof may be present as a hydrate or a solvate. Any hydrate and solvate formed from the urea derivative represented by the general formula (I) above, including any of the preferred compounds specifically described above, or a salt thereof are included in the scope of the present invention. Examples of the solvent that can form the solvate may include methanol, ethanol, 2-propanol, acetone, ethyl acetate, dichloromethane, diisopropyl ether and the like.

The compound (I) of the present embodiment or a pharmacologically acceptable salt thereof may be a racemate and also includes their optically active substances, stereoisomers, and rotational isomers.

When the compound (I) of the present embodiment is one of its optical isomers having one or more asymmetric carbon atom, the configuration of each asymmetric carbon atom in the compound (I) of the present embodiment may be any one of the R configuration and the S configuration. Any one of the optical isomers is included in the present invention, and a mixture of these optical isomers is also included in the present invention. A mixture of optically active substances may be a racemate formed of equal amounts of the optical isomers, and this racemate is also included in the scope of the present invention. When the compound (I) of the present embodiment is a solid or crystalline racemate, the racemate, racemic mixture, and racemic solid solution are included in the scope of the present invention.

When the compound (I) of the present embodiment includes geometrical isomers, all the geometrical isomers are included in the present invention.

When the compound (I) of the present embodiment includes tautomers, all the tautomers are included in the present invention.

Pharmacologically acceptable salts of the compound (I) include proton tautomers thereof.

The compound (I) of the present embodiment or a pharmacologically acceptable salt thereof may be a compound labeled with an isotope (for example, $^3$H, $^{14}$C, $^{35}$S and the like). Such a compound is also included in the present invention.

The compound (I) of the present embodiment or a pharmacologically acceptable salt thereof may be a deuterium-substituted compound in which $^1$H is substituted with $^2$H(D). Such a compound is also included in the present invention.

The term "FPRL1 agonist effect" in the present embodiment means agonist activity obtained by the action on formyl peptide receptor like 1 (FPRL1).

The compound (I) of the present embodiment or a pharmacologically acceptable salt thereof exhibits superior agonist activity in, for example, a test of calcium influx into FPRL1-overexpressing cells. Therefore, it can be understood that the compound (I) of the present embodiment or a pharmacologically acceptable salt thereof is useful as a therapeutic or prophylactic agent for inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

Method of Producing the Compound (I) of the Present Embodiment

The compound (I) of the present embodiment or a pharmacologically acceptable salt thereof can be produced, for example, in accordance with processes described in the following schemes 1 to 30, methods similar thereto, methods described in other literatures, and methods similar thereto.

Synthesis of Compound (Ia)

Among Compound (I) of the present embodiment, Compound (Ia) wherein A is a hydrogen atom, cyano group, hydroxy group, a $C_1$ to $C_6$ alkyloxycarbonyl group optionally having substituent(s), a 5-membered aromatic heterocyclyl group optionally having substituent(s), a 5-membered non-aromatic heterocyclyl group optionally having substituent(s), a 6-membered aromatic heterocyclyl group optionally having substituent(s),a 6-membered non-aromatic heterocyclyl group optionally having substituent(s), —CONHZ, or —C(NH$_2$)=NZ, and Z is a $C_1$ to $C_6$ alkyloxy group optionally having substituent(s), or a $C_1$ to $C_6$ alkylsulfonyl group optionally having substituent(s) can be produced in accordance with methods described in Scheme 1, methods similar thereto, methods described in other literatures, and methods similar thereto.

triethylamine, and N-methylmorpholine; an aromatic amine such as pyridine, picoline, and N,N-dimethylaniline; and the like. The amount of the base used is about 1-100 molar equivalents, preferably about 1-5 molar equivalents, per 1 mole of the compound. The reaction temperature can generally be performed at −20° C. to the reflux temperature of the solvent and is performed preferably at 0° C. to 50° C. The reaction time varies depending on the starting materials used, the solvent used, the reaction temperature, or the like, but is generally 10 minutes to 48 hours.

Further, Compound (1b) used in this step may be a commercially available, or can be produced in accordance with methods described in other literatures, and methods similar thereto.

Step 1-2

Compound (Ia) can be also prepared in the process mentioned below.

This step is a step of reacting Compound (1a) and Compound (1c) to produce Compound (Ia). Compound (Ia) can be produced by, for example, reacting Compound (1c) in a solvent with carbonyldiimidazole (CDI) and then reacting the obtained product with Compound (1a). The solvent used may include dimethylsulfoxide and the like. The reaction temperature can generally be performed at 10° C. to the reflux temperature of the solvent and is performed preferably at 10° C. to 50° C. The reaction time varies depending on the starting materials used, the solvent used, the reaction temperature, or the like, but is generally 10 minutes to 3 hours.

Scheme 1

[Chem.19]

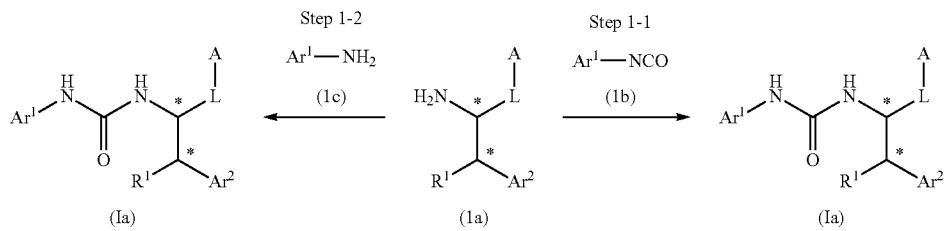

In the above formulas, Ar$^1$, Ar$^2$, R$^1$, L, and A are as described above, and each carbon atom marked with an asterisk is an asymmetric carbon atom when the carbon is a tertiary carbon atom.

Step 1-1

This step is a step of reacting Compound (1a) and Compound (1b) to produce Compound (Ia). Compound (Ia) can be produced by, for example, reacting Compound (1a) in a solvent with Compound (1b) in the presence or absence of a base. The amount of Compound (1b) used is about 0.5-10 molar equivalents, preferably about 1-2 molar equivalents, per 1 mole of Compound (1a).

Examples of the solvent used may include dichloromethane, 1,2-dichloroethane, benzene, toluene, tetrahydrofuran, ethyl acetate, methanol, water, mixed solvents thereof and the like. Examples of the base used may include an alkali metal hydride such as lithium hydride, sodium hydride, and potassium hydride; an alkali metal hydroxide such as sodium hydroxide and potassium hydroxide; a hydrogen carbonate such as sodium hydrogen carbonate and potassium hydrogen carbonate; a carbonate such as sodium carbonate and potassium carbonate; an organic acid salt such as sodium acetate; a tertiary amine such as trimethylamine, Further, Compound (1c) used in this step may be a commercially available, or can be produced in accordance with methods described in other literatures, and methods similar thereto.

Synthesis of Compound (1a)

Compound (1a) can be produced from Compound (2a) in accordance with methods described in Scheme 2, methods similar thereto, methods described in other literatures, and methods similar thereto.

Scheme 2

[Chem.20]

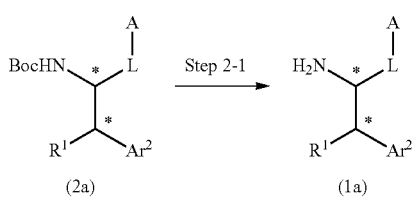

In the above formulas, $Ar^2$, $R^1$, L, and A are as described above, and each carbon atom marked with an asterisk is an asymmetric carbon atom when the carbon is a tertiary carbon atom.

Step 2-1

This step is a step of deprotecting the tert-butoxycarbonyl (Boc) group in Compound (2a) to produce Compound (1a). Compound (1a) can be produced by, for example, reacting Compound (2a) in a solvent with an acid such as trifluoroacetic acid (TFA) and hydrogen chloride. The solvent used can include dichloromethane, dioxane, ethyl acetate, methanol, water, mixed solvents thereof and the like. The reaction temperature can generally be performed at −78° C. to the reflux temperature of the solvent and is performed preferably at 0° C. to 60° C. The reaction time varies depending on the starting materials used, the solvent used, the reaction temperature, or the like, but is generally 30 minutes to 3 days.

Synthesis of Compound (3d)

Compound (3d) can be produced from Compound (3a) in accordance with methods described in Scheme 3, methods similar thereto, methods described in other literatures, and methods similar thereto.

Step 3-2

This step is a step of reducing the unsaturated part in Compound (3c) to produce Compound (3d). Compound (3d) can be produced by, for example, hydrogenating Compound (3c) in a solvent under ordinary or increased pressure in the presence of a catalyst such as 10t palladium carbon (10% Pd—C) and (S,S)-Et-DUPHOS-Rh. The solvent used can include methanol, ethanol, dichloromethane, tetrahydrofuran, ethyl acetate, mixed solvents thereof and the like. The reaction temperature can generally be performed at −78° C. to the reflux temperature of the solvent and is performed preferably at 20° C. to 40° C. The reaction time varies depending on the starting materials used, the solvent used, the reaction temperature, or the like, but is generally 30 minutes to 3 days.

Synthesis of Compound (4f)

Compound (4f) can be produced in accordance with methods described in Scheme 4, methods similar thereto, methods described in other literatures, and methods similar thereto.

Scheme 3

[Chem.21]

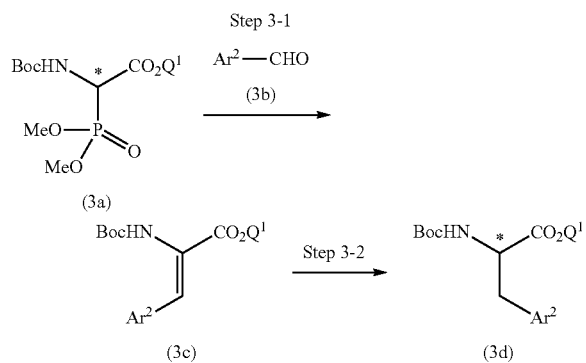

In the above formulas, $Ar^2$ is as described above, $Q^1$ is a $C_1$ to $C_6$ alkyl group, and each carbon atom marked with an asterisk is an asymmetric carbon atom.

Step 3-1

This step is a step of reacting Compound (3a) and Compound (3b) to produce Compound (3c). Compound (3c) can be produced by, for example, reacting Compound (3a) and Compound (3b) in a solvent in the presence of a base. The solvent used can include dichloromethane, N,N-dimethylformamide, tetrahydrofuran, mixed solvents thereof and the like. The base used can include 1,8-diazabicyclo[5.4.0]undec-7-ene (DBU), sodium methoxide, sodium ethoxide, sodium hydride, potassium tert-butoxide, and the like. The reaction temperature can generally be performed at −78° C. to the reflux temperature of the solvent and is performed preferably at 0° C. to the reflux temperature of the solvent. The reaction time varies depending on the starting materials used, the solvent used, the reaction temperature, or the like, but is generally 30 minutes to 3 days. Further, Compound (3a) and (3b) used in this step may be a commercially available, or can be produced in accordance with methods described in other literatures, and methods similar thereto.

Scheme 4

[Chem.22]

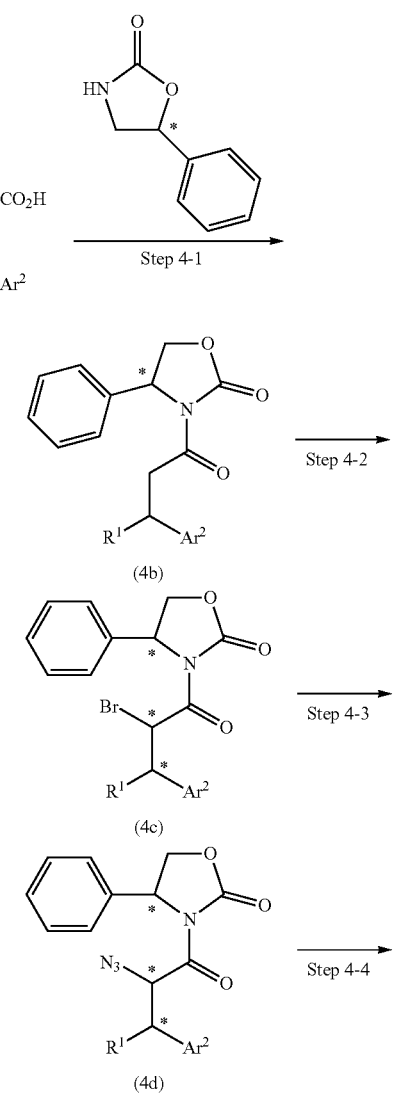

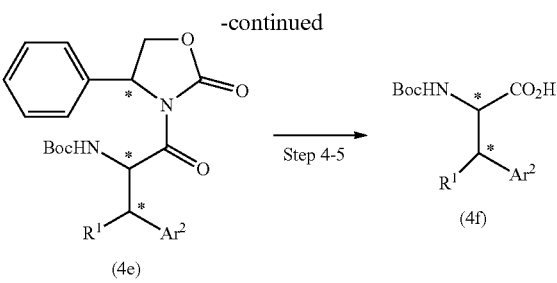

In the above formulas, $Ar^2$ and $R^1$ are as described above, and each carbon atom marked with an asterisk is an asymmetric carbon atom when the carbon is a tertiary carbon atom.

Step 4-1

This step is a step of producing Compound (4b) from Compound (4a). Compound (4b) can be produced by, for example, reacting Compound (4a) in a solvent with pivaloyl chloride in the presence of a base such as triethylamine to produce a mixed anhydride and then reacting the obtained mixed anhydride with 4-phenyl-2-oxazolidinone in the presence of lithium chloride. The solvent used can include tetrahydrofuran and the like. The reaction temperature can generally be performed at −78° C. to the reflux temperature of the solvent and is performed preferably at −10° C. to room temperature. The reaction time varies depending on the starting materials used, the solvent used, the reaction temperature, or the like, but is generally 30 minutes to 3 days. Further, Compound (4a) used in this step may be a commercially available, or can be produced in accordance with methods described in other literatures, and methods similar thereto.

Step 4-2

This step is a step of producing Compound (4c) from Compound (4b). Compound (4c) can be produced by, for example, reacting Compound (4b) in a solvent with dibutylboryl trifluoromethanesulfonate ("Bu$_2$BOTf) and then brominating the obtained product with N-bromosuccinimide. The solvent used can include dichloromethane, chloroform, mixed solvents thereof and the like. The reaction temperature can generally be performed at −78° C. to the reflux temperature of the solvent and is performed preferably at −78° C. to 0° C. The reaction time varies depending on the starting materials used, the solvent used, the reaction temperature, or the like, but is generally 30 minutes to 3 days.

Step 4-3

This step is a step of producing Compound (4d) from Compound (4c). Compound (4d) can be produced by, for example, reacting Compound (4c) in a solvent with sodium azide. The solvent used can include dimethylsulfoxide, N,N-dimethylformamide, mixed solvents thereof, and the like. The reaction temperature can generally be performed at −78° C. to the reflux temperature of the solvent and is performed preferably at 0° C. to room temperature. The reaction time varies depending on the starting materials used, the solvent used, the reaction temperature, or the like, but is generally 30 minutes to 3 days.

Step 4-4

This step is a step of producing Compound (4e) from Compound (4d). Compound (4e) can be produced by, for example, hydrogenating Compound (4d) in a solvent under ordinary or increased pressure in the presence of a catalyst such as 10 palladium carbon (10% Pd—C) and simultaneously reacting the hydrogenated product with di-tert-butyl dicarbonate. The solvent used can include dichloromethane, tetrahydrofuran, ethyl acetate, mixed solvents thereof, and the like. The reaction temperature can generally be performed at 0° C. to the reflux temperature of the solvent and is performed preferably at 20° C. to 40° C. The reaction time varies depending on the starting materials used, the solvent used, the reaction temperature, or the like, but is generally 30 minutes to 3 days.

Step 4-5

This step is a step of making the oxidative cleavage of the chiral auxiliary group in Compound (4e) to produce Compound (4f). Compound (4f) can be produced by, for example, treating Compound (4e) in a solvent with aqueous hydrogen peroxide followed by lithium hydroxide. The solvent used can include tetrahydrofuran, water, mixed solvents thereof, and the like. The reaction temperature can generally be performed at 0° C. to the reflux temperature of the solvent and is performed preferably at 0° C. to room temperature. The reaction time varies depending on the starting materials used, the solvent used, the reaction temperature, or the like, but is generally 30 minutes to 3 days.

Synthesis of Compounds (5e), (5f)

Compounds (5e, 5f) can be produced, for example, from Compound (5a) in accordance with methods described in Scheme 5, methods similar thereto, methods described in other literatures, and methods similar thereto.

Scheme 5

[Chem.23]

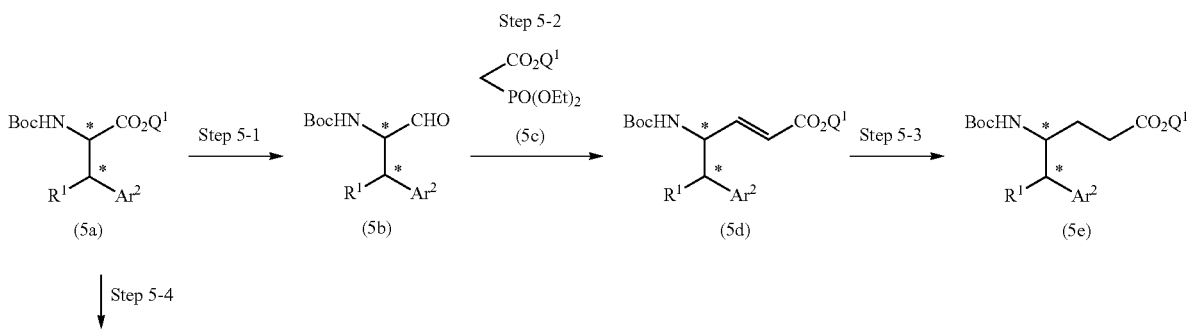

-continued

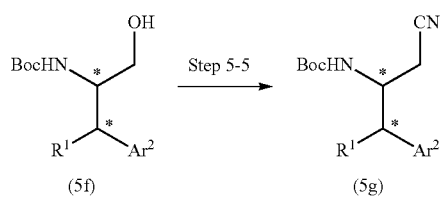
(5f)

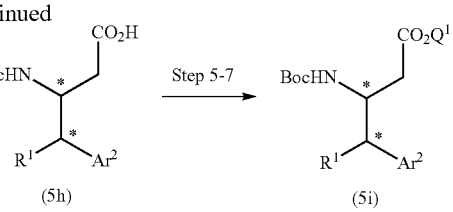
(5g) (5h) (5i)

In the above formulas, $Ar^2$, $R^1$, and $Q^1$ are as described above, and each carbon atom marked with an asterisk is an asymmetric carbon atom when the carbon is a tertiary carbon atom.

Step 5-1

This step is a step of reducing the ester part in Compound (5a) to the corresponding aldehyde to produce Compound (5b). Compound (5b) can be produced by, for example, reacting Compound (5a) in a solvent with a reducing agent such as diisobutylaluminum hydride (DIBAL). The solvent used can include tetrahydrofuran, toluene, mixed solvents thereof, and the like. The reaction temperature can generally be performed at $-78°$ C. to the reflux temperature of the solvent and is performed preferably at $0°$ C. to room temperature. The reaction time varies depending on the starting materials used, the solvent used, the reaction temperature, or the like, but is generally 30 minutes to 3 days.

Compound (5a) in this step can be prepared from (4f) according to a conventional esterification of a carboxylic acid.

Step 5-2

This step is a step of reacting Compound (5b) and Compound (5c) to produce Compound (5d). Compound (5d) can be produced by, for example, reacting Compound (5b) in a solvent with Compound (5c) in the presence of a base. The solvent used can include tetrahydrofuran and the like. Examples of the base used may include sodium hydride (NaH) and the like. The reaction temperature can generally be performed at $-78°$ C. to the reflux temperature of the solvent and is performed preferably at $-78°$ C. to $30°$ C. The reaction time varies depending on the starting materials used, the solvent used, the reaction temperature, or the like, but is generally 30 minutes to 3 days.

Further, Compound (5c) used in this step may be a commercially available, or can be produced in accordance with methods described in other literatures, and methods similar thereto.

Step 5-3

This step is a step of reducing the olefin part in Compound (5d) to produce Compound (5e). Compound (5e) can be produced by, for example, hydrogenating Compound (5d) in a solvent under ordinary or increased pressure in the presence of a catalyst such as 10% palladium carbon (10% Pd—C). The solvent used can include methanol, ethanol, dichloromethane, tetrahydrofuran, ethyl acetate, N,N-dimethylformamide, mixed solvents thereof, and the like. The reaction temperature can generally be performed at $0°$ C. to the reflux temperature of the solvent and is performed preferably at $20°$ C. to $40°$ C. The reaction time varies depending on the starting materials used, the solvent used, the reaction temperature, or the like, but is generally 30 minutes to 3 days.

Step 5-4

This step is a step of reducing the ester part in Compound (5a) to the corresponding alcohol to produce Compound (5f). Compound (5f) can be produced by, for example, reacting Compound (5a) in a solvent with a reducing agent such as sodium borohydride ($NaBH_4$) and lithium borohydride ($LiBH_4$). The solvent used can include methanol, ethanol, tetrahydrofuran, water, mixed solvents thereof, and the like. The reaction temperature can generally be performed at $-78°$ C. to the reflux temperature of the solvent and is performed preferably at $0°$ C. to the reflux temperature of the solvent. The reaction time varies depending on the starting materials used, the solvent used, the reaction temperature, or the like, but is generally 30 minutes to 3 days.

Step 5-5

This step is a step of converting the alcohol part in Compound (5f) to the corresponding cyano group to produce Compound (5g). Compound (5g) can be produced by, for example, reacting Compound (5f) in Solvent A with mesyl chloride (MsCl) in the presence of a base and then reacting the mesylated compound in Solvent B with sodium cyanide. Solvent A used can include dichloromethane, tetrahydrofuran, mixed solvents thereof, and the like. Examples of the base used may include triethylamine, N,N-diisopropylethylamine, and the like. Solvent B used can include N,N-dimethylformamide, dimethylsulfoxide, and the like. The reaction temperature can generally be performed at $-78°$ C. to the reflux temperature of the solvent and is performed preferably at $0°$ C. to $60°$ C. The reaction time varies depending on the starting materials used, the solvent used, the reaction temperature, or the like, but is generally 30 minutes to 3 days.

Step 5-6

This step is a step of hydrolyzing the cyano group in Compound (5g) to the corresponding carboxylic acid to produce Compound (5h). Compound (5h) can be produced by, for example, reacting Compound (5g) in a solvent with 2N aqueous sodium hydroxide. The solvent used can include methanol, ethanol, tetrahydrofuran, water, mixed solvents thereof, and the like. The reaction temperature can generally be performed at $0°$ C. to the reflux temperature of the solvent and is performed preferably at $70°$ C. to the reflux temperature of the solvent. The reaction time varies depending on the starting materials used, the solvent used, the reaction temperature, or the like, but is generally 30 minutes to 3 days.

Step 5-7

This step is a step of converting the carboxylic acid part in Compound (5h) to the corresponding ester to produce Compound (5i). Compound (5i) can be produced by, for example, reacting Compound (5h) in a solvent with trimethylsilyldiazomethane. The solvent used can include methanol and the like. The reaction temperature can generally be performed at $0°$ C. to the reflux temperature of the solvent and is performed preferably at $0°$ C. to $30°$ C. The reaction time varies depending on the starting materials used, the solvent used, the reaction temperature, or the like, but is generally 30 minutes to 3 days.

Synthesis of Compounds (6d), (6e), (6g), (6i), (6k), (6m)

Compounds (6d), (6e), (6g), (6i), (6k), and (6m) can be produced, for example, from Compound (6a) in accordance with methods described in Scheme 6, methods similar thereto, methods described in other literatures, and methods similar thereto.

generally be performed at 0° C. to the reflux temperature of the solvent. Examples of the base used may include an alkali metal salt such as lithium hydroxide and sodium hydroxide. The reaction time varies depending on the starting materials used, the solvent used, the reaction temperature, or the like, but is generally 30 minutes to 3 days.

Scheme 6

[Chem. 24]

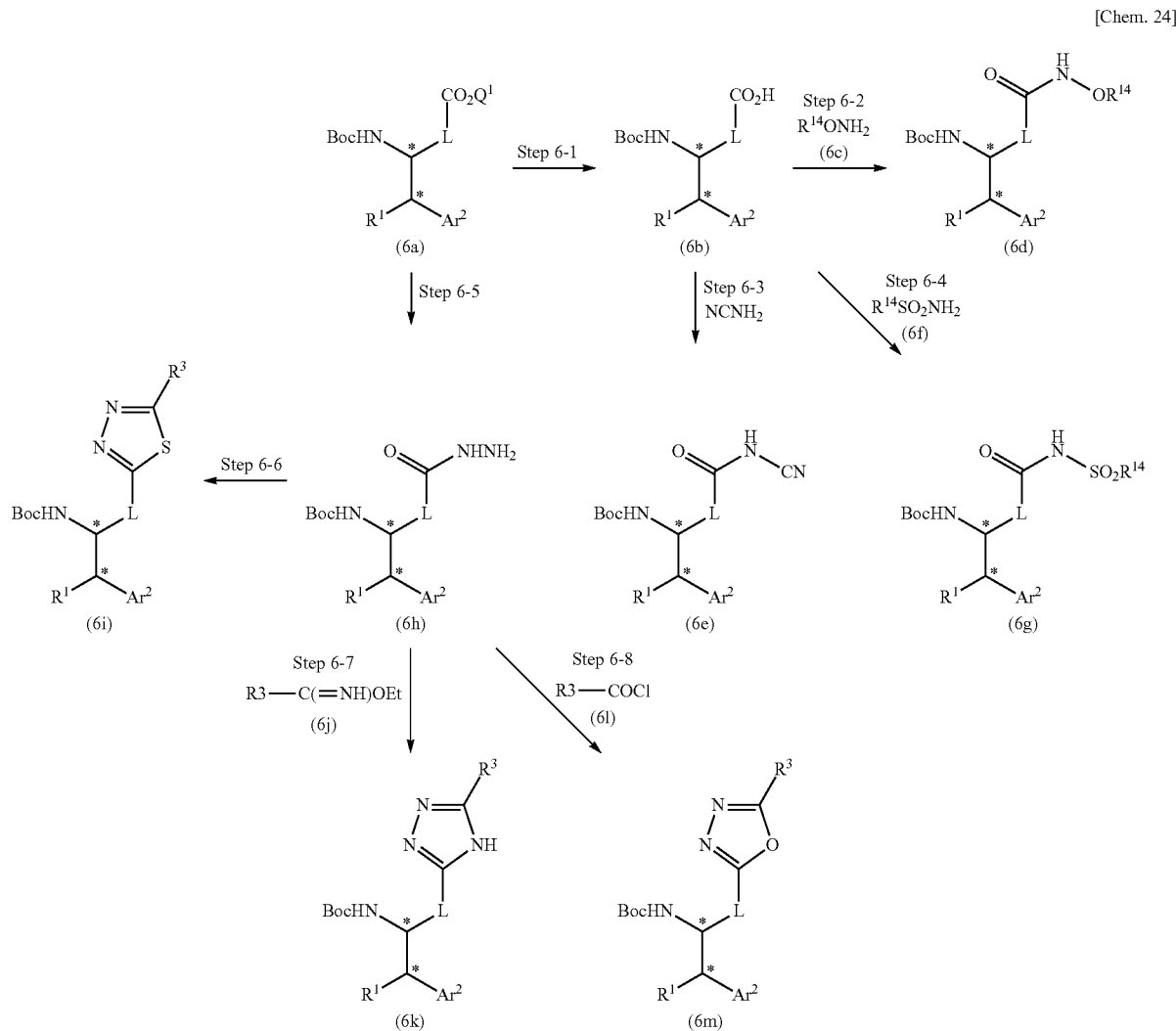

In the above formulas, $Ar^2$, $R^1$, $R^3$, L, and $Q^1$ are as described above, $R^{14}$ is a $C_1$ to $C_6$ alkyl group optionally having substituent(s), and each carbon atom marked with an asterisk is an asymmetric carbon atom when the carbon is a tertiary carbon atom.

Step 6-1

This step is a step of hydrolyzing the ester part in Compound (6a) to produce Compound (6b). Compound (6b) can be produced by, for example, reacting Compound (6a) in a solvent in the presence of a base. The solvent used can include water, or mixed solvents thereof with tetrahydrofuran, 1,4-dioxane, diethyl ether, methanol, ethanol, propanol, 2-propanol, and butanol. The reaction temperature can Compound (6a) used in this step can be produced according to the above Step 5, or can be produced in accordance with methods described in other literatures, and methods similar thereto.

Step 6-2

This step is a step of producing Compound (6d) from Compound (6b). Compound (6d) can be produced by, for example, reacting Compound (6b) in a solvent with hydroxyamine Compound (6c) in the presence of a condensing agent in the presence or absence of a base. The solvent used can include N,N-dimethylformamide, dichloromethane, 1,4-dioxane, tetrahydrofuran, mixed solvents thereof, and the like. Examples of the condensing agent used may include 1-ethyl-3-(3-dimethylaminopropyl)carbodiimide (EDCI), dicyclohexylcarbodiimide (DCC), 2-(1H-7-azabenzotriazol-1-yl)-1,1,3,3-tetramethyluronium hexafluorophosphate methanaminium (HATU), and the like. As necessary, N,N-dimethylaminopyridine, pyridine, 1-hydroxybenzotriazole (HOBT), and the like can be used as a reaction accelerator. The reaction temperature can generally be performed at −78° C. to the reflux temperature of the solvent and is performed preferably at 0° C. to 30° C. The base used can include potassium carbonate, sodium carbonate, triethylamine, N,N-diisopropylethylamine, and the like. The reaction time varies depending on the starting materials used, the solvent used, the reaction temperature, or the like, but is generally 30 minutes to 3 days.

Further, Compound (6c) used in this step may be a commercially available, or can be produced in accordance with methods described in other literatures, and methods similar thereto.

Step 6-3

This step is a step of producing Compound (6e) from Compound (6b). Compound (6e) can be produced by, for example, reacting Compound (6b) in a solvent with cyanamide in the presence of a condensing agent in the presence or absence of a base. The solvent used can include N,N-dimethylformamide, dichloromethane, 1,4-dioxane, tetrahydrofuran, mixed solvents thereof, and the like. Examples of the condensing agent used may include 1-ethyl-3-(3-dimethylaminopropyl)carbodiimide (EDCI), dicyclohexylcarbodiimide (DCC), 2-(1H-7-azabenzotriazol-1-yl)-1,1,3,3-tetramethyluronium hexafluorophosphate methanaminium (HATU), and the like. As necessary, N,N-dimethylaminopyridine, pyridine, 1-hydroxybenzotriazole (HOBT), and the like can be used as a reaction accelerator. The reaction temperature can generally be performed at −78° C. to the reflux temperature of the solvent and is performed preferably at 0° C. to 30° C. The base used can include potassium carbonate, sodium carbonate, triethylamine, N,N-diisopropylethylamine, and the like. The reaction time varies depending on the starting materials used, the solvent used, the reaction temperature, or the like, but is generally 30 minutes to 3 days.

Step 6-4

This step is a step of producing Compound (6g) from Compound (6b). Compound (6g) can be produced by, for example, reacting Compound (6b) in a solvent with sulfonylamine compound (6f) and N,N-dimethylaminopyridine (DMAP) in the presence of condensing agent. The solvent used can include N,N-dimethylformamide, dichloromethane, tetrahydrofuran, mixed solvents thereof, and the like. Examples of the condensing agent used may include 1-ethyl-3-(3-dimethylaminopropyl)carbodiimide (EDCI), dicyclohexylcarbodiimide (DCC), and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days.

Further, Compound (6f) used in this step may be a commercially available, or can be produced in accordance with methods described in other literatures, and methods similar thereto.

Step 6-5

This step is a step of producing Compound (6h) from Compound (6a). Compound (6h) can be produced by, for example, reacting Compound (6a) in a solvent with hydrazine or hydrazine monohydrate. The solvent used can include methanol, ethanol, propanol, tetrahydrofuran, mixed solvents thereof, and the like. The reaction temperature can generally be performed at −78° C. to the reflux temperature of the solvent and is performed preferably at 0° C. to 90° C. The reaction time varies depending on the starting materials used, the solvent used, the reaction temperature, or the like, but is generally 30 minutes to 3 days.

Step 6-6

This step is a step of producing Compound (6i) from Compound (6h). Compound (6i) can be produced by, for example, reacting Compound (6h) in a solvent with an acyl chloride in the presence of a base and then reacting the obtained product with Lawesson's reagent. The solvent used can include tetrahydrofuran and the like. The base used can include triethylamine, N,N-diisopropylethylamine, and the like. The reaction temperature can generally be performed at −78° C. to the reflux temperature of the solvent and is performed preferably at 0° C. to 50° C. The reaction time varies depending on the starting materials used, the solvent used, the reaction temperature, or the like, but is generally 30 minutes to 3 days.

Step 6-7

This step is a step of producing Compound (6k) from Compound (6h). Compound (6k) can be produced by, for example, reacting Compound (6h) in Solvent A with an ethyl imidate (6j) in the presence of a base and then ring-closing the obtained product in Solvent B under heating in the presence of a base. Solvent A used can include water, acetonitrile, mixed solvents thereof, and the like. Solvent B used can include water, acetonitrile, mixed solvents thereof, and the like. The base used can include sodium acetate, potassium carbonate, sodium carbonate, triethylamine, N,N-diisopropylethylamine, and the like. The reaction temperature can generally be performed at −78° C. to the reflux temperature of the solvent and is performed preferably at 0° C. to 110° C. The reaction time varies depending on the starting materials used, the solvent used, the reaction temperature, or the like, but is generally 30 minutes to 3 days.

Further, Compound (6j) used in this step may be a commercially available, or can be produced in accordance with methods described in other literatures, and methods similar thereto.

Step 6-8

This step is a step of producing Compound (6m) from Compound (6h). Compound (6m) can be produced by, for example, reacting Compound (6h) in a solvent with an acyl chloride (6l) in the presence of a base and then ring-closing the obtained condensed product in the presence or absence of an acid. The solvent used can include tetrahydrofuran, dichloromethane, and the like. The base used can include triethylamine, N,N-diisopropylethylamine, and the like. The acid used can include p-toluenesulfonic acid, and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days.

Further, Compound (6l) used in this step may be a commercially available, or can be produced in accordance with methods described in other literatures, and methods similar thereto.

Synthesis of Compounds (7f), (7h), (7j)

Compounds (7f), (7h), and (7j) can be produced, for example, from Compound (7a) in accordance with methods described in Scheme 7, methods similar thereto, methods described in other literatures, and methods similar thereto.

Scheme 7

[Chem. 25]

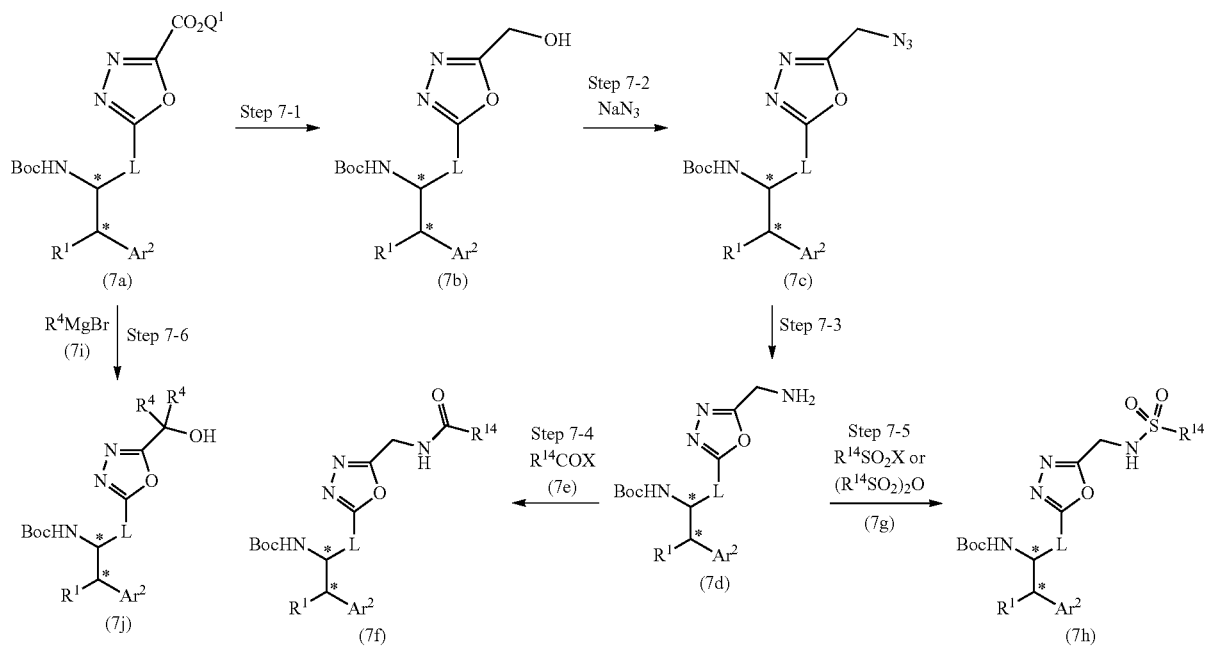

In the above formulas, $Ar^2$, $R^1$, $R^{14}$, L, and $Q^1$ are as described above, $R^{14}$ is a $C_1$ to $C_3$ alkyl group, X is a halogen atom, and each carbon atom marked with an asterisk is an asymmetric carbon atom when the carbon is a tertiary carbon atom.

Step 7-1

This step is a step of reducing the ester part in Compound (7a) to the corresponding alcohol to produce Compound (7b). This step can be done according to the above Step 5-4. Compound (7a) used in this step can be produced according to the above Step 6-8.

Step 7-2

This step is a step of converting the alcohol part in Compound (7b) to the corresponding azide to produce Compound (7c). Compound (7c) can be produced by, for example, reacting Compound (7b) in Solvent A with mesyl chloride in the presence of a base and then reacting the mesylated compound in Solvent B with sodium azide. Solvent A used can include dichloromethane, ethyl acetate, and the like. Solvent B used can include N,N-dimethylformamide, acetonitrile, 1,4-dioxane, mixed solvents thereof, and the like. The base used can include triethylamine, N,N-diisopropylethylamine, and the like. The reaction temperature can generally be performed at −78° C. to the reflux temperature of the solvent and is performed preferably at 20° C. to 90° C. The reaction time varies depending on the starting materials used, the solvent used, the reaction temperature, or the like, but is generally 30 minutes to 3 days.

Step 7-3

This step is a step of reducing the azide part in Compound (7c) to the corresponding amine to produce Compound (7d). Compound (7d) can be produced by, for example, reacting Compound (7c) in a solvent with triphenylphosphine in the presence of water. The solvent used can include tetrahydrofuran and the like. The reaction temperature can generally be performed at 0° C. to the reflux temperature of the solvent and is performed preferably at 20° C. to 50° C. The reaction time varies depending on the starting materials used, the solvent used, the reaction temperature, or the like, but is generally 30 minutes to 3 days.

Step 7-4

This step is a step of producing Compound (7f) from Compound (7d). Compound (7f) can be produced by, for example, reacting Compound (7d) in a solvent with Acyl chloride compound (7e) in the presence of a base. The solvent used can include dichloromethane, tetrahydrofuran, ethyl acetate, acetonitrile, 1,4-dioxane, mixed solvents thereof, and the like. The base used can include potassium carbonate, sodium carbonate, triethylamine, N,N-diisopropylethylamine, and the like. The reaction temperature can generally be performed at −78° C. to the reflux temperature of the solvent and is performed preferably at 20° C. to 90° C. The reaction time varies depending on the starting materials used, the solvent used, the reaction temperature, or the like, but is generally 30 minutes to 3 days.

Further, Compound (7e) used in this step may be a commercially available, or can be produced in accordance with methods described in other literatures, and methods similar thereto.

Step 7-5

This step is a step of producing Compound (7h) from Compound (7d). Compound (7h) can be produced by, for example, reacting Compound (7d) in a solvent with a sulfonyl halide compound or sulfonic anhydride (7g) in the presence of a base. The solvent used can include dichloromethane, tetrahydrofuran, ethyl acetate, acetonitrile, 1,4-dioxane, mixed solvents thereof, and the like. The base used can include potassium carbonate, sodium carbonate, triethylamine, N,N-diisopropylethylamine, and the like. The reaction temperature can generally be performed at −78° C. to the reflux temperature of the solvent and is performed preferably at 20° C. to 90° C. The reaction time varies depending on the starting materials used, the solvent used, the reaction temperature, or the like, but is generally 30 minutes to 3 days.

Further, sulfonyl halide compound and sulfonic anhydride (7g) used in this step may be a commercially available, or Synthesis of Compounds (8c), (8f), (8g), (8i)

Compounds (8c), (8f), (8g), and (8i) can be produced, for example, from Compound (6h) in accordance with methods described in Scheme 8, methods similar thereto, methods described in other literatures, and methods similar thereto.

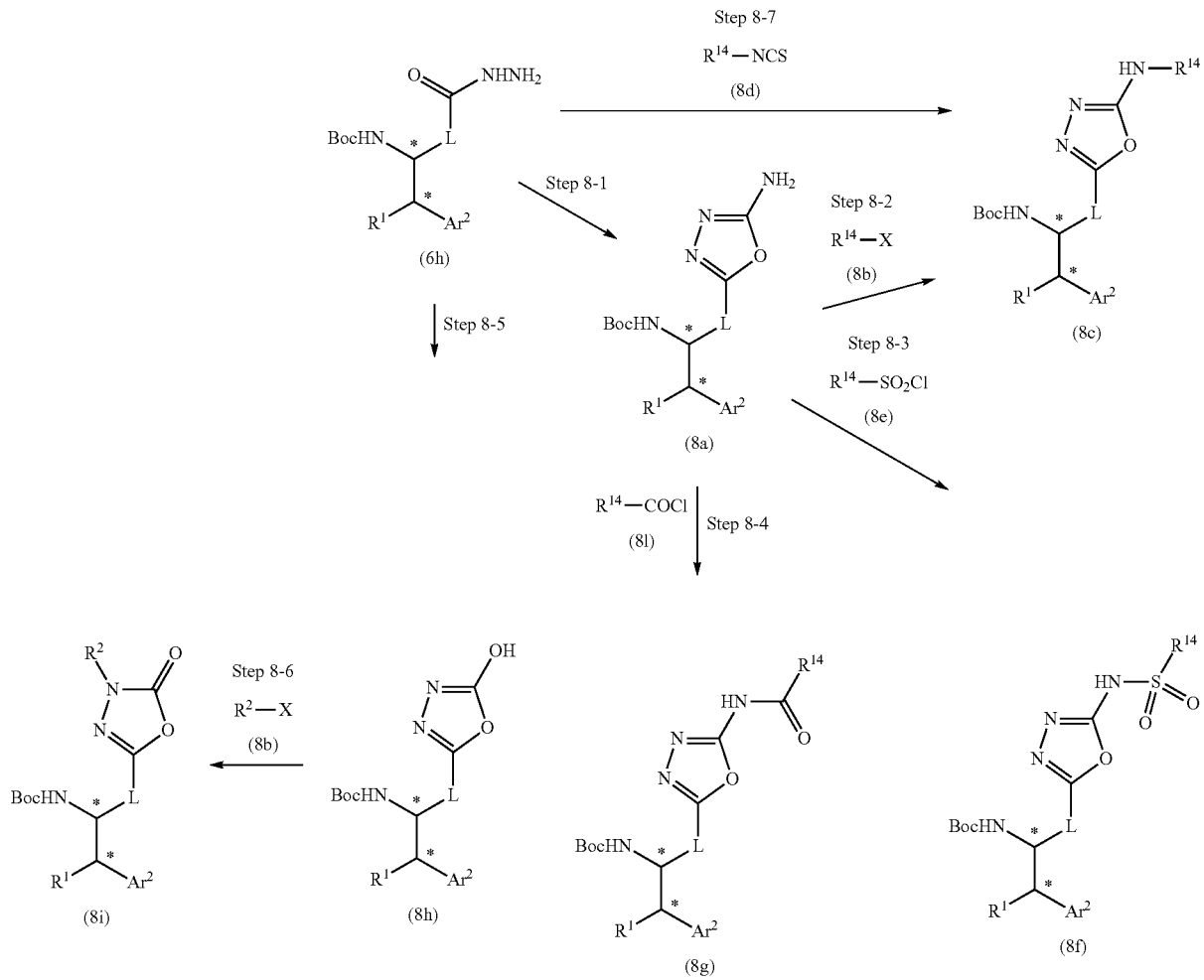

can be produced in accordance with methods described in other literatures, and methods similar thereto.
Step 7-6
This step is a step of producing Compound (7j) from Compound (7a). Compound (7j) can be produced by, for example, reacting Compound (7a) in a solvent with Grignard Compound (7i). The solvent used can include tetrahydrofuran and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days. Further, Compound (7i) used in this step may be a commercially available, or can be produced in accordance with methods described in other literatures, and methods similar thereto.

In the above formulas, $Ar^2$, $R^1$, $R^2$, $R^{14}$, and L are as described above, and each carbon atom marked with an asterisk is an asymmetric carbon atom when the carbon is a tertiary carbon atom.
Step 8-1
This step is a step of producing Compound (8a) from Compound (6h). Compound (8a) can be produced by, for example, reacting Compound (6h) in a solvent with cyanogen bromide (BrCN). The solvent used can include methanol and the like. The reaction temperature can generally be performed at −78° C. to the reflux temperature of the solvent and is performed preferably at 20° C. to 100° C. The reaction time varies depending on the starting materials used, the solvent used, the reaction temperature, or the like, but is generally 30 minutes to 3 days.

Step 8-2

This step is a step of producing Compound (8c) from Compound (8a). Compound (8c) can be produced by, for example, reacting Compound (Ba) in a solvent with Halogen compound (8b) in the presence of a base. The solvent used can include N,N-dimethylformamide, acetonitrile, 1,4-dioxane, mixed solvents thereof, and the like. The base used can include potassium carbonate, sodium carbonate, cesium carbonate, triethylamine, N,N-diisopropylethylamine, and the like. The reaction temperature can generally be performed at −78° C. to the reflux temperature of the solvent and is performed preferably at 20° C. to 90° C. The reaction time varies depending on the starting materials used, the solvent used, the reaction temperature, or the like, but is generally 30 minutes to 3 days.

Further, Compound (8b) used in this step may be a commercially available, or can be produced in accordance with methods described in other literatures, and methods similar thereto.

Step 8-3

This step is a step of producing Compound (8f) from Compound (8a). Compound (8f) can be produced by, for example, reacting Compound (8a) in a solvent with Sulfonyl chloride (8e) in the presence of a base. The solvent used can include dichloromethane, tetrahydrofuran, ethyl acetate, acetonitrile, 1,4-dioxane, mixed solvents thereof, and the like. The base used can include potassium carbonate, sodium carbonate, triethylamine, N,N-diisopropylethylamine, and the like. The reaction temperature can generally be performed at −78° C. to the reflux temperature of the solvent and is performed preferably at 20° C. to 90° C. The reaction time varies depending on the starting materials used, the solvent used, the reaction temperature, or the like, but is generally 30 minutes to 3 days.

Further, Compound (8e) used in this step may be a commercially available, or can be produced in accordance with methods described in other literatures, and methods similar thereto.

Step 8-4

This step is a step of producing Compound (8g) from Compound (8a). Compound (8g) can be produced by, for example, reacting Compound (8a) in a solvent with Acyl chloride (8l) in the presence of a base. The solvent used can include dichloromethane, tetrahydrofuran, ethyl acetate, acetonitrile, 1,4-dioxane, mixed solvents thereof, and the like. The base used can include potassium carbonate, sodium carbonate, triethylamine, N,N-diisopropylethylamine, and the like. The reaction temperature can generally be performed at −78° C. to the reflux temperature of the solvent and is performed preferably at 20° C. to 90° C. The reaction time varies depending on the starting materials used, the solvent used, the reaction temperature, or the like, but is generally 30 minutes to 3 days.

Further, Compound (8l) used in this step may be a commercially available, or can be produced in accordance with methods described in other literatures, and methods similar thereto.

Step 8-5

This step is a step of producing Compound (8h) from Compound (6h). Compound (8h) can be produced by, for example, reacting Compound (6h) in a solvent with carbonyldiimidazole (CDI). The solvent used can include acetonitrile and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days.

Step 8-6

This step is a step of producing Compound (8i) from Compound (8h). Compound (8i) can be produced by, for example, reacting Compound (8h) in a solvent with halogen compound (8b) in the presence of a base. The solvent used can include N,N-dimethylformamide, acetonitrile, 1,4-dioxane, mixed solvents thereof, and the like. The base used can include potassium carbonate, sodium carbonate, cesium carbonate, triethylamine, N,N-diisopropylethylamine, and the like. The reaction temperature can generally be performed at −78° C. to the reflux temperature of the solvent and is performed preferably at 20° C. to 90° C. The reaction time varies depending on the starting materials used, the solvent used, the reaction temperature, or the like, but is generally 30 minutes to 3 days.

Step 8-7

This step is a step of producing Compound (8c) from Compound (6h). Compound (8c) can be produced by, for example, reacting Compound (6h) in a solvent with Isocyanate compound (8d) in the presence of a base and then ring-closing the obtained condensed product in pyridine in the presence of p-toluenesulfonic acid. The solvent used can include tetrahydrofuran, dichloromethane, and the like. The reaction temperature can generally be performed at −78° C. to the reflux temperature of the solvent and is performed preferably at 20° C.-70° C. The reaction time varies depending on the starting materials used, the solvent used, the reaction temperature, or the like, but is generally 30 minutes to 3 days.

Further, Compound (8d) used in this step may be a commercially available, or can be produced in accordance with methods described in other literatures, and methods similar thereto.

Synthesis of Compounds (9d), (9e), (9g)

Compounds (9d), (9e), and (9g) can be produced, for example, from Compound (6a) or Compound (6b) in accordance with methods described in Scheme 9, methods similar thereto, methods described in other literatures, and methods similar thereto.

Scheme 9

[Chem.27]

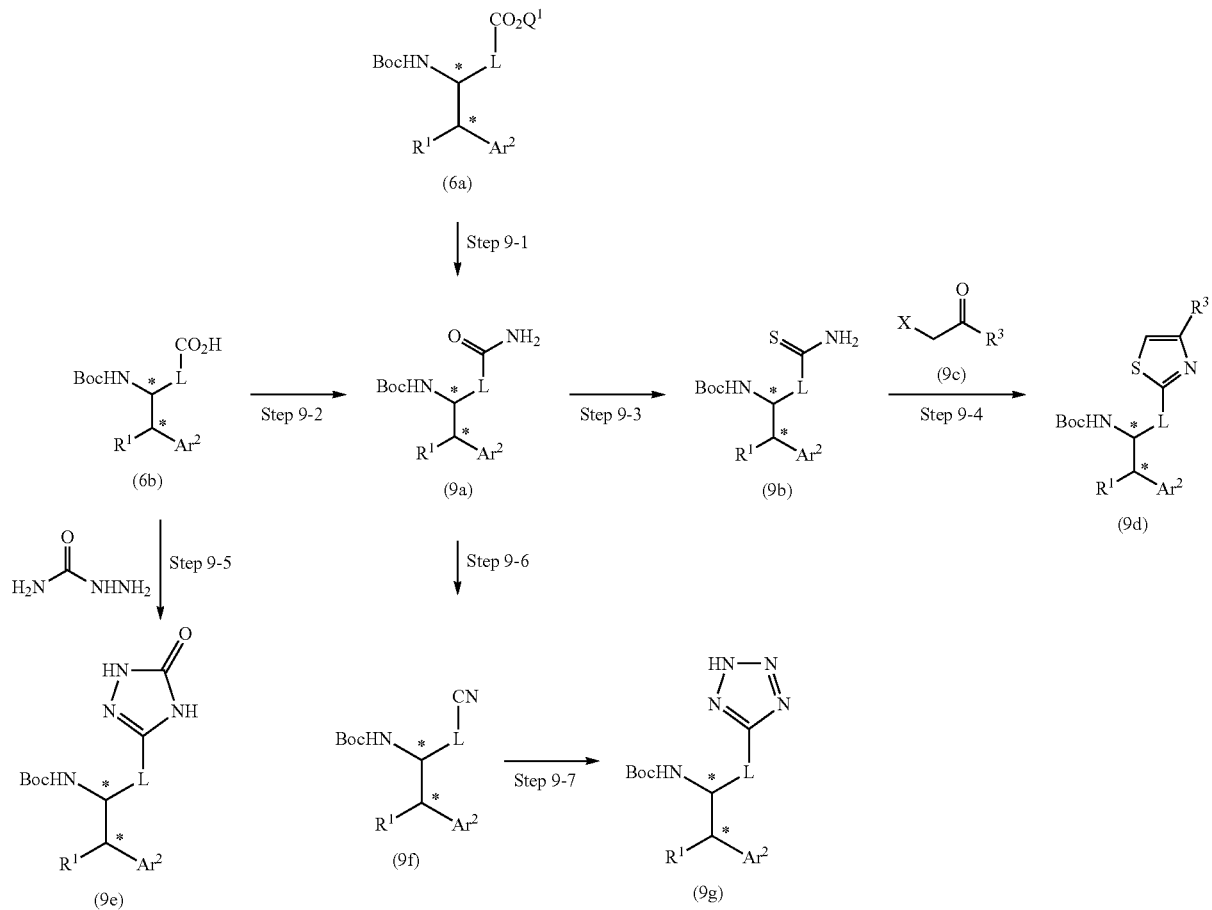

In the above formulas, $Ar^2$, $R^1$, $R^3$, L, and X are as described above, and each carbon atom marked with an asterisk is an asymmetric carbon atom when the carbon is a tertiary carbon atom.

Step 9-1

This step is a step of producing Compound (9a) from Compound (6a). Compound (9a) can be produced by, for example, reacting Compound (6a) in a solvent with ammonia. The solvent used can include methanol and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 5 days.

Step 9-2

This step is a step of producing Compound (9a) from Compound (6b). Compound (9a) can be produced by, for example, reacting Compound (6b) and aqueous ammonia in a solvent in the presence of condensing agent. The solvent used can include N,N-dimethylformamide, dichloromethane, 1,4-dioxane, tetrahydrofuran, mixed solvents thereof, and the like. Examples of the condensing agent used may include 1-ethyl-3-(3-dimethylaminopropyl)carbodiimide (EDCI), dicyclohexylcarbodiimide (DCC), 2-(1H-7-azabenzotriazol-1-yl)-1,1,3,3-tetramethyluronium hexafluorophosphate methanaminium (HATU), and the like. As necessary, N,N-dimethylaminopyridine, pyridine, 1-hydroxybenzotriazole (HOBT), and the like can be used as a reaction accelerator. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days.

Step 9-3

This step is a step of producing Compound (9b) from Compound (9a). Compound (9b) can be produced by, for example, reacting Compound (9a) and Lawesson's reagent in a solvent. The solvent used can include dichloromethane and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days.

Step 9-4

This step is a step of producing Compound (9d) from Compound (9b). Compound (9d) can be produced by, for example, reacting Compound (9b) and α-Haloketone (9c) in a solvent. The solvent used can include ethanol and the like. The reaction temperature can generally be performed at −78° C. to the reflux temperature of the solvent and is performed preferably at 50° C. to the reflux temperature of the solvent. The reaction time varies depending on the starting materials used, the solvent used, the reaction temperature, or the like, but is generally 30 minutes to 5 days.

Further, Compound (9c) used in this step may be a commercially available, or can be produced in accordance with methods described in other literatures, and methods similar thereto.

Step 9-5

This step is a step of producing Compound (9e) from Compound (6b). Compound (9e) can be produced by, for example, reacting Compound (6b) in a solvent A with semicarbazide in the presence of a condensing agent in the presence or absence of a base such as N,N-diisopropylethylamine and then treating the obtained product in Solvent B with a base such as sodium hydroxide. Solvent A used can include N,N-dimethylformamide and the like. Examples of the condensing agent used may include 2-(1H-7-azabenzotriazol-1-yl)-1,1,3,3-tetramethyluronium hexafluorophosphate methanaminium (HATU), and the like. Solvent B used can include water and the like. The reaction temperature can generally be performed at −78° C. to the reflux temperature of the solvent and is performed preferably at 0° C. to 100° C. The reaction time varies depending on the starting materials used, the solvent used, the reaction temperature, or the like, but is generally 30 minutes to 3 days.

Step 9-6

This step is a step of dehydrating Amide compound (9a) to produce Nitrile compound (9f). Compound (9f) can be produced by, for example, reacting Compound (9a) in a solvent with trifluoroacetic anhydride or the like in the presence of a base. The solvent used can include N,N-dimethylformamide, dichloromethane, 1,4-dioxane, tetrahydrofuran, toluene, mixed solvents thereof, and the like. The base used can include pyridine, triethylamine, and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days.

Step 9-7

This step is a step of producing Compound (9g) from Compound (9f). Compound (9g) can be produced by, for example, reacting Compound (9f) in a solvent with sodium azide in the presence of a base. The solvent used can include toluene, isopropanol, water, mixed solvents thereof, and the like. The reaction temperature can generally be performed at −78° C. to the reflux temperature of the solvent and is performed preferably at 50° C. to 110° C. The reaction time varies depending on the starting materials used, the solvent used, the reaction temperature, or the like, but is generally 30 minutes to 3 days.

Synthesis of Compound (10c)

Compound (10c) can be produced, for example, from Compound (6a) in accordance with methods described in Scheme 10, methods similar thereto, methods described in other literatures, and methods similar thereto.

Scheme 10

[Chem.28]

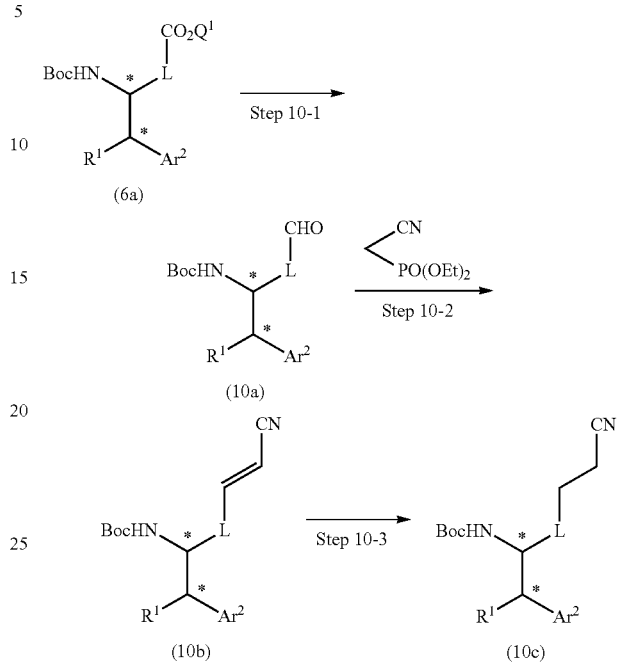

In the above formulas, $Ar^2$, $R^1$, and L are as described above, and each carbon atom marked with an asterisk is an asymmetric carbon atom when the carbon is a tertiary carbon atom.

Step 10-1

This step is a step of reducing the ester part in Compound (6a) to the corresponding aldehyde to produce Compound (10a). Compound (10a) can be produced by, for example, reacting Compound (6a) in a solvent with a reducing agent such as diisobutylaluminum hydride (DIBAL). The solvent used can include dichloromethane, tetrahydrofuran, toluene, mixed solvents thereof, and the like. The reaction temperature can generally be performed at −78° C. to the reflux temperature of the solvent and is performed preferably at −78° C. to 0° C. The reaction time varies depending on the starting materials used, the solvent used, the reaction temperature, or the like, but is generally 30 minutes to 3 days.

Step 10-2

This step is a step of producing Compound (10b) from Compound (10a). This step can be done according to the above Step 5-2.

Step 10-3

This step is a step of producing Compound (10c) from Compound (10b). This step can be done according to the above Step 5-3.

Synthesis of Compound (11c)

Compound (11c) can be produced, for example, from Compound (9a) in accordance with methods described in Scheme 11, methods similar thereto, methods described in other literatures, and methods similar thereto.

Scheme 11

[Chem.29]

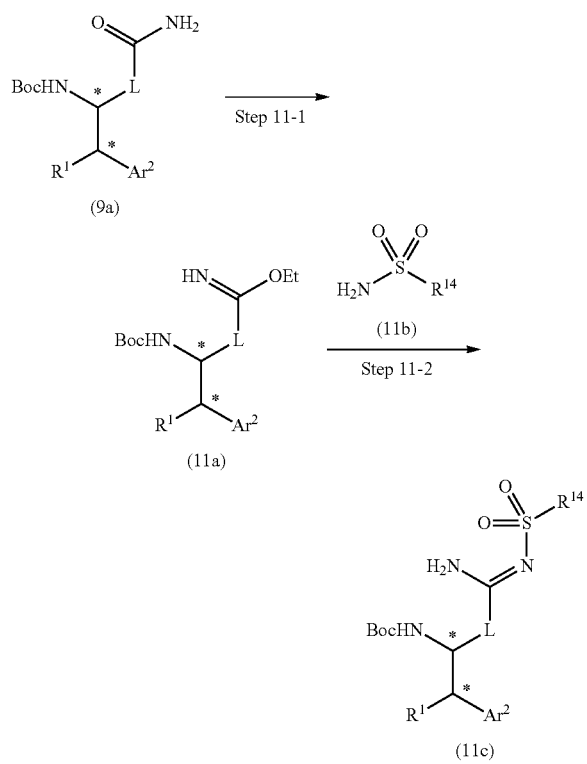

In the above formulas, $Ar^2$, $R^1$, L, and $R^{14}$ are as described above, and each carbon atom marked with an asterisk is an asymmetric carbon atom when the carbon is a tertiary carbon atom.

Step 11-1

This step is a step of producing Compound (11a) from Compound (9a). Compound (11a) can be produced by, for example, reacting Compound (9a) in a solvent with triethyloxonium hexafluorophosphate ($Et_3OPF_6$). The solvent used can include dichloromethane and the like. The reaction temperature can generally be performed at 0° C. to the reflux temperature of the solvent and is performed preferably at 10° C. to 40° C. The reaction time varies depending on the starting materials used, the solvent used, the reaction temperature, or the like, but is generally 30 minutes to 3 days.

Step 11-2

This step is a step of reacting Compound (11a) and Compound (1b) to produce Compound (1c). Compound (1c) can be produced by, for example, reacting Compound (11a) in a solvent with Compound (11b) in the presence of a base. The solvent used can include tetrahydrofuran, N,N-dimethylformamide, mixed solvents thereof, and the like. Examples of the base used may include sodium hydride, potassium carbonate, cesium carbonate, and the like. The reaction temperature can generally be performed at 0° C. to the reflux temperature of the solvent and is performed preferably at 0° C. to 60° C. The reaction time varies depending on the starting materials used, the solvent used, the reaction temperature, or the like, but is generally 30 minutes to 3 days.

Further, Compound (1b) used in this step may be a commercially available, or can be produced in accordance with methods described in other literatures, and methods similar thereto.

Synthesis of Compound (12c)

Compound (12c) can be produced, for example, from Compound (9a) in accordance with methods described in Scheme 12, methods similar thereto, methods described in other literatures, and methods similar thereto.

Scheme 12

[Chem.30]

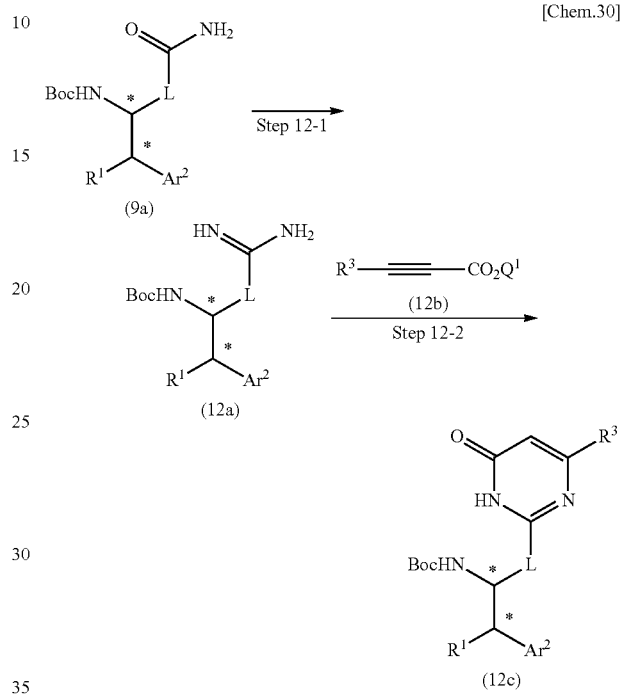

In the above formulas, $Ar^2$, $R^1$, L, and $R^3$ are as described above, and each carbon atom marked with an asterisk is an asymmetric carbon atom when the carbon is a tertiary carbon atom.

Step 12-1

This step is a step of producing Compound (12a) from Compound (9a). Compound (12a) can be produced by, for example, reacting Compound (9a) in Solvent A with triethyloxonium hexafluorophosphate ($Et_3OPF_6$) and then reacting the obtained product in Solvent B with ammonia. Solvent A used can include dichloromethane and the like. Solvent B used can include methanol and the like. The reaction temperature can generally be performed at 0° C. to the reflux temperature of the solvent and is performed preferably at 10° C. to 40° C. The reaction time varies depending on the starting materials used, the solvent used, the reaction temperature, or the like, but is generally 30 minutes to 3 days.

Step 12-2

This step is a step of reacting Compound (12a) and Compound (12b) to produce Compound (12c). Compound (12c) can be produced by, for example, reacting Compound (12a) in a solvent with Compound (12b) in the presence of a base. The solvent used can include ethanol and the like. The base used can include N,N-diisopropylethylamine and the like. The reaction temperature can generally be performed at 0° C. to the reflux temperature of the solvent and is performed preferably at 100° C. to 120° C. by using a microwave device. The reaction time varies depending on the starting materials used, the solvent used, the reaction temperature, or the like, but is generally 30 minutes to 3 days.

Further, Compound (12b) used in this step may be a commercially available, or can be produced in accordance with methods described in other literatures, and methods similar thereto.

Synthesis of Compounds (13b), (13d), (13e), (13h)

Compounds (13b), (13d), (13e), (13h) can be produced, for example, from Compound (9f) in accordance with methods described in Scheme 13, methods similar thereto, methods described in other literatures, and methods similar thereto.

In the above formulas, $Ar^2$, $R^1$, L, $R^3$, $R^5$, and $R^6$ are as described above, and each carbon atom marked with an asterisk is an asymmetric carbon atom when the carbon is a tertiary carbon atom.

Step 13-1

This step is a step of reacting Compound (9f) and hydroxylamine to produce Compound (13a). Compound (13a) can be produced by, for example, reacting Compound (9f) in a solvent with hydroxylamine hydrochloride in the presence of a base such as triethylamine. The solvent used can include ethanol and the like. The reaction temperature can generally be performed at −78° C. to the reflux temperature of the solvent and is performed preferably at 30° C. to the reflux temperature of the solvent. The reaction time varies depend- Scheme 13

[Chem.31]

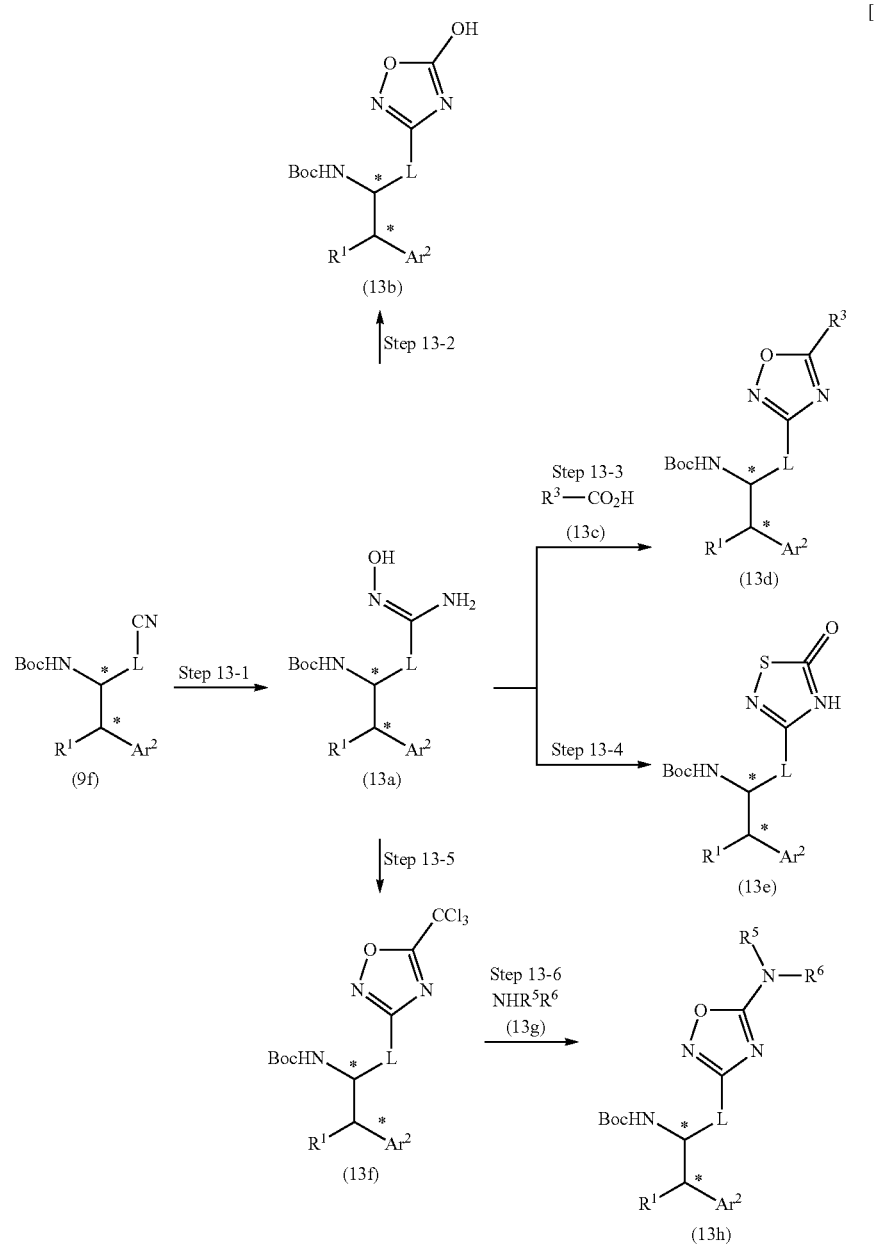

ing on the starting materials used, the solvent used, the reaction temperature, or the like, but is generally 30 minutes to 3 days.

Step 13-2

This step is a step of producing Compound (13b) from Compound (13a). Compound (13b) can be produced by, for example, reacting Compound (13a) and N,N-carbonyldiimidazole (CDI) in a solvent. The solvent used can include tetrahydrofuran and the like. The reaction temperature can generally be performed at −78° C. to the reflux temperature of the solvent and is performed preferably at 20° C. to 100° C. The reaction time varies depending on the starting materials used, the solvent used, the reaction temperature, or the like, but is generally 30 minutes to 5 days.

Step 13-3

This step is a step of producing Compound (13d) from Compound (13a). Compound (13d) can be produced by, for example, reacting Compound (13a) in Solvent A with Carboxylic acid compound (13c) in the presence of a condensing agent in the presence or absence of a base and then heating the obtained product in Solvent B in the presence or absence of a base. Solvent A used can include dichloromethane, N,N-dimethylformamide, and the like. Examples of the condensing agent used in the reaction with a carboxylic acid compound may include 1-ethyl-3-(3-dimethylaminopropyl) carbodiimide (EDCI), 2-(1H-7-azabenzotriazol-1-yl)-1,1,3,3-tetramethyluronium hexafluorophosphate methanaminium (HATU), and the like. The reaction temperature can generally be performed at −78° C. to the reflux temperature of the solvent and is performed preferably at 0° C. to 30° C. The base used can include potassium carbonate, sodium carbonate, triethylamine, N,N-diisopropylethylamine, and the like. The reaction time varies depending on the starting materials used, the solvent used, the reaction temperature, or the like, but is generally 30 minutes to 3 days. Solvent B used can include N,N-dimethylformamide, xylene, and the like. The base used can include potassium carbonate, sodium carbonate, triethylamine, N,N-diisopropylethylamine, and the like. The reaction temperature can generally be performed at −78,C to the reflux temperature of the solvent and is performed preferably at 0° C. to 100° C. The reaction time varies depending on the starting materials used, the solvent used, the reaction temperature, or the like, but is generally 30 minutes to 3 days.

Further, Compound (13c) used in this step may be a commercially available, or can be produced in accordance with methods described in other literatures, and methods similar thereto.

Step 13-4

This step is a step of producing Compound (13e) from Compound (13a). Compound (13e) can be produced by, for example, reacting Compound (13a) and thiocarbonyldiimidazole (TCDI) in Solvent A and then cyclizing the obtained product in Solvent B in the presence of silica gel. Solvent A used can include tetrahydrofuran and the like. Solvent B used can include chloroform, methanol, mixed solvents thereof, and the like. The reaction temperature can generally be performed at −78° C. to the reflux temperature of the solvent and is performed preferably at 20° C. to 100° C. The reaction time varies depending on the starting materials used, the solvent used, the reaction temperature, or the like, but is generally 30 minutes to 5 days.

Step 13-5

This step is a step of producing Compound (13f) from Compound (13a). Compound (13f) can be produced by, for example, reacting Compound (13a) and trichloroacetic anhydride in a solvent. The solvent used can include toluene and the like. The reaction temperature can generally be performed at −78° C. to the reflux temperature of the solvent and is performed preferably at 20° C. to 100° C. The reaction time varies depending on the starting materials used, the solvent used, the reaction temperature, or the like, but is generally 30 minutes to 5 days.

Step 13-6

This step is a step of producing Compound (13h) from Compound (13f). Compound (13h) can be produced by, for example, reacting Compound (13f) and Amine ingredient (13g) such as aqueous ammonia in a solvent. The solvent used can include water and the like. The reaction temperature can generally be performed at −78° C. to the reflux temperature of the solvent and is performed preferably at 20° C. to 100° C. The reaction time varies depending on the starting materials used, the solvent used, the reaction temperature, or the like, but is generally 30 minutes to 5 days.

Further, Compound (13g) used in this step may be a commercially available, or can be produced in accordance with methods described in other literatures, and methods similar thereto.

Synthesis of Compound (14a)

Compound (14a) can be produced, for example, from Compound (9f) or Compound (13a) in accordance with methods described in Scheme 14, methods similar thereto, methods described in other literatures, and methods similar thereto.

Scheme 14

[Chem.32]

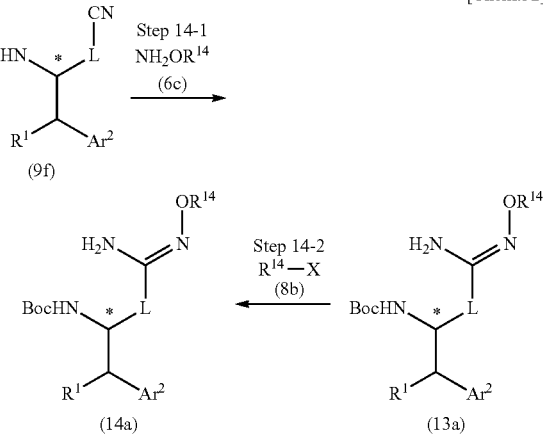

In the above formulas, $Ar^2$, $R^1$, L, and $R^{14}$ are as described above, and each carbon atom marked with an asterisk is an asymmetric carbon atom when the carbon is a tertiary carbon atom.

Step 14-1

This step is a step of reacting Compound (9f) and Compound (6c) to produce Compound (14a). Compound (14a) can be produced by, for example, reacting Compound (9f) in a solvent with Compound (6c) in the presence of a base such as triethylamine in the presence or absence of mercaptoacetic acid and ethylenediaminetetraacetate (EDTA). The solvent used can include ethanol, tetrahydrofuran, N,N-dimethylformamide, mixed solvents thereof, and the like. The reaction temperature can generally be performed at 0° C. to the reflux temperature of the solvent and is performed preferably at 70° C. to 90° C. The reaction time varies depending on the starting materials used, the solvent used, the reaction temperature, or the like, but is generally 30 minutes to 3 days.

Further, Compound (6c) used in this step may be a commercially available, or can be produced in accordance with methods described in other literatures, and methods similar thereto.

Step 14-2

This step is a step of reacting Compound (13a) and Compound (8b) to produce Compound (14a). Compound (14a) can be produced by, for example, reacting Compound (13a) in a solvent with Compound (8b) in the presence of a base. The solvent used can include tetrahydrofuran, N,N-dimethylformamide, mixed solvents thereof, and the like. Examples of the base used may include an alkali metal hydride such as lithium hydride and sodium hydride; an alkali metal hydroxide such as sodium hydroxide and potassium hydroxide; a carbonate such as potassium carbonate and cesium carbonate; and the like. The reaction temperature can generally be performed at −10° C. to the reflux temperature of the solvent and is performed preferably at 0° C. to 60° C. The reaction time varies depending on the starting materials used, the solvent used, the reaction temperature, or the like, but is generally 30 minutes to 3 days.

Further, Compound (8b) used in this step may be a commercially available, or can be produced in accordance with methods described in other literatures, and methods similar thereto.

Synthesis of Compounds (15a), (15b)

Compounds (15a) and (15b) can be produced, for example, from Compound (9g) in accordance with methods described in Scheme 15, methods similar thereto, methods described in other literatures, and methods similar thereto.

Scheme 15

[Chem.33]

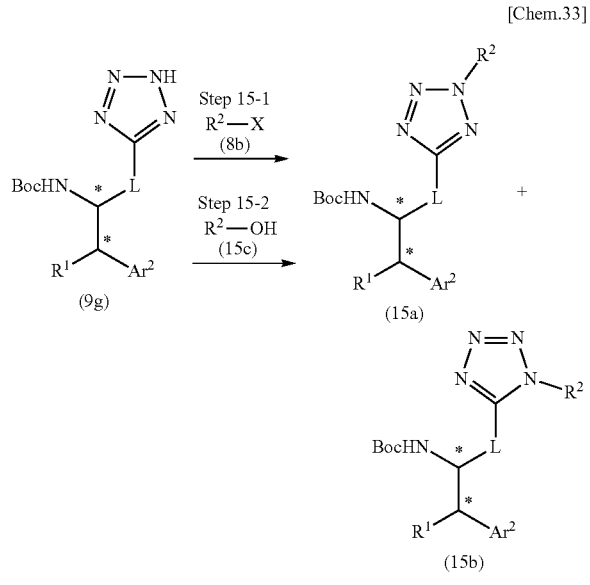

In the above formulas, $Ar^2$, $R^1$, L, and $R^2$ are as described above, and each carbon atom marked with an asterisk is an asymmetric carbon atom when the carbon is a tertiary carbon atom.

Step 15-1

This step is a step of producing Compound (15a) and Compound (15b) from Compound (9g). Compound (15a) and Compound (15b) can be produced by, for example, reacting Compound (9g) and Halogen compound (8b) in a solvent in the presence of a base. The solvent used can include N,N-dimethylformamide and the like. The base used can include potassium carbonate, sodium carbonate, triethylamine, N,N-diisopropylethylamine, and the like. The reaction temperature can generally be performed at −78° C. to the reflux temperature of the solvent and is performed preferably at 0° C. to 80° C. The reaction time varies depending on the starting materials used, the solvent used, the reaction temperature, or the like, but is generally 30 minutes to 5 days.

Further, Compound (8b) used in this step may be a commercially available, or can be produced in accordance with methods described in other literatures, and methods similar thereto.

Step 15-2

Compound (15a) and Compound (15b) can be prepared in the process mentioned below. Compound (15a) and Compound (15b) can be produced by, for example, reacting Compound (9g) in a solvent with alcohol (15c) in the presence of diethyl azodicarboxylate (DEAD) and triphenylphosphine. The solvent used can include tetrahydrofuran, toluene, mixed solvents thereof, and the like. The reaction temperature can generally be performed at −78° C. to the reflux temperature of the solvent and is performed preferably at 0° C. to 40° C. The reaction time varies depending on the starting materials used, the solvent used, the reaction temperature, or the like, but is generally 30 minutes to 3 days.

Further, Compound (15c) used in this step may be a commercially available, or can be produced in accordance with methods described in other literatures, and methods similar thereto.

Synthesis of Compound (16c)

Compound (16c) can be produced, for example, from Compound (6b) in accordance with methods described in Scheme 16, methods similar thereto, methods described in other literatures, and methods similar thereto.

Scheme 16

[Chem.34]

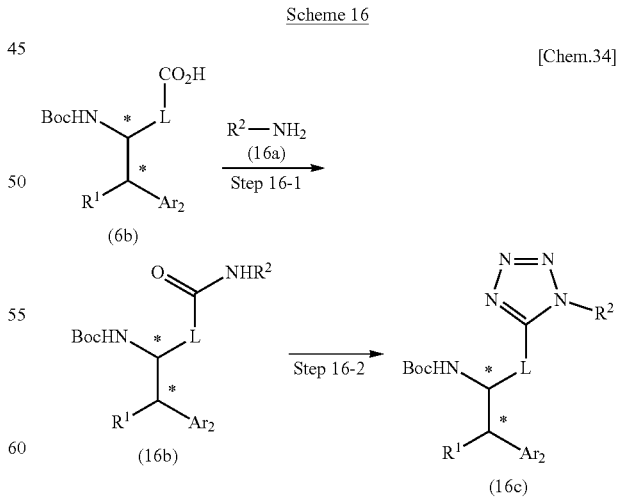

In the above formulas, $Ar^2$, $R^1$, L, and $R^2$ are as described above, and each carbon atom marked with an asterisk is an asymmetric carbon atom when the carbon is a tertiary carbon atom.

Step 16-1

This step is a step of producing Compound (16b) from Compound (6b). Compound (16b) can be produced by, for example, reacting Compound (6b) in a solvent with Primary amine (16a) in the presence of a condensing agent in the presence or absence of a base. The solvent used can include dichloromethane, N,N-dimethylformamide, and the like. Examples of the condensing agent used may include 1-ethyl-3-(3-dimethylaminopropyl)carbodiimide (EDCI), 2-(1H-7-azabenzotriazol-1-yl)-1,1,3,3-tetramethyluronium hexafluorophosphate methanaminium (HATU), and the like. The reaction temperature can generally be performed at −78° C. to the reflux temperature of the solvent and is performed preferably at 0° C. to 30° C. The base used can include triethylamine, N,N-diisopropylethylamine, and the like. The reaction time varies depending on the starting materials used, the solvent used, the reaction temperature, or the like, but is generally 30 minutes to 3 days.

Further, Compound (16a) used in this step may be a commercially available, or can be produced in accordance with methods described in other literatures, and methods similar thereto.

Step 16-2

This step is a step of producing Compound (16c) from Compound (16b). Compound (16c) can be produced by, for example, reacting Compound (16b) in a solvent with trimethylsilyl azide in the presence of di-2-methoxyethyl azodicarboxylate (DMEAD) and triphenylphosphine. The solvent used can include tetrahydrofuran, toluene, mixed solvents thereof, and the like. The reaction temperature can generally be performed at −78° C. to the reflux temperature of the solvent and is performed preferably at 0° C. to 40° C. The reaction time varies depending on the starting materials used, the solvent used, the reaction temperature, or the like, but is generally 30 minutes to 3 days.

Synthesis of Compounds (17e), (17h), (17i), (17k)

Compounds (17e), (17h), (17i), and (17k) can be produced, for example, from Compound (17a) in accordance with methods described in Scheme 17, methods similar thereto, methods described in other literatures, and methods similar thereto.

Scheme 17

[Chem.35]

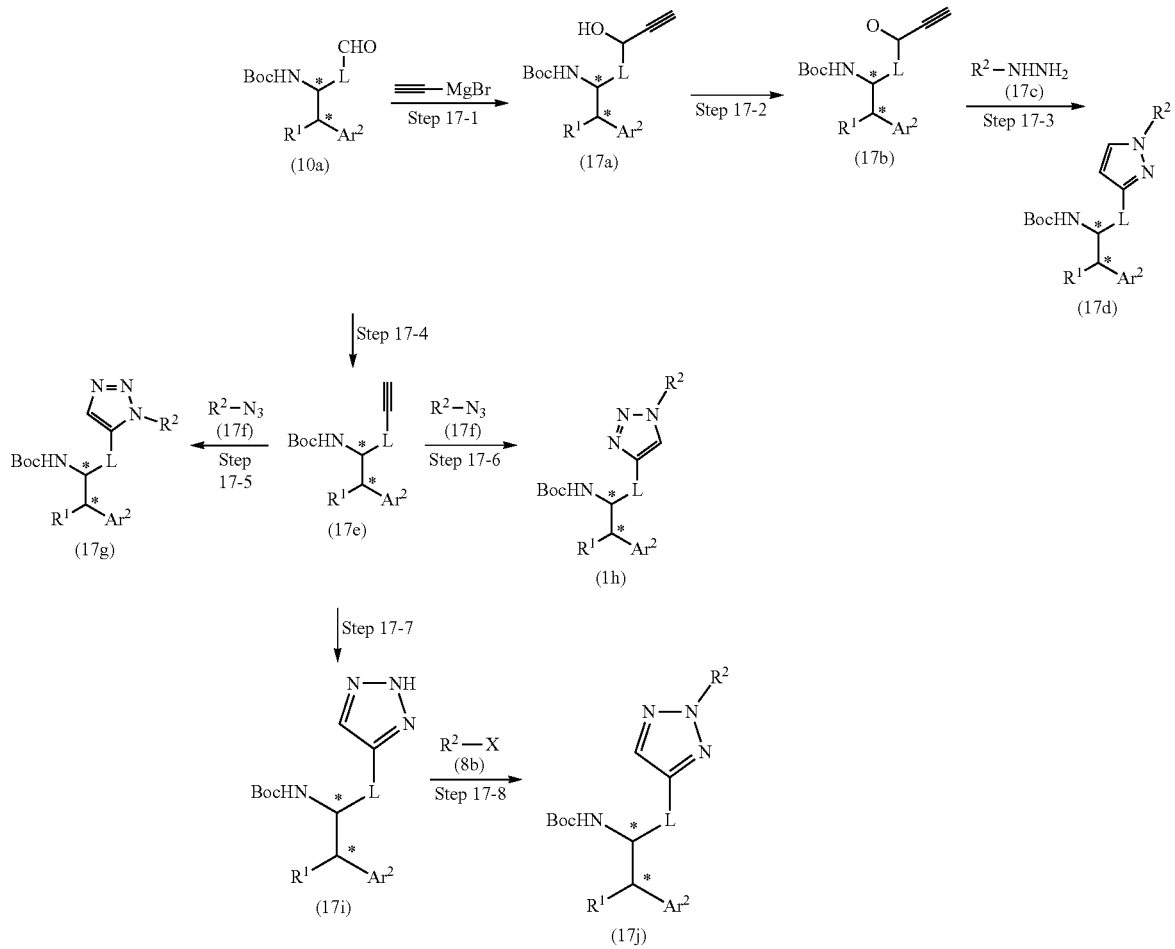

In the above formulas, Ar$^2$, R$^1$, L, and R$^2$ are as described above, and each carbon atom marked with an asterisk is an asymmetric carbon atom when the carbon is a tertiary carbon atom.

Step 17-1

This step is a step of producing Compound (17a) from Compound (10a). Compound (17a) can be produced by, for example, reacting Compound (10a) and ethynylmagnesium bromide in a solvent. The solvent used can include tetrahydrofuran and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 5 days.

Step 17-2

This step is a step of producing Compound (17b) from Compound (17a). Compound (17b) can be produced by, for example, reacting Compound (17a) in a solvent with Dess-Martin reagent. The solvent used can include dichloromethane and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 5 days.

Step 17-3

This step is a step of producing Compound (17d) from Compound (17b). Compound (17d) can be produced by, for example, reacting Compound (17b) in a solvent with Hydrazine compound (17c). The solvent used can include methanol and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 5 days.

Further, Compound (17c) used in this step may be a commercially available, or can be produced in accordance with methods described in other literatures, and methods similar thereto.

Step 17-4

This step is a step of converting the aldehyde part in Compound (10a) to Acetylene (17e). Compound (17e) can be produced by, for example, reacting Compound (10a) in a solvent with Ohira-Bestmann Reagent in the presence of a base. The solvent used can include methanol and the like. The reaction temperature can generally be performed at −78° C. to the reflux temperature of the solvent and is performed preferably at 0° C.-30° C. The base used can include potassium carbonate and the like. The reaction time varies depending on the starting materials used, the solvent used, the reaction temperature, or the like, but is generally 30 minutes to 3 days.

Step 17-5

This step is a step of producing Compound (17g) from Compound (17e). Compound (17g) can be produced by, for example, reacting Compound (17e) in a solvent with Azide compound (17f) in the presence of a ruthenium catalyst such as RuClCp(PPh$_3$)$_2$ by using a microwave device. The solvent used can include N,N-dimethylacetamide and the like. The reaction temperature can generally be performed at −78° C. to the reflux temperature of the solvent and is performed preferably at 100° C. The reaction time varies depending on the starting materials used, the solvent used, the reaction temperature, or the like, but is generally 30 minutes to 3 days.

Further, Compound (17f) used in this step may be a commercially available, or can be produced in accordance with methods described in other literatures, and methods similar thereto.

Step 17-6

This step is a step of producing Compound (17h) from Compound (17e). Compound (17h) can be produced by, for example, reacting Compound (17e) in a solvent with azide compound (17f) in the presence of copper iodide (CuI) by using a microwave device. The solvent used can include N,N-dimethylformamide, methanol, mixed solvents thereof, and the like. The reaction temperature can generally be performed at −78° C. to the reflux temperature of the solvent and is performed preferably at 100° C. The reaction time varies depending on the starting materials used, the solvent used, the reaction temperature, or the like, but is generally 30 minutes to 3 days.

Step 17-7

This step is a step of producing Compound (17i) from Compound (17e). Compound (17i) can be produced by, for example, reacting Compound (17e) in a solvent with trimethysilyl azide. The solvent used can include N,N-dimethylformamide, methanol, mixed solvents thereof, and the like. The reaction temperature can generally be performed at −78° C. to the reflux temperature of the solvent and is performed preferably at 100° C. The reaction time varies depending on the starting materials used, the solvent used, the reaction temperature, or the like, but is generally 30 minutes to 3 days.

Step 17-8

This step is a step of producing Compound (17j) from Compound (17i). Compound (17j) can be produced by, for example, reacting Compound (17i) and Halogen compound (8b) in a solvent in the presence of a base. The solvent used can include N,N-dimethylformamide and the like. The base used can include potassium carbonate, sodium carbonate, cesium carbonate, triethylamine, N,N-diisopropylethylamine, and the like. The reaction temperature can generally be performed at −78° C. to the reflux temperature of the solvent and is performed preferably at 0° C.-80° C. The reaction time varies depending on the starting materials used, the solvent used, the reaction temperature, or the like, but is generally 30 minutes to 5 days. Further, Compound (8b) used in this step may be a commercially available, or can be produced in accordance with methods described in other literatures, and methods similar thereto.

Synthesis of Compounds (18f), (18g)

Compounds (18f), (18g) can be produced, for example, from Compound (3a) in accordance with methods described in Scheme 18, methods similar thereto, methods described in other literatures, and methods similar thereto.

Scheme 18

[Chem.36]

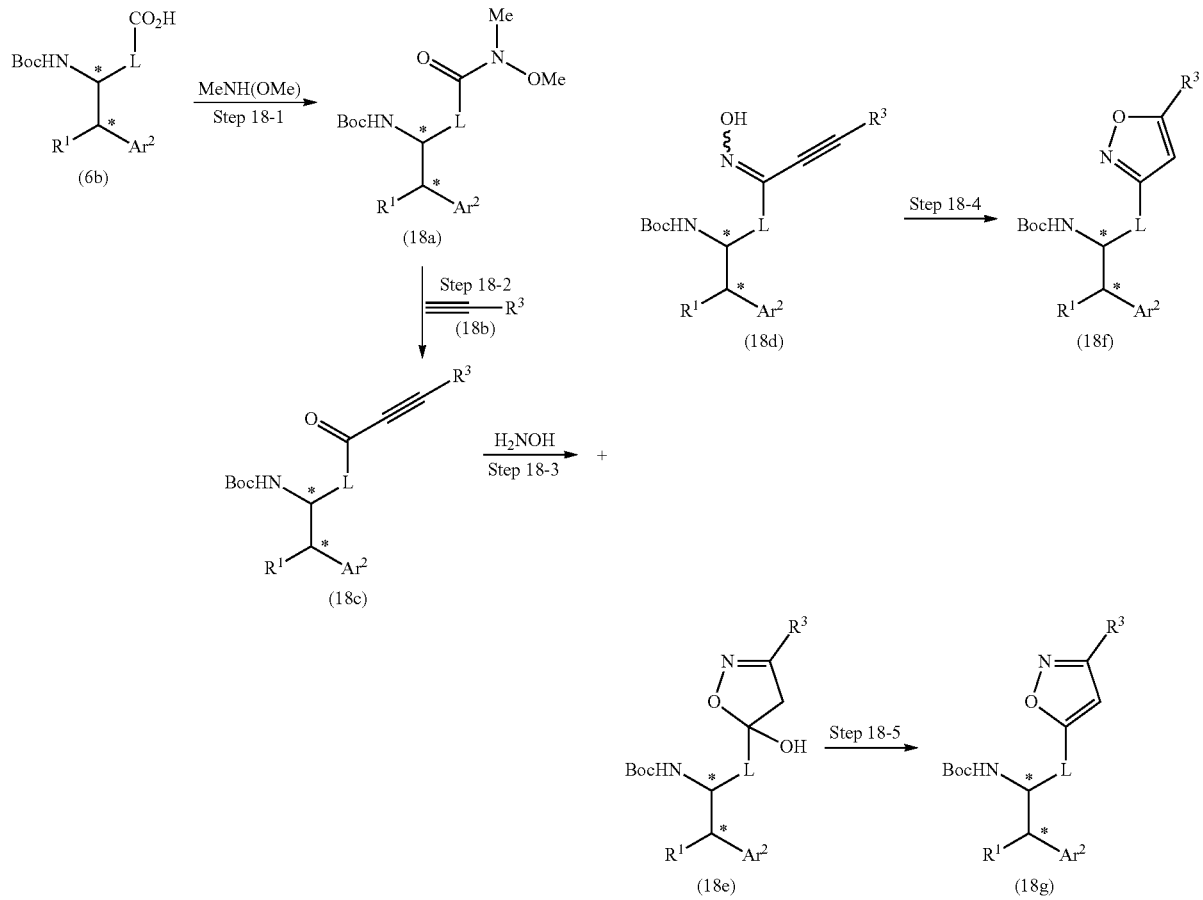

In the above formulas, $Ar^2$, $R^1$, L, and $R^3$ are as described above, and each carbon atom marked with an asterisk is an asymmetric carbon atom when the carbon is a tertiary carbon atom.

Step 18-1

This step is a step of producing Compound (18a) from Compound (6b). Compound (18a) can be produced by, for example, reacting Compound (6b) in a solvent with N,O-dimethylhydroxylamine hydrochloride in the presence of a condensing agent in the presence or absence of a base. The solvent used can include dichloromethane, N,N-dimethylformamide, and the like. Examples of the condensing agent used may include 1-ethyl-3-(3-dimethylaminopropyl)carbodiimide (EDCI), 2-(1H-7-azabenzotriazol-1-yl)-1,1,3,3-tetramethyluronium hexafluorophosphate methanaminium (HATU), and the like. The reaction temperature can generally be performed at −78° C. to the reflux temperature of the solvent and is performed preferably at 0° C. to 30° C. The base used can include triethylamine, N,N-diisopropylethylamine, and the like. The reaction time varies depending on the starting materials used, the solvent used, the reaction temperature, or the like, but is generally 30 minutes to 3 days.

Step 18-2

This step is a step of producing Compound (18c) from Compound (18a). Compound (18c) can be produced by, for example, making the lithionation of Alkyne (18b) in a solvent with a base such as n-butyllithium (n-BuLi) and then reacting Compound (18a). The solvent used can include tetrahydrofuran and the like. The reaction temperature can generally be performed at −78° C. to the reflux temperature of the solvent and is performed preferably at −78° C. to −20° C. The reaction time varies depending on the starting materials used, the solvent used, the reaction temperature, or the like, but is generally 30 minutes to 5 days. Further, Compound (18b) used in this step may be a commercially available, or can be produced in accordance with methods described in other literatures, and methods similar thereto.

Step 18-3

This step is a step of producing Compound (18d) and Compound (18e) from Compound (18c). Compound (18d) and Compound (18e) can be produced by, for example, reacting Compound (18c) in a solvent with hydroxylamine hydrochloride in the presence of a base. The solvent used can include methanol and the like. The base used can include potassium carbonate, sodium carbonate, triethylamine, N,N-diisopropylethylamine, and the like. The reaction temperature can generally be performed at −78° C. to the reflux temperature of the solvent and is performed preferably at 0° C. to 40° C. The reaction time varies depending on the starting materials used, the solvent used, the reaction temperature, or the like, but is generally 30 minutes to 5 days.

Step 18-4

This step is a step of producing Compound (18f) from Compound (18d). Compound (18f) can be produced by, for example, reacting Compound (18d) in a solvent in the presence of gold(III) chloride ($AuCl_3$). The solvent used can include dichloromethane and the like. The reaction temperature can generally be performed at −78° C. to the reflux temperature of the solvent and is performed preferably at 0° C. to 40° C. The reaction time varies depending on the starting materials used, the solvent used, the reaction temperature, or the like, but is generally 30 minutes to 5 days.

Step 18-5

This step is a step of producing Compound (18g) from Compound (18e). Compound (18g) can be produced by, for example, reacting Compound (18e) in a solvent in the presence of an acid. The solvent used can include ethyl acetate and the like. The acid used can include hydrogen chloride and the like. The reaction temperature can generally be performed at −78° C. to the reflux temperature of the solvent and is performed preferably at 0° C. to 40° C. The reaction time varies depending on the starting materials used, the solvent used, the reaction temperature, or the like, but is generally 30 minutes to 5 days.

Synthesis of Compounds (19c), (19e)

Compounds (19c) and (19e) can be produced, for example, from Compound (6b) in accordance with methods described in Scheme 19, methods similar thereto, methods described in other literatures, and methods similar thereto.

ester hydrochloride (19a) in the presence of a condensing agent in the presence or absence of a base. The solvent used can include dichloromethane, N,N-dimethylformamide, and the like. Examples of the condensing agent used may include 1-ethyl-3-(3-dimethylaminopropyl)carbodiimide (EDCI), 2-(1H-7-azabenzotriazol-1-yl)-1,1,3,3-tetramethyluronium hexafluorophosphate methanaminium (HATU), and the like. The reaction temperature can generally be performed at −78° C. to the reflux temperature of the solvent and is performed preferably at 0° C. to 30° C. The base used can include triethylamine, N,N-diisopropylethylamine, and the like. The reaction time varies depending on the starting materials used, the solvent used, the reaction temperature, or the like, but is generally 30 minutes to 3 days.

Further, Compound (19a) used in this step may be a commercially available, or can be produced in accordance with methods described in other literatures, and methods similar thereto.

Step 19-2

This step is a step of producing Compound (19c) from Compound (19b). Compound (19c) can be produced by, for example, reacting Compound (19b) in a solvent with Deoxo-Fluor and then reacting the obtained product with bromotrichloromethane ($BrCCl_3$) and 1,8-diazabicyclo[5.4.0]undec-7-ene (DBU). The solvent used can include dichloromethane and the like. The reaction temperature can generally be performed at −78° C. to the reflux temperature of the solvent and is performed preferably at 0° C. to 30° C.

Scheme 19

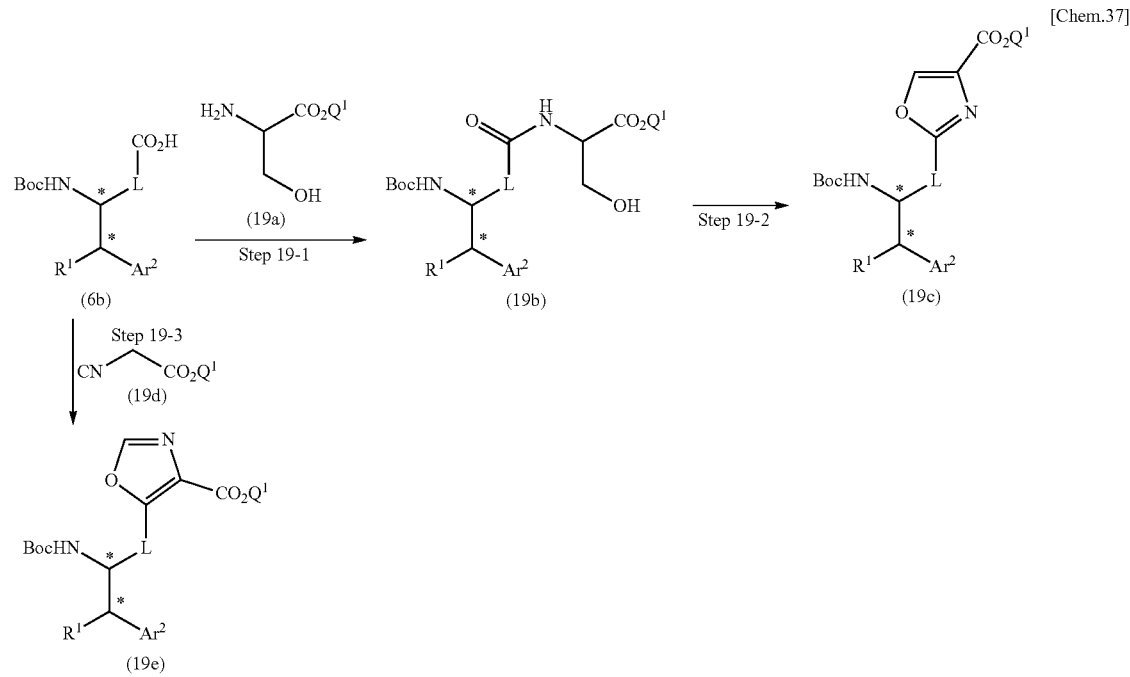

[Chem.37]

In the above formulas, $Ar^2$, $R^1$, L, and $Q^1$ are as described above, and each carbon atom marked with an asterisk is an asymmetric carbon atom when the carbon is a tertiary carbon atom.

Step 19-1

This step is a step of producing Compound (19b) from Compound (6b). Compound (19b) can be produced by, for example, reacting Compound (6b) in a solvent with Serine The base used can include triethylamine, N,N-diisopropylethylamine, and the like. The reaction time varies depending on the starting materials used, the solvent used, the reaction temperature, or the like, but is generally 30 minutes to 3 days.

Step 19-3

This step is a step of producing Compound (19e) from Compound (6b). Compound (19e) can be produced by, for example, reacting Compound (6b) in a solvent with diphenylphosphoryl azide (DPPA) and then reacting the obtained product with Isocyanoacetate (19d). The solvent used can include N,N-dimethylformamide and the like. The reaction temperature can generally be performed at −78° C. to the reflux temperature of the solvent and is performed preferably at 0° C. to 40° C. The reaction time varies depending on the starting materials used, the solvent used, the reaction temperature, or the like, but is generally 30 minutes to 5 days.

Further, Compound (19d) used in this step may be a commercially available, or can be produced in accordance with methods described in other literatures, and methods similar thereto.

Synthesis of Compounds (20a), (20d)

Compounds (20a) and (20d) can be produced, for example, from Compound (19e) in accordance with methods described in Scheme 20, methods similar thereto, methods described in other literatures, and methods similar thereto.

Synthesis of Compound (21h)

Compound (21h) can be produced, for example, from Compound (21a) in accordance with methods described in Scheme 21, methods similar thereto, methods described in other literatures, and methods similar thereto.

Scheme 21

[Chem. 38]

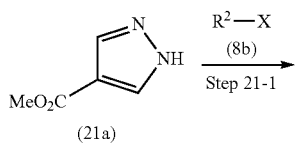

Scheme 20

[Chem. 38]

In the above formulas, $Ar^2$, $R^1$, L, and $Q^1$ are as described above, $R^4$ is a $C_1$ to $C_3$ alkyl group, and each carbon atom marked with an asterisk is an asymmetric carbon atom when the carbon is a tertiary carbon atom.

Step 20-1

This step is a step of producing Compound (20a) from Compound (19e). This step can be done according to the above Step 7-6.

Step 20-2

This step is a step of producing Compound (20b) from Compound (19e). This step can be done according to the above Step 6-1.

Step 20-3

This step is a step of producing Compound (20c) from Compound (20b). This step can be done according to the above Step 9-2.

Step 20-4

This step is a step of producing Compound (20d) from Compound (20c). This step can be done according to the above Step 9-6.

-continued

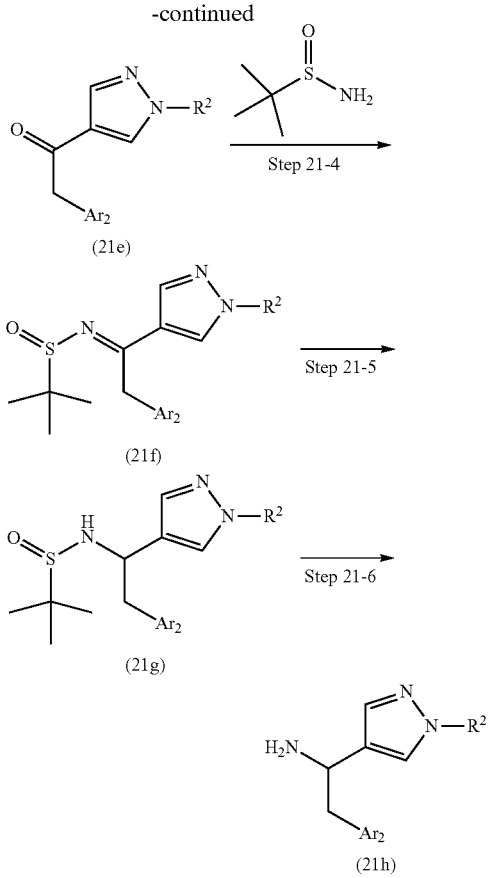

In the above formulas, Ar² and R² are as described above, and each carbon atom marked with an asterisk is an asymmetric carbon atom when the carbon is a tertiary carbon atom.

Step 21-1

This step is a step of producing Compound (21b) from Compound (21a). Compound (21b) can be produced by, for example, reacting Compound (21a) and Halogen compound (8b) in a solvent in the presence of a base. The solvent used can include N,N-dimethylformamide and the like. The base used can include potassium carbonate, cesium carbonate, and the like. The reaction temperature can generally be performed at −78° C. to the reflux temperature of the solvent and is performed preferably at 0° C. to 80° C. The reaction time varies depending on the starting materials used, the solvent used, the reaction temperature, or the like, but is generally 30 minutes to 5 days.

Further, Compound (8b) used in this step may be a commercially available, or can be produced in accordance with methods described in other literatures, and methods similar thereto.

Step 21-2

This step is a step of producing Compound (21c) from Compound (21b). Compound (21c) can be produced by, for example, reacting Compound (21b) and N,O-dimethylhydroxylamine hydrochloride in a solvent in the presence of isopropylmagnesium chloride. The solvent used can include tetrahydrofuran and the like. The reaction temperature can generally be performed at −78° C. to the reflux temperature of the solvent and is performed preferably at −20° C. The reaction time varies depending on the starting materials used, the solvent used, the reaction temperature, or the like, but is generally 30 minutes to 5 days.

Step 21-3

This step is a step of producing Compound (21e) from Compound (21c). Compound (21e) can be produced by, for example, reacting Compound (21c) and Grignard Compound (21d) in a solvent. The solvent used can include tetrahydrofuran and the like. The reaction temperature can generally be performed at −78° C. to the reflux temperature of the solvent and is performed preferably at −78° C. to 20° C. The reaction time varies depending on the starting materials used, the solvent used, the reaction temperature, or the like, but is generally 30 minutes to 5 days.

Further, Compound (21d) used in this step may be a commercially available, or can be produced in accordance with methods described in other literatures, and methods similar thereto.

Step 21-4

This step is a step of producing Compound (21f) from Compound (21e). Compound (21f) can be produced by, for example, reacting Compound (21e) and tert-butyl sulfinamide in a solvent in the presence of Ti(O$^i$Pr)$_4$. The solvent used can include tetrahydrofuran and the like. The reaction temperature can generally be performed at −78° C. to the reflux temperature of the solvent and is performed preferably at 0° C. to 80° C. The reaction time varies depending on the starting materials used, the solvent used, the reaction temperature, or the like, but is generally 30 minutes to 5 days.

Step 21-5

This step is a step of producing Compound (21g) from Compound (21f). Compound (21g) can be produced by, for example, reacting Compound (21f) and L-Selectride in a solvent. The solvent used can include tetrahydrofuran and the like. The reaction temperature can generally be performed at −78° C. to the reflux temperature of the solvent and is performed preferably at −78° C. to 0° C. The reaction time varies depending on the starting materials used, the solvent used, the reaction temperature, or the like, but is generally 30 minutes to 5 days.

Step 21-6

This step is a step of producing Compound (21h) from Compound (21g). Compound (21h) can be produced by, for example, reacting Compound (21g) and an acid such as hydrogen chloride in a solvent. The solvent used can include dioxane and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 5 days.

Synthesis of Compounds (Ia), (Ib), (Ic), (Id)

Compounds (Ia), (Ib), (Ic), and (Id) can be produced, for example, from Compound (22a) in accordance with methods described in Scheme 22, methods similar thereto, methods described in other literatures, and methods similar thereto.

Scheme 22

[Chem. 40]

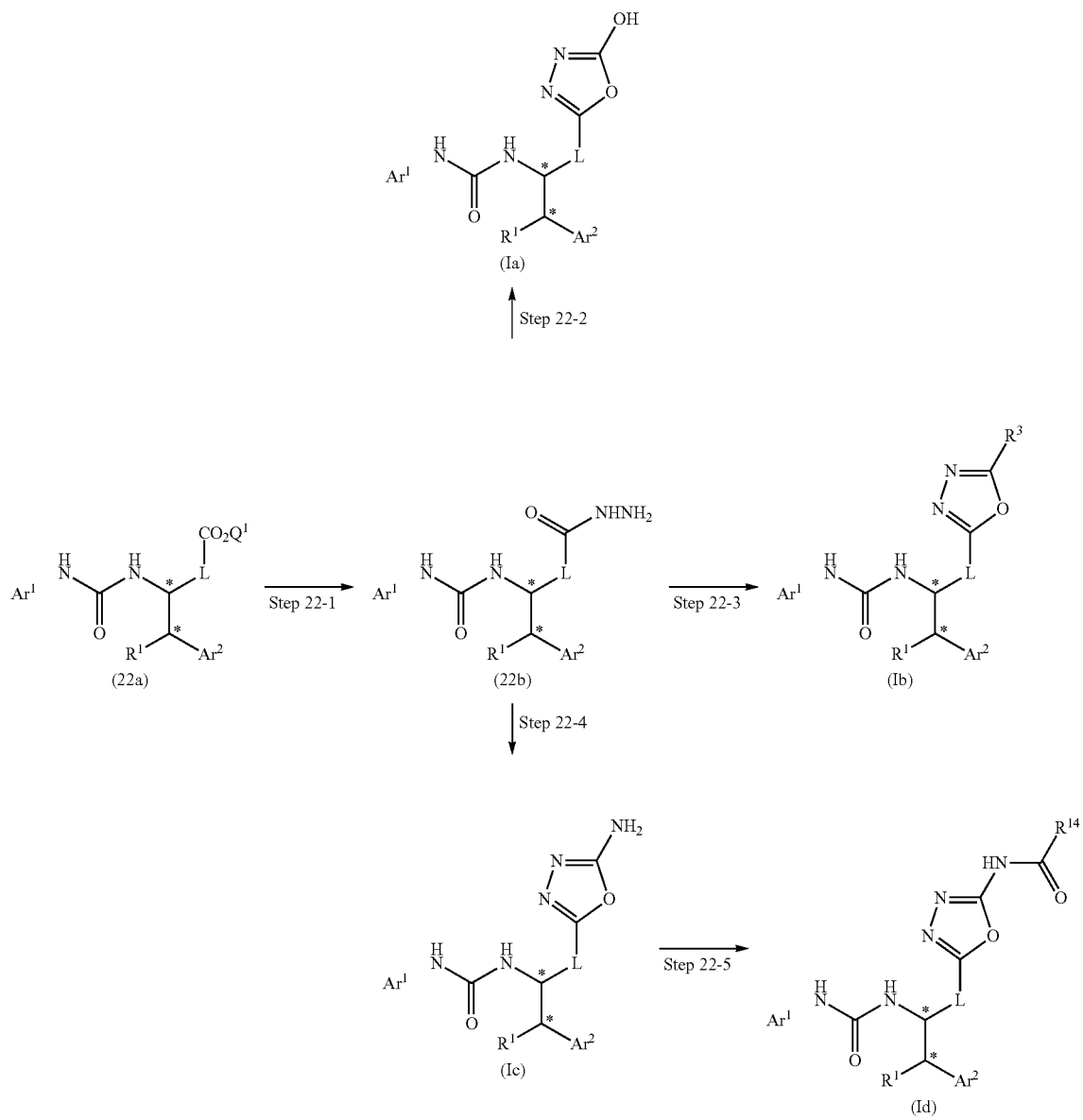

In the above formulas, $Ar^1$, $Ar^2$, $R^1$, $R^3$, L, and $R^{14}$ are as described above, and each carbon atom marked with an asterisk is an asymmetric carbon atom when the carbon is a tertiary carbon atom.

Step 22-1

This step is a step of producing Compound (22b) from Compound (22a). This step can be done according to the above Step 6-5. Compound (22a) used in this step can be produced from Compound (6a) according to the above Step 2-1, followed by the above Step 1-1 or 1-2.

Step 22-2

This step is a step of producing Compound (Ia) from Compound (22b). This step can be done according to the above Step 8-5.

Step 22-3

This step is a step of producing Compound (Ib) from Compound (22b). This step can be done according to the above Step 6-8.

Step 22-4

This step is a step of producing Compound (Ic) from Compound (22b). This step can be done according to the above Step 8-1.

Step 22-5

This step is a step of producing Compound (Id) from Compound (Ic). This step can be done according to the above Step 8-4.

Synthesis of Compounds (Ie), (If), (Ig), (Ih)

Compounds (Ie), (If), (Ig), (Ih) can be produced, for example, from Compound (23a) in accordance with methods described in Scheme 23, methods similar thereto, methods described in other literatures, and methods similar thereto.

Scheme 23

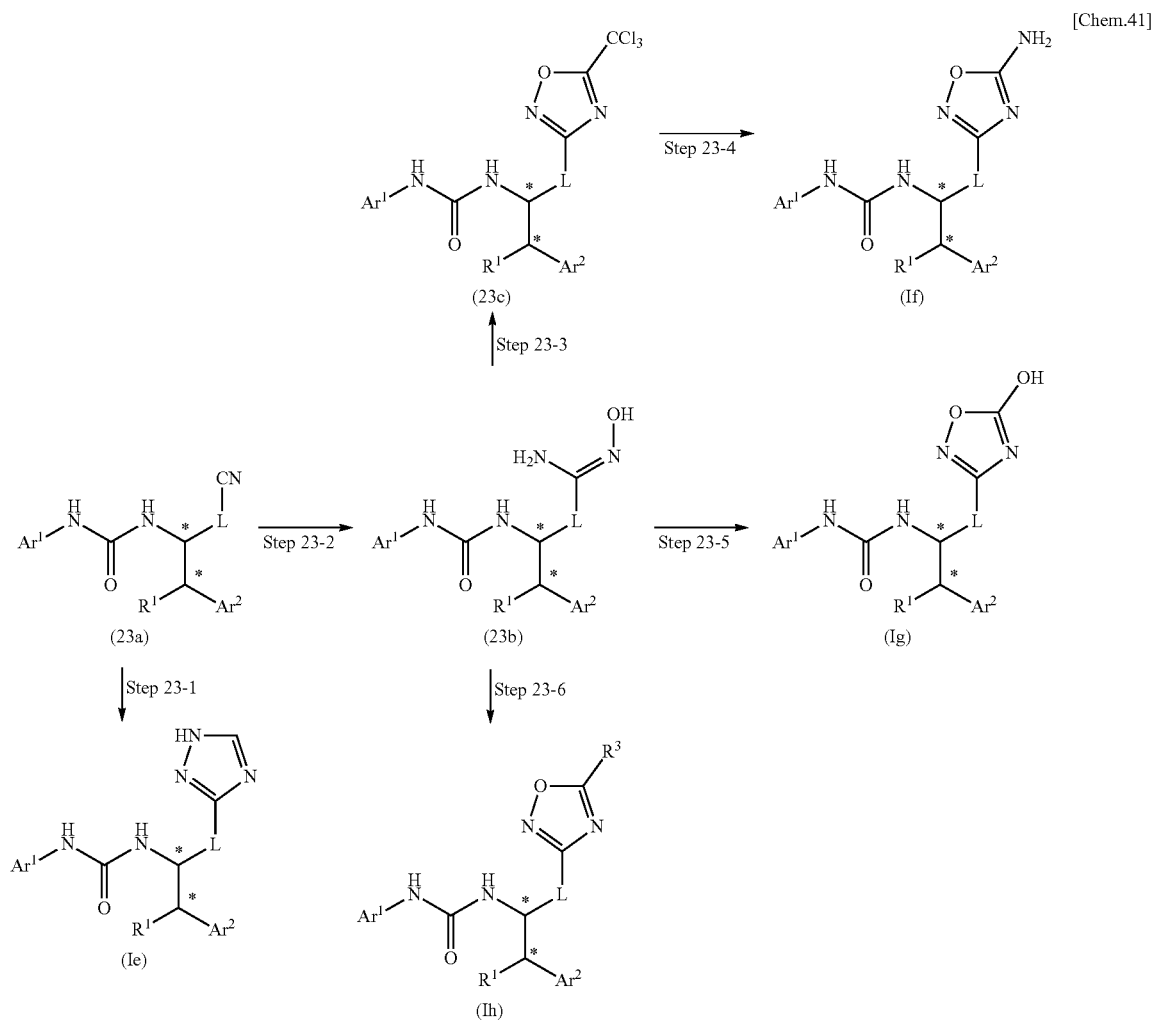

In the above formulas, $Ar^1$, $Ar^2$, $R^1$, $R^3$, and L are as described above, and each carbon atom marked with an asterisk is an asymmetric carbon atom when the carbon is a tertiary carbon atom.

Step 23-1

This step is a step of producing Compound (Ie) from Compound (23a). Compound (Ie) can be produced by, for example, reacting Compound (23a) and formylhydrazide in a solvent in the presence of a base. The solvent used can include ethanol and the like. The base used can include sodium ethoxide and the like. The reaction temperature can generally be performed at −78° C. to the reflux temperature of the solvent and is performed preferably at 0° C. to 140° C. The reaction time varies depending on the starting materials used, the solvent used, the reaction temperature, or the like, but is generally 30 minutes to 5 days.

Further, Compound (23a) used in this step can be produced from Compound (9f) according to the above Step 2-1, followed by the above Step 1-1 or 1-2.

Step 23-2

This step is a step of producing Compound (23b) from Compound (23a). This step can be done according to the above Step 13-1.

Step 23-3

This step is a step of producing Compound (23c) from Compound (23b). This step can be done according to the above Step 13-5.

Step 23-4

This step is a step of producing Compound (If) from Compound (23c). This step can be done according to the above Step 13-6.

Step 23-5

This step is a step of producing Compound (Ig) from Compound (23b). This step can be done according to the above Step 13-2.

Step 23-6

This step is a step of producing Compound (Ih) from Compound (23b). This step can be done according to the above Step 13-3.

Synthesis of Compounds (Ii), (Ij)

Compounds (Ii) and (Ij) can be produced, for example, from Compound (24a) in accordance with methods described in Scheme 24, methods similar thereto, methods described in other literatures, and methods similar thereto.

Scheme 24

[Chem.42]

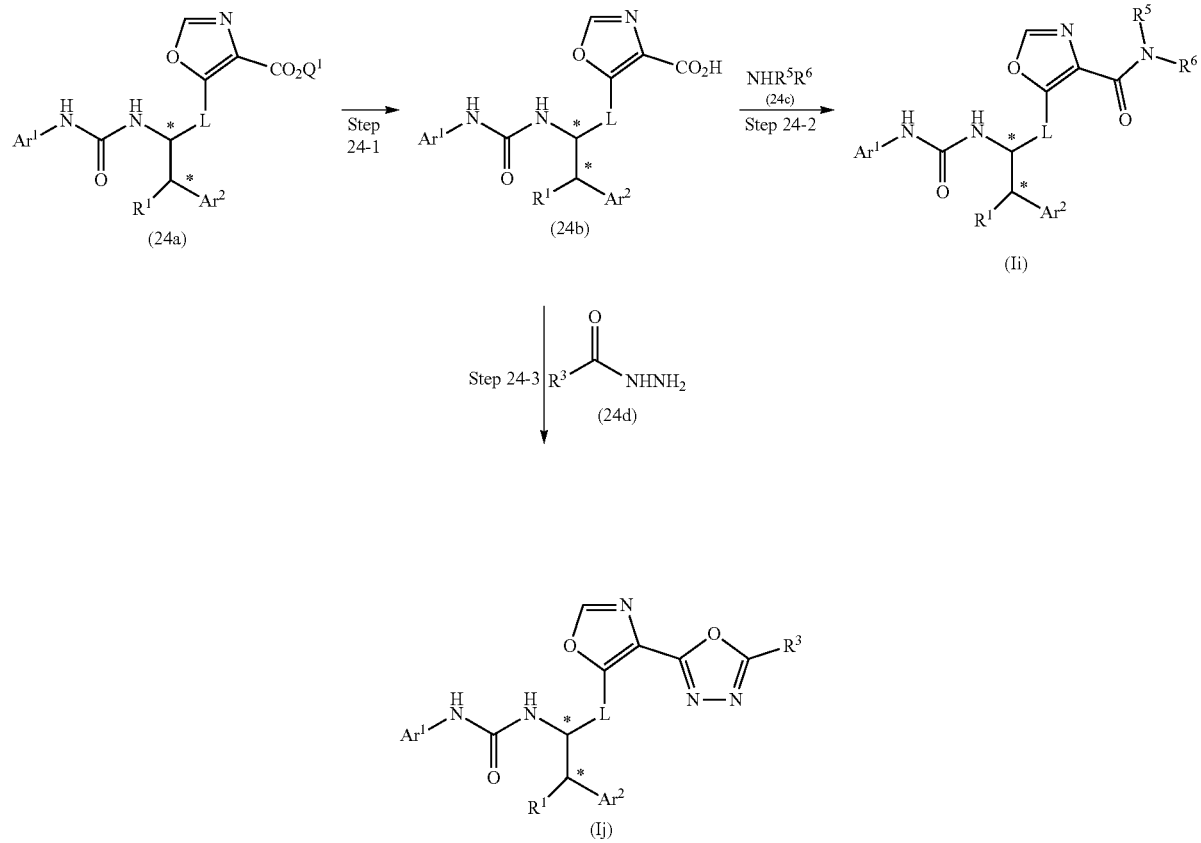

In the above formulas, $Ar^1$, $Ar^2$, $R^1$, $R^3$, $R^5$, $R^6$, and L are as described above, and each carbon atom marked with an asterisk is an asymmetric carbon atom when the carbon is a tertiary carbon atom.

Step 24-1

This step is a step of producing Compound (24b) from Compound (24a). This step can be done according to the above Step 6-1.

Compound (24a) used in this step can be produced from Compound (19e) according to the above Step 2-1, followed by the above Step 1-1 or 1-2.

Step 24-2

This step is a step of producing Compound (Ii) from Compound (24b). Compound (Ii) can be produced by, for example, reacting Compound (24b) in a solvent with Amine compound (24c) in the presence of a condensing agent in the presence or absence of a base. The solvent used can include dichloromethane, N,N-dimethylformamide, and the like. Examples of the condensing agent used may include 1-ethyl-3-(3-dimethylaminopropyl)carbodiimide (EDCI), 2-(1H-7-azabenzotriazol-1-yl)-1,1,3,3-tetramethyluronium hexafluorophosphate methanaminium (HATU), and the like. The reaction temperature can generally be performed at −78° C. to the reflux temperature of the solvent and is performed preferably at 0° C. to 30° C. The base used can include triethylamine, N,N-diisopropylethylamine, and the like. The reaction time varies depending on the starting materials used, the solvent used, the reaction temperature, or the like, but is generally 30 minutes to 3 days.

Further, Compound (24c) used in this step may be a commercially available, or can be produced in accordance with methods described in other literatures, and methods similar thereto.

Step 24-3

This step is a step of producing Compound (Ij) from Compound (24b). Compound (Ij) can be produced by, for example, reacting Compound (24b) in Solvent A with Hydrazine compound (24d) in the presence of a condensing agent in the presence or absence of a base to produce a condensed product and cyclizing the obtained condensed product in Solvent B in the presence or absence of an acid. Solvent A used can include dichloromethane, N,N-dimethylformamide, and the like. Examples of the condensing agent used may include 1-ethyl-3-(3-dimethylaminopropyl) carbodiimide (EDCI), 2-(1H-7-azabenzotriazol-1-yl)-1,1,3,3-tetramethyluronium hexafluorophosphate methanaminium (HATU), and the like. The base used can include triethylamine, N,N-diisopropylethylamine, and the like. Solvent B used can include tetrahydrofuran, dichloromethane, and the like. The acid used can include p-toluenesulfonic acid and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days.

Synthesis of Compound (Ik)

Compound (Ik) can be produced, for example, from Compound (Ih) in accordance with methods described in Scheme 25, methods similar thereto, methods described in other literatures, and methods similar thereto.

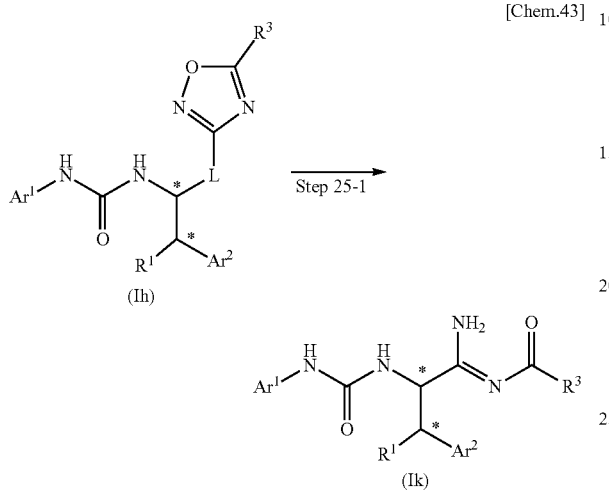

Scheme 25

[Chem. 43]

(Ih)

(Ik)

In the above formulas, $Ar^1$, $Ar^2$, $R^1$, and $R^3$ are as described above, L is a single bond, and each carbon atom marked with an asterisk is an asymmetric carbon atom when the carbon is a tertiary carbon atom.

Step 25-1

This step is a step of producing Compound (Ik) from Compound (Ih). Compound (Ik) can be produced by, for example, reacting Compound (Ih) in a solvent with a reducing agent such as sodium borohydride ($NaBH_4$). The solvent used can include methanol and the like. The reaction temperature can generally be performed at 0° C. to the reflux temperature of the solvent and is performed preferably at 20° C. to 80° C. The reaction time varies depending on the starting materials used, the solvent used, the reaction temperature, or the like, but is generally 30 minutes to 3 days.

Synthesis of Compound (Il)

Compound (Il) can be produced, for example, from Compound (26a) in accordance with methods described in Scheme 26, methods similar thereto, methods described in other literatures, and methods similar thereto.

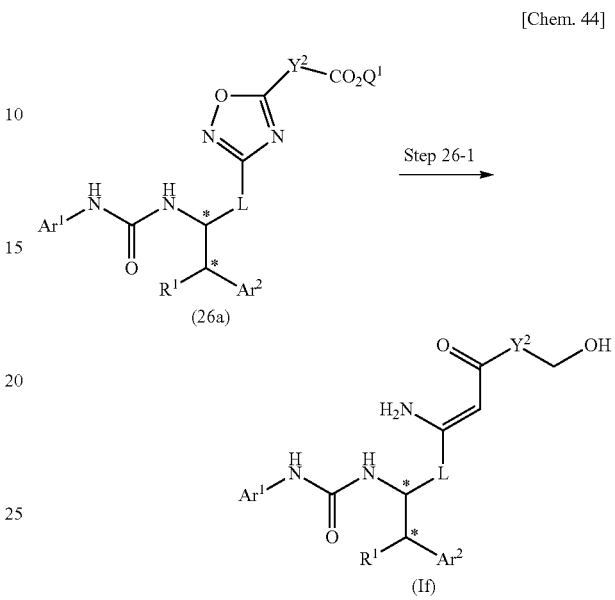

Scheme 26

[Chem. 44]

(26a)

(If)

In the above formulas, $Ar^1$, $Ar^2$, $R^1$, and $Q^1$ are as described above, $Y^2$ is a single bond or $C_1$-$C_5$ alkylene, and each carbon atom marked with an asterisk is an asymmetric carbon atom when the carbon is a tertiary carbon atom.

Step 26-1

This step is a step of reducing the oxadiazole ring and the ester part in Compound (26a) simultaneously to produce Compound (Il). This step can be done according to the above Step 25-1.

Compound (26a) used in this step can be produced from Compound (23b) according to the above Step 13-3 by using a dicarboxylic acid monoester compound (HOOC—$Y^2$—COOQ$^1$).

Synthesis of Compounds (In), (Io), (Ip)

Compounds (In), (Io), and (Ip) can be produced, for example, from Compound (Im) in accordance with methods described in Scheme 27, methods similar thereto, methods described in other literatures, and methods similar thereto.

Scheme 27

[Chem. 45]

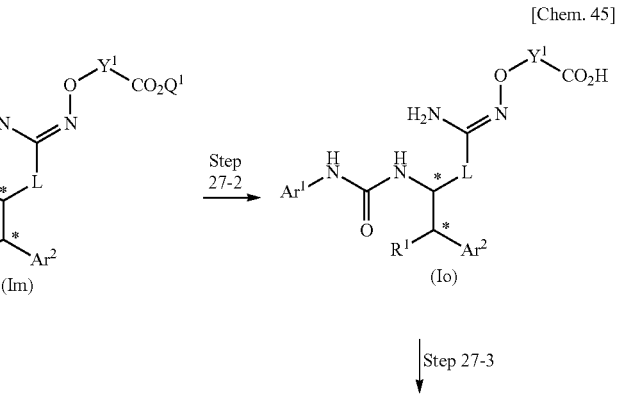

(In)    (Im)    (Io)

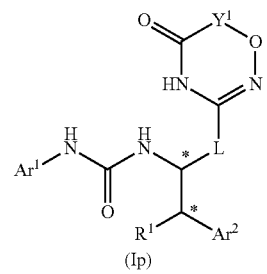
(Ip)

In the above formulas, $Ar^1$, $Ar^2$, $R^1$, L, and $Q^1$ are as described above, $Y^1$ is a single bond or a $C_1$ to $C_3$ alkylene, and each carbon atom marked with an asterisk is an asymmetric carbon atom when the carbon is a tertiary carbon atom.

Step 27-1

This step is a step of producing Compound (In) from Compound (Im). Compound (In) can be produced by, for example, reacting Compound (Im) in a solvent with a reducing agent such as lithium borohydride ($LiBH_4$). The solvent used can include tetrahydrofuran and the like. The reaction temperature can generally be performed at 0° C. to the reflux temperature of the solvent and is performed preferably at 0° C. to 30° C. The reaction time varies depending on the starting materials used, the solvent used, the reaction temperature, or the like, but is generally 30 minutes to 3 days.

Compound (Im) used in this step can be produced from Compound (23a) by using a 0-substituted hydroxylamine compound ($H_2N$—O—$Y^1$—$COOQ^1$) according to Step 14-1, or alternatively can be produced from Compound (23b) by using a halogen compound (X—$Y^1$—$COOQ^1$) according to Step 14-2.

Step 27-2

This step is a step of producing Compound (Io) from Compound (Im). This step can be done according to the above Step 6-1.

Step 27-3

This step is a step of producing Compound (Ip) from Compound (Io). Compound (Ip) can be produced by, for example, reacting Compound (Io) in a solvent in the presence of a condensing agent in the presence or absence of a base. The solvent used can include dichloromethane, N,N-dimethylformamide, and the like. Examples of the condensing agent used may include 1-ethyl-3-(3-dimethylaminopropyl)carbodiimide (EDCI), 2-(1H-7-azabenzotriazol-1-yl)-1,1,3,3-tetramethyluronium hexafluorophosphate methanaminium (HATU), and the like. The reaction temperature can generally be performed at −78° C. to the reflux temperature of the solvent and is performed preferably at 0° C. to 30° C. The base used can include triethylamine, N,N-diisopropylethylamine, and the like. The reaction time varies depending on the starting materials used, the solvent used, the reaction temperature, or the like, but is generally 30 minutes to 3 days.

Synthesis of Compound (Iq)

Compound (Iq) can be produced, for example, from Compound (28a) in accordance with methods described in Scheme 28, methods similar thereto, methods described in other literatures, and methods similar thereto.

Scheme 28

[Chem. 46]

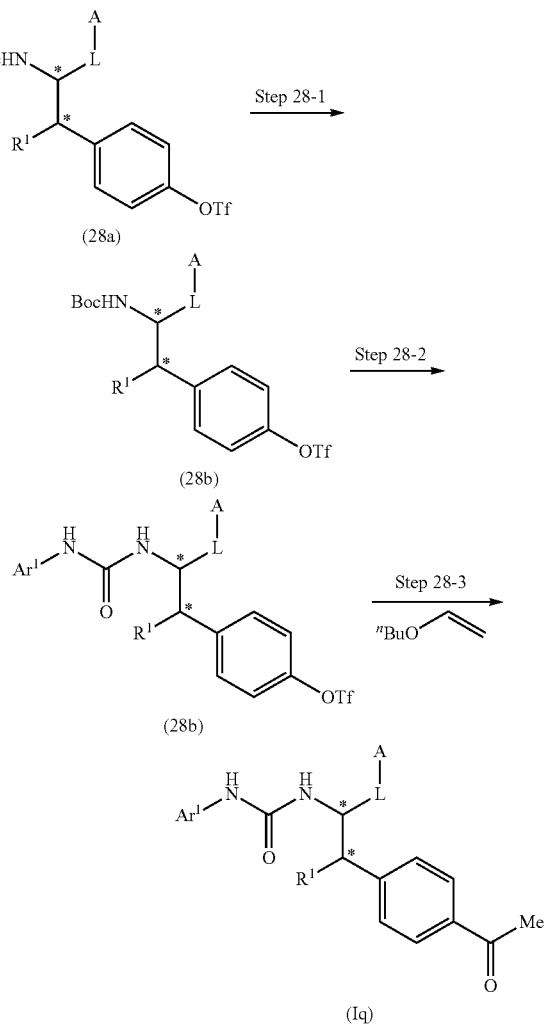

In the above formulas, $Ar^1$, L, A, and $R^1$ are as described above, Tf is trifluoromethanesulfonyl, and each carbon atom marked with an asterisk is an asymmetric carbon atom when the carbon is a tertiary carbon atom.

Step 28-1

This step is a step of producing Compound (28b) from Compound (28a). This step can be done according to the above Step 2-1.

Further, Compound (28a) used in this step may be a commercially available, or can be produced in accordance with methods described in other literatures, and methods similar thereto.

Step 28-2

This step is a step of producing Compound (28c) from Compound (28b). This step can be done by using Isocyanate compound (1b) according to the above Step 1-1, or can be also done by using Amine compound (1c) according to the above Step 1-2.

Step 28-3

This step is a step of producing Compound (Iq) from Compound (28c). Compound (Iq) can be produced by, for example, reacting Compound (28c) and butyl vinyl ether in a solvent with a palladium reagent as a catalyst in the presence of a base such as triethylamine. The solvent used can include 1,4-dioxane, toluene, N,N-dimethylformamide, mixed solvent thereof, and the like. The palladium reagent used can include palladium(II) acetate ($Pd(OAc)_2$) with 1,3-bis(diphenylphosphino)propane (DPPP) as a ligand, and the like. The reaction temperature can generally be performed at 20[ro] C. to the reflux temperature of the solvent and is performed preferably at 60° C. to 100° C. The reaction time varies depending on the starting materials used, the solvent used, the reaction temperature, or the like, but is generally 30 minutes to 3 days.

Synthesis of Compounds (Is), (It)

Compound (Is) and (It) can be produced, for example, from Compound (Ir) in accordance with methods described in Scheme 29, methods similar thereto, methods described in other literatures, and methods similar thereto.

xantphos. The solvent used can include 1,4-dioxane and the like. The reaction temperature can generally be performed at 0° C. to the reflux temperature of the solvent and is performed preferably at 20,C to 100° C. The reaction time varies depending on the starting materials used, the solvent used, the reaction temperature, or the like, but is generally 30 minutes to 3 days.

Further, Compound (29a) used in this step may be a commercially available, or can be produced in accordance with methods described in other literatures, and methods similar thereto.

Step 29-2

This step is a step of producing Compound (29d) from Compound (29c). This step can be done according to the above Step 2-1.

Step 29-3

This step is a step of producing Compound (Ir) from Compound (29d). This step can be done by using Isocyanate compound (1b) according to the above Step 1-1, or can be also done by using Amine compound (1c) according to the above Step 1-2.

Step 29-4

This step is a step of converting the sulfanyl group in Compound (Ir) to the corresponding sulfinyl group to produce Compound (Is). Compound (Is) can be produced by, for example, reacting Compound (Ir) in a solvent with an oxidizer such as meta-chloroperbenzoic acid (m-CPBA). The solvent used can include dichloromethane, acetonitrile, tetrahydrofuran, mixed solvents thereof, and the like. The amount of the oxidizer used is about 1-2 molar equivalents per 1 mole of the compound. The reaction temperature can Scheme 29

[Chem. 47]

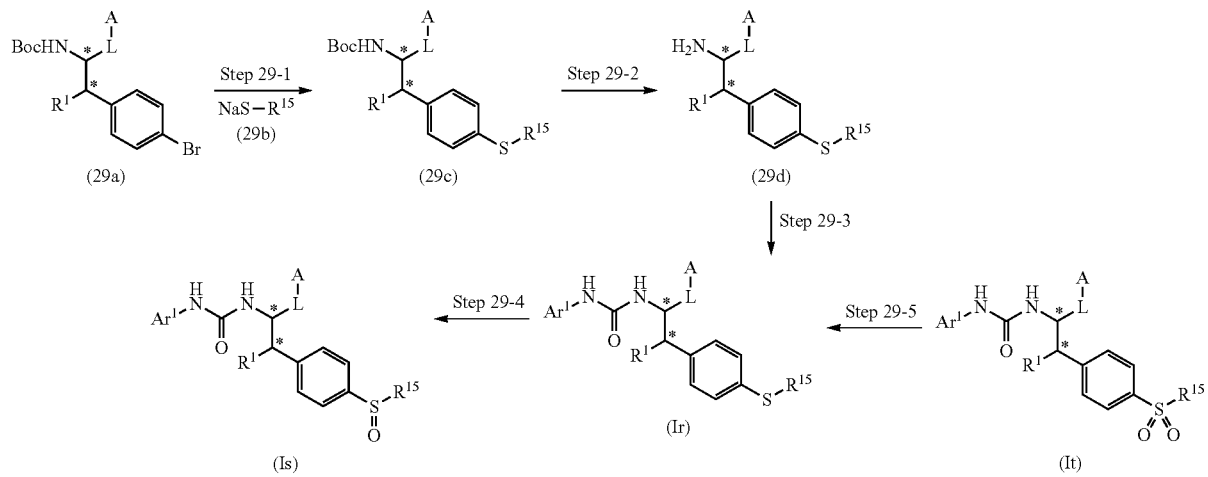

In the above formulas, $Ar^1$, $R^1$, L, and A are as described above, $R^{15}$ is a $C_{1-6}$ alkyl group or the like, and each carbon atom marked with an asterisk is an asymmetric carbon atom when the carbon is a tertiary carbon atom.

Step 29-1

This step is a step of reacting Compound (29a) and Compound (29b) to produce Compound (29c). Compound (29c) can be produced by, for example, reacting Compound (29a) in a solvent with Sodium mercaptan (29b) in the presence of a palladium catalyst such as tris(dibenzylideneacetone) dipalladium(0), and a phosphine ligand such as generally be performed at 0° C. to the reflux temperature of the solvent and is performed preferably at 20° C. to 30° C. The reaction time varies depending on the starting materials used, the solvent used, the reaction temperature, or the like, but is generally 30 minutes to 3 days.

Step 29-5

This step is a step of converting the sulfanyl group in Compound (Ir) to the corresponding sulfonyl group to produce Compound (It). Compound (It) can be produced by, for example, reacting Compound (Ir) in a solvent with an oxidizer such as meta-chloroperbenzoic acid (m-CPBA).

The solvent used can include dichloromethane, acetonitrile, tetrahydrofuran, mixed solvents thereof, and the like. The amount of the oxidizer used is about 2-5 molar equivalents per 1 mole of the compound. The reaction temperature can generally be performed at 0° C. to the reflux temperature of the solvent and is performed preferably at 20° C. to 30° C. The reaction time varies depending on the starting materials used, the solvent used, the reaction temperature, or the like, but is generally 30 minutes to 3 days.

Synthesis of Compounds (30d), (30f), (30g)

Compound (30d), (30f), and (30g) can be produced, for example, from Compound (30a) in accordance with methods described in Scheme 30, methods similar thereto, methods described in other literatures, and methods similar thereto.

C. to the reflux temperature of the solvent and is performed preferably at 60° C. to 100° C. The reaction time varies depending on the starting materials used, the solvent used, the reaction temperature, or the like, but is generally 30 minutes to 3 days.

Step 30-3

This step is a step of producing Compound (30d) from Compound (30c). Compound (30d) can be produced by, for example, reacting Compound (30c) in a solvent with dimethylamine in the presence of a condensing agent in the presence or absence of a base. The solvent used can include N,N-dimethylformamide, dichloromethane, 1,4-dioxane, tetrahydrofuran, mixed solvents thereof, and the like. Examples of the condensing agent used may include 1-ethyl- Scheme 30

[Chem. 48]

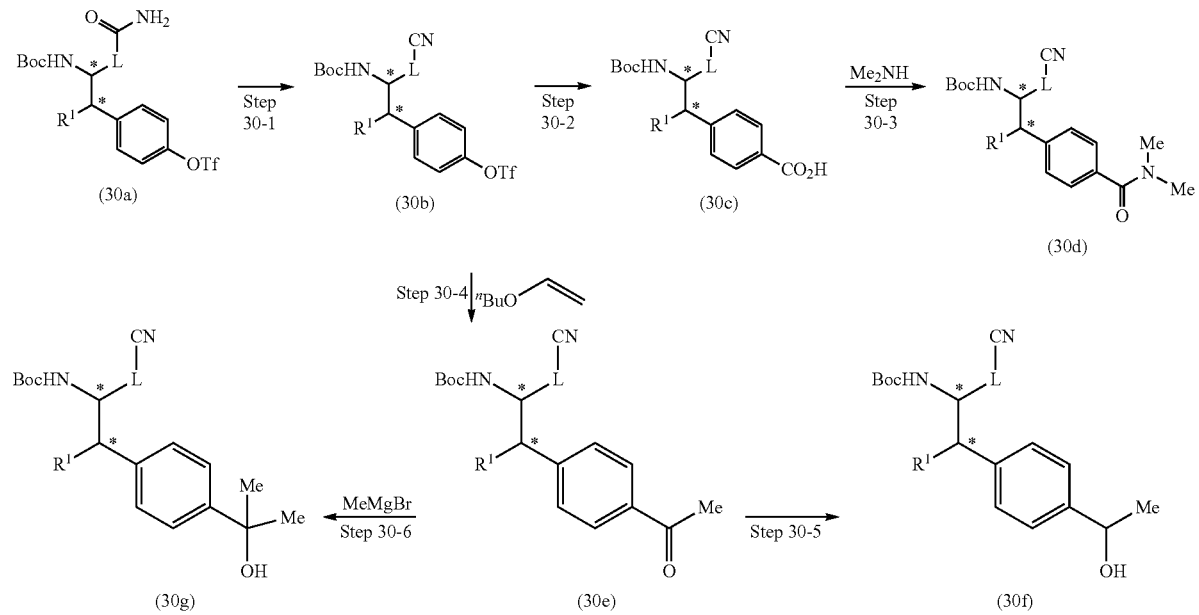

In the above formulas, $R^1$, L, and Tf are as described above, and each carbon atom marked with an asterisk is an asymmetric carbon atom when the carbon is a tertiary carbon atom.

Step 30-1

This step is a step of producing Compound (30b) from Compound (30a). This step can be done according to the above Step 9-6.

Further, Compound (30a) used in this step may be a commercially available, or can be produced in accordance with methods described in other literatures, and methods similar thereto.

Step 30-2

This step is a step of producing Compound (30c) from Compound (30b). Compound (30c) can be produced by, for example, reacting Compound (30b) in a solvent with a palladium reagent as a catalyst under carbon monoxide atmosphere in the presence of a base such as potassium carbonate. The solvent used can include N,N-dimethylformamide, and the like. The palladium reagent used can include palladium(II) acetate ($Pd(OAc)_2$) with 1,1'-bis(diphenylphophino)ferrocene (DPPF) as a ligand, and the like. The reaction temperature can generally be performed at 20°

3-(3-dimethylaminopropyl)carbodiimide (EDCI), dicyclohexylcarbodiimide (DCC), 2-(1H-7-azabenzotriazol-1-yl)-1,1,3,3-tetramethyluronium hexafluorophosphate methanaminium (HATU), and the like. As necessary, N,N-dimethylaminopyridine, pyridine, 1-hydroxybenzotriazole (HOBT), and the like can be used as a reaction accelerator. The reaction temperature can generally be performed at −78° C. to the reflux temperature of the solvent and is performed preferably at 0° C. to 40° C. The base used can include potassium carbonate, sodium carbonate, triethylamine, N,N-diisopropylethylamine, and the like. The reaction time varies depending on the starting materials used, the solvent used, the reaction temperature, or the like, but is generally 30 minutes to 3 days.

Step 30-4

This step is a step of producing Compound (30e) from Compound (30b). This step can be done according to the above Step 28-1.

Step 30-5

This step is a step of reducing the ketone part in Compound (30e) to produce Compound (30f). Compound (30f) can be produced by, for example, reacting Compound (30e) in a solvent with a reducing agent such as sodium borohydride (NaBH$_4$). The solvent used can include methanol, tetrahydrofuran, mixed solvents thereof, and the like. The reaction temperature can generally be performed at 0° C. to the reflux temperature of the solvent and is performed preferably at 0° C. to 30° C.

The reaction time varies depending on the starting materials used, the solvent used, the reaction temperature, or the like, but is generally 30 minutes to 3 days.

Step 30-6

This step is a step of producing Compound (30g) from Compound (30e). Compound (30g) can be produced by, for example, reacting Compound (30e) in a solvent with methylmagnesium bromide. The solvent used can include tetrahydrofuran and the like. The reaction temperature can generally be performed at −78° C. to the reflux temperature of the solvent and is performed preferably at 0° C. to 30° C. The reaction time varies depending on the starting materials used, the solvent used, the reaction temperature, or the like, but is generally 30 minutes to 3 days.

A pharmacologically acceptable salt of Compound (I) of the present embodiment can be produced using the compound (I) of the present embodiment according to a conventional method.

The schemes described above are examples of the method of producing Compound (I) of the present embodiment or a production intermediate thereof. These schemes can be modified to various schemes that can be readily understood by a person skilled in the art.

Also, in the case that there is a need of a protective group according to the kind of the functional group, an appropriate combination of introduction and removal procedures may be performed according to a conventional method. For the types of protective groups and introduction and removal of the protective groups, see, for example, methods described in "Greene's Protective Groups in Organic Synthesis," Theodra W. Green & Peter G. M. Wuts, ed., fourth edition, Wiley-Interscience, 2006.

The intermediates used for preparation of Compound (I) of the present embodiment or a pharmacologically acceptable salt thereof can be isolated/purified, as necessary, by solvent extraction, crystallization, recrystallization, chromatography, or preparative high-performance liquid chromatography or the like, that is an isolation/purification means well-known to a skilled person in the art.

The term "FPRL1 agonist effect" used in the present embodiment means that agonist activity exhibits through the action on formyl peptide receptor like 1 (FPRL1).

As described above, it is known that LXA4 and peptides reported as endogenous agonists of FPRL1 contribute to resolution of inflammation.

Compound (I) of the present embodiment or a pharmacologically acceptable salt thereof exhibits superior agonist activity in, for example, a test of calcium influx into FPRL1-overexpressing cells. Therefore, Compound (I) of the present embodiment or a pharmacologically acceptable salt thereof is useful as a therapeutic or prophylactic agent for inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

Compound (I) of the present embodiment or a pharmacologically acceptable salt thereof can also be used to produce pharmaceuticals for treatment or prevention of inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

In addition, pharmaceuticals containing, as an active ingredient, Compound (I) of the present embodiment or a pharmacologically acceptable salt thereof can be used as, for example, prophylactic or therapeutic agents for various disease states associated with the FPRL1 receptor (such as Behcet's disease, Sweet disease, systemic lupus erythematosus (SLE), Wegener's granulomatosis, virus infection, diabetes, amputations, cancers, bacterial infection, physical external injuries, physical disorders including exposure to radiation, vasoconstriction, anaphylactic reactions, allergic reactions, rhinitis, shocks (endotoxic, hemorrhagic, traumatic, splanchnic ischemia, and circulatory shocks), rheumatoid arthritis, gout, psoriasis, benign prostatic hyperplasia, myocardial ischemia, myocardial infarction, brain injuries, pulmonary diseases, COPD, COAD, COLD, acute lung injury, acute respiratory distress syndrome, chronic bronchitis, pulmonary emphysema, asthma (allergic asthma and non-allergic asthma), cystic pulmonary fibrosis, nephropathy, renal glomerular diseases, ulcerative colitis, IBD, Crohn's disease, periodontitis, pains, Alzheimer's disease, AIDS, uveitic glaucoma, conjunctivitis, Sjoegren's syndrome, rhinitis and the like).

Pharmaceutical containing Compound (I) of the Present Embodiment or Pharmacologically Acceptable Salt Thereof A pharmaceutical containing, as an active ingredient, Compound (I) of the present embodiment or a pharmacologically acceptable salt thereof can have various forms according to the usages. Examples of the forms may include powders, granules, fine granules, dry syrups, tablets, capsules, injections, liquids, ointments, suppositories, patches, sublingual tablets and the like, which are administered orally or parenterally.

Such a pharmaceutical can be formed as a pharmaceutical composition containing, as an active ingredient, Compound (I) of the present embodiment or a pharmacologically acceptable salt thereof and a pharmacologically acceptable additive using a well-known method according to the form of the pharmaceutical. Examples of the additive contained in the pharmaceutical composition may include an excipient, a disintegrant, a binder, a lubricant, a diluent, a buffering agent, an isotonizing agent, an antiseptic, a humectant, an emulsifier, a dispersant, a stabilizer, a solubilizing agent and the like. The pharmaceutical composition can be prepared by appropriately mixing Compound (I) of the present embodiment or a pharmacologically acceptable salt thereof with an additive or by diluting Compound (I) or a pharmacologically acceptable salt thereof with an additive and dissolving it in the additive. When Compound (I) of the present embodiment or a pharmacologically acceptable salt thereof is used in combination with agents other than the FPRL1 receptor agonist, a pharmaceutical composition can be produced by forming active ingredients of these components into a formulation simultaneously or separately in the manner described above.

The pharmaceutical according to the present embodiment can be systemically or locally administered orally or parenterally (transnasally, pulmonarily, intravenously, intrarectally, hypodermically, intramuscularly, percutaneously and the like).

When a pharmaceutical composition containing, as an active ingredient, Compound (I) of the present embodiment or a pharmacologically acceptable salt thereof is used for practical treatment, the dose of Compound (I) of the present embodiment or the pharmacologically acceptable salt thereof used as the active ingredient is appropriately determined according to the age, sex, and body weight of the patient, the disease of the patient, the degree of the treatment and the like. For example, in the case of oral administration, it may be appropriately administered to an adult (the body weight is assumed to be 60 kg) at a daily dose within the range of about 0.03 to about 1,000 mg/body in one portion or several divided portions. The dose per day as an oral administration is preferably 0.06 to 540 mg/body and more preferably 0.18 to 180 mg/body. In the case of parenteral administration, it may be appropriately administered to an adult at a daily dose within the range of about 0.01 to about 300 mg/body in one portion or several divided portions. The dose per day as a parenteral administration is preferably 0.01 to 100 mg/body and more preferably 0.06 to 60 mg/body. The dose of Compound (I) of the present embodiment or a pharmacologically acceptable salt thereof may be reduced according to the dose of agents other than the FPRL1 receptor agonist.

EXAMPLES

Hereinafter, the present invention will be described in more detail on the basis of Test Examples, Examples, and Reference Examples. Starting materials used in production of Compound (I) include a novel compound, and therefore Production examples for the starting materials will be also described as Reference Examples. The present invention is not limited to compounds described in the following Examples, and may be modified without departing from the scope of the present invention.

Among symbols used in each Reference Example, each Example, and each Table; Ref. No. represents Reference Example Number, Ex. No. represents Example Number, P.D. represents physical chemical data, Str. represents a structural formula, and $^1$H-NMR represents a proton nuclear magnetic resonance spectrum. $CDCl_3$ represents chloroform-d, and $DMSO-d_6$ represents dimethyl sulfoxide-do. MS(ESI$^+$) represents mass spectral data measured by electron-spray ionization. An optical rotation represents a specific optical rotation, which measured in described solvent at described concentration and temperature using sodium D-line as light source.

Wedge-shaped solid line and dashed line in a structural formula represent absolute configuration in an optically active substance. A carbon atom marked with "*" represents an asymmetric carbon when the carbon is a tertiary carbon atom.

Both R and S in the name of a compound represent absolute steric configuration about an asymmetric carbon atom.

In order to represent isomers about a double bond and a double bond of imine in the name of a compound, a cis-isomer is expressed as "Z," and a trans-isomer is expressed as "E."

Reference Example 1-1

Methyl (Z)-2-((tert-butoxycarbonyl)amino)-3-(2,3-dihydrobenzofuran-5-yl)acrylate

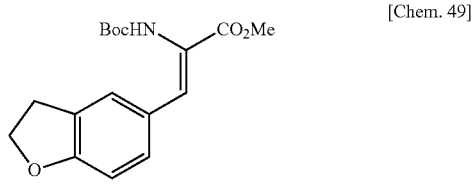 [SMILES: COC(=O)/C(=C/c1ccc2c(c1)CCO2)NC(=O)OC(C)(C)C]

[Chem. 49]

To a solution of trimethyl N-(tert-butoxycarbonyl)-2-phosphonoglycine (488 mg) and 2,3-dihydrobenzofuran-5-carboxyaldehyde (187 mg) in dichloromethane (6 mL) was added 1,8-diazabicyclo[5.4.0]undec-7-ene (DBU) (0.24 mL) to produce a reaction solution. The reaction solution was stirred at room temperature for 12 hours. The solvent was removed under reduced pressure, and the obtained residue was then purified by silica gel column chromatography (hexane:ethyl acetate=3:1) to obtain the title compound as a white solid (400 mg).

$^1$H-NMR (400 MHz, $CDCl_3$) δ 1.43 (9H, s), 3.20 (2H, t, J=8.5 Hz), 3.83 (3H, s), 4.61 (2H, t, J=8.5 Hz), 6.15 (1H, brs), 6.77 (1H, d, J=8.5 Hz), 7.28 (1H, brs), 7.35 (1H, d, J=8.5 Hz), 7.47 (1H, brs).

Reference Examples 1-2 to 1-8

The following Reference Examples 1-2 to 1-8 were obtained using each corresponding starting material in the same method as in Reference Example 1-1.

The structures and spectral data thereof are shown in Tables 1 and 2.

TABLE 1

| Ref. No | Str. | Chemical name | P.D. |
|---|---|---|---|
| 1-2 | BocHN-CO$_2$Me (chroman structure) | methyl (Z)-2-[(tert-butoxycarbonyl)amino]-3-(chroman-6-yl)acrylate | $^1$H-NMR (400 MHz, $CDCl_3$) δ 1.43 (9H, s), 1.97-2.40 (2H, m), 2.77 (2H, t, J = 6.4 Hz), 3.83 (3H, s), 4.20 (2H, t, J = 5.4 Hz), 6.76 (1H, d, J = 8.5 Hz), 7.24 (1H, s), 7.26 (1H, s), 7.33 (1H, d, J = 8.5 Hz). |
| 1-3 | BocHN-CO$_2$Me (MeO, Me phenyl) | methyl (Z)-2-[(tert-butoxycarbonyl)amino]-3-(4-methoxy-2-methylphenyl)-acrylate | $^1$H NMR (400 MHz, $CDCl_3$) δ 1.38 (9H, s), 2.34 (3H, s), 3.81 (3H, s), 3.85 (3H, s), 6.01 (1H, brs), 6.70-6.75 (2H, m), 7.28 (1H, s), 7.52 (1H, d, J = 8.5 Hz). |

TABLE 1-continued

| Ref. No | Str. | Chemical name | P.D. |
|---|---|---|---|
| 1-4 | BocHN, CO₂Me, NC-phenyl | methyl (Z)-2-[(tert-butoxycarbonyl)amino]-3-(4-cyanophenyl)acrylate | ¹H-NMR (400 MHz, CDCl₃) δ 1.38 (9H, s), 3.88 (3H, s), 6.50 (1H, brs), 7.20 (1H, s), 7.57 (2H, d, J = 8.5 Hz), 7.62 (2H, d, J = 8.5 Hz). |
| 1-5 | BocHN, CO₂Me, MeO, F | methyl (Z)-2-[(tert-butoxycarbonyl)amino]-3-(2-fluoro-4-methoxyphenyl)acrylate | ¹H-NMR (400 MHz, CDCl₃) δ 1.41 (9H, s), 3.81 (3H, s), 3.85 (3H, s), 6.23 (1H, brs), 6.62 (1H, dd, J = 12.4, 2.7 Hz), 6.68 (1H, dd, J = 9.1, 2.7 Hz), 7.37 (1H, brs), 7.60 (1H, brs). |

TABLE 2

| Ref. No | Str. | Chemical name | P.D. |
|---|---|---|---|
| 1-6 | BocHN, CO₂Me, Me-CF₂-phenyl | methyl (Z)-2-[(tert-butoxycarbonyl)amino]-3-[4-(1,1-difluoroethyl)phenyl]acrylate | ¹H-NMR (400 MHz, CDCl₃) δ 1.39 (9H, s), 1.91 (3H, t, J = 18.0 Hz), 3.87 (3H, s), 6.28 (1H, br s), 7.25 (1H, s), 7.49 (2H, d, J = 7.9 Hz), 7.57 (2H, d, J = 7.9 Hz). |
| 1-7 | BocHN, CO₂Me, MeO-thiophene | methyl (Z)-2-[(tert-butoxycarbonyl)amino]-3-(5-methoxythiophen-2-yl)acrylate | 1H-NMR (400 MHz, CDCl₃) δ 1.50 (9H, s), 3.80 (3H, s), 3.93 (3H, s), 5.71 (1H, brs), 6.20 (1H, d, J = 4.2 Hz), 7.03 (1H, d, J = 4.2 Hz), 7.64 (1H, brs). |
| 1-8 | BocHN, CO₂Me, F₂CHO-phenyl | methyl (Z)-2-[(tert-butoxycarbonyl)amino]-3-[4-(difluoromethoxy)phenyl]acrylate | 1H-NMR (400 MHz, CDCl₃) δ 1.40 (9H, s), 3.86 (3H, s), 6.53 (1H, t, J = 73.6 Hz), 7.10 (2H, d, J = 9.1 Hz), 7.24 (1H, s), 7.55 (2H, d, J = 9.1 Hz). |

Reference Example 2-1

Methyl 2-[(tert-butoxycarbonyl)amino]-3-(2,3-dihydrobenzofuran-5-yl)propanoate

[Chem.50]

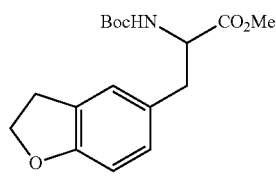

To a solution of methyl (Z)-2-[(tert-butoxycarbonyl)amino]-3-(2,3-dihydrobenzofuran-5-yl)acrylate (330 mg) in ethanol (6 mL) was added 10, palladium carbon (30 mg) to produce a reaction solution. The reaction solution was stirred under a hydrogen atmosphere for 2 hours. The reaction solution was filtered over Celite, and the solvent of the filtrate was removed under reduced pressure. The obtained residue was then purified by silica gel column chromatography (hexane:ethyl acetate=1:1) to obtain the title compound as a white solid (325 mg).

¹H-NMR (400 MHz, CDCl₃) δ 1.42 (9H, s), 2.93-3.07 (2H, m), 3.18 (2H, t, J=8.8 Hz), 3.72 (3H, s), 4.48-4.55 (1H, m), 4.55 (2H, t, J=8.8 Hz), 4.96 (1H, brs), 6.69 (1H, d, J=8.5 Hz), 6.84 (1H, d, J=8.5 Hz), 6.95 (1H, s).

Reference Examples 2-2 to 2-8

The following Reference Examples 2-2 to 2-8 were obtained using each corresponding starting material in the same method as in Reference Example 2-1.

The structures and spectral data thereof are shown in Tables 3 and 4.

TABLE 3

| Ref. No | Str. | Chemical name | P.D. |
|---|---|---|---|
| 2-2 | | methyl 2-[(tert-butoxycarbonyl)-amino]-3-(chroman-6-yl)propanoate | ¹H-NMR (400 MHz, CDCl₃) δ 1.42 (9H, s), 1.95-2.02 (2H, m), 2.74 (2H, t, J = 6.4 Hz), 2.90-3.04 (2H, m), 3.72 (3H, s), 4.16 (2H, t, J = 5.1 Hz), 4.46-4.56 (1H, m), 4.94 (1H, brs), 6.70 (1H, d, J = 8.5 Hz), 6.78 (1H, s), 6.81 (1H, d, J = 8.5 Hz). |
| 2-3 | | methyl 2-[(tert-butoxycarbonyl)-amino]-3-(4-methoxy-2-methylphenyl)-propanoate | ¹H-NMR (400 MHz, CDCl₃) δ 1.40 (9H, s), 2.31 (3H, s), 2.92 (1H, dd, J = 13.9, 8.8 Hz), 3.07 (1H, dd, J = 13.9, 6.9 Hz), 3.69 (3H, s), 3.77 (3H, s), 4.47-4.56 (1H, m), 4.96 (1H, brs), 6.66 (1H, dd, J = 8.5, 2.4 Hz), 6.71 (1H, d, J = 2.4 Hz), 6.95 (1H, d, J = 8.5 Hz). |
| 2-4 | | methyl 2-[(tert-butoxycarbonyl)-amino]-3-(4-cyanophenyl)-propanoate | ¹H-NMR (400 MHz, CDCl₃) δ 1.41 (9H, s), 3.06 (1H, dd, J = 13.9, 6.1 Hz), 3.22 (1H, dd, J = 13.9, 5.4 Hz), 3.73 (3H, s), 4.57-4.66 (1H, m), 5.02 (1H, brs), 7.26 (2H, d, J = 8.5 Hz), 7.59 (2H, d, J = 8.5 Hz). |
| 2-5 | | methyl 2-[(tert-butoxycarbonyl)-amino]-3-(2-fluoro-4-methoxyphenyl)-propanoate | ¹H-NMR (400 MHz, CDCl₃) δ 1.41 (9H, s), 2.97-3.15 (2H, m), 3.72 (3H, s), 3.78 (3H, s), 4.49-4.58 (1H, m), 5.02 (1H, brs), 6.57-6.65 (2H, m), 7.03 (1H, t, J = 8.5 Hz). |

TABLE 4

| Ref. No | Str. | Chemical name | P.D. |
|---|---|---|---|
| 2-6 | | methyl 2-[(tert-butoxycarbonyl)-amino]-3-[4-(1,1-difluoro-ethyl)phenyl]-propanoate | 1H-NMR (400 MHz, CDCl₃) δ 1.41 (9H, s), 1.91 (3H, t, J = 18.0 Hz), 3.06 (1H, dd, J = 13.4, 6.1 Hz), 3.17 (1H, dd, J = 13.4, 5.5 Hz), 3.73 (3H, s), 4.61 (1H, q, J = 7.9 Hz), 4.97 (1H, d, J = 7.9 Hz), 7.18 (2H, d, J = 7.9 Hz), 7.43 (2H, d, J = 7.9 Hz). |
| 2-7 | | methyl 2-[(tert-butoxycarbonyl)-amino]-3-(5-methoxythiophen-2-yl)propanoate | 1H-NMR (400 MHz, CDCl3) δ 1.45 (9H, s), 3.17 (2H, d, J = 4.8 Hz), 3.75 (3H, s), 3.84 (3H, s), 4.48-4.56 (1H, m), 5.13 (1H, brs), 6.00 (1H, d, J = 3.6 Hz), 6.40 (1H, d, J = 3.6 Hz). |
| 2-8 | | methyl 2-[(tert-butoxycarbonyl)-amino]-3-[4-(difluoro-methoxy)phenyl]-propanoate | ¹H-NMR (400 MHz, CDCl₃) δ 1.42 (9H, s), 3.02 (1H, dd, J = 13.9, 6.1 Hz), 3.12 (1H, dd, J = 13.9, 6.1 Hz), 3.72 (3H, s), 4.58 (1H, dd, J = 13.9, 7.3 Hz), 4.98 (1H, d, J = 7.3 Hz), 6.48 (1H, t, J = 73.9 Hz), 7.05 (2H, d, J = 8.5 Hz), 7.12 (2H, d, J = 8.5 Hz). |

Reference Example 3

Methyl (S)-2-[(tert-butoxycarbonyl)amino]-3-(2,3-dihydrobenzofuran-5-yl)propanoate

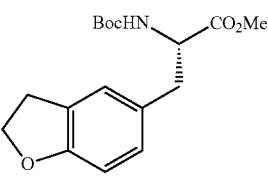
[Chem.51]

To a solution of methyl (Z)-2-[(tert-butoxycarbonyl)amino]-3-(2,3-dihydrobenzofuran-5-yl)acrylate (713 mg) in a mixed solvent of methanol and dichloromethane (20 mL-20 mL) was added 1,2-bis[(2S,5S)-2,5-dimethylphospholano]benzene(cyclooctadiene)rhodium(I) tetrafluoroborate (30 mg) to produce a reaction solution. The reaction solution was stirred under hydrogen atmosphere at 0.25 MPa for 6 hours. The reaction solution was filtered over Celite, and the solvent of the filtrate was removed under reduced pressure. The residue was then purified by silica gel column chromatography (hexane:ethyl acetate=4:1) to obtain the title compound as a colorless oil (715 mg).

$^1$H-NMR (400 MHz, CDCl$_3$) δ 1.42 (9H, s), 2.93-3.07 (2H, m), 3.18 (2H, t, J=8.8 Hz), 3.72 (3H, s), 4.48-4.55 (1H, m), 4.55 (2H, t, J=8.8 Hz), 4.96 (1H, brs), 6.69 (1H, d, J=8.5 Hz), 6.84 (1H, d, J=8.5 Hz), 6.95 (1H, s).

Reference Example 4-1

Methyl 2-amino-3-(2,3-dihydrobenzofuran-5-yl)propanoate

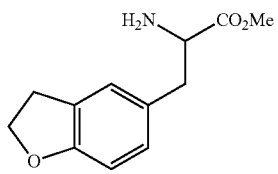
[Chem.52]

To a solution of methyl 2-((tert-butoxycarbonyl)amino)-3-(2,3-dihydrobenzofuran-5-yl)propanoate (400 mg) in ethyl acetate (5 mL) was added 4N hydrogen chloride/ethyl acetate (1 mL) to produce a reaction solution. The reaction solution was stirred at room temperature for 1 hour. The reaction solution was concentrated under reduced pressure, a saturated aqueous sodium hydrogen carbonate solution was added thereto, and the mixture was extracted with ethyl acetate. The organic layer was washed with water and then a brine, and dried over anhydrous sodium sulfate. The solvent was removed under reduced pressure to obtain the title compound as a colorless oil (250 mg).

$^1$H-NMR (400 MHz, CDCl$_3$) δ 2.78 (1H, dd, J=13.6, 7.9 Hz), 3.02 (1H, dd, J=13.6, 5.1 Hz), 3.18 (2H, t, J=8.8 Hz), 3.68 (1H, dd, J=7.9, 5.1 Hz), 3.72 (3H, s), 4.55 (2H, t, J=8.8 Hz), 6.71 (1H, d, J=8.5 Hz), 6.91 (1H, d, J=8.5 Hz), 7.02 (1H, s).

Reference Examples 4-2 to 4-7

The following Reference Examples 4-2 to 4-7 were obtained using each corresponding starting material in the same method as in Reference Example 4-1.

The structures and spectral data thereof are shown in Tables 5 and 6.

TABLE 5

| Ref. No | Str. | Chemical name | P.D. |
|---|---|---|---|
| 4-2 | (structure: H$_2$N-CH(CO$_2$Me)-CH$_2$-chroman-6-yl) | methyl 2-amino-3-(chroman-6-yl)propanoate | $^1$H-NMR (400 MHz, CDCl$_3$) δ 1.95-2.02 (2H, m), 2.71-2.78 (3H, m), 2.99 (1H, dd, J = 13.9, 4.8 Hz), 3.65-3.70 (1H, m), 3.72 (3H, s), 4.16 (2H, t, J = 5.1 Hz), 6.72 (1H, d, J = 8.1 Hz), 6.84-6.91 (2H, m). |
| 4-3 | (structure: H$_2$N-CH(CO$_2$Me)-CH$_2$-(4-methoxy-2-methylphenyl)) | methyl 2-amino-3-(4-methoxy-2-methylphenyl)-propanoate | $^1$H-NMR (400 MHz, CDCl$_3$) δ 2.32 (3H, s), 2.73 (1H, dd, J = 13.6, 8.5 Hz), 3.08 (1H, dd, J = 13.6, 5.4 Hz), 3.67 (1H, dd, J = 8.5, 5.4 Hz), 3.71 (3H, s), 3.78 (3H, s), 6.69 (1H, dd, J = 8.5, 2.4 Hz), 6.73 (1H, d, J = 2.4 Hz), 7.04 (1H, d, J = 8.5 Hz). |
| 4-4 | (structure: H$_2$N-CH(CO$_2$Me)-CH$_2$-(2-fluoro-4-methoxyphenyl)) | methyl 2-amino-3-(2-fluoro-4-methoxyphenyl)-propanoate | $^1$H-NMR (400 MHz, CDCl$_3$) δ 2.85 (1H, dd, J = 13.3, 7.9 Hz), 3.04 (1H, dd, J = 13.3, 5.4 Hz), 3.72 (3H, s), 3.69-3.74 (1H, m), 3.78 (3H, s), 6.57-6.66 (2H, m), 7.09 (1H, t, J = 8.5 Hz). |

TABLE 5-continued

| Ref. No | Str. | Chemical name | P.D. |
|---|---|---|---|
| 4-5 | (structure with H₂N, CO₂Me, thiophene, MeO) | methyl 2-amino-3-(5-methoxy-thiophen-2-yl)propanoate | $^1$H-NMR (400 MHz, CDCl$_3$) δ 2.99 (1H, dd, J = 15.1, 7.3 Hz), 3.11 (1H, dd, J = 15.1, 4.3 Hz), 3.67 (1H, dd, J = 7.3, 4.3 Hz), 3.75 (3H, s), 3.85 (3H, s), 6.01 (1H, d, J = 3.6 Hz), 6.46 (1H, d, J = 3.6 Hz). |

TABLE 6

| Ref. No | Str. | Chemical name | P.D. |
|---|---|---|---|
| 4-6 | (structure with H₂N, CO₂Me, difluoromethoxyphenyl) | methyl 2-amino-3-(4-(difluoromethoxy)phenyl)-propanoate | $^1$H-NMR (400 MHz, CDCl$_3$) δ 1.50 (2H, s), 2.86 (1H, dd, J = 13.9, 7.9 Hz), 3.07 (1H, dd, J = 13.9, 5.4 Hz), 3.68-3.74 (1H, m), 3.71 (3H, s), 6.49 (1H, t, J = 73.9 Hz), 7.06 (2H, d, J = 9.1 Hz), 7.19 (2H, d, J = 9.1 Hz). |
| 4-7 | (structure with H₂N, CO₂Me, methoxypyridine) | methyl 2-amino-3-(5-methoxy-pyridin-2-yl)propanoate | $^1$H NMR (400 MHz, CDCl$_3$) δ 2.99 (1H, dd, J = 13.9, 7.8 Hz), 3.21 (1H, dd, J = 13.9, 4.2 Hz), 3.72 (3H, s), 3.84 (3H, s), 3.94 (1H, dd, J = 7.9, 4.2 Hz), 7.08-7.15 (2H, m), 8.24 (1H, d, J = 3.0 Hz). |

Reference Example 5-1

2-Amino-3-(2,3-dihydrobenzofuran-5-yl)propan-1-ol

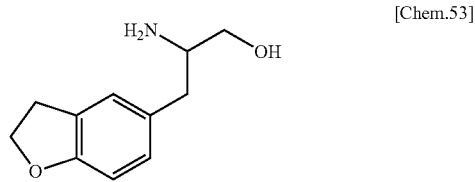 [SMILES: NC(CO)Cc1ccc2c(c1)CCO2]

[Chem.53]

To a solution of methyl 2-amino-3-(2,3-dihydrobenzofuran-5-yl)propanoate (250 mg) in methanol (8 mL) was added sodium borohydride (214 mg) to produce a reaction solution. The reaction solution was stirred at room temperature for 12 hours. The reaction solution was concentrated under reduced pressure, water was added thereto, and the mixture was extracted with ethyl acetate. The organic layer was washed with water and then a brine, and dried over anhydrous sodium sulfate. The solvent was removed under reduced pressure to obtain the title compound as a colorless oil (193 mg).

$^1$H-NMR (400 MHz, CDCl$_3$) δ 2.45 (1H, dd, J=13.6, 8.5 Hz), 2.72 (1H, dd, J=13.6, 5.1 Hz), 3.03-3.10 (1H, m), 3.19 (2H, t, J=8.5 Hz), 3.36 (1H, dd, J=10.3, 7.3 Hz), 3.63 (1H, dd, J=10.3, 3.9 Hz), 4.56 (2H, t, J=8.5 Hz), 6.72 (1H, d, J=8.1 Hz), 6.91 (1H, d, J=8.1 Hz), 7.02 (1H, s).

Reference Examples 5-2 to 5-7

The following Reference Examples 5-2 to 5-7 were obtained using each corresponding starting material in the same method as in Reference Example 5-1.

The structures and spectral data thereof are shown in Tables 7 and 8.

TABLE 7

| Ref. No | Str. | Chemical name | P.D. |
|---|---|---|---|
| 5-2 | (structure with H₂N, OH, chroman) | 2-amino-3-(chroman-6-yl)propan-1-ol | $^1$H-NMR (400 MHz, CDCl$_3$) δ 1.96-2.03 (2H, m), 2.41 (1H, dd, J = 13.9, 8.5 Hz), 2.68 (1H, dd, J = 13.9, 5.4 Hz), 2.76 (2H, t, J = 6.4 Hz), 3.03-3.10 (1H, m), 3.37 (1H, dd, J = 10.9, 7.3 Hz), 3.63 (1H, dd, J = 10.9, 3.6 Hz), 4.17 (2H, t, J = 5.1 Hz), 6.73 (1H, d, J = 8.5 Hz), 6.84-6.91 (2H, m). |

TABLE 7-continued

| Ref. No | Str. | Chemical name | P.D. |
|---|---|---|---|
| 5-3 | H₂N, OH, MeO, Me | 2-amino-3-(4-methoxy-2-methylphenyl)-propan-1-ol | ¹H-NMR (400 MHz, CDCl₃) δ 2.30 (3H, s), 2.48 (1H, dd, J = 13.9, 8.5 Hz), 2.74 (1H, dd, J = 13.9, 5.4 Hz), 3.04-3.12 (1H, m), 3.37 (1H, dd, J = 10.6, 7.3 Hz), 3.63 (1H, dd, J = 10.6, 3.9 Hz), 3.78 (3H, s), 6.69 (1H, dd, J = 8.5, 2.4 Hz), 6.73 (1H, d, J = 2.4 Hz), 7.04 (1H, d, J = 8.5 Hz). |
| 5-4 | H₂N, OH, NC | 2-amino-3-(4-cyanophenyl)-propan-1-ol | ¹H-NMR (400 MHz, CDCl₃) δ 2.62 (1H, dd, J = 13.3, 8.2 Hz), 2.87 (1H, dd, J = 13.3, 5.4 Hz), 3.11-3.18 (1H, m), 3.39 (1H, dd, J = 10.9, 6.7 Hz), 3.62 (1H, dd, J = 10.9, 4.2 Hz), 7.32 (2H, d, J = 8.5 Hz), 7.61 (2H, d, J = 8.5 Hz). |
| 5-5 | H₂N, OH, MeO, F | 2-amino-3-(2-fluoro-4-methoxyphenyl)-propan-1-ol | ¹H-NMR (400 MHz, CDCl₃) δ 2.55 (1H, dd, J = 13.6, 8.2 Hz), 2.73 (1H, dd, J = 13.6, 5.8 Hz), 3.05-3.12 (1H, m), 3.34 (1H, dd, J = 10.6, 7.0 Hz), 3.61 (1H, dd, J = 10.6, 3.6 Hz), 3.78 (3H, s), 6.58-6.68 (2H, m), 7.08 (1H, t, J = 8.5 Hz). |

TABLE 8

| Ref. No | Str. | Chemical name | P.D. |
|---|---|---|---|
| 5-6 | H₂N, OH, MeO, S | 2-amino-3-(5-methoxythiophen-2-yl)propan-1-ol | ¹H-NMR (400 MHz, CDCl₃) δ 2.61 (1H, dd, J = 15.2, 7.9 Hz), 2.82 (1H, dd, J = 15.2, 4.8 Hz), 3.00-3.10 (1H, m), 3.38 (1H, dd, J = 10.6, 7.0 Hz), 3.63 (1H, dd, J = 10.6, 3.6 Hz), 3.85 (3H, s), 6.01 (1H, d, J = 3.6 Hz), 6.43 (1H, d, J = 3.6 Hz). |
| 5-7 | H₂N, OH, F, F, O | 2-amino-3-[4-(difluoro-methoxy)phenyl]-propan-1-ol | ¹H-NMR (400 MHz, CDCl₃) δ 1.41 (1H, s), 1.61 (2H, s), 2.53 (1H, dd, J = 13.9, 8.5 Hz), 2.78 (1H, dd, J = 13.9, 5.4 Hz), 3.05-3.14 (1H, m), 3.38 (1H, dd, J = 10.6, 6.7 Hz), 3.63 (1H, dd, J = 10.6, 3.9 Hz), 6.49 (1H, t, J = 74.2 Hz), 7.07 (2H, d, J = 8.5 Hz), 7.19 (2H, d, J = 8.5 Hz). |

Reference Example 6-1

Tert-Butyl (S)-[1-amino-3-(4-methoxyphenyl)-1-oxopropan-2-yl]carbamate

[Chem.54]

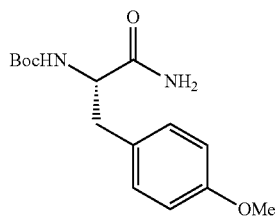

To a solution of (S)-2-[(tert-butoxycarbonyl)amino]-3-(4-methoxyphenyl)propanoic acid (29 g) in dichloromethane (485 mL) were added 1-hydroxybenzotriazole (16.5 g) and 1-ethyl-3-(3-dimethylaminopropyl)carbodiimide (20.4 g) to produce a reaction solution. To the reaction solution under ice-cooling was added 25% aqueous ammonia (29.4 mL) over 10 minutes, and the mixture was stirred at room temperature for 1 hour. To the reaction solution was added water, and the mixture was extracted with dichloromethane. The organic layer was washed with water, a saturated aqueous sodium hydrogen carbonate solution, and then a brine, and dried over anhydrous sodium sulfate. The solvent was removed under reduced pressure, and the obtained residue was then washed with hexane to obtain the title compound as a white solid (26.5 g).

¹H-NMR (400 MHz, DMSO-d₆) δ 1.42 (9H, s), 2.98 (1H, dd, J=13.9, 7.3 Hz), 3.06 (1H, dd, J=13.9, 6.1 Hz), 3.79 (3H, s), 4.30 (1H, m), 5.02 (1H, m), 5.25 (1H, s), 5.68 (1H, s), 6.85 (2H, d, J=8.5 Hz), 7.15 (2H, d, J=8.5 Hz).

Reference Examples 6-2 to 6-7

The following Reference Examples 6-2 to 6-7 were obtained using each corresponding starting material in the same method as in Reference Example 6-1.

The structures and spectral data thereof are shown in Tables 9 and 10.

TABLE 9

| Ref. No | Str. | Chemical name | P.D. |
|---|---|---|---|
| 6-2 | BocHN-CH(CH2-C6H4-Cl)-C(O)NH2 | tert-butyl (S)-[1-amino-3-(4-chlorophenyl)-1-oxopropan-2-yl]carbamate | $^1$H NMR (400 MHz, DMSO-d$_6$) δ 1.28 (9H, s), 2.70 (1H, dd, J = 14.0, 9.8 Hz), 2.93 (1H, dd, J = 13.6, 3.9 Hz), 4.01-4.08 (1H, m), 6.81 (1H, d, J = 8.5 Hz), 7.00 (1H. s), 7.26 (2H, d, J = 8.5 Hz), 7.31 (2H, d, J = 7.9 Hz), 7.35 (1H, s). |
| 6-3 | BocHN-CH(CH2-C6H4-Br)-C(O)NH2 | tert-butyl (S)-[1-amino-3-(4-bromophenyl)-1-oxopropan-2-yl]carbamate | $^1$H NMR (400 MHz, DMSO-d$_6$) δ 1.30 (9H, s), 2.68 (1H, dd, J = 13.3, 10.4 Hz), 2.91 (1H, dd, J = 13.3, 4.2 Hz), 4.05 (1H, td, J = 9.2, 4.2 Hz), 6.81 (1H, d, J = 9.2 Hz), 7.00 (1H, s), 7.20 (2H, d, J = 8.5 Hz), 7.36 (1H, s), 7.45 (2H, d, J = 7.9 Hz). |
| 6-4 | BocHN-CH(CH2-C6H4-CF2Me)-C(O)NH2 | tert-butyl {1-amino-3-[4-(1,1-difluoroethyl)-phenyl]-1-oxopropan-2-yl}carbamate | $^1$H-NMR (400 MHz, DMSO-d$_6$) δ 1.28 (9H, s), 1.94 (3H, t, J = 19.0 Hz), 2.76 (1H, dd, J = 13.5, 10.4 Hz), 2.95-3.05 (1H, m), 4.05-4.16 (1H, m), 6.85 (1H, d, J = 8.6 Hz), 7.03 (1H, s), 7.32-7.40 (3H, m), 7.45 (2H, d, J = 8.3 Hz). |
| 6-5 | BocHN-CH(CH2-(2,3-dihydrobenzofuran-5-yl))-C(O)NH2 | tert-butyl (S)-(1-amino-3-(2,3-dihydrobenzofuran-5-yl)-1-oxopropan-2-yl]carbamate | $^1$H-NMR (400 MHz, CDCl$_3$) δ 1.43 (9H, s), 2.95 (1H, dd, J = 13.9, 7.1 Hz), 3.05 (1H, dd, J = 13.9, 6.7 Hz), 3.18 (2H, t, J = 8.5 Hz), 4.24-4.34 (1H, m), 4.55 (2H, t, J = 8.5 Hz), 5.04 (1H, brs), 5.26 (1H, brs), 5.69 (1H, brs), 6.72 (1H, d, J = 7.9 Hz), 6.95 (1H, d, J = 7.9 Hz), 7.08 (1H, s). |

TABLE 10

| Ref. No | Str. | Chemical name | P.D. |
|---|---|---|---|
| 6-6 | MeO-C6H4-CH(Me)-CH(NHBoc)-C(O)NH2 | tert-butyl ((2S,3S)-1-amino-3-(4-methoxy-phenyl)-1-oxobutan-2-yl)carbamate | $^1$H-NMR (400 MHz, CDCl$_3$) δ 1.31 (3H, d, J = 7.2 Hz), 1.41 (9H, s), 3.40-3.46 (1H, m), 3.80 (3H, s), 4.18-4.27 (1H, m), 4.94-5.03 (1H, m), 5.38 (1H, br), 5.61 (1H, br), 6.87 (2H, d, J = 8.5 Hz), 7.21 (2H, d, J = 8.5 Hz). |
| 6-7 | MeO-C6H4-CH(Me)-CH(NHBoc)-C(O)NH2 | tert-butyl ((2S,3R)-1-amino-3-(4-methoxy-phenyl)-1-oxobutan-2-yl)carbamate | $^1$H-NMR (400 MHz, CDCl$_3$) δ 1.33 (3H, d, J = 6.7 Hz), 1.41 (9H, s), 3.11 (1H, br), 3.78 (3H, s), 4.20 (1H, t, J = 8.5 Hz), 5.15 (2H, br), 5.37 (1H, br), 6.85 (2H, d, J = 8.5 Hz), 7.18 (2H, d, J = 8.5 Hz). |

Reference Example 7-1

Tert-Butyl (S)-[1-cyano-2-(4-methoxyphenyl)ethyl]carbamate

[Chem.55]

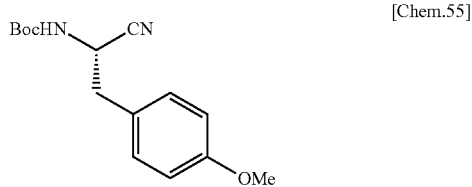 [SMILES: COc1ccc(C[C@@H](C#N)NC(=O)OC(C)(C)C)cc1]

To a solution of tert-butyl (S)-[1-amino-3-(4-methoxyphenyl)-1-oxopropan-2-yl]carbamate (23 g) in tetrahydrofuran (390 mL) at −10° C. were added trifluoroacetic anhydride (16.7 mL) and pyridine (19.1 mL) to produce a reaction solution. The reaction solution was stirred at the same temperature for 4 hours. The reaction solution was concentrated under reduced pressure, a saturated aqueous sodium hydrogen carbonate solution was added to the obtained residue, and the mixture was extracted with ethyl acetate. The organic layer was washed with water and then a brine, and dried over anhydrous sodium sulfate. The solvent was removed under reduced pressure, and the obtained residue was washed with hexane to obtain the title compound as a white solid (19.8 g).

$^1$H-NMR (400 MHz, CDCl$_3$) δ 1.45 (9H, s), 2.98 (1H, dd, J=13.9, 6.7 Hz), 3.06 (1H, dd, J=13.9, 4.8 Hz), 3.81 (3H, s), 4.77 (2H, m), 6.90 (2H, d, J=8.5 Hz), 7.21 (2H, d, J=8.5 Hz).

Reference Examples 7-2 to 7-10

The following Reference Examples 7-2 to 7-10 were obtained using each corresponding starting material in the same method as in Reference Example 7-1.

The structures and spectral data thereof are shown in Tables 11 and 12.

TABLE 11

| Ref. No | Str. | Chemical name | P.D. |
| --- | --- | --- | --- |
| 7-2 | BocHN-CN, 4-Cl-phenyl | tert-butyl (S)-[2-(4-chlorophenyl)-1-cyanoethyl]-carbamate | $^1$H-NMR (400 MHz, CDCl$_3$) δ 1.46 (9H, s), 3.05 (2H, dq, J = 23.8, 6.8 Hz), 4.78 (2H, s), 7.21-7.24 (2H, m). 7.33-7.37 (2H, m). |
| 7-3 | BocHN-CN, 4-Br-phenyl | tert-butyl (S)-[2-(4-bromophenyl)-1-cyanoethyl]-carbamate | $^1$H-NMR (400 MHz, CDCl$_3$) δ 1.42 (9H, s), 3.02 (2H, ddd, J = 23.5, 13.8, 6.5 Hz), 4.75 (1H, brs), 7.14 (2H, d, J = 8.5 Hz), 7.48 (2H, d, J = 8.0 Hz). |
| 7-4 | BocHN-CN, 4-OTf-phenyl | (S)-4-{2-[(tert-butoxycarbonyl)-amino]-2-cyanoethyl}phenyl trifluoromethanesulfonate | $^1$H-NMR (400 MHz, CDCl$_3$) δ 1.44 (9H, s), 3.11 (2H, dd, J = 2.4, 6.1 Hz), 4.81 (br, 2H), 7.32 (2H, d, J = 9.1 Hz), 7.39 (2H, d, J = 9.1 Hz). |
| 7-5 | BocHN-CN, 4-(1,1-difluoroethyl)-phenyl | tert-butyl (S)-{1-cyano-2-[4-(1,1-difluoroethyl)-phenyl]ethyl}-carbamate | $^1$H-NMR (400 MHz, DMSO-d$_6$) δ 1.35 (9H, s), 1.93 (3H, t, J = 19.0 Hz), 3.00-3.15 (2H, m), 4.68 (1H, q, J = 7.9 Hz), 7.40 (2H, d, J = 8.6 Hz), 7.50 (2H, d, J = 7.9 Hz), 7.81 (1H, d, J = 7.9 Hz). |
| 7-6 | BocHN-CN, 4-OCHF$_2$-phenyl | tert-butyl (S)-{1-cyano-2-[4-(difluoromethoxy)-phenyl]ethyl}-carbamate | $^1$H-NMR (400 MHz, CDCl$_3$) δ 1.44 (9H, s), 3.04 (1H, dd, J = 13.9, 7.3 Hz), 3.10 (1H, dd, J = 13.9, 6.1 Hz), 4.78 (2H, br s), 6.51 (1H, t, J = 73.9 Hz), 7.13 (2H, d, J = 8.5 Hz), 7.29 (2H, d, J = 8.5 Hz). |

TABLE 12

| Ref. No | Str. | Chemical name | P.D. |
|---|---|---|---|
| 7-7 | BocHN—CH₂—*CH(CN)—[2,3-dihydrobenzofuran-5-yl] | tert-butyl (S)-[1-cyano-2-(2,3-dihydrobenzofuran-5-yl)ethyl]-carbamate | ¹H-NMR (400 MHz, CDCl₃) δ 1.45 (9H, s), 2.91-3.07 (2H, m), 3.21 (2H, t, J = 8.8 Hz), 4.58 (2H, t, J = 8.8 Hz), 4.70-4.80 (1H, m), 4.75 (1H, brs), 6.76 (1H, d, J = 8.5 Hz), 7.00 (1H, d, J = 8.5 Hz), 7.13 (1H, s). |
| 7-8 | BocHN—CH₂—*CH(CN)—[4-(CF₃)phenyl] | tert-butyl (S)-{1-cyano-2-[4-(trifluoromethyl)phenyl]ethyl}-carbamate | ¹H-NMR (400 MHz, CDCl₃) δ 1.44 (9H, s), 3.09-3.21 (2H, m), 4.78 (1H, br s), 4.86 (1H, br s), 7.41 (2H, d, J = 7.9 Hz), 7.64 (2H, d, J = 7.9 Hz). |
| 7-9 | MeO-C₆H₄-*CH(CH₃)-*CH(CN)-NHBoc | tert-butyl ((1S,2S)-1-cyano-2-(4-methoxyphenyl)propyl)-carbamate | ¹H-NMR (400 MHz, CDCl₃) δ 1.41 (9H, s), 1.45 (3H, d, J = 7.2 Hz), 3.16 (1H, br), 3.81 (3H, s), 4.69 (2H, br), 6.89 (2H, d, J = 9.1 Hz), 7.20 (2H, d, J = 9.1 Hz). |
| 7-10 | MeO-C₆H₄-*CH(CH₃)-*CH(CN)-NHBoc | tert-butyl ((1S,2R)-1-cyano-2-(4-methoxyphenyl)propyl)-carbamate | ¹H-NMR (400 MHz, CDCl₃) δ 1.45-1.47 (12H, m), 3.04-3.11 (1H, m), 3.83 (3H, s), 4.66 (1H, br), 4.77 (1H, br), 6.93 (2H, d, J = 8.5 Hz), 7.26 (2H, d, J = 8.5 Hz). |

Reference Example 8

Tert-Butyl (S)-[1-cyano-2-(4-methylthiophenyl)ethyl]carbamate

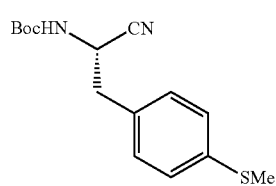

[Chem.56]

To a solution of tert-butyl (S)-[2-(4-bromophenyl)-1-cyanoethyl]carbamate (100 mg) in dioxane (9 mL) were added sodium methyl mercaptan (26 mg), tris(dibenzylideneacetone) dipalladium(0) (28 mg), and xantphos (36 mg) to produce a reaction solution. The reaction solution was stirred under an argon atmosphere at 100° C. for 3 hours. The reaction solution was filtered over Celite, and the Celite was washed with ethyl acetate.

The organic layer was washed with water and then a brine, and dried over anhydrous sodium sulfate. The solvent was removed under reduced pressure, and the obtained residue was then purified by silica gel column chromatography (hexane:ethyl acetate=6:1) to obtain the title compound as a white solid (40 mg).

¹H-NMR (400 MHz, CDCl₃) δ 1.44 (9H, s), 2.49 (3H, s), 3.00 (1H, dd, J=13.9, 7.3 Hz), 3.07 (1H, dd, J=13.9, 5.4 Hz), 4.75-4.77 (2H, m), 7.20 (2H, d, J=7.9 Hz), 7.25 (2H, d, J=7.9 Hz).

Reference Example 9

(S)-4-{2-[(tert-Butoxycarbonyl)amino]-2-cyanoethyl}benzoic Acid

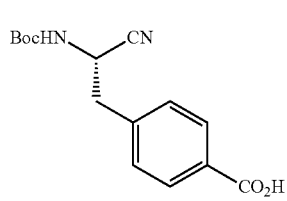

[Chem.57]

To a solution of tert-butyl (S)-[2-(4-bromophenyl)-1-cyanoethyl]carbamate (118 mg) in N,N-dimethylformamide (0.75 mL) were added palladium acetate (118 mg), (diphenylphosphino)ferrocene (33 mg), and potassium carbonate (207 mg) to produce a reaction solution. The reaction solution was stirred under a carbon monoxide atmosphere at 60° C. for 20 hours. The reaction solution was filtered over Celite, and the Celite was washed with ethyl acetate. The organic layer was washed with water and then a brine, and dried over anhydrous sodium sulfate. The solvent was removed under reduced pressure, and the obtained residue was then purified by silica gel column chromatography (ethyl acetate:methanol=4:1) to obtain the title compound as a white solid (64 mg).

¹H-NMR (400 MHz, CDCl₃) δ 1.45 (9H, s), 3.11-3.23 (2H, m), 4.79 (1H, br s), 4.87 (1H, br s), 7.40 (2H, d, J=7.9 Hz), 8.09 (2H, d, J=7.9 Hz).

Reference Example 10

Tert-Butyl (S)-{1-cyano-2-[4-(dimethylcarbamoyl)phenyl]ethyl}carbamate

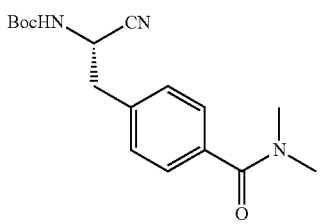

[Chem.58]

To a solution of (S)-4-{2-[(tert-butoxycarbonyl)amino]-2-cyanoethyl}benzoic acid (600 mg) in dichloromethane (10 mL) were added 1-hydroxybenzotriazole (349 mg) and 1-ethyl-3-(3-dimethylaminopropyl)carbodiimide (437 mg) to produce a reaction solution. To the reaction solution was added a solution of dimethylamine in tetrahydrofuran (2 mol/L, 1.2 mL), and the reaction mixture was stirred at room temperature for 16 hours. Water was added to the reaction solution, and the mixture was extracted with ethyl acetate. The organic layer was washed with water, a saturated aqueous sodium hydrogen carbonate, and then a brine, and dried over anhydrous sodium sulfate. The solvent was removed under reduced pressure, and the residue was then purified by silica gel column chromatography (hexane:ethyl acetate=2:1) to obtain the title compound as a white solid (554 mg).

$^1$H-NMR (CDCl$_3$) δ 1.45 (9H, s), 2.99 (3H, s), 3.08 (1H, dd, J=14.1, 6.7 Hz), 3.12 (3H, s), 3.14 (1H, dd, J=14.1, 5.5 Hz), 4.77 (1H, br s), 4.84 (1H, br s), 7.33 (2H, d, J=8.6 Hz), 7.44 (2H, d, J=8.6 Hz).

Reference Example 11

Tert-Butyl (S)-[2-(4-acetylphenyl)-1-cyanoethyl]carbamate

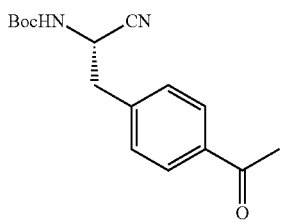

[Chem.59]

To a solution of (S)-4-{2-[(tert-butoxycarbonyl)amino]-2-cyanoethyl}phenyl trifluoromethanesulfonate (2.0 g) in N,N-dimethylformamide (50.7 mL) were added butyl vinyl ether (3.3 mL), triethylamine (3.53 mL), palladium acetate (228 mg), and (diphenylphosphino)ferrocene (837 mg) to produce a reaction solution. The reaction solution was stirred under an argon atmosphere at 80° C. for 7 hours. The solvent was removed under reduced pressure, tetrahydrofuran (40 mL) was added thereto, the mixture was cooled, 1N hydrochloric acid (10 mL) was added thereto, and the mixture was stirred for 1 hour. The solvent was removed under reduced pressure, and the obtained residue was extracted with ethyl acetate. The organic layer was washed with water and then a brine, and dried over anhydrous sodium sulfate. The solvent was removed under reduced pressure, and the obtained residue was then purified by silica gel column chromatography (hexane:ethyl acetate=2:1) to obtain the title compound as a pale yellow solid (1.24 g).

$^1$H-NMR (400 MHz, CDCl$_3$) δ 1.44 (9H, s), 2.61 (3H, s), 3.09-3.22 (2H, m), 4.79 (1H, brs), 4.86 (1H, brs), 7.39 (2H, d, J=8.5 Hz), 7.97 (2H, d, J=8.5 Hz).

Reference Example 12

Tert-Butyl (±)-{(S)-1-cyano-2-[4-(1-hydroxyethyl)phenyl]ethyl}carbamate

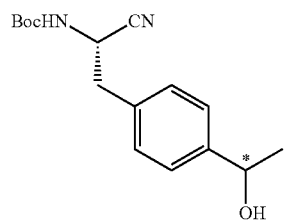

[Chem.60]

To a solution of tert-butyl (S)-[2-(4-acetylphenyl)-1-cyanoethyl]carbamate (500 mg) in tetrahydrofuran (11.6 mL) were added sodium borohydride (98.4 mg) and then methanol (0.32 mL) to produce a reaction solution. The reaction solution was stirred under an argon atmosphere at room temperature for 2 hours. To the reaction solution was added a saturated aqueous sodium hydrogen carbonate solution, and the mixture was extracted with ethyl acetate. The organic layer was washed with water, a saturated aqueous sodium hydrogen carbonate solution, and then a brine, and dried over anhydrous sodium sulfate. The solvent was removed under reduced pressure, and the obtained residue was then purified by silica gel column chromatography (hexane:ethyl acetate=1:1) to obtain the title compound of a 1:1 diastereomer mixture as a pale yellow solid (480 mg). Data for Diastereomer Mixture (1:1)

$^1$H-NMR (400 MHz, DMSO-d$_6$) δ 1.27 (3H, s), 1.29 (3H, s), 1.36 (18H, s), 1.98 (2H, s), 3.00 (4H, d, J=8.9 Hz), 4.59 (2H, q, J=8.6 Hz), 4.64-4.70 (2H, m), 5.10 (2H, d, J=4.8 Hz), 7.22 (2H, d, J=8.5 Hz), 7.27 (2H, d, J=8.5 Hz), 7.79 (1H, brs), 7.81 (1H, brs).

Reference Example 13

Tert-Butyl (S)-{1-cyano-2-[4-(2-hydroxypropan-2-yl)phenyl]ethyl}carbamate

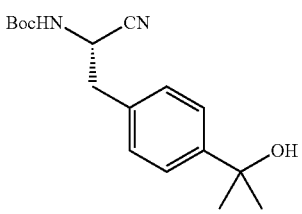

[Chem.61]

To a solution of tert-butyl (S)-[2-(4-acetylphenyl)-1-cyanoethyl]carbamate (100 mg) in tetrahydrofuran (1.7 mL) at −78° C. was added a solution of methylmagnesium bromide in tetrahydrofuran (0.97 mol/L, 0.86 mL) to produce a reaction solution. The reaction solution was stirred under an argon atmosphere at the same temperature for 4 hours and then under ice-cooling for 2 hours. To the reaction solution was added a saturated aqueous ammonium chloride, and the mixture was extracted with ethyl acetate. The organic layer was washed with water and then a brine, and dried over anhydrous sodium sulfate. The solvent was removed under reduced pressure, and the residue was then purified by silica gel column chromatography (hexane:ethyl acetate=2:1) to obtain the title compound (60 mg).

$^1$H-NMR (400 MHz, DMSO-d$_6$) δ 1.34 (9H, s), 1.37 (6H, s), 2.98 (2H, d, J=7.9 Hz), 4.58 (1H, q, J=8.1 Hz), 4.94 (1H, s), 7.19 (2H, d, J=8.5 Hz), 7.37 (2H, d, J=8.5 Hz), 7.78 (1H, brd, J=7.9 Hz).

Reference Example 14-1

Tert-Butyl (S,Z)-[1-amino-1-(hydroxyimino)-3-(4-methoxyphenyl)propan-2-yl]carbamate To a solution of tert-butyl (S)-[1-cyano-2-(4-methoxyphenyl)ethyl]carbamate (666 mg) in ethanol (10 mL) were added hydroxylamine hydrochloride (419 mg) and triethylamine (0.84 mL) to produce a reaction solution. The reaction solution was heated to reflux under an argon atmosphere for 4 hours. The solvent was removed under reduced pressure, water was added to the obtained residue, and the mixture was extracted with ethyl acetate. The organic layer was washed with water and a brine, and dried over anhydrous sodium sulfate. The solvent was removed under reduced pressure, and the resulting crude product was washed with a hexane-ethyl acetate mixture to obtain the title compound as a white solid (640 mg).

$^1$H NMR (400 MHz, DMSO-d$_6$) δ 1.29 (9H, s), 2.71 (1H, dd, J=13.9, 9.1 Hz), 2.81 (1H, dd, J=13.9, 6.1 Hz), 3.69 (3H, s), 3.99-4.11 (1H, m), 5.30 (2H, s), 6.75-6.83 (3H, m), 7.09 (2H, d, J=9.1 Hz), 8.91 (1H, s).

[Chem.62]

Reference Examples 14-2 to 14-10

The following Reference Examples 14-2 to 14-10 were obtained using each corresponding starting material in the same method as in Reference Example 14-1.

The structures and spectral data thereof are shown in Tables 13 and 14.

TABLE 13

| Ref. No | Str. | Chemical name | P.D. |
|---|---|---|---|
| 14-2 | | tert-butyl (S,Z)-[1-amino-3-(4-chlorophenyl)-1-(hydroxyimino)-propan-2-yl]carbamate | $^1$H-NMR (400 MHz, DMSO-d$_6$) δ 1.28 (9H, s), 2.77 (1H, dd, J = 13.3, 9.1 Hz), 2.89 (1H, dd, J = 13.3, 6.1 Hz), 4.06-4.14 (1H, m), 5.33 (2H, s), 6.84 (1H, d, J = 9.7 Hz), 7.20 (2H, d, J = 8.5 Hz), 7.30 (2H, d, J = 8.5 Hz), 8.96 (1H, s). |
| 14-3 | | tert-butyl (S,Z)-[1-amino-3-(4-bromophenyl)-1-(hydroxyimino)-propan-2-yl]carbamate | $^1$H NMR (400 MHz, DMSO-d$_6$) δ 1.28 (9H, s), 2.75 (1H, dd, J = 13.3, 9.7 Hz), 2.8 7 (1H, dd, J = 13.3, 6.1 Hz), 4.10 (1H, dd, J = 15.7, 9.1 Hz), 5.33 (2H, s), 6.84 (1H, d, J = 9.7 Hz), 7.14 (2H, d, J = 8.5 Hz), 7.43 (2H, d, J = 7.9 Hz), 8.96 (1H, s). |
| 14-4 | | tert-butyl (S,Z)-[1-amino-3-(4-ethylphenyl)-1-(hydroxyimino)-propan-2-yl]carbamate | $^1$H NMR (400 MHz, DMSO-d$_6$) δ 1.13 (3H, t, J = 8.0 Hz), 1.28 (9H, s), 2.53 (2H, q, J = 8.0 Hz), 2.79 (2H, dq, J = 37.5, 7.2 Hz), 4.10 (1H, dd, J = 15.4, 9.1 Hz), 5.31 (2H, s), 6.79 (1H, d, J = 9.1 Hz), 7.07 (4H, s), 8.92 (1H, s). |

TABLE 13-continued

| Ref. No | Str. | Chemical name | P.D. |
|---|---|---|---|
| 14-5 | | (S,Z)-4-{3-amino-2-[(tert-butoxy-carbonyl)amino]-3-(hydroxy-imino)propyl}phenyl trifluoro-methanesulfonate | $^1$H-NMR (400 MHz, CDCl$_3$) δ 1.25 (9H, s), 2.82 (1H, dd, J = 14.1, 9.8 Hz), 2.96 (1H, dd, J = 14.1, 5.6 Hz), 4.16 (1H, td, J = 9.6, 5.6 Hz), 5.35 (2H, s), 6.88 (1H, d, J = 9.7 Hz), 7.37 (4H, s), 9.00 (1H, s). |
| 14-6 | | tert-butyl (±)-{(2S,Z)-1-amino-3-[4-(1-hydroxy-ethyl)phenyl]-1-(hydroxyimino)-propan-2-yl}carbamate | Data for diastereomer mixture (1:1) $^1$H-NMR (400 MHz, DMSO-d$_6$) δ 1.27 (3H, d, J = 6.7 Hz), 1.29 (9H, s), 2.73-2.88 (2H, m), 4.07-4.14 (1H, m), 4.62-4.68 (1H, m), 5.04 (1H, d, J = 4.3 Hz), 5.31 (2H, brs), 6.81 (1H, d, J = 9.1 Hz), 7.11 (2H, d, J = 7.9 Hz), 7.20 (2H, d, J = 7.9 Hz), 8.92 (1H, brs). |

TABLE 14

| Ref. No | Str. | Chemical name | P.D. |
|---|---|---|---|
| 14-7 | | tert-butyl (S,Z)-[1-amino-3-(4-trifluoromethyl-phenyl)-1-(hydroxyimino)-propan-2-yl]carbamate | $^1$H-NMR (400 MHz, CDCl$_3$) δ 1.26 (9H, s), 2.87 (1H, dd, J = 13.3, 9.7 Hz), 3.00 (1H, dd, J = 13.3, 6.1 Hz), 4.17 (1H, td, J = 9.7, 6.1 Hz), 5.36 (2H, s), 6.89 (1H, d, J = 9.7 Hz), 7.41 (2H, d, J = 7.9 Hz), 7.61 (2H, d, J = 7.9 Hz), 8.99 (1H, s). |
| 14-8 | | tert-butyl (1-amino-1-(hydroxy-imino)-3-(4-methoxyphenyl)-propan-2-yl)carbamate | $^1$H NMR (400 MHz, DMSO-d$_6$) δ 1.29 (9H, s), 2.71 (1H, dd, J = 13.9, 9.1 Hz), 2.81 (1H, dd, J = 13.9, 6.1 Hz), 3.69 (3H, s), 3.99-4.11 (1H, m), 5.30 (2H, s), 6.75-6.83 (3H, m), 7.09 (2H, d, J = 9.1 Hz), 8.91 (1H, s). |
| 14-9 | | tert-butyl (Z)-(4-amino-4-(hydroxyimino)-1-(4-methoxy-phenyl)butan-2-yl)carbamate | $^1$H-NMR (400 MHz, CDCl$_3$) δ 1.43 (9H, s), 2.63 (1H, dd, J = 15.1, 7.3 Hz), 2.73-2.82 (2H, m), 2.89 (1H, dd, J = 13.3, 6.7 Hz), 3.81 (3H, s), 4.10-4.22 (1H, m), 4.65 (1H, d, J = 8.5 Hz), 6.87 (2H, d, J = 8.5 Hz), 7.12 (2H, d, J = 8.5 Hz), 8.27 (1H, s). |

TABLE 14-continued

| Ref. No | Str. | Chemical name | P.D. |
|---|---|---|---|
| 14-10 | 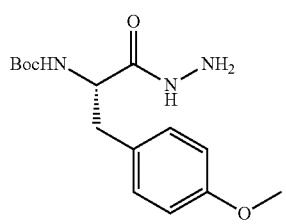 | tert-butyl (S,Z) [4-amino-1-(4-chlorophenyl)-4-(hydroxyimino)-butan-2-yl]carbamate | $^1$H-NMR (400 MHz, DMSO-d$_6$) δ 1.28 (9H, s), 2.55 (1H, dd, J = 13.6, 8.6 Hz), 2.75 (1H, dd, J = 13.6, 4.5 Hz), 3.85-3.90 (1H, m), 5.35 (2H, s), 6.58 (1H, d, J = 8.5 Hz), 7.17 (2H, d, J = 7.9 Hz), 7.30 (2H, d, J = 8.5 Hz), 8.84 (1H, s). |

Reference Example 15-1

Tert-Butyl (S)-[1-hydrazinyl-(4-methoxyphenyl)-1-oxopropan-2-yl]carbamate

[Chem.63]

To a solution of methyl (S)-2-[(tert-butoxycarbonyl)amino]-3-(4-methoxyphenyl)propionate (1.00 g, 3.23 mmol) in methanol (16.0 mL) was added hydrazine monohydrate (784 µL, 16.2 mmol), and the mixture was stirred at room temperature for a day. Then, to the reaction mixture under ice-cooling was added ethyl acetate (50 mL) and water (25 mL), the mixture of organic layer was separated, and the combined aqueous layer was extracted with ethyl acetate (50 mL). The organic layer was washed with a brine (20 mL), dried over anhydrous sodium sulfate, and then filtrated. The filtrate was concentrated under reduced pressure to obtain the title compound a white solid (1.00 g, quant.).

$^1$H-NMR (400 MHz, DMSO-d$_6$) δ 1.29 (9H, s), 2.66 (1H, m), 2.78 (1H, m), 3.70 (3H, s), 4.02 (1H, m), 4.34-4.74 (2H, br s), 6.81 (2H, d, J=8.5 Hz), 6.86 (1H, d, J=8.5 Hz), 7.14 (2H, d, J=8.5 Hz), 9.15 (1H, br s).

Reference Examples 15-2 to 15-6

The following Reference Examples 15-2 to 15-6 were obtained using each corresponding starting material in the same method as in Reference Example 15-1.

The structures and spectral data thereof are shown in Table 15.

TABLE 15

| Ref. No | Str. | Chemical name | P.D. |
|---|---|---|---|
| 15-2 | | tert-butyl (S)-(3-(4-ethylphenyl)-1-hydrazinyl-1-oxopropan-2-yl)carbamate | $^1$H-NMR (400 MHz, DMSO-d$_6$) δ 1.22 (3H, t, J = 8.0 Hz), 1.41 (9H, s), 2.61 (2H, dd, J = 15.3, 8.0 Hz), 3.01 (2H, d, J = 7.3 Hz), 3.79 (2H, s), 4.28 (1H, dd, J = 17.1, 7.4 Hz), 4.96 (1H, brs), 7.01 (1H, s), 7.11 (4H, dd, J = 17.8, 8.6 Hz). |
| 15-3 | | tert-butyl (S)-(3-(4-bromophenyl)-1-hydrazinyl-1-oxopropan-2-yl)carbamate | $^1$H-NMR (400 MHz, CDCl$_3$) δ 1.41 (9H, s), 2.96-3.07 (2H, m), 3.80 (2H, d, J = 3.7 Hz), 4.28 (1H, dd, J = 7.4, 14.7 Hz), 4.90 (1H, s), 7.07 (2H, d, J = 8.6 Hz), 7.43 (2H, d, J = 8.6 Hz). |

TABLE 15-continued

| Ref. No | Str. | Chemical name | P.D. |
|---|---|---|---|
| 15-4 | (structure: BocHN-CH(CH2-C6H4-Cl)-C(O)-NH-NH2) | tert-butyl (S)-(3-(4-chlorophenyl)-1-hydrazinyl-1-oxopropan-2-yl)carbamate | $^1$H-NMR (400 MHz, CDCl$_3$) δ 1.41 (9H, s), 2.97-3.09 (2H, m), 3.81 (2H, brs), 4.22-4.32 (1H, m), 4.91 (1H, brs), 7.06 (1H, brs), 7.13 (2H, d, J = 8.1 Hz), 7.28 (2H, d, J = 8.1 Hz). |
| 15-5 | (structure: BocHN-CH(CH2-C6H4-OMe)-CH2-C(O)-NHNH2) | tert-butyl [4-hydrazinyl-1-(4-methoxyphenyl)-4-oxobutan-2-yl]carbamate | $^1$H-NMR (400 MHz, DMSO-d$_6$) δ 1.29 (9H, s), 2.09 (1H, dd, J = 14.5, 7.3 Hz), 2.14 (1H, dd, J = 14.3, 7.3 Hz), 2.52-2.65 (2H, m), 3.68 (3H, s), 3.78-3.89 (1H, m), 4.14 (2H, d, J = 3.6 Hz), 6.59 (1H, d, J = 8.5 Hz), 6.80 (2H, d, J = 8.5 Hz), 7.03 (2H, d, J = 8.5 Hz), 8.88 (1H, s). |
| 15-6 | (structure: BocHN-CH(CH2-C6H4-OMe)-CH2CH2-C(O)-NH-NH2) | tert-butyl [5-hydrazinyl-1-(4-methoxyphenyl)-5-oxopentan-2-yl]carbamate | $^1$H-NMR (400 MHz, CDCl$_3$) δ 1.40 (9H, s), 1.57-1.68 (1H, m), 1.81-1.92 (1H, m), 2.09-2.27 (2H, m), 2.70 (2H, s), 3.79 (4H, s), 3.88 (2H, s), 4.39 (1H, d, J = 7.9 Hz), 6.83 (2H, d, J = 8.5 Hz), 7.07 (2H, d, J = 8.5 Hz), 7.38 (1H, s). |

Reference Example 16-1

Ethyl (S,Z)-5-amino-6-(4-methoxybenzyl)-10,10-dimethyl-8-oxo-3,9-dioxa-4,7-diazaundec-4-en-1-oate

[Chem.64]

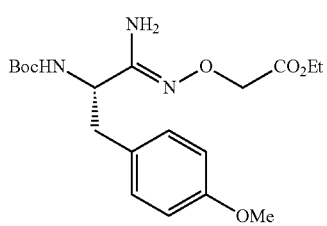 [SMILES: CCOC(=O)CO/N=C(\N)[C@H](Cc1ccc(OS(=O)(=O)C(F)(F)F)cc1)NC(=O)OC(C)(C)C]

To a solution of tert-butyl (S,Z)-[1-amino-1-(hydroxyimino)-3-(4-methoxyphenyl)propan-2-yl]carbamate (640 mg) in N,N-dimethylformamide (10 mL) were added cesium carbonate (2.02 g) and ethyl bromoacetate (0.69 mL) to produce a reaction solution. The reaction solution was stirred under an argon atmosphere at room temperature for 12 hours. Water was added to the reaction solution, and the mixture was extracted with ethyl acetate. The organic layer was washed with water and then a brine, and dried over anhydrous sodium sulfate. The solvent was removed under reduced pressure, and the obtained residue was then purified by silica gel column chromatography (hexane:ethyl acetate=2:1) to obtain the title compound as a pale yellow solid (570 mg).

$^1$H-NMR (400 MHz, CDCl$_3$) δ 1.28 (3H, t, J=7.3 Hz), 1.40 (9H, s), 3.02 (2H, d, J=6.6 Hz), 3.78 (3H, s), 4.18-4.26 (3H, m), 4.49 (2H, s), 4.87 (2H, brs), 6.83 (2H, d, J=8.6 Hz), 7.15 (2H, d, J=8.6 Hz).

Reference Examples 16-2 to 16-6

The following Reference Examples 16-2 to 16-6 were obtained using each corresponding starting material in the same method as in Reference Example 16-1.

The structures and spectral data thereof are shown in Table 16.

TABLE 16

| Ref. No | Str. | Chemical name | P.D. |
|---|---|---|---|
| 16-2 | (structure) | ethyl (S,Z)-5-amino-6-(4-chlorobenzyl)-10,10-dimethyl-8-oxo-3,9-dioxa-4,7-diazaundec-4-en-1-oate | 1H-NMR (400 MHz, CDCl$_3$) δ 1.26 (3H, t, J = 7.4 Hz), 1.40 (9H, s), 3.02-3.09 (2H, m), 4.19 (3H, q, J = 7.4 Hz), 4.16-4.26 (1H, m), 4.45 (2H, s), 4.87 (2H, brs), 7.14 (2H, d, J = 8.5 Hz), 7.23 (2H, d, J = 8.5 Hz). |
| 16-3 | (structure) | ethyl (S,Z)-5-amino-6-(4-bromobenzyl)-10,10-dimethyl-8-oxo-3,9-dioxa-4,7-diazaundec-4-en-1-oate | $^1$H NMR (400 MHz, DMSO-d$_6$) δ 1.26 (3H, t, J = 6.7 Hz), 1.36 (9H, s), 3.00-3.07 (2H, m), 4.16-4.26 (3H, m), 4.45 (2H, s), 4.87 (2H, brs), 7.08 (2H, d, J = 8.5 Hz), 7.38 (2H, d, J = 8.5 Hz). |
| 16-4 | (structure) | ethyl (S,Z)-5-amino-6-(4-ethylbenzyl)-10,10-dimethyl-8-oxo-3,9-dioxa-4,7-diazaundec-4-en-1-oate | $^1$H NMR (400 MHz, DMSO-d$_6$) δ 1.22 (3H, t, J = 7.6 Hz), 1.28 (3H, t, J = 7.4 Hz), 1.39 (9H, s), 2.61 (2H, q, J = 7.6 Hz), 3.05 (2H, d, J = 6.1 Hz), 4.22 (2H, q, J = 7.4 Hz), 4.19-4.29 (1H, m), 4.49 (2H, s), 4.87 (2H, brs), 7.13 (4H, d, J = 3.7 Hz). |
| 16-5 | (structure) | ethyl (S,Z)-5-amino-10,10-dimethyl-8-oxo-6-(4-{[(trifluoromethyl)sulfonyl]oxy}benzyl)-3,9-dioxa-4,7-diazaundec-4-en-1-oate | $^1$H-NMR (400 MHz, CDCl$_3$) δ 1.25 (9H, s), 2.82 (1H, dd, J =14.1, 10.4 Hz), 2.93 (1H, dd, J = 14.1, 5.5 Hz), 4.01-4.17 (3H, m), 4.29-4.38 (2H, m), 5.76 (2H, brs), 6.90 (1H, d, J = 9.7 Hz), 7.37 (4H, s). |
| 16-6 | (structure) | ethyl (S,Z)-5-amino-6-(4-trifluoromethyl-benzyl)-10,10-dimethyl-8-oxo-3,9-dioxa-4,7-diazaundec-4-en-1-oate | $^1$H-NMR (400 MHz, CDCl$_3$) δ 1.28 (3H, t, J = 7.3 Hz), 1.40 (9H, s), 3.02-3.14 (1H, m), 3.19 (1H, dd, J = 13.9, 6.7 Hz), 4.17-4.35 (4H, m), 4.48 (2H, s), 4.91 (2H, br s), 7.35 (2H, d, J = 7.9 Hz), 7.54 (2H, d, J = 7.9 Hz). |

125

Reference Example 17

Ethyl (6S,Z)-5-amino-6-[4-(1-hydroxyethyl)benzyl]-10,10-dimethyl-8-oxo-3,9-dioxa-4,7-diazaundec-4-en-1-oate

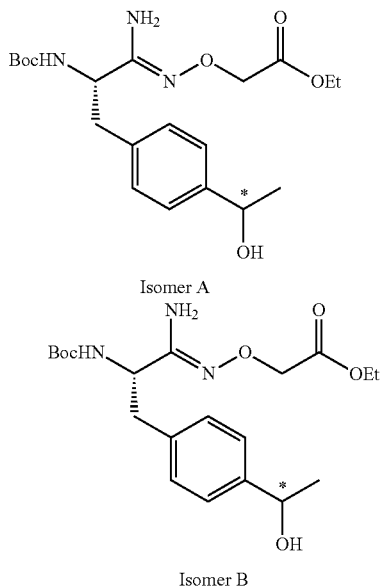

Isomer A

Isomer B

[Chem.65]

Ethyl (±)-(6S,Z)-5-amino-6-(4-(1-hydroxyethyl)benzyl)-10,10-dimethyl-8-oxo-3,9-dioxa-4,7-diazaundec-4-en-1-oate that was obtained in the same method as in Reference Example 16-1 using tert-butyl (±)-{(2S,Z)-1-amino-3-[4-(1-hydroxyethyl)phenyl]-1-(hydroxyimino)propan-2-yl}carbamate instead of tert-butyl (S,Z)-[1-amino-1-(hydroxyimino)-3-(4-methoxyphenyl)propan-2-yl]carbamate was subjected to optical resolution by high performance liquid chromatography (hexane:IPA=90:10, flow rate: 20.0 mL) using a column for separation of enantiomers (CHIRALPAK IA) to obtain the title compounds of two isomers: Isomer A with a retention time of 23.6 minutes, and Isomer B with a retention time of 27.2 minutes.

Isomer A:
Data for 1$^{st}$ Peak A
$^1$H-NMR (400 MHz, DMSO-d$_6$) δ 1.20-1.30 (4H, m), 1.39 (9H, s), 1.48 (3H, d, J=6.7 Hz), 3.08 (2H, brd, J=6.7 Hz), 3.72 (1H, q, J=7.1 Hz), 4.19-4.30 (3H, m), 4.48 (2H, s), 4.85-4.91 (3H, m), 7.21 (2H, d, J=8.5 Hz), 7.30 (2H, d, J=8.5 Hz).

126

Isomer B:
Data for 2$^{nd}$ Peak B
$^1$H-NMR (400 MHz, DMSO-d$_6$) δ 1.19-1.30 (4H, m), 1.40 (9H, s), 1.49 (3H, d, J=6.7 Hz), 3.08 (2H, brd, J=6.7 Hz), 3.69-3.76 (1H, m), 4.19-4.30 (3H, m), 4.48 (2H, s), 4.85-4.91 (3H, m), 7.22 (2H, d, J=8.5 Hz), 7.30 (2H, d, J=8.5 Hz).

Reference Example 18-1

Tert-Butyl (S,Z)-{1-amino-3-(4-ethylphenyl)-1-[(2-hydroxyethoxy)imino]propan-2-yl}carbamate

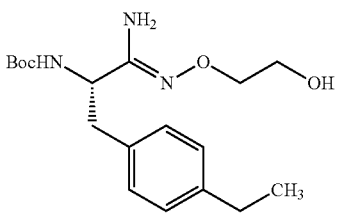

[Chem.66]

To a solution of ethyl (S,Z)-5-amino-6-(4-ethylbenzyl)-10,10-dimethyl-8-oxo-3,9-dioxa-4,7-diazaundec-4-en-1-oate (486 mg) in tetrahydrofuran (2.5 mL) under ice-cooling was added lithium borohydride (1M tetrahydrofuran solution, 3.7 mL) to produce a reaction solution. The reaction solution was stirred under an argon atmosphere at room temperature for 7 hours. A 10% citric acid aqueous solution was added to the reaction solution, and the mixture was extracted with ethyl acetate. The organic layer was washed with water and then a brine, and dried over anhydrous sodium sulfate. The solvent was removed under reduced pressure, and the obtained residue was then purified by silica gel column chromatography (hexane:ethyl acetate=1:1) to obtain the title compound as a white solid (173 mg).
$^1$H-NMR (400 MHz, CDCl$_3$) δ 1.22 (3H, t, J=7.6 Hz), 1.40 (9H, s), 2.62 (2H, q, J=7.6 Hz), 2.81 (1H, br), 3.02-3.10 (2H, m), 3.82 (2H, brd, J=3.6 Hz), 4.05-4.08 (2H, m), 4.27 (1H, q, J=7.5 Hz), 4.84 (2H, br), 7.13 (4H, s).

Reference Examples 18-2 to 18-3

The following Reference Examples 18-2 to 18-3 were obtained using each corresponding starting material in the same method as in Reference Example 18-1.

The structures and spectral data thereof are shown in Table 17.

TABLE 17

| Ref. No | Str. | Chemical name | P.D. |
|---|---|---|---|
| 18-2 | [structure with BocHN, NH2, N-O, OH, Cl-phenyl] | tert-butyl (S,Z)-{1-amino-3-(4-chlorophenyl)-1-[(2-hydroxyethoxy)imino]propan-2-yl}carbamate | $^1$H-NMR (400 MHz, CDCl$_3$) δ 1.40 (9H, s), 3.02 (1H, brd, J = 8.0 Hz), 3.09 (1H, dd, J = 14.1, 6.1 Hz), 3.83 (2H, dd, J = 4.3, 4.3 Hz), 4.05-4.07 (2H, m), 4.26 (2H, q, J = 7.5 Hz), 4.81 (1H, brs), 4.88 (1H, brs), 7.15 (2H, d, J = |

TABLE 17-continued

| Ref. No | Str. | Chemical name | P.D. |
|---|---|---|---|
| | | | 8.5 Hz), 7.27 (2H, d, J = 8.5 Hz). |
| 18-3 | ![structure](BocHN-NH2-N-O-OH, 4-bromophenyl) | tert-butyl (S,Z)-{1-amino-3-(4-bromophenyl)-1-[(2-hydroxyethoxy)imino]propan-2-yl}carbamate | ¹H-NMR (400 MHz, CDCl₃) δ 1.40 (9H, s), 2.75 (1H, t, J = 5.8 Hz), 2.95-3.03 (1H, m), 3.08 (1H, dd, J = 14.1, 6.1 Hz), 3.81-3.85 (2H, m), 4.05-4.07 (2H, m), 4.45 (2H, s), 4.80 (1H, brs), 4.87 (1H, brs), 7.09 (2H, d, J = 8.5 Hz), 7.42 (2H, d, J = 8.5 Hz). |

Reference Example 19-1

Tert-Butyl (S,Z)-{1-amino-3-(4-cyanophenyl)-1-[(2-hydroxyethoxy)imino]propan-2-yl}carbamate

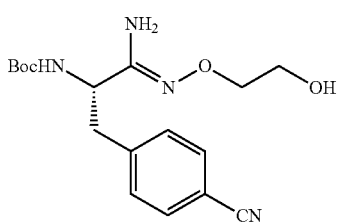 [SMILES: CC(C)(C)OC(=O)N[C@@H](Cc1ccc(Cl)cc1)/C(N)=N/OCCO]

[Chem.67]

To a solution of tert-butyl (S,Z)-{1-amino-3-(4-bromophenyl)-1-[(2-hydroxyethoxy)imino]propan-2-yl}carbamate (368 mg) in N,N-dimethylformamide (9.2 mL) were added zinc cyanide (215 mg) and tetrakis-triphenylphosphine palladium (218 mg) to produce a reaction solution. The reaction solution was stirred under an argon atmosphere at 90° C. for 7 hours. Water was added to the reaction solution, and the mixture was washed with ethyl acetate. The organic layer was washed with water and then a brine, and dried over anhydrous sodium sulfate. The solvent was removed under reduced pressure, and the obtained residue was then purified by silica gel column chromatography (hexane:ethyl acetate=1:2) to obtain the title compound (130 mg).

¹H-NMR (400 MHz, CDCl₃) δ 1.40 (9H, s), 2.67 (1H, br), 3.22 (1H, dd, J=14.1, 6.1 Hz), 3.82 (2H, br), 4.05-4.07 (2H, m), 4.33 (1H, q, J=7.5 Hz), 4.83-4.90 (3H, m), 7.33 (2H, d, J=8.5 Hz), 7.59 (2H, d, J=8.5 Hz).

Reference Example 19-2

The following Reference Example 19-2 was obtained using the corresponding starting material in the same method as in Reference Example 19-1.

The structure and spectral data thereof are shown in Table 18.

TABLE 18

| Ref. No | Str. | Chemical name | P.D. |
|---|---|---|---|
| 19-2 | ![structure with oxadiazole, BocHN, CN] | tert-butyl (S)-(2-(4-cyanophenyl)-1-(5-(2-hydroxyethyl)-1,3,4-oxadiazol-2-yl)carbamate | ¹H-NMR (400 MHz, CDCl₃) δ 1.40 (9H, s), 2.36 (1H, t, J = 6.1 Hz), 3.05 (2H, t, J = 5.5, Hz), 3.22-3.27 (2H, dd, J = 7.4, 14.1 Hz), 3.35-3.40 (1H, dd, J = 6.7, 14.1 Hz), 4.05 (2H, dd, J = 5.5, 11.6 Hz), 5.09 (1H, d, J = 7.3 Hz), 5.28 (1H, d, J = 7.4 Hz), 7.28 (2H, d, J = 12.8 Hz), 7.59 (2H, d, J = 8.6 Hz). |

Reference Example 20-1

Tert-Butyl (S,Z)-{1-amino-3-(2,3-dihydrobenzofuran-5-yl)-1-[(2-hydroxyethoxy)imino]propan-2-yl}carbamate

[Chem.68]

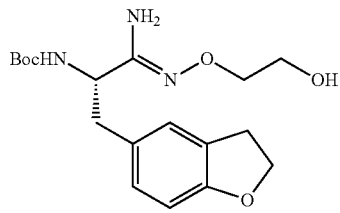

To a solution of tert-butyl (S)-[1-cyano-2-(2,3-dihydrobenzofuran-5-yl)ethyl]carbamate (310 mg) in ethanol (5 mL) were added 2-aminooxyethanol (83 mg), triethylamine (0.38 mL), mercaptoacetic acid (0.075 mL), and then ethylenediaminetetraacetate (32 mg) to produce a reaction solution. The reaction solution was heated to reflux under an argon atmosphere for 4 hours. The solvent was removed under reduced pressure, water was added to the obtained residue, and the mixture was extracted with ethyl acetate. The organic layer was washed with water and then a brine, and dried over anhydrous sodium sulfate. The solvent was removed under reduced pressure, and the residue was then purified by silica gel column chromatography (hexane:ethyl acetate=3:1) to obtain the title compound (165 mg).

$^1$H-NMR (400 MHz, CDCl$_3$) δ 1.29 (9H, s), 2.65-2.83 (2H, m), 3.10 (2H, t, J=8.8 Hz), 3.46-3.52 (2H, m), 3.75 (2H, t, J=5.2 Hz), 3.97-4.05 (1H, m), 4.45 (2H, t, J=8.8 Hz), 4.40-4.50 (1H, m), 5.61 (2H, brs), 6.61 (1H, d, J=7.9 Hz), 6.78 (1H, d, J=8.8 Hz), 6.89 (1H, d, J=8.8 Hz), 7.04 (1H, s).

Reference Examples 20-2 to 20-12

The following Reference Examples 20-2 to 20-12 were obtained using each corresponding starting material in the same method as in Reference Example 20-1.

The structures and spectral data thereof are shown in Tables 19-21.

TABLE 19

| Ref. No | Str. | Chemical name | P.D. |
|---|---|---|---|
| 20-2 | | tert-butyl S,Z)-(1-amino-3-(4-chlorophenyl)-1-{[(1-hydroxy-2-methoxypropan-2-yl)oxy]imino}-propan-2-yl)carbamate | $^1$H-NMR (400 MHz, CDCl$_3$) δ 1.22 (6H, s), 1.41 (9H, s), 2.98 (1H, dd, J = 13.9, 6.7 Hz), 3.10 (1H, dd, J = 13.9, 6.7 Hz), 3.61 (2H, br s), 4.24-4.36 (1H, m), 4.77 (1H, br s), 4.82 (2H, br s), 7.15 (2H, d, J = 8.5 Hz), 7.26 (2H, d, J = 8.5 Hz). |
| 20-3 | | tert-butyl (S,Z)-{1-amino-3-(4-chlorophenyl)-1-[(2-hydroxy-2-methylpropoxy)-imino]propan-2-yl}carbamate | $^1$H-NMR (400 MHz, CDCl$_3$) δ 1.18 (3H, s), 1.19 (3H, s), 1.40 (9H, s), 3.00 (1H, dd, J = 13.9, 7.9 Hz), 3.09 (1H, dd, J = 13.9, 6.7 Hz), 3.64 (1H, br s), 3.82 (2H, s), 4.27 (1H, dt, J = 7.9, 6.7 Hz), 4.79 (1H, br s), 4.91 (2H, br s), 7.14 (2H, d, J = 8.6 Hz), 7.26 (2H, d, J = 8.6 Hz). |
| 20-4 | | tert-butyl (S,Z){1-amino-3-[4-(difluoromethoxy)phenyl]-1-[(2-hydroxyethoxy)imino]-propan-2-yl}carbamate | $^1$H-NMR (400 MHz, CDCl$_3$) δ 1.27 (9H, s), 2.77 (1H, dd, J = 13.9, 9.7 Hz), 2.88 (1H, J = 13.9, 5.4 Hz), 3.49 (2H, q, J = 5.4 Hz), 3.75 (2H, t, J = 5.4 Hz), 4.07 (1H, td, J = 9.7, 5.4 Hz), 4.44 (1H, t, J = 5.4 Hz), 5.64 (2H, s), 6.85 (1H, d, J = 9.7 Hz), 7.06 (2H, d, J = 8.5 Hz), 7.15 (1H, t, J = 74.5 Hz), 7.18 (2H, d, J = 8.5 Hz). |

TABLE 19-continued

| Ref. No | Str. | Chemical name | P.D. |
|---|---|---|---|
| 20-5 | (structure: BocHN-CH(CH2-C6H4-SMe)-C(=N-O-CH2CH2-OH)-NH2) | tert-butyl (S,Z){1-amino-1-[(2-hydroxyethoxy)imino]-3-(4-methylthiophenyl)propan-2-yl}carbamate | $^1$H NMR (400 MHz, DMSO-$d_6$) δ 1.28 (9H, s), 2.42 (3H, s), 2.74 (1H, dd, J = 13.9, 9.8 Hz), 2.84 (1H, J = 13.9, 5.5 Hz), 3.49 (2H, q, J = 5.3 Hz), 3.75 (2H, t, J = 5.4 Hz), 3.98-4.10 (1H, m), 4.45 (1H, t, J = 5.4 Hz), 5.63 (2H, s), 6.82 (1H, d, J = 9.8 Hz), 7.14 (4H, s). |

TABLE 20

| Ref. No | Str. | Chemical name | P.D. |
|---|---|---|---|
| 20-6 | (structure: BocHN-CH(CH2-C6H4-C(=O)N(Me)2)-C(=N-O-CH2CH2-OH)-NH2) | tert-butyl (S,Z)-{1-amino-3-[4-(dimethylcarbamoyl)phenyl]-1-[(2-hydroxyethoxy)imino]propan-2-yl}carbamate | $^1$H-NMR (400 MHz, CDCl$_3$) δ 1.41 (9H, s), 2.90 (1H, s), 2.98 (3H, s), 3.04-3.13 (5H, m), 3.73-3.79 (2H, m), 4.02-4.06 (2H, m), 4.30 (1H, q, J = 7.3 Hz), 4.89 (2H, br s), 7.25 (6H, d, J = 7.9 Hz), 7.36 (2H, d, J = 7.9 Hz). |
| 20-7 | (structure: BocHN-CH(CH2-C6H4-C(Me)2-OH)-C(=N-O-CH2CH2-OH)-NH2) | tert-butyl (S,Z)-{1-amino-1-[(2-hydroxyethoxy)imino]-3-[4-(2-hydroxypropan-2-yl)phenyl]propan-2-yl}carbamate | $^1$H-NMR (400 MHz, CDCl$_3$) δ 1.41 (9H, s), 1.575 (3H, s), 1.583 (3H, s), 2.00 (1H, brs), 2.63 (1H, brs), 2.98-3.04 (1H, m), 3.12 (1H, dd, J = 14.0, 6.7 Hz), 3.75 (2H, brs), 4.02-4.04 (2H, m), 4.27 (1H, q, J = 7.3 Hz), 4.86 (2H, brs), 7.18 (2H, d, J = 8.5 Hz), 7.32 (2H, d, J = 8.5 Hz) |
| 20-8 | (structure: BocHN-CH(CH2-C6H4-OTf)-C(=N-O-CH2CH2-OH)-NH2) | (S, Z)-4-(3-amino-2-((tert-butoxycarbonyl)amino)-3-((2-hydroxyethoxy)imino)propyl)phenyl trifluoromethanesulfonate | $^1$H-NMR (400 MHz, CDCl$_3$) δ 1.40 (9H, S), 2.68 (1H, t, J = 5.8 Hz), 3.03-3.19 (1H, m), 3.18 (1H, dd, J = 14.1, 6.1 Hz) 3.31 (2H, dd, J = 8.5, 5.4 Hz), 4.04-4.07 (2H, m), 4.30 (1H, q, J = 7.5 Hz), 4.81-4.90 (3H, m), 7.21 (2H, d, J = 8.5 Hz), 7.30 (2H, d, J = 8.5 Hz). |

TABLE 20-continued

| Ref. No | Str. | Chemical name | P.D. |
|---|---|---|---|
| 20-9 | (structure) | tert-butyl (Z)-{1-amino-3-[4-(1,1-difluoroethyl)phenyl]-1-[(2-hydroxyethoxy)imino]-propan-2-yl}carbamate | $^1$H-NMR (400 MHz, CDCl$_3$) δ 1.40 (9H, s), 1.91 (3H, t, J = 18.3 Hz), 2.75 (1H, t, J = 5.5 Hz), 3.00-3.12 (1H, m), 3.16 (1H, dd, J = 13.9, 6.7 Hz), 3.80-3.83 (2H, m), 4.05-4.08 (2H, m), 4.31 (1H, q, J = 6.7 Hz), 4.70-5.00 (3H, m), 7.27 (2H, d, J = 7.3 Hz), 7.44 (2H, d, J = 8.6 Hz). |

TABLE 21

| Ref. No. | Str. | Chemical name | P.D. |
|---|---|---|---|
| 20-10 | (structure) | tert-butyl (S,Z) {1-amino-1-[(2-hydroxyethoxy)-imino]-3-[4-(2-hydroxyethyl)-phenyl]propan-2-yl}carbamate | $^1$H-NMR (400 MHz, CDCl$_3$) δ 1.44 (9H, s), 2.42 (1H, br s), 2.81 (3H, t, J = 6.1 Hz), 2.98 (1H, dd, J = 13.9, 6.1 Hz), 3.14 (1H, br s), 3.63 (2H, dd, J = 7.3, 3.0 Hz), 3.84 (2H, t, J = 5.4 Hz), 3.94 (2H, dd, J = 5.4, 3.0 Hz), 4.21-4.30 (1H, m), 4.87 (1H, br s), 7.12 (2H, d, J = 8.5 Hz), 7.18 (2H, d, J = 8.5 Hz). |
| 20-11 | (structure) | (2R,6S,Z)-ethyl 5-amino-6-(4-chlorobenzyl)-2,10,10-trimethyl-8-oxo-3,9-dioxa-4,7-diazaundec-4-en-1-oate | $^1$H NMR (400 MHz, DMSO-d$_6$) δ 1.15 (3H, t, J = 7.3 Hz), 1.26 (3H, d, J = 5.2 Hz), 1.27 (9H, s), 2.75 (1H, dd, J = 13.4, 9.8 Hz), 2.84 (1H, dd, J = 13.4, 5.5 Hz), 4.04 (2H, q, J = 7.3 Hz), 4.06-4.11 (1H, m), 4.32 (1H, q, J = 6.9 Hz), 5.70 (2H, s), 6.83 (1H, d, J = 9.8 Hz), 7.20 (2H, d, J = 8.6 Hz), 7.29 (2H, d, J = 8.6 (Hz). |
| 20-12 | (structure) | (2S,6S,Z)-methyl 5-amino-6-(4-chlorobenzyl)-2,10,10-trimethyl-8-oxo-3,9-dioxa-4,7-diazaundec-4-en-1-oate | $^1$H NMR (400 MHz, DMSO-d$_6$) δ 1.26 (3H, d, J = 7.3 Hz), 1.27 (9H, s), 2.75 (1H, dd, J = 13.4, 9.8 Hz), 2.85 (1H, dd, J = 13.4, 5.5 Hz), 3.60 (3H, s), 3.99-4.08 (1H, m), 4.32 (1H, q, J = 7.3 Hz), 5.70 (2H, s), 6.86 (1H, d, J = 8.6 Hz), 7.21 (2H, d, J = 8.6 Hz), 7.29 (2H, d, J = 8.6 Hz). |

Reference Example 21

Tert-Butyl (5,Z)-{1-amino-3-(4-chlorophenyl)-1-[(methylsulfonyl)imino]propan-2-yl}carbamate

[Chem.69]

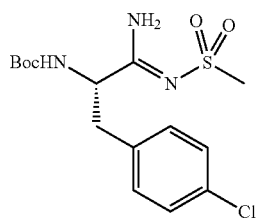

To a suspension of tert-butyl (S)-[1-amino-3-(4-chlorophenyl)-1-oxopropan-2-yl]carbamate (1.0 g) in dichloromethane (8.4 mL) was added triethyloxonium hexafluorophosphate (1.0 g) to produce a reaction solution. The reaction solution was stirred at room temperature for 20 hours. A saturated aqueous sodium hydrogen carbonate solution was added to the reaction solution, and the mixture was stirred at room temperature for 30 minutes. The mixture was extracted with dichloromethane. The organic layer was dried over anhydrous sodium sulfate. The solvent was removed under reduced pressure to obtain ethyl (S)-2-[(tert-butoxycarbonyl)amino]-3-(4-chlorophenyl)-propanimidate that is an intermediate.

To a solution of ethyl (S)-2-[(tert-butoxycarbonyl)amino]-3-(4-chlorophenyl)propanimidate (587 mg) in methanol (9.0 mL) was added methanesulfonamide (1.92 g), and the reaction mixture was stirred for 2 days. The reaction solution was concentrated under reduced pressure, and the obtained residue was then purified by silica gel column chromatography (ethyl acetate:hexane=1:1) to obtain the title compound as a colorless oil (72.0 mg).

$^1$H-NMR (400 MHz, DMSO-$d_6$) δ 1.30 (9H, s), 2.76 (1H, m), 2.81 (3H, s), 2.91 (1H, m), 4.19 (1H, m), 7.07 (1H, d, J=8.5 Hz), 7.33 (2H+2H, s), 7.82 (1H, s), 8.53 (1H, s).

Reference Example 22-1

(S)-5-(1-((tert-Butoxycarbonyl)amino)-2-(4-chlorophenyl)ethyl)-1,3,4-oxadiazol-2-ethyl Ester

[Chem.70]

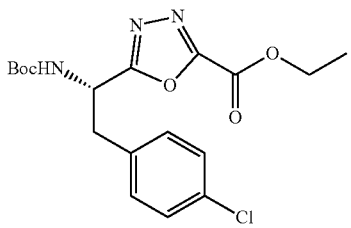

To a solution of (S)-tert-butyl (3-(4-chlorophenyl)-1-hydrazinyl-1-oxopropan-2-yl)carbamate (2.00 g) in tetrahydrofuran (16 mL) at −30° C. were added triethylamine (1.10 mL) and ethyl oxalyl chloride (850 μL), and the reaction mixture was stirred at −30° C. for 5 minutes. The reaction mixture was warmed to room temperature, and was stirred for 15 minutes. A saturated aqueous sodium hydrogen carbonate solution was added to the reaction solution, ethyl acetate was added thereto, the mixture was washed with water and then a brine, and then the organic layer was dried over anhydrous sodium sulfate. The solvent was removed, and the obtained residue was dissolved in dichloromethane (25 mL). To the solution under ice-cooling were added triethylamine (1.80 mL) and tosyl chloride (1.46 g), and the reaction mixture was warmed to room temperature and was stirred for 4 hours. To the reaction solution was added dichloromethane, and the mixture was washed with a saturated aqueous sodium hydrogen carbonate solution, water and then a brine. The organic layer was dried over anhydrous sodium sulfate. The solvent was removed under reduced pressure, and the obtained residue was then purified by silica gel column chromatography (ethyl acetate:hexane=1:2) to obtain the title compound as a colorless solid (1.79 g).

$^1$H-NMR (400 MHz, CDCl$_3$) δ 1.41 (9H, s), 1.46 (3H, t, J=7.4 Hz), 3.17-3.32 (2H, m), 4.51 (2H, dd, J=6.7, 15.2 Hz), 5.33 (1H, brs), 5.09 (1H, brs), 7.05 (2H, d, J=8.0 Hz), 7.26 (2H, d, J=8.6 Hz).

Reference Examples 22-2 to 22-4

The following Reference Examples 22-2 to 22-4 were obtained using each corresponding starting material in the same method as in Reference Example 22-1.

The structures and spectral data thereof are shown in Table 22.

TABLE 22

| Ref. No | Str. | Chemical name | P.D. |
|---|---|---|---|
| 22-2 | ![structure] | ethyl 5-{1-[(tert-butoxycarbonyl)amino]-2-(4-methoxyphenyl)ethyl}-1,3,4-oxadiazol-2-carboxylate | $^1$H-NMR (400 MHz, CDCl$_3$) δ 1.41 (9H, s), 1.45 (3H, t, J = 7.0 Hz), 3.12-3.28 (2H, m) 3.77 (3H, s), 4.51 (2H, q, J = 7.1 Hz), 5.08 (1H, m), 5.31 (1H, m), 6.81 (2H, d, J = 8.5 Hz), 7.00 (2H, d, J = 8.5 Hz). |

TABLE 22-continued

| Ref. No | Str. | Chemical name | P.D. |
|---|---|---|---|
| 22-3 | 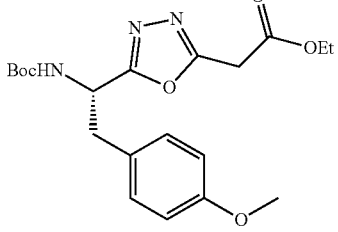 | ethyl (S)-2-(5-{1-[(tert-buroxy carbonyl)amino]-2-(4-methoxy-phenyl)ethyl}-1,3,4-oxadiazol-2-yl)acetate | $^{1}$H-NMR (400 MHz, CDCl$_{3}$) δ 1.28 (3H, t, J = 7.3 Hz), 1.41 (9H, s), 3.06-3.24 (2H, m), 3.77 (3H, s), 3.90 (1H, d, J = 17.6 Hz), 3.95 (1H, d, J = 17.6 Hz), 4.23 (2H, q, J = 7.3 Hz), 5.08 (1H, m), 5.24 (1H, m), 6.80 (2H, d, J = 9.1 Hz), 6.99 (2H, d, J = 9.1 Hz). |
| 22-4 | 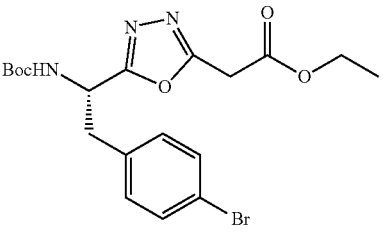 [SMILES: CCOC(=O)Cc1nnc([C@H](Cc2ccc(Br)cc2)NC(=O)OC(C)(C)C)o1] | ethyl (S)-2-(5-{1-[(tert-butoxy-carbonyl)amino]-2-(4-chloro-phenyl)ethyl}-1,3,4-oxadiazol-2-yl)acetate | $^{1}$H-NMR (400 MHz, CDCl$_{3}$) δ 1.28 (3H, t, J = 7.3 Hz), 1.41. (9H, s), 3.13-3.27 (2H, m), 3.92 (2H, d, J = 3.6 Hz), 4.24 (2H, dd, J = 7.3, 14.1 Hz), 5.09 (1H, d, J = 7.4 Hz), 5.27 (1H, d, J = 8.0 Hz) 6.78 (2H, d, J = 8.0 Hz), 7.40 (2H, d, J = 8.0 Hz). |

Reference Example 23-1

Tert-Butyl (S)-{1-[5-(2-hydroxyethyl)-1,3,4-oxadiazol-2-yl]-2-(4-methoxyphenyl)ethyl}carbamate

[Chem.71]

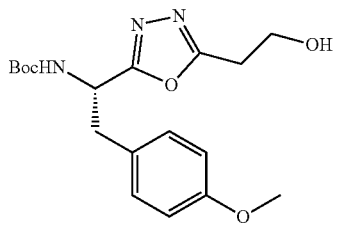

Using ethyl (S)-2-(5-{1-[(tert-butoxycarbonyl)amino]-2-(4-methoxyphenyl)ethyl}-1,3,4-oxazol-2-yl)acetate (528 mg) as a starting material, the same method as in Reference Example 5-1 was performed to obtain the title compound as a white solid (380 mg).

$^{1}$H-NMR (400 MHz, DMSO-d$_{6}$) δ 1.30 (9H, s), 2.92-3.01 (3H, m), 3.09 (1H, m), 3.70 (3H, s), 3.72 (2H, m), 4.83-4.92 (2H, m), 6.82 (2H, d, J=8.5 Hz), 7.13 (2H, d, J=8.5 Hz), 7.60 (1H, d, J=8.5 Hz).

Reference Examples 23-2 to 23-4

The following Reference Examples 23-2 to 23-4 were obtained using each corresponding starting material in the same method as in Reference Example 23-1.

The structures and spectral data thereof are shown in Table 23.

TABLE 23

| Ref. No | Str. | Chemical name | P.D. |
|---|---|---|---|
| 23-2 | 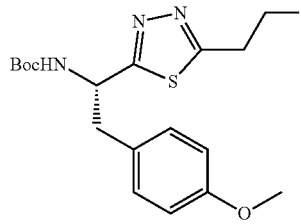 | tert-butyl (S)-{1-[5-(2-hydroxy-ethyl)-1,3,4-thiadiazol-2-yl]-2-(4-methoxy-phenyl)ethyl}-carbamate | $^{1}$H-NMR (400 MHz, CDCl$_{3}$) δ 1.41 (9H, s), 2.60 (1H, m), 3.20-3.30 (4H, m), 3.78 (3H, s), 4.04 (2H, br t, J = 5.4 Hz), 5.22-5.36 (2H, m), 6.81 (2H, d, J = 8.5 Hz), 7.06 (2H, d, J = 8.5 Hz). |

TABLE 23-continued

| Ref. No | Str. | Chemical name | P.D. |
|---|---|---|---|
| 23-3 | BocHN, N-N, OH, Cl structure | tert-butyl (S)-{2-(4-chlorophenyl)-1-[5-(hydroxymethyl)-1,3,4-oxadiazol-2-yl]ethyl}-carbamate | $^1$H-NMR (400 MHz, CDCl$_3$) δ 1.42 (9H, s), 2.47 (1H, s), 3.15-3.30 (2H, m), 4.82 (2H, d, J = 5.5 Hz), 5.10 (1H, s), 5.25 (1H, s), 7.06 (2H, d, J = 8.6 Hz), 7.24 (2H, d, J = 5.5 Hz). |
| 23-4 | BocHN, N-N, OH, Br structure | tert-butyl (S)-{2-(4-bromophenyl)-1-[5-(2-hydroxyethyl)-1,3,4-oxadiazol-2-yl]ethyl}-carbamate | $^1$H-NMR (400 MHz, CDCl$_3$) δ 1.41 (9H, s), 2.38 (1H, s), 3.04 (2H, t, J = 5.5 Hz), 3.12-3.26 (2H, m), 4.03 (2H, d, J = 6.1 Hz), 5.08 (1H, s), 5.22 (1H, s), 7.00 (2H, d, J = 8.0 Hz), 7.40 (2H, d, J = 8.0 Hz). |

Reference Example 24

Tert-Butyl (S)-(1-(5-acetamidemethyl)-1,3,4-oxadiazol-2-yl)-2-(4-ethylphenyl)ethyl)carbamate

[Chem.72]

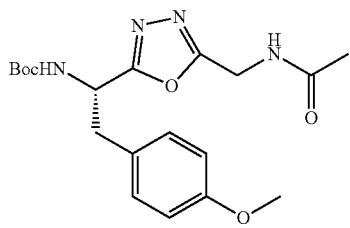

To a solution of N-acetylglycine (177 mg) in dichloromethane (6.50 mL) under ice-cooling were added 1-hydroxybenzotriazole (231 mg) and 1-ethyl-3-(3-dimethylaminopropyl)carbodiimide hydrochloride (290 mg). The reaction mixture was warmed to room temperature, and was stirred for 1 hour. To the reaction solution was added tert-butyl (S)-(3-(4-ethylphenyl)-1-hydrazinoyl-1-oxopropan-2-yl)carbamate (343 mg), and the reaction mixture was stirred at room temperature for 2 hours. To the reaction solution was added ethyl acetate, and the mixture was washed with a saturated aqueous sodium hydrogen carbonate solution, water and then a brine. The organic layer was dried over anhydrous sodium sulfate. The solvent was removed under reduced pressure, and the residue was then purified by silica gel column chromatography (methanol:chloroform=1:4). The purified product was dissolved in N,N-dimethylformamide (2.50 mL). To the solution under ice-cooling were added triethylamine (160 µL) and tosyl chloride (131 mg), and the reaction mixture was warmed to room temperature and stirred for 2 hours. To the reaction mixture under ice-cooling were added triethylamine (160 µL) and tosyl chloride (140 mg), and the reaction mixture was warmed to room temperature and stirred for a day. To the reaction solution was added ethyl acetate, and the mixture was washed with water and then a brine. The organic layer was dried over anhydrous sodium sulfate. The solvent was removed under reduced pressure, and the residue was then purified by silica gel column chromatography (methanol:chloroform=1:24) to obtain the title compound as a yellow foam (52.7 mg), $^1$H-NMR (400 MHz, CDCl$_3$) δ 1.21 (3H, t, J=8.0 Hz), 1.40. (9H, s), 2.07 (3H, s), 2.60 (2H, dd, J=8.0, 15.3 Hz), 3.12-3.21 (2H, m), 4.63 (2H, d, J=5.5 Hz), 5.06 (1H, s), 5.23 (1H, s), 6.06 (1H, s), 7.00 (2H, d, J=8.0 Hz), 7.11 (2H, d, J=8.0 Hz).

Reference Example 25

Tert-Butyl (S)-(1-(5-(2-((tert-butyldiphenylsilyl)oxy)ethyl)-1,3,4-oxadiazol-2-yl)-2-(4-ethylphenyl)ethyl)carbamate

[Chem.73]

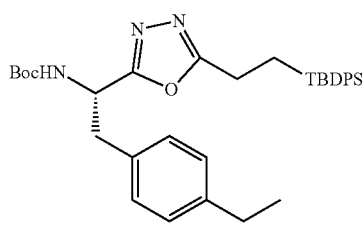

To a solution of (S)-2-((tert-butoxycarbonyl)-3-(4-ethylphenyl)propionic acid (1.13 g) in dichloromethane (20.0 mL) under ice-cooling were added 1-hydroxybenzotriazole (733 mg) and 1-ethyl-3-(3-dimethylaminopropyl)carbodiimide hydrochloride (918 mg), and the reaction mixture was warmed to room temperature and stirred for 1 hour. To the reaction solution was added 3-((tert-butyldiphenylsilyl)oxy)propionic acid hydrazide (1.58 g), and the reaction mixture was stirred at room temperature for 1 hour. To the reaction solution was added ethyl acetate, and the mixture was washed with a saturated aqueous sodium hydrogen carbonate solution, water and then a brine. The organic layer was dried over anhydrous sodium sulfate. The solvent was removed, and the obtained residue was dissolved in dichloromethane (16.0 mL). To the solution under ice-cooling were added triethylamine (1.20 mL) and tosyl chloride (914 mg), and the reaction mixture was warmed to room temperature and stirred for 6 hours. To the reaction solution was added dichloromethane, and the mixture was washed with a saturated aqueous sodium hydrogen carbonate solution. The organic layer was dried over anhydrous sodium sulfate. The solvent was removed under reduced pressure, and the obtained residue was then purified by silica gel column chromatography (ethyl acetate:hexane=3:2) to obtain the title compound as a colorless solid (1.60 g).

$^1$H-NMR (400 MHz, CDCl$_3$) δ 1.02 (9H, s), 1.18 (3H, t, J=7.3 Hz), 1.39 (9H, s), 2.57 (2H, dd, J=7.3, 15.3 Hz), 3.06 (2H, t, J=6.7 Hz), 3.10-3.22 (2H, m), 4.01 (2H, t, J=6.1 Hz), 5.02 (1H, brs), 5.21 (1H, brs), 6.98 (2H, d, J=7.9 Hz), 7.06 (2H, d, J=7.3 Hz), 7.36-7.45 (6H, m), 7.61 (4H, d, J=7.9 Hz).

Reference Example 26

Tert-Butyl (S)-1-(5-(azidomethyl)-1,3,4-oxadiazol-2-yl)-2-(4-chlorophenyl)ethyl)carbamate

[Chem.74]

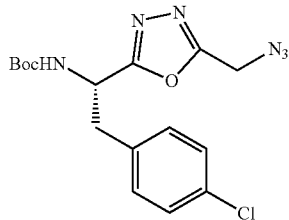

To a solution of tert-butyl (S)-(2-(4-chlorophenyl)-1-(5-hydroxymethyl)-1,3,4-oxadiazol-2-yl)ethyl)carbamate (49.3 mg) in ethyl acetate (2.00 mL) under ice-cooling were added triethylamine (30.0 μL) and methanesulfonyl chloride (11.0 μL), and the mixture was stirred at 0° C. for 10 minutes. The insoluble was removed by filtration, the solvent of the filtrate was removed under reduced pressure, and the residue was then purified by silica gel column chromatography (ethyl acetate:hexane=1:1). The purified product was dissolved in N,N-dimethylformamide (650 μL). To the solution was added sodium azide (40.6 mg), and the reaction mixture was stirred at 70° C. for 5 hours. To the reaction solution was added ethyl acetate, and the mixture was washed with water and then a brine, and the organic layer was dried over anhydrous sodium sulfate. The solvent was removed under reduced pressure to obtain the title compound as a colorless solid (55.3 mg).

1H-NMR (400 MHz, CDCl$_3$) δ 1.42 (9H, s), 3.17-3.29 (2H, m), 4.51 (2H, s), 5.08 (1H, brs), 5.28 (1H, brs), 7.05 (2H, d, J=8.6 Hz), 7.26 (2H, d, J=8.6 Hz), Reference Example 27

Tert-Butyl (S)-(1-(5-(aminomethyl)-1,3,4-oxadiazol-2-yl)-2-(4-chlorophenyl)ethyl)carbamate

[Chem.75]

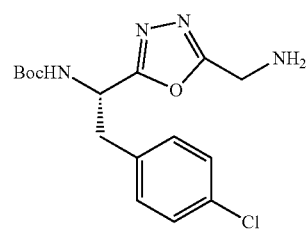

To a solution of tert-butyl (S)-1-(5-(azidomethyl)-1,3,4-oxadiazol-2-yl)-2-(4-chlorophenyl)ethyl)carbamate (48.4 mg) in tetrahydrofuran (650 μL) was added triphenylphosphine (78.1 mg), and the mixture was stirred at room temperature for 1 hour. Water (50.0 μL) was added to the reaction solution, and the mixture was stirred at 40° C. for a day.
The solvent was removed under reduced pressure, and the residue was then purified by silica gel column chromatography (methanol:chloroform=1:4) to obtain the title compound as a yellow solid (35.6 mg).

$^1$H-NMR (400 MHz, CDCl$_3$) δ 1.41 (9H, s), 3.14-3.28 (2H, m), 4.03 (2H, s), 5.10 (1H, brs), 5.23 (1H, brs), 7.06 (2H, d, J=8.6 Hz), 7.25 (2H, d, J=6.7 Hz).

Reference Example 28

Tert-Butyl (S)-(1-(5-acetamidemethyl)-1,3,4-oxadiazol-2-yl)-2-(4-chlorophenyl)ethyl)carbamate

[Chem.76]

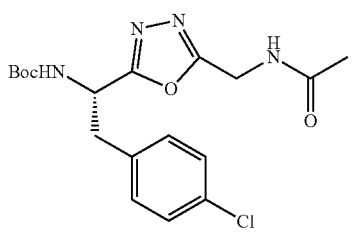

To a solution of tert-butyl (S)-(1-(5-(aminomethyl)-1,3,4-oxadiazol-2-yl)-2-(4-chlorophenyl)ethyl)carbamate (29.9 mg) in pyridine (850 μL) was added acetic anhydride (12.0 μL), and the mixture was stirred at room temperature for 2 hours. To the reaction solution was added ethyl acetate, and the mixture was washed with a 10% citric acid aqueous solution, water and then a brine. The organic layer was dried over anhydrous sodium sulfate. The solvent was removed under reduced pressure, and the obtained residue was then purified by silica gel column chromatography (methanol:chloroform=1:9) to obtain the title compound as an orange solid (27.5 mg).

$^1$H-NMR (400 MHz, CDCl$_3$) δ 1.41 (9H, s), 2.08 (3H, s), 3.13-3.27 (2H, m), 4.63 (2H, d, J=6.1 Hz), 5.06 (1H, s), 5.23 (1H, s), 6.03 (1H, s), 7.05 (2H, d, J=8.0 Hz), 7.26 (2H, d, J=8.6 Hz).

Reference Example 29

Tert-Butyl (S)-(2-(4-chlorophenyl)-1-(5-(methylsulfonamidemethyl)-1,3,4-oxadiazol-2-yl)ethyl)carbamate

[Chem.77]

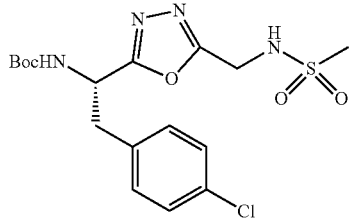

To a solution of tert-butyl (S)-(1-(5-(aminomethyl)-1,3,4-oxadiazol-2-yl)-2-(4-chlorophenyl)ethyl)carbamate (121 mg) in pyridine (3.40 mL) was added methanesulfonyl anhydride (90.2 mg), and the mixture was stirred at 70° C. for 2 hours. To the reaction solution was added methanesulfonyl anhydride (59.7 mg), and the reaction mixture was stirred at 70° C. for a day. To the reaction solution was added ethyl acetate, and the mixture was washed with water and then a brine. The organic layer was dried over anhydrous sodium sulfate. The solvent was removed under reduced pressure, and the obtained residue was then purified by silica gel column chromatography (methanol:chloroform=1:3) to obtain the title compound as a brown solid (82.4 mg).

$^1$H-NMR (400 MHz, CDCl$_3$) δ 1.41 (9H, s), 3.03 (3H, s), 3.16-3.29 (2H, m), 4.56 (2H, d, J=6.1 Hz), 4.99 (1H, s), 5.05 (1H, d, J=8.0 Hz), 5.23 (1H, s), 7.08 (2H, d, J=8.0 Hz), 7.27 (2H, d, J=6.7 Hz).

Reference Example 30

Tert-Butyl (S)-(2-(4-chlorophenyl)-1-(5-(2-hydroxypropan-2-yl)-1,3,4-oxadiazol-2-yl)ethyl)carbamate

[Chem.78]

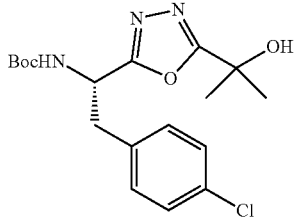

To a solution of ethyl (S)-5-(1-((tert-butoxycarbonyl)amino)-2-(4-chlorophenyl)ethyl)-1,3,4-oxadiazol-2-carboxylate (152 mg) in tetrahydrofuran (2.00 mL) at −78° C. was added methylmagnesium bromide (1.60 mL, 1 mol/L tetrahydrofuran solution), and the mixture was stirred at −78° C. for 20 minutes. The reaction mixture was warmed to 0° C. and stirred for 1.5 hours. The reaction mixture was warmed to room temperature and stirred for 5 hours. To the reaction solution were added a saturated aqueous ammonia chloride and the mixture was extracted with ethyl acetate. The organic layer was washed with water and then a brine. The organic layer was dried over anhydrous sodium sulfate. The solvent was removed under reduced pressure, and the obtained residue was purified by preparative thin-layer chromatography (ethyl acetate hexane=2:1) to obtain the title compound as a colorless solid (60.8 mg).

$^1$H-NMR (400 MHz, CDCl$_3$) δ 1.42 (9H, s), 1.64 (6H, s), 2.64 (1H, s), 3.20 (2H, d, J=6.7 Hz), 5.15 (1H, s), 5.24 (1H, s), 7.04 (2H, d, J=8.6 Hz), 7.25 (2H, d, J=9.8 Hz).

Reference Example 31-1

Tert-Butyl (1-(5-hydroxy-1,2,4-oxadiazol-3-yl)-2-(4-methoxyphenyl)ethyl)carbamate

[Chem.79]

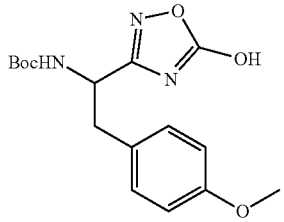

To a solution of tert-butyl (Z)-(1-amino-1-(hydroxyimino)-3-(4-methoxyphenyl)propan-2-yl)carbamate (901 mg) in tetrahydrofuran (20 mL) was added carbodiimidazole (708 mg), and the mixture was stirred under reflux for 7 hours. The reaction solution was concentrated under reduced pressure, and the obtained residue was then purified by silica gel column chromatography (ethyl acetate) to obtain the title compound as a white solid (714 mg).

$^1$H NMR (400 MHz, CDCl$_3$) δ 1.43 (9H, s), 3.21 (2H, d, J=6.1 Hz), 3.81 (3H, s), 4.56 (1H, dd, J=14.5, 7.9 Hz), 4.92 (1H, bs), 6.88 (2H, d, J=8.5 Hz), 7.14 (2H, d, J=8.5 Hz).

Reference Example 31-2

The following Reference Example 31-2 was obtained using the corresponding starting material in the same method as in Reference Example 31-1.

The structure and spectral data thereof are shown in Table 24.

TABLE 24

| Ref. No | Str. | Chemical name | P.D. |
|---|---|---|---|
| 31-2 | HO⟶O⟵N=N⟵BocHN⟵⟶OMe | tert-butyl (1-(5-hydroxy-1,2,4-oxazol-3-yl)-3-(4-methoxyphenyl)-propan-2-yl)carbamate | $^1$H-NMR (400 MHz, DMSO-d$_6$) δ 1.27 (9H, s), 2.38-2.45 (1H, m), 2.50-2.58 (1H, m), 2.64 (2H, d, J = 7.3 Hz), 3.69 (3H, s), 3.91 (1H, br s), 6.82 (2H, d, J = 8.5 Hz), 6.85 (1H, s), 7.08 (2H, d, J = 8.5 Hz), 12.11 (1H, s). |

Reference Example 32-1

Ethyl (S)-2-(3-{1-[(tert-butoxycarbonyl)amino]-2-(4-methoxyphenyl)ethyl}-1,2,4-oxadiazol-5-yl)acetate

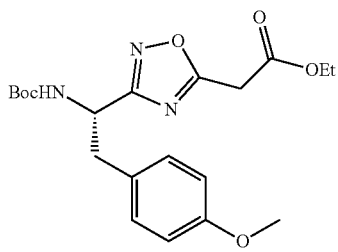 [SMILES: CCOC(=O)Cc1nc([C@H](Cc2ccc(Cl)cc2)NC(=O)OC(C)(C)C)no1]

[Chem.80]

To tert-butyl (S,Z)-[1-amino-1-(hydroxyimino)-3-(4-methoxyphenyl)propan-2-yl]carbamate (434 mg) was added tert-butyl ethyl malonate (2.8 mL) to produce a reaction solution. The reaction solution was stirred at 120° C. for 4.5 hours. The reaction solution was cooled to room temperature, and then purified by silica gel column chromatography (ethyl acetate:hexane=1:2) to obtain the title compound as a pale yellow oil (290 mg).

$^1$H-NMR (400 MHz, CDCl$_3$) δ 1.30 (3H, t, J=7.3 Hz), 1.41 (9H, s), 3.13 (2H, m), 3.77 (3H, s), 3.97 (2H, s), 4.25 (2H, q, J=7.3 Hz), 5.04 (1H, m), 5.19 (1H, m), 6.79 (2H, d, J=8.5 Hz), 6.99 (2H, d, J=8.5 Hz).

Reference Example 32-2

The following Reference Example 32-2 was obtained using the corresponding starting material in the same method as in Reference Example 32-1.

The structures and spectral data thereof are shown in Table 25.

Reference Example 33-1

Ethyl (S)-2-(3-{1-[(tert-butoxycarbonyl)amino]-2-(4-chlorophenyl)ethyl}-1,2,4-oxadiazol-5-yl)-2-methylpropanoate

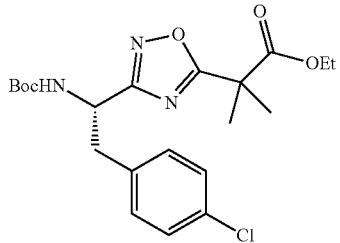 [SMILES: CCOC(=O)C1(c2nc([C@H](Cc3ccc(Cl)cc3)NC(=O)OC(C)(C)C)no2)CC1]

[Chem.81]

To a solution of tert-butyl (S,Z)-[1-amino-3-(4-chlorophenyl)-1-(hydroxyimino)propan-2-yl]carbamate (200 mg) in N,N-dimethylformamide (2.1 mL) under ice-cooling were added 3-ethoxy-2,2-dimethyl-3-oxopropanoic acid (102 mg), N,N-diisopropylethylamine (271 µL), and O-(7-azabenzotriazol-1-yl)-N,N,N',N'-tetramethyluronium hexafluorophosphate (300 mg) to produce a reaction solution. The reaction solution was stirred at room temperature for 3 hours, warmed to 120° C., and then stirred for further 1 hour. Water was added to the reaction solution, and the mixture was extracted with ethyl acetate. The organic layer was washed with water and then a brine, and dried over anhydrous sodium sulfate. The solvent was removed under reduced pressure, and the obtained residue was then purified by silica gel column chromatography (hexane:ethyl acetate=4:1) to obtain the title compound as a pale yellow oil (135 mg).

$^1$H-NMR (400 MHz, CDCl$_3$) δ 1.23 (3H, t, J=7.3 Hz), 1.42 (9H, s), 1.69 (6H, s), 3.16 (2H, m), 4.20 (2H, q, J=7.3 Hz), 5.07 (1H, m), 5.21 (1H, m), 7.00 (2H, d, J=7.9 Hz), 7.21 (2H, d, J=7.9 Hz).

Reference Examples 33-2 to 33-3

The following Reference Examples 33-2 to 33-3 were obtained using each corresponding starting material and reactant in the same method as in Reference Example 33-1.

TABLE 25

| Ref. No | Str. | Chemical name | P.D. |
|---|---|---|---|
| 32-2 | | ethyl (S)-2-(3-{1-[(tert-butoxycarbonyl)-amino]-2-(4-chlorophenyl)-ethyl}-1,2,4-oxadiazol-5-yl)acetate | $^1$H-NMR (400 MHz, CDCl$_3$) δ 1.30 (3H, t, J = 7.3 Hz), 1.41 (9H, s), 3.07-3.24 (2H, m), 3.97 (2H, s), 4.26 (2H, q, J = 7.3 Hz), 5.05 (1H, d, J = 7.3 Hz), 5.17-5.28 (1H, m), 7.02 (2H, d, J = 7.9 Hz), 7.23 (2H, d, J = 7.9 Hz). |

The structures and spectral data thereof are shown in Table 26.

TABLE 26

| Ref. No | Str. | Chemical name | P.D. |
|---|---|---|---|
| 33-2 | ![structure] | ethyl (S)-1-(3-{1-[(tert-butoxycarbonyl)amino]-2-(4-chlorophenyl)ethyl}-1,2,4-oxadiazol-5-yl)cyclopropane-carboxylate | $^1$H-NMR (400 MHz, DMSO-$d_6$) δ 1.16 (3H, t, J = 7.3 Hz), 1.28 (9H, s), 1.61 (2H, m), 1.72 (2H, m), 2.98 (1H, m), 3.09 (1H, m), 4.15 (2H, q, J = 7.3 Hz), 4.83 (1H, m), 7.24 (2H, d, J = 8.5 Hz), 7.32 (2H, d, J = 8.5 Hz), 7.52 (1H, d, J = 9.1 Hz). |
| 33-3 | ![structure] | tert-butyl (S)-(2-(4-chlorophenyl)-1-{5-[(methylthio)methyl]-1,2,4-oxadiazol-3-yl}ethyl)-carbamate | $^1$H-NMR (400 MHz, CDCl$_3$) δ 1.41 (9H, s), 2.21 (3H, s), 3.08-3.23 (2H, m), 3.81 (2H, s), 5.05 (1H, d, J = 7.3 Hz), 5.17-5.25 (1H, m), 7.03 (2H, d, J = 8.5 Hz), 7.23 (2H, d, J = 3.5 Hz). |

Reference Example 34-1

Ethyl 3-{1-[(tert-butoxycarbonyl)amino]-2-(4-methoxyphenyl)ethyl}-1,2,4-oxadiazol-5-carboxylate

[Chem.82]

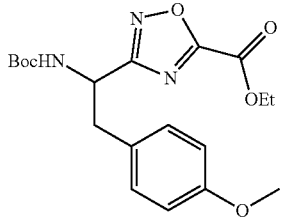

To a solution of tert-butyl (S,Z)-[1-amino-1-(hydroxyimino)-3-(4-methoxyphenyl)propan-2-yl]carbamate (450 mg) in 1,2-dichloroethane (4.8 mL) under ice-cooling were added pyridine (355 μL) and ethyl 2-chloro-2-oxo acetate (247 μL) to produce a reaction solution. The reaction solution was stirred at room temperature for 30 minutes and then at 80° C. for 1.5 hours. Water was added to the reaction solution, and the mixture was extracted with dichloromethane. The organic layer was washed with water and then a brine, and dried over anhydrous sodium sulfate. The solvent was removed under reduced pressure, and the residue was then purified by silica gel column chromatography (hexane:ethyl acetate=2:1) to obtain the title compound as a colorless oil (401 mg).

$^1$H-NMR (400 MHz, CDCl$_3$) δ 1.39 (9H, s), 1.47 (3H, t, J=7.0 Hz), 3.15 (2H, m), 3.77 (3H, s), 4.55 (2H, m), 5.08 (1H, m), 5.28 (1H, m), 6.80 (2H, d, J=8.5 Hz), 6.99 (2H, d, J=8.5 Hz).

Reference Examples 34-2 to 34-3

The following Reference Examples 34-2 to 34-3 were obtained using each corresponding starting material in the same method as in Reference Example 34-1.

The structures and spectral data thereof are shown in Table 27.

TABLE 27

| Ref. No | Str. | Chemical name | P.D. |
|---|---|---|---|
| 34-2 | ![structure] | ethyl (S)-3-{1-[(tert-butoxycarbonyl)amino]-2-(4-chlorophenyl)ethyl}-1,2,4-oxadiazol-5-carboxylate | $^1$H-NMR (400 MHz, CDCl$_3$) δ 1.39 (9H, s), 1.47 (3H, t, J = 7.3 Hz), 3.09-3.25 (2H, m), 4.55 (2H, q, J = 7.3 Hz), 5.02-5.14 (1H, m), 5.25-5.36 (1H, m), 7.03 (2H, d, J = 7.9 Hz), 7.24 (2H, d, J = 7.9 Hz). |

149

TABLE 27-continued

| Ref. No | Str. | Chemical name | P.D. |
|---|---|---|---|
| 34-3 | BocHN, structure with 4-chlorophenyl and ethyl carboxylate oxadiazole | ethyl (S)-3-(2-((tert-butoxycarbonyl)amino)-3-(4-chlorophenyl)propyl)-1,2,4-oxadiazol-5-carboxylate | $^1$H-NMR (400 MHz, CDCl$_3$) δ 1.38 (9H, s), 1.47 (3H, t, J = 7.1 Hz), 2.79 (2H, dd, J = 14.1, 7.3 Hz), 2.89-3.06 (3H, m), 4.25 (1H, br), 4.53 (2H, q, J = 7.1 Hz), 4.76 (1H, br), 7.14 ( 2H, d, J = 8.5 Hz), 7.28 (2H, d, J = 8.5 Hz). |

Reference Example 35-1

Tert-Butyl (2-(4-methoxyphenyl)-1-(5-(tetrahydro-2H-pyran-4-yl)-1,2,4-oxadiazol-3-yl)ethyl)carbamate

[Chem.83]

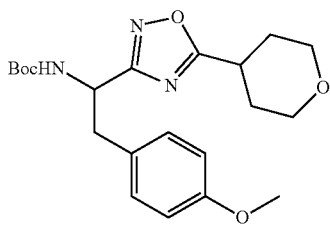

To a solution of tert-butyl (Z)-[1-amino-1-(hydroxyimino)-3-(4-methoxyphenyl)propan-2-yl]carbamate (200 mg) in dichloromethane (3.2 mL) were added tetrahydro-2H-pyran-4-carboxylic acid (84 mg), 4-dimethylaminopyridine (94.8 mg), and 1-ethyl-3-(3-dimethylaminopropyl)carbodiimide hydrochloride (149 mg), and the mixture was stirred at room temperature for 40 minutes. The solvent was removed under reduced pressure, N,N-dimethylformamide (3.2 mL) was added to the obtained residue, and the mixture was stirred at 120° C. for 2 hours. Water was added to the reaction solution, extracted with ethyl acetate. The organic layer was washed with water and then a brine, and dried over anhydrous sodium sulfate. The solvent was removed under reduced pressure, and the obtained residue was then purified by silica gel column chromatography (hexane:ethyl acetate=5:1) to obtain the title compound as a yellow solid (168 mg).

$^1$H NMR (400 MHz, DMSO-d$_6$) δ 1.41 (9H, s), 1.90-2.06 (4H, m), 3.02-3.24 (3H, m), 3.55 (2H, td, J=11.5, 3.0 Hz), 3.77 (3H, s), 4.02 (2H, dt, J=11.5, 3.6 Hz), 5.04 (1H, s), 5.16 (1H, s), 6.78 (2H, d, J=8.5 Hz), 6.99 (2H, d, J=8.5 Hz).

Reference Example 35-2

The following Reference Example 35-2 was obtained using the corresponding starting material in the same method as in Reference Example 35-1.

The structure and spectral data thereof are shown in Table 28.

TABLE 28

| Ref.No | Str. | Chemical name | P.D. |
|---|---|---|---|
| 35-2 | structure with Boc-NH, 4-methoxyphenyl, oxadiazole, 1-methylpiperidine | tert-butyl (2-(4-methoxyphenyl)-1-(5-(1-methylpiperidine-4-yl)-1,2,4-oxadiazol-3-yl)ethyl)carbamate | $^1$H NMR (400 MHz, DMSO-d$_6$) δ 1.41 (9H, s), 1.94-2.30 (6H, m), 2.37 (3H, s), 2.91 (3H, s), 3.11 (2H, s), 3.76 (3H, s), 5.03 (1H, d, J = 7.9 Hz), 5.17 (1H, d, J = 7.3 Hz), 6.78 (2H, d, J = 8.5 Hz), 6.98 (2H, d, J = 8.5 Hz). |

Reference Example 36

Tert-Butyl (S)-(1-(5-acetamide-1,3,4-oxadiazol-2-yl)-2-(4-ethylphenyl)ethyl)carbamate

[Chem.84]

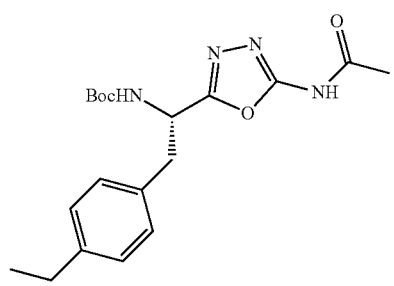

To a solution of tert-butyl (S)-(3-(4-ethylphenyl)-1-hydrazinoyl-1-oxopropan-2-yl)carbamate (494 mg) in 1,4-dioxane (8.93 mL) were added sodium hydrogen carbonate (162 mg) and water (3.74 mL), and the mixture was stirred at room temperature for 10 minutes. Then, cyanogen bromide (215 mg) was added thereto, and the reaction mixture was stirred at room temperature for 4 hours. Water was added to the reaction mixture, and the mixture was extracted with ethyl acetate (z 2). The organic layer was washed with water and then a brine, and the organic layer was dried over anhydrous sodium sulfate. The filtrate was concentrated under reduced pressure to obtain the resulting crude product (540 mg).

The resulting crude product (540 mg) was dissolved in pyridine (1.61 mL), acetic anhydride (235 µL) was added thereto, and the mixture was stirred at 60° C. for 1 hour. The reaction solution was concentrated under reduced pressure, and the obtained residue was triturated with ethyl acetate:hexane=1:5 to obtain the title compound as a white solid (365 mg).

$^1$H-NMR (400 MHz, DMSO-$d_6$) δ 1.13 (3H, t, J=7.3 Hz), 1.29 (9H, s), 2.09 (3H, s), 2.54 (2H, q, J=7.3 Hz), 3.01 (1H, dd, J=13.9, 9.7 Hz), 3.13 (1H, dd, J=13.9, 6.1 Hz), 4.87 (1H, m), 7.09 (2H, d, J=8.5 Hz), 7.14 (2H, d, J=8.5 Hz), 7.61 (1H, d, J=8.5 Hz), 11.52 (1H, br s).

Reference Example 37

Tert-Butyl (S)-[2-(4-chlorophenyl)-1-(5-methyl-1,2,4-oxadiazol-3-yl)ethyl]carbamate

[Chem.85]

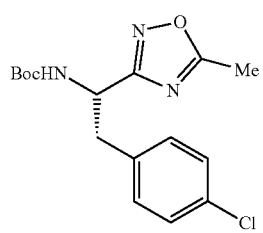

To a suspension of tert-butyl (S,Z)-[1-amino-3-(4-chlorophenyl)-1-(hydroxyimino)propan-2-yl]carbamate (300 mg) in toluene (4.8 mL) were added pyridine (1 mL) and acetic anhydride (1 mL) to produce a reaction solution. The reaction solution was heated to reflux for 3 hours. To the reaction solution was added ethyl acetate, and the precipitated solid was collected by filtration. The precipitated solid was dissolved in tetrahydrofuran solution (1.5 mL), tetrabutylammonium fluoride (1 mol/L tetrahydrofuran solution, 0.56 mL) was added thereto, and the mixture was stirred at 50° C. for 30 minutes. Water was added to the reaction solution, and the mixture was extracted with ethyl acetate. The organic layer was washed with water and then a brine, and dried over anhydrous sodium sulfate. The solvent was removed under reduced pressure, and the residue was then purified by silica gel column chromatography (hexane:ethyl acetate=20:1-2:1) to obtain the title compound as a colorless oil (188 mg).

$^1$H-NMR (400 MHz, DMSO-$d_6$) δ 1.28 (9H, s), 2.57 (3H, s), 2.97 (1H, dd, J=13.9, 9.7 Hz), 3.09 (1H, dd, J=13.9, 5.4 Hz), 4.77-4.86 (1H, m), 7.26 (2H, d, J=8.5 Hz), 7.32 (2H, d, J=8.5 Hz), 7.50 (1H, d, J=8.5 Hz).

Reference Example 38

Tert-Butyl (S)-(2-(4-chlorophenyl)-1-{5-[(methylsulfonyl)methyl]-1,2,4-oxadiazol-3-yl}ethyl)carbamate

[Chem.86]

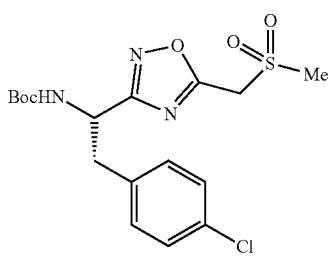

To a solution of tert-butyl (S)-(2-(4-chlorophenyl)-1-{5-[(methylthio)methyl]-1,2,4-oxadiazol-3-yl}ethyl)carbamate (150 mg) in dichloromethane (2.0 mL) was added meta-chloroperbenzoic acid (mCPBA) (245 mg) to produce a reaction solution. The reaction solution was stirred at room temperature for 1 hour. To the reaction solution was added an aqueous sodium thiosulfate, and the mixture was extracted with ethyl acetate. The organic layer was washed with water and then a brine, and dried over anhydrous sodium sulfate. The solvent was removed under reduced pressure, and the obtained residue was then washed with diisopropyl ether to obtain the title compound as a white solid (157 mg).

$^1$H-NMR (400 MHz, DMSO-$d_6$) δ 1.29 (9H, s), 3.03 (1H, dd, J=13.3, 9.7 Hz), 3.11 (1H, dd, J=13.3, 6.1 Hz), 3.20 (3H, s), 4.85-4.94 (1H, m), 5.20 (2H, s), 7.25 (2H, d, J=8.5 Hz), 7.32 (2H, d, J=8.5 Hz), 7.61 (1H, d, J=8.5 Hz).

Reference Example 39

Ethyl (S)-2-(5-(1-((tert-butoxycarbonyl)amino)-2-(4-methoxyphenyl)ethyl)-2-oxo-1,3,4-oxadiazol-3(2H)-yl)acetate

[Chem.87]

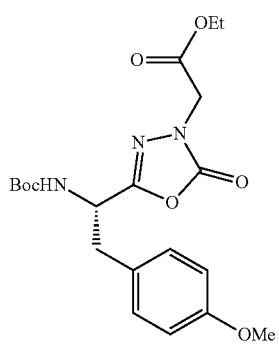

tert-Butyl (S)-(1-(5-hydroxy-1,3,4-oxadiazol-2-yl)-2-(4-methoxyphenyl)ethyl)carbamate (800 mg) was dissolved in N,N-dimethylformamide (11.9 mL); potassium carbonate (396 mg) and ethyl bromoacetate (0.32 mL) were added thereto; and the mixture was stirred at room temperature for 2 hours. Water was added to the reaction solution, and the mixture was extracted with ethyl acetate. The organic layer was washed with water and a brine, and dried over anhydrous sodium sulfate. The solvent was removed under reduced pressure, and the residue was then purified by silica gel column chromatography (hexane:ethyl acetate=5:2) to obtain the title compound (1.0 g).

$^1$H-NMR (400 MHz, CDCl$_3$) δ 1.28 (3H, t, J=7.3 Hz), 1.41 (9H, s), 3.08-3.3.13 (2H, m), 3.79 (3H, s), 4.23 (2H, q, J=7.3 Hz), 4.41 (2H, d, J=1.2 Hz), 4.81 (1H, brs), 4.92 (1H, brs), 6.84 (2H, d, J=8.5 Hz), 7.05 (2H, d, J=8.5 Hz).

Reference Example 40

(S)-2-(5-(1-((tert-Butoxycarbonyl)amino)-2-(4-methoxyphenyl)ethyl)-4H-1,2,4-triazol-3-yl)acetic Acid

[Chem.88]

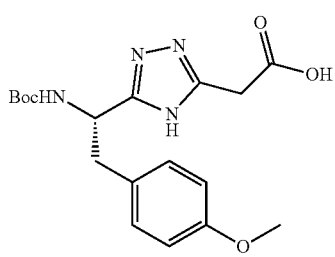

To a solution of sodium acetate (159 mg) in acetonitrile (1.62 mL)-water (0.5 mL) was added ethyl 3-ethoxy-3-iminopropionate (317 mg), and the reaction mixture was stirred at room temperature for 5 minutes. To the reaction solution was added tert-butyl (S)-[1-hydrazinyl-(4-methoxyphenyl)-1-oxopropan-2-yl]carbamate (500 mg), and the reaction mixture was stirred at room temperature for 2 hours. After, sodium carbonate (343 mg) and water (2.8 mL) were added thereto, and the mixture was heated to reflux for 3 hours. The reaction mixture was allowed to cool to room temperature, then citric acid was added thereto to adjust the pH of the reaction mixture to 3-4. The mixture was extracted with ethyl acetate. The organic layer was washed with a brine, and dried over anhydrous sodium sulfate. The solvent was removed under reduced pressure, and the obtained residue was triturated with ethanol:water=1:10 to obtain the title compound as a colorless solid (344 mg).

$^1$H-NMR (400 MHz, DMSO-d$_6$) δ 1.29 (9H, s), 2.80-2.93 (1H, m), 3.00-3.08 (1H, m), 3.64-3.70 (2H, m), 3.68 (3H, s), 4.73 (1H, s), 6.78 (2H, d, J=8.5 Hz), 7.08 (2H, d, J=8.5 Hz), 7.24 (1H, s), 13.45 (1H, s).

Reference Example 41

Methyl (S)-2-(5-(1-((tert-butoxycarbonyl)amino)-2-(4-methoxyphenyl)ethyl)-4H-1,2,4-triazol-3-yl)acetate

[Chem.89]

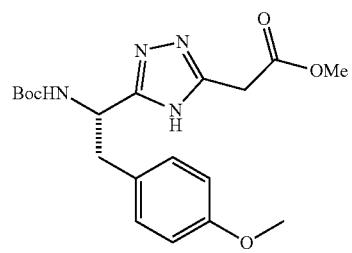

To a solution of (S)-2-(5-(1-((tert-butoxycarbonyl)amino)-2-(4-methoxyphenyl)ethyl)-4H-1,2,4-triazol-3-yl)acetic acid (100 mg) in methanol (1 mL) was added thionyl chloride (38.3 μL), and the mixture was stirred at room temperature for 3 hours. Sodium hydrogen carbonate was added thereto, and then the mixture was extracted with ethyl acetate. The organic layer was washed with a brine, and dried over anhydrous sodium sulfate. The solvent was removed under reduced pressure, and the residue was then purified by silica gel column chromatography (hexane:ethyl acetate=1:1-1:20) to obtain the title compound as a colorless oil (36.9 mg).

$^1$H-NMR (400 MHz, CDCl$_3$) δ 1.38 (9H, s), 3.15 (2H, d, J=6.1 Hz), 3.74 (3H, s), 3.76 (3H, s), 3.87 (2H, s), 5.05 (1H, dd, J=6.7, 6.1 Hz), 5.49 (1H, d, J=6.7 Hz), 6.76 (2H, dd, J=11.5, 3.0 Hz), 6.99 (2H, dd, J=11.5, 3.0 Hz), 12.12 (1H, s).

Reference Example 42

(S)-2-(5-(1-((tert-Butoxycarbonyl)amino)-2-(4-methoxyphenyl)ethyl)-1,3,4-oxadiazol-2-yl)acetic Acid

[Chem.90]

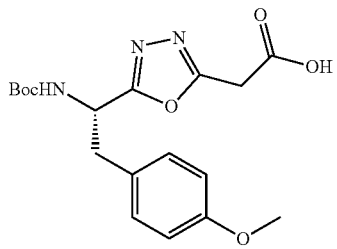

To a solution of ethyl (S)-2-(5-(1-((tert-butoxycarbonyl)amino)-2-(4-methoxyphenyl)ethyl)-1,3,4-oxadiazol-2-yl) acetate (182 mg) in methanol (1.0 mL) was added 0.539 mol/L aqueous lithium hydroxide (1.0 mL), and the mixture was stirred at room temperature for 1 hour. To the reaction solution was added a 10% aqueous citric acid to adjust the pH of the reaction solution to 3-4, and the precipitated solid was collected by filtration. The precipitated solid was washed with water and hexane to obtain the title compound as a light brown solid (136 mg).

$^1$H-NMR (400 MHz, DMSO-$d_6$) δ 1.30 (9H, s), 2.99 (1H, dd, J=13.9, 9.7 Hz), 3.09 (1H, dd, J=13.9, 6.1 Hz), 3.70 (3H, s), 4.01 (2H, s), 4.89 (1H, m), 6.81 (2H, d, J=9.1 Hz), 7.14 (2H, d, J=9.1 Hz), 7.63 (1H, d, J=8.5 Hz), 13.11 (1H, br s).

Reference Example 43

Tert-Butyl (S)-(2-(4-methoxyphenyl)-1-(5-(2-(methylamino)-2-oxoethyl)-1,3,4-oxadiazol-2-yl)ethyl) carbamate

[Chem.91]

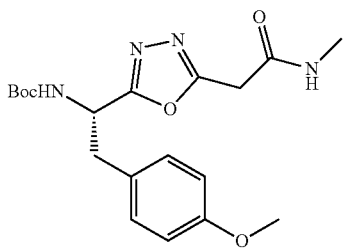

To a solution of (S)-2-(5-(1-((tert-butoxycarbonyl)amino)-2-(4-methoxyphenyl)ethyl)-1,3,4-oxadiazol-2-yl) acetic acid (130 mg) in tetrahydrofuran (1.7 mL) under ice-cooling were added 1-hydroxybenzotriazole (63.9 mg), 2 mol/L methylamine-tetrahydrofuran (689 μL), and 1-ethyl-3-(3-dimethylaminopropyl)carbodiimide hydrochloride (79.2 mg), and the mixture was stirred under ice-cooling for 3 minutes and then at room temperature for 2 days. To the reaction mixture was added ethyl acetate, the organic layer was washed with water, a saturated aqueous sodium hydrogen carbonate, and then a brine, and the organic layer was dried over anhydrous sodium sulfate. The filtrate was concentrated under reduced pressure to obtain the title compound as a pale yellow amorphous (127 mg).

$^1$H-NMR (400 MHz, CDCl$_3$) δ 1.41 (9H, s), 2.86 (3H, d, J=4.8 Hz), 3.17 (2H, m), 3.78 (3H, s), 3.81 (2H, s), 5.04 (1H, m), 5.20 (1H, m), 6.81 (3H, m), 7.01 (2H, d, J=8.5 Hz).

Reference Example 44-1

Ethyl (S)-5-(1-((tert-butoxycarbonyl)amino)-2-(4-methoxyphenyl)ethyl)oxazole-4-carboxylate

[Chem.92]

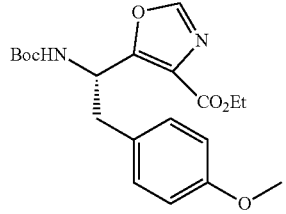

To a solution of (S)-2-((tert-butoxycarbonyl)amino)-3-(4-methoxyphenyl)propionic acid (1.0 g) in N,N-dimethylformamide (15 mL) were added potassium carbonate (955 mg) and ethyl 2-isocyanoacetate (510 μL), and the mixture was stirred at room temperature for 5 minutes. To the reaction mixture was added diphenylphosphoryl azide (894 μL), and the mixture was stirred at room temperature for 22 hours. A cold water was added to the reaction mixture under ice-cooling, and the mixture was extracted with ethyl acetate (×3). The organic layer was washed with water and then a brine, and the organic layer was dried over anhydrous sodium sulfate. The filtrate was concentrated under reduced pressure, and the obtained residue was then purified by silica gel column chromatography (ethyl acetate:hexane=1:1) to obtain the title compound as a colorless oil (291 mg).

$^1$H-NMR (400 MHz, DMSO-$d_6$) δ 1.25 (3H, m), 1.30 (9H, br s), 2.85 (1H, m), 2.97 (1H, dd, J=13.3, 8.5 Hz), 3.68 (3H, s), 4.21 (2H, m), 5.40 (1H, m), 6.80 (2H, d, J=8.5 Hz), 7.05 (2H, d, J=8.5 Hz), 7.60 (1H, d, J=8.5 Hz), 8.42 (1H, s).

Reference Example 44-2

The following Reference Example 44-2 was obtained using the corresponding starting material in the same method as in Reference Example 44-1.

The structure and spectral data thereof are shown in Table 29.

TABLE 29

| Ref.No | Str. | Chemical name | P.D. |
|---|---|---|---|
| 44-2 | BocHN-...-EtO$_2$C-N-O-MeO (structure) | ethyl (S)-5-(2-((tert-butoxycarbonyl)amino)-3-(4-methoxyphenyl)propyl)-oxazole-4-carboxylate | $^1$H-NMR (400 MHz, CDCl$_3$) δ 1.34 (9H, s), 1.37 (3H, t, J = 7.1 Hz), 2.74 (1H, dd, J = 14.4, 7.1 Hz), 2.91 (1H, dd, J = 13.9, 5.4 Hz), 3.15 (2H, ddd, |

| Ref.No | Str. | Chemical name | P.D. |
|---|---|---|---|
| | | | J = 46.5, 14.4, 7.1 Hz), 3.80 (3H, s), J = 4.16 (1H, brs), 4.36 (2H, q, J = 7.1 Hz), 4.74 (1H, d, J = 8.5 Hz), 6.86 (2H, d, J = 8.5 Hz), 7.13 (2H, d, J = 8.5 Hz), 7.76 (1H, s). |

Reference Example 45

Tert-Butyl (S)-(1-(4-(2-hydroxypropan-2-yl)oxazol-5-yl)-2-(4-methoxyphenyl)ethyl)carbamate

[Chem.93]

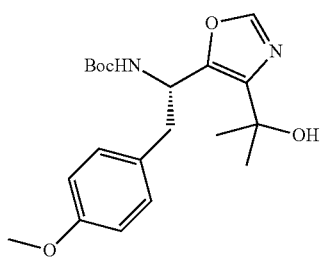

To a solution of ethyl (S)-5-(1-((tert-butoxycarbonyl)amino)-2-(4-methoxyphenyl)ethyl)oxazole-4-carboxylate (100 mg) in tetrahydrofuran (1.28 mL) under ice-cooling was added 0.99 mol/L methylmagnesium bromide/tetrahydrofuran solution (854 μL), and the mixture was stirred under ice-cooling for 2 hours. To the reaction mixture was added a saturated aqueous ammonium chloride, and the mixture was extracted with ethyl acetate. The organic layer was washed with a brine, and dried over anhydrous sodium sulfate. The filtrate was concentrated under reduced pressure, and the residue was then purified by silica gel column chromatography (ethyl acetate:hexane=1:2) to obtain the title compound as a colorless oil (37.2 mg).

$^1$H-NMR (400 MHz, CDCl$_3$) δ 1.24 (3H, s), 1.39 (9H, s), 1.47 (3H, s), 3.01-3.13 (2H, m), 3.75 (3H, s), 4.46 (1H, br s), 5.02 (1H, d, J=8.5 Hz), 5.55 (1H, m), 6.77 (2H, d, J=8.5 Hz), 7.01 (2H, d, J=8.5 Hz), 7.69 (1H, s).

Reference Example 46

Tert-Butyl (S)-(1-(4-carbamoyloxazol-5-yl)-2-(4-methoxyphenyl)ethyl)carbamate

[Chem.94]

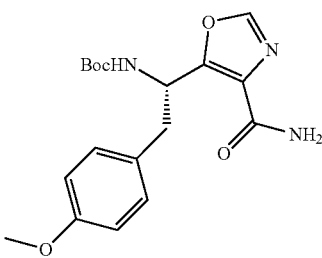

Using ethyl (S)-5-(1-((tert-butoxycarbonyl)amino)-2-(4-methoxyphenyl)ethyl)oxazole-4-carboxylate (1.38 g) as a starting material, the same method as in Reference Example 42 followed by the same method as in Reference Example 6-1 to obtain the title compound as a white amorphous (800 mg).

$^1$H-NMR (400 MHz, DMSO-d$_6$) δ 1.30 (9H, br s), 2.82-2.97 (2H, m), 3.69 (3H, s), 5.36 (1B, m), 6.79 (2H, d, J=8.5 Hz), 7.07 (2H, d, J=8.5 Hz), 7.50 (2H, br s), 7.59 (1H, br s), 8.33 (1H, s).

Reference Example 47

Tert-Butyl (S)-(1-(4-cyanooxazol-5-yl)-2-(4-methoxyphenyl)ethyl)carbamate

[Chem. 95]

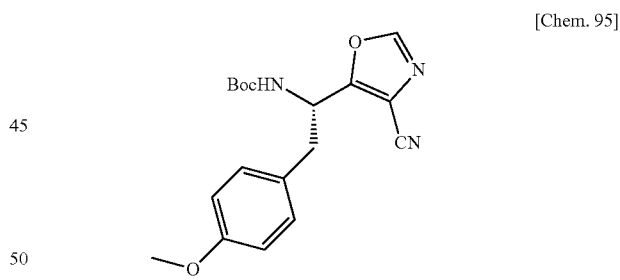

Using tert-butyl (S)-(1-(4-carbamoyloxazol-5-yl)-2-(4-methoxyphenyl)ethyl)carbamate (800 mg) as a starting material, the same method as in Reference Example 7-1 to obtain the title compound as a white solid (101 mg).

$^1$H-NMR (400 MHz, DMSO-d$_6$) δ 1.32 (9H, br s), 3.02 (2H, d, J=7.9 Hz), 3.70 (3H, s), 4.89 (1H, m), 6.82 (2H, d, J=8.5 Hz), 7.11 (2H, d, J=8.5 Hz), 7.80 (1H, d, J=7.3 Hz), 8.60 (1H, s).

Reference Example 48

Methyl 2-(2-((tert-butoxycarbonyl)amino)-3-(4-methoxyphenyl)propanamide)-3-hydroxypropionate

[Chem. 96]

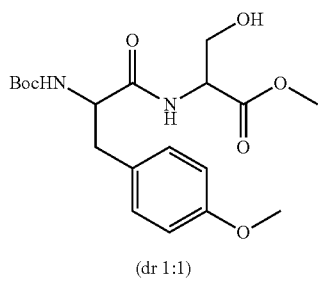

(dr 1:1)

To a solution of 2-((tert-butoxycarbonyl)amino)-3-(4-methoxyphenyl)propionic acid (1.49 g) in N,N-dimethylformamide (13.0 mL) under ice-cooling were added serine methyl ester hydrochloride (887 mg), diisopropylethylamine (3.11 mL), and O-(7-azabenzotriazol-1-yl)-N,N,N',N'-tetramethyluronium hexafluorophosphate (2.39 g), and the mixture was stirred at room temperature for 22 hours. To the reaction mixture under ice-cooling were added a saturated aqueous sodium hydrogen carbonate and water, and the mixture was extracted with ethyl acetate (×3). The organic layer was washed with water and then a brine, and dried over anhydrous sodium sulfate. The filtrate was concentrated under reduced pressure, and the residue was then purified by silica gel column chromatography (ethyl acetate hexane=2:1) to obtain the title compound as a white amorphous (1.78 g).

$^1$H-NMR (400 MHz, CDCl$_3$) δ 1.42 (9H, s), 2.11 (0.5H, m), 2.63 (0.5H, m), 2.99-3.09 (2H, m), 3.77 (3H, m), 3.79 (3H, s), 3.86 (1H, m), 3.87 (0.5H, m), 3.97 (0.5H, m), 4.21-4.34 (1H, m), 4.58 (1H, m), 4.88-5.02 (1H, m), 6.60 (0.5H, m), 6.69 (0.5H, d, J=6.7 Hz), 6.86 (2H, m), 7.14 (2H, m).

Reference Example 49

Methyl 2-(1-((tert-butoxycarbonyl)amino)-2-(4-methoxyphenyl)ethyl)oxazole-4-carboxylate

[Chem. 97]

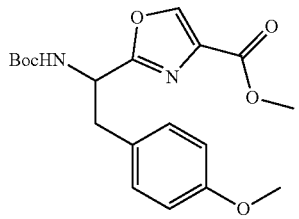

To a solution of methyl 2-(2-((tert-butoxycarbonyl)amino)-3-(4-methoxyphenyl)propanamide)-3-hydroxypropionate (1.76 g) in dichloromethane (32.0 mL) at −20° C. was added Deoxo-Fluor (0.9 mL), and the mixture was stirred at the same temperature for 45 minutes. To the reaction mixture were added bromotrichloromethane (1.6 mL) and 1,8-diazabicyclo[5.4.0]undec-7-ene (4.73 mL), and the mixture was stirred at room temperature for 2.5 hours. To the reaction solution was added a saturated aqueous sodium hydrogen carbonate. The organic layer was separated, and the aqueous layer was extracted with dichloromethane (×2). The combined organic layer was washed with a brine, and dried over anhydrous sodium sulfate. The filtrate was concentrated under reduced pressure, and the residue was then purified by silica gel column chromatography (ethyl acetate:hexane=1:2) to obtain the title compound as a white amorphous (1.41 g).

$^1$H-NMR (400 MHz, CDCl$_3$) δ 1.41 (9H, br s), 3.16 (2H, d, J=5.4 Hz), 3.77 (3H, s), 3.92 (3H, s), 5.16 (1H, m), 5.19 (1H, m), 6.78 (2H, d, J=8.5 Hz), 6.93 (2H, d, J=8.5 Hz), 8.13 (1H, s).

Reference Example 50

Tert-Butyl (1-amino-3-(4-methoxyphenyl)-1-thioxopropan-2-yl)carbamate

[Chem. 98]

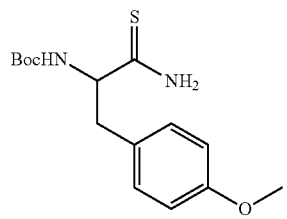

To a solution of tert-butyl (1-amino-3-(4-methoyphenyl)-1-oxopropan-2-yl)carbamate (500 mg) in dichloromethane (17.0 mL) was added Lawesson's reagent (405 mg), and the mixture was stirred at room temperature for 19 hours. The reaction mixture was concentrated under reduced pressure, and the obtained residue was then purified by silica gel column chromatography (ethyl acetate:hexane=1:2) to obtain the title compound as a white solid (501 mg).

$^1$H-NMR (400 MHz, CDCl$_3$) δ 1.42 (9H, s), 3.07 (1H, m), 3.17 (1H, m), 3.79 (3H, s), 4.52 (1H, m), 5.26 (1H, m), 6.84 (2H, d, J=8.5 Hz), 7.01 (1H, br s), 7.17 (2H, d, J=8.5 Hz), 7.26 (1H, m).

Reference Example 51

Ethyl 2-(2-(1-((tert-butoxycarbonyl)amino)-2-(4-methoxyphenyl)ethyl)thiazol-4-yl)acetate

[Chem. 99]

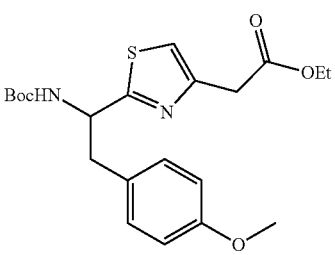

To a solution of tert-butyl (1-amino-3-(4-methoxyphenyl)-1-thioxopropan-2-yl)carbamate (100 mg) in ethanol (645 µL) was added ethyl 4-chloro-3-oxobutyrate (46.1 µL), and the reaction mixture was stirred under reflux for 30 minutes. To the reaction mixture under ice-cooling was added ethyl acetate and water. The organic layer was separated, and the aqueous layer was extracted with ethyl acetate (×2). The combined organic layer was washed with a brine, and dried over anhydrous sodium sulfate. The filtrate was concentrated under reduced pressure, and the obtained residue was then purified by silica gel column chromatography (ethyl acetate:hexane=1:2-ethyl acetate:methanol=20:1) to obtain the title compound as a yellow oil (49.5 mg).

$^1$H-NMR (400 MHz, DMSO-d$_6$) δ 1.19 (3H, t, J=7.3 Hz), 1.30 (9H, s), 2.87 (1H, dd, J=13.9, 10.9 Hz), 3.18 (1H, dd, J=13.9, 4.2 Hz), 3.70 (3H, s), 3.78 (2H, s), 4.09 (2H, q, J=7.3 Hz), 4.85 (1H, m), 6.82 (2H, d, J=8.5 Hz), 7.17 (2H, d, J=8.5 Hz), 7.34 (1H, s), 7.67 (1H, d, J=8.5 Hz).

Reference Example 52

Ethyl (S)-2-(5-(1-((tert-butoxycarbonyl)amino)-2-(4-methoxyphenyl)ethyl)-1,3,4-thiadiazol-2-yl)acetate

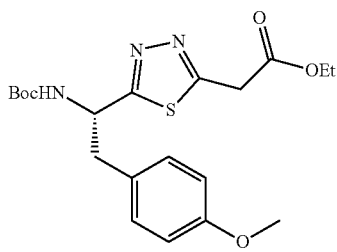

[Chem. 100]

To a solution of tert-butyl (S)-[1-hydrazinyl-(4-methoxyphenyl)-1-oxopropan-2-yl]carbamate (200 mg) in tetrahydrofuran (2.15 mL) was added triethylamine (110 µL). To the reaction mixture was added ethyl malonyl chloride (101 µL) at −15° C. The reaction mixture was stirred at room temperature for 3.5 hours. To the reaction mixture was added a saturated aqueous sodium hydrogen carbonate, and the mixture was extracted with ethyl acetate (×2). The organic layer was washed with a brine. The combined organic layer was dried over anhydrous sodium sulfate. The filtrate was concentrated under reduced pressure to obtain the resulting crude product (277 mg).

The resulting crude product (274 mg) was dissolved in tetrahydrofuran (6.50 mL), and Lawesson's reagent (320 mg) was added thereto, and the mixture was stirred at 50° C. for 3.5 hours. The reaction solution was concentrated under reduced pressure, and the obtained residue was then purified by silica gel column chromatography (ethyl acetate: hexane=1:1) to obtain the title compound as a colorless oil (205 mg).

$^1$H-NMR (400 MHz, CDCl$_3$) δ 1.29 (3H, t, J=7.3 Hz), 1.41 (9H, s), 3.27 (2H, br d, J=5.4 Hz), 3.78 (3H, s), 4.12 (2H, m), 4.23 (2H, q, J=7.3 Hz), 5.29 (1H, m), 5.33 (1H, m), 6.81 (2H, d, J=8.5 Hz), 7.06 (2H, d, J=8.5 Hz).

Reference Example 53

(S)-2-(1-(5-amino-1,3,4-thiadiazol-2-yl)-2-(4-methoxyphenyl)ethyl)isoindoline-1,3-dione

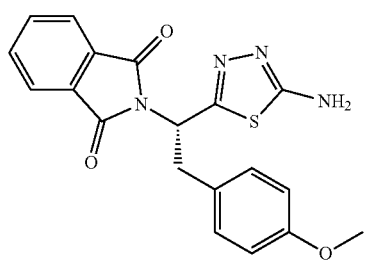

[Chem. 101]

To a solution of (S)-2-(1,3-dioxoisoindolin-2-yl)-3-(4-methoxyphenyl)propionic acid (490 mg) in N,N-dimethylformamide (5.0 mL) under ice-cooling were added thiosemicarbazide (154 mg), diisopropylethylamine (640 µL), and O-(7-azabenzotriazol-1-yl)-N,N,N',N',-tetramethyluronium hexafluorophosphate (709 mg), and the reaction mixture was stirred at room temperature for 21 hour. Under ice-cooling, water was added hereto, and the mixture was extracted with ethyl acetate (×2). The combined organic layer was washed with water and a brine, and the organic layer was dried over anhydrous sodium sulfate. The filtrate was concentrated under reduced pressure to obtain a crude product as a pale yellow amorphous (1.15 g).

To the solution of the crude product (1.15 g) in toluene (15.1 mL) was added methanesulfonic acid (294 µL) was added thereto, and the mixture was stirred under reflux for 3 hours. To the mixture was added a saturated aqueous sodium hydrogen carbonate, and the mixture was extracted with ethyl acetate (×2). The combined organic layer was washed with a saturated aqueous sodium hydrogen carbonate, and dried over anhydrous sodium sulfate. The filtrate was concentrated under reduced pressure, and the obtained residue was triturated with chloroform to obtain the title compound as a white solid (246 mg).

$^1$H-NMR (400 MHz, DMSO-d$_6$) δ 3.47 (1H, dd, J=13.9, 6.7 Hz), 3.57 (1H, dd, J=13.9, 10.3 Hz), 3.63 (3H, s), 5.73 (1H, dd, J=10.3, 6.7 Hz), 6.76 (2H, d, J=8.5 Hz), 7.11 (2H, d, J=8.5 Hz), 7.22 (2H, s), 7.84 (4H, s).

Reference Example 54

Tert-Butyl (2-(4-methoxyphenyl)-1-(5-oxo-4,5-dihydro-1,2,4-thiadiazol-3-yl)ethyl)carbamate

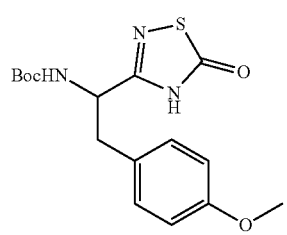

[Chem. 102]

To a solution of tert-butyl (Z)-[1-amino-1-(hydroxyimino)-3-(4-methoxyphenyl)propan-2-yl]carbamate (100 mg) in tetrahydrofuran solution (1.6 mL) was added 1,1'-thiocarbonyldiimidazole (86.0 mg), and the reaction mixture was stirred at room temperature for 1 hour. Water was added to the reaction solution, and the mixture was extracted with ethyl acetate. The organic layer was washed with water and then a brine, and dried over anhydrous sodium sulfate. The solvent was removed under reduced pressure, and the resulting solid was washed with diisopropyl ether to obtain a pale yellow solid.

The obtained pale yellow solid was dissolved in chloroform (8.00 mL)-methanol (1.60 mL), silica gel (1.50 g, Merck ART 7734) was added thereto, and the mixture was stirred at room temperature for 1 day. The insoluble was removed by filtration, the solvent was removed under reduced pressure, and then the obtained residue was then purified by silica gel column chromatography (hexane: acetone=3:1) to obtain the title compound as a colorless solid (46.1 mg).

$^1$H NMR (400 MHz, DMSO-$d_6$) δ 1.30 (9H, s), 2.80 (1H, dd, J=13.3, 9.1 Hz), 2.99 (1H, dd, J=13.3, 5.4 Hz), 3.70 (3H, s), 4.46 (1H, s), 6.79-6.68 (2H, m), 7.08-7.16 (2H, m), 7.24 (1H, s), 12.84 (1H, s).

Reference Example 55-1

2-((t-Butoxycarbonyl)amino)-3-(4-methoxyphenyl) propyl Methanesulfonate

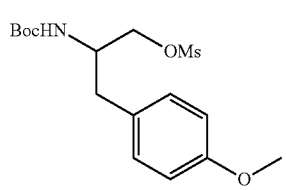

[Chem. 103]

To a solution of tert-butyl (1-hydroxy-3-(4-methoxyphenyl)propan-2-yl)carbamate (2.82 g) in dichloromethane (40 mL) at 0$^1$C were added triethylamine (2.24 mL) and methanesulfonyl chloride (1.16 mL), and the reaction mixture was stirred at the same temperature for 30 minutes. Water was added to the reaction solution, and the mixture was extracted with ethyl acetate. The organic layer was washed with a brine, and the organic layer was dried over anhydrous sodium sulfate. The solvent was removed under reduced pressure to obtain the title compound as a white solid (3.59 g).

$^1$H-NMR (400 MHz, CDCl$_3$) δ 1.43 (9H, s), 2.79 (1H, dd, J=13.9, 7.9 Hz), 2.87 (1H, dd, J=13.9, 6.7 Hz), 3.02 (3H, s), 3.79 (3H, s), 4.05 (1H, br s), 4.11 (1H, dd, J=10.3, 4.2 Hz), 4.19-4.29 (1H, m), 4.71 (1H, m), 6.86 (2H, d, J=8.5 Hz), 7.13 (2H, d, J=8.5 Hz).

Reference Examples 55-2 to 55-3

The following Reference Examples 55-2 to 55-3 were obtained using each corresponding starting material in the same method as in Reference Example 55-1.

The structures and spectral data thereof are shown in Table 30.

TABLE 30

| Ref. No | Str. | Chemical name | P.D. |
|---|---|---|---|
| 55-2 | BocHN— (S)—OMs, benzyl-OMe | (S)-2-[(tert-butoxy-carbonyl)-amino]-3-(4-methoxy-phenyl)-propyl methane-sulfonate | $^1$H-NMR (400 MHz, CDCl$_3$) δ 1.43 (9H, s), 2.76-2.89 (2H, m), 3.02 (3H, s), 3.79 (3H, s), 4.05 (1H, brs), 4.09-4.13 (1H, m), 4.24 (1H, dd, J = 10.3, 3.6 Hz), 4.72 (1H, d, J = 6.7 Hz), 6.85 (2H, d, J = 8.5 Hz), 7.13 (2H, d, J = 8.5 Hz). |
| 55-3 | BocHN— (S)—OMs, benzyl-Cl | (S)-2-[(tert-butoxy-carbonyl)-amino]-3-(4-chlorophenyl)-propyl methane-sulfonate | $^{1H}$-NMR (400 MHz, CDCl$_3$) δ 1.41 (9H, s), 2.31-2.92 (2H, m), 3.03 (3H, s), 4.07 (1H, s), 4.11-4.14 (1H, m), 4.24 (1H, dd, J = 9.8, 3.7 Hz), 4.73 (1H, d, J = 7.3 Hz), 7.16 (2H, d, J = 3.5 Hz), 7.29 (2H, d, J = 8.5 Hz). |

Reference Example 56-1

Tert-Butyl (1-cyano-3-(4-methoxyphenyl)propan-2-yl)carbamate

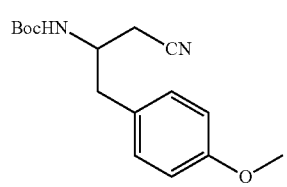

[Chem. 104]

To a solution of 2-((t-butoxycarbonyl)amino)-3-(4-methoxyphenyl)propyl methanesulfonate (3.6 g) in N,N-dimethylformamide (120 mL) was added sodium cyanide (1.47 g), and the reaction mixture was warmed to 50° C. and stirred for 18 hours. The reaction solution was cooled, water was added thereto, and the resulting solid precipitated was collected by filtration to obtain the title compound as a white solid (2.44 g).

$^1$H-NMR (400 MHz, CDCl$_3$) δ 1.43 (9H, s), 2.41 (1H, dd, J=17.0, 4.2 Hz), 2.69 (1H, dd, J=17.0, 4.2 Hz), 2.80 (1H, dd, J=13.9, 8.5 Hz), 2.95 (1H, dd, J=13.9, 6.1 Hz), 3.80 (3H, s), 4.02 (1H, br s), 4.71 (1H, d, J=6.1 Hz), 6.87 (2H, d, J=8.5 Hz), 7.14 (2H, d, J=8.5 Hz).

Reference Examples 56-2 to 56-3

The following Reference Examples 56-2 to 56-3 were obtained using each corresponding starting material in the same method as in Reference Example 56-1.

The structures and spectral data thereof are shown in Table 31.

The organic layer was washed with a brine, and dried over anhydrous sodium sulfate. The solvent was removed under reduced pressure to obtain the title compound as a white solid (214 mg).

$^1$H-NMR (400 MHz, DMSO-d$_6$) δ 1.31 (9H, s), 2.29 (2H, t, J=7.0 Hz), 2.60 (2H, d, J=7.3 Hz), 3.70 (3H, s), 3.85 (1H, d, J=7.3 Hz), 6.73 (1H, d, J=8.5 Hz), 6.82 (2H, d, J=8.5 Hz), 7.06 (2H, d, J=8.5 Hz), 12.10 (1H, brs).

Reference Example 57-2

The following Reference Example 57-2 was obtained using the corresponding starting material in the same method as in Reference Example 57-1.

The structure and spectral data thereof are shown in Table 32.

TABLE 31

| Ref. No | Str. | Chemical name | P.D. |
|---|---|---|---|
| 56-2 | 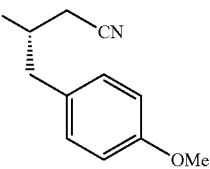 | tert-butyl (S)-(1-cyano-3-(4-methoxyphenyl)-propan-2-yl)carbamate | $^1$H-NMR (400 MHz, CDCl$_3$) δ 1.43 (9H, s), 2.41 (1H, dd, J = 16.7, 4.5 Hz), 2.69 (1H, dd, J = 16.7, 4.5 Hz), 2.80 (1H, dd, J = 13.9, 8.5 Hz), 2.95 (1H, dd, J = 13.9, 7.1 Hz), 3.80 (3H, s), 4.02 (1H, brs), 4.71 (1H, brs), 6.87 (2H, d, J = 8.5 Hz), 7.14 (2H, d, J = 8.5 Hz). |
| 56-3 | 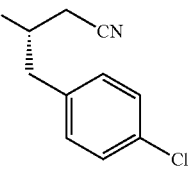 | tert-butyl (S)-[1-(4-chlorophenyl)-3-cyclopropan-2-yl]carbamate | $^1$H-NMR (400 MHz, CDCl$_3$) δ1.43 (9H, s), 2.43 (1H, dd, J = 16.5, 4.3 Hz), 2.71 (1H, dd, J = 16.5, 4.3 Hz), 2.85 (1H, dd, J = 13.6, 8.6 Hz), 2.97 (1H, dd, J = 13.6, 7.4 Hz), 4.04 (1H, brs), 4.70 (1H, brs), 7.16 (2H, d, J = 7.9 Hz), 7.31 (2H, d, J = 7.9 Hz). |

Reference Example 57-1

(S)-3-((tert-butoxycarbonyl)amino)-4-(4-methoxyphenyl)butyric Acid

[Chem. 105]

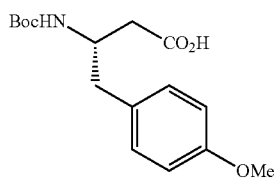

To a solution of tert-butyl (S)-(1-cyano-3-(4-methoxyphenyl)propan-2-yl)carbamate (800 mg) in ethanol (13.8 mL) was added an aqueous sodium hydroxide (2N, 6.9 mL), and the reaction mixture was heated to reflux for 5 hours. The reaction solution was cooled, hydrochloric acid was added thereto, and the mixture was extracted with ethyl acetate.

TABLE 32

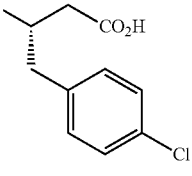

| Ref. No | Str. | Chemical name | P.D. |
|---|---|---|---|
| 57-2 | | (S)-3-((tert-butoxycarbonyl)amino)-4-(4-chlorophenyl)-butyric acid | $^1$H-NMR (400 MHz, CDCl$_3$) δ 1.40 (9H, s), 2.45-2.61 (2H, m), 2.80-2.94 (2H, m), 4.13 (1H, br), 5.01 (1H, br), 7.14 (2H, d, J = 8.5 Hz), 7.27 (2H, d, J = 8.5 Hz). |

Reference Example 58

Tert-Butyl (S)-1-(methoxycarbonyl)-3-(4-chlorophenyl)propan-2-ylcarbamate

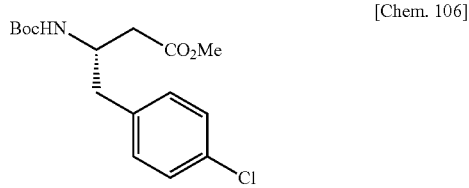 [SMILES: COC(=O)C[C@H](Cc1ccc(Cl)cc1)NC(=O)OC(C)(C)C]

[Chem. 106]

To a solution of (S)-3-((tert-butoxycarbonyl)amino)-4-(4-chlorophenyl)butyric acid (1.34 g) in N,N-dimethylformamide (22.7 mL) were added potassium carbonate (755 mg) and iodomethane (0.34 mL), and the reaction mixture was stirred at room temperature for 4 hours. Water was added to the reaction solution, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=2:1) to obtain the title compound (1.22 g).

$^1$H-NMR (400 MHz, CDCl$_3$) δ 1.38 (9H, s), 2.46 (2H, qd, J=16.5, 6.1 Hz), 2.76 (1H, dd, J=13.4, 7.3 Hz), 2.87 (1H, br), 3.67 (3H, s), 4.09 (1H, br), 5.01 (1H, br), 7.10 (2H, d, J=8.5 Hz), 7.24 (2H, d, J=8.5 Hz).

Reference Example 59

Ethyl (S)-3-(2-(3-((tert-butoxycarbonyl)amino)-4-(4-chlorophenyl)butanoyl)hydrazinyl)-3-oxopropionate

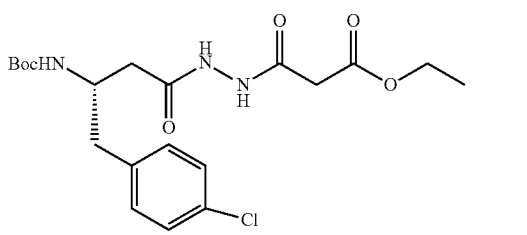

[Chem. 107]

To a solution of tert-butyl (S)-[4-hydrazinyl-1-(4-chlorophenyl)-4-oxobutan-2-yl]carbamate (350 mg) in tetrahydrofuran (3.6 mL) was added triethylamine (0.18 mL), and the reaction mixture was cooled to −17° C. Ethyl malonyl chloride (0.16 mL) was added thereto, and the reaction mixture was stirred at room temperature for 5.5 hours. A saturated aqueous sodium hydrogen carbonate was added to the reaction solution, and the mixture was extracted with ethyl acetate. The organic layer was washed with a brine, and dried over anhydrous sodium sulfate. The solvent was removed under reduced pressure to obtain the title compound as a light brown solid (361 mg).

$^1$H-NMR (400 MHz, DMSO-d$_6$) δ 1.17 (3H, t, J=7.3 Hz), 1.27 (9H, s), 2.22-2.34 (2H, m), 2.50 (1H, dd, J=13.3, 9.2 Hz), 2.77 (1H, dd, J=13.3, 4.8 Hz), 3.91 (1H, brs), 4.07 (2H, q, J=7.3 Hz), 6.72 (1H, d, J=9.1 Hz), 7.16 (2H, d, J=8.5 Hz), 7.31 (2H, d, J=8.5 Hz), 9.99 (1H, s), 10.09 (1H, s).

Reference Example 60

Ethyl (S)-2-(5-(2-((tert-butoxycarbonyl)amino)-3-(4-chlorophenyl)propyl)-1,3,4-oxadiazol-2-yl)acetate

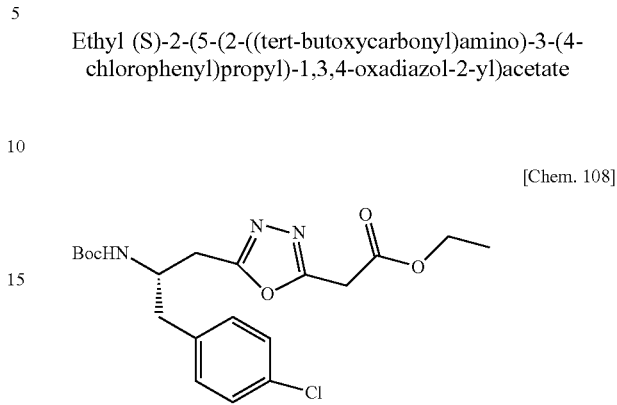

[Chem. 108]

To a solution of ethyl (S)-3-(2-(3-((tert-butoxycarbonyl)amino)-4-(4-chlorophenyl)butanoyl)hydrazinyl)-3-oxopropionate (352 mg) in dichloromethane (3.2 mL) were added triethylamine (0.22 mL), p-toluenesulfonyl chloride (182 mg), and the reaction mixture was stirred at 0° C. for 8 days. A saturated aqueous sodium hydrogen carbonate was added to the reaction solution, and the mixture was extracted with dichloromethane. The organic layer was washed with a brine, and dried over anhydrous sodium sulfate. The solvent was removed under reduced pressure, and the obtained residue was then purified by silica gel column chromatography (hexane:ethyl acetate=2:1) to obtain the title compound as a white solid (160 mg).

$^1$H-NMR (400 MHz, CDCl$_3$) δ 1.26 (3H, t, J=7.4 Hz), 1.39 (9H, s), 2.80-3.09 (4H, m), 3.93 (2H, s), 4.23 (2H, q, J=7.4 Hz), 4.26 (1H, brs), 4.96 (1H, d, J=9.7 Hz), 7.14 (2H, d, J=8.5 Hz), 7.28 (2H, d, J=8.5 Hz).

Reference Example 61

Ethyl (E)-4-((tert-butoxycarbonyl)amino)-5-(4-methoxyphenyl)-2-pentenoate

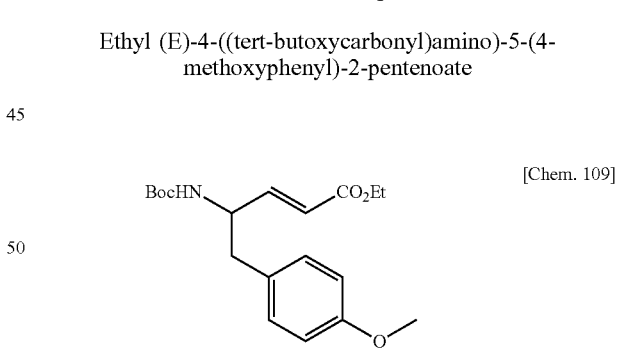

[Chem. 109]

To a solution of ethyl diethylphosphonoacetate (1.7 mL) in tetrahydrofuran (28 mL) under ice-cooling was added sodium hydride (60%, 344 mg), and the reaction mixture was stirred under ice-cooling for 30 minutes. To the reaction solution was added a solution of tert-butyl (1-(4-methoxyphenyl)-3-oxopropan-2-yl)carbamate (2.0 g) in tetrahydrofuran (8 mL), and the reaction mixture was stirred under ice-cooling for 3 hours. To the reaction solution was added an aqueous saturated ammonium chloride, and the mixture was extracted with ethyl acetate. The organic layer was washed with water and then a brine, and dried over anhydrous sodium sulfate. The solvent was removed under reduced pressure, and the obtained residue was then purified by silica gel column chromatography (hexane:ethyl acetate=1:1) to obtain the title compound as a pale yellow solid (2.13 g).

$^1$H-NMR (400 MHz, CDCl$_3$) δ 1.28 (3H, t, J=7.3 Hz), 1.40 (9H, s), 3.83 (2H, d, J=6.7 Hz), 3.79 (3H, s), 4.18 (2H, q, J=7.3 Hz), 4.49 (1H, br s), 4.55 (1H, br s), 5.84 (1H, dd, J=15.7, 1.8 Hz), 6.84 (2H, d, J=8.5 Hz), 6.90 (1H, dd, J=15.7, 5.4 Hz), 7.08 (2H, d, J=8.5 Hz).

Reference Example 62

Ethyl 4-((tert-butoxycarbonyl)amino)-5-(4-methoxyphenyl)pentanoate

[Chem. 110]

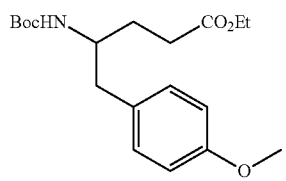

To a solution of ethyl (E)-4-((tert-butoxycarbonyl)amino)-5-(4-methoxyphenyl)-2-pentenoate (1.8 g) in ethanol (20 mL) was added 10 palladium-carbon (360 mg), and the reaction mixture was stirred under hydrogen atmosphere at room temperature for 4 hours. The reaction solution was filtered over Celite, the filtrate was concentrated under reduced pressure, and the obtained residue was then purified by silica gel column chromatography (hexane:ethyl acetate=1:1) to obtain the title compound as a white amorphous (1.73 g).

$^1$H-NMR (400 MHz, CDCl$_3$) δ 1.25 (3H, t, J=7.3 Hz), 1.41 (9H, s), 1.56-1.68 (1H, m), 1.79-1.92 (1H, m), 2.30-2.43 (2H, m), 2.69 (1H, dd, J=13.3, 7.3 Hz), 2.78 (1H, dd, J=13.3, 4.8 Hz), 3.73-3.79 (1H, m), 3.80 (3H, s), 4.13 (2H, q, J=7.3 Hz), 4.35 (1H, d, J=8.5 Hz), 6.84 (2H, d, J=8.5 Hz), 7.10 (2H, d, J=8.5 Hz).

Reference Example 63-1

Tert-Butyl (1-(5-hydroxy-1,3,4-oxadiazol-2-yl)-3-(4-methoxyphenyl)propan-2-yl)carbamate

[Chem. 111]

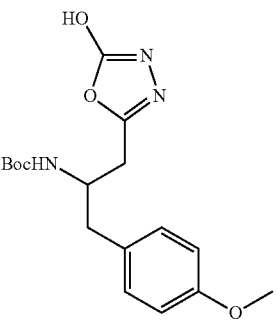

Using tert-butyl [4-hydrazinyl-1-(4-methoxyphenyl)-4-oxobutan-2-yl]carbamate as a starting material, the same method as in Reference Example 31-1 to obtain the title compound.

$^1$H-NMR (400 MHz, CDCl$_3$) δ 1.43 (9H, s), 2.63 (1H, dd, J=15.1, 7.3 Hz), 2.73-2.82 (2H, m), 2.89 (1H, dd, J=13.3, 6.7 Hz), 3.81 (3H, s), 4.10-4.22 (1H, m), 4.65 (1H, d, J=8.5 Hz), 6.87 (2H, d, J=8.5 Hz), 7.12 (2H, d, J=8.5 Hz), 8.27 (1H, s).

Reference Example 63-2

The following Reference Example 63-2 was obtained using the corresponding starting material in the same method as in Reference Example 63-1.

The structure and spectral data thereof are shown in Table 33.

TABLE 33

| Ref.No | Str. | Chemical name | P.D. |
|---|---|---|---|
| 63-2 | (structure shown) | tert-butyl (4-(5-hydroxy-1,3,4-oxadiazol-2-yl)-1-(4-methoxyphenyl)-butan-2-yl)carbamate | $^1$H-NMR (400 MHz, DMSO-d$_6$) δ 1.32 (9H, s), 1.50-1.64 (1H, m), 1.65-1.76 (1H, m), 2.59 (2H, s), 3.28 (2H, s), 3.56 (1H, s), 3.70 (3H, s), 6.76 (1H, d, J = 8.5 Hz), 6.82 (2H, d, J = 8.5 Hz), 7.07 (2H, d, J = 8.5 Hz), 11.97 (1H, s). |

Reference Example 64

Tert-Butyl (E)-(4-cyano-1-(4-methoxyphenyl)-3-buten-2-yl)carbamate

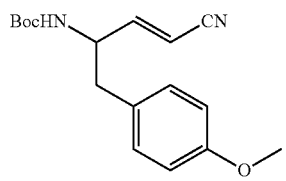

[Chem. 112]

To a solution of diethyl cyanomethylphosphonate (0.68 mL) in acetonitrile (36 mL) under ice-cooling were added lithium chloride (182 mg), 1,8-diazabicyclo[5.4.0]undec-7-ene (0.54 mL), and tert-butyl (1-(4-methoxyphenyl)-3-oxo-propan-2-yl)carbamate (1.0 g), and the reaction mixture was stirred at room temperature for 4 hours. The reaction solution was concentrated under reduced pressure, and the obtained residue was then purified by silica gel column chromatography (hexane:ethyl acetate=3:1) to obtain the title compound as a white solid (818 mg).

$^1$H-NMR (400 MHz, CDCl$_3$) δ 1.43 (9H, s), 2.78-2.96 (2H, m), 3.80 (3H, s), 4.59-4.68 (1H, m), 5.38 (1H, d, J=9.5 Hz), 6.42 (1H, s), 6.84 (2H, d, J=8.5 Hz), 6.88 (1H, d, J=9.5 Hz), 7.11 (2H, d, J=8.5 Hz).

Reference Example 65

Tert-Butyl (E)-(4-cyano-1-(4-methoxyphenyl)butan-2-yl)carbamate

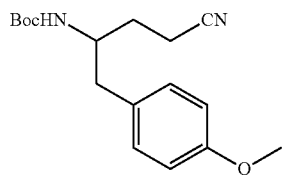

[Chem. 113]

To a solution of tert-butyl (E)-(4-cyano-1-(4-methoxyphenyl)-3-buten-2-yl)carbamate (400 mg) in ethanol (10 mL) was added 105 palladium-carbon (40 mg), and the reaction mixture was stirred under hydrogen atmosphere at room temperature for 5 hours. The reaction solution was filtered over Celite, and the residue was washed with ethyl acetate. The filtrate was concentrated under reduced pressure to obtain the title compound as a white amorphous (404 mg).

$^1$H-NMR (400 MHz, CDCl$_3$) δ 1.42 (9H, s), 1.60-1.73 (1H, m), 1.85-1.97 (1H, m), 2.30-2.47 (2H, m), 2.70 (1H, dd, J=13.3, 6.7 Hz), 2.80 (1H, dd, J=13.3, 4.7 Hz), 3.75-3.85 (1H, m), 3.80 (3H, s), 4.33 (1H, d, J=8.5 Hz), 6.85 (2H, d, J=8.5 Hz), 7.08 (2H, d, J=8.5 Hz).

Reference Example 66

Tert-Butyl (4-(5-hydroxy-1,2,4-oxadiazol-3-yl)-1-(4-methoxyphenyl)butan-2-yl) carbamate

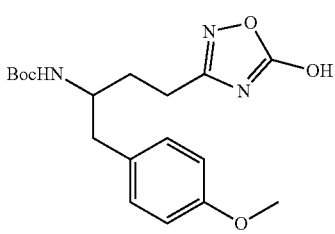

[Chem. 114]

Using tert-butyl (E)-(4-cyano-1-(4-methoxyphenyl)butan-2-yl)carbamate as a starting material, the same method as in Reference Example 14-1 followed by the same method as in Reference Example 31-1 were performed to obtain the title compound.

$^1$H-NMR (400 MHz, CDCl$_3$) δ 1.41 (9H, s), 1.61-1.71 (1H, m), 1.79-1.89 (1H, m), 2.38-2.48 (1H, m), 2.66-2.84 (3H, m), 3.81 (3H, s), 3.82-3.89 (1H, m), 4.49 (1H, d, J=8.5 Hz), 6.87 (2H, d, J=8.5 Hz), 7.06 (2H, d, J=8.5 Hz), 10.96 (1H, s).

Reference Example 67-1

Tert-Butyl (S)-(2-(4-bromophenyl)-1-(5-(trichloromethyl)-1,2,4-oxadiazol-3-yl)ethyl)carbamate

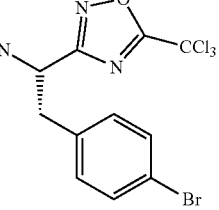

[Chem. 115]

To a suspension of tert-butyl (S,Z)-[1-amino-3-(4-bromophenyl)-1-(hydroxyimino)propan-2-yl]carbamate (1.41 g) in toluene under ice-cooling were added pyridine (0.38 mL) and trichloroacetic anhydride (0.863 mL), and the reaction mixture was stirred at room temperature for 10 minutes. And, the reaction mixture was heated to 80° C. and stirred for 1.5 hours. The reaction mixture was allowed to cool to room temperature, and a saturated aqueous sodium hydrogen carbonate was added to the reaction solution. The mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=20:1-1:3) to obtain the title compound as a colorless solid (1.34 g).

$^1$H-NMR (400 MHz, CDCl$_3$) δ 1.41 (9H, s), 3.09-3.25 (2H, m), 4.96-5.09 (1H, m), 5.28 (1H, br s), 6.99 (2H, d, J=8.5 Hz), 7.41 (2H, d, J=8.5 Hz).

Reference Examples 67-2 to 67-4

The following Reference Examples 67-2 to 67-4 were obtained using each corresponding starting material in the same method as in Reference Example 67-1.

The structures and spectral data thereof are shown in Table 34.

TABLE 34

| Ref.No | Str. | Chemical name | P.D. |
|---|---|---|---|
| 67-2 | BocHN—[CH(CH2-4-Cl-C6H4)]—(5-CCl3-1,2,4-oxadiazol-3-yl) | tert-butyl (S)-(2-(4-chlorophenyl)-1-(5-(trichloromethyl)-1,2,4-oxadiazol-3-yl)ethyl)-carbamate | $^1$H-NMR (400 MHz, CDCl$_3$) δ 1.41 (9H, s), 3.11-3.28 (2H, m), 5.04 (1H, d, J = 4.8 Hz), 5.23-5.33 (1H, m), 7.05 (2H, d, J = 7.9 Hz), 7.24 (2H, d, J = 7.9 Hz). |
| 67-3 | BocHN—[CH(CH2-4-Et-C6H4)]—(5-CCl3-1,2,4-oxadiazol-3-yl) | tert-butyl (S)-(2-(4-ethylphenyl)-1-(5-(trichloromethyl)-1,2,4-oxadiazol-3-yl)ethyl)-carbamate | 1H-NMR (400 MHz, CDCl$_3$) δ 1.21 (3H, t, J = 7.3 Hz), 1.41 (9H, s), 2.61 (2H, q, J = 7.3 Hz), 3.11-3.23 (2H, m), 5.05 (1H, br s), 5.28 (1H, br s), 7.00 (2H, d, J = 7.9 Hz), 7.11 (2H, d, J = 7.9 Hz). |
| 67-4 | BocHN—[CH(CH2-4-MeO-C6H4)]—(5-CCl3-1,2,4-oxadiazol-3-yl) | tert-butyl (S)-(2-(4-methoxyphenyl)-1-(5-(trichloromethyl)-1,2,4-oxadiazol-3-yl)ethyl)-carbamate | $^1$H-NMR (400 MHz, CDCl$_3$) δ 1.46 (9H, s), 2.99 (1H, dd, J = 13.9, 7.3 Hz), 3.07 (1H, dd, J = 13.9, 4.8 Hz), 3.82 (3H, s), 4.78 (2H, s), 6.91 (2H, d, J = 8.6 Hz), 7.22 (2H, d, J = 8.6 Hz). |

Reference Example 68-1

Tert-Butyl (S)-(2-(4-bromophenyl)-1-(5-((hydroxyethyl)amino)-1,2,4-oxadiazol-3-yl)ethyl)carbamate

[Chem. 116]

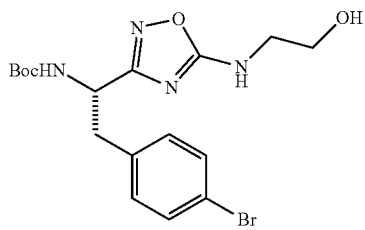

To a solution of tert-butyl (S)-(2-(4-bromophenyl)-1-(5-(trichloromethyl)-1,2,4-oxadiazol-3-yl)ethyl)carbamate (100 mg) in N,N-dimethylformamide was added ethanolamine (37.7 mg), and the reaction mixture was stirred at room temperature for 1 hour. Water was added to the reaction solution, and the mixture was extracted with ethyl acetate:hexane=2:1. The organic layer was washed with a brine, and dried over anhydrous sodium sulfate. The solvent was removed under reduced pressure, and the obtained residue was then purified by silica gel column chromatography (hexane:ethyl acetate=1:1-1:20) to obtain the title compound as a colorless solid (69.0 mg).

$^1$H-NMR (400 MHz, CDCl$_3$) δ 1.40 (9H, s), 2.04 (1H, br s), 2.99-3.18 (2H, m), 3.57 (2H, dd, J=5.4, 5.4 Hz), 3.85 (2H, dd, J=5.4, 5.4 Hz), 4.96-5.04 (2H, m), 5.61 (1H, br s), 7.02 (2H, d, J=8.5 Hz), 7.38 (2H, d, J=8.5 Hz).

Reference Examples 68-2 to 68-6

The following Reference Examples 68-2 to 68-6 were obtained using each corresponding starting material in the same method as in Reference Example 68-1.

The structures and spectral data thereof are shown in Table 35.

TABLE 35

| Ref.No | Str. | Chemical name | P.D. |
| --- | --- | --- | --- |
| 68-2 | | tert-butyl (S)-(2-(4-ethyl-phenyl)-1-(5-((hydroxyethyl)-amino)-1,2,4-oxadiazol-3-yl)ethyl)-carbamate | ¹H-NMR (400 MHz, CDCl₃) δ 1.20 (3H, t, J = 7.9 Hz), 1.39 (9H, s), 2.42 (1H, s), 2.60 (2H, q, J = 7.9 Hz), 2.99-3.18 (2H, m), 3.55 (2H, q, J = 5.0 Hz), 3.79-3.86 (2H, m), 4.92-5.09 (2H, m), 5.93 (1H, s), 7.03-7.13 (4H, m). |
| 68-3 | | tert-butyl (S)-(1-(5-amino-1,2,4-oxadiazol-3-yl)-2-(4-methoxyphenyl)-ethyl)carbamate | ¹H-NMR (400 MHz, CDCl₃) δ 1.29 (9H, s), 2.83 (1H, dd, J = 13.9, 9.1 Hz), 2.95 (1H, dd, J = 13.9, 5.4 Hz), 3.69 (3H, s), 4.48-4.58 (1H, m), 6.31 (2H, d, J = 8.6 Hz), 7.11 (2H, d, J = 8.6 Hz), 7.23 (1H, d, J = 8.5 Hz), 7.71 (2H, s). |
| 68-4 | | tert-butyl (S)-(2-(4-methoxy-phenyl)-1-(5-(methylamino)-1,2,4-oxadiazol-3-yl)ethyl)-carbamate | ¹H-NMR (400 MHz, CDCl₃) δ 1.57 (9H, s), 3.07 (3H, s), 3.08-3.18 (2H, m), 3.77 (3H, s), 4.99 (2H, br s), 5.10 (1H, br s), 6.80 (2H, d, J = 8.6 Hz), 7.05 (2H, d, J = 8.6 Hz). |
| 68-5 | | tert-butyl (S)-(1-(5-(dimethyl-amino)-1,2,4-oxadiazol-3-yl)-2-(4-methoxy-phenyl)ethyl)-carbamate | ¹H-NMR (400 MHz, CDCl₃) δ 1.57 (9H, s), 3.03-3.12 (2H, m), 3.14 (6H, s), 3.77 (3H, s), 4.91-5.05 (2H, m), 6.80 (2H, d, J = 8.6 Hz), 7.06 (2H, d, J = 8.6 Hz). |
| 68-6 | | tert-butyl (S)-(1-(5-(3-hydroxy-azetidin-1-yl)-1,2,4-oxadiazol-3-yl)-2-(4-methoxyphenyl)-ethyl)carbamate | ¹H-MMR (400 MHz, CDCl₃) δ 1.41 (9H, s), 2.99-3.08 (1H, m), 3.08-3.17 (1H, m), 3.79 (3H, s), 4.15 (2H, dd, J = 9.7, 4.2 Hz), 4.48 (2H, dd, J = 9.7, 6.7 Hz), 4.82-4.92 (2H, m), 4.96-5.03 (2H, m), 6.82 (2H, d, J = 8.6 Hz), 7.05 (2H, d, J = 3.6 Hz). |

Reference Example 69

Tert-Butyl (S)-(1-(5-((2-tert-butyldimethylsilyl)oxy)ethyl)amino)-1,2,4-oxadiazol-3-yl)-2-(4-ethylphenyl)ethyl)carbamate

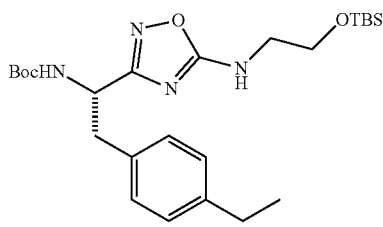

[Chem. 117]

To a solution of tert-butyl (S)-(2-(4-ethylphenyl)-1-(5-((hydroxyethyl)amino)-1,2,4-oxadiazol-3-yl)ethyl)carbamate (400 mg) in dichloromethane (2.6 mL) were added diisopropylethylamine (0.26 mL) and tert-butyldimethylchlorosilane (156 mg), and the reaction mixture was stirred at room temperature for 16 hours. The reaction solution was purified by silica gel column chromatography (hexane:ethyl acetate=20:1-1:2) to obtain the title compound as a colorless oil (366 mg).

$^1$H-NMR (400 MHz, CDCl$_3$) δ 0.08 (6H, s), 0.91 (9H, s), 1.20 (3H, t, J=7.9 Hz), 1.39 (9H, s), 2.60 (2H, q, J=7.9 Hz), 3.00-3.10 (1H, m), 3.10-3.21 (1H, m), 3.51 (2H, q, J=5.4 Hz), 3.78 (2H, t, J=5.4 Hz), 4.93-5.05 (2H, m), 5.47 (1H, br s), 7.05 (2H, d, J=7.9 Hz), 7.09 (2H, d, J=7.9 Hz).

Reference Example 70

Tert-Butyl (S)-(1-(5-((2-((tert-butyldimethylsilyl)oxy)ethyl(methyl)amino)-1,2,4-oxadiazol-3-yl)-2-(4-ethylphenyl)ethyl)carbamate

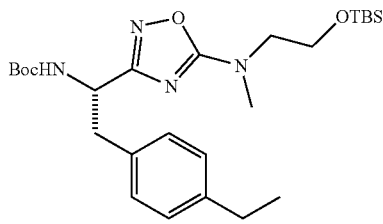

[Chem. 118]

To a solution of tert-butyl (S)-(1-(5-((2-tert-butyldimethylsilyl)oxy)ethyl)amino)-1,2,4-oxadiazol-3-yl)-2-(4-ethylphenyl)ethyl)carbamate (360 mg) in N,N-dimethylformamide (3.7 mL) were added potassium carbonate (203 mg) and iodomethane (91.2 μL), and the reaction mixture was stirred at 50° C. for 8 hours. Water was added to the reaction solution, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=1:4) to obtain the title compound as a colorless oil (200 mg).

$^1$H-NMR (400 MHz, CDCl$_3$) δ 0.05 (6H, s), 0.88 (9H, s), 1.20 (3H, t, J=7.9 Hz), 1.39 (9H, s), 2.60 (2H, q, J=7.9 Hz), 3.01-3.09 (1H, m), 3.10-3.18 (1H, m), 3.21 (3H, s), 3.56 (2H, t, J=5.4 Hz), 3.82 (2H, t, J=5.4 Hz), 4.74-5.04 (2H, m), 7.05 (2H, d, J=7.9 Hz), 7.09 (2H, d, J=7.9 Hz).

Reference Example 71

Tert-Butyl (S)-(2-(4-ethylphenyl)-1-(5-((2-hydroxyethyl(methyl)amino)-1,2,4-oxadiazol-3-yl)ethyl)carbamate

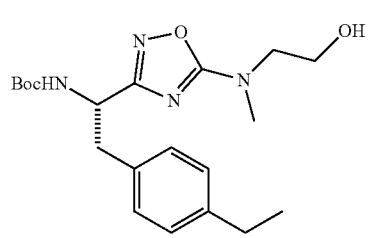

[Chem. 119]

To a solution of tert-butyl (S)-(1-(5-((2-((tert-butyldimethylsilyl)oxy)ethyl(methyl)amino)-1,2,4-oxadiazol-3-yl)-2-(4-ethylphenyl)ethyl)carbamate (200 mg) in tetrahydrofuran (2.0 mL) was added tetrabutylammonium fluoride (1 mol/L tetrahydrofuran solution, 0.475 mL), and the reaction mixture was stirred at 0° C. for 30 minutes. Water was added to the reaction solution, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=1:20-20:1) to obtain the title compound as a colorless solid (135 mg).

$^1$H-NMR (400 MHz, DMSO-d$_6$) δ 1.13 (3H, t, J=7.9 Hz), 1.28 (9H, s), 2.54 (2H, q, J=7.9 Hz), 2.88 (1H, dd, J=13.3, 9.7 Hz), 2.97 (1H, dd, J=13.3, 5.4 Hz), 3.09 (3H, s), 3.46 (2H, t, J=5.4 Hz), 3.55-3.61 (2H, m), 4.53-4.62 (1H, m), 4.84 (1H, t, J=5.4 Hz), 7.08 (2H, d, J=7.9 Hz), 7.13 (2H, d, J=7.9 Hz), 7.27 (1H, d, J=9.1 Hz).

Reference Example 72-1

Tert-Butyl (S)-(2-(4-methoxyphenyl)-1-(2H-tetrazol-5-yl)ethyl)carbamate

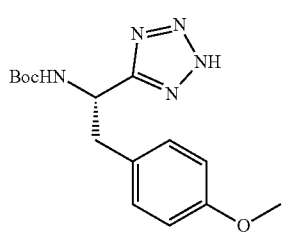

[Chem. 120]

To a mixture of tert-butyl (S)-[1-cyano-2-(4-methoxyphenyl)ethyl]carbamate (19.8 g) and sodium azide (18.6 g) were added a solution of triethylamine (39.7 mL)-acetic acid (16.4 mL) in toluene (72 mL), and the reaction mixture was stirred at 100° C. for 15 minutes and then under reflux for 1.5 hours. The reaction mixture was allowed to cool to room temperature, a 10k aqueous citric acid and ethyl acetate were added thereto, the organic layer was separated, and the aqueous layer was extracted with ethyl acetate (×2). The combined organic layer was washed with water and then a brine, and dried over anhydrous sodium sulfate. The filtrate was concentrated under reduced pressure, and the obtained residue was triturated with diisopropyl ether to obtain the title compound as a light brown solid (19.1 g).

$^1$H-NMR (400 MHz, DMSO-$d_6$) δ 1.30 (9H, s), 3.04 (1H, m), 3.13 (1H, m), 3.69 (3H, s), 4.95 (1H, m), 6.80 (2H, d, J=8.5 Hz), 7.09 (2H, d, J=8.5 Hz), 7.55 (1H, m), 16.16 (1H, br s).

Reference Examples 72-2 to 72-7

The following Reference Examples 72-2 to 72-7 were obtained using each corresponding starting material in the same method as in Reference Example 72-1.

The structures and spectral data thereof are shown in Tables 36 and 37.

TABLE 36

| Ref.No | Str. | Chemical name | P.D. |
| --- | --- | --- | --- |
| 72-2 | (BocHN, 4-bromophenyl-CH2-CH-tetrazole) | tert-butyl (S)-(2-(4-bromophenyl)-1-(2H-tetrazol-5-yl)ethyl)-carbamate | $^1$H-NMR (400 MHz, DMSO-$d_6$) δ 1.23 (9H, s), 3.07 (1H, dd, J = 13.3, 9.7 Hz), 3.21 (1H, dd, J = 13.3, 6.1 Hz), 4.98-5.09 (1H, m), 7.17 (2H, d, J = 8.5 Hz), 7.45 (2H, d, J = 8.5 Hz), 7.58 (1H, d, J = 7.9 Hz), 16.24 (1H, s). |
| 72-3 | (BocHN, 4-chlorophenyl-CH2-CH-tetrazole) | tert-butyl (S)-(2-(4-chlorophenyl)-1-(2H-tetrazol-5-yl)-ethyl)carbamate | $^1$H-NMR (400 MHz, CDCl$_3$) δ 1.28 (9H, s), 3.09 (1H, dq, J = 13.5, 9.8 Hz), 3.23 (1H, dd, J = 13.5, 13.5 Hz), 5.04 (1H, s), 7.23 (2H, d, J = 8.5 Hz), 7.32 (2H, d, J = 8.5 Hz), 7.60 (1H, d, J = 7.9 Hz), 16.22 (1H, s). |
| 72-4 | (BocHN, 2,3-dihydrobenzofuran-5-yl-CH2-CH-tetrazole) | tert-butyl (S)-(2-(2,3-dihydrobenzofuran-5-yl)-1-(2H-tetrazol-5-yl)ethyl)-carbamate | $^1$H-NMR (400 MHz, DMSO-$d_6$) δ 1.30 (9H, s), 2.98-3.15 (2H, m), 3.09 (2H, t, J = 8.8 Hz), 4.45 (2H, t, J = 8.8 Hz), 4.91-5.00 (1H, m), 6.62 (1H, d, J = 7.3 Hz), 6.87 (1H, d, J = 7.3 Hz), 7.05 (1H, s), 7.56 (1H, d, J = 7.9 Hz), 16.2 (1H, brs). |
| 72-5 | (CbzHN, 4-methoxyphenyl-CH2-CH-tetrazole) | benzyl (S)-(2-(4-methoxyphenyl)-1-(2H-tetrazol-5-yl)ethyl)-carbamate | $^1$H-NMR (400 MHz, DMSO-$d_6$) δ 3.05 (1H, dd, J = 13.4, 9.8 Hz), 3.20 (1H, dd, J = 13.4, 7.6 Hz), 3.69 (3H, s), 4.96 (2H, q, J = 12.8 Hz), 5.06 (1H, q, J = 9.2 Hz), 6.81 (2H, d, J = 8.5 Hz), 7.12 (2H, d, J = 8.5 Hz), 7.23-7.33 (5H, m), 8.08 (1H, d, J = 7.9 Hz), 16.27 (1H, brs). |

TABLE 37

| Ref.No | Str. | Chemical name | P.D. |
|---|---|---|---|
| 72-6 | | tert-butyl ((1S,2S)-2-(4-methoxyphenyl)-1-(2H-tetrazol-5-yl)propyl)-carbamate | ¹H-NMR (400 MHz, CDCl₃) δ 1.44-1.47 (12H, m), 3.39-3.42 (1H, m), 3.74 (3H, s), 5.04-5.08 (1H, m), 5.44 (1H, br), 6.75 (2H, d, J = 9.1 Hz), 6.98 (2H, d, J = 9.1 Hz). |
| 72-7 | | tert-butyl ((1S,2R)-2-(4-methoxyphenyl)-1-(2H-tetrazol-5-yl)propyl)-carbamate | ¹H-NMR (400 MHz, CDCl₃) δ 1.20 (3H, d, J = 6.7 Hz), 1.40 (9H, s), 3.69 (1H, br), 3.32 (3H, s), 4.91 (1H, br), 5.08-5.10 (1H, m), 6.89 (2H, d, J = 8.5 Hz), 7.13-7.16 (2H, m). |

Reference Example 73-1

Tert-Butyl (S)-(1-(2-(2-hydroxyethyl)-2H-tetrazol-5-yl)-2-(4-methoxyphenyl)ethyl)carbamate

[Chem. 121]

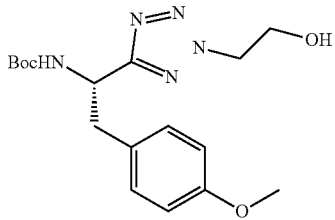

To a solution of tert-butyl (S)-(2-(4-methoxyphenyl)-1-(2H-tetrazol-5-yl)ethyl)carbamate (15.0 g) in N,N-dimethylformamide (118 mL) were added potassium carbonate (7.95 g) and 2-bromoethane (4.24 mL), and the reaction mixture was stirred at 50° C. Every 2 hours later, potassium carbonate (3.98 g) and 2-bromoethane (2.12 mL) were added thereto (totally 5 times), and the mixture was stirred at 50° C. for a day. The reaction mixture was allowed to cool to room temperature, water and ethyl acetate were added thereto, and the organic layer was separated. The organic layer was washed with water and then a brine, and dried over anhydrous sodium sulfate. The filtrate was concentrated under reduced pressure, and the obtained residue was then purified by silica gel column chromatography (ethyl acetate:hexane=2:3) to obtain the title compound as a colorless oil (10.6 g).

¹H-NMR (400 MHz, CDCl₃) δ 1.41 (9H, s), 2.22 (1H, m), 3.18 (2H, d, J=6.1 Hz), 3.76 (3H, s), 4.09 (2H, m), 4.69 (2H, m), 5.20 (1H, m), 5.32 (1H, m), 6.77 (2H, d, J=8.5 Hz), 6.94 (2H, d, J=8.5 Hz).

Reference Examples 73-2 to 73-14

The following Reference Examples 73-2 to 73-14 were obtained using each corresponding starting material in the same method as in Reference Example 73-1.

The structures and spectral data thereof are shown in Tables 38-41.

TABLE 38

| Ref.No | Str. | Chemical name | P.D. |
|---|---|---|---|
| 73-2 | | tert-butyl (S)-(2-(4-bromophenyl)-1-(2-(2-hydroxyethyl)-2H-tetrazol-5-yl)ethyl)carbamate | ¹H-NMR (400 MHz, DMSO-d₆) δ 1.28 (9H, s), 3.02 (1H, dd, J = 13.6, 9.7 Hz), 3.15 (1H, dd, J = 13.6, 5.4 Hz), 3.84-3.90 (2H, m), 4.65 (2H, t, J = 5.1 Hz), 4.97-5.05 (2H, m), 7.19 (2H, d, J = 8.5 Hz), 7.44 (2H, d, J = 8.5 Hz), 7.51 (1H, d, J = 9.1 Hz). |

TABLE 38-continued

| Ref.No | Str. | Chemical name | P.D. |
|---|---|---|---|
| 73-3 | | tert-butyl (S)-(2-(4-chlorophenyl)-1-(2-(2-hydroxyethyl)-2H-tetrazol-5-yl)ethyl)carbamate | $^1$H-NMR (400 MHz, CDCl$_3$) δ 1.39 (9H, s), 2.25 (1H, t, J = 5.8 Hz), 3.22 (2H, t, J = 5.4 Hz), 4.12 (2H, q, J = 5.4 Hz), 4.70 (2H, t, J = 5.4 Hz), 5.20 (1H, d, J = 7.3 Hz), 5.35 (1H, d, J = 7.3 Hz), 6.99 (2H, d, J = 7.9 Hz), 7.21 (2H, d, J = 7.9 Hz). |
| 73-4 | | tert-butyl (S)-(2-(2,3-dihydro-benzofuran-5-yl)-1-(2-(2-hydroxyethyl)-2H-tetrazol-5-yl)ethyl)carbamate | $^1$H-NMR (400 MHz, CDCl$_3$) δ 1.42 (9H, s), 2.20 (1H, brs), 3.10-3.19 (4H, m), 4.07-4.14 (2H, m), 4.52 (2H, t, J = 8.5 Hz), 4.69 (2H, t, J = 5.1 Hz), 5.15-5.22 (1H, m), 5.31 (1H, brs), 6.63 (1H, d, J = 8.1 Hz), 6.72 (1H, d, J = 8.1 Hz), 6.89 (1H, s). |
| 73-5 | | tert-butyl ((1S,2S)-1-(2-(2-hydroxyethyl)-2H-tetrazol-5-yl)-2-phenyl)propyl)-carbamate | $^1$H-NMR (400 MHz, CDCl$_3$) δ 1.29 (3H, d, J = 6.7 Hz), 1.37 (9H, s), 2.47 (1H, br), 3.36-3.38 (1H, m), 3.77 (3H, s), 4.09-4.10 (2H, m), 4.68-4.70 (2H, m), 5.06-5.08 (1H, m), 5.23-5.28 (1H, m), 6.79 (2H, d, J = 8.5 Hz), 6.98 (2H, d, J = 8.5 Hz). |

TABLE 39

| Ref.No | Str. | Chemical name | P.D. |
|---|---|---|---|
| 73-6 | | tert-butyl ((1S,2R)-1-(2-(2-hydroxyethyl)-2H-tetrazol-5-yl)-2-(4-methoxy-phenyl)propyl)-carbamate | $^1$H-NMR (400 MHz, CDCl$_3$) δ 1.39-1.42 (12H, m), 2.37 (1H, br), 3.21-3.28 (1H, m), 3.74 (3H, s), 3.98 (2H, br), 4.60-4.62 (2H, m), 5.19-5.23 (1H, m), 5.33-5.36 (1H, m), 6.73 (2H, d, J = 8.5 Hz), 6.91 (2H, d, J = 8.5 Hz). |
| 73-7 | | (S)-tert-butyl (1-(2-(3-hydroxypropyl)-2H-tetrazol-5-yl)-2-(4-methoxyphenyl)-ethyl)carbamate | $^1$H-NMR (400 MHz, CDCl$_3$) δ 1.41 (9H, s), 2.12-2.18 (2H, m), 3.18 (2H, d, J = 6.1 Hz), 3.58 (2H, d, J = 6.1 Hz), 3.76 (3H, s), 4.71 (2H, t, J = 6.7Hz), 5.20 (1H, s), 5.31 (1H, brs), 6.75 (2H, d, J = 8.6 Hz), 6.93 (2H, d, J = 8.6 Hz). |

TABLE 39-continued

| Ref.No | Str. | Chemical name | P.D. |
|---|---|---|---|
| 73-8 | BocHN, tetrazole-CH2CH2CH2CH2OH, 4-methoxyphenyl | (S)-tert-butyl (1-(2-(4-hydroxybutyl)-2H-tetrazol-5-yl)-2-(4-methoxyphenyl)-ethyl)carbamate | ¹H-NMR (400 MHz, CDCl₃) δ 1.40 (9H, s), 1.46-1.51 (2H, m), 2.00-2.08 (2H, m), 3.18 (2H, d, J = 6.1 Hz), 3.63 (2H, d, J = 6.1 Hz), 3.75 (3H, s), 4.59 (2H, d, J = 6.7 Hz), 5.20 (1H, brs), 5.32 (1H, J = brs), 6.75 (2H, d, J = 8.6 Hz), 6.92 (2H, d, J = 8.6 Hz). |
| 73-9 | BocHN, tetrazole-CH2SMe, 4-methoxyphenyl, regioisomers mixture (1:1) | tert-butyl (S)-(2-(4-methoxyphenyl)-1-(2-((methylthio)-methyl)-2H-tetrazol-5-yl)-ethyl)carbamate | ¹H-NMR (400 MHz, CDCl₃) δ 1.38 (9H, s), 1.42 (9H, s), 1.97 (3H, s,), 2.19 (3H, s), 3.19 (2H, d, J = 6.1 Hz), 3.27 (2H, d, J = 6.1 Hz), 3.75 (3H, s), 3.76 (3H, s), 5.01 (1H, d, J = 14.5 Hz), 5.21-5.34 (5H, m), 5.50 (2H, s), 6.77 (4H, t, J = 8.5 Hz), 6.93 (2H, d, J = 8.5 Hz), 7.04 (2H, d, J = 8.5 Hz). |

TABLE 40

| Ref.No | Str. | Chemical name | P.D. |
|---|---|---|---|
| 73-10 | BocHN, tetrazole-CH2CH2SMe, 4-methoxyphenyl, regioisomers mixture (1:1) | tert-butyl (S)-(2-(4-methoxyphenyl)-1-(2-(2-(methylthio)-ethyl)-2H-tetrazol-5-yl)-ethyl)carbamate | ¹H-NMR (400 MHz, CDCl₃) δ 1.37 (9H, s), 1.39 (9H, s), 1.98 (3H, s), 2.07 (3H, s), 2.42-2.49 (1H, m), 2.68-2.72 (1H, m), 2.99 (2H, t, J = 7.0 Hz), 3.14-3.31 (4H, m), 3.74 (6H, s), 4.12-4.22 (2H, m), 4.72 (2H, t, J = 7.0 Hz), 5.06-5.32 (4H, m), 6.74 (2H, d, J = 7.9 Hz), 6.75 (2H, d, J = 7.9 Hz), 6.91 (2H, d, J = 7.9 Hz), 6.95 (2H, d, J = 7.9 Hz). |
| 73-11 | BocHN, tetrazole-CH2CH2NHSO2Me, 4-chlorophenyl | tert-butyl (S)-(2-(4-chlorophenyl)-1-(2-(2-(methyl-sulfonamide)-ethyl)-2H-tetrazol-5-yl)-ethyl)carbamate | 1H-NMR (400 MHz, CDCl₃) δ 1.39 (9H, s), 2.94 (3H, s), 3.22 (2H, d, J = 6.7 Hz), 3.71 (2H, q, J = 6.7 Hz), 4.74 (2H, t, J = 5.4 Hz), 4.87 (1H, s), 5.20 (1H, d, J = 3.5 Hz), 5.33 (1H, d, J = 8.5 Hz), 7.01 (2H, d, J = 8.5 Hz), 7.23 (2H, d, J = 8.5 Hz). |

TABLE 40-continued

| Ref.No | Str. | Chemical name | P.D. |
|---|---|---|---|
| 73-12 | | tert-butyl (S)-3-(5-(1-((benzyloxy)carbonyl)-amino)-2-(4-methoxyphenyl)-ethyl)-2H-tetrazol-2-yl)-ethyl)carbamate | $^1$H-NMR (400 MHz, CDCl$_3$) δ 1.44 (9H, s), 3.21 (2H, s), 3.63 (2H, d, J = 4.8 Hz), 3.75 (3H, s), 4.65 (3H, brs), 5.10 (2H, dd, J = 21.8, 12.1 Hz), 5.41 (2H, s), 6.75 (2H, d, J = 8.5 Hz), 6.91 (2H, d, J = 8.5 Hz), 7.31-7.35 (5H, m). |
| 73-13 | | tert-butyl (S)-3-(5-(1-((benzyloxy)-carbonyl)amino)-2-(4-methoxy-phenyl)ethyl)-2H-tetrazol-2-yl)azetidin-1-carboxylate | $^1$H-NMR (400 MHz, CDCl$_3$) δ 1.47 (9H, s), 3.22 (2H, brs), 3.76 (3H, s), 4.37 (1H, brs), 4.46 (2H, t, J = 8.8 Hz), 5.05-5.14 (2H, m), 5.40-5.54 (3H, m), 6.75 (2H, d, J = 8.5 Hz), 6.92 (2H, d, J = 8.5 Hz), 7.33 (5H, brs). |

30

TABLE 41

| Ref.No | Str. | Chemical name | P.D. |
|---|---|---|---|
| 73-14 | | ethyl (S)-2-(5-(1-((tert-butoxycarbonyl)-amino)-2-(4-methoxyphenyl)-ethyl)-2H-tetrazol-2-yl)acetate | $^1$H-NMR (400 MHz, CDCl$_3$) δ 1.29 (3H, t, J = 7.4 Hz), 1.41 (9H, s), 3.21 (2H, s), 3.76 (3H, s), 4.25 (2H, dd, J = 6.8, 14.1 Hz), 5.18 (1H, s), 5.35 (2H, s), 6.77 (2H, d, J = 8.6 Hz), 6.93 (2H, d, J = 8.6 Hz). |

Reference Example 74

Tert-Butyl (S)-(2-(4-cyanophenyl)-1-(2-(2-hydroxyethyl)-2H-tetrazol-5-yl)ethyl)carbamate

[Chem. 122]

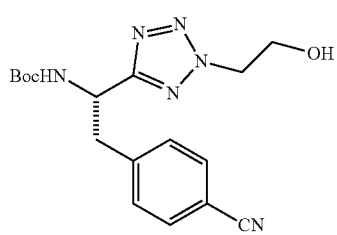

To a solution of tert-butyl (S)-(2-(4-bromophenyl)-1-(2-(2-hydroxyethyl)-2H-tetrazol-5-yl)ethyl)carbamate (216 mg) in N,N-dimethylformamide (6 mL) was added zinc cyanide (87.5 mg). Tetrakis(triphenylphosphine)palladium (0) (121 mg) was added thereto, and the reaction mixture was stirred under heating at 110° C. for 4 hours. The reaction mixture was allowed to cool to room temperature, water was added thereto, and the mixture was extracted with ethyl acetate. The organic layer was washed with water and then a brine, and dried over anhydrous sodium sulfate. The solvent was removed under reduced pressure, and the obtained residue was then purified by silica gel column chromatography (hexane:ethyl acetate=20:1-1:4) to obtain the title compound as a colorless solid (166 mg).

$^1$H-NMR (400 MHz, CDCl$_3$) δ 1.41 (9H, s), 2.16 (1H, t, J=6.1 Hz), 3.27 (1H, dd, J=13.3, 6.1 Hz), 3.35 (1H, dd, J=13.3, 6.1 Hz), 4.11-4.16 (2H, m), 4.71 (2H, t, J=5.1 Hz), 5.22 (1H, d, J=7.3 Hz), 5.35-5.44 (1H, m), 7.20 (2H, d, J=7.9 Hz), 7.54 (2H, d, J=7.9 Hz).

Reference Example 75-1

Tert-Butyl (S)-(2-(5-(1-amino-(4-methoxyphenyl)ethyl)-2H-tetrazol-2-yl)ethyl)carbamate

[Chem. 123]

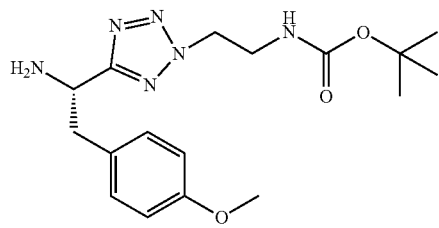

To a solution of tert-butyl (S)-3-(5-(1-((benzyloxy)carbonyl)amino)-2-(4-methoxyphenyl)ethyl)-2H-tetrazol-2-yl)ethyl)carbamate (1.0 g) in methanol (10 mL) was added 10% palladium-carbon (100 mg), and the reaction mixture was stirred under hydrogen atmosphere at room temperature for 1 hour. The reaction solution was filtered over Celite, the solvent of the filtrate was concentrated under reduced pressure to obtain the title compound as a light yellow liquid (868 mg).

$^1$H-NMR (400 MHz, CDCl$_3$) δ 1.44 (9H, s), 1.67 (2H, brs), 3.00 (1H, dd, J=13.9, 8.5 Hz), 3.25 (1H, dd, J=13.9, 5.4 Hz), 3.70 (2H, q, J=5.7 Hz), 3.78 (3H, s), 4.49 (2H, dd, J=8.5, 5.4 Hz), 4.68 (1H, t, J=5.4 Hz), 4.77 (1H, s), 6.83 (2H, d, J=8.5 Hz), 7.09 (2H, d, J=8.5 Hz).

Reference Example 75-2

The following Reference Example 75-2 was obtained using the corresponding starting material in the same method as in Reference Example 75-1.

The structure and spectral data thereof are shown in Table 42.

Reference Example 76-1

Tert-Butyl (S)-(2-(4-methoxyphenyl)-1-(2-(2-(methylsulfonyl)methyl)-2H-tetrazol-5-yl)ethyl)carbamate

[Chem. 124]

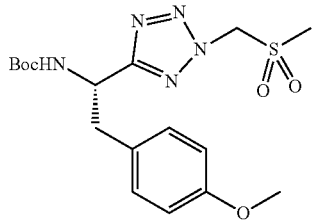

To a solution of tert-butyl (S)-(2-(4-methoxyphenyl)-1-(2-((methylthio)methyl)-2H-tetrazol-5-yl)ethyl)carbamate (300 mg) in dichloromethane (4.0 mL) under ice-cooling was added meta-chloroperbenzoic acid (432 mg), and the reaction mixture was stirred at room temperature for 2 hours. The reaction solution was ice-cooled, an aqueous sodium sulfite was added thereto, and the mixture was extracted with chloroform. The organic layer was washed with a saturated sodium hydrogen carbonate and a brine, and the organic layer was dried over anhydrous sodium sulfate. The solvent was removed under reduced pressure, and the residue was then purified by silica gel column chromatography (hexane ethyl acetate=2:1) to obtain the title compound as a white solid (157 mg).

$^1$H-NMR (400 MHz, CDCl$_3$) δ 1.42 (9H, s), 2.89 (3H, s), 3.15-3.23 (2H, m), 3.75 (3H, s), 5.21 (1H, brs), 5.34 (1H, brs), 6.76 (2H, d, J=8.5 Hz), 6.91 (2H, d, J=8.5 Hz).

Reference Example 76-2

The following Reference Example 76-2 was obtained using the corresponding starting material in the same method as in Reference Example 76-1.

The structure and spectral data thereof are shown in Table 43.

TABLE 42

| Ref.No | Str. | Chemical name | P.D. |
|---|---|---|---|
| 75-2 | | tert-butyl (S)-3-(5-(1-amino-2-(4-methoxyphenyl)-ethyl)-2H-tetrazol-2-yl)azetidin-1-carboxylate | $^1$H-NMR (400 MHz, CDCl$_3$) δ 1.47 (9H, s), 2.98 (2H, dd, J = 13.6, 8.8 Hz), 3.26 (2H, dd, J = 13.6, 5.1 Hz), 3.79 (3H, s), 4.42-4.53 (5H, m), 5.55-5.62 (1H, m), 6.83 (2H, d, J = 8.6 Hz), 7.10 (2H, d, J = 8.6 Hz). |

TABLE 43

| Ref. No | Str. | Chemical name | P.D. |
|---|---|---|---|
| 76-2 | | tert-butyl (S)-(2-(4-methoxyphenyl)-1-(2-(2-(methylsulfonyl)ethyl)-2H-tetrazol-5-yl)ethyl)carbamate | $^1$H-NMR (400 MHz, CDCl$_3$) δ 1.36 (9H, s), 2.75 (3H, s), 3.04-3.10 (1H, m), 3.18 (1H, dd, J = 13.3, 10.3 Hz), 3.28-3.40 (2H, m), 3.74 (3H, s), 4.38-4.45 (1H, m), 4.48-4.58 (1H, m), 5.02 (1H, ddd, J = 12.1, 6.1, 3.6 Hz), 5.27 (1H, brd, J = 8.5 Hz), 6.77 (2H, d, J = 8.5 Hz), 6.95 (2H, d, J = 8.5 Hz). |

Reference Example 77

Tert-Butyl ((1S)-2-(4-methoxyphenyl)-1-(2-((methylsulfinyl)methyl)-2H-tetrazol-5-yl)ethyl)carbamate

[Chem. 125]

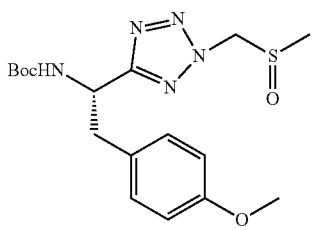

To a solution of tert-butyl (S)-(2-(4-methoxyphenyl)-1-(2-((methylthio)methyl)-2H-tetrazol-5-yl)ethyl)carbamate (730 mg) in dichloromethane (9.62 mL) under ice-cooling was added dropwise a solution of meta-chloroperbenzoic acid (432 mg) in dichloromethane (9.62 mL) over 1 hour, and the reaction mixture was stirred at the same temperature for 10 minutes. To the reaction solution was added an aqueous sodium sulfite, and the mixture was extracted with chloroform. The organic layer was washed with a saturated sodium hydrogen carbonate and a brine, and dried over anhydrous sodium sulfate. The solvent was removed under reduced pressure, and the residue was then purified by silica gel column chromatography (hexane:ethyl acetate=1:2-1:5) to obtain the title compound (regioisomers 1:1 mixture) as a white amorphous (378 mg).

$^1$H-NMR (400 MHz, CDCl$_3$) δ 1.41 (18H, s), 2.54 (3H, s), 2.57 (3H, s), 3.19 (4H, brs), 3.76 (6H, s), 5.20 (2H, brs), 5.35 (2H, brs), 5.51-5.62 (4H, m), 6.76 (4H, d, J=8.6 Hz), 6.93 (4H, d, J=8.6 Hz).

Reference Example 78

Tert-Butyl (S)-(1-amino-3-(4-methoxyphenyl)-1-((2-(methylthio)acetoxy)imino)propan-2-yl)carbamate

[Chem. 126]

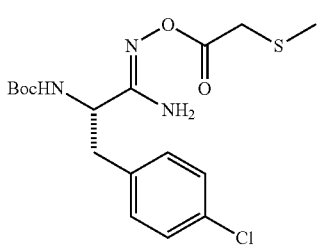

To a solution of 2-methylthioacetic acid (169 mg) in N,N-dimethylformamide (5.2 mL) was added tert-butyl (S,Z)-[1-amino-3-(4-chlorophenyl)-1-(hydroxyimino)propan-2-yl]carbamate (500 mg), and the reaction mixture was ice-cooled. To the reaction mixture were added diisopropylethylamine (0.68 mL) and O-(7-azabenzotriazol-1-yl)-N,N,N',N'-tetramethyluronium hexafluorophosphate (750 mg), and the reaction mixture was stirred at room temperature for 1 hour. Water was added thereto, and the precipitated solid was collected by filtration to obtain the title compound as a colorless solid (535 mg).

$^1$H-NMR (400 MHz, DMSO-d$_6$) δ 1.27 (9H, s), 2.12 (3H, s), 2.82 (1H, dd, J=13.9, 9.7 Hz), 2.93 (1H, dd, J=13.9, 4.8 Hz), 3.33 (2H, s), 4.14-4.25 (1H, m), 6.42 (2H, s), 6.98 (1H, d, J=9.7 Hz), 7.26 (2H, d, J=8.5 Hz), 7.32 (2H, d, J=8.5 Hz).

Reference Example 79

Tert-Butyl (S)-(2-(4-chlorophenyl)-1-(5-((methylthio)methyl)-1,2,4-oxadiazol-3-yl)ethyl)carbamate

[Chem. 127]

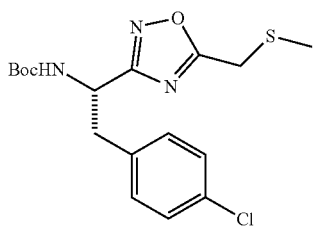

To a solution of tert-butyl (S)-(1-amino-3-(4-methoxyphenyl)-1-((2-(methylthio)acetoxy)imino)propan-2-yl)carbamate (500 mg) in tetrahydrofuran (3 mL) was added tetrabutylammonium fluoride (1 mol/L tetrahydrofuran solution, 1.25 mL), and the reaction mixture was stirred at 50° C. for 30 minutes. The reaction mixture was allowed to cool to room temperature, water was added thereto, and the mixture was extracted with ethyl acetate. The solvent was removed under reduced pressure, and the obtained residue was then purified by silica gel column chromatography (hexane:ethyl acetate=8:1-2:1) to obtain the title compound as a colorless solid (317 mg).

$^1$H-NMR (400 MHz, CDCl$_3$) δ 1.41 (9H, s), 2.21 (3H, s), 3.08-3.23 (2H, m), 3.81 (2H, s), 5.05 (1H, d, J=7.3 Hz), 5.17-5.25 (1H, m), 7.03 (2H, d, J=8.5 Hz), 7.23 (2H, d, J=8.5 Hz).

Reference Example 80

Tert-Butyl (3-(4-methoxyphenyl)-1-(methylsulfona-mide)-1-oxopropan-2-yl)carbamate

[Chem. 128]

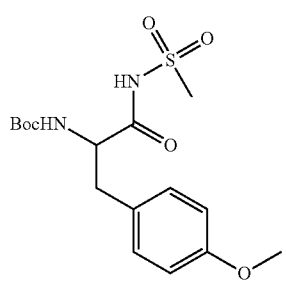

To a solution of 2-((tert-butoxycarbonyl)amino)-3-(4-methoxyphenyl)propionic acid (300 mg) in dichloromethane (10.0 mL) were added methanesulfonamide (100 mg) and 4-dimethylaminopyridine (120 mg) at room temperature and then N,N'-dicyclohexylcarbodiimide (210 mg) under ice-cooling, and the reaction mixture was stirred at room temperature for 80 minutes. The insoluble was removed by filtration, the solvent was removed under reduced pressure, and the obtained residue was then purified by silica gel column chromatography (hexane:acetone=2:1) to obtain the title compound as a colorless solid (109 mg).

$^1$H NMR (400 MHz, DMSO-$d_6$) δ 1.30 (9H, s), 2.66 (1H, dd, J=13.3, 10.9 Hz), 2.88 (1H, dd, J=13.3, 3.6 Hz), 3.18 (3H, s), 3.70 (3H, s), 4.12 (1H, s), 6.83 (2H, d, J=8.5 Hz), 7.15 (1H, s), 7.21 (2H, d, J=8.5 Hz), 11.96 (1H, s).

Reference Example 81

Tert-Butyl (1-((1H-tetrazol-5-yl)amino)-3-(4-methoxyphenyl)-1-oxopropan-2-yl)carbamate

[Chem. 129]

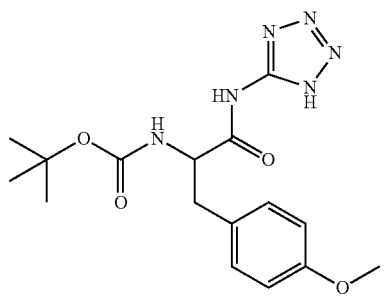

To a solution of 2-((tert-butoxycarbonyl)amino)-3-(4-methoxyphenyl)propionic acid (100 mg) in N,N-dimethylformamide (1.7 mL) were added 5-amino-1H-tetrazole (144 mg), 4-dimethylaminopyridine (49.6 mg) and 1-ethyl-3-(3-dimethylaminopropyl)carbodiimide hydrochloride (77.9 mg), and the reaction mixture was stirred at room temperature for 2 days. Water was added to the reaction solution, and the mixture was extracted with ethyl acetate. The organic layer was washed with water and then a brine, and dried over anhydrous sodium sulfate. The solvent was removed under reduced pressure to obtain the title compound as a colorless solid (73.7 mg).

$^1$H NMR (400 MHz, DMSO-$d_6$) δ 1.31 (9H, s), 2.69-2.79 (1H, m), 2.86-2.98 (1H, m), 3.70 (3H, s), 4.32 (1H, s), 6.84 (2H, d, J=9.1 Hz), 7.23-7.30 (3H, m), 12.20 (1H, brs), 15.91 (1H, S).

Reference Example 82-1

Ethyl (R)-2-(aminooxy)propionate

[Chem. 130]

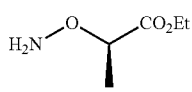

To a solution of ethyl (R)-2-((1,3-dioxoisoindolin-2-yl)oxy)propionate (2.63 g) in methanol (30 mL) was added hydrazine monohydrate (1.46 mL), and the reaction mixture was stirred at room temperature for 3 hours. To the reaction solution was added ethyl acetate, the insoluble was removed by filtration, and the filtrate was concentrated under reduced pressure. The residue was dissolved in ethyl acetate, 1 mol/L hydrochloric acid was added thereto, and the mixture was extracted. To the obtained aqueous layer was added a saturated aqueous sodium hydrogen carbonate to make the solution basic, and the mixture was was extracted with ethyl acetate. The extract was washed with water and a brine, and the organic layer was dried over anhydrous sodium sulfate. The solvent was removed under reduced pressure to obtain the title compound as a colorless oil (780 mg), $^1$H-NMR (400 MHz, DMSO-$d_6$) δ 1.18 (3H, d, J=6.7 Hz), 1.20 (3H, t, J=6.7 Hz), 3.31 (1H, s), 4.10 (2H, q, J=6.7 Hz), 6.15 (2H, s).

Reference Example 82-2

The title compound was obtained using the corresponding starting material in the same method as in Reference Example 82-1.

The structure and spectral data thereof are shown in Table 44.

TABLE 44

| Ref. No | Str. | Chemical name | P.D. |
|---|---|---|---|
| 82-2 | H$_2$N-O-CH(CH$_3$)-CO$_2$Me | methyl-(S)-2-(aminooxy)-propionate | $^1$H-NMR (400 MHz, DMSO-$d_6$) δ 1.19 (3H, d, J = 7.3 Hz), 3.64 (3H, s), 4.11 (1H, q, J = 7.3 Hz), 6.16 (2H, s). |

Reference Example 83

Tert-Butyl (S)-(1-(4-methoxyphenyl)-3-oxopent-4-yn-2-yl)carbamate

[Chem. 131]

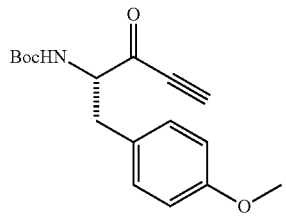

To a solution of tert-butyl (S)-(1-(methoxy(methyl)amino)-3-(4-methoxyphenyl)-1-oxopropan-2-yl)carbamate (500 mg) in tetrahydrofuran (4.5 mL) at −78° C. was added ethynylmagnesium bromide (0.5M tetrahydrofuran solution, 5.4 mL), and the reaction mixture was stirred at −78° C. for 30 minutes. The reaction mixture was warmed to room temperature and then was stirred for 15 hours. To the reaction mixture was added a saturated aqueous ammonium chloride, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=20:1-1:20) to obtain the title compound as a pale yellow oil (190 mg).

$^1$H-NMR (400 MHz, CDCl$_3$) δ 1.42 (9H, s), 3.16-3.18 (2H, m), 3.40 (1H, s), 3.79 (3H, s), 4.64 (1H, q, J=6.7 Hz), 4.97 (1H, d, J=6.7 Hz), 6.83 (2H, d, J=8.5 Hz), 7.07 (2H, d, J=8.5 Hz).

Reference Example 84

Tert-Butyl (S)-(1-(1-(2-hydroxyethyl)-1H-pyrazol-3-yl)-2-(4-methoxyphenyl)ethyl)carbamate

[Chem. 132]

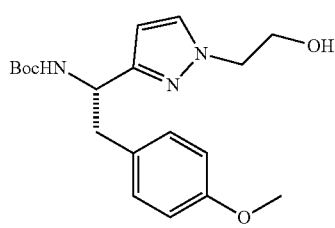

To a solution of tert-butyl (S)-(1-(4-methoxyphenyl)-3-oxopent-4-yn-2-yl)carbamate (143 mg) in methanol (4.7 mL) was added 2-hydrazino-ethanol (47 μL), and the reaction mixture was stirred at room temperature for 1 hour. The solvent was removed under reduced pressure, and the obtained residue was then purified by silica gel column chromatography (hexane:ethyl acetate=20:1-1:20) to obtain the title compound as a colorless solid (87.6 mg).

$^1$H-NMR (400 MHz, CDCl$_3$) δ 1.42 (9H, s), 2.96 (1H, s), 3.07 (2H, d, J=6.1 Hz), 3.77 (3H, s), 3.94 (2H, dd, J=9.7, 5.4 Hz), 4.17 (2H, t, J=4.8 Hz), 4.99 (1H, s), 5.07 (1H, s), 5.98 (1H, d, J=2.4 Hz), 6.76 (2H, d, J=8.5 Hz), 6.97 (2H, d, J=8.5 Hz), 7.29 (1H, d, J=2.4 Hz).

Reference Example 85

Tert-Butyl (S)-(7-((tert-butyldimethylsilyl)oxy)-1-(4-methoxyphenyl)-3-oxohept-4-yn-2-yl) carbamate

[Chem. 133]

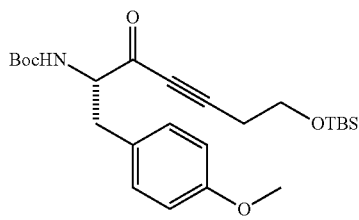

To a solution of 4-(tert-butyldimethylsilyloxy)-1-butyne (737 mg) in tetrahydrofuran (4 mL) at −78° C. was added n-butyllithium (1.67 mol/L, 2.28 mL), and the reaction mixture was stirred for 45 minutes. The reaction mixture was warmed to −30° C. and stirred for further 30 minutes, and then cooled to −78° C. A solution of tert-butyl (S)-(1-(methoxy(methyl)amino)-3-(4-methoxyphenyl)-1-oxopropan-2-yl)carbamate (338 mg) in tetrahydrofuran (2.6 mL) was added thereto, and the reaction mixture was stirred at −78° C. for 1 hour. The reaction mixture was warmed to −20° C. and stirred for further 2 hours. Then, a saturated aqueous ammonium chloride was added thereto, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=20:1-3:1) to obtain the title compound as a colorless oil (400 mg).

$^1$H-NMR (400 MHz, CDCl$_3$) δ 0.08 (6H, s), 0.90 (9H, s), 1.42 (9H, s), 2.62 (2H, t, J=6.7 Hz), 3.16 (2H, s), 3.78 (3H, s), 3.79 (2H, t, J=6.7 Hz), 4.56-4.65 (1H, m), 5.01 (1H, d, J=8.5 Hz), 6.81 (2H, d, J=8.5 Hz), 7.06 (2H, d, J=8.5 Hz).

Reference Example 86

Tert-Butyl ((1S)-1-(3-(2-((tert-butyldimethylsilyl)oxy)ethyl)-5-hydroxy-4,5-dihydroisoxazol-5-yl)-2-(4-methoxyphenyl)ethyl)carbamate Tert-Butyl (S)-(7-((tert-butyldimethylsilyl)oxy)-3-(hydroxyimino)-1-(4-methoxyphenyl)hept-4-yn-2-yl)carbamate

[Chem. 134]

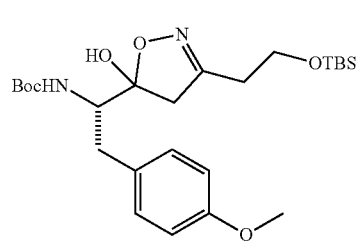

-continued

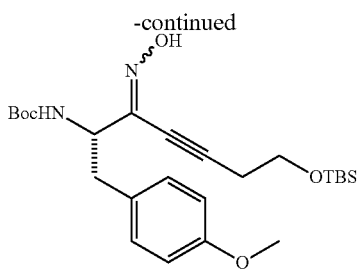

To a solution of tert-butyl (S)-(7-((tert-butyldimethylsilyl)oxy)-1-(4-methoxyphenyl)-3-oxohept-4-yn-2-yl)carbamate (200 mg) in methanol (2.6 mL) were added hydroxylamine hydrochloride (36.1 mg) and triethylamine (66.5 μL), and the reaction mixture was stirred at room temperature for 15 hours. The reaction solution was concentrated under reduced pressure, water was added thereto, and the mixture was was extracted with dichloromethane. The organic layer was washed with a brine, and dried over anhydrous sodium sulfate. The solvent was removed under reduced pressure, and the obtained residue was then purified by silica gel column chromatography (hexane:ethyl acetate=20:1-1:1) to obtain the title compounds tert-butyl ((1S)-1-(3-(2-((tert-butyldimethylsilyl)oxy)ethyl)-5-hydroxy-4,5-dihydroisoxazol-5-yl)-2-(4-methoxyphenyl)ethyl)carbamate (178 mg), and tert-butyl (S)-(7-((tert-butyldimethylsilyl)oxy)-3-(hydroxyimino)-1-(4-methoxyphenyl)hept-4-yn-2-yl)carbamate (21.8 mg) as each colorless oil.

Tert-butyl ((1S)-1-(3-(2-((tert-butyldimethylsilyl)oxy)-ethyl)-5-hydroxy-4,5-dihydroisoxazol-5-yl)-2-(4-methoxy-phenyl)ethyl)carbamate $^1$H-NMR (400 MHz, CDCl$_3$) δ 0.06 (6H, s), 0.87-0.89 (9H, m), 1.33 (9H, s), 2.58 (2H, t, J=6.1 Hz), 2.88-3.07 (3H, m), 3.77-3.80 (3H, m), 3.81-3.85 (2H, m), 4.00 (1H, s), 6.81-6.85 (2H, m), 7.14 (2H, d, J=8.5 Hz).

Tert-butyl (S)-(7-((tert-butyldimethylsilyl)oxy)-3-(hydroxyimino)-1-(4-methoxyphenyl)hept-4-yn-2-yl)carbamate $^1$H-NMR (400 MHz, CDCl$_3$) δ 0.08-0.09 (6H, m), 0.89-0.91 (9H, m), 1.40 (9H, s), 2.55 (1H, t, J=7.0 Hz), 2.70 (1H, t, J=7.0 Hz), 3.73 (1H, t, J=7.3 Hz), 3.77 (1H, s), 3.78 (2H, s), 3.82 (1H, t, J=6.7 Hz), 4.54-5.32 (2H, m), 6.82 (2H, q, J=4.6 Hz), 7.08 (1H, d, J=8.5 Hz), 7.14 (1H, d, J=8.5 Hz), 7.31-7.52 (1H, m).

Reference Example 87

Tert-Butyl (S)-(1-(3-(2-hydroxyethyl)isoxazol-5-yl)-2-(4-methoxyphenyl)ethyl)carbamate

[Chem. 135]

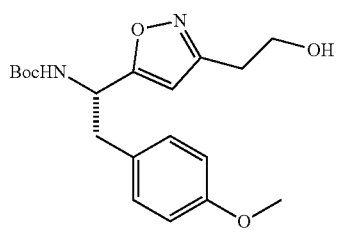

To a solution of tert-butyl ((1S)-1-(3-(2-((tert-butyldimethylsilyl)oxy)ethyl)-5-hydroxy-4,5-dihydro-isoxazol-5-yl)-2-(4-methoxyphenyl)ethyl)carbamate (24.0 mg) in ethyl acetate (1 mL) was added hydrogen chloride (4 mol/L ethyl acetate, 12 μL), and the reaction mixture was stirred at room temperature for 4 hours. Further, hydrogen chloride (4 mol/L ethyl acetate, 12 μL) was added thereto, and the reaction mixture was stirred at room temperature for 1 hour. A saturated aqueous sodium hydrogen carbonate was added to the reaction solution, and the mixture was extracted with ethyl acetate. The organic layer was washed with a brine, and dried over anhydrous sodium sulfate. The solvent was removed under reduced pressure to obtain the title compound as a colorless oil (16.6 mg).

$^1$H-NMR (400 MHz, CDCl$_3$) δ 1.41 (9H, s), 2.86 (2H, t, J=6.1 Hz), 3.04-3.13 (2H, m), 3.77 (3H, s), 3.92 (2H, t, J=6.1 Hz), 4.88 (1H, s), 5.09 (1H, s), 5.87 (1H, s), 6.80 (2H, d, J=8.5 Hz), 6.97 (2H, d, J=8.5 Hz).

Reference Example 88

Tert-Butyl (S)-(1-(5-(2-((tert-butyldimethylsilyl)oxy)ethyl)isoxazol-3-yl)-2-(4-methoxyphenyl)ethyl)carbamate

[Chem. 136]

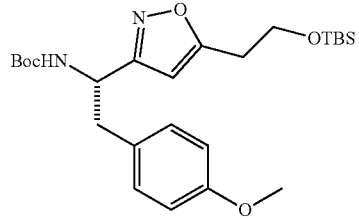

To a solution of tert-butyl (S)-(7-((tert-butyl-dimethylsilyl)oxy)-3-(hydroxyimino)-1-(4-methoxyphenyl)hept-4-yn-2-yl)carbamate (88.5 mg) in dichloromethane (1.5 mL) was added gold(III) chloride (0.5 mg), and the reaction mixture was heated to reflux for 1 hour. The reaction solution was purified by silica gel column chromatography (hexane:ethyl acetate=20:1-1:20) to obtain the title compound as a brown oil (34.8 mg).

$^1$H-NMR (400 MHz, CDCl$_3$) δ 0.00 (6H, s), 0.85 (9H, s), 1.38 (9H, s), 2.89 (2H, t, J=6.7 Hz), 3.09 (2H, d, J=5.4 Hz), 3.75 (3H, s), 3.85 (2H, t, J=6.7 Hz), 4.94-5.09 (2H, m), 5.80 (1H, s), 6.78 (2H, d, J=8.5 Hz), 7.03 (2H, d, J=8.5 Hz).

Reference Example 89

Tert-Butyl (S)-(1-(5-(2-hydroxyethyl)isoxazol-3-yl)-2-(4-methoxyphenyl)ethyl)carbamate

[Chem. 137]

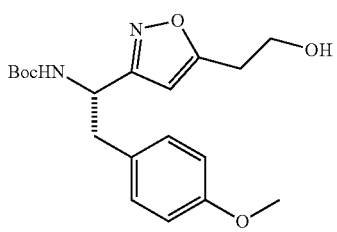

To a solution of tert-butyl (S)-(1-(5-(2-((tert-butyldimethylsilyl)oxy)ethyl)isoxazol-3-yl)-2-(4-methoxyphenyl)ethyl)carbamate (34.8 mg) in tetrahydrofuran (1 mL) was added tetrabutylammonium fluoride (1 mol/L tetrahydrofuran solution, 0.146 mL), and the reaction mixture was stirred at room temperature for 10 minutes. Water was added to the reaction solution, and the mixture was extracted with ethyl acetate. The organic layer was washed with a brine, and was dried over anhydrous sodium sulfate. The solvent was removed under reduced pressure, and the obtained residue was then purified by silica gel column chromatography (hexane:ethyl acetate=2:1-1:2) to obtain the title compound as a pale yellow oil (13.6 mg).

$^1$H-NMR (400 MHz, CDCl$_3$) δ 1.40 (9H, s), 1.78 (1H, s), 2.97 (2H, t, J=6.1 Hz), 3.09 (2H, d, J=6.1 Hz), 3.78 (3H, s), 3.91 (2H, t, J=6.1 Hz), 4.96-5.13 (2H, m), 5.84 (1H, s), 6.80 (2H, d, J=8.5 Hz), 7.05 (2H, d, J=8.5 Hz).

Reference Example 90

Tert-Butyl (S)-(1-(4-methoxyphenyl)-3-butyn-2-yl)carbamate

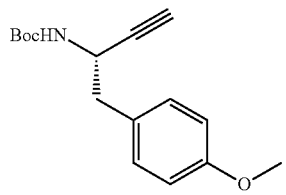

[Chem. 138]

under an argon atmosphere, a solution of methyl (S)-2-((tert-butoxycarbonyl)amino)-3-(4-methoxyphenyl)propionate (3.09 g) in dichloromethane (10 mL) and toluene (30 mL) was cooled to −78° C., 1 mol/L diisobutylaluminum hydride/toluene solution (22 mL) was added thereto, and the reaction mixture was stirred at the same temperature for 2 hours. To the reaction solution was added methanol (10 mL), and the mixture was stirred under ice-cooling for 10 minutes. The reaction solution was concentrated under reduced pressure to make its volume a half. To the concentrated solution was added methanol (30 mL), then Ohira-Bestmann Reagent (1.95 mL) and potassium carbonate (2.76 g). The reaction mixture was stirred at room temperature overnight. The reaction solution was concentrated under reduced pressure, and ethyl acetate and an aqueous saturated Rochelle salt were added thereto. The mixture was stirred at room temperature for 1 hour, and then extracted. The organic layer was washed with a brine, and dried over anhydrous sodium sulfate. The solvent was removed under reduced pressure to obtain the title compound as a white solid (2.1 g).

$^1$H-NMR (400 MHz, CDCl$_3$) δ 1.43 (9H, s), 2.27 (1H, s), 2.87 (1H, dd, J=13.9, 6.7 Hz), 2.94 (1H, dd, J=13.9, 4.8 Hz), 3.80 (3H, s), 4.63 (2H, br s), 6.85 (2H, d, J=8.5 Hz), 7.19 (2H, d, J=8.5 Hz).

Reference Example 91

Tert-Butyl (S)-(2-(4-methoxyphenyl)-1-(1H-1,2,3-triazol-4-yl)ethyl)carbamate

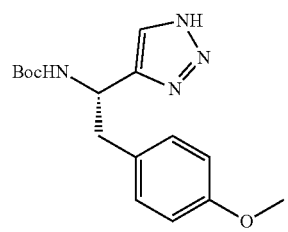

[Chem. 139]

To a solution of tert-butyl (S)-(1-(4-methoxyphenyl)-3-butyn-2-yl)carbamate (100 mg) in methanol-dimethylformamide (1:9, 0.73 mL) were added copper iodide (3.4 mg) and trimethylsilylazide (72.3 μL), and the reaction mixture was stirred at 100° C. for 1 hour. The reaction mixture was ice-cooled, water was added thereto, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=1:1) to obtain the title compound as a white solid (90 mg).

$^1$H-NMR (400 MHz, CDCl$_3$) δ 1.43 (9H, s), 3.02-3.21 (2H, m), 3.77 (3H, s), 5.02-5.16 (2H, m), 6.78 (2H, d, J=8.5 Hz), 6.99 (2H, d, J=8.5 Hz), 7.35 (1H, s).

Reference Example 92

Tert-Butyl (S)-(1-(2-(2-hydroxyethyl)-2H-1,2,3-triazol-4-yl)-2-(4-methoxyphenyl)ethyl)carbamate

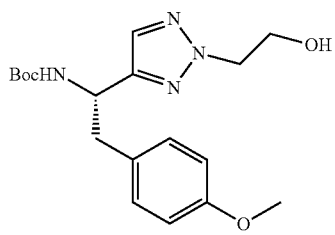

[Chem.140]

To a solution of tert-butyl (S)-(2-(4-methoxyphenyl)-1-(1H-1,2,3-triazol-4-yl)ethyl)carbamate (200 mg) in N,N-dimethylformamide (3 mL) were added potassium carbonate (104 mg) and 2-bromoethanol (57 μL), and the reaction mixture was stirred at 50° C. for 3 hours. The reaction mixture was ice-cooled, water was added thereto, and the mixture was extracted with ethyl acetate. The organic layer was washed with a brine, and dried over anhydrous sodium sulfate. The solvent was removed under reduced pressure, and the residue was then purified by silica gel column chromatography (hexane:ethyl acetate=1:1) to obtain the title compound as a white solid (141 mg).

$^1$H-NMR (400 MHz, CDCl$_3$) δ 1.43 (9H, s), 2.72 (1H, s), 3.05 (1H, dd, J=13.3, 7.3 Hz), 3.11 (1H, dd, J=13.3, 5.4 Hz), 3.77 (3H, s), 4.03-4.10 (2H, m), 4.51 (2H, t, J=4.8 Hz), 4.95-5.11 (2H, m), 6.79 (2H, d, J=9.1 Hz), 6.98 (2H, d, J=9.1 Hz), 7.28 (1H, s).

Reference Example 93

Tert-Butyl (S)-(1-(1-(2-hydroxyethyl)-1H-1,2,3-triazol-4-yl)-2-(4-methoxyphenyl)ethyl)carbamate

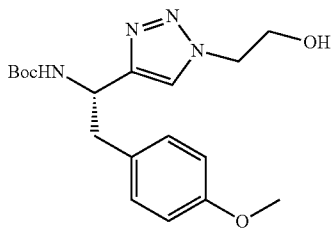

[Chem.141]

To a solution of tert-butyl (S)-(1-(4-methoxyphenyl)-3-butyn-2-yl)carbamate (200 mg) in methanol (0.3 mL)/N,N-dimethylformamide (2.6 mL) were added copper iodide (6.9 mg) and 2-azidoethanol (126 mg), and the reaction mixture was irradiated to microwave at 100° C. for 2 hours. The reaction mixture was ice-cooled, water was added thereto, and the mixture was extracted with ethyl acetate. The organic layer was washed with a brine, and dried over anhydrous sodium sulfate. The solvent was removed under reduced pressure, and the obtained residue was then purified by silica gel column chromatography (hexane ethyl acetate=2:1) to obtain the title compound as a colorless oil (187 mg).

$^1$H-NMR (400 MHz, CDCl$_3$) δ 1.41 (9H, s), 2.14 (1H, s), 3.06 (1H, dd, J=12.7, 8.5 Hz), 3.18-3.29 (1H, m), 3.77 (3H, s), 3.96-4.04 (2H, m), 4.39 (2H, t, J=4.8 Hz), 4.96-5.04 (1H, m), 5.29 (1H, br s), 6.77 (2H, d, J=8.5 Hz), 6.99 (2H, d, J=8.5 Hz), 7.18 (1H, s).

Reference Example 94

Tert-Butyl (S)-(1-(1-(2-hydroxyethyl)-1H-1,2,3-triazol-5-yl)-2-(4-methoxyphenyl)ethyl)carbamate

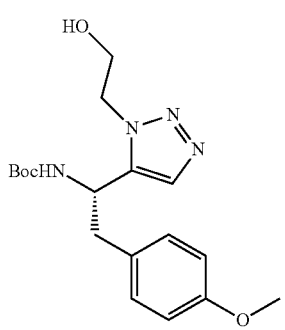

[Chem.142]

To a solution of tert-butyl (S)-(1-(4-methoxyphenyl)-3-butyn-2-yl)carbamate (200 mg) in N,N-dimethylacetamide (3 ML) were added pentamethylcyclopentadienylbis(triphenyl-phosphine)ruthenium(II) chloride (35 mg) and 2-azidoethanol (126 mg), and the reaction mixture was irradiated microwave at 100° C. for 30 minutes. The reaction mixture was ice-cooled, water was added thereto, and the mixture was extracted with ethyl acetate. The organic layer was washed with a brine, and dried over anhydrous sodium sulfate. The solvent was removed under reduced pressure, and the residue was then purified by silica gel column chromatography (hexane:ethyl acetate=1:2) to obtain the title compound as a colorless oil (118 mg).

$^1$H-NMR (400 MHz, CDCl$_3$) δ 1.41 (9H, s), 2.96 (1H, dd, J=13.3, 8.5 Hz), 3.06 (1H, dd, J=13.3, 6.7 Hz), 3.46 (1H, s), 3.77 (3H, s), 3.90-4.02 (3H, m), 4.20-4.30 (1H, m), 4.93 (1H, s), 5.10 (1H, s), 6.80 (2H, d, J=8.5 Hz), 6.95 (2H, d, J=8.5 Hz), 7.60 (1H, s).

Reference Example 95

1-(2-((tert-Butyldimethylsilyl)oxy)ethyl)-N-methoxy-N-methyl-1H-pyrazole-4-carboxamide

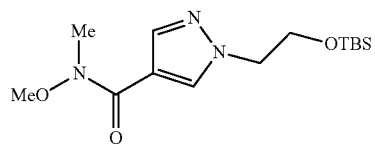

[Chem.143]

To a solution of ethyl 1-(2-((tert-butyldimethylsilyl)oxy)ethyl)-1H-pyrazole-4-carboxylate (100 mg) in tetrahydrofuran (1.4 mL) at −20° C. were added N,O-dimethylhydroxylamine hydrochloride (49 mg) and 2 mol/L isopropylmagnesium chloride/tetrahydrofuran solution (0.5 mL), and the reaction mixture was stirred at the same temperature for 2 hours. An aqueous saturated ammonium chloride was added thereto, and the mixture was extracted with ethyl acetate. The organic layer was washed with a brine, and dried over anhydrous sodium sulfate. The solvent was removed under reduced pressure, and the residue was then purified by silica gel column chromatography (hexane: ethyl acetate=1:2) to obtain the title compound as a colorless oil (105 mg).

$^1$H-NMR (400 MHz, CDCl$_3$) δ 0.05 (6H, s), 0.89 (9H, s), 3.38 (3H, s), 3.77 (3H, s), 4.02 (2H, t, J=5.1 Hz), 4.28 (2H, t, J=5.1 Hz), 8.05 (1H, s), 8.06 (1H, s).

Reference Example 96

1-(1-(2-((tert-Butyldimethylsilyl)oxy)ethyl)-1H-pyrazol-4-yl)-2-(4-methoxyphenyl)ethanone

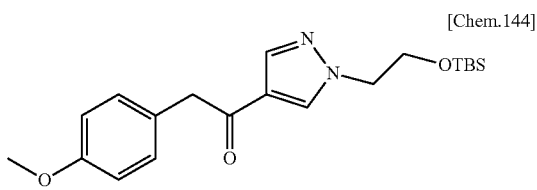 [SMILES: COc1ccc(CC(=O)c2cnn(CCO[Si](C)(C)C(C)(C)C)c2)cc1]

[Chem.144]

To a solution of 1-(2-((tert-butyldimethylsilyl)oxy)ethyl)-N-methoxy-N-methyl-1H-pyrazole-4-carboxamide (2.44 g) in tetrahydrofuran (16 mL) at −20° C. was added 0.25 mol/L p-methoxybenzylmagnesium chloride/tetrahydrofuran solution (78 mL), and the reaction mixture was stirred at room temperature for 5 hours. An aqueous saturated ammonium chloride was added thereto, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=1:2) to obtain the title compound as a colorless oil (2.9 g).

$^1$H-NMR (400 MHz, CDCl$_3$) δ −0.08 (6H, s), 0.82 (9H, s), 3.78 (3H, s), 3.93 (2H, t, J=4.8 Hz), 3.95 (2H, s), 4.20 (2H, t, J=4.8 Hz), 6.85 (2H, d, J=8.5 Hz), 7.18 (2H, d, J=8.5 Hz), 7.92 (2H, s).

Reference Example 97

(R,E)-N-(1-(1-(2-((tert-Butyldimethylsilyl)oxy)ethyl)-1H-pyrazol-4-yl)-2-(4-methoxyphenyl)ethylidene)-2-methylpropane-2-sulfinamide

[Chem.145]

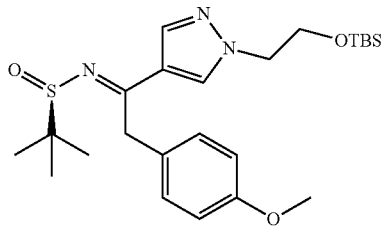

To a solution of 1-(1-(2-((tert-butyldimethylsilyl)oxy)ethyl)-1H-pyrazol-4-yl)-2-(4-methoxyphenyl)ethanone (1.12 g) in tetrahydrofuran (15 mL) at room temperature were added (R)-(+)-tert-butylsulfinamide (400 mg) and titanium(IV) isopropoxide (4.0 mL), and the reaction mixture was heated to reflux for 5 hours. Water was added to the reaction solution, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=1:2) to obtain the title compound as a colorless oil (990 mg).

$^1$H-NMR (400 MHz, CDCl$_3$) δ −0.10 (6H, s), 0.81 (9H, s), 1.28 (9H, s), 3.77 (3H, s), 3.88-3.96 (2H, m), 4.14-4.21 (2H, m), 4.22-4.31 (2H, m), 6.81 (2H, d, J=8.5 Hz), 7.18 (2H, d, J=8.5 Hz), 7.82 (2H, s).

Reference Example 98

(R)—N—((S)-1-(1-(2-((tert-butyldimethylsilyl)oxy)ethyl)-1H-pyrazol-4-yl)-2-(4-methoxyphenyl)ethyl)-2-methylpropane-2-sulfinamide

[Chem.146]

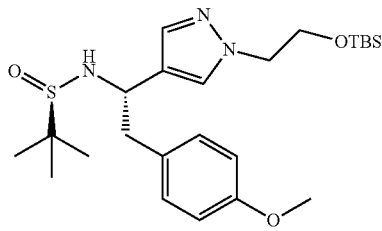

To a solution of (R,E)-N-(1-(1-(2-((tert-butyl-dimethylsilyl)oxy)ethyl)-1H-pyrazol-4-yl)-2-(4-methoxyphenyl)ethylidene)-2-methylpropane-2-sulfinamide (400 mg) in tetrahydrofuran (10 mL) at −78° C. were added 1 mol/L L-Selectride in tetrahydrofuran (1.67 mL), and the reaction mixture was stirred at −78° C. for 2 hours, under ice-cooling for 2 hours, and then at room temperature for 1 hour. Water was added to the reaction solution, and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=1:1) to obtain the title compound as a colorless oil (240 mg).

$^1$H-NMR (400 MHz, CDCl$_3$) δ −0.06 (3H, s), −0.05 (3H, s), 0.84 (9H, s), 1.1$^3$ (9H, s), 2.95 (1H, dd, J=13.4, 7.9 Hz), 3.05 (1H, dd, J=13.4, 6.1 Hz), 3.46 (1H, d, J=3.1 Hz), 3.78 (3H, s), 3.92 (2H, t, J=5.5 Hz), 4.16 (2H, t, J=5.5 Hz), 4.58-4.65 (1H, m), 6.82 (2H, d, J=8.6 Hz), 7.08 (2H, d, J=8.6 Hz), 7.32 (1H, s), 7.42 (1H, s).

Reference Example 99

Methyl (S)-2-((tert-butoxycarbonyl)amino)-3-(4-vinyl phenyl)propionate

[Chem.147]

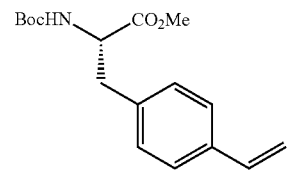

To a solution of methyl (S)-3-(4-bromophenyl)-2-((tert-butoxycarbonyl)amino)propionate (1.28 g) in N,N-dimethylformamide (9 mL) were added tributyl(vinyl)tin (876 μL), lithium chloride (254 mg) and bis(triphenyl-phosphine)palladium(II) dichloride (105 mg), and the reaction mixture was stirred at 90° C. for 16 hours. The reaction mixture was allowed to cool to room temperature, and filtered over Celite. Ethyl acetate and water were added thereto, and the mixture was extracted. The organic layer was washed with water and a brine, and dried over anhydrous sodium sulfate. The solvent was removed under reduced pressure, and the obtained residue was then purified by silica gel column chromatography (hexane:ethyl acetate=2:1) to obtain the title compound (862 mg).

$^1$H-NMR (400 MHz, CDCl$_3$) δ 1.42 (9H, s), 3.04 (1H, dd, J=13.9, 6.1 Hz), 3.11 (1H, dd, J=13.9, 6.1 Hz), 3.72 (3H, s), 4.53-5.63 (1H, m), 4.96 (1H, d, J=6.7 Hz), 5.22 (1H, J=10.9 Hz), 5.72 (1H, J=17.6 Hz), 6.69 (1H, d, J=17.6, 10.9 Hz), 7.08 (2H, d, J=7.9 Hz), 7.34 (2H, d, J=7.9 Hz).

Reference Example 100

Methyl (S)-2-((tert-butoxycarbonyl)amino)-3-(4-(2-hydroxyethyl)phenyl)propionate

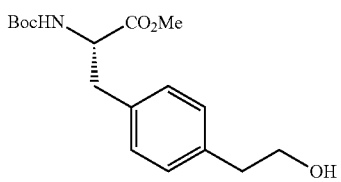

[Chem.148]

To a solution of methyl (S)-2-((tert-butoxycarbonyl)amino)-3-(4-vinylphenyl)propionate (862 mg) in tetrahydrofuran (4.7 mL) under ice-cooling was added borane-tetrahydrofuran complex in tetrahydrofuran (0.9 mol/L, 1.05 mL), and the reaction mixture was stirred at room temperature for 3 hours. To the reaction solution was added a solution of sodium perborate tetrahydrate (434 mg) in water (23 mL), and the reaction mixture was stirred at room temperature for 1 hour. To the reaction solution were added ethyl acetate and water, and the mixture was extracted. The organic layer was washed with water and a brine, and dried over anhydrous sodium sulfate. The solvent was removed under reduced pressure, and the obtained residue was then purified by silica gel column chromatography (hexane:ethyl acetate=1:2) to obtain the title compound as a colorless oil (653 mg).

$^1$H-NMR (400 MHz, CDCl$_3$) δ 1.42 (9H, s), 2.85 (2H, t, J=6.7 Hz), 3.02 (1H, dd, J=13.9, 6.1 Hz), 3.10 (1H, dd, J=13.9, 6.1 Hz), 3.73 (3H, s), 3.86 (2H, q, J=6.7 Hz), 4.58 (1H, q, J=6.7 Hz), 4.96 (1H, d, J=7.9 Hz), 7.07 (2H, d, J=7.9 Hz), 7.16 (2H, d, J=7.9 Hz).

Reference Example 101

(S)-2-((tert-Butoxycarbonyl)amino)-3-(4-(2-hydroxyethyl)phenyl)propionic Acid

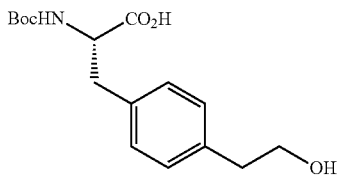

[Chem.149]

To a solution of methyl (S)-2-((tert-butoxycarbonyl)amino)-3-(4-(2-hydroxyethyl)phenyl)propionate (653 mg) in methanol (2 mL) was added a solution of lithium hydroxide (53 mg) in water (2 mL), and the reaction mixture was stirred at room temperature for 1 hour. To the reaction solution was added 1 mol/L hydrochloric acid to neutralize the solution, and the mixture was was extracted with ethyl acetate. The organic layer was washed with water and a brine, and dried over anhydrous sodium sulfate. The solvent was removed under reduced pressure to obtain the title compound as a colorless amorphous (620 mg).

$^1$H-NMR (400 MHz, CDCl$_3$) δ 1.42 (9H, s), 2.85 (2H, t, J=6.7 Hz), 3.07 (1H, dd, J=14.2, 5.4 Hz), 3.16 (1H, dd, J=14.2, 5.4 Hz), 3.86 (2H, t, J=6.7 Hz), 4.58 (1H, d, J=6.1 Hz), 4.96 (1H, d, J=6.1 Hz), 7.13 (2H, d, J=7.9 Hz), 7.17 (2H, d, J=7.9 Hz).

Reference Example 102

(S)-4-{2-[(tert-Butoxycarbonyl)amino]-2-cyanoethyl}phenethyl 2,2,2-trifluoroacetate

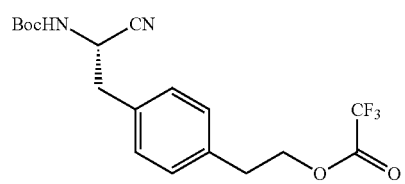

[Chem.150]

Using (S)-2-((tert-butoxycarbonyl)amino)-3-(4-(2-hydroxyethyl)phenyl)propionic acid (620 mg) as a starting material, the same method as in Reference Example 6-1 followed by the same method as in Reference Example 7-1 to obtain the title compound as a white solid (237 mg).

$^1$H-NMR (400 MHz, CDCl$_3$) δ 1.44 (9H, s), 2.99-3.14 (4H, m), 4.54 (1H, t, J=7.3 Hz), 4.76 (1H, br s), 4.81 (1H, br s), 7.23 (2H, d, J=8.5 Hz), 7.26 (2H, d, J=8.5 Hz).

Reference Example 103

(R)-3-((2R,3S)-2-Bromo-3-(4-methoxyphenyl)butanoyl)-4-phenyloxazolidin-2-one (R)-3-((2R,3R)-2-Bromo-3-(4-methoxyphenyl)butanoyl)-4-phenyloxazolidin-2-one

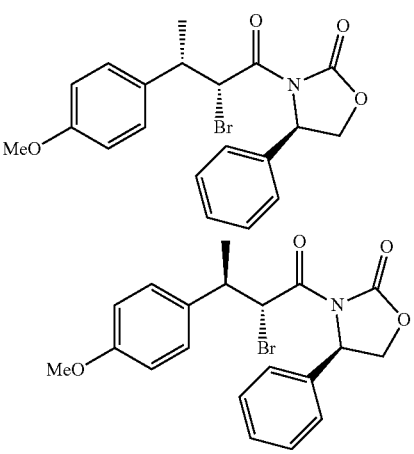

[Chem.151]

To a solution of 3-(3-(4-methoxyphenyl)butanoyl)-4-phenyloxazolidin-2-one (1.55 g) in dichloromethane (30 mL) at −78° C. were added diisopropylethylamine (952 μL) and dibutylboryl trifluoromethanesulfonate (nBu$_2$BOTf) (1.0 M dichloromethane solution, 4.78 mL), and the reaction mixture was stirred at the same temperature for 20 minutes and then at room temperature for 1 hour to obtain a pale yellow solution. To a solution of N-bromosuccinimide (1.79 g) in dichloromethane (16.7 mL) at −78° C. was added the above-prepared solution, and the reaction mixture was stirred at the same temperature for 1 hour and then at 0° C. for 1 hour. To the reaction solution was added 1M aqueous sodium thiosulfate (50 mL), and the mixture was was extracted with dichloromethane. The organic layer was dried over anhydrous magnesium sulfate, and the solvent was removed under reduced pressure. The obtained residue was then purified by silica gel column chromatography (hexane:ethyl acetate=92:8-60:40) to obtain (R)-3-((2R,3S)-2-bromo-3-(4-methoxyphenyl)butanoyl)-4-phenyloxazolidin-2-one (822 mg) and (R)-3-((2R,3R)-2-bromo-3-(4-methoxyphenyl)butanoyl)-4-phenyloxazolidin-2-one (854 mg) as pale yellow amorphouses.

(R)-3-((2R,3S)-2-bromo-3-(4-methoxyphenyl)butanoyl)-4-phenyloxazolidin-2-one $^1$H-NMR (400 MHz, CDCl$_3$) δ 1.48 (3H, d, J=7.3 Hz), 3.35-3.42 (1H, m), 3.78 (3H, s), 4.14 (1H, dd, J=4.2, 9.1 Hz), 4.43 (1H, t, J=8.5 Hz), 5.14 (1H, dd, J=4.2, 9.1 Hz), 6.00 (1H, d, J=10.9 Hz), 6.83 (2H, d, J=8.5 Hz), 7.15 (2H, d, J=8.5 Hz), 7.26-7.40 (5H, m).

(R)-3-((2R,3R)-2-bromo-3-(4-methoxyphenyl)butanoyl)-4-phenyloxazolidin-2-one $^1$H-NMR (400 MHz, CDCl$_3$) δ 1.33 (3H, d, J=6.7 Hz), 3.36-3.45 (1H, m), 3.80 (3H, s), 4.28 (1H, dd, J=4.8, 9.1 Hz), 4.73 (1H, d, J=9.1 Hz), 5.49 (1H, dd, J=4.8, 8.5 Hz), 5.91 (1H, d, J=10.3 Hz), 6.87 (2H, d, J=8.5 Hz), 7.16 (2H, d, J=8.5 Hz), 7.35-7.40 (5H, m).

Reference Example 104-1

(R)-3-((2S,3S)-2-azido-3-(4-methoxyphenyl)butanoyl)-4-phenyloxazolidin-2-one

[Chem.152]

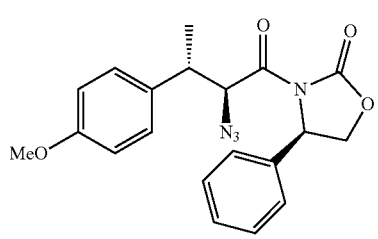

To a solution of (R)-3-((2R,3S)-2-bromo-3-(4-methoxyphenyl)butanoyl)-4-phenyloxazolidin-2-one (807 mg) in dimethylsulfoxide (19.3 mL) was added sodium azide (376 mg), and the reaction mixture was stirred at room temperature for 4 hours. Water was added to the reaction solution, and the mixture was extracted with diethyl ether. The organic layer was washed with water and a brine, and dried over anhydrous magnesium sulfate. The solvent was removed under reduced pressure. The residue was then purified by silica gel column chromatography (hexane:ethyl acetate=92:8-60:40) to obtain the title compound as a colorless oil (657 mg).

$^1$H-NMR (400 MHz, CDCl$_3$) δ 1.15 (3H, d, J=7.2 Hz), 3.16-3.23 (1H, m), 3.77 (3H, s), 4.45 (1H, dd, J=3.6, 9.1 Hz), 4.78 (1H, t, J=9.1 Hz), 5.23 (1H, d, J=8.5 Hz), 5.51 (1H, dd, J=3.6, 9.1 Hz), 6.75 (2H, d, J=8.5 Hz), 7.01 (2H, d, J=8.5 Hz), 7.35-7.44 (5H, m).

Reference Example 104-2

The following Reference Example 104-2 was obtained using the corresponding starting material in the same method as in Reference Example 104-1.

The structure and spectral data thereof are shown in Table 45.

TABLE 45

| Ref. No | Str. | Chemical name | P.D. |
|---|---|---|---|
| 104-2 | | (R)-3-((2S,3R)-2-azido-3-(4-methoxyphenyl)butanoyl)-4-phenyloxazolidin-2-one | $^1$H-NMR (400 MHz, CDCl$_3$) δ 1.27 (3H, d, J = 6.7 Hz), 3.24-3.32 (1H, m), 3.81 (3H, s), 4.18 (1H, dd, J = 4.2, 9.1 Hz), 4.67 (1H, t, J = 8.5 Hz), 5.36 (1H, d, J = 8.5 Hz), 5.40 (1H, dd, J = 4.2, 9.1 Hz), 6.74 (2H, d, J = 9.1 Hz), 6.80-6.82 (2H, m), 7.09 (2H, d, J = 9.1 Hz), 7.22-7.27 (3H, m). |

Reference Example 105-1

Tert-Butyl ((2S,3S)-3-(4-methoxyphenyl)-1-oxo-1-((R)-2-oxo-4-phenyloxazolidin-3-yl)butan-2-yl Carbamate

[Chem.153]

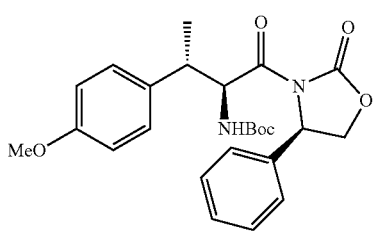

To a solution of (R)-3-((2S,3S)-2-azido-3-(4-methoxyphenyl)butanoyl)-4-phenyloxazolidin-2-one (649 mg) in ethyl acetate (17.1 mL) were added di-tert-butyl dicarbonate (558 mg) and 10 palladium-carbon (195 mg), and the reaction mixture was stirred under hydrogen atmosphere at room temperature for 8 hours. The insoluble was filtered off through Celite pad, and the filtrate was concentrated under reduced pressure. The obtained residue was then purified by silica gel column chromatography (hexane:ethyl acetate=98: 2-60:40) to obtain the title compound as a colorless amorphous (632 mg).

$^1$H-NMR (400 MHz, CDCl$_3$) δ 1.36-1.39 (12H, m), 3.18-3.20 (1H, m), 3.71 (3H, m), 4.53 (1H, dd, J=3.0, 9.1 Hz), 4.59 (1H, d, J=9.7 Hz), 4.78 (1H, t, J=9.1 Hz), 5.47 (1H, dd, J=3.0, 8.5 Hz), 5.54 (1H, dd, J=3.0, 9.7 Hz), 6.46 (4H, m), 7.44-7.47 (5H, m).

Reference Example 105-2

The following Reference Example 105-2 was obtained using the corresponding starting material in the same method as in Reference Example 1-1.

The structure and spectral data thereof are shown in Table 46.

TABLE 46

| Ref. No | Str. | Chemical name | P.D. |
|---|---|---|---|
| 105-2 | 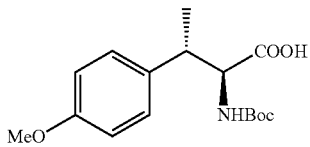 | tert-butyl ((2S,3R)-3-(4-methoxyphenyl)-1-oxo-1-((R)-2-oxo-4-phenyl-oxazolidin-3-yl)carbamate | $^1$H-NMR (400 MHz, CDCl$_3$) δ 0.97 (3H, d, J = 6.7 Hz), 1.35 (9H, s), 3.26 (1H, br), 3.79 (3H, s), 4.28 (1H, dd, J = 3.6, 8.65 Hz), 4.71 (1H, t, J = 9.1 Hz), 5.00 (1H, br), 5.41-5.54 (1H, m), 5.78 (1H, dd, J = 5.5, 9.1 Hz), 6.78 (2H, d, J = 8.5 Hz), 7.10-7.12 (2H, m), 7.18 (2H, d, J = 9.1 Hz), 7.32-7.33 (3H, m). |

Reference Example 106-1

(2S,3S)-2-((tert-Butoxycarbonyl)amino)-3-(4-methoxyphenyl)butyric Acid

[Chem.154]

To a solution of tert-butyl ((2S,3S)-3-(4-methoxyphenyl)-1-oxo-1-((R)-2-oxo-4-phenyloxazolidin-3-yl) butan-2-yl carbamate (626 mg) in tetrahydrofuran-water (3:1, 19.7 mL) at 0° C. were added dropwise 30% aqueous hydrogen peroxide (781 μL). 1M aqueous lithium hydroxide (2.76 mL) was added thereto, and the reaction mixture was stirred at 0° C. for 1 hour, and then warmed to room temperature. To the reaction mixture was added a solution of sodium hydrogen sulfite (869 mg) in water (5.3 mL), and the reaction solution was concentrated under reduced pressure. Water was added to the obtained residue, and the mixture was washed with dichloromethane. Then, the aqueous layer was made acidic with 0.3M hydrochloric acid, and the mixture was extracted with ethyl acetate. The organic layer was washed with a brine, and dried over anhydrous magnesium sulfate. The solvent was removed under reduced pressure to obtain the title compound as a colorless oil (350 mg).

¹H-NMR (400 MHz, CDCl₃) δ 1.37 (3H, d, J=7.3 Hz), 1.41 (9H, s), 3.36-3.42 (1H, m), 3.79 (3H, s), 4.43-4.76 (1H, m), 4.73-4.76 (1H, m), 6.86 (2H, d, J=8.5 Hz), 7.12 (2H, d, J=8.5 Hz).

Reference Example 106-2

The following Reference Example 106-2 was obtained using each corresponding starting material in the same method as in Reference Example 106-1.
The structure and spectral data thereof are shown in Table 47.

TABLE 47

| Ref. No | Str. | Chemical name | P.D. |
|---|---|---|---|
| 106-2 | MeO-C₆H₄-CH(—)-CH(NHBoc)-COOH | (2S,3R)-2-((tert-butoxycarbonyl)-amino)-3-(4-methoxyphenyl)-butyric acid | ¹H-NMR (400 MHz, CDCl₃) δ 1.35 (3H, d, J = 7.2 Hz), 1.41 (9H, s), 3.22-3.29 (1H, m), 3.78 (3H, s), 4.47-4.50 (1H, m), 4.99-5.02 (1H, m), 6.84 (2H, d, J = 9.1 Hz), 7.15 (2H, d, J = 9.1 Hz). |

Reference Example 107

Tert-Butyl (S)-(1-(4-(2-((tert-butyldimethylsilyl)oxy)ethyl)-6-oxo-1,6-dihydropyrimidin-2-yl)-2-(4-chlorophenyl)ethyl)carbamate

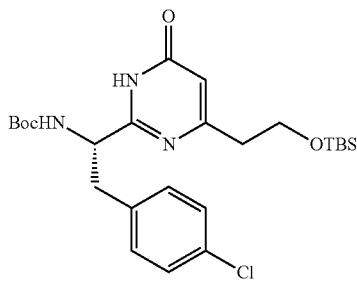

[Chem. 155]

To a solution of tert-butyl (S)-(1-amino-3-(4-chlorophenyl)-1-oxopropan-2-yl)carbamate (500 mg) in dichloromethane (4.2 mL) at room temperature was added triethyloxonium hexafluorophosphate (460 mg), and the reaction mixture was heated at room temperature for 23 hours. To the reaction solution was added an saturated potassium carbonate, and the mixture was extracted with dichloromethane. The organic layer was dried over sodium sulfate, and filtered, and the filtrate was concentrated under reduced pressure. The obtained residue was dissolved in methanol (4.2 mL), ammonium chloride (358 mg) and ammonia/methanol (7.0 mol/L, 1.0 mL) were added thereto, and the mixture was stirred at room temperature for 15 hours. The insoluble was removed, the solution was concentrated under reduced pressure, and the obtained residue was then purified by silica gel column chromatography (ethyl acetate 100%-ethyl acetate:methanol=4:1) to obtain tert-butyl (S)-(1-amino-3-(4-chlorophenyl)-1-iminopropan-2-yl)carbamate as a colorless amorphous (310 mg).

To a solution of tert-butyl (S)-(1-amino-3-(4-chlorophenyl)-1-iminopropan-2-yl)carbamate (450 mg) in ethanol (2.9 mL) at room temperature were added ethyl 5-((tert-butyldimethylsilyl)oxy)pent-2-ynoate (260 mg) and diisopropylethylamine (0.3 mL), and the mixture was heated at 125° C. with microwave for 20 minutes. The reaction solution was concentrated under reduced pressure, and the obtained residue was purified by silica gel column chromatography (hexane:ethyl acetate=2:1-1:1) to obtain the title compound as a colorless solid (99.0 mg).

¹H-NMR (400 MHz, CDCl₃) δ 0.04 (6H, s), 0.87 (9H, s), 1.39 (9H, s), 2.72 (2H, t, J=6.7 Hz), 2.98-3.12 (1H, m), 3.16-3.28 (1H, m), 3.90 (2H, t, J=6.7 Hz), 4.70-4.88 (1H, m), 5.32 (1H, d, J=7.9 Hz), 6.22 (1H, s), 7.09 (2H, d, J=7.6 Hz), 7.22-7.27 (3H, m).

Reference Example 108

Tert-Butyl (S)-(2-(4-chlorophenyl)-1-(4-(2-hydroxyethyl)-6-oxo-1,6-dihydropyrimidin-2-yl)ethyl)carbamate

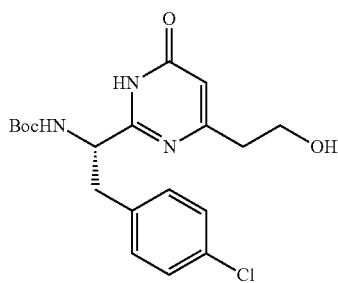

[Chem. 156]

To a solution of tert-butyl (S)-(1-(4-(2-((tert-butyldimethylsilyl)oxy)ethyl)-6-oxo-1,6-dihydropyrimidin-2-yl)-2-(4-chlorophenyl)ethyl)carbamate (102 mg) in tetrahydrofuran (0.25 mL) were added acetic acid (1.0 mL) and water (0.25 mL), and the reaction mixture was stirred at room temperature for 30 minutes and then at 50° C. for 52 hours. The reaction solution was concentrated under reduced pressure, and the obtained residue was then purified by silica gel column chromatography (hexane:ethyl acetate=1:4-ethyl acetate 100%) to obtain the title compound as a colorless solid (57.0 mg).

¹H-NMR (400 MHz, CDCl₃) δ 1.39 (9H, s), 2.77 (2H, t, J=5.4 Hz), 2.98-3.10 (1H, m), 3.16-3.26 (1H, m), 3.90 (2H, q, J=5.7 Hz), 4.76-4.84 (1H, m), 5.20-5.40 (1H, m), 6.20 (1H, s), 7.08 (2H, d, J=8.5 Hz), 7.22-7.27 (2H, m).

Reference Example 109-1

Ethyl (S)-2-(5-(1-(3-(4-chlorophenyl)ureido)-2-(4-methoxyphenyl)ethyl)-2H-tetrazol-2-yl)acetate

[Chem. 157]

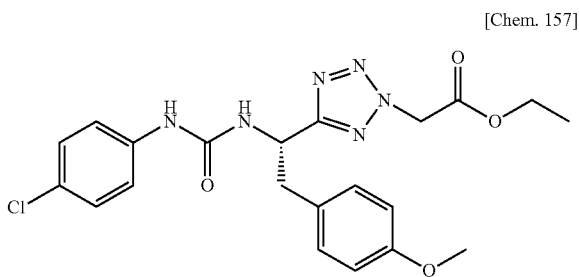 [SMILES: CCOC(=O)Cn1nnc([C@H](Cc2ccc(OC)cc2)NC(=O)Nc2ccc(Cl)cc2)n1]

To a solution of ethyl (S)-2-(5-(1-((tert-butoxycarbonyl)amino)-2-(4-methoxyphenyl)ethyl)-2H-tetrazol-2-yl)acetate (454 mg) in dioxane (1.20 mL) was added hydrogen chloride (2.8 mL, 4 mol/L dioxane solution), and the reaction mixture was stirred at room temperature for 1 hour. The reaction solution was concentrated to obtain ethyl (S)-2-(5-(1-amino-2-(4-methoxyphenyl)ethyl)-2H-tetrazol-2-yl)acetate hydrochloride as a yellow oil (383 mg). To a solution of ethyl (S)-2-(5-(1-amino-2-(4-methoxyphenyl)ethyl)-2H-tetrazol-2-yl)acetate hydrochloride (342 mg) in ethyl acetate (4.00 mL) were added a saturated aqueous sodium hydrogen carbonate (1.70 mL) and p-chlorophenyl isocyanate (172 mg), and the reaction mixture was stirred at room temperature for 1 hour. To the reaction solution was added p-chlorophenyl isocyanate (34.2 mg), and the reaction mixture was stirred at room temperature for 30 minutes. To the reaction solution was added ethyl acetate, and the mixture was washed with water and then a brine. The organic layer was dried over anhydrous sodium sulfate. The solvent was removed under reduced pressure, and the obtained residue was then purified by silica gel column chromatography (acetone:hexane=1:5), and the resulting crude product was washed with ethyl acetate-hexane to obtain the title compound as a colorless solid (377 mg).

$^1$H-NMR (400 MHz, DMSO-d$_6$) δ 1.17 (3H, t, J=7.4 Hz), 3.05-3.16 (2H, m), 3.69 (3H, s), 4.18 (2H, dd, J=6.7, 14.1 Hz), 5.31 (1H, dd, J=7.3, 15.3 Hz), 5.78 (2H, s), 6.78 (3H, m), 7.01 (2H, d, J=8.6 Hz), 7.23 (2H, d, J=8.6 Hz), 7.36 (2H, d, J=8.6 Hz), 8.74 (1H, s).

Reference Examples 109-2 to 109-40

The following Reference Examples 109-2 to 109-40 were obtained using each corresponding starting material in the same method as in Reference Example 109-1.

The structures and spectral data thereof are shown in Tables 48 and 57.

TABLE 48

| Ref. No. | Str. | Chemical name | P.D. |
|---|---|---|---|
| 109-2 | | ethyl (S)-2-(3-{1-[3-(4-chlorophenyl)ureido]-2-(4-methoxyphenyl)ethyl}-1,2,4-oxadiazol-5-yl)acetate | $^1$H-NMR (400 MHz, CDCl$_3$) δ 1.30 (3H, t, J = 7.3 Hz), 3.09-3.23 (2H, m), 3.76 (3H, s), 3.96 (2H, s), 4.25 (2H, q, J = 7.3 Hz), 5.19 (1H, m), 5.44 (1H, m), 6.48 (1H, m), 6.77 (2H, d, J = 8.5 Hz), 6.96 (2H, d, J = 8.5 Hz), 7.14-7.24 (4H, m). |
| 109-3 | | methyl 2-(1-(3-(4-chlorophenyl)-ureido)-2-(4-methoxyphenyl)-ethyl)oxazole-4-carboxylate | $^1$H-NMR (400 MHz, CDCl$_3$) δ 3.01 (1H, m), 3.14 (1H, m), 3.74 (3H, s), 3.82 (3H, s), 5.35 (1H, m), 5.73 (1H, d, J = 8.5 Hz), 6.72 (2H, d, J = 8.5 Hz), 6.86 (2H, d, J = 8.5 Hz), 6.97 (1H, s), 7.11 (4H, m), 8.22 (1H, s). |
| 109-4 | | ethyl (S)-2-(5-(1-(3-(4-chlorophenyl)ureido)-2-(4-methoxyphenyl)ethyl)-1,3,4-thiadiazol-2-yl)acetate | $^1$H-NMR (400 MHz, CDCl$_3$) δ 1.28 (3H, t, J = 7.3 Hz), 3.27 (1H, dd, J = 13.9, 7.9 Hz), 3.37 (1H, dd, J = 13.9, 6.7 Hz), 3.76 (3H, s), 4.11 (2H, s), 4.22 (2H, q, J = 7.3 Hz), 5.67 (1H, m), 6.41 (1H, br d, J = 7.9 Hz), 6.78 (2H, d, J = 9.1 Hz), 7.04 (2H, d, J = 8.5 Hz), 7.23 (2H, d, J = 9.1 Hz), 7.28 (2H, d, J = 8.5 Hz), 7.39 (1H, br s). |

TABLE 48-continued

| Ref. No. | Str. | Chemical name | P.D. |
|---|---|---|---|
| 109-5 | | ethyl 5-(1-(3-(4-chlorophenyl)-ureido)-2-(4-methoxyphenyl)-ethyl)oxazole-4-carboxylate | $^1$H-NMR (400 MHz, DMSO-d$_6$) δ 1.28 (3H, t, J = 7.0 Hz), 2.96 (1H, m), 3.04 (1H, m), 3.69 (3H, s), 4.24 (2H, m), 5.64 (1H, m), 6.81 (2H, d, J = 8.5 Hz), 6.86 (1H, d, J = 7.9 Hz), 7.02 (2H, d, J = 8.5 Hz), 7.23 (2H, d, J = 9.1 Hz), 7.34 (2H, d, J = 9.1 Hz), 8.41 (1H, s), 8.74 (1H, s). |

TABLE 49

| Ref. No | Str. | Chemical name | P.D. |
|---|---|---|---|
| 109-6 | | ethyl 2-(2-(1-(3-(4-chlorophenyl)-ureido)-2-(4-methoxyphenyl)-ethyl)thiazol-4-yl)acetate | $^1$H-NMR (400 MHz, DMSO-d$_6$) 1.19 (3H, t, J = 7.3 Hz), 3.05 (1H, dd, J = 13.9, 8.5 Hz), 3.17 (1H, dd, J = 13.9, 5.4 Hz), 3.69 (3H, s), 3.80 (2H, s), 4.10 (2H, q, J = 7.3 Hz), 5.19 (1H, m), 6.80 (2H, d, J = 8.5 Hz), 6.85 (1H, m), 7.08 (2H, d, J = 9.1 Hz), 7.24 (2H, d, J = 9.1 Hz), 7.34 (1H, s), 7.36 (2H, d, J = 8.5 Hz), 8.79 (1H, br s). |
| 109-7 | | ethyl 5-(1-(3-(4-chlorophenyl)-ureido)-2-(4-methoxyphenyl)-ethyl)-1,3,4-oxadiazol-2-carboxylate | $^1$H-NMR (400 MHz, CDCl$_3$) δ 1.47 (3H, t, J = 7.3 Hz), 3.16-3.30 (2H, m), 3.76 (3H, s), 4.53 (2H, q, J = 7.1 Hz), 5.36 (1H, br d, J = 8.5 Hz), 5.58 (1H, m), 6.56 (1H, br s), 6.79 (2H, d, J = 8.5 Hz), 6.95 (2H, d, J = 9.1 Hz), 7.23 (4H, m). |
| 109-8 | | ethyl (S)-2-(5-(1-(3-(4-chlorophenyl)ureido)-2-(4-methoxyphenyl)ethyl)-2-oxo-1,3,4-oxadiazol-3(2H)-yl)acetate | $^1$H-NMR (400 MHz, DMSO-d$_6$) δ 1.18 (3H, t, J = 7.1 Hz), 2.94-3.08 (2H, m), 3.70 (3H, s), 4.14 (2H, q, J = 7.1 Hz), 4.61 (2H, s), 4.91-4.96 (1H, m), 6.74 (1H, d, J = 8.5 Hz), 6.85 (1H, d, J = 8.5 Hz), 7.14 (2H, d, J = 8.5 Hz), 7.25 (2H, d, J = 9.1 Hz), 7.37 (2H, d, J = 9.1 Hz), 8.73 (1H, brs). |
| 109-9 | | ethyl 3-(1-(3-(4-chlorophenyl)-ureido)-2-(4-methoxyphenyl)-ethyl)-1,2,4-oxadiazol-5-carboxylate | $^1$H-NMR (400 MHz, CDCl$_3$) δ 1.47 (3H, t, J = 7.0 Hz), 3.20 (2H, m), 3.78 (3H, s), 4.55 (2H, q, J = 7.0 Hz), 5.05 (1H, d, J = 9.1 Hz), 5.52 (1H, m), 6.22 (1H, s), 6.80 (2H, d, J = 8.5 Hz), 6.98 (2H, d, J = 8.5 Hz), 7.18 (2H, d, J = 9.1 Hz), 7.24 (2H, d, J = 9.1 Hz). |

TABLE 50

| Ref. No | Str. | Chemical name | P.D. |
|---|---|---|---|
| 109-10 | | ethyl (S)-2-(3-{1-[3-(4-fluorophenyl)ureido]-2-(4-methoxyphenyl)ethyl}-1,2,4-oxadiazol-5-yl)acetate | $^1$H-NMR (400 MHz, CDCl$_3$) δ 1.26 (3H, t, J = 7.3 Hz), 3.03 (1H, dd, J = 13.9, 6.7 Hz), 3.14 (1H, dd, J = 13.9, 6.1 Hz), 3.70 (3H, s), 3.90 (2H, s), 4.20 (2H, q, J = 7.3 Hz), 5.39-5.47 (1H, m), 5.85 (1H, d, J = 8.5 Hz), 6.71 (2H, d, J = 8.5 Hz), 6.87 (2H, t, J = 8.5 Hz), 6.93 (2H, d, J = 8.5 Hz), 7.09-7.12 (2H, m), 7.37 (1H, s). |
| 109-11 | | ethyl (S)-2-(3-{1-[3-(4-cyanophenyl)ureido]-2-(4-methoxyphenyl)ethyl}-1,2,4-oxadiazol-5-yl)acetate | $^1$H-NMR (400 MHz, CDCl$_3$) δ 1.30 (3H, t, J = 7.3 Hz), 3.01 (1H, dd, J = 13.9, 6.7 Hz), 3.17 (1H, dd, J = 13.9, 5.4 Hz), 3.72 (3H, s), 3.97 (2H, s), 4.24 (2H, q, J = 7.3 Hz), 5.38-5.48 (1H, m), 5.76 (1H, d, J = 7.9 Hz), 6.74 (2H, d, J = 8.5 Hz), 6.94 (2H, d, J = 8.5 Hz), 7.29 (2H, d, J = 8.5 Hz), 7.40 (2H, d, J = 8.5 Hz), 7.50 (1H, s). |
| 109-12 | | ethyl (S)-2-(3-(2-(4-chlorophenyl)-1-(3-(4-cyanophenyl)-ureido)ethyl)1,2,4-oxadiazol-5-yl)acetate | $^1$H-NMR (400 MHz, CDCl$_3$) δ 1.31 (3H, t, J = 7.3 Hz), 3.16-3.28 (2H, m), 3.99 (2H, s), 4.26 (2H, q, J = 7.3 Hz), 5.45-5.50 (2H, m), 7.00 (2H, dt, J = 7.9, 1.8 Hz), 7.03 (1H, s), 7.22 (2H, dt, J = 7.9, 1.8 Hz), 7.41 (2H, dt, J = 8.5, 1.8 Hz), 7.51 (2H, dt, J = 8.5, 1.8 Hz). |
| 109-13 | | ethyl (S)-2-(3-{2-(4-chlorophenyl)-1-[3-(4-chlorophenyl)-ureido]ethyl}-1,2,4-oxadiazol-5-yl)acetate | $^1$H-NMR (400 MHz, CDCl$_3$) δ 1.30 (3H, t, J = 7.3 Hz), 3.15 (1H, dd, J = 13.9, 6.1 Hz), 3.22 (1H, dd, J = 13.9, 6.1 Hz), 3.96 (2H, s), 4.24 (2H, q, J = 7.3 Hz), 5.37-5.43 (1H, m), 5.45-5.50 (1H, m), 6.72-6.79 (1H, m), 6.98 (2H, d, J = 8.5 Hz), 7.16-7.23 (6H, m). |

TABLE 51

| Ref. No | Str. | Chemical name | P.D. |
|---|---|---|---|
| 109-14 | | ethyl (S)-2-(3-{2-(4-chlorophenyl)-1-[3-(4-fluorophenyl)-ureido]ethyl}-1,2,4-oxadiazol-5-yl)acetate | $^1$H-NMR (400 MHz, CDCl$_3$) δ 1.31 (3H, t, J = 7.3 Hz), 3.16-3.28 (2H, m), 3.99 (2H, s), 4.26 (2H, q, J = 7.3 Hz), 5.45-5.50 (2H, m), 7.00 (2H, dt, J = 7.9, 1.8 Hz), 7.03 (1H, s), 7.22 (2H, dt, J = 7.9, 1.8 Hz), 7.41 (2H, dt, J = 8.5, 1.8 Hz), 7.51 (2H, dt, J = 8.5, 1.8 Hz). |
| 109-15 | | ethyl (S)-2-(3-{2-(4-chlorophenyl)-1-[3-(4-chlorophenyl)-ureido]ethyl}-1,2,4-oxadiazol-5-yl)-2-methylpropanoate | $^1$H-NMR (400 MHz, DMSO-d$_6$) δ 1.11 (3H, t, J = 7.1 Hz), 1.62 (6H, s), 3.11 (2H, d, J = 7.3 Hz), 4.12 (2H, q, J = 7.1 Hz), 5.20 (1H, m), 6.88 (1H, d, J = 8.5 Hz), 7.16 (2H, d, J = 8.5 Hz), 7.24 (2H, d, J = 8.5 Hz), 7.31 (2H, d, J = 8.5 Hz), 7.36 (2H, d, J = 8.5 Hz), 8.80 (1H, s). |

TABLE 51-continued

| Ref. No | Str. | Chemical name | P.D. |
|---|---|---|---|
| 109-16 | | ethyl (S)-2-(3-{2-(4-chlorophenyl)-1-[3-(4-fluorophenyl)-ureido]ethyl}-1,2,4-oxadiazol-5-yl)-2-methyl-propionate | ¹H-NMR (400 MHz, DMSO-d₆) δ 1.11 (3H, t, J = 7.3 Hz), 1.62 (6H, s), 3.11 (2H, d, J = 7.3 Hz), 4.12 (2H, 2, J = 7.3 Hz), 5.20 (1H, m), 6.79 (1H, d, J = 9.1 Hz), 7.03 (2H, m), 7.15 (2H, d, J = 8.5 Hz), 7.31 (2H, d, J = 8.5 Hz), 7.34 (2H, m), 8.65 (1H, s). |
| 109-17 | | ethyl (S)-1-(3-{2-(4-chlorophenyl)-1-[3-(4-chlorophenyl)-ureido]ethyl}-1,2,4-oxadiazol-5-yl)cyclopropane-carboxylate | ¹H-NMR (400 MHz, CDCl₃) δ 1.27 (3H, t, J = 7.3 Hz), 1.60 (2H, m), 1.84 (2H, m), 3.15-3.27 (2H, m), 4.24 (2H, q, J = 7.3 Hz), 5.15 (1H, d, J = 8.5 Hz), 5.45 (1H, m), 6.39 (1H, s), 6.98 (2H, d, J = 8.5 Hz), 7.19-7.26 (6H, m). |

TABLE 52

| Ref. No | Str. | Chemical name | P.D. |
|---|---|---|---|
| 109-18 | | ethyl (S)-1-(3-{2-(4-chlorophenyl)-1-[3-(4-fluorophenyl)-ureido]ethyl}-1,2,4-oxadiazol-5-yl)cyclopropane-carboxylate | ¹H-NMR (400 MHz, CDCl₃) δ 1.27 (3H, t, J = 7.3 Hz), 1.60 (2H, m), 1.83 (2H, m), 3.12-3.26 (2H, m), 4.23 (2H, q, J = 7.3 Hz), 5.16 (1H, d, J = 8.5 Hz), 5.45 (1H, m), 6.39 (1H, s), 6.94-7.02 (4H, m), 7.17-7.24 (4H, m). |
| 109-19 | | ethyl (S)-3-{1-[3-(4-chloro-phenyl)ureido]-2-(4-methoxy-phenyl)ethyl}-1,2,4-oxadiazol-5-carboxylate | ¹H-NMR (400 MHz, CDCl₃) δ 1.47 (3H, t, J = 7.0 Hz), 3.20 (2H, m), 3.78 (3H, s), 4.55 (2H, q, J = 7.0 Hz), 5.05 (1H, d, J = 9.1 Hz), 5.52 (1H, m), 6.22 (1H, s), 6.80 (2H, d, J = 8.5 Hz), 6.98 (2H, d, J = 8.5 Hz), 7.18 (2H, d, J = 9.1 Hz), 7.24 (2H, d, J = 9.1 Hz). |
| 109-20 | | ethyl (S)-3-{2-(4-chlorophenyl)-1-{3-(4-chloro-phenyl)ureido]-ethyl}-1,2,4-oxadiazol-5-carboxylate | ¹H-NMR (400 MHz, DMSO-d₆) δ 1.33 (3H, t, J = 7.3 Hz), 3.15 (2H, d, J = 7.9 Hz), 4.41 (2H, q, J = 7.3 Hz), 5.22-5.30 (1H, m), 6.92 (1H, d, J = 8.5 Hz), 7.21-7.26 (4H, m), 7.31-7.37 (4H, m), 8.72 (1H, s). |
| 109-21 | | ethyl (S)-3-{2-(4-chlorophenyl)-1-[3-(4-fluoro-phenyl)ureido]-ethyl}-1,2,4-oxadiazol-5-carboxylate | ¹H-NMR (400 MHz, DMSO-d₆) δ 1.34 (3H, t, J = 7.3 Hz), 3.14 (2H, d, J = 7.9 Hz), 4.41 (2H, q, J = 7.3 Hz), 5.22-5.29 (1H, m), 6.86 (1H, d, J = 8.5 Hz), 6.99-7.06 (2H, m), 7.23 (2H, d, J = 8.5 Hz), 7.30-7.35 (4H, m), 8.60 (1H, s). |

TABLE 53

| Ref. No | Str. | Chemical name | P.D. |
|---|---|---|---|
| 109-22 | 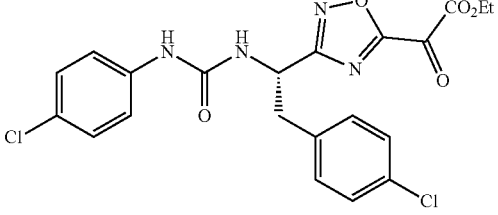 | ethyl (S)-3-{2-(4-chlorophenyl)-1-[3-(4-cyano-phenyl)ureido]-ethyl}-1,2,4-oxadiazol-5-carboxylate | $^1$H-NMR (400 MHz, DMSO-$d_6$) δ 1.33 (3H, t, J = 7.3 Hz), 3.13-3.19 (2H, m), 4.41 (2H, q, J = 7.3 Hz), 5.23-5.31 (1H, m), 7.13 (1H, d, J = 8.5 Hz), 7.23 (2H, d, J = 8.5 Hz), 7.33 (2H, d, J = 8.5 Hz), 7.50 (2H, d, J = 8.5 Hz), 7.65 (2H, d, J = 8.5 Hz), 9.12 (1H, s). |
| 109-23 | 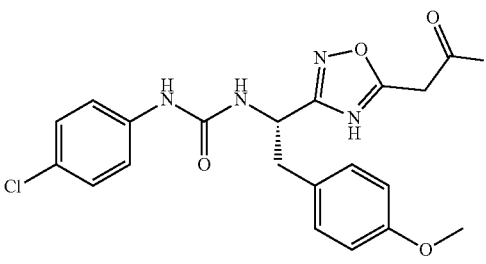 | methyl (S)-2-(5-(1-(3-(4-chloro-phenyl)ureido)-2-(4-methoxy-phenyl)ethyl)-4H-1,2,4-triazol-3-yl)acetate | $^1$H-NMR (400 MHz, DMSO-$d_6$) δ 2.98 (1H, dd, J = 13.9, 7.3 Hz), 3.05 (1H, dd, J = 13.9, 6.7 Hz), 3.64 (3H, s), 3.68 (3H, s), 3.79 (2H, s), 4.98-5.07 (1H, m), 6.65 (1H, s), 6.77 (2H, d, J = 8.5 Hz), 6.97 (2H, d, J = 8.5 Hz), 7.23 (2H, dt, J = 8.5, 1.8 Hz), 7.37 (2H, dt, J = 8.5, 1.8 Hz), 8.78 (1H, s), 13.63 (1H, s). |
| 109-24 | 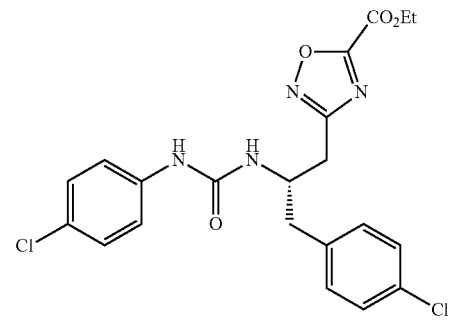 [SMILES: CCOC(=O)c1nc(C[C@H](Cc2ccc(Cl)cc2)NC(=O)Nc2ccc(Cl)cc2)no1] | ethyl (S)-3-{3-(4-chlorophenyl)-2-[3-(4-chloro-phenyl)ureido]-propyl}-1,2,4-oxadiazol-5-carboxylate | $^1$H-NMR (400 MHz, DMSO-$d_6$) δ 1.31 (3H, t, J = 7.0 Hz), 2.79-2.89 (2H, m), 2.94-3.04 (2H, m), 4.24 (1H, q, J = 6.9 Hz), 4.39 (2H, q, J = 7.0 Hz), 6.23 (1H, d, J = 8.5 Hz), 7.23 (4H, dd, J = 12.4, 8.2 Hz), 7.33 (4H, dd, J = 12.4, 8.2 Hz), 8.53 (1H, s). |
| 109-25 | 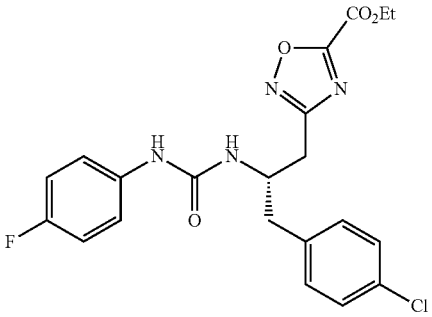 [SMILES: CCOC(=O)c1nc(C[C@H](Cc2ccc(Cl)cc2)NC(=O)Nc2ccc(F)cc2)no1] | ethyl (S)-3-(3-(4-chlorophenyl)-2-(3-(4-fluoro-phenyl)ureido)-propyl)-1,2,4-oxadiazol-5-carboxylate | $^1$H-NMR (400 MHz, DMSO-$d_6$) δ 1.31 (3H, t, J = 7.0 Hz), 2.79-2.87 (2H, m), 2.96-3.00 (2H, m), 4.24 (1H, q, J = 7.1 Hz), 4.39 (2H, q, J = 7.0 Hz), 6.17 (1H, d, J = 8.5 Hz), 7.01 (2H, t, J = 9.1 Hz), 7.24-7.28 (4H, m), 7.35 (2H, d, J = 8.5 Hz), 8.42 (1H, s). |

TABLE 54

| Ref. No | Str. | Chemical name | P.D. |
|---|---|---|---|
| 109-26 | 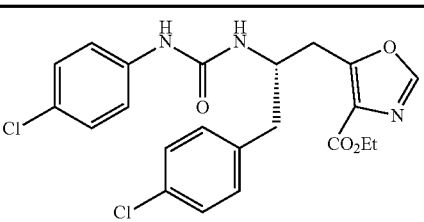 | ethyl (S)-5-(2-(3-(4-chloro-phenyl)ureido)-3-(4-methoxy-phenyl)propyl)-oxazole-4-carboxylate | $^1$H-NMR (400 MHz, DMSO-$d_6$) δ 1.19 (3H, t, J = 7.3 Hz), 2.72 (2H, dq, J = 26.9, 7.0 Hz), 3.08-3.35 (2H, m), 3.70 (3H, s), 4.14-4.25 (3H, m), 6.05 (1H, d, J = 9.1 Hz), 6.85 (2H, d, J = 8.5 Hz), 7.13 (2H, d, J = 9.1 Hz), 7.21 (2H, d, J = 9.1 Hz), 7.29 (2H, d, J = 9.1 Hz), 8.35 (1H, s), 8.47 (1H, s). |

TABLE 54-continued

| Ref. No | Str. | Chemical name | P.D. |
|---|---|---|---|
| 109-27 | 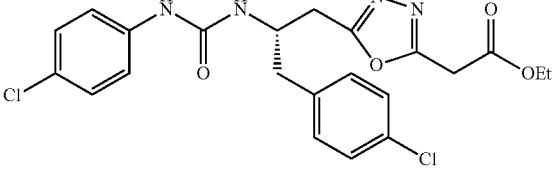 | ethyl (S)-2-(5-(3-(4-chlorophenyl)-2-(3-(4-chlorophenyl)ureido)propyl)-1,3,4-oxadiazol-2-yl)acetate | $^{1}$H-NMR (400 MHz, DMSO-d$_{6}$) δ 1.15 (3H, t, J = 7.0 Hz), 2.82 (2H, t, J = 7.9 Hz), 3.00-3.15 (2H, m), 4.09 (2H, q, J = 7.0 Hz), 4.10 (2H, s), 6.28 (1H, d, J = 8.5 Hz), 7.23 (4H, dd, J = 11.2, 8.8 Hz), 7.33 (4H, t, J = 9.1 Hz), 8.58 (1H, s). |
| 109-28 | 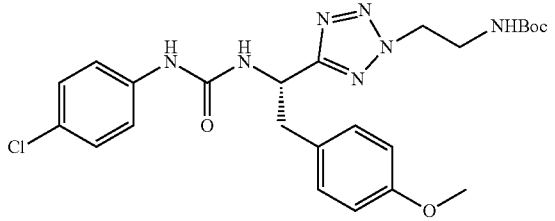 [SMILES: COc1ccc(C[C@H](NC(=O)Nc2ccc(Cl)cc2)c2nnn(CCNC(=O)OC(C)(C)C)n2)cc1] | tert-butyl (S)-(2-(5-(1-(3-(4-chlorophenyl)ureido)-2-(4-methoxyphenyl)ethyl)-2H-tetrazol-2-yl)ethyl)carbamate | $^{1}$H-NMR (400 MHz, CDCl$_{3}$) δ 1.33 (9H, s), 3.00-3.12 (2H, m), 3.41 (2H, q, J = 6.1 Hz), 3.69 (3H, s), 4.64 (2H, t, J = 6.1 Hz), 5.28 (1H, q, J = 7.9 Hz), 6.75 (1H, d, J = 8.5 Hz), 6.80 (2H, d, J = 9.1 Hz), 6.96-7.05 (1H, m), 7.00 (2H, d, J = 9.1 Hz), 7.23 (2H, d, J = 8.5 Hz), 7.35 (2H, d, J = 9.1 Hz), 8.72 (1H, brs). |
| 109-29 | 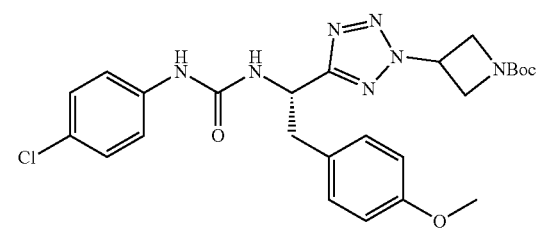 [SMILES: COc1ccc(C[C@H](NC(=O)Nc2ccc(Cl)cc2)c2nnn(C3CN(C(=O)OC(C)(C)C)C3)n2)cc1] | tert-butyl (S)-3-(5-(1-(3-(4-chlorophenyl)ureido)-2-(4-methoxyphenyl)ethyl)-2H-tetrazol-2-yl)azetidin-1-carboxylate | $^{1}$H-NMR (400 MHz, CDCl$_{3}$) δ 1.47 (9H, s), 3.17-3.28 (2H, m), 3.75 (3H, s), 4.37 (2H, dd, J = 9.8, 5.5 Hz), 4.43-4.49 (2H, m), 5.46 (1H, d, J = 8.5 Hz), 6.65 (1H, s), 6.75 (2H, d, J = 8.5 Hz), 6.92 (2H, d, J = 8.5 Hz), 7.24 (4H, d, J = 13.9 Hz). |

TABLE 55

| Ref. No | Str. | Chemical name | P.D. |
|---|---|---|---|
| 109-30 | 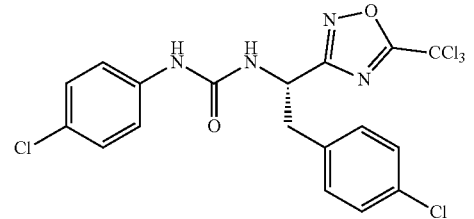 | (S)-1-(4-chlorophenyl)-3-(2-(4-chlorophenyl)-1-(5-(trichloromethyl)-1,2,4-oxadiazol-3-yl)ethyl)urea | $^{1}$H-NMR (400 MHz, CDCl$_{3}$) δ 3.18-3.31 (2H, m), 5.12 (1H, d, J = 8.6 Hz), 5.55 (1H, dt, J = 8.6, 6.7 Hz), 6.37 (1H, s), 7.01 (2H, td, J = 5.2, 3.1 Hz), 7.19-7.28 (6H, m). |
| 109-31 | 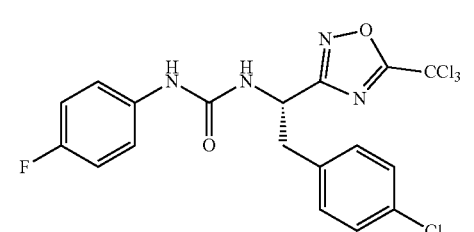 | (S)-1-(2-(4-chlorophenyl)-1-(5-(trichloromethyl)-1,2,4-oxadiazol-3-yl)ethyl)-3-(4-fluorophenyl)urea | $^{1}$H-NMR (400 MHz, DMSO-d$_{6}$) δ 3.16-3.22 (2H, m), 5.27 (1H, dd, J = 8.0, 15.3 Hz), 6.90 (1H, d, J = 8.6 Hz), 7.04 (2H, d, J = 9.2 Hz), 7.24 (2H, d, J = 8.6 Hz), 7.31-7.35 (4H, m), 8.63 (1H, brs). |
| 109-32 | 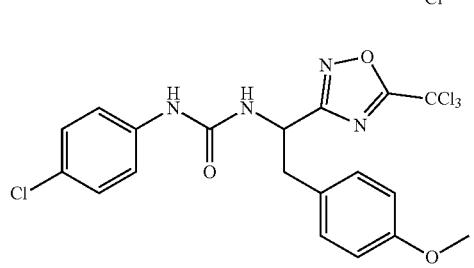 | 1-(4-chlorophenyl)-3-(2-(4-methoxyphenyl)-1-(5-(trichloromethyl)-1,2,4-oxadiazol-3-yl)ethyl)urea | $^{1}$H-NMR (400 MHz, DMSO-d$_{6}$) δ 3.11 (2H, d, J = 7.3 Hz), 3.70 (3H, s), 5.21 (1H, q, J = 7.3 Hz), 6.83 (2H, d, J = 8.6 Hz), 6.96 (1H, d, J = 7.9 Hz), 7.10 (2H, d, J = 8.6 Hz), 7.24 (2H, d, J = 8.4 Hz), 7.37 (2H, d, J = 8.6 Hz), 8.79 (1H, s). |

TABLE 55-continued

| Ref. No | Str. | Chemical name | P.D. |
|---|---|---|---|
| 109-33 | | ethyl 4-(3-(4-chlorophenyl)-ureido)-5-(4-methoxyphenyl)-pentanoate | $^1$H-NMR (400 MHz, CDCl$_3$) δ 1.23 (3H, t, J = 7.3 Hz), 1.65-1.77 (1H, m), 1.80-1.91 (1H, m), 2.32-2.49 (2H, m), 2.71-2.82 (2H, m), 3.79 (3H, s), 3.98 (1H, d, J = 5.4 Hz), 4.11 (2H, q, J = 7.3 Hz), 4.54 (1H, d, J = 8.5 Hz), 6.34 (1H, s), 6.83 (2H, d, J = 8.5 Hz), 7.10 (2H, d, J = 8.5 Hz), 7.23 (4H, d, J = 8.5 Hz). |

TABLE 56

| Ref. No | Str. | Chemical name | P.D. |
|---|---|---|---|
| 109-34 | | ethyl (S,Z)-2-(((1-amino-2-[3-(4-chlorophenyl)-ureido]-3-(4-{[(trifluoro-methyl)sulfonyl]-oxy}phenyl)-propylidene)amino)oxy)acetate | $^1$H-NMR (400 MHz, CDCl$_3$) δ 1.26 (3H, t, J = 7.3 Hz), 3.15-3.17 (2H, m), 4.17 (2H, q, J = 7.1 Hz), 4.41 (2H, s), 4.43 (1H, q, J = 7.1 Hz), 5.15 (2H, brs), 5.40 (1H, d, J = 7.3 Hz), 6.80 (1H, brs), 7.16-7.30 (8H, m). |
| 109-35 | | ethyl (S,Z)-2-(({1-amino-2-[3-(4-chlorophenyl)-ureido]-3-(4-methoxyphenyl)-propylidene}amino)oxy)acetate | $^1$H-NMR (400 MHz, DMSO-d$_6$) δ 1.15 (3H, t, J = 7.1 Hz), 2.76 (1H, dd, J = 13.8, 7.3 Hz), 2.92 (1H, dd, J = 13.8, 5.8 Hz), 3.69 (3H, s), 4.07 (2H, q, J = 7.1 Hz), 4.34 (2H, s), 4.34-4.40 (1H, m), 5.90 (2H, brs), 6.19 (1H, d, J = 8.6 Hz), 6.80 (2H, d, J = 8.6 Hz), 7.11 (2H, d, J = 8.6 Hz), 7.23 (2H, d, J = 8.9 Hz), 7.35 (2H, d, J = 8.9 Hz), 8.75 (1H, s). |
| 109-36 | | ethyl (S)-2-({3-(4-chlorophenyl)-2-[3-(4-chloro-phenyl)ureido]-propanimidamide}-oxy)acetate | $^1$H-NMR (400 MHz, DMSO-d$_6$) δ 1.15 (3H, t, J = 7.0 Hz), 2.81-3.01 (2H, m), 4.07 (2H, q, J = 7.0 Hz), 4.35 (2H, s), 4.42 (1H, q, J = 7.3 Hz), 5.94 (2H, s), 6.22 (1H, d, J = 9.1 Hz), 7.20-7.26 (4H, m), 7.28-7.36 (4H, m), 8.75 (1H, s). |
| 109-37 | From 1$^{st}$ peak | ethyl 2-(((Z)-{(2S)-1-amino-2-[3-(4-chloro-phenyl)ureido]-3-[4-(1-hydroxy-ethyl)phenyl]-propylidene}amino)oxy)acetate | $^1$H-NMR (400 MHz, CDCl$_3$) δ 1.25 (3H, t, J = 7.3 Hz), 1.46 (3H, d, J = 6.7 Hz), 2.06 (1H, d, J = 3.1 Hz), 3.04-3.16 (2H, m), 4.17 (2H, q, J = 7.3 Hz), 4.35-4.43 (3H, m), 4.76-4.90 (1H, m), 5.15 (2H, s), 5.34 (1H, d, J = 6.7 Hz), 6.86 (1H, s), 7.16-7.30 (8H, m). |

TABLE 57

| Ref. No | Str. | Chemical name | P.D. |
|---|---|---|---|
| 109-38 | (From 2nd peak) | ethyl 2-(((Z)-{(2S)-1-amino-2-[3-(4-chloro-phenyl)ureido]-3-[4-(1-hydroxy-ethyl)phenyl]-propylidene}amino)oxy)acetate | $^1$H-NMR (400 MHz, CDCl$_3$) δ 1.22-1.28 (3H, m), 1.42-1.47 (3H, m), 2.07-2.17 (1H, m), 2.95-3.18 (2H, m), 4.15-4.19 (2H, m), 4.34-4.42 (3H, m), 4.76-4.88 (1H, m), 5.18 (2H, s), 5.43 (1H, d, J = 6.7 Hz), 6.90 (0.5H, s), 7.02 (0.5H, s), 7.15-7.27 (8H, m). |
| 109-39 | | ethyl (R)-2-(((Z)-{(S)-1-amino-3-(4-chlorophenyl)-2-[3-(4-chloro-phenyl)ureido]-propylidene}amino)oxy)propanoate | $^1$H-NMR (400 MHz, DMSO-d$_6$) δ 1.10 (3H, t, J = 7.3 Hz), 1.27 (3H, d, J = 7.3 Hz), 2.82 (1H, dd, J = 14.1, 7.9 Hz), 2.97 (1H, dd, J = 14.1, 6.1 Hz), 3.95-4.05 (2H, m), 4.32 (1H, q, J = 7.3 Hz), 4.37-4.45 (1H, m), 5.88 (2H, s), 6.18 (1H, d, J = 8.6 Hz), 7.20 (2H, d, J = 8.6 Hz), 7.23 (2H, d, J = 8.6 Hz), 7.30 (2H, d, J = 8.6 Hz), 7.35 (2H, d, J = 8.6 Hz), 8.75 (1H, s). |
| 109-40 | | methyl (S)-2-(((Z)-{(S)-1-amino-3-(4-chlorophenyl)-2-[3-(4-chloro-phenyl)ureido]-propylidene}amino)oxy)propanoate | $^1$H-NMR (400 MHz, DMSO-d$_6$) δ 1.28 (3H, d, J = 7.3 Hz), 2.82 (1H, dd, J = 13.4, 7.3 Hz), 2.96 (1H, dd, J = 13.4, 6.1 Hz), 3.60 (3H, s), 4.36 (1H, q, J = 7.3 Hz), 4.37-4.44 (1H, m), 5.90 (2H, s), 6.21 (1H, d, J = 8.6 Hz), 7.19 (2H, d, J = 8.6 Hz), 7.23 (2H, d, J = 8.6 Hz), 7.29 (2H, d, J = 8.6 Hz), 7.35 (2H, d, J = 8.6 Hz), 8.77 (1H, s). |

Reference Example 110

(S,Z)-4-(3-Amino-2-(3-(4-chlorophenyl) ureido)-3-((2-hydroxyethoxy)imino)propyl)phenyl Trifluoromethanesulfonate

[Chem. 158]

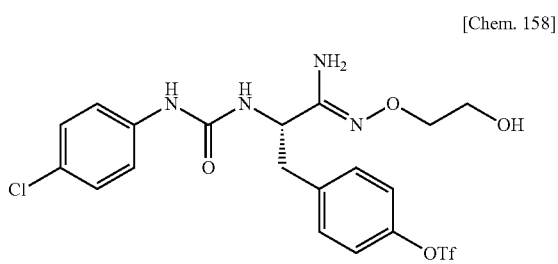 [SMILES: N/C(=N\OCCO)[C@H](Cc1ccc(OS(=O)(=O)C(F)(F)F)cc1)NC(=O)Nc1ccc(Cl)cc1]

To a solution of ethyl (S,Z)-2-(((1-amino-2-[3-(4-chlorophenyl)ureido]-3-(4-{[(trifluoromethyl)sulfonyl]oxy}phenyl)propylidene)amino)ox y)acetate (580 mg) in tetrahydrofuran (4.1 mL) under ice-cooling was added lithium borohydride (3M tetrahydrofuran solution, 1.71 mL), and the reaction mixture was stirred at the same temperature for 2 hours. To the reaction solution was added 10% citric acid aqueous solution, and the mixture was extracted with ethyl acetate. The organic layer was washed with water and a brine, and dried over anhydrous sodium sulfate. The solvent was removed under reduced pressure, and the obtained residue was then purified by silica gel column chromatography (hexane:ethyl acetate=4:1) to obtain the title compound (350 mg).

$^1$H-NMR (400 MHz, DMSO-d$_6$) δ 2.91 (1H, dd, J=14.1, 8.0 Hz), 3.07 (1H, dd, J=14.1, 5.4 Hz), 3.48 (2H, q, J=5.4 Hz), 3.75 (2H, t, J=5.4 Hz), 4.43-4.49 (2H, m), 5.87 (2H, brs), 6.28 (1H, J=8.5 Hz), 7.22-7.24 (2H, m), 7.34-7.40 (6H, m), 8.79 (1H, brs).

Example 1-1

(−)-(S)-1-(4-Chlorophenyl)-3-{1-[2-(2-hydroxyethyl)-2H-tetrazol-5-yl]-2-(4-methoxyphenyl)ethyl}urea

[Chem. 159]

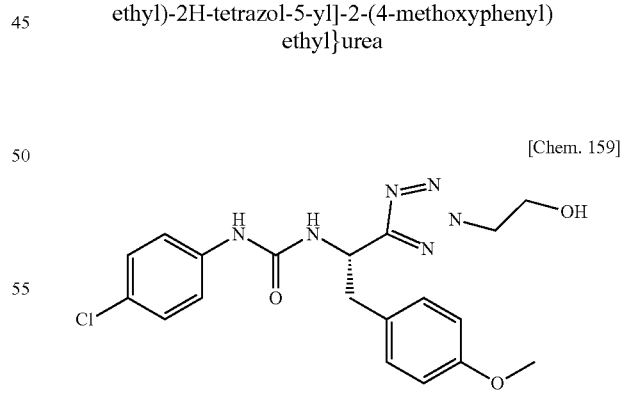

To a solution of tert-butyl (S)-{1-[2-(2-hydroxyethyl)-2H-tetrazol-5-yl]-2-(4-methoxyphenyl)ethyl}carbamate (9.31 g) in 1,4-dioxane (26.0 mL) was added 4 mol/L hydrogen chloride-1,4-dioxane (64.0 ML), and the reaction mixture was stirred at room temperature for 2 hours. The reaction solution was concentrated under reduced pressure to obtain the resulting crude product.

To a suspension of the resulting crude product in ethyl acetate (85.3 mL) were added a saturated aqueous sodium hydrogen carbonate (40.0 mL) and 4-chlorophenyl isocyanate (4.06 g), and the mixture was stirred at room temperature for 1 hour. Then, ethyl acetate (100 mL) and water (50 mL) were added to the reaction mixture, and the organic layer was separated. The organic layer was washed with a brine (90 mL), and dried over anhydrous sodium sulfate, and filtered. The filtrate was concentrated under reduced pressure, and the obtained residue was triturated with ethyl acetate:hexane=1:1 (90 mL) to obtain the title compound as a white solid (10.2 g).

$^1$H-NMR (400 MHz, DMSO-$d_6$) δ 3.01-3.15 (2H, m), 3.68 (3H, s), 3.86 (2H, m), 4.65 (2H, m), 5.03 (1H, t, J=5.4 Hz), 5.29 (1H, m), 6.76-6.82 (3H, m), 7.01 (2H, d, J=9.1 Hz), 7.24 (2H, d, J=9.1 Hz), 7.36 (2H, d, J=9.1 Hz), 8.73 (1H, s).

ESIMS (+) 417[M+H]$^+$.

$[α]_D^{26}$ −19 (c 0.34, EtOH).

Examples 1-2 to 1-79

The following Examples 1-2 to 1-78 were obtained using each corresponding starting material and reactant in the same method as in Example 1-1.

The structures and spectral data thereof are shown in Tables 58-78.

TABLE 58

| Ex. No | Str. | Chemical name | P.D. |
|---|---|---|---|
| 1-2 | | (S)-1-(4-fluorophenyl)-3-{1-[2-(2-hydroxyethyl)-2H-tetrazol-5-yl]-2-(4-methoxyphenyl)ethyl}urea | $^1$H-NMR (400 MHz, DMSO-$d_6$) δ 2.87-3.14 (2H, m), 3.68 (3H, s), 3.86 (2H, m), 4.65 (2H, m), 5.05 (1H, m), 5.28 (1H, m), 6.77-6.85 (3H, m), 6.99-7.06 (4H, m), 7.34 (2H, m), 8.71 (1H, br s). ESIMS (+) 401 [M − H]$^+$. |
| 1-3 | | (S)-1-(4-cyanophenyl)-3-{1-[2-(2-hydroxyethyl)-2H-tetrazol-5-yl]-2-(4-methoxyphenyl)ethyl}urea | $^1$H-NMR (400 MHz, DMSO-$d_6$) δ 3.06 (1H, m), 3.14 (1H, m), 3.68 (3H, s), 3.86 (2H, m), 4.65 (2H, m), 5.05 (1H, t, J = 5.5 Hz), 5.29 (1H, m), 6.79 (2H, d, J = 8.6 Hz), 7.02 (3H, m), 7.51 (2H, d, J = 8.6 Hz), 7.64 (2H, d, J = 8.6 Hz), 9.16 (1H, br s). ESIMS (+) 408 [M + H]$^+$. |
| 1-4 | | (S)-1-(4-chlorophenyl)-3-{1-[2-(2-hydroxyethyl)-2H-tetrazol-5-yl]-2-phenylethyl}urea | $^1$H-NMR (400 MHz, CDCl$_3$) δ 2.58-3.22 (1H, m), 3.87 (2H, q, J = 5.5 Hz), 4.65 (2H, t, J = 5.5 Hz), 5.03 (1H, t, J = 5.4 Hz), 5.32-5.38 (1H, m), 6.80-6.83 (1H, m), 7.10-7.13 (2H, m), 7.17-7.19 (1H, m), 7.22-7.26 (1H, m), 7.22-7.26 (4H, m), 7.35-7.37 (2H, m), 8.72 (br, 1H). ESIMS (+) 387 [M + H]$^+$. |
| 1-5 | | (S)-1-(4-chlorophenyl)-3-{2-(4-cyanophenyl)-1-[2-(2-hydroxyethyl)-2H-tetrazol-5-yl]ethyl}urea | $^1$H-NMR (400 MHz, DMSO-$d_6$) δ 3.19-3.36 (2H, m), 3.86 (2H, q, J = 5.4 Hz), 4.66 (2H, t, J = 5.4 Hz), 5.03 (1H, t, J = 5.4 Hz), 5.36-5.44 (1H, m), 6.88 (1H, d, J = 8.5 Hz), 7.24 (2H, d, J = 8.5 Hz), 7.32-7.37 (4H, m), 7.71 (2H, d, J = 8.5 Hz), 8.69 (1H, s). ESIMS (+) 412 [M + H]$^+$. |

TABLE 59

| Ex. No | Str. | Chemical name | P.D. |
|---|---|---|---|
| 1-6 | | (S)-1-{2-(4-cyanophenyl)-1-[2-(2-hydroxyethyl)-2H-tetrazol-5-yl]ethyl}-3-(4-fluorophenyl)-urea | $^1$H-NMR (400 MHz, DMSO-$d_6$) δ 3.19-3.33 (2H, m), 3.86 (2H, q, J = 5.4 Hz), 4.66 (2H, t, J = 5.4 Hz), 5.03 (1H, t, J = 5.4 Hz), 5.36-5.44 (1H, m), 6.82 (1H, d, J = 8.5 Hz), 6.99-7.06 (2H, m), 7.30-7.36 (4H, m), 7.72 (2H, d, J = 8.5 Hz), 8.57 (1H, s). ESIMS (+) 396 [M + H]$^+$. |
| 1-7 | | (−)-(S)-1-(4-chlorophenyl)-3-{2-(4-chlorophenyl)-1-[2-(2-hydroxyethyl)-2H-tetrazol-5-yl]ethyl}urea | $^1$H-NMR (400 MHz, DMSO-$d_6$) δ 3.09-3.22 (2H, m), 3.86 (2H, q, J = 5.4 Hz), 4.65 (2H, t, J = 5.4 Hz), 5.03 (1H, t, J = 5.4 Hz), 5.34 (1H, q, J = 7.5 Hz), 6.83 (1H, d, J = 9.1 Hz), 7.13 (2H, d, J = 8.5 Hz), 7.24 (2H, d, J = 8.5 Hz), 7.29 (2H, d, J = 7.9 Hz), 7.36 (2H, d, J = 9.1 Hz), 8.70 (1H, s). ESIMS (+) 421 [M + H]$^+$. $[α]_D^{28}$ −19.0° (c 0.346, EtOH) |
| 1-8 | | (−)-(S)-1-(4-chlorophenyl)-1-[2-(2-hydroxyethyl)-2H-tetrazol-5-yl]ethyl}-3-(4-fluorophenyl)-urea | $^1$H-NMR (400 MHz, DMSO-$d_6$) δ 3.09-3.21 (2H, m), 3.86 (2H, q, J = 5.4 Hz), 4.65 (2H, t, J = 5.4 Hz), 5.04 (1H, t, J = 5.4 Hz), 5.34 (1H, q, J = 7.5 Hz), 6.76 (1H, d, J = 8.5 Hz), 7.03 (2H, t, J = 8.5 Hz), 7.13 (2H, d, J = 8.5 Hz), 7.28-7.35 (4H, m), 8.59 (1H, s). ESIMS (+) 405 [M + H]$^+$. $[α]_D^{29}$ −12.8° (c 0.349, EtOH) |
| 1-9 | | (S)-1-{2-(4-chlorophenyl)-1-[2-(2-hydroxyethyl)-2H-tetrazol-5-yl]ethyl}-3-(4-cyanophenyl)urea | $^1$H-NMR (400 MHz, DMSO-$d_6$) δ 3.12-3.22 (2H, m), 3.86 (2H, q, J = 5.4 Hz), 4.66 (2H, t, J = 5.4 Hz), 5.04 (1H, t, J = 5.4 Hz), 5.35 (1H, q, J = 7.5 Hz), 7.02 (1H, d, J = 8.5 Hz), 7.14 (2H, t, J = 8.5 Hz), 7.29 (2H, d, J = 8.5 Hz), 7.51 (2H, d, J = 9.1 Hz), 7.65 (2H, d, J = 8.5 Hz), 9.09 (1H, s). ESIMS (+) 412 [M + H]$^+$. $[α]_D^{27}$ −14.6° (c 0.349, EtOH) |

TABLE 60

| Ex. No | Str. | Chemical name | P.D. |
|---|---|---|---|
| 1-10 | | (S)-1-(4-chlorophenyl)-3-{2-(2,3-dihydrobenzofuran-5-yl)-1-[2-(2-hydroxyethyl)-2H-tetrazol-5-yl]ethyl}urea | $^1$H-NMR (400 MHz, CDCl$_3$) δ 2.31 (1H, t, J = 6.7 Hz), 3.11 (2H, t, J = 8.8 Hz), 3.19 (2H, d, J = 6.7 Hz), 4.08-4.13 (2H, m), 4.52 (2H, t, J = 8.8 Hz), 4.69 (2H, t, J = 5.1 Hz), 5.40 (1H, d, J = 7.9 Hz), 5.51-5.57 (1H, m), 6.50 (1H, s), 6.61 (1H, d, J = 7.9 Hz), 6.70 (1H, d, J = 7.9 Hz), 6.87 (1H, s), 7.20 (2H, d, J = 9.1 Hz), 7.23 (2H, d, J = 9.1 Hz). ESIMS (+) 429 [M + H]$^+$. |
| 1-11 | | (S)-1-(4-chlorophenyl)-3-{2-(4-ethylphenyl)-1-[2-(2-hydroxyethyl)-2H-tetrazol-5-yl]ethyl}urea | $^1$H-NMR (400 MHz, DMSO-$d_6$) δ 1.23 (3H, t, J = 7.9 Hz), 2.53 (2H, q, J = 7.8 Hz), 3.05-3.17 (2H, m), 3.86 (2H, q, J = 5.5 Hz), 4.65 (2H, t, J = 5.5 Hz), 5.03 (1H, t, J = 5.5 Hz), 5.32 (1H, q, J = 7.8 Hz), 6.78 (1H, d, J = 8.5 Hz), 7.00 (2H, d, J = 7.8 Hz), 7.07 (2H, d, J = 7.9 Hz), 7.23 (2H, d, J = 9.1 Hz), 7.36 (2H, d, J = 9.1 Hz), 8.72 (1H, s). ESIMS (+) 415 [M + H]$^+$. |

TABLE 60-continued

| Ex. No | Str. | Chemical name | P.D. |
|---|---|---|---|
| 1-12 | | (−)-(S)-1-(4-cyanophenyl)-3-{2-(2,3-dihydro-benzofuran-5-yl)-1-[2-(2-hydroxyethyl)-2H-tetrazol-5-yl]ethyl}urea | $^1$H-NMR (400 MHz, DMSO-d$_6$) δ 3.01-3.16 (4H, m), 3.86 (2H, q, J = 5.4 Hz), 4.45 (2H, t, J = 8.8 Hz), 4.65 (2H, t, J = 5.4 Hz), 5.03 (1H, t, J = 5.4 Hz), 5.28 (1H, q, J = 7.3 Hz), 6.60 (1H, d, J = 7.9 Hz), 6.79 (1H, d, J = 7.9 Hz), 6.95 (2H, s), 7.51 (2H, d, J = 8.5 Hz), 7.65 (2H, t, J = 8.5 Hz), 9.11 (1H, s). ESIMS (+) 420 [M + H]$^+$. [α]$_D^{27}$ −27.0° (c 0.351, EtOH) |

TABLE 61

| Ex. No | Str. | Chemical name | P.D. |
|---|---|---|---|
| 1-13 | | 1-(4-chlorophenyl)-3-{(1S,2R)-1-[2-(2-hydroxyethyl)-2H-tetrazol-5-yl]-2-(4-methoxyphenyl)propyl}urea | $^1$H-NMR (400 MHz, DMSO-d$_6$) δ 1.25 (3H, d, J = 7.3 Hz), 3.22-3.31 (1H, m), 3.68 (3H, s), 3.81 (2H, q, J = 5.5 Hz), 4.60 (2H, q, J = 5.5 Hz), 5.01 (1H, t, J = 5.4 Hz), 5.25 (1H, dd, J = 6.7, 9.1 Hz), 6.76 (2H, d, J = 8.5 Hz), 6.84 (1H, d, J = 9.7 Hz), 6.96 (2H, d, J = 8.5 Hz), 7.24 (2H, d, J = 9.1 Hz), 7.37 (2H, d, J = 9.1 Hz), 8.80 (1H, br). ESIMS (+) 431 [M + H]$^+$. |
| 1-14 | | 1-(4-chlorophenyl)-3-{(1S,2S)-1-[2-(2-hydroxyethyl)-2H-tetrazol-5-yl]-2-(4-methoxyphenyl)propyl}urea | $^1$H-NMR (400 MHz, DMSO-d$_6$) δ 1.12 (3H, d, J = 7.2 Hz), 3.20-3.28 (1H, m), 3.69 (3H, s), 3.86 (2H, q, J = 5.5 Hz), 4.65 (2H, t, J = 5.5 Hz), 5.03 (1H, t, J = 5.5 Hz), 5.28 (1H, dd, J = 7.9, 9.1 Hz), 6.54-6.58 (1H, m), 6.81 (2H, d, J = 8.5 Hz), 7.03 (2H, d, J = 8.5 Hz), 7.22 (2H, d, J = 9.1 Hz), 7.32 (2H, d, J = 9.1 Hz), 8.71 (1H, s). ESIMS (+) 431 [M + H]$^+$. |
| 1-15 | | (S)-1-(4-chlorophenyl)-3-(2-(4-ethylphenyl)-1-{5-[(2-hydroxyethyl)(methyl)amino]-1,2,4-oxadiazol-3-yl}ethyl)urea | $^1$H-NMR (400 MHz, DMSO-d$_6$) δ 1.13 (3H, t, J = 7.9 Hz), 2.54 (2H, q, J = 7.9 Hz), 2.92-3.06 (2H, m), 3.10 (3H, s), 3.44-3.50 (2H, m), 3.56-3.63 (2H, m), 4.85 (1H, t, J = 5.4 Hz), 4.87-4.94 (1H, m), 6.61 (1H, d, J = 8.5 Hz), 7.06 (2H, d, J = 8.5 Hz), 7.10 (2H, d, J = 8.5 Hz), 7.23 (2H, d, J = 9.1 Hz), 7.36 (2H, d, J = 9.1 Hz), 8.73 (1H, s). ESIMS (+) 444 [M + H]$^+$. |

TABLE 62

| Ex. No | Str. | Chemical name | P.D. |
|---|---|---|---|
| 1-16 | | (+)-(S)-1-(4-chlorophenyl)-3-{1-[2-(3-hydroxypropyl)-2H-tetrazol-5-yl]-2-(4-methoxyphenyl)ethyl}urea | $^1$H-NMR (400 MHz, DMSO-d$_6$) δ 1.95-2.02 (2H, m), 3.08 (2H, d, J = 8.0 Hz), 3.36 (2H, dd, J = 5.5, 17.1 Hz), 3.68 (3H, s), 4.66 (3H, t, J = 7.4 Hz), 5.27 (1H, dd, J = 7.4, 15.3 Hz), 6.78 (3H, d, J = 8.6 Hz), 6.97 (2H, d, J = 8.6 Hz), 7.23 (2H, d, J = 9.2 Hz), 7.36 (2H, d, J = 8.6 Hz), 8.72 (1H, s). ESIMS (+) 431 [M + H]$^+$. [α]$_D^{25}$ +12 (c 0.304, THF). |

TABLE 62-continued

| Ex. No | Str. | Chemical name | P.D. |
|---|---|---|---|
| 1-17 | | (+)-(S)-1-(4-chlorophenyl)-3-(1-(2-(3-hydroxybutyl)-2H-tetrazol-5-yl)-2-(4-methoxyphenyl)-ethyl)urea | $^1$H-NMR (400 MHz, DMSO-$d_6$) δ 1.28-1.35 (2H, m), 1.84-1.91 (2H, m), 3.08 (2H, d, J = 6.8 Hz), 3.37 (2H, dd, J = 6.1, 11.6 Hz), 3.68 (3H, s), 4.47 (1H, t, J = 4.9 Hz), 4.62 (2H, t, J = 7.3 Hz), 5.27 (1H, dd, J = 7.3, 15.9 Hz), 6.77 (3H, m), 6.96 (2H, d, J = 9.2 Hz), 7.23 (2H, d, J = 8.6 Hz), 7.36 (2H, d, J = 9.2 Hz), 8.74 (1H, s). ESIMS (+) 445 [M + H]$^+$. $[α]_D^{25}$ +11 (c 0.364, THF). |
| 1-18 | | (S)-1-(4-fluoro-phenyl)-3-{1-[5-(2-hydroxyethyl)-1,3,4-thiadiazol-2-yl]-2-(4-methoxyphenyl)-ethyl}urea | $^1$H-NMR (400 MHz, DMSO-$d_6$) δ 3.07-3.16 (3H, m), 3.24 (1H, dd, J = 13.9, 5.4 Hz), 3.66-3.71 (5H, m), 4.99 (1H, t, J = 5.1 Hz), 5.32 (1H, m), 6.84 (2H, d, J = 8.5 Hz), 6.93 (1H, m), 7.03 (2H, m), 7.15 (2H, d, J = 9.1 Hz), 7.40 (2H, m), 8.65 (1H, br s). ESIMS (+) 417 [M + H]$^+$. |

TABLE 63

| Ex. No | Str. | Chemical name | P.D. |
|---|---|---|---|
| 1-19 | | (S)-1-(4-cyano-phenyl)-3-{1-[5-(2-hydroxyethyl)-1,3,4-thiadiazol-2-yl]-2-(4-methoxyphenyl)-ethyl}urea | $^1$H-NMR (400 MHz, DMSO-$d_6$) δ 3.09-3.17 (3H, m), 3.25 (1H, m), 3.66-3.71 (5H, m), 5.00 (1H, t, J = 4.8 Hz), 5.35 (1H, m), 6.83 (2H, d, J = 9.1 Hz), 7.15 (2H, d, J = 8.5 Hz), 7.21 (1H, m), 7.52 (2H, d, J = 8.5 Hz), 7.65 (2H, d, J = 9.1 Hz), 9.17 (1H, br s). ESIMS (+) 424 [M + H]$^+$. |
| 1-20 | | (S)-1-(4-chloro-phenyl)-3-{1-[5-(2-hydroxyethyl)-1,3,4-oxadiazol-2-yl]-2-(4-methoxy-phenyl)ethyl}urea | $^1$H-NMR (400 MHz, DMSO-$d_6$) δ 2.95 (2H, t, J = 6.1 Hz), 3.03-3.16 (2H, m), 3.70 (3H, s), 3.73 (2H, m), 4.92 (1H, t, J = 5.4 Hz), 5.20 (1H, m), 6.82 (3H, m), 7.08 (2H, d, J = 8.5 Hz), 7.25 (2H, d, J = 9.1 Hz), 7.37 (2H, d, J = 9.1 Hz), 8.77 (1H, s). ESIMS (+) 417 [M + H]$^+$. |
| 1-21 | | (S)-1-(4-fluoro-phenyl)-3-{1-[5-(2-hydroxyethyl)-1,3,4-oxadiazol-2-yl]-2-(4-methoxy-phenyl)ethyl}urea | $^1$H-NMR (400 MHz, DMSO-$d_6$) δ 2.95 (2H, t, J = 6.1 Hz), 3.03-3.16 (2H, m), 3.70 (3H, s), 3.73 (2H, m), 4.92 (1H, t, J = 5.4 Hz), 5.20 (1H, m), 6.77 (1H, br d, J = 7.3 Hz), 6.82 (2H, d, J = 8.5 Hz), 7.01-7.10 (4H, m), 7.34 (2H, m), 8.66 (1H, s). ESIMS (+) 401 [M + H]$^+$. |
| 1-22 | | (S)-1-(4-cyano-phenyl)-3-{1-[5-(2-hydroxyethyl)-1,3,4-oxadiazol-2-yl]-2-(4-methoxy-phenyl)ethyl}urea | $^1$H-NMR (400 MHz, DMSO-$d_6$) δ 2.95 (2H, t, J = 6.1 Hz), 3.04-3.18 (2H, m), 3.69 (3H, s), 3.73 (2H, m), 4.92 (1H, t, J = 5.4 Hz), 5.22 (1H, m), 6.82 (2H, d, J = 8.5 Hz), 7.02 (1H, d, J = 8.5 Hz), 7.08 (2H, d, J = 8.5 Hz), 7.52 (2H, d, J = 8.5 Hz), 7.66 (2H, d, J = 8.5 Hz), 9.16 (1H, s). ESIMS (+) 408 [M + H]$^+$. |

TABLE 64

| Ex. No | Str. | Chemical name | P.D. |
|---|---|---|---|
| 1-23 | | (S)-2-(5-{1-[3-(4-chlorophenyl)ureido]-2-(4-methoxyphenyl)ethyl}-1,3,4-oxadiazol-2-yl)-N-methylacetamide | $^1$H-NMR (400 MHz, DMSO-$d_6$) δ 2.61 (3H, d, J = 4.8 Hz), 3.03-3.16 (2H, m), 3.70 (3H, s), 3.81 (2H, s), 5.21 (1H, m), 6.81 (2H, d, J = 8.5 Hz), 6.87 (1H, m), 7.08 (2H, d, J = 8.5 Hz), 7.25 (2H, d, J = 9.1 Hz), 7.37 (2H, d, J = 9.1 Hz), 8.19 (1H, br d, J = 4.8 Hz), 8.79 (1H, m). ESIMS (+) 444 [M + H]$^+$. |
| 1-24 | | (S)-2-(5-{1-[3-(4-fluorophenyl)ureido]-2-(4-methoxyphenyl)ethyl}-1,3,4-oxadiazol-2-yl)-N-methylacetamide | $^1$H-NMR (400 MHz, DMSO-$d_6$) δ 2.61 (3H, d, J = 4.2 Hz), 3.02-3.16 (2H, m), 3.70 (3H, s), 3.81 (2H, s), 5.21 (1H, m), 6.81 (3H, m), 7.04 (2H, m), 7.09 (2H, d, J = 8.5 Hz), 7.34 (2H, m), 8.19 (1H, m), 8.69 (1H, s). ESIMS (+) 428 [M + H]$^+$. |
| 1-25 | | (S)-1-(4-chlorophenyl)-3-{1-[4-(2-hydroxypropan-2-yl)oxazol-5-yl]-2-(4-methoxyphenyl)ethyl}urea | $^1$H-NMR (400 MHz, DMSO-$d_6$) δ 1.15 (3H, s), 1.36 (3H, s), 3.00 (2H, m), 3.67 (3H, s), 5.30 (1H, br s), 5.54 (1H, m), 6.79 (3H, m), 7.00 (2H, d, J = 8.5 Hz), 7.24 (2H, d, J = 9.1 Hz), 7.35 (2H, d, J = 9.1 Hz), 8.13 (1H, s), 8.65 (1H, s). ESIMS (+) 430 [M + H]$^+$. |
| 1-26 | | (S)-1-(4-chlorophenyl)-3-[1-(4-cyanooxazol-5-yl)-2-(4-methoxyphenyl)ethyl]urea | $^1$H-NMR (400 MHz, DMSO-$d_6$) δ 3.10 (2H, m), 3.70 (3H, s), 5.16 (1H, m), 6.84 (2H, d, J = 8.5 Hz), 6.98 (1H, m), 7.10 (2H, d, J = 8.5 Hz), 7.24 (2H, d, J = 8.5 Hz), 7.36 (2H, d, J = 8.5 Hz), 8.62 (1H, s), 8.79 (1H, m). ESIMS (+) 397 [M + H]$^+$. |

TABLE 65

| Ex. No | Str. | Chemical name | P.D. |
|---|---|---|---|
| 1-27 | | (S)-1-{1-[4-(1H-tetrazol-5-yl)-oxazol-5-yl]-2-(4-methoxyphenyl)ethyl}-3-(4-chlorophenyl)urea | $^1$H-NMR (400 MHz, DMSO-$d_6$) δ 3.11 (2H, m), 3.67 (3H, s), 5.72 (1H, m), 6.78 (2H, d, J = 8.5 Hz), 6.94 (1H, d, J = 7.3 Hz), 7.08 (2H, d, J = 8.5 Hz), 7.21 (2H, d, J = 8.5 Hz), 7.33 (2H, d, J = 8.5 Hz), 8.59 (1H, s), 8.79 (1H, s), 17.06 (1H, br s). ESIMS (+) 440 [M + H]$^+$. |

TABLE 65-continued

| Ex. No | Str. | Chemical name | P.D. |
| --- | --- | --- | --- |
| 1-28 | | (S)-N-(5-{1-[3-(4-chlorophenyl)ureido]-2-(4-ethylphenyl)ethyl}-1,3,4-oxadiazol-2-yl)acetamide | $^1$H-NMR (400 MHz, DMSO-$d_6$) δ 1.13 (3H, t, J = 7.3 Hz), 2.08 (3H, s), 2.54 (2H, q, J = 7.3 Hz), 3.09 (1H, dd, J = 13.9, 7.9 Hz), 3.17 (1H, dd, J = 13.9, 6.1 Hz), 5.18 (1H, m), 6.84 (1H, d, J = 8.5 Hz), 7.10 (2H+2H, s), 7.24 (2H, d, J = 9.1 Hz), 7.37 (2H, d, J = 9.1 Hz), 8.76 (1H, s), 11.54 (1H, br s). ESIMS (+) 428 [M + H]$^+$. |
| 1-29 | | (S)-1-(4-chlorophenyl)-3-(2-(4-chlorophenyl)-1-{5-[(methylsulfonyl)methyl]-1,2,4-oxadiazol-3-yl}ethyl)urea | $^1$H-NMR (400 MHz, DMSO-$d_6$) δ 3.15 (2H, d, J = 7.3 Hz), 3.21 (3H, s), 5.20-5.26 (3H, m), 6.84 (1H, d, J = 8.5 Hz), 7.18 (2H, d, J = 8.5 Hz), 7.24 (2H, d, J = 9.1 Hz), 7.30 (2H, d, J = 8.5 Hz), 7.36 (2H, d, J = 9.1 Hz), 8.75 (1H, s). ESIMS (+) 467 [M + H]$^+$. |
| 1-30 | | (S)-1-(2-(4-chlorophenyl)-1-{5-[(methylsulfonyl)methyl]-1,2,4-oxadiazol-3-yl}ethyl)-3-(4-fluorophenyl)urea | $^1$H-NMR (400 MHz, DMSO-$d_6$) δ 3.15 (2H, d, J = 7.3 Hz), 3.21 (3H, s), 5.21-5.27 (1H, m), 5.21 (2H, s), 6.76 (1H, d, J = 9.1 Hz), 7.01-7.07 (2H, m), 7.18 (2H, d, J = 8.5 Hz), 7.29-7.35 (4H, m), 8.62 (1H, s). ESIMS (+) 453 [M + H]$^+$. |

TABLE 66

| Ex. No | Str. | Chemical name | P.D. |
| --- | --- | --- | --- |
| 1-31 | | (S)-1-(4-chlorophenyl)-3-[2-(4-chlorophenyl)-1-(5-methyl-1,2,4-oxadiazol-3-yl)ethyl]urea | $^1$H-NMR (400 MHz, DMSO-$d_6$) δ 2.58 (3H, s), 3.03-3.15 (2H, m), 5.10-5.18 (1H, m), 6.77 (1H, d, J = 9.1 Hz), 7.19 (2H, d, J = 8.5 Hz), 7.24 (2H, d, J = 9.1 Hz), 7.32 (2H, d, J = 8.5 Hz), 7.35 (2H, d, J = 9.1 Hz), 8.69 (1H, s). ESIMS (+) 391 [M + H]$^+$. |
| 1-32 | | 1-(4-chloro-3-methylphenyl)-3-[1-(5-hydroxy-1,2,4-oxadiazol-3-yl)-2-(4-methoxyphenyl)-ethyl]urea | $^1$H-NMR (400 MHz, DMSO-$d_6$) δ 2.24 (3H, s), 2.96 (1H, dd, J = 14.5, 8.5 Hz), 3.06 (1H, dd, J = 14.5, 6.1 Hz), 3.70 (3H, s), 4.82-4.87 (1H, m), 6.56 (1H, d, J = 7.8 Hz), 6.86 (2H, d, J = 8.5 Hz), 7.12 (1H, d, J = 8.5 Hz), 7.17-7.33 (3H, m), 8.69 (1H, s), 12.5 (1H, bs). ESIMS (+) 401 [M + H]$^+$. |

TABLE 66-continued

| Ex. No | Str. | Chemical name | P.D. |
|---|---|---|---|
| 1-33 | | 1-(4-chloro-2-methylphenyl)-3-[1-(5-hydroxy-1,2,4-oxadiazol-3-yl)-2-(4-methoxyphenyl)-ethyl]urea | $^1$H-NMR (400 MHz, DMSO-d$_6$) δ 2.15 (3H, d, J = 11.5 Hz), 2.95 (1H, q, J = 7.3 Hz), 3.05 (1H, q, J = 7.3 Hz), 3.70 (3H, s), 4.84 (1H, q, J = 7.3 Hz), 6.86 (2H, d, J = 8.5 Hz), 7.04 (1H, d, J = 8.5 Hz), 7.12 (3H, d, J = 8.5 Hz), 7.20 (1H, s), 7.75 (1H, d, J = 8.5 Hz), 7.91 (1H, bs), 12.5 (1H, bs). ESIMS (+) 401 [M + H]$^+$. |
| 1-34 | | 1-[1-(5-hydroxy-1,2,4-oxadiazol-3-yl)-2-(4-methoxyphenyl)-ethyl]-3-(naphthalen-1-yl)urea | $^1$H-NMR (400 MHz, DMSO-d$_6$) δ 3.00 (1H, dd, J = 14.5, 7.3 Hz), 3.09 (1H, dd, J = 14.5, 7.3 Hz), 3.71 (3H, s), 4.91 (1H, q, J = 7.3 Hz), 6.87 (2H, d, J = 8.5 Hz), 7.00 (1H, d, J = 8.5 Hz), 7.16 (2H, d, J = 8.5 Hz), 7.40 (1H, t, J = 7.9 Hz), 7.49-7.58 (3H, m), 7.88 (2H, dd, J = 1.2, 8.5 Hz), 8.01 (1H, d, J = 8.5 Hz), 8.69 (1H, bs), 12.5 (1H, bs). ESIMS (+) 403 [M + H]$^+$. |

TABLE 67

| Ex. No | Str. | Chemical name | P.D. |
|---|---|---|---|
| 1-35 | | 1-[1-(5-hydroxy-1,2,4-oxadiazol-3-yl)-2-(4-methoxyphenyl)-ethyl]-3-(naphthalen-2-yl)urea | $^1$H-NMR (400 MHz, DMSO-d$_6$) δ 2.98 (1H, dd, J = 13.3, 8.5 Hz), 3.06 (1H, dd, J = 13.3, 6.7 Hz), 3.70 (3H, s), 4.80-4.86 (1H, m), 6.59 (1H, d, J = 7.3 Hz), 6.86 (2H, d, J = 8.5 Hz), 7.13 (2H, d, J = 8.5 Hz), 7.29-7.52 (4H, m), 7.71-7.86 (2H, m), 7.99 (1H, d, J = 1.2 Hz), 8.86 (1H, s), 12.5 (1H, bs). ESIMS (+) 403 [M + H]$^+$. |
| 1-36 | | 1-(4-bromophenyl)-3-[1-(5-hydroxy-1,2,4-oxadiazol-3-yl)-2-(4-methoxyphenyl)ethyl]-urea | $^1$H-NMR (400 MHz, DMSO-d$_6$) δ 2.96 (1H, q, J = 7.5 Hz), 3.06 (1H, q, J = 7.5 Hz), 3.71 (3H, s), 4.87 (1H, q, J = 7.5 Hz), 6.58 (1H, d, J = 7.5 Hz), 6.86 (2H, d, J = 9.7 Hz), 7.13 (2H, d, J = 9.7 Hz), 7.31 (2H, d, J = 9.7 Hz), 7.38 (2H, d, J = 9.7 Hz), 8.79 (1H, bs), 12.53 (1H, bs). ESIMS (+) 432 [M + H]$^+$. |
| 1-37 | | 1-[1-(5-hydroxy-1,2,4-oxadiazol-3-yl)-2-(4-methoxyphenyl)-ethyl]-3-(p-tolyl)urea | $^1$H-NMR (400 MHz, DMSO-d$_6$) δ 2.19 (3H, s), 2.96 (1H, q, J = 7.5 Hz), 3.05 (1H, q, 7.5 Hz), 3.71 (3H, s), 4.85 (1H, q, J = 7.5 Hz), 6.47 (1H, d, J = 8.5 Hz), 6.86 (2H, d, J = 9.1 Hz), 7.01 (2H, d, J = 8.5 Hz), 7.13 (2H, d, J = 9.1 Hz), 7.21 (2H, d, J = 8.5 Hz), 8.53 (1H, bs), 12.54 (1H, bs). ESIMS (+) 369 [M + H]$^+$. |
| 1-38 | | 1-[1-(5-hydroxy-1,2,4-oxadiazol-3-yl)-2-(4-methoxyphenyl)-ethyl]-3-(4-phenoxyphenyl)-urea | $^1$H-NMR (400 MHz, DMSO-d$_6$) δ 2.97 (1H, q, J = 7.3 Hz), 3.06 (1H, dd, J = 13.6, 5.1 Hz), 3.71 (3H, s), 4.86 (1H, q, J = 7.3 Hz), 6.49 (1H, d, J = 8.5 Hz), 6.86 (2H, d, J = 8.5 Hz), 6.90-6.92 (4H, m), 7.06 (1H, t, J = 7.3 Hz), 7.13 (2H, d, J = 7.9 Hz), 7.31-7.36 (4H, m), 8.66 (1H, bs), 12.5 (1H, bs). ESIMS (+) 447 [M + H]$^+$. |

TABLE 68

| Ex. No | Str. | Chemical name | P.D. |
|---|---|---|---|
| 1-39 | | 1-(3,4-dichlorophenyl)-3-[1-(5-hydroxy-1,2,4-oxadiazol-3-yl)-2-(4-methoxyphenyl)ethyl]urea | $^1$H-NMR (400 MHz, DMSO-$d_6$) δ 2.97 (1H, q, J = 7.3 Hz), 3.07 (1H, q, J = 7.3 Hz), 3.70 (3H, s), 4.86 (1H, q, 7.5 Hz), 6.70 (1H, d, J = 9.1 Hz), 6.86 (2H, d, J = 9.1 Hz), 7.13 (2H, d, J = 9.1 Hz), 7.19 (1H, dd, J = 9.1, 2.4 Hz), 7.44 (1H, d, J = 9.1 Hz), 7.78 (1H, d, J = 1.8 Hz), 8.97 (1H, s), 12.4 (1H, bs). ESIMS (+) 422 [M + H]$^+$. |
| 1-40 | | 1-[4-(tert-butyl)phenyl]-3-[1-(5-hydroxy-1,2,4-oxadiazol-3-yl)-2-(4-methoxyphenyl)ethyl]urea | $^1$H-NMR (400 MHz, DMSO-$d_6$) δ 1.22 (9H, s), 2.96 (1H, dd, J = 13.9, 9.1 Hz), 3.05 (1H, q, J = 7.5 Hz), 3.70 (3H, s), 4.85 (1H, q, J = 7.5 Hz), 6.45 (1H, d, J = 7.5 Hz), 6.86 (2H, d, J = 9.1 Hz), 7.12 (2H, d, J = 9.1 Hz), 7.23 (4H, dd, J = 8.8, 11.2 Hz), 8.54 (1H, bs), 12.45 (1H, bs). ESIMS (−) 411 [M + H]$^+$. |
| 1-41 | | 1-(4-chloro-2-fluorophenyl)-3-[1-(5-hydroxy-1,2,4-oxadiazol-3-yl)-2-(4-methoxyphenyl)ethyl]urea | $^1$H-NMR (400 MHz, DMSO-$d_6$) δ 2.95 (1H, q, J = 7.5 Hz), 3.07 (1H, q, J = 6.7 Hz), 3.71 (3H, s), 4.84-4.89 (1H, m), 6.87 (2H, q, J = 8.5 Hz), 7.08 (1H, d, J = 7.3 Hz), 7.12-7.16 (3H, m), 7.40 (1H, dd, J = 11.5, 3.0 Hz), 8.07 (1H, t, J = 9.1 Hz), 8.62 (1H, d, J = 2.4 Hz), 12.5 (1H, bs). ESIMS (+) 407 [M + H]$^+$. |
| 1-42 | | 1-[(1,1′-biphenyl)-4-yl]-3-[1-(5-hydroxy-1,2,4-oxadiazol-3-yl)-2-(4-methoxyphenyl)ethyl]urea | $^1$H-NMR (400 MHz, DMSO-$d_6$) δ 2.98 (1H, dd, J = 13.9, 8.5 Hz), 3.07 (1H, q, J = 6.7 Hz), 3.71 (3H, s), 4.86-4.91 (1H, m), 6.57 (2H, q, J = 8.5 Hz), 6.87 (1H, d, J = 8.5 Hz), 7.14 (2H, d, J = 8.5 Hz), 7.29 (1H, t, J = 7.3 Hz), 7.42 (4H, dd, J = 8.5, 14.5 Hz), 7.54 (1H, d, J = 8.5 Hz), 7.59 (2H, d, J = 7.3 Hz), 8.76 (1H, s), 12.5 (1H, bs). ESIMS (+) 413 [M + H]$^+$. |

TABLE 69

| Ex. No | Str. | Chemical name | P.D. |
|---|---|---|---|
| 1-43 | | 1-(4-acetylphenyl)-3-[1-(5-hydroxy-1,2,4-oxadiazol-3-yl)-2-(4-methoxyphenyl)ethyl]urea | $^1$H-NMR (400 MHz, DMSO-$d_6$) δ 2.49 (3H, s), 2.99 (1H, q, J = 7.5 Hz), 3.09 (1H, q, J = 6.7 Hz), 3.72 (3H, s), 4.87-4.92 (1H, m), 6.71 (1H, d, J = 8.5 Hz), 6.88 (2H, d, J = 9.1 Hz), 7.15 (2H, d, J = 8.5 Hz), 7.48 (2H, d, J = 9.1 Hz), 7.85 (1H, d, J = 9.1 Hz), 9.09 (1H, bs), 12.5 (1H, bs). ESIMS (+) 397 [M + H]$^+$. |
| 1-44 | | 1-(4-chlorophenyl)-3-[1-cyano-2-(4-methoxyphenyl)ethyl]urea | $^1$H-NMR (400 MHz, DMSO-$d_6$) δ 3.05 (2H, d, J = 7.9 Hz), 3.73 (3H, s), 4.81 (1H, q, J = 7.9 Hz), 6.90 (3H, d, J = 8.5 Hz), 7.24 (2H, d, J = 8.5 Hz), 7.28 (2H, d, J = 9.1 Hz), 7.41 (2H, d, J = 9.1 Hz), 8.90 (1H, s). ESIMS (+) 330 [M + H]$^+$. |

TABLE 69-continued

| Ex. No | Str. | Chemical name | P.D. |
|---|---|---|---|
| 1-45 | | 1-(4-chloro-phenyl)-3-{2-(4-methoxy-phenyl)-1-[5-(tetrahydro-2H-pyran-4-yl)-1,2,4-oxadiazol-3-yl]ethyl}urea | $^1$H-NMR (400 MHz, DMSO-$d_6$) δ 1.89-2.06 (4H, m), 3.10-3.25 (3H, m), 3.55 (2H, td, J = 11.5, 3.0 Hz), 3.77 (3H, s), 4.03 (2H, dt, J = 11.5, 3.6 Hz), 5.09 (1H, d, J = 8.5 Hz), 5.41 (1H, dd, J = 14.5, 6.7 Hz), 6.34 (1H, s), 6.78 (2H, d, J = 8.5 Hz), 6.96 (2H, d, J = 8.5 Hz), 7.17-7.26 (4H, m). ESIMS (+) 457 [M + H]$^+$. |
| 1-46 | | 1-(4-chloro-phenyl)-3-{2-(4-methoxy-phenyl)-1-[5-(1-methyl-piperazin-4-yl)-1,2,4-oxadiazol-3-yl]ethyl}urea | $^1$H-NMR (400 MHz, DMSO-$d_6$) δ 1.66-1.80 (2H, m), 1.93-2.08 (4H, m), 2.16 (3H, s), 2.72 (2H, d, J = 7.9 Hz), 2.94-3.06 (3H, m), 3.69 (3H, s), 5.11 (1H, q, J = 7.3 Hz), 6.72 (1H, d, J = 8.6 Hz), 6.80 (2H, d, J = 8.6 Hz), 7.03 (2H, d, J = 8.6 Hz), 7.24 (2H, d, J = 8.6 Hz), 7.36 (2H, d, J = 8.6 Hz), 8.72 (1H, s). ESIMS (+) 470 [M + H]$^+$. |

TABLE 70

| Ex. No | Str. | Chemical name | P.D. |
|---|---|---|---|
| 1-47 | | (S)-1-(1-(5-amino-1,2,4-oxadiazol-3-yl)-2-(4-methoxy-phenyl)ethyl)-3-(4-fluoro-phenyl)urea | $^1$H-NMR (400 MHz, DMSO-$d_6$) δ 2.87-3.02 (2H, m), 3.69 (3H, s), 4.81-4.90 (1H, m), 6.43 (1H, d, J = 9.1 Hz), 6.82 (2H, d, J = 8.5 Hz), 7.00-7.07 (4H, m), 7.30-7.37 (2H, m), 7.78 (2H, s), 8.59 (1H, s). HRESIMS (+): 372.14693 (372.12719 calculated for C18H19FN5O3). |
| 1-48 | | (S)-1-(1-(5-amino-1,2,4-oxadiazol-3-yl)-2-(4-methoxy-phenyl)ethyl)-3-(4-cyanophenyl)-urea | $^1$H-NMR (400 MHz, DMSO-$d_6$) δ 2.91-3.03 (2H, m), 3.69 (3H, s), 4.87 (1H, q, J = 7.3 Hz), 6.69 (1H, d, J = 8.5 Hz), 6.82 (2H, d, J = 8.5 Hz), 7.05 (2H, d, J = 8.5 Hz), 7.51 (2H, d, J = 8.5 Hz), 7.65 (2H, d, J = 8.5 Hz), 7.81 (2H, s), 9.09 (1H, s). HRESIMS (+): 379.15126 (379.15186 calculated for C19H19N5O3). |
| 1-49 | | (S)-1-(4-chloro-phenyl)-3-(2-(4-methoxyphenyl)-1-(5-(methylamino)-1,2,4-oxadiazol-3-yl)ethyl)urea | $^1$H-NMR (400 MHz, DMSO-$d_6$) δ 2.93 (3H, d, J = 4.8 Hz), 2.98-3.10 (2H, m), 3.77 (3H, s), 4.95 (1H, dt, J = 8.5, 7.3 Hz), 6.62 (1H, d, J = 8.5 Hz), 6.89 (2H, d, J = 8.5 Hz), 7.13 (2H, d, J = 8.5 Hz), 7.31 (2H, d, J = 8.5 Hz), 7.43 (2H, d, J = 8.5 Hz), 8.26 (1H, q, J = 4.8 Hz), 8.76 (1H, s). HRESIMS (+): 402.13356 (402.13329 calculated for C19H21ClN5O4). |
| 1-50 | | (S)-1-(4-chloro-phenyl)-3-(1-(5-(dimethylamino)-1,2,4-oxadiazol-3-yl)-2-(4-methoxyphenyl)-ethyl)urea | $^1$H-NMR (400 MHz, DMSO-$d_6$) δ 2.93-3.02 (2H, m), 3.07 (6H, s), 3.69 (3H, s), 4.87 (1H, dt, J = 8.5, 7.3 Hz), 6.56 (1H, d, J = 8.5 Hz), 6.82 (2H, d, J = 8.5 Hz), 7.07 (2H, d, J = 8.5 Hz), 7.24 (2H, d, J = 8.5 Hz), 7.35 (2H, d, J = 8.5 Hz), 8.68 (1H, s). HRESIMS (+): 416.14885 (416.14894 calculated for C20H23ClN5O4). |

TABLE 71

| Ex. No | Str. | Chemical name | P.D. |
|---|---|---|---|
| 1-51 | | (S)-1-(4-chlorophenyl)-3-(1-(5-(3-hydroxyazetidin-1-yl)-1,2,4-oxadiazol-3-yl)-2-(4-methoxyphenyl)ethyl)urea | $^1$H-NMR (400 MHz, DMSO-d$_6$) δ 2.91-2.99 (2H, m), 3.69 (3H, s), 3.90-3.96 (2H, m), 4.32-4.39 (2H, m), 4.57-4.66 (1H, m), 4.89 (1H, q, J = 7.3 Hz), 5.90 (1H, q, J = 7.3 Hz), 6.59 (1H, d, J = 8.5 Hz), 6.82 (2H, d, J = 8.5 Hz), 7.06 (2H, d, J = 8.5 Hz), 7.24 (2H, d, J = 8.5 Hz), 7.35 (2H, d, J = 8.5 Hz), 8.66 (1H, s). HRESIMS (+): 444.14459 (444.14386 calculated for C21H23ClN5O4). |
| 1-52 | | (S)-1-(4-chlorophenyl)-3-(1-(1-(2-hydroxyethyl)-1H-pyrazol-3-yl)-2-(4-methoxyphenyl)ethyl)urea | $^1$H-NMR (400 MHz, DMSO-d$_6$) δ 2.93 (1H, dd, J = 13.9, 7.3 Hz), 3.01 (1H, dd, J = 13.9, 6.7 Hz), 3.65-3.72 (2H, m), 3.68 (3H, s), 4.07 (2H, t, J = 5.4 Hz), 4.84 (1H, t, J = 5.4 Hz), 4.96 (1H, q, J = 7.3 Hz), 6.03 (1H, d, J = 2.4 Hz), 6.42 (1H, d, J = 8.5 Hz), 6.77 (2H, d, J = 8.5 Hz), 7.00 (2H, d, J = 8.5 Hz), 7.23 (2H, d, J = 8.5 Hz), 7.36 (2H, d, J = 8.5 Hz), 7.57 (1H, d, J = 2.4 Hz), 8.64 (1H, s). ESIMS (+) 415 [M + H]$^+$. |
| 1-53 | | (S)-1-(4-chlorophenyl)-3-(1-(3-(2-hydroxyethyl)isoxazol-5-yl)-2-(4-methoxyphenyl)ethyl)urea | $^1$H-NMR (400 MHz, DMSO-d$_6$) δ 2.71 (2H, t, J = 6.4 Hz), 2.99 (1H, dd, J = 13.4, 8.6 Hz), 3.07 (1H, dd, J = 13.4, 6.1 Hz), 3.61-3.67 (2H, m), 3.71 (3H, s), 4.77 (1H, t, J = 5.2 Hz), 5.08-5.17 (1H, m), 6.25 (1H, s), 6.75 (1H, d, J = 8.6 Hz), 6.83 (2H, d, J = 8.6 Hz), 7.10 (2H, d, J = 8.6 Hz), 7.25 (2H, d, J = 9.2 Hz), 7.37 (2H, d, J = 9.2 Hz), 8.64 (1H, s). ESIMS (+) 416 [M + H]$^+$. |

TABLE 72

| Ex. No | Str. | Chemical name | P.D. |
|---|---|---|---|
| 1-54 | | (S)-1-(4-chlorophenyl)-3-(1-(5-(2-hydroxyethyl)isoxazol-3-yl)-2-(4-methoxyphenyl)ethyl)urea | $^1$H-NMR (400 MHz, DMSO-d6) δ 2.85 (2H, t, J = 6.4 Hz), 2.96 (1H, dd, J = 13.9, 7.9 Hz), 3.05 (1H, dd, J = 13.9, 6.1 Hz), 3.63-3.69 (2H, m), 3.69 (3H, s), 4.84 (1H, t, J = 5.4 Hz), 5.00-5.09 (1H, m), 6.25 (1H, s), 6.63 (1H, d, J = 9.1 Hz), 6.81 (2H, d, J = 9.1 Hz), 7.09 (2H, d, J = 8.5 Hz), 7.23 (2H, d, J = 8.5 Hz), 7.36 (2H, d, J = 9.1 Hz), 8.66 (1H, s). ESIMS (+) 416 [M + H]$^+$. |
| 1-55 | | (S)-1-(4-chlorophenyl)-3-(1-(2-(2-hydroxyethyl)-2H-1,2,3-triazol-4-yl)-2-(4-methoxyphenyl)ethyl)urea | $^1$H-NMR (400 MHz, DMSO-d$_6$) δ 2.69 (1H, br s), 3.09 (1H, dd, J = 13.9, 6.7 Hz), 3.15 (1H, dd, J = 13.9, 6.7 Hz), 3.78 (3H, s), 4.06 (2H, t, J = 4.8 Hz), 4.51 (2H, t, J = 4.8 Hz), 5.11 (1H, s), 5.26-5.34 (1H, m), 6.27 (1H, s), 6.79 (2H, d, J = 8.5 Hz), 6.98 (2H, d, J = 8.5 Hz), 7.19 (2H, d, J = 8.5 Hz), 7.25 (2H, d, J = 8.5 Hz), 7.33 (1H, s). HRESIMS (+): 416.14910 (416.14894 calculated for C20H23ClN5O3). |
| 1-56 | | (S)-1-(4-chlorophenyl)-3-(1-(1-(2-hydroxyethyl)-1H-1,2,3-triazol-4-yl)-2-(4-methoxyphenyl)ethyl)urea | $^1$H-NMR (400 MHz, DMSO-d$_6$) δ 3.00 (1H, dd, J = 13.9, 6.7 Hz), 3.08 (1H, dd, J = 13.9, 6.7 Hz), 3.68 (3H, s), 3.69-3.76 (2H, m), 4.34 (2H, t, J = 5.4 Hz), 4.99 (1H, t, J = 5.4 Hz), 5.00-5.10 (1H, m), 6.60 (1H, d, J = 8.5 Hz), 6.79 (2H, d, J = 8.5 Hz), 7.04 (2H, d, J = 8.5 Hz), 7.23 (2H, d, J = 8.5 Hz), 7.36 (2H, d, J = 8.5 Hz), 7.81 (1H, s), 8.61 (1H, s). HRESIMS (+): 416.14967 (416.14894 calculated for C20H23ClN5O3). |

TABLE 73

| Ex. No | Str. | Chemical name | P.D. |
|---|---|---|---|
| 1-57 | | (S)-1-(4-chlorophenyl)-3-(1-(1-(2-hydroxyethyl)-1H-1,2,3-triazol-5-yl)-2-(4-methoxyphenyl)ethyl)urea | $^1$H-NMR (400 MHz, DMSO-d$_6$) δ 3.00-3.09 (1H, m), 3.57-3.68 (1H, m), 3.69 (3H, s), 4.28-4.32 (2H, m), 4.42-4.52 (2H, m), 5.06 (1H, t, J = 5.4 Hz), 5.17-5.20 (1H, m), 6.71 (1H, d, J = 8.5 Hz), 7.15 (2H, d, J = 8.5 Hz), 7.22 (2H, d, J = 8.5 Hz), 7.32 (2H, d, J = 8.5 Hz), 7.52-7.63 (2H, m), 7.70 (1H, s), 8.53 (1H, s). HRESIMS (+): 416.14998 (416.14894 calculated for C20H23ClN5O3). |
| 1-58 | | (S)-1-(4-chlorophenyl)-3-(1-(1-(2-hydroxyethyl)-1H-pyrazol-4-yl)-2-(4-methoxyphenyl)ethyl)urea | $^1$H-NMR (400 MHz, DMSO-d$_6$) δ 2.87-3.02 (2H, m), 3.64-3.71 (2H, m), 3.69 (3H, s), 4.05 (2H, t, J = 5.4 Hz), 4.83 (1H, t, J = 5.4 Hz), 4.86-4.93 (1H, m), 6.37 (1H, d, J = 8.5 Hz), 6.80 (2H, d, J = 8.5 Hz), 7.09 (2H, d, J = 8.5 Hz), 7.22 (2H, d, J = 8.5 Hz), 7.32 (1H, s), 7.36 (2H, d, J = 8.5 Hz), 7.55 (1H, s), 8.46 (1H, s). HRESIMS (+): 415.15360 (415.15369 calculated for C21H24ClN4O3). |
| 1-59 | | 1-(4-chlorophenyl)-3-(2-(4-methoxyphenyl)-1-(5-oxo-4,5-dihydro-1,2,4-thiadiazol-3-yl)ethyl)urea | $^1$H-NMR (400 MHz, DMSO-d$_6$) δ 2.92 (1H, dd, J = 13.9, 7.9 Hz), 3.05 (1H, dd, J = 13.9, 5.4 Hz), 3.70 (3H, s), 4.81 (1H, dd, J = 13.9, 7.9 Hz), 6.57 (1H, d, J = 7.9 Hz), 6.84 (2H, d, J = 8.5 Hz), 7.06 (2H, d, J = 8.5 Hz), 7.24 (2H, d, J = 9.1 Hz), 7.36 (2H, d, J = 9.1 Hz), 8.82 (1H, s), 12.98 (1H, s). ESIMS (+) 405 [M + H]$^+$. |

TABLE 74

| Ex. No | Str. | Chemical name | P.D. |
|---|---|---|---|
| 1-60 | | 2-(3-(4-chlorophenyl)ureido)-3-(4-methoxyphenyl)-N-(methylsulfonyl)propanamide | $^1$H NMR (400 MHz, DMSO-d$_6$) δ 2.78 (1H, dd, J = 13.9, 8.5 Hz), 2.97 (1H, dd, J = 13.9, 4.8 Hz), 3.18 (3H, s), 3.70 (3H, s), 4.43 (1H, s), 6.38 (1H, d, J = 7.9 Hz), 6.85 (2H, d, J = 8.5 Hz), 7.14 (2H, d, J = 8.5 Hz), 7.24 (2H, d, J = 9.1 Hz), 7.35 (2H, d, J = 9.1 Hz), 8.83 (1H, s), 1.207 (1H, s). ESIMS (−) 424 [M − 1]$^+$. |

TABLE 74-continued

| Ex. No | Str. | Chemical name | P.D. |
|---|---|---|---|
| 1-61 | | 2-(3-(4-chloro-phenyl)ureido)-3-(4-methoxy-phenyl)-N-(1H-tetrazol-5-yl)propanamide | $^1$H NMR (400 MHz, DMSO-d$_6$) δ 2.75-2.85 (1H, m), 2.96-3.08 (1H, m), 3.69 (3H, s), 4.61 (1H, s), 6.41 (2H, s), 6.82 (2H, d, J = 7.9 Hz), 7.17 (2H, d, J = 7.9 Hz), 7.22 (2H, d, J = 8.5 Hz), 7.35 (2H, d, J = 8.5 Hz), 8.85 (1H, s), 10.59 (1H, brs). ESIMS (+) 416 [M + H]$^+$. |
| 1-62 | | (−)-(S)-1-(4-chlorophenyl)-3-(2-(4-methoxyphenyl)-1-(2-((methylsulfonyl)methyl)-2H-tetrazol-5-yl)ethyl)urea | $^1$H NMR (400 MHz, DMSO-d$_6$) δ 3.09 (3H, s), 3.13 (2H, d, J = 7.3 Hz), 3.69 (3H, s), 5.33 (1H, q, J = 7.3 Hz), 6.45 (2H, s), 6.78 (2H, d, J = 8.5 Hz), 6.85 (1H, d, J = 7.9 Hz), 7.01 (2H, d, J = 8.5 Hz), 7.24 (2H, d, J = 9.1 Hz), 7.36 (2H, d, J = 8.5 Hz), 8.76 (1H, s). ESIMS (+) 465 [M + H]$^+$. [α]$_D^{26}$ −27.5° (c 0.349, DMSO) |
| 1-63 | | (−)-(S)-1-(4-chlorophenyl)-3-(2-(4-methoxyphenyl)-1-(2-(2-(methylsulfonyl)methyl)-2H-tetrazol-5-yl)ethyl)urea | $^1$H-NMR (400 MHz, DMSO-d$_6$) δ 2.99 (3H, s), 3.08 (2H, t, J = 7.6 Hz), 3.69 (3H, s), 3.85 (2H, t, J = 6.7 Hz), 5.08 (2H, t, J = 6.7 Hz), 5.29 (1H, q, J = 7.5 Hz), 6.78 (3H, t, J = 8.5 Hz), 7.01 (2H, d, J = 8.5 Hz), 7.24 (2H, d, J = 8.5 Hz), 7.36 (2H, d, J = 9.1 Hz), 8.72 (1H, s). LRMS (ESI+) [M + H+] 479. ESIMS (+) 479 [M + H]$^+$. [α]$_D^{29.1}$ −13.49 (c 0.348, DMSO) |

TABLE 75

| Ex. No | Str. | Chemical name | P.D. |
|---|---|---|---|
| 1-64 | | (−)-(S)-N-(2-(5-(2-(4-chlorophenyl)-1-(3-(4-chlorophenyl)ureido)ethyl)-2H-tetrazol-2-yl)ethyl)methane-sulfonamide | $^1$H-NMR (400 MHz, DMSO-d$_6$) δ 2.86 (3H, s), 3.17 (2H, qd, J = 13.4, 7.9 Hz), 3.51 (2H, t, J = 5.8 Hz), 4.73 (1H, t, J = 5.8 Hz), 5.34 (1H, q, J = 7.5 Hz), 6.84 (2H, d, J = 9.1 Hz), 7.14 (2H, d, J = 8.5 Hz), 7.24 (2H, d, J = 8.5 Hz), 7.31 (2H, d, J = 8.5 Hz), 7.35 (2H, d, J = 9.1 Hz), 8.73 (1H, s). ESIMS (+) 498 [M + H]$^+$. [α]$_D^{27}$ −18.2° (c 0.348, DMSO) |

TABLE 75-continued

| Ex. No | Str. | Chemical name | P.D. |
|---|---|---|---|
| 1-65 | 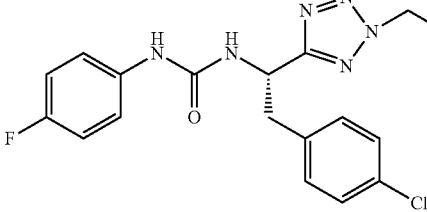 | (−)-(S)-N-(2-(5-(2-(4-chlorophenyl)-1-(3-(4-fluorophenyl)ureido)ethyl)-2H-tetrazol-2-yl)ethyl)methanesulfonamide | $^1$H-NMR (400 MHz, DMSO-d$_6$) δ 2.86 (3H, s), 3.09-3.21 (2H, m), 3.51 (2H, s), 4.73 (1H, t, J = 6.1 Hz), 5.34 (1H, q, J = 7.5 Hz), 6.77 (2H, d, J = 9.1 Hz), 7.03 (2H, t, J = 9.1 Hz), 7.14 (2H, d, J = 8.5 Hz), 7.29-7.34 (5H, m), 8.61 (1H, s).<br><br>ESIMS (+) 482 [M + H]$^+$.<br>[α]$_D^{27}$ −18.6° (c 0.345, DMSO) |
| 1-66 | 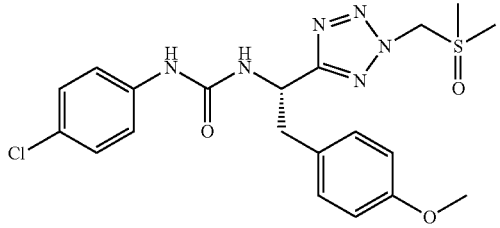<br>Stereoisomer A | (−)-1-(4-chlorophenyl)-3-((1S)-2-(4-methoxyphenyl)-1-(2-((methylsulfinyl)methyl)-2H-tetrazol-5-yl)ethyl)urea | $^1$H-NMR (400 MHz, DMSO-d$_6$) δ 2.63 (3H, s), 3.10-3.14 (2H, m), 3.68 (3H, s), 5.32 (1H, q, J = 7.5 Hz), 5.91 (2H, d, J = 13.3 Hz), 6.09 (1H, d, J = 13.3 Hz), 6.78 (2H, d, J = 8.5 Hz), 7.01 (2H, d, J = 8.5 Hz), 7.24 (2H, d, J = 8.5 Hz), 7.36 (2H, d, J = 8.5 Hz), 8.74 (1H, s).<br>ESIMS (+) 449 [M + H]$^+$.<br>[α]$_D^{29}$ −119.6° (c 0.350, DMSO) |
| 1-67 | 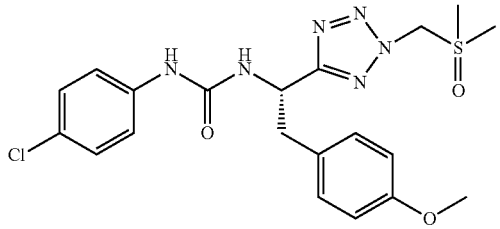<br>Stereoisomer B | (+)-1-(4-chlorophenyl)-3-((1S)-2-(4-methoxyphenyl)-1-(2-((methylsulfinyl)methyl)-1H-tetrazol-5-yl)ethyl)urea | $^1$H-NMR (400 MHz, DMSO-d$_6$) δ 2.67 (3H, s), 3.11-3.16 (2H, m), 3.68 (3H, s), 5.33 (1H, q, J = 7.5 Hz), 5.92 (2H, d, J = 12.7 Hz), 6.10 (1H, d, J = 12.7 Hz), 6.77-6.82 (2H, m), 7.01 (2H, d, J = 8.5 Hz), 7.24 (2H, d, J = 8.5 Hz), 7.36 (2H, d, J = 8.5 Hz), 8.73 (1H, brs).<br>ESIMS (+) 449 [M + H]$^+$.<br>[α]$_D^{29}$ +72.01° (c 0.345, DMSO) |

TABLE 76

| Ex. No | Str. | Chemical name | P.D. |
|---|---|---|---|
| 1-68 | 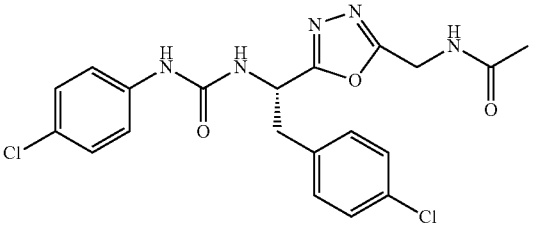 [SMILES: CC(=O)NCc1nnc([C@H](Cc2ccc(Cl)cc2)NC(=O)Nc2ccc(Cl)cc2)o1] | (−)-(S)-N-((5-(2-(4-chlorophenyl)-1-(3-(4-chlorophenyl)ureido)ethyl)-1,3,4-oxadiazol-2-yl)methyl)acetamide | $^1$H-NMR (400 MHz, DMSO-d$_6$) δ 1.86 (3H, s), 3.12-3.31 (2H, m), 4.45 (2H, d, J = 5.5 Hz), 5.26 (1H, dd, J = 7.3, 14.7 Hz), 6.93 (1H, s), 7.20-7.25 (4H, m), 7.23-7.37 (4H, m), 8.58 (1H, t, J = 6.1 Hz), 8.76 (1H, s).<br><br>ESIMS (+) 448 [M + H]$^+$.<br>[α]$_D^{27}$ −37 (c 0.295, DMSO). |

TABLE 76-continued

| Ex. No | Str. | Chemical name | P.D. |
|---|---|---|---|
| 1-69 | | (−)-(S)-N-((5-(2-(4-chlorophenyl)-1-(3-(4-chlorophenyl)-ureido)ethyl)-1,3,4-oxadiazol-2-yl)methyl)methane-sulfonamide | $^1$H-NMR (400 MHz, DMSO-$d_6$) δ 2.95 (3H, s), 3.14-3.30 (2H, m), 4.45 (2H, s), 5.28 (1H, dd, J = 8.0, 14.7 Hz), 6.91 (1H, d, J = 8.0 Hz), 7.23-7.25 (4H, m), 7.32-7.37 (4H, m), 7.94 (1H, s), 8.76 (1H, s). ESIMS (+) 483 [M + H]$^+$. [α]$_D^{27}$ −33 (c 0.254, DMSO). |
| 1-70 | | (S)-1-(4-chlorophenyl)-3-(2-(4-chlorophenyl)-1-(5-(2-hydroxypropan-2-yl)-1,3,4-oxadiazol-2-yl)ethyl)urea | $^1$H-NMR (400 MHz, DMSO-$d_6$) δ 1.47 (3H, s), 1.50 (3H, s), 3.19 (2H, d, J = 7.3 Hz), 5.27 (1H, dd, J = 6.7, 14.7 Hz), 5.82 (1H, s), 6.95 (1H, s), 7.19-7.26 (4H, m), 7.32-7.38 (4H, m), 8.77 (1H, s). ESIMS (+) 435 [M + H]$^+$. |
| 1-71 | | (−)-(S)-1-(4-chlorophenyl)-3-(2-(4-cyanophenyl)-1-(5-(2-hydroxyethyl)-1,3,4-oxadiazol-2-yl)ethyl)urea | $^1$H-NMR (400 MHz, CDCl$_3$) δ 3.08-3.11 (2H, m), 3.24 (1H, dd, J = 6.7, 14.1 Hz), 3.33 (1H, dd, J = 6.7, 14.1 Hz), 4.07 (2H, t, J = 5.5 Hz), 5.59 (1H, dd, J = 6.7, 15.3 Hz), 5.94 (1H, d, J = 8.6 Hz), 7.06 (1H, s), 7.22-7.24 (6H, m), 7.55 (2H, d, J = 8.0 Hz). ESIMS (+) 412 [M + H]$^+$. [α]$_D^{26}$ −27 (c 0.261, EtOH). |

TABLE 77

| Ex. No | Str. | Chemical name | P.D. |
|---|---|---|---|
| 1-72 | | (S)-N-((5-(3-(4-chlorophenyl)ureido)-2-(4-ethylphenyl)ethyl)-1,3,4-oxadiazol-2-yl)methyl)-acetamide | $^1$H-NMR (400 MHz, DMSO-$d_6$) δ 1.35 (3H, t, J = 7.9 Hz), 2.54 (2H, dd, J = 7.4, 15.3 Hz), 4.45 (2H, d, J = 5.5 Hz), 6.90 (1H, d, J = 8.0 Hz), 7.08 (4H, dd, J = 4.9, 13.5 Hz), 7.25 (2H, d, J = 9.2 Hz), 7.36 (2H, d, J = 9.2 Hz), 8.59 (1H, t, J = 5.5 Hz), 8.82 (1H, s). FDMS (+) 441 [M]$^+$. |
| 1-73 | | (−)-(S)-1-(4-chlorophenyl)-3-(2-(4-ethylphenyl)-1-(5-(3-hydroxyethyl)-1,3,4-oxadiazol-2-yl)ethyl)urea | $^1$H-NMR (400 MHz, CDCl$_3$) δ 1.17 (3H, t, J = 8.0 Hz), 2.56 (2H, dd, J = 7.4, 15.3 Hz), 3.05 (2H, t, J = 6.1 Hz), 3.13 (2H, t, J = 6.8 Hz), 4.00 (2H, s), 5.50 (1H, dd, J = 6.7, 15.3 Hz), 6.21 (1H, d, J = 8.6 Hz), 6.96 (2H, d, J = 8.0 Hz), 7.06 (2H, d, J = 8.6 Hz), 7.13-7.19 (4H, m), 7.39 (1H, s). ESIMS (+) 415 [M + H]$^−$. [α]$_D^{26}$ −15 (c 0.141, EtOH). |

TABLE 77-continued

| Ex. No | Str. | Chemical name | P.D. |
|---|---|---|---|
| 1-74 | | 1-(4-chlorophenyl)-3-(1-(5-hydroxy-1,2,4-oxadiazol-3-yl)-3-(4-methoxyphenyl)propan-2-yl)urea | $^1$H-NMR (400 MHz, DMSO-d$_6$) δ 2.59 (1H, dd, J = 15.1, 7.9 Hz), 2.69 (1H, dd, J = 15.1, 4.8 Hz), 2.72-2.83 (2H, m), 3.70 (3H, s), 4.13-4.24 (1H, m), 6.16 (1H, d, J = 8.5 Hz), 6.86 (2H, d, J = 8.5 Hz), 7.14 (2H, d, J = 8.5 Hz), 7.23 (2H, d, J = 8.5 Hz), 7.34 (2H, d, J = 8.5 Hz), 8.55 (1H, s), 12.21 (1H, s). HRESIMS (+): 403.11766 (403.11731 calculated for C19H20ClN4O4). |
| 1-75 | | 1-(4-chlorophenyl)-3-(1-(5-hydroxy-1,3,4-oxadiazol-2-yl)-3-(4-methoxyphenyl)propan-2-yl)urea | $^1$H-NMR (400 MHz, DMSO-d$_6$) δ 2.60 (1H, dd, J = 15.1, 7.9 Hz), 2.68-2.81 (3H, m), 3.70 (3H, s), 4.04-4.15 (1H, m), 6.19 (1H, d, J = 8.5 Hz), 6.86 (2H, d, J = 8.5 Hz), 7.14 (2H, d, J = 8.5 Hz), 7.22 (2H, d, J = 8.5 Hz), 7.34 (2H, d, J = 8.5 Hz), 8.58 (1H, s), 12.02 (1H, s). HRESIMS (+): 403.11694 (403.11731 calculated for C19H20ClN4O4). |

TABLE 78

| Ex. No | Str. | Chemical name | P.D. |
|---|---|---|---|
| 1-76 | | 1-(4-chlorophenyl)-3-(4-(5-hydroxy-1,3,4-oxadiazol-2-yl)-1-(4-methoxyphenyl)butan-2-yl)urea | $^1$H-NMR (400 MHz, DMSO-d$_6$) δ 1.54-1.66 (1H, m), 1.73-1.85 (2H, m), 2.51-2.62 (2H, m), 2.68 (2H, d, J = 6.7 Hz), 3.70 (3H, s), 3.79-3.90 (1H, m), 6.09 (1H, d, J = 8.5 Hz), 6.84 (1H, s), 7.12 (2H, d, J = 8.5 Hz), 7.23 (2H, d, J = 8.5 Hz), 7.37 (2H, d, J = 8.5 Hz), 8.46 (1H, s) 12.13 (1H, s). HRESIMS (+): 413.13318 (417.13296 calculated for C20H22ClN4O4). |
| 1-77 | | 1-(4-chlorophenyl)-3-(4-(5-hydroxy-1,2,4-oxadiazol-3-yl)-1-(4-methoxyphenyl)butan-2-yl)urea | $^1$H-NMR (400 MHz, DMSO-d$_6$) δ 1.54-1.66 (1H, m), 1.76-1.86 (2H, m), 2.46-2.60 (2H, m), 2.68 (2H, d, J = 6.7 Hz), 3.70 (3H, s), 3.77-3.90 (1H, m), 6.08 (1H, d, J = 8.5 Hz), 6.84 (1H, s), 7.12 (2H, d, J = 8.5 Hz), 7.23 (2H, d, J = 8.5 Hz), 7.37 (2H, d, J = 8.5 Hz), 8.48 (1H, s), 12.10 (1H, s). HRESIMS (+): 413.13393 (417.13296 calculated for C20H22ClN4O4). |

TABLE 78-continued

| Ex. No | Str. | Chemical name | P.D. |
|---|---|---|---|
| 1-78 | | (S)-1-(4-chlorophenyl)-3-(2-(4-chlorophenyl)-1-(4-(2-hydroxyethyl)-6-oxo-1,6-dihydropyrimidin-2-yl)ethyl)urea | $^1$H-NMR (400 MHz, DMSO-$d_6$) δ 2.54 (2H, t, J = 6.7 Hz), 2.92 (1H, dd, J = 13.6, 8.2 Hz), 3.06 (1H, dd, J = 13.3, 5.4 Hz), 3.26 (2H, t, J = 6.7 Hz), 4.54-4.72 (m, 1H), 4.80-4.89 (m, 1H), 6.04 (1H, s), 6.60 (1H, d, J = 8.5 Hz), 7.15 (2H, d, J = 8.5 Hz), 7.24 (2H, d, J = 9.1 Hz), 7.31 (2H, d, J = 8.5 Hz), 7.35 (2H, d, J = 8.5 Hz), 8.91 (1H, s), 12.45 (1H, s). |

Example 2-1

1-(4-Ethynylphenyl)-3-(1-(5-hydroxy-1,2,4-oxadiazol-3-yl)-2-(4-methoxyphenyl)ethyl)urea

[Chem. 160]

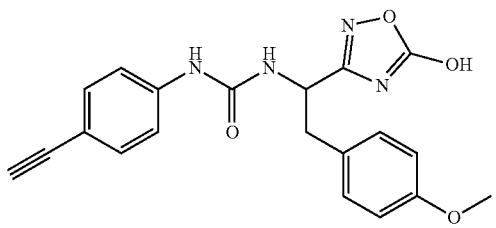

To a solution of 4-ethynylaniline (43.1 mg) in dimethylsulfoxide (1.0 mL) was added carbodiimidazole (65.5 mg), and the reaction mixture was stirred at ambient temperature for 4 hours. After confirming the disappearance of the starting material, a solution of 3-[1-amino-2-(4-methoxyphenyl)ethyl]1,2,4-oxadiazol-5-ol hydrochloride (100 mg) in dimethylsulfoxide (1.0 mL) was added to the reaction solution, and the reaction mixture was stirred at ambient temperature for 3 hours. The reaction solution was adjusted pH 3 by addition of 1 mol/L hydrochloric acid. The mixture was stirred at room temperature for 5 minutes, and then extracted with ethyl acetate (30 mL). The organic layer was washed with water (15 mL) and then a brine (15 mL), dried over anhydrous sodium sulfate, and filtrated. The solvent was removed under reduced pressure, and the obtained residue was then purified by silica gel column chromatography (chloroform:methanol=10:1) to obtain the title compound as a white solid (30.2 mg).

$^1$H NMR (400 MHz, DMSO-$d_6$) δ 2.97 (1H, dd, J=13.6, 8.2 Hz), 3.06 (1H, dd, J=13.6, 5.4 Hz), 3.70 (3H, s), 3.99 (1H, s), 4.86 (1H, q, J=7.3 Hz), 6.61 (1H, d, J=7.5 Hz), 6.86 (2H, d, J=8.5 Hz), 7.12 (2H, d, J=8.5 Hz), 7.31 (2H, q, J=8.3 Hz), 7.36 (2H, d, J=8.3 Hz), 8.86 (1H, bs), 12.5 (1H, bs).

ESIMS (+) 379[M+H]$^+$.

Examples 2-2 to 2-10

The following Examples 2-2 to 2-10 were obtained using each corresponding starting material and reactant in the same method as in Example 2-1.

The structures and spectral data thereof are shown in Tables 79-81.

TABLE 79

| Ex. No | Str. | Chemical name | P.D. |
|---|---|---|---|
| 2-2 | | 1-(6-chlorobenzo[d]thiazol-2-yl)-3-(1-(5-hydroxy-1,2,4-oxadiazol-3-yl)-2-(4-methoxyphenyl)ethyl)urea | $^1$H NMR (400 MHz, CDCl$_3$) δ 3.03 (1H, dd, J = 13.9, 8.5 Hz), 3.13 (1H, dd, J = 13.9, 5.8 Hz), 3.70 (3H, s), 4.94-5.00 (1H, m), 6.87 (2H, d, J = 8.5 Hz), 7.14-7.21 (3H, m), 7.37 (1H, dd, J = 8.5, 2.1 Hz), 7.61 (1H, d, J = 8.5 Hz), 8.01 (1H, d, J = 2.1 Hz), 10.9 (1H, bs), 12.6 (1H, bs). ESIMS (+) 446 [M + H]$^+$. |

TABLE 79-continued

| Ex. No | Str. | Chemical name | P.D. |
|---|---|---|---|
| 2-3 | | 1-(5-chloro-thiazol-2-yl)-3-(1-(5-hydroxy-1,2,4-oxadiazol-3-yl)-2-(4-methoxyphenyl)-ethyl)urea | 1H NMR (400 MHz, DMSO-d$_6$) δ 2.99 (1H, dd, J = 13.9, 8.5 Hz), 3.09 (1H, q, J = 6.7 Hz), 3.70 (3H, s), 4.88-4.94 (1H, m), 6.86 (2H, d, J = 8.5 Hz), 6.91 (1H, d, J = 7.3 Hz), 7.12 (2H, d, J = 8.5 Hz), 7.34 (1H, s), 10.83 (1H, bs), 12.50 (1H, bs). <br><br>ESIMS (+) 395 [M + H]$^-$. |
| 2-4 | | 1-(4-chloro-3-fluoropehnyl)-3-(1-(5-hydroxy-1,2,4-oxadiazol-3-yl)-2-(4-methoxyphenyl)-ethyl)urea | H NMR (400 MHz, DMSO-d$_6$) δ 2.96 (1H, dd, J = 13.3, 8.5 Hz), 3.06 (1H, dd, J = 13.2, 5.8 Hz), 3.70 (3H, s), 4.82-4.88 (1H, m), 6.68 (1H, d, J = 7.3 Hz), 6.85 (2H, d, J = 8.5 Hz), 7.04 (1H, dd, J = 8.5, 2.4 Hz), 7.12 (2, d, J = 8.5 Hz), 7.39 (1H, t, J = 8.5 Hz), 7.56 (1H, dd, J = 12.7, 2.4 Hz), 9.01 (1H, bs), 12.52 (1H, bs). <br><br>ESIMS (+) 407 [M + H]$^+$. |
| 2-5 | | 1-(1-(5-hydroxy-1,2,4-oxadiazol-3-yl)-2-(4-methoxyphenyl)-ethyl)-3-(4-morpholino-phenyl)urea | $^1$H NMR (400 MHz, DMSO-d$_6$) δ 2.91-3.05 (6H, m), 3.68-3.70 (7H, m), 4.81 (1H, q, J = 7.3 Hz), 6.37 (1H, d, J = 9.1 Hz), 6.80-6.86 (4H, m), 7.11 (2H, d, J = 9.1 Hz), 7.19 (2H, d, J = 9.1 Hz), 8.38 (1H, bs), 12.48 (1H, bs). <br>ESIMS (+) 438 [M + H]$^+$. |

TABLE 80

| Ex. No | Str. | Chemical name | P.D. |
|---|---|---|---|
| 2-6 | | 1-(4-(cyclo-hexyloxy)phenyl)-3-(1-(5-hydroxy-1,2,4-oxadiazol-3-yl)-2-(4-methoxyphenyl)-ethyl)urea | $^1$H NMR (400 MHz, DMSO-d$_6$) δ 1.21-1.41 (5H, m), 1.49-1.53 (1H, m), 1.67-1.69 (2H, m), 1.85-1.88 (2H, m), 2.92-2.98 (1H, m), 3.01-3.06 (1H, m), 3.71 (3H, s), 4.15-4.20 (1H, m), 4.81-4.86 (1H, m), 6.40 (1H, d, J = 7.9 Hz), 6.79 (2H, d, J = 8.5 Hz), 6.86 (2H, d, J = 9.1 Hz), 7.12 (2H, d, J = 8.5 Hz), 7.20 (2H, d, J = 9.1 Hz), 8.42 (1H, bs), 12.48 (1H, bs). <br>ESIMS (+) 451 [M + H]$^+$. |

TABLE 80-continued

| Ex. No | Str. | Chemical name | P.D. |
| --- | --- | --- | --- |
| 2-7 | | 1-(1-(5-hydroxy-1,2,4-oxadiazol-3-yl)-2-(4-methoxyphenyl)-ethyl)-3-(4-(3-methyl-1,2,4-oxadiazol-5-yl)phenyl)urea | $^1$H NMR (400 MHz, DMSO-$d_6$) δ 2.36 (3H, m), 2.99 (1H, q, J = 7.5 Hz), 3.09 (1H, dd, J = 13.9, 5.4 Hz), 3.71 (3H, s), 4.88-4.93 (1H, m), 6.74 (1H, d, J = 7.9 Hz), 6.87 (2H, d, J = 7.9 Hz), 7.14 (2H, d, J = 8.5 Hz), 7.58 (2H, d, J = 7.9 Hz), 7.94 (2H, d, J = 8.5 Hz), 9.15 (1H, bs), 12.52 (1H, bs). ESIMS (+) 437 [M + H]$^+$. |
| 2-8 | | 1-(4-cyclopropyl-phenyl)-3-(1-(5-hydroxy-1,2,4-oxadiazol-3-yl)-2-(4-methoxy-phenyl)ethyl)urea | $^1$H NMR (400 MHz, DMSO-$d_6$) δ 0.53-0.57 (2H, m), 0.83-0.87 (2H, m), 1.77-1.84 (1H, m), 2.95 (1H, q, J = 7.3 Hz), 3.04 (1H, q, J = 7.3 Hz), 3.70 (3H, s), 4.84 (1H, m, J = 7.3 Hz), 6.45 (1H, d, J = 7.9 Hz), 6.86 (2H, d, J = 8.5 Hz), 6.92 (2H, d, J = 8.5 Hz), 7.12 (2H, d, J = 8.5 Hz), 7.20 (2H, d, J = 8.5 Hz), 8.52 (1H, bs), 12.51 (1H, bs). ESIMS (+) 395 [M + H]$^+$. |

TABLE 81

| Ex. No | Str. | Chemical name | P.D. |
| --- | --- | --- | --- |
| 2-9 | | 1-(1-(5-hydroxy-1,2,4-oxadiazol-3-yl)-2-(4-methoxyphenyl)ethyl)-3-(4-(5-methyl-1,2,4-oxadiazol-3-yl)phenyl)urea | $^1$H NMR (400 MHz, DMSO-$d_6$) δ 2.62 (3H, s), 2.99 (1H, q, J = 7.3 Hz), 3.08 (1H, dd, J = 13.9, 5.4 Hz), 3.71 (3H, s), 4.89 (1H, q, J = 7.3 Hz), 6.67 (1H, d, J = 7.3 Hz), 6.87 (2H, d, J = 9.1 Hz), 7.14 (2H, d, J = 9.1 Hz), 7.52 (2H, d, J = 9.1 Hz), 7.84 (2H, d, J = 9.1 Hz), 8.99 (1H, bs), 12.51 (1H, bs). ESIMS (+) 437 [M + H]$^+$. |

TABLE 81-continued

| Ex. No | Str. | Chemical name | P.D. |
|---|---|---|---|
| 2-10 | | 1-(4-(cyclo-propyloxy)phenyl)-3-(1-(5-hydroxy-1,2,4-oxadiazol-3-yl)-2-(4-methoxyphenyl)-ethyl)urea | $^1$H NMR (400 MHz, DMSO-$d_6$) δ 0.58-0.62 (2H, m), 0.70-0.75 (2H, m), 2.96 (1H, dd, J = 13.8, 8.3 Hz), 3.05 (1H, q, J = 6.5 Hz), 3.72 (3H, s), 3.75 (1H, td, J = 6.0, 3.3 Hz), 4.84 (1H, dd, J = 14.4, 8.3 Hz), 6.42 (1H, d, J = 7.9 Hz), 6.87 (2H, d, J = 8.6 Hz), 6.91 (2H, d, J = 8.6 Hz), 7.13 (2H, d, J = 8.6 Hz), 7.24 (2H, d, J = 8.6 Hz), 8.47 (1H, bs), 12.46 (1H, bs). ESIMS (+) 411 [M + H]$^+$. |

Example 3

1-(4-Chlorophenyl)-3-(2-(4-methoxyphenyl)-1-(1H-1,2,4-triazol-3-yl)ethyl)urea

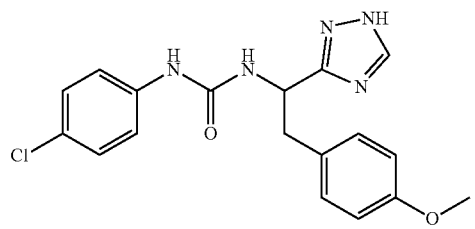

[Chem. 161]

To a solution of 1-(4-chlorophenyl)-3-[1-cyano-2-(4-methoxyphenyl)ethyl]urea (100 mg) in ethanol (0.15 mL) were added formohydrazide (36.4 μL) and sodium ethoxide (0.60 mol/L ethanol solution, 0.15 mL), and the reaction mixture was stirred at ambient temperature for 2 hours, then at 140° C. for 1.5 hours. The reaction solution was cooled to ambient temperature, water was added thereto, and the mixture was extracted with chloroform:methanol=10:1. The organic layer was washed with water, dried over anhydrous sodium sulfate, and filtrated. The solvent was removed under reduced pressure, and the precipitated solid was washed with ethyl acetate to obtain the title compound as a pale yellow solid (57.1 mg).

$^1$H NMR (400 MHz, DMSO-$d_6$) δ 2.96-3.10 (2H, m), 3.67 (3H, s), 4.82-4.88 (1H, m), 5.07 (1H, q, J=7.3 Hz), 6.57 (1H, brs), 6.77 (2H, d, J=8.5 Hz), 6.95 (2H, d, J=7.3 Hz), 7.24 (2H, d, J=9.1 Hz), 7.36 (2H, d, J=9.1 Hz), 8.73 (1H, s), 13.77 (1H, s).

ESIMS (+) 372[M+H]*.

Example 4

2-(3-(4-chlorophenyl)ureido-N'-hydroxy-3-(4-methoxyphenyl)propanimidamide

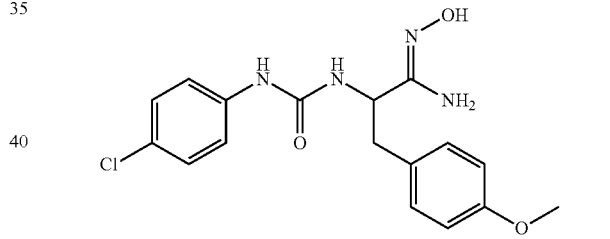

[Chem. 162]

To a solution of 1-(4-chlorophenyl)-3-[1-cyano-2-(4-methoxyphenyl)ethyl]urea (300 mg) in ethanol (4.5 mL) were added hydroxylammonium chloride (126 mg) and triethylamine (0.25 mL), and the reaction mixture was stirred under reflux for 8.5 hours. Water was added to the reaction solution, and the mixture was extracted with ethyl acetate. The organic layer was washed with an aqueous saturated ammonium chloride and then a brine, dried over anhydrous sodium sulfate, and filtrated. The solvent was removed under reduced pressure, and the precipitated solid was washed with hexane:ethyl acetate=1:1 to obtain the title compound as a colorless solid (252 mg).

$^1$H NMR (400 MHz, DMSO-$d_6$) δ 2.78 (1H, dd, J=13.9, 7.9 Hz), 2.97 (1H,dd, J=13.9, 6.1 Hz), 3.69 (3H, s), 4.33-4.42 (1H, m), 5.50 (2H, s), 6.19 (1H, d, J=8.5 Hz), 6.80 (2H, d, J=8.5 Hz), 7.11 (2H, d, J=8.5 Hz), 7.23 (2H, d, J=8.5 Hz), 7.36 (2H, d, J=8.5 Hz), 8.77 (1H, s), 8.94 (1H, s).

ESIMS (+) 363[M+H]$^+$.

Example 5

1-(4-Chlorophenyl)-3-(1-(5-hydroxy-1,2,4-oxadiazol-3-yl)-(2-(4-methoxyphenyl)ethyl)urea

[Chem. 163]

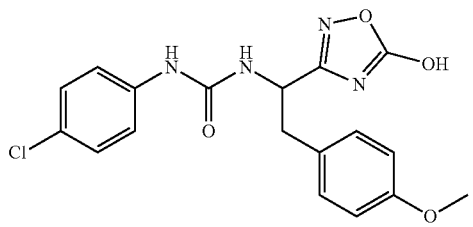

To a solution of 2-(3-(4-chlorophenyl)ureido-N'-hydroxy-3-(4-methoxyphenyl)propanimidamide (100 mg) in N,N-dimethylformamide (1.4 mL) under ice-cooling was added pyridine (0.03 mL), and then ethyl chloroformate (0.03 mL), and the reaction mixture was stirred at the same temperature for 30 minutes. Water was added to the reaction solution, and the mixture was extracted with ethyl acetate. The organic layer was washed with water and then a brine, dried over anhydrous sodium sulfate, and filtrated. The solvent was removed under reduced pressure to obtain a pale yellow liquid.

To a solution of the obtained pale yellow liquid in zylene (1.4 mL) was added 1,8-diazabicyclo[5.4.0]undec-7-ene (0.04 mL), and the mixture was stirred at 80° C. for 30 minutes. To the reaction solution was added a 10% aqueous citric acid solution, and the mixture was extracted with ethyl acetate. The organic layer was washed with water and then a brine, dried over anhydrous sodium sulfate, and filtrated. The solvent was removed under reduced pressure, the precipitated solid was washed with diisopropyl ether, and the residue was then purified by silica gel column chromatography (hexane:ethyl acetate=2:1) to obtain the title compound as a pale yellow solid (21.0 mg).

$^1$H NMR (400 MHz, DMSO-$d_6$) δ 2.95 (1H, dd, J=13.9, 7.9 Hz), 3.05 (1H, dd, J=13.9, 6.1 Hz), 3.70 (3H, s), 4.83 (1H, q, J=7.3 Hz), 6.54 (1H, d, J=7.9 Hz), 6.85 (2H, d, J=8.5 Hz), 7.12 (2H, d, J=8.5 Hz), 7.25 (2H, d, J=9.1 Hz), 7.37 (2H, d, J=9.1 Hz), 8.78 (1H, s), 12.45 (1H, brs). ESIMS (+) 389[M+H]$^+$.

Example 6

1-(4-Chlorophenyl)-3-(2-(4-methoxyphenyl)-1-(5-methyl-1,2,4-oxadiazol-3-yl)ethyl)urea

[Chem. 164]

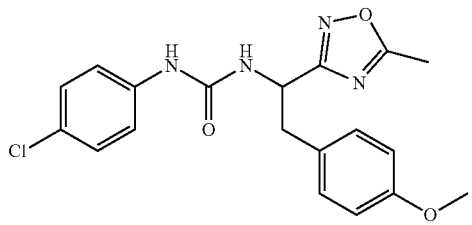

To a solution of 2-(3-(4-chlorophenyl)ureido-N'-hydroxy-3-(4-methoxyphenyl)propanimidamide (100 mg) in ethanol (4.5 mL) were added ethyl acetate (0.11 mL) and a solution of sodium ethoxide (188 mg) in ethanol (1.0 mL), and the reaction mixture was stirred under reflux for 2 hours. The solvent was removed under reduced pressure, water was added to the resulting solution, and the mixture was extracted with ethyl acetate. The organic layer was washed with water and then a brine, dried over anhydrous sodium sulfate, and filtrated. The solvent was removed under reduced pressure, water was added to the resulting solution, and the mixture was extracted with ethyl acetate. The organic layer was washed with water and then a brine, dried over anhydrous sodium sulfate, and filtrated. and the precipitated solid was washed with hexane:ethyl acetate=1:1 to obtain the title compound as a pale yellow solid (47.0 mg).

$^1$H NMR (400 MHz, DMSO-$d_6$) δ 2.58 (3H, s), 2.96-3.08 (2H, m), 3.69 (3H, s), 5.09 (1H, dd, J=15.7, 7.3 Hz), 6.71 (1H, d, J=8.5 Hz), 6.82 (2H, d, J=8.5 Hz), 7.06 (2H, d, J=8.5 Hz), 7.24 (2H, d, J=9.1 Hz), 7.35 (2H, d, J=9.1 Hz), 8.71 (1H, s).
ESIMS (+) 387 [M+H]$^+$.

Example 7

1-(4-Chlorophenyl)-3-(2-(4-methoxyphenyl)-1-(5-oxo-4,5-dihydro-1H-1,2,4-triazol-3-yl)ethyl)urea

[Chem. 165]

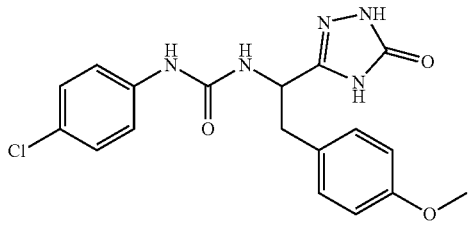

tert-Butyl 1-[(2-carbamoylhydrazinyl)-3-(4-methoxyphenyl)-1-oxopropan-2-yl]carbamate (100 mg) was stirred in 2 mol/L aqueous sodium hydroxide (1.14 mL) under reflux for 20 minutes. The reaction solution was adjusted pH 3 by addition of 1 mol/L hydrochloric acid, and the precipitated solid was collected by filtration to obtain the resulting crude product (66.6 mg). The resulting crude product (66.6 mg) was dissolved in ethyl acetate (2 mL), 4 mol/L hydrogen chloride/ethyl acetate (295 µL) was added thereto, and the mixture was stirred at room temperature for 1 day. The reaction mixture was concentrated under reduced pressure, and the obtained residue was triturated with ethyl acetate to obtain a white solid (45.0 mg). The obtained solid (40.0 mg) was dissolved in methanol (420 µL)-triethylamine (41.2 µL). To the solution under ice-cooling was added 4-chlorophenyl isocyanate (23.4 mg), and the mixture was stirred at room temperature for 1 hour. The reaction solution was adjusted pH 2 by addition of 2 mol/L hydrochloric acid, and the mixture was extracted with ethyl acetate (2 mL, ×3). The combined organic layer was washed with a brine (2 mL), dried with anhydrous sodium sulfate, and filtrated. The filtrate was concentrated under reduced pressure, and the residue was then purified by silica gel column chromatography (ethyl acetate:methanol=10:1) to obtain the title compound as a white solid (5.7 mg).

$^1$H-NMR (400 MHz, DMSO-d$_5$) δ 2.89 (1H, m), 3.00 (1H, m), 3.69 (3H, s), 4.74 (1H, m), 6.76-6.86 (3H, m), 7.05 (2H, d, J=9.1 Hz), 7.23 (2H, d, J=9.1 Hz), 7.37 (2H, d, J=9.1 Hz), 8.98 (1H, s), 11.14 (1H, s), 11.48 (1H, br s).
ESIMS (+) 388[M+H]$^+$.

Example 8

(S)-1-[1-(5-Amino-1,3,4-thiadiazol-2-yl)-2-(4-methoxyphenyl)ethyl]-3-(4-chlorophenyl)urea

[Chem. 166]

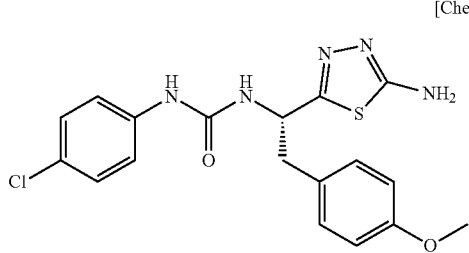

To a solution of (S)-2-[1-(5-amino-1,3,4-thiaziazol-2-yl)-2-(4-methoxyphenyl)ethyl]isoindoline-1,3-dione (240 mg) in ethanol (2.1 mL) was added hydrazine monohydrate (46.8 μL), and the reaction mixture was stirred under reflux for 30 minutes. The reaction mixture was concentrated under reduced pressure, ethyl acetate (6 mL) was added thereto, and the insoluble solid was filtered off. The filtrate was concentrated under reduced pressure to obtain the resulting crude product (169 mg).

The resulting crude product (58.9 mg) was dissolved in tetrahydrofuran (730 μL), 4-chlorophenyl isocyanate (31.7 mg) was added to the solution, and the mixture was stirred at room temperature for 4.5 hours. The reaction solution was concentrated under reduced pressure, and the obtained residue was then purified by silica gel column chromatography (chloroform:methanol=10:1) to obtain the title compound as a white solid (56.8 mg).

$^1$H-NMR (400 MHz, DMSO-d$_6$) δ 3.04 (1H, dd, J=13.9, 7.9 Hz), 3.14 (1H, dd, J=13.9, 6.1 Hz), 3.70 (3H, s), 5.09 (1H, m), 6.78 (1H, d, J=7.9 Hz), 6.83 (2H, d, J=9.1 Hz), 7.05 (2H, s), 7.13 (2H, d, J=8.5 Hz), 7.24 (2H, d, J=9.1 Hz), 7.37 (2H, d, J=8.5 Hz), 8.69 (1H, br s).
ESIMS (+) 404[M+H]$^+$.

Example 9-1

5-(1-(3-(4-Chlorophenyl)ureido)-2-(4-methoxyphenyl)ethyl)-1,3,4-oxadiazol-2-carboxylic Acid

[Chem. 167]

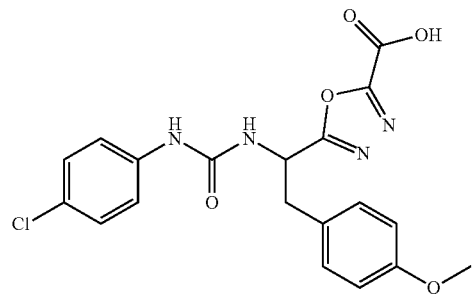

To a solution of ethyl 5-{1-[3-(4-chlorophenyl)ureido]-2-(4-methoxyphenyl)ethyl}-1,3,4-oxadiazol-2-carboxylate (120 mg) in tetrahydrofuran (270 μL)-methanol (270 μL) was added 2 mol/L aqueous sodium hydroxide (270 μL), and the reaction mixture was stirred at room temperature for 5 hours. The reaction solution was adjusted pH 2 by addition of 1 mol/L hydrochloric acid, and the mixture was extracted with ethyl acetate (2 mL, ×3). The organic layer was washed with a brine (2 mL), dried with anhydrous sodium sulfate, and filtrated. The filtrate was concentrated under reduced pressure, and the obtained residue was triturated with ethyl acetate:hexane=1:4 to obtain the title compound as a white solid (78.1 mg).

$^1$H-NMR (400 MHz, DMSO-d$_6$) δ 2.89 (1H, dd, J=13.9, 3.6 Hz), 3.07 (1H, m), 3.73 (3H, s), 5.06 (1H, m), 6.83 (2H, d, J=8.5 Hz), 7.00 (2H, d, J=8.5 Hz), 7.16 (2H, d, J=8.5 Hz), 7.30 (1H, m), 7.39 (2H, d, J=8.5 Hz), 8.03 (1H, s), 10.80 (1H, br s).
ESIMS (−) 415[M−H]$^-$.

Examples 9-2 to 9-7

The following Examples 9-2 to 9-7 were obtained using each corresponding starting material in the same method as in Example 9-1.

The structures and spectral data thereof are shown in Tables 82 and 83.

TABLE 82

| Ex. No | Str. | Chemical name | P.D. |
| --- | --- | --- | --- |
| 9-2 | | 2-(1-(3-(4-chlorophenyl)-ureido)-2-(4-methoxyphenyl)-ethyl)oxazole-4-carboxylic acid | $^1$H-NMR (400 MHz, DMSO-d$_6$) δ 3.02-3.16 (2H, m), 3.69 (3H, s), 5.10 (1H, m), 6.82 (2H, d, J = 8.5 Hz), 6.88 (1H, m), 7.03 (2H, d, J = 8.5 Hz), 7.24 (2H, d, J = 9.1 Hz), 7.38 (2H, d, J = 9.1 Hz), 8.62 (1H, s), 8.84 (1H, s), 13.06 (1H, br s). ESIMS (+) 416 [M + H]$^+$. |

TABLE 82-continued

| Ex. No | Str. | Chemical name | P.D. |
| --- | --- | --- | --- |
| 9-3 | | 3-(1-(3-(4-chlorophenyl)ureido)-2-(4-methoxyphenyl)ethyl)-1,2,4-oxadiazole-5-carboxylic acid | $^1$H-NMR (400 MHz, DMSO-$d_6$) δ 3.05 (2H, m), 3.72 (3H, s), 4.81 (1H, m), 6.89 (2H, d, J = 8.5 Hz), 7.21-7.30 (5H, m), 7.41 (2H, d, J = 8.5 Hz), 8.91 (1H, s), 10.90 (1H, br s). ESIMS (−) 415 [M − H]$^-$. |
| 9-4 | | 5-(1-(3-(4-chlorophenyl)ureido)-2-(4-methoxyphenyl)ethyl)oxazole-4-carboxylic acid | $^1$H-NMR (400 MHz, DMSO-$d_6$) δ 2.99 (2H, m), 3.69 (3H, s), 5.64 (1H, m), 6.77-6.83 (3H, m), 7.01 (2H, d, J = 9.1 Hz), 7.23 (2H, d, J = 8.5 Hz), 7.34 (2H, d, J = 9.1 Hz), 8.35 (1H, s), 8.74 (1H, s), 13.14 (1H, br s). ESIMS (+) 416 [M + H]$^+$. |
| 9-5 | | (S)-5-(1-(3-(4-chlorophenyl)ureido)-2-(4-methoxyphenyl)ethyl)oxazole-4-carboxylic acid | $^1$H-NMR (400 MHz, DMSO-$d_6$) δ 2.99 (2H, m), 3.69 (3H, s), 5.64 (1H, m), 6.77-6.83 (3H, m), 7.01 (2H, d, J = 9.1 Hz), 7.23 (2H, d, J = 8.5 Hz), 7.34 (2H, d, J = 9.1 Hz), 8.35 (1H, s), 8.74 (1H, s), 13.14 (1H, br s). ESIMS (+) 416 [M + H]$^+$. |

TABLE 83

| Ex. No | Str. | Chemical name | P.D. |
| --- | --- | --- | --- |
| 9-6 | | (S)-2-(5-(1-(3-(4-chlorophenyl)ureido)-2-(4-methoxy-phenyl)ethyl)-2H-tetrazol-2-yl)acetic acid | $^1$H-NMR (400 MHz, DMSO-$d_6$) δ 3.12-3.23 (2H, m), 3.76 (3H, s), 5.38 (1H, dd, J = 15.9, 7.4 Hz), 5.70 (2H, s), 6.85 (3H, m), 7.07 (2H, d, J = 8.6 Hz), 7.31 (2H, d, J = 8.6 Hz), 7.43 (2H, d, J = 9.2 Hz), 8.80 (1H, s). ESIMS (+) 431[M + H]$^+$ |

TABLE 83-continued

| Ex. No | Str. | Chemical name | P.D. |
|---|---|---|---|
| 9-7 | (structure) | 4-(3-(4-chlorophenyl)ureido)-5-(4-methoxyphenyl)pentane-carboxylic | $^1$H-NMR (400 MHz, DMSO-$d_6$) δ 1.42-1.55 (1H, m), 1.64-1.78 (1H, m), 2.14-2.32 (2H, m), 2.65 (2H, t, J = 6.7 Hz), 3.70 (3H, s), 3.79 (1H, d, J = 3.6 Hz), 6.34 (1H, s), 6.84 (2H, d, J = 8.5 Hz), 7.11 (2H, d, J = 8.5 Hz), 7.23 (2H, d, J = 8.5 Hz), 7.37 (2H, d, J = 8.5 Hz), 8.45 (1H, s), 12.01 (1H, s). HRESIMS (+): 375.11168 (375.11116 calculated for C19H20ClN2O4). |

Example 10-1

(−)-(S)-5-(2-(3-(4-Chlorophenyl)ureido)-3-(4-methoxyphenyl)propyl)oxazole-4-carboxylic Acid

[Chem. 168]

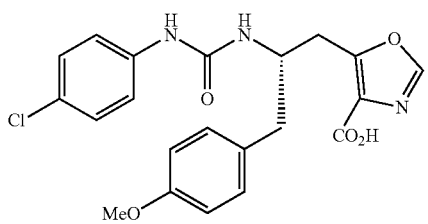

To a solution of ethyl (S)-5-(2-(3-(4-chlorophenyl)ureido)-3-(4-methoxyphenyl)propyl)oxazole-4-carboxylate (80 mg) in methanol (0.87 mL) under ice-cooling was added a solution of lithium hydroxide (5.0 mg) in water (0.87 mL), and the reaction mixture was stirred at room temperature for 21 hours. The reaction solution was ice-cooled, 1 mol/L hydrochloric acid (0.4 mL) was added thereto, and the precipitated solid was collected by filtration to obtain the title compound as a white solid (59 mg).

$^1$H-NMR (400 MHz, DMSO-$d_6$) δ 2.71 (2H, t, J=5.8 Hz), 3.16 (3H, ddd, J=28.0, 14.7, 6.5 Hz), 3.70 (3H, s), 4.20 (1H, q, J=6.9 Hz), 6.14 (1H, d, J=8.5 Hz), 6.83 (2H, d, J=8.5 Hz), 7.12 (2H, d, J=9.1 Hz), 7.20 (2H, d, J=9.1 Hz), 7.30 (2H, d, J=8.5 Hz), 8.29 (1H, s), 8.49 (1H, s).

ESIMS (+) 430[M+H]*.

$[α]_D^{25}$ −19.80° (c 0.347, DMSO)

Example 10-2

The following Example 10-2 was obtained using the corresponding starting material in the same method as in Example 10-1.

The structure and spectral data thereof are shown in Table 84.

TABLE 84

| Ex. No | Str. | Chemical name | P.D. |
|---|---|---|---|
| 10-2 | (structure) | (−)-(S)-2-(5-(1-(3-(4-chlorophenyl)ureido)-2-(4-methoxyphenyl)ethyl)-2-oxo-1,3,4-oxadiazol-3(2H)-yl)acetic acid | $^1$H-NMR (400 MHz, DMSO-$d_6$) δ 2.96-3.09 (2H, m), 3.70 (3H, s), 4.47 (2H, s), 4.94 (1H, td, J = 8.2, 6.3 Hz), 6.73 (1H, d, J = 8.5 Hz), 6.84 (2H, d, J = 8.5 Hz), 7.14 (2H, d, J = 9.1 Hz), 7.25 (2H, d, J = 9.1 Hz), 7.36 (2H, d, J = 9.1 Hz), 8.72 (1H, s). ESIMS (+) 445 [M + H]$^+$. $[α]_D^{27}$ −50.6° (c 0.345, EtOH) |

Example 11-1

1-(4-Chlorophenyl)-3-(1-(5-(hydroxymethyl)-1,3,4-oxadiazol-2-yl)-2-(4-methoxyphenyl)ethyl)urea

[Chem. 169]

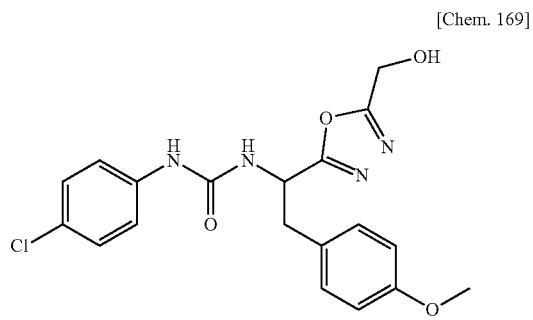 [SMILES: COc1ccc(CC(NC(=O)Nc2ccc(Cl)cc2)C(=N)OC(=N)CO)cc1]

To a solution of ethyl 5-{1-[3-(4-chlorophenyl)ureido]-2-(4-methoxyphenyl)ethyl}-1,3,4-oxadiazole-2-carboxylate (120 mg) in tetrahydrofuran (540 µL)-methanol (540 µL) under ice-cooling was added sodium borohydride (33.3 mg), and the reaction mixture was stirred at the same temperature for 2.5 hours. Under ice-cooling, water (1 mL), an aqueous saturated citric acid (130 µL), and ethyl acetate (1 mL) were added to the reaction solution, and the mixture was stirred. The precipitated solid was collected by filtration to obtain the title compound as a white solid (90.5 mg).

$^1$H-NMR (400 MHz, DMSO-$d_6$) δ 3.08 (1H, m), 3.16 (1H, m), 3.70 (3H, s), 4.60 (2H, d, J=6.1 Hz), 5.22 (1H, br q, J=7.5 Hz), 5.87 (1H, t, J=6.1 Hz), 6.83 (2H, d, J=8.5 Hz), 6.92 (1H, m), 7.10 (2H, d, J=8.5 Hz), 7.24 (2H, d, J=9.1 Hz), 7.37 (2H, d, J=9.1 Hz), 8.80 (1H, br s).
ESIMS (+) 403[M+H]$^+$.

Examples 11-2 to 11-9

The following Examples 11-2 to 11-9 were obtained using each corresponding starting material in the same method as in Example 11-1.

The structures and spectral data thereof are shown in Tables 85 and 86.

TABLE 85

| Ex. No | Str. | Chemical name | P.D. |
|---|---|---|---|
| 11-2 | | 1-(4-chlorophenyl)-3-(1-(4-(hydroxymethyl)oxazol-2-yl)-2-(4-methoxyphenyl)ethyl)urea | $^1$H-NMR (400 MHz, DMSO-$d_6$) δ 3.06 (1H, m), 3.13 (1H, m), 3.71 (3H, s), 4.35 (2H, d, J = 5.4 Hz), 4.86 (1H, t, J = 5.4 Hz), 5.10 (1H, m), 6.58 (1H, d, J = 7.9 Hz), 6.81 (2H, d, J = 8.5 Hz), 7.03 (2H, d, J = 8.5 Hz), 7.20-7.25 (2H, m), 7.34-7.38 (2H, m), 7.75 (1H, s), 8.59 (1H, s). ESIMS (+) 401 [M + H]$^+$ |
| 11-3 | | 1-(4-chlorophenyl)-3-(1-(5-(hydroxymethyl)-1,2,4-oxadiazol-3-yl)-2-(4-methoxyphenyl)ethyl)urea | $^1$H-NMR (400 MHz, DMSO-$d_6$) δ 3.03 (2H, m), 3.69 (3H, s), 4.71 (2H, d, J = 6.1 Hz), 5.11 (1H, br q, J = 7.5 Hz), 6.00 (1H, t, J = 6.1 Hz), 6.82 (2H, d, J = 8.5 Hz), 7.02 (1H, m), 7.08 (2H, d, J = 8.5 Hz), 7.23 (2H, d, J = 9.1 Hz), 7.37 (2H, d, J = 9.1 Hz), 8.98 (1H, br s). ESIMS (+) 403 [M + H]$^+$. |
| 11-4 | | 1-(4-chlorophenyl)-3-(2-(2,3-dihydrobenzofuran-5-yl)-1-(5-(2-hydroxyethyl)-1,2,4-oxadiazol-3-yl)ethyl)urea | $^1$H-NMR (400 MHz, DMSO-$d_6$) δ 2.94-3.13 (6H, m), 3.80 (2H, q, J = 6.1 Hz), 4.45 (2H, t, J = 8.5 Hz), 4.96 (1H, t, J = 5.4 Hz), 5.04-5.13 (1H, m), 6.61 (1H, d, J = 8.5 Hz), 6.73 (1H, d, J = 8.5 Hz), 6.83 (1H, d, J = 8.5 Hz), 7.00 (1H, s), 7.24 (2H, dt, J = 9.1, 2.4 Hz), 7.36 (2H, d,t J = 9.1, 2.4 Hz), 8.75 (1H, s). ESIMS (+) 429 [M + H]$^+$. |

TABLE 85-continued

| Ex. No | Str. | Chemical name | P.D. |
|---|---|---|---|
| 11-5 | | (S)-1-(4-chlorophenyl)-3-(1-(5-(2-hydroxyethyl)-1,3,4-thiadiazol-2-yl)-2-(4-methoxyphenyl)ethyl)urea | $^1$H-NMR (400 MHz, DMSO-d$_6$) δ 3.08-3.16 (3H, m), 3.24 (1H, m), 3.66-3.71 (5H, m), 4.99 (1H, t, J = 5.1 Hz), 5.33 (1H, m), 6.83 (2H, d, J = 8.5 Hz), 6.95 (1H, m), 7.15 (2H, d, J = 8.5 Hz), 7.24 (2H, d, J = 9.1 Hz), 7.36 (2H, d, J = 9.1 Hz), 8.72 (1H, m). ESIMS (+) 433 [M + H]$^+$. |

TABLE 86

| Ex. No | Str. | Chemical name | P.D. |
|---|---|---|---|
| 11-6 | | 1-(4-chlorophenyl)-3-(1-(4-(hydroxymethyl)oxazol-5-yl)-2-(4-methoxyphenyl)ethyl)urea | $^1$H-NMR (400 MHz, DMSO-d$_6$) δ 2.94 (1H, m), 3.03 (1H, m), 3.69 (3H, s), 4.24 (2H, m), 4.99 (1H, m), 5.18 (1H, m), 6.75 (1H, d, J = 8.5 Hz), 6.80 (2H, d, J = 8.5 Hz), 7.05 (2H, d, J = 8.5 Hz), 7.23 (2H, d, J = 9.1 Hz), 7.35 (2H, d, J = 9.1 Hz), 8.20 (1H, s), 8.60 (1H, s). ESIMS (+) 402 [M + H]$^-$. |
| 11-7 | | 1-(4-chlorophenyl)-3-(1-(4-(hydroxyethyl)thiazol-5-yl)-2-(4-methoxyphenyl)ethyl)urea | $^1$H-NMR (400 MHz, DMSO-d$_6$) δ 2.84 (2H, t, J = 7.0 Hz), 3.03 (1H, dd, J = 13.9, 8.5 Hz), 3.19 (1H, dd, J = 13.9, 5.5 Hz), 3.66-3.72 (5H, m), 4.64 (1H, t, J = 5.4 Hz), 5.18 (1H, m), 6.81 (2H, d, J = 9.1 Hz), 6.86 (1H, m), 7.08 (2H, d, J = 9.1 Hz), 7.16 (1H, s), 7.24 (2H, d, J = 9.1 Hz), 7.36 (2H, d, J = 9.1 Hz), 8.79 (1H, br s). ESIMS (+) 432 [M + H]$^+$. |
| 11-8 | | (S)-1-(4-chlorophenyl)-3-(1-(5-(2-hydroxyethyl)-4H-1,2,4-triazol-3-yl)-2-(4-methoxyphenyl)ethyl)urea | $^1$H-NMR (400 MHz, DMSO-d$_6$) δ 2.81 (2H, t, J = 6.8 Hz), 2.98 (1H, dd, J = 13.4, 7.4 Hz), 3.05 (1H, dd, J = 13.4, 6.7 Hz), 3.68 (3H, s), 3.71 (3H, t, J = 6.8 Hz), 4.98-5.07 (1H, m), 6.60 (1H, d, J = 8.5 Hz), 6.77 (2H, d, J = 8.5 Hz), 6.99 (2H, d, J = 8.5 Hz), 7.23 (2H, dt, J = 8.5, 1.8 Hz), 7.35 (2H, dt, J = 8.5, 1.8 Hz), 8.78 (1H, s). ESIMS (+) 416 [M + H]$^+$. |
| 11-9 | | (−)-(S)-1-(4-chlorophenyl)-3-(1-(4-chlorophenyl)-3-(5-(2-hydroxyethyl)-1,3,4-oxadiazol-2-yl)propan-2-yl)urea | $^1$H-NMR (400 MHz, DMSO-d$_6$) δ 2.81-3.08 (6H, m), 3.71 (2H, t, J = 6.7 Hz), 4.23 (1H, q, J = 7.3 Hz), 4.85 (1H, s), 6.26 (1H, d, J = 8.5 Hz), 7.23 (4H, dd, J = 14.2, 8.8 Hz), 7.30-7.36 |

(4H, m), 8.56 (1H, s).
ESIMS (+) 435 [M + H]$^+$.
[α]$_D^{28}$ −18.5° (c 0.351, DMSO)

Example 12

5-(1-(3-(4-Chlorophenyl)ureido)-2-(4-methoxyphenyl)ethyl)-1,3,4-oxadiazole-2-carboxamide

[Chem. 170]

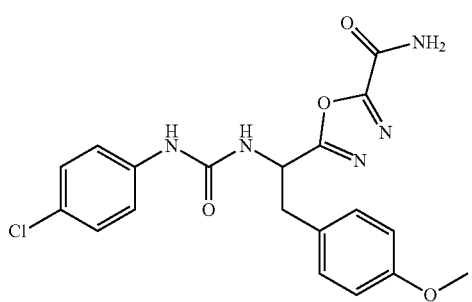

To a solution of ethyl 5-{1-[3-(4-chlorophenyl)ureido]-2-(4-methoxyphenyl)ethyl}-1,3,4-oxadiazole-2-carboxylate (50.0 mg) in methanol (200 μL) was added 7 mol/L ammonia/methanol (500 μL), and the reaction mixture was stirred at room temperature for 4 hours. The reaction solution was concentrated under reduced pressure, and the obtained residue was triturated with diisopropyl ether to obtain the title compound as a white solid (43.9 mg).

$^1$H-NMR (400 MHz, DMSO-d$_6$) δ 2.89 (1H, dd, J=13.9, 3.6 Hz), 3.07 (1H, m), 3.73 (3H, s), 5.11 (1H, t, J=3.6 Hz), 6.83 (2H, d, J=8.5 Hz), 7.02 (2H, d, J=8.5 Hz), 7.16 (2H, d, J=9.1 Hz), 7.39 (2H, d, J=9.1 Hz), 7.59 (1H, m), 7.84 (1H, br s), 8.03 (1H, s), 10.77 (1H, br s).
ESIMS (+) 416[M+H]$^+$.

Example 13

5-(1-(3-(4-Chlorophenyl)ureido)-2-(4-methoxyphenyl)ethyl)-N-methyl-1,3,4-oxadiazole-2-carboxamide

[Chem. 171]

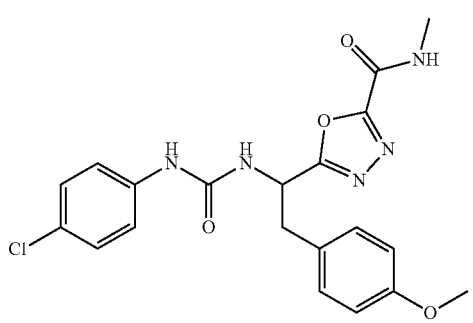

To a solution of ethyl 5-{1-[3-(4-chlorophenyl)ureido]-2-(4-methoxyphenyl)ethyl}-1,3,4-oxadiazole-2-carboxylate (19.2 mg) in tetrahydrofuran (112 μL) was added 2 mol/L methylamine/tetrahydrofuran (250 μL), and the reaction mixture was stirred at room temperature for 17 hours. The reaction suspension was filtered, and the solid on the filter was washed with tetrahydrofuran to obtain the title compound as a white solid (8.7 mg).

$^1$H-NMR (400 MHz, DMSO-d$_6$) δ 2.69 (3H, d, J=4.8 Hz), 2.82 (1H, m), 3.04 (1H, m), 3.71 (3H, s), 5.13 (1H, m), 6.82 (2H, d, J=8.5 Hz), 6.94 (2H, d, J=8.5 Hz), 7.14 (2H, d, J=8.5 Hz), 7.42 (2H, d, J=8.5 Hz), 8.26 (1H, s), 8.73 (1H, m), 11.12 (1H, br s).
ESIMS (+) 430[M+H]$^+$.

Example 14-1

(+)-(S)-2-(5-{1-[3-(4-Chlorophenyl)ureido]-2-(4-methoxyphenyl)ethyl}-2H-tetrazol-2-yl)acetamide

[Chem. 172]

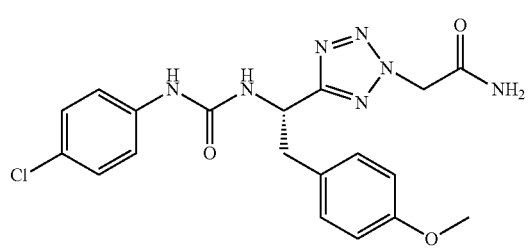

To a solution of (S)-2-(5-{1-[3-(4-chlorophenyl)ureido]-2-(4-methoxyphenyl)ethyl}-2H-tetrazol-2-yl)acetic acid (100 mg) in a mixed solvent of dichloromethane (1.00 mL) and DMF (1.00 mL) under ice-cooling were added 1-hydroxybenzotriazole (39.9 mg) and 1-ethyl-3-(3-dimethylaminopropyl)carbodiimide hydrochloride (50.3 mg), and the reaction mixture was warmed to room temperature and stirred for 1 hour. To the reaction mixture under ice-cooling was added 25% aqueous ammonia (80.0 μL), and the reaction mixture was warmed to room temperature and stirred for a day. To the reaction mixture under ice-cooling were added 1-hydroxybenzotriazole (34.9 mg) and 1-ethyl-3-(3-dimethylaminopropyl)carbodiimide hydrochloride (44.7 mg), and the reaction mixture was warmed to room temperature and stirred for 1 hour. To the reaction solution was added ethyl acetate, and the organic layer was washed with water and then a brine, and dried over anhydrous sodium sulfate. The solvent was removed, and the obtained residue was then purified by silica gel column chromatography (ethyl acetate:hexane=1:3) to obtain the title compound as a colorless solid (19.5 mg).

$^1$H-NMR (400 MHz, DMSO-d$_6$) δ 3.02-3.12 (2H, m), 3.68 (3H, s), 5.29 (1H, dd, J=15.8, 8.6 Hz), 5.37 (2H, s), 6.76-6.80 (3H, m), 7.01 (2H, d, J=8.6 Hz), 7.23 (2H, d, J=9.2 Hz), 7.36 (2H, d, J=8.6 Hz), 7.49 (1H, s), 7.80 (1H, s), 8.72 (1H, s).
ESIMS (+) 430[M+H]$^+$.
[α]$_D^{26}$ +14 (c 0.092, DMSO).

Examples 14-2 to 14-6

The following Examples 14-2 to 14-6 were obtained using each corresponding starting material and reactant in the same method as in Example 14-1.

The structures and spectral data thereof are shown in Tables 87 and 88.

TABLE 87

| Ex. No | Str. | Chemical name | P.D. |
|---|---|---|---|
| 14-2 | | (S)-5-(1-(3-(4-chlorophenyl)ureido)-2-(4-methoxyphenyl)ethyl)oxazole-4-carboxamide | $^1$H-NMR (400 MHz, DMSO-$d_6$) δ 3.02 (2H, d, J = 7.3 Hz), 3.68 (3H, s), 5.53 (1H, m), 6.79 (2H, d, J = 8.5 Hz), 6.96-7.08 (3H, m), 7.22 (2H, d, J = 8.5 Hz), 7.37 (2H, d, J = 8.5 Hz), 7.59 (1H, s), 7.69 (1H, s), 8.31 (1H, s), 8.99 (1H, brs). ESIMS (+) 415 [M + H]$^+$. |
| 14-3 | | (S)-5-(1-(3-(4-chlorophenyl)ureido)-2-(4-methoxyphenyl)ethyl)-N-methyloxazole-4-carboxamide | $^1$H-NMR (400 MHz, DMSO-$d_6$) δ 2.77 (3H, d, J = 4.8 Hz), 3.02 (2H, d, J = 7.9 Hz), 3.68 (3H, s), 5.52 (1H, m), 6.80 (2H, d, J = 8.5 Hz), 6.96-7.06 (3H, m), 7.22 (2H, d, J = 8.5 Hz), 7.37 (2H, d, J = 8.5 Hz), 8.30 (1H, m), 8.32 (1H, s), 8.99 (1H, br s). ESIMS (+) 429 [M + H]$^+$. |
| 14-4 | | (S)-5-(1-(3-(4-chlorophenyl)ureido)-2-(4-methoxyphenyl)ethyl)-N,N-dimethyloxazole-4-carboxamide | $^1$H-NMR (400 MHz, DMSO-$d_6$) δ 2.92 (3H, br s), 2.94-3.03 (5H, m), 3.69 (3H, s), 5.34 (1H, m), 6.80 (2H, d, J = 8.5 Hz), 6.86 (1H, m), 7.02 (2H, d, J = 8.5 Hz), 7.23 (2H, d, J = 8.5 Hz), 7.37 (2H, d, J = 8.5 Hz), 8.35 (1H, s), 8.88 (1H, br s). ESIMS (+) 443 [M + H]$^+$. |
| 14-5 | | (S)-2-(5-(1-(3-(4-chlorophenyl)ureido)-2-(4-methoxyphenyl)ethyl)-2H-tetrazol-2-yl)-N-methylacetamide | $^1$H-NMR (400 MHz, DMSO-$d_6$) δ 2.64 (3H, d, J = 4.9 Hz), 3.02-3.15 (2H, m), 3.69 (3H, s), 5.29 (1H, d, J = 7.4 Hz), 5.37 (2H, s), 6.79 (3H, m), 7.01 (2H, d, J = 9.2 Hz), 7.23 (2H, d, J = 9.2 Hz), 7.35 (2H, d, J = 8.6 Hz), 8.34 (1H, s), 8.72 (1H, s). ESIMS (+) 444 [M + H]$^+$. |

TABLE 88

| Ex. No | Str. | Chemical name | P.D. |
|---|---|---|---|
| 14-6 | | (S)-1-(4-chlorophenyl)-3-(2-(4-methoxyphenyl)-1-(2-(2-morpholino-2-oxoethyl)-2H-tetrazol-5-yl)ethyl)urea | ¹H-NMR (400 MHz, DMSO-d₆) δ 3.04-3.16 (2H, m), 3.41-3.49 (4H, m), 3.56-3.64 (4H, m), 3.68 (3H, s), 5.29 (1H, dd, J = 7.4, 15.3 Hz), 5.96 (2H, s), 6.77-6.79 (3H, m), 7.02 (2H, d, J = 8.6 Hz), 7.23 (2H, d, J = 9.2 Hz), 7.36 (2H, d, J = 6.7 Hz), 8.77 (1H, s). ESIMS (+) 500 [M + H]⁺. |

Example 15-1

(−)-(S)-1-{1-[2-(2-Aminoethyl)-2H-tetrazol-5-yl]-2-(4-methoxyphenyl)ethyl}-3-(4-chlorophenyl)urea

[Chem. 173]

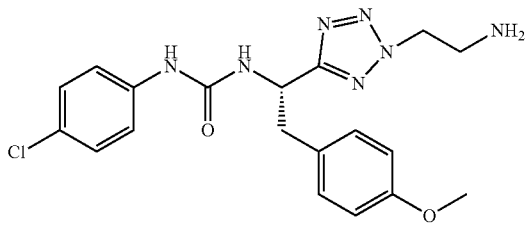

To a solution of tert-butyl (S)-(2-(5-(1-(3-(4-chlorophenyl)ureido)-2-(4-methoxyphenyl)ethyl)-2H-tetrazol-2-yl)ethyl)carbamate (513 mg) in 1,4-dioxane (0.99 mL) was added 4N hydrogen chloride/dioxane (1.99 mL), and the reaction mixture was stirred at room temperature for 2 hours. The solvent was removed under reduced pressure to obtain the hydrochloride as a white solid (535 mg).

The obtained hydrochloride (346 mg) was dissolved in ethanol (7.7 mL). Under ice-cooling, aqueous sodium hydroxide (0.5M, 1.53 mL) was added to the solution. The solvent was removed, and the resulting white solid was washed with water and diethyl ether to obtain the title compound.

¹H-NMR (400 MHz, DMSO-d₆) θ 1.48 (2H, s), 3.00 (2H, t, J=6.1 Hz), 3.04-3.13 (2H, m), 3.68 (3H, s), 4.55 (2H, t, J=6.1 Hz), 5.28 (1H, q, J=7.5 Hz), 6.78 (3H, d, J=9.2 Hz), 6.99 (2H, d, J=8.5 Hz), 7.24 (2H, d, J=8.5 Hz), 7.36 (2H, d, J=6.7 Hz), 8.74 (1H, s).

ESIMS (+) 416[M+H]⁺.

$[\alpha]_D^{28}$ −17.7° (c 0.348, EtOH)

Example 15-2

The following Example 15-2 was obtained using the corresponding starting material in the same method as in Example 15-1.

The structure and spectral data thereof are shown in Table 89.

TABLE 89

| Ex. No | Str. | Chemical name | P.D. |
|---|---|---|---|
| 15-2 | | (−)-(S)-1-(1-(2-(azetidin-3-yl)-2H-tetrazol-5-yl)-2-(4-methoxyphenyl)ethyl)-3-(4-chlorophenyl)urea | ¹H-NMR (400 MHz, CDCl₃) δ 3.16-3.27 (2H, m), 3.75 (3H, s), 4.08 (2H, t, J = 8.3 Hz), 4.19 (2H, t, J = 7.3 Hz), 5.53-5.61 (2H, m), 5.68 (1H, t, J = 6.7 Hz), 6.73 (1H, s), 6.74 (2H, d, J = 8.6 Hz), 6.92 (2H, d, J = 8.6 Hz), 7.22 (4H, s). ESIMS (+) 428 [M + H]⁺. $[\alpha]_D^{28}$ −16.38° (c 0.348, EtOH) |

Example 16

(−)-(S)—N-(2-(5-(1-(3-(4-Chlorophenyl)ureido)-2-(4-methoxyphenyl)ethyl)-2H-tetrazol-2-yl)ethyl)acetamide

[Chem. 174]

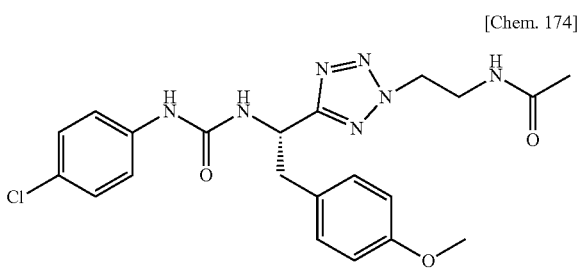 [SMILES: COc1ccc(C[C@H](NC(=O)Nc2ccc(Cl)cc2)c2nnn(CCNC(C)=O)n2)cc1]

To a solution of (S)-1-{1-[2-(2-aminoethyl)-2H-tetrazol-5-yl]-2-(4-methoxyphenyl)ethyl}-3-(4-chlorophenyl)urea hydrochloride (100 mg) in pyridine (0.44 mL) under ice-cooling was added acetic anhydride (0.22 mL), and the reaction mixture was stirred at the same temperature for 1 hour. To the reaction solution were added ice and a dilute hydrochloric acid (1%), and the mixture was extracted with ethyl acetate. The organic layer was washed with a brine, dried over anhydrous sodium sulfate, and filtrated. The solvent was removed under reduced pressure, and the resulting crude product was purified by silica gel column chromatography (hexane:ethyl acetate=1:1) to obtain the title compound as a white solid (79.1 mg).

$^1$H-NMR (400 MHz, CDCl$_3$) δ 1.90 (3H, s), 3.22 (2H, d, J=6.1 Hz), 3.37-3.77 (2H, m), 3.76 (3H, s), 4.66 (2H, t, J=5.4 Hz), 5.49-5.55 (2H, m), 5.80 (1H, brs), 6.69 (1H, brs), 6.76 (2H, d, J=8.5 Hz), 6.95 (2H, d, J=8.5 Hz), 7.24 (4H d, J=8.5 Hz).

ESIMS (+) 458[M+H]$^+$.

$[\alpha]_D^{28}$ −30.1 (c 0.345, EtOH)

Example 17

(−)-(S)—N-(2-(5-(1-(3-(4-Chlorophenyl)ureido)-2-(4-methoxyphenyl)ethyl)-2H-tetrazol-2-yl)ethyl)methanesulfonamide

[Chem. 175]

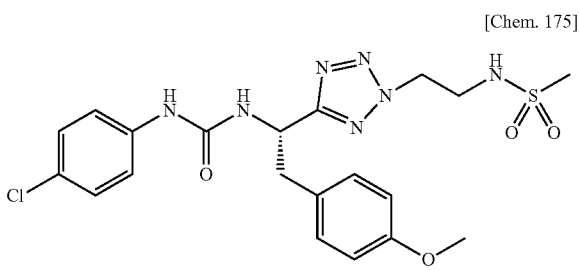 [SMILES: COc1ccc(C[C@H](NC(=O)Nc2ccc(Cl)cc2)c2nnn(CCNS(C)(=O)=O)n2)cc1]

To a solution of (S)-1-{1-[2-(2-aminoethyl)-2H-tetrazol-5-yl]-2-(4-methoxyphenyl)ethyl}-3-(4-chlorophenyl)urea hydrochloride (200 mg) in dichloromethane (2.21 mL) under ice-cooling were added triethylamine (0.13 mL) and methanesulfonyl chloride (0.034 mL), and the reaction mixture was stirred at the same temperature for 2 hours. To the reaction solution was added ice, and the mixture was extracted with chloroform. The organic layer was washed with a brine, and dried over anhydrous sodium sulfate. The solvent was removed under reduced pressure, and the obtained residue was then purified by silica gel column chromatography (hexane:ethyl acetate=1:3) to obtain the title compound as a white solid (81.5 mg).

$^1$H-NMR (400 MHz, DMSO-d$_6$) δ 2.85 (3H, s), 3.02-3.13 (2H, m), 3.50 (2H, d, J=5.4 Hz), 3.68 (3H, s), 4.72 (2H, t, J=6.1 Hz), 5.29 (1H, q, J=7.5 Hz), 6.77 (1H, d, J=9.1 Hz), 6.80 (2H, d, J=9.1 Hz), 7.01 (2H, d, J=8.5 Hz), 7.24 (2H, d, J=9.1 Hz), 7.31 (1H, s), 7.36 (2H, d, J=9.1 Hz), 8.72 (1H, s).

ESIMS (+) 494[M+H]$_+$.

$[\alpha]_D^{29}$ −17.7 (c 0.350, EtOH)

Example 18-1

(−)-(S)-1-(4-Chlorophenyl)-3-(2-(4-chlorophenyl)-1-(5-((2-hydroxyethyl)amino)-1,2,4-oxadiazol-3-yl)ethylurea

[Chem. 176]

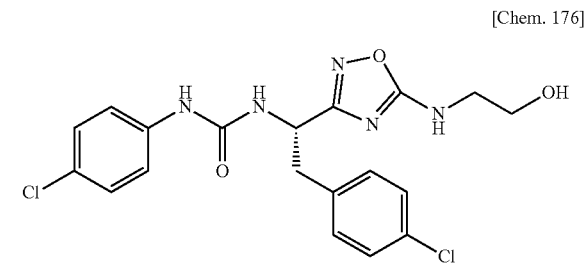 [SMILES: O=C(Nc1ccc(Cl)cc1)N[C@@H](Cc1ccc(Cl)cc1)c1noc(NCCO)n1]

To a solution of (S)-1-(4-chlorophenyl)-3-(2-(4-chlorophenyl)-1-(5-trichloromethyl)-1,2,4-oxadiazol-3-yl)ethyl)urea (200 mg) in N,N-dimethylformamide (2.00 mL) was added hydroxyethylamine (80.0 μL), and the reaction mixture was stirred at room temperature for 4 hours. To the reaction solution was added ethyl acetate, and the organic layer was washed with water and then a brine, and dried over anhydrous sodium sulfate. The solvent was removed, and the obtained residue was then purified by silica gel column chromatography (methanol:ethyl acetate=1:9) to obtain the title compound as a colorless solid (134 mg).

$^1$H-NMR (400 MHz, DMSO-d$_6$) δ 2.98-3.08 (2H, m), 3.27-3.31 (2H, m), 3.49-3.53 (2H, m), 4.80 (1H, t, J=5.5 Hz), 4.92 (1H, dd, J=16.5, 7.4 Hz), 6.59 (1H, d, J=8.6 Hz), 7.17 (2H, d, J=8.6 Hz), 7.24 (2H, d, J=9.2 Hz), 7.30-7.37 (4H, m), 8.34 (1H, t, J=5.5 Hz), 8.68 (1H, s).

ESIMS (+) 436[M+H]$^+$.

$[\alpha]_D^{25}$ −64 (c 0.137, DMSO).

Examples 18-2 to 18-18

The following Examples 18-2 to 18-18 were obtained using each corresponding starting material and reactant in the same method as in Example 18-1.

The structures and spectral data thereof are shown in Tables 90-94.

TABLE 90

| Ex. No | Str. | Chemical name | P.D. |
|---|---|---|---|
| 18-2 | | 1-(1-(5-amino-1,2,4-oxadiazol-3-yl)-2-(4-methoxyphenyl)ethyl)-3-(4-chlorophenyl)urea | $^1$H-NMR (400 MHz, DMSO-$d_6$) δ 2.96 (2H, t, J = 13.9, 7.9 Hz), 3.69 (3H, s), 4.85 (1H, q, J = 6.7 Hz), 6.51 (1H, d, J = 8.6 Hz), 6.82 (2H, d, J = 8.6 Hz), 7.04 (2H, d, J = 8.6 Hz), 7.24 (2H, d, J = 8.6 Hz), 7.36 (2H, d, J = 8.6 Hz), 7.79 (2H, s), 8.72 (1H, s). ESIMS (+) 388 [M + H]$^+$ |
| 18-3 | | (+)-(S)-1-(4-chlorophenyl)-3-(2-(4-chlorophenyl)1-1(5-((2-fluoroethyl)amino)-1,2,4-oxadiazol-3-yl)urea | $^1$H-NMR (400 MHz, DMSO-$d_6$) δ 2.99-3.09 (2H, m), 3.50-3.54 (1H, m), 3.57-3.61 (1H, m), 4.47 (1H, t, J = 4.9 Hz), 4.59 1H, t, J = 4.9 Hz), 4.93 (1H, dd, J = 7.4, 15.9 Hz), 6.60 (1H, d, J = 8.6 Hz), 7.17 (2H, d, J = 8.6 Hz), 7.24 (2H, d, J = 8.6 Hz), 7.30-7.37 (4H, m), 8.62 (1H, t, J = 1.5 Hz), 8.68 (1H, s). ESIMS (+) 438 [M − H]$^+$ $[α]_D^{26}$ +20 (c 0.096, THF). |
| 18-4 | | (+)-(S)-1-(4-chlorophenyl)-3-(2-(4-chlorophenyl)-1-(5-morpholino-1,2,4-oxadiazol-3-yl)ethyl)urea | 1H-NMR (400 MHz, DMSO-$d_6$) δ 2.98-3.09 (2H, m), 3.50-3.53 (4H, m), 3.67-3.69 (4H, m), 5.95 (1H, q, J = 7.9 Hz), 6.64 (1H, d, J = 9.2 Hz), 7.19-7.25 (4H, m), 7.32-7.36 (4H, m), 8.68 (1H, s). ESIMS (+) 462 [M + H]$^+$ $[α]_D^{26}$ +7 (c 0.099, THF). |
| 18-5 | | (S)-1-(1-(5-amino-1,2,4-oxadiazol-3-yl)-2-(4-chlorophenyl)ethyl)-3-(4-chlorophenyl)urea | $^1$H-NMR (400 MHz, DMSO-$d_6$) δ 2.98-3.10 (2H, m), 4.88-4.96 (1H, m), 6.58 (1H, d, J = 8.5 Hz), 7.18 (2H, d, J = 8.5 Hz), 7.25 (2H, d, J = 8.5 Hz), 7.34 (2H, d, J = 8.5 Hz), 7.37 (2H, d, J = 8.5 Hz), 7.83 (2H, s), 8.71 (1H, s). HRESIMS (+): 392.06880 (392.06810 calculated for C17H16C12N5O2). |

TABLE 91

| Ex. No | Str. | Chemical name | P.D. |
|---|---|---|---|
| 18-6 | | (+)-(S)-1-(4-chlorophenyl)-3-(2-(4-chlorophenyl)-1-(5-(methylamino)-1,2,4-oxadiazol-3-yl)ethyl)urea | $^1$H-NMR (400 MHz, DMSO-d$_6$) δ 2.85 (3H, d, J = 4.9 Hz), 2.98-3.08 (2H, m), 4.92 (1H, dd, J = 7.4, 15.3 Hz), 6.62 (1H, d, J = 8.6 Hz), 7.17 (2H, d, J = 8.0 Hz), 7.23 (2H, d, J = 8.0 Hz), 7.31-7.36 (4H, m), 8.21 (1H, dd, J = 4.3 Hz, 9.2 Hz), 8.69 (1H, s). ESIMS (+) 406 [M + H]$^+$ [α]$_D^{29}$ +8 (c 0.367, THF). |
| 18-7 | | (+)-(S)-1-(4-chlorophenyl)-3-(2-(4-chlorophenyl)-1-(5-(ethylamino)-1,2,4-oxadiazol-3-yl)ethyl)urea | $^1$H-NMR (400 MHz, DMSO-d$_6$) δ 1.14 (3H, t, J = 7.3 Hz), 2.98-3.08 (2H, m), 3.23-3.31 (2H, m), 4.92 (1H, dd, J = 7.3, 15.9 Hz), 6.60 (1H, d, J = 9.2 Hz), 7.17 (2H, d, J = 8.6 Hz), 7.23 (2H, d, J = 9.2 Hz), 7.31-7.36 (4H, m), 8.31 (1H, t, J = 5.5 Hz), 8.70 (1H, s). ESIMS (+) 420 [M + H]$^+$ [α]$_D^{29}$ +8 (c 0.283, THF). |
| 18-8 | | (+)-(S)-1-(4-chlorophenyl)-3-(2-(4-chlorophenyl)-1-(5-(isopropylamino)-1,2,4-oxadiazol-3-yl)ethyl)urea | $^1$H-NMR (400 MHz, DMSO-d$_6$) δ 1.17 (6H, d), 2.99-3.09 (2H, m), 3.35-3.79 (1H, m), 4.92 (1H, dd, J = 7.4, 15.9 Hz), 6.60 (1H, d, J = 8.6 Hz), 7.17 (2H, d, J = 8.6 Hz), 7.23 (2H, d, J = 9.2 Hz), 7.31 (2H, d, J = 8.6 Hz), 7.35 (2H, d, J = 9.2 Hz), 8.26 (1H, d, J = 8.0 Hz), 8.70 (1H, s). ESIMS (+) 434 [M + H]$^+$ [α]$_D^{29}$ +4 (c 0.265, THF). |
| 18-9 | | (S)-1-(4-chlorophenyl)-3-(2-(4-chlorophenyl)-1-(5-(cyclopropylamino)-1,2,4-oxadiazol-3-yl)ethyl)urea | $^1$H-NMR (400 MHz, DMSO-d$_6$) δ 0.50-0.55 (2H, m), 0.68-0.76 (2H, m), 2.63-2.71 (1H, m), 2.98-3.10 (2H, m), 4.90-4.98 (1H, m), 6.66 (1H, d, J = 8.6 Hz), 7.18 (2H, d, J = 8.6 Hz), 7.24 (2H, d, J = 8.6 Hz), 7.32 (2H, d, J = 8.6 Hz), 7.36 (2H, d, J = 8.6 Hz), 8.61 (1H, d, J = 2.4 Hz), 8.71 (1H, s). HRESIMS (+): 432.09907 (432.09940 calculated for C20H20Cl2N5O2). |

TABLE 92

| Ex. No | Str. | Chemical name | P.D. |
|---|---|---|---|
| 18-10 | | (S)-1-(4-chlorophenyl)-3-(2-(4-chlorophenyl)-1-(5-(dimethylamino)-1,2,4-oxadiazol-3-yl)ethyl)urea | $^1$H-NMR (400 MHz, DMSO-$d_6$) δ 2.97-3.07 (2H, m), 3.08 (6H, s), 4.89-4.97 (1H, m), 6.63 (1H, d, J = 8.5 Hz), 7.20 (2H, d, J = 8.5 Hz), 7.25 (2H, d, J = 8.5 Hz), 7.33 (2H, d, J = 8.5 Hz), 7.36 (2H, d, J = 8.5 Hz), 8.68 (1H, s).<br><br>HRESIMS (+): 420.09861 (420.09940 calculated for C18H20Cl2N5O2). |
| 18-11 | | (S)-1-(4-chlorophenyl)-3-(2-(4-chlorophenyl)-1-(5-((2-hydroxyethyl)(methyl)amino)-1,2,4-oxadiazol-3-yl)ethyl)urea | 1H-NMR (400 MHz, DMSO-$d_6$) δ 2.98-3.07 (2H, m), 3.10 (3H, s), 3.47 (2H, d, J = 5.5 Hz), 3.58 (2H, dd, J = 11.0, 5.5 Hz), 4.85 (1H, t, J = 4.9 Hz), 4.92 (1H, dd, J = 15.3, 7.3 Hz), 6.62 (1H, d, J = 9.2 Hz), 7.18-7.25 (4H, m),<br><br>7.30-7.36 (4H, m), 8.69 (1H, s).<br><br>ESIMS (+) 450 [M + H]$^+$. |
| 18-12 | | (S)-1-(4-chlorophenyl)-3-(2-(4-chlorophenyl)-1-(5-(piperidine-1-yl)-1,2,4-oxadiazol-3-yl)ethyl)urea | $^1$H-NMR (400 MHz, DMSO-$d_6$) δ 1.52-1.62 (6H, m), 2.96-3.10 (2H, m), 3.47-3.55 (4H, m), 4.89-4.97 (1H, m), 6.64 (1H, d, J = 9.2 Hz), 7.19 (2H, d, J = 9.2 Hz), 7.24 (2H, d, J = 9.2 Hz), 7.32 (2H, d, J = 9.2 Hz), 7.35 (2H, d, J = 9.2 Hz), 8.70 (1H, s).<br><br>HRESIMS (+): 460.013080 (460.13070 calculated for C22H24Cl2N5O2). |
| 18-13 | | (S)-1-(4-chlorophenyl)-3-(2-(4-chlorophenyl)-1-(5-(3-hydroxyazetidin-1-yl)-1,2,4-oxadiazol-3-yl)ethyl)urea | $^1$H-NMR (400 MHz, DMSO-$d_6$) δ 1.23 (1H, br s), 2.96-3.07 (2H, m), 3.90-3.97 (2H, m), 4.32-4.39 (2H, m), 4.88-4.98 (1H, m), 5.90 (1H, q, J = 7.3 Hz), 6.65 (1H, d, J = 8.5 Hz), 7.18 (2H, d, J = 8.5 Hz), 7.24 (2H, d, J = 8.5 Hz), 7.30-7.38<br><br>(4H, m), 8.65 (1H, s).<br><br>HRESIMS (+): 448.09507 (448.09432 calculated for C20H20Cl2N5O3). |

TABLE 93

| Ex. No | Str. | Chemical name | P.D. |
|---|---|---|---|
| 18-14 | | (S)-1-(4-chlorophenyl)-3-(2-(4-chlorophenyl)-1-(5-((1-hydroxy-2-methylpropan-2-yl)amino)-1,2,4-oxadiazol-3-yl)ethyl)urea | $^1$H-NMR (400 MHz, DMSO-$d_6$) δ 1.26 (6H, s), 3.01-3.07 (2H, m), 3.46 (2H, d, J = 6.1 Hz), 4.85 (1H, t, J = 6.1 Hz), 4.90-4.98 (1H, m), 6.54 (1H, d, J = 8.6 Hz), 7.16 (2H, d, J = 8.6 Hz), 7.24 (2H, d, J = 8.6 Hz), 7.31 (2H, d, J = 8.6 Hz), 7.36 (2H, d, J = 8.6 Hz), 8.00 (1H, s), 8.75 (1H, s). HRESIMS (+): 464.12525 (464.12562 calculated for C21H24Cl2N5O3). |
| 18-15 | | (−)-(S)-1-(2-(4-chlorophenyl)-1-(5-((2-hydroxyethyl)amino)-1,2,4-oxadiazol-3-yl)ethyl)-3-(4-fluorophenyl)urea | $^1$H-NMR (400 MHz, DMSO-$d_6$) δ 2.97-3.08 (2H, m), 3.27-3.31 (3H, m), 3.51 (2H, dd, J = 11.6, 6.1 Hz), 4.81 (1H, t, J = 5.6 Hz), 4.92 (1H, dd, J = 15.9, 7.3 Hz), 6.52 (1H, d, J = 9.2 Hz), 7.03 (2H, t, J = 9.2 Hz), 7.17 (2H, d, J = 8.6 Hz), 7.30-7.35 (4H, m), 8.41 (1H, t, J = 5.5 Hz), 8.58 (1H, s). ESIMS (+) 420 [M + H]$^+$ $[α]_D^{26}$ −18 (c 0.405, DMSO) |
| 18-16 | | (−)-(S)-1-(4-chlorophenyl)-3-(2-(4-chlorophenyl)-1-(5-((1,3-dihydroxypropan-2-yl)amino)-1,2,4-oxadiazol-3-yl)ethyl)urea | 1H-NMR (400 MHz, DMSO-$d_6$) δ 3.01-3.05 (2H, m), 3.39-3.54 (4H, m), 3.59-3.63 (1H, m), 4.74-4.78 (2H, m), 4.92 (1H, q, J = 7.7 Hz), 6.57 (1H, d, J = 9.1 Hz), 7.18 (2H, d, J = 8.5 Hz), 7.24 (2H, d, J = 9.1 Hz), 7.31 (2H, d, J = 8.5 Hz), 7.35 (2H, d, J = 8.5 Hz), 8.14 (1H, d, J = 7.9 Hz), 8.68 (1H, s). ESIMS (+) 466 [M + H]$^+$ $[α]_D^{31.8}$ −23.20 (c 0.350, DMSO) |

TABLE 94

| Ex. No | Str. | Chemical name | P.D. |
|---|---|---|---|
| 18-17 | | (−)-(S)-1-(4-chlorophenyl)-3-(1-(5-((1,3-dihydroxypropan-2-yl)amino)-1,2,4-oxadiazol-3-yl)-2-(4-methoxyphenyl)ethyl)urea | $^1$H-NMR (400 MHz, DMSO-d$_6$) δ 2.91-3.02 (2H, m), 3.44-3.64 (5H, m), 3.69 (3H, s), 4.76 (2H, q, J = 4.5 Hz), 4.87 (1H, q, J = 8.5 Hz), 6.52 (1H, d, J = 9.1 Hz), 6.81 (2H, d, J = 8.5 Hz), 7.06 (2H, d, J = 8.5 Hz), 7.24 (2H, d, J = 9.1 Hz), 7.36 (2H, d, J = 9.1 Hz), 8.12 (1H, d, J = 7.9 Hz), 8.70 (1H, s). ESIMS (+) 462 [M + H]$^+$ [α]$_D^{27.3}$ −12.94 (c 0.348, EtOH) |
| 18-18 | | (−)-(S)-1-(4-chlorophenyl)-3-(1-(5-(cyclopropylamino)-1,2,4-oxadiazol-3-yl)-2-(4-methoxyphenyl)ethyl)urea | $^1$H-NMR (400 MHz, DMSO-d$_6$) δ 0.51-0.55 (2H, m), 0.69-0.73 (2H, m), 2.66-2.70 (1H, m), 2.97 (2H, t, J = 7.3 Hz), 3.69 (3H, s), 4.89 (1H, q, J = 7.9 Hz), 6.56 (1H, d, J = 8.5 Hz), 6.82 (2H, d, J = 8.5 Hz), 7.06 (2H, d, J = 8.5 Hz), 7.24 (2H, dd J = 7.0, 2.1 Hz), 7.36 (2H, dd, J = 7.0, 2.1 Hz), 8.58 (1H, d, J = 2.4 Hz), 8.69 (1H, s). ESIMS (+) 428 [M + H]$^+$ [α]$_D^{28}$ −10.9 (c 0.347, EtOH) |

Example 19-1

(+)-(S,Z)-2-[3-(4-Chlorophenyl) ureido]-3-(4-ethylphenyl)-N'-(2-hydroxyethoxy)propanimidamide

[Chem. 177]

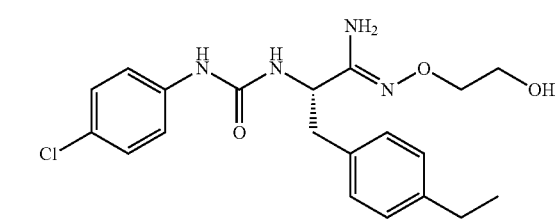 [SMILES: N/C(=N\OCCO)[C@H](Cc1ccc2c(c1)CCO2)NC(=O)Nc1ccc(Cl)cc1]

Using tert-butyl (S,Z)-{1-amino-3-(4-ethylphenyl)-1-[(2-hydroxyethoxy)imino]propan-2-yl}carbamate instead of tert-butyl (S)-{1-[2-(2-hydroxyethyl)-2H-tetrazol-5-yl]-2-(4-methoxyphenyl)ethyl}carbamate, the same method as in Example 1-1 was performed to obtain the title compound.

$^1$H NMR (400 MHz, DMSO-d$_6$) δ 1.14 (3H, t, J=7.6 Hz), 2.54 (2H, q, J=7.6 Hz), 2.81 (1H, dd, J=14.0, 8.0 Hz), 2.97 (1H, dd, J=14.0, 6.7 Hz), 3.49 (2H, q, J=5.4 Hz), 3.75 (2H, t, J=5.4 Hz), 4.37-4.42 (1H, m), 4.45 (1H, t, J=5.8 Hz), 5.81 (2H, brs), 6.25 (1H, brd, J=7.9 Hz), 7.07-7.11 (4H, m), 7.21-7.25 (2H, m), 7.34-7.37 (2H, m), 8.80 (1H, brs).

ESIMS (+) 405[M+H]$^+$

[α]$_D^{26}$ +9.48 (c 0.349, DMSO)

Examples 19-2 to 19-11

The following Examples 19-2 to 19-11 were obtained using each corresponding starting material and reactant in the same method as in Example 19-1.

The structures and spectral data thereof are shown in Tables 95-97.

TABLE 95

| Ex. No | Str. | Chemical name | P.D. |
|---|---|---|---|
| 19-2 | | (+)-(S,Z)-2-[3-(4-chlorophenyl)-ureido]-3-(2,3-dihydrobenzofuran-5-yl)-N'-(2-hydroxyethoxy)-propanimidamide | $^1$H-NMR (400 MHz, DMSO-$d_6$) δ 2.76 (1H, dd, J = 13.8, 7.3 Hz), 2.94 (1H, dd, J = 13.8, 5.8 Hz), 3.10 (2H, t, J = 8.6 Hz), 3.49 (2H, q, J = 5.5 Hz), 3.76 (2H, t, J = 5.5 Hz), 4.32-4.38 (1H, m), 4.42-4.49 (3H, m), 5.81 (2H, brs), 6.18 (1H, d, J = 8.6 Hz), 6.62 (1H, d, J = 7.9 Hz), 6.89 (1H, d, J = 7.9 Hz), 7.04 (1H, s), 7.23 (2H, d, J = 8.9 Hz), 7.36 (2H, d, J = 8.9 Hz), 8.78 (1H, s). ESIMS (+) 419 [M + H]$^+$ $[α]_D^{24}$ +8 (c 0.13, EtOH). |
| 19-3 | | (+)-(S,Z)-2-[3-(4-chlorophenyl)-ureido]-3-(4-cyanophenyl)-N'-(2-hydroxy-ethoxy)-propanimidamide | $^1$H NMR (400 MHz, DMSO-$d_6$) δ 2.95 (1H, dd, J = 13.6, 5.8 Hz), 3.10 (1H, dd, J = 13.6, 5.8 Hz), 3.47 (2H, q, J = 5.4 Hz), 3.75 (2H, t, J = 5.4 Hz), 3.45 (1H, t, J = 5.5 Hz), 4.45-4.51 (1H, m), 5.88 (2H, s), 6.36 (1H, d, J = 9.1 Hz), 7.23 (2H, d, J = 9.2 Hz), 7.36 (4H, dd, J = 13.5, 8.5 Hz), 7.73 (2H, d, J = 8.5 Hz), 8.83 (1H, s). ESIMS (+) 402 [M + H]$^+$ $[α]_D^{26}$ +16.4 (c 0.352, DMSO) |
| 19-4 | | (S,Z)-2-[3-(4-chlorophenyl)ureido]-3-[4-(difluoromethoxy)phenyl]-N'-(2-hydroxyethoxy)-propanimidamide | $^1$H NMR (400 MHz, DMSO-$d_6$) δ 2.84 (1H, dd, J = 13.9, 7.3 Hz), 2.99 (1H, dd, J = 13.9, 6.1 Hz), 3.47 (2H, q, J = 5.4 Hz), 3.74 (2H, t, J = 5.4 Hz), 4.40 (1H, dd, J = 7.9, 6.1 Hz), 4.44 (1H, t, J = 6.1 Hz), 5.83 (2H, s), 6.24 (1H, d, J = 8.5 Hz), 7.05 (2H, d, J = 8.5 Hz), 7.14 (1H, t, J = 73.9 Hz), 7.22 (4H, d, J = 9.1 Hz), 7.34 (2H, d, J = 8.5 Hz), 8.76 (1H, s). ESIMS (+) 443 [M + H]$^+$ |

TABLE 96

| Ex. No | Str. | Chemical name | P.D. |
|---|---|---|---|
| 19-5 | | (S,Z)-2-[3-(4-chlorophenyl)ureido]-N'-(2-hydroxyethoxy)-3-(4-methylthio-phenyl)-propanimidamide | $^1$H NMR (400 MHz, DMSO-$d_6$) δ 2.42 (3H, s), 2.81 (1H, dd, J = 14.1, 7.9 Hz), 2.97 (1H, dd, J = 14.1, 5.8 Hz), 3.50 (2H, q, J = 5.5 Hz), 3.76 (2H, t, J = 5.4 Hz), 4.37-4.44 (1H, m), 4.46 (1H, t, J = 5.5 Hz), 5.83 (2H, s), 6.21 (1H, d, J = 8.5 Hz), 7.10-7.17 (4H, m), 7.23 (2H, d, J = 8.6 Hz), 7.35 (2H, d, |

TABLE 96-continued

| Ex. No | Str. | Chemical name | P.D. |
|---|---|---|---|
| | | | J = 8.6 Hz), 8.76 (1H, s). ESIMS (+) 423 [M + H]⁺ |
| 19-6 | | (S,Z)-4-{3-amino-2-[3-(4-chlorophenyl)ureido]-3-[(2-hydroxyethoxy)imino]-propyl}-N,N-dimethylbenzamide | ¹H NMR (400 MHz, DMSO-d₆) δ 2.86 (3H, s), 2.89 (1H, dd, J = 13.4, 7.9 Hz), 2.94 (3H, s), 3.05 (1H, dd, J = 13.4, 6.1 Hz), 3.48 (2H, q, J = 5.5 Hz), 3.75 (2H, t, J = 5.5 Hz), 4.42-4.50 (2H, m), 5.86 (2H, s), 6.25 (1H, d, J = 8.6 Hz), 7.19-7.25 (4H, m), 7.28 (2H, d, J = 8.6 Hz), 7.35 (2H, d, J = 8.6 Hz), 8.79 (1H, s). ESIMS (+) 448 [M + H]⁺ |
| 19-7 | | (Z)-2-[3-(4-chlorophenyl)-ureido]-3-[4-(1,1-difluoro-ethyl)phenyl]-N'-(2-hydroxy-ethoxy)-propanimidamide | ¹H NMR (400 MHz, DMSO-d₆) δ 1.93 (3H, t, J = 18.3 Hz), 2.91 (1H, dd, J = 14.1, 7.9 Hz), 3.06 (1H, dd, J = 14.1, 6.1 Hz), 3.47 (2H, q, J = 5.5 Hz), 3.75 (2H, t, J = 5.2 Hz), 4.44-4.49 (2H, m), 5.87 (2H, s), 6.25 (1H, q, J = 8.6 Hz), 7.23 (2H, d, J = 9.2 Hz), 7.30 (2H, d, J = 7.9 Hz), 7.36 (2H, d, J = 9.2 Hz), 7.45 (2H, d, J = 7.9 Hz), 8.79 (1H, s) |
| 19-8 | | (S,Z)-2-(3-(4-chlorophenyl)ureido)-N'-(2-hydroxyethoxy)-3-(4-(2-hydroxy-ethyl)phenyl)-propanimidamide | ¹H NMR (400 MHz, DMSO-d₆) δ: 2.65 (2H, t, J = 7.3 Hz), 2.81 (1H, dd, J = 13.9, 7.9 Hz), 2.97 (1H, dd, J = 13.9, 6.1 Hz), 3.28 (1H, s), 3.48 (2H, q, J = 5.4 Hz), 3.52-3.59 (2H, m), 3.75 (2H, t, J = 5.4 Hz), 4.44 (1H, t, J = 5.4 Hz), 5.58 (1H, t, J = 5.4 Hz), 5.61 (2H, s), 6.21 (1H, d, J = 8.5 Hz), 7.09 (4H, s), 7.23 (2H, d, J = 9.1 Hz), 7.36 (2H, d, J = 9.1 Hz), 8.76 (1H, s). HRESIMS (−): 421.16350 (421.16426 calculated for C20H26ClN4O4). |

TABLE 97

| Ex. No | Str. | Chemical name | P.D. |
|---|---|---|---|
| 19-9 | | (S,Z)-3-(4-chlorophenyl)-2-[3-(4-chlorophenyl)ureido]-N'-[{1-hydroxy-2-methylpropan-2-yl}oxy]-propanimidamide | ¹H NMR (400 MHz, DMSO-d₆) δ 1.03 (3H, s), 1.04 (3H, s), 1.22 (1H, s), 2.86 (1H, dd, J = 13.9, 6.7 Hz), 3.01 (1H, dd, J = 13.9, 6.7 Hz), 3.30-3.31 (1H, m), 4.28-4.32 (1H, m), 4.39-4.46 (1H, m), 5.72 (2H, s), 6.19 (1H, d, J = 8.5 Hz), 7.19 (2H, d, J = 8.5 Hz), 7.24 (2H, d, J = 8.5 Hz), 7.29 (2H, d, J = 8.5 Hz), |

TABLE 97-continued

| Ex. No | Str. | Chemical name | P.D. |
|---|---|---|---|
| | | | 7.37 (2H, d, J = 8.5 Hz), 8.82 (1H, s). ESIMS (+) 439 [M + H]+ |
| 19-10 | | (S,Z)-3-(4-chlorophenyl)-2-[3-(4-chlorophenyl)ureido]-N'-(2-hydroxy-2-methylpropoxy)-propanimidamide | 1H NMR (400 MHz, DMSO-d6) δ 1.03 (3H, s), 1.04 (3H, s), 1.22 (1H, s), 2.84 (1H, dd, J = 13.9, 7.9 Hz), 3.00 (1H, dd, J = 13.9, 6.7 Hz), 3.53 (1H, d, J = 9.7 Hz), 3.56 (1H, d, J = 9.7 Hz), 4.42 (1H, td, J = 8.5, 5.4 Hz), 5.90 (2H, s), 6.25 (1H, d, J = 8.5 Hz), 7.21 (2H, d, J = 8.5 Hz), 7.23 (2H, d, J = 8.5 Hz), 7.30 (2H, d, J = 8.5 Hz), 7.35 (2H, d, J = 8.5 Hz), 8.75 (1H, s). ESIMS (+) 439 [M + H]+ |
| 19-11 | | (S,Z)-3-(4-chlorophenyl)-2-[3-(4-chlorophenyl)ureido]-N'-(methanesulfonyl)-propanimidamide | 1H NMR (400 MHz, DMSO-d6 80° C.) δ 2.83 (3H, s), 2.90 (1H, dd, J = 13.9, 7.9 Hz), 3.03 (1H, m), 4.61 (1H, m), 6.33 (1H, d, J = 8.5 Hz), 7.23 (2H, d, J = 8.5 Hz), 7.27 (2H, d, J = 8.5 Hz), 7.33 (2H, d, J = 8.5 Hz), 7.36 (2H, d, J = 8.5 Hz), 7.72 (1H, br s), 8.46 (1H, br s), 8.70 (1H, s). FDMS (+) 428 [M]+ |

Example 20

(S,Z)-2-[3-(4-Chlorophenyl)ureido]-N'-(2-hydroxyethoxy)-3-[4-(2-hydroxypropan-2-yl)phenyl]propanimidamide (Fraction 1)

(+)-(S,Z)-2-[3-(4-Chlorophenyl)ureido]-N'-(2-hydroxyethoxy)-3-[4-(propen-2-yl)phenyl]propanimidamide (Fraction 2)

[Chem. 178]

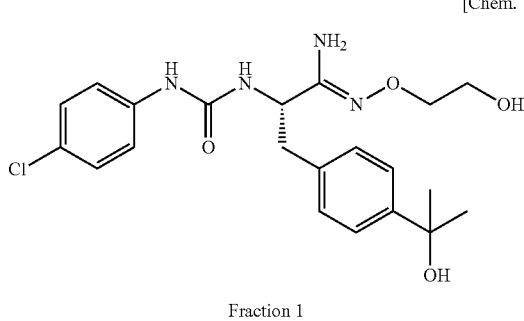

Fraction 1

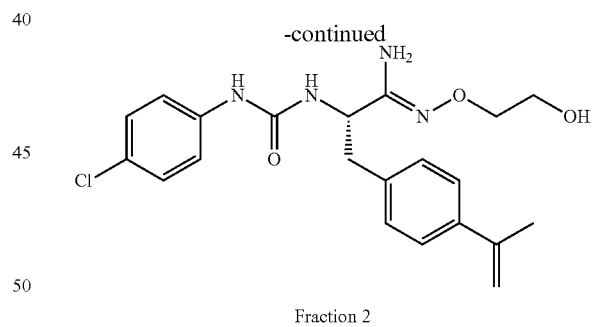

Fraction 2

To a solution of tert-butyl (S,Z)-{1-amino-1-[(2-hydroxyethoxy)imino]-3-[4-(2-hydroxypropan-2-yl)phenyl]propan-2-yl}carbamate (128 mg) in 1,4-dioxane (0.34 mL) was added 4N hydrogen chloride in dioxane (0.67 mL) to produce a reaction solution. The reaction solution was stirred at room temperature for 3 hours. The reaction solution was concentrated under reduced pressure, and a saturated aqueous sodium hydrogen carbonate was added to the obtained residue to adjust the pH of the aqueous layer to 9. And then, ethyl acetate (5 mL) was added thereto. To the resulting bilayer reaction solution was added 4-chlorophenyl isocyanate (46 mg), and the mixture was stirred at room temperature for 4 hours. Water was added to the reaction solution, and the mixture was extracted with ethyl acetate. The organic layer was washed with water and a brine, and dried over anhydrous sodium sulfate. The solvent was removed under reduced pressure, and the obtained residue was then purified by silica gel column chromatography (hexane ethyl acetate=3:1-ethyl acetate-ethyl acetate methanol=50:1) to obtain the title compounds (S,Z)-2-[3-(4-chlorophenyl)ureido]-N'-(2-hydroxyethoxy)-3-[4-(2-hydroxypropan-2-yl)phenyl]propanimidamide (23 mg) as Fraction 1 and (+)-(S,Z)-2-[3-(4-chlorophenyl)ureido]-N'-(2-hydroxyethoxy)-3-[4-(propen-2-yl)phenyl]propanimidamide (50 mg) as Fraction 2, each as a white solid.

Fraction 1:

$^1$H-NMR (400 MHz, DMSO-d$_6$) δ 1.37 (6H, s), 2.83 (1H, dd, J=14.1, 8.0 Hz), 2.98 (1H, dd, J=14.1, 6.1 Hz), 3.48 (2H, q, J=5.4 Hz), 3.76 (2H, t, J=5.4 Hz), 4.38-4.46 (2H, m), 4.89 (1H, s), 5.82 (2H, brs), 6.23 (1H, d, J=8.5 Hz), 7.12 (2H, d, J=8.5 Hz), 7.23 (2H, d, J=9.1 Hz), 7.32-7.37 (4H, m), 8.77 (1H, brs).

ESIMS (+) 435[M+H]$^+$

Fraction 2:

$^1$H-NMR (400 MHz, DMSO-d$_6$) δ 1.96 (3H, s), 2.84 (1H, dd, J=13.4, 8.0 Hz), 2.99 (1H, dd, J=12.9, 4.9 Hz), 3.46-3.50 (2H, m), 3.75 (2H, t, J=5.4 Hz), 4.41-4.45 (2H, m), 5.02 (1H, s), 5.35 (1H, s), 5.82 (2H, brs), 6.21 (1H, brd, J=8.5 Hz), 7.16 (2H, d, J=7.9 Hz), 7.21 (2H, d, J=8.6 Hz), 7.34 (2H, d, J=8.6 Hz), 7.3$^7$ (2H, d, J=7.9 Hz), 8.75 (1H, brs).

ESIMS (+) 417[M+H]$^+$ $[α]_D^{24}$ +14.48 (c 0.302, DMSO)

Example 21

(S,Z)-2-[3-(4-Chlorophenyl)ureido]-N'-(2-hydroxyethoxy)-3-[4-(methylsulfonyl)phenyl]propanimidamide

[Chem. 179]

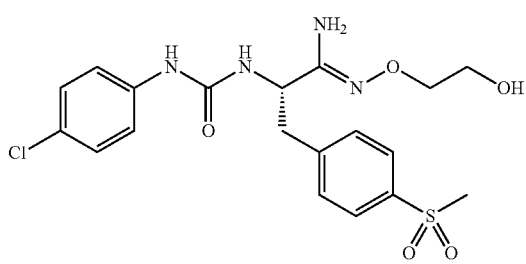

To a solution of (S,Z)-2-[3-(4-chlorophenyl)ureido]-N'-(2-hydroxyethoxy)-3-[4-(methylthio)phenyl]propanimidamide (121 mg) in dichloromethane (6 mL) was added meta-chloroperbenzoic acid (mCPBA)(114 mg) to produce a reaction solution. The reaction solution was stirred at room temperature for 1 hour. A saturated aqueous sodium hydrogen carbonate was added to the reaction solution, and the mixture was extracted with a dichloromethane-methanol mixture. The organic layer was washed with water and then a brine, and dried over anhydrous sodium sulfate. The solvent was removed under reduced pressure, and the residue was then purified by silica gel column chromatography (hexane:ethyl acetate=1:2) to obtain the title compound as a white solid (31 mg).

$^1$H NMR (400 MHz, DMSO-d$_6$) δ 1.22 (1H, s), 2.98 (1H, dd, J=13.1, 7.3 Hz), 3.16 (3H, s), 3.46 (2H, d, J=5.5 Hz), 3.75 (2H, q, J=5.5 Hz), 4.45 (1H, t, J=5.5 Hz), 4.50 (1H, q, J=7.3 Hz), 5.89 (2H, s), 6.31 (1H, d, J=8.6 Hz), 7.23 (2H, d, J=8.6 Hz), 7.36 (2H, d, J=8.6 Hz), 7.45 (2H, d, J=8.6 Hz), 7.82 (2H, d, J=8.6 Hz), 8.80 (1H, s).

ESIMS (+) 455[M+H]$_+$

Example 22-1

(+)-(S,Z)-2-[3-(4-Chlorophenyl)ureido]-N'-(2-hydroxyethoxy)-3-(4-methoxyphenyl)propanimidamide

[Chem. 180]

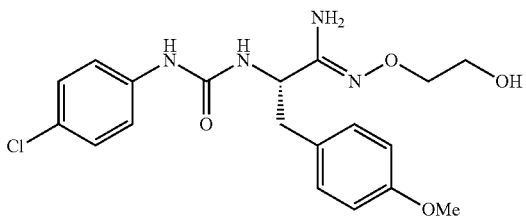 [SMILES: CSc1ccc(C[C@H](NC(=O)Nc2ccc(Cl)cc2)/C(N)=N/OCCO)cc1]

To a solution of ethyl (S,Z)-2-(({1-amino-2-[3-(4-chlorophenyl)ureido]-3-(4-methoxyphenyl)propylidene}amino)oxy)acetate (320 mg) in tetrahydrofuran (5 mL) under ice-cooling was added lithium borohydride (0.72 mL, 3 mol/L tetrahydrofuran solution) to produce a reaction solution. The reaction solution was stirred at the same temperature for 2 hours. To the reaction solution was added methanol (0.5 mL), and the mixture was stirred for 30 minutes. To the reaction solution was added an aqueous saturated ammonium chloride, and the mixture was extracted with ethyl acetate. The organic layer was washed with water and then a brine, and dried over anhydrous sodium sulfate. The solvent was removed under reduced pressure, and the obtained residue was then purified by silica gel column chromatography (hexane:ethyl acetate=4:1) to obtain the title compound as a white solid (235 mg).

$^1$H-NMR (400 MHz, DMSO-d$_6$) δ 2.78 (1H, dd, J=13.8, 7.1 Hz), 2.94 (1H, dd, J=13.8, 5.8 Hz), 3.49 (2H, q, J=5.3 Hz), 3.69 (3H, s), 3.76 (2H, t, J=5.2 Hz), 4.46 (1H, t, J=5.8 Hz), 4.50 (1H, q, J=7.3 Hz), 5.81 (2H, brs), 6.19 (1H, d, J=8.6 Hz), 6.81 (2H, d, J=8.6 Hz), 7.10 (2H, d, J=8.6 Hz), 7.23 (2H, d, J=8.9 Hz), 7.36 (2H, d, J=8.9 Hz), 8.76 (1H, s).

ESIMS (+) 407[M+H]$_+$ $[α]_D^{24}$ +13 (c 0.19, EtOH)

Examples 22-2 to 22-7

The following Examples 22-2 to 22-7 were obtained using each corresponding starting material and reactant in the same method as in Example 22-1.

The structures and spectral data thereof are shown in Tables 98 and 99.

TABLE 98

| Ex. No | Str. | Chemical name | P.D. |
|---|---|---|---|
| 22-2 | | (+)-(S,Z)-3-(4-chlorophenyl)-2-(3-(4-chlorophenyl)ureido)-N'-(2-hydroxyethoxy)propanimidamide | $^1$H-NMR (400 MHz, DMSO-$d_6$) δ 2.85 (1H, dd, J = 13.9, 7.1 Hz), 3.00 (1H, dd, J = 13.9, 5.4 Hz), 3.49 (2H, q, J = 5.4 Hz), 3.76 (2H, t, J = 5.4 Hz), 4.40-4.45 (1H, m), 4.45 (1H, t, J = 6.3 Hz), 5.85 (2H, s), 6.23 (1H, d, J = 8.5 Hz), 7.22 (4H, dd, J = 11.5, 8.5 Hz), 7.33 (4H, dd, J = 17.8, 8.9 Hz), 8.77 (1H, s). ESIMS (+) 411 [M + H]$^+$ $[α]_D^{25}$ −13.61 (c 0.352, DMSO) |
| 22-3 | | (S,Z)-3-(4-chlorophenyl)-2-[3-(4-chlorophenyl)ureido]-N'-(((R)-1-hydroxypropan-2-yl)oxy]propanimidamide | $^1$H-NMR (400 MHz, DMSO-$d_6$) δ 1.02 (3H, d, J = 6.7 Hz), 2.85 (1H, dd, J = 14.1, 7.3 Hz), 3.01 (1H, dd, J = 14.1, 5.8 Hz), 3.23-3.30 (1H, m), 3.36-3.44 (1H, m), 3.78-3.87 (1H, m), 4.39-4.47 (2H, m), 5.77 (2H, s), 6.22 (1H, d, J = 8.6 Hz), 7.20 (2H, d, J = 8.6 Hz), 7.23 (2H, d, J = 8.6 Hz), 7.30 (2H, d, J = 8.6 Hz), 7.36 (2H, d, J = 8.6 Hz), 8.80 (1H, s). ESIMS (+) 425 [M + H]$^+$ |
| 22-4 | | (S,Z)-3-(4-chlorophenyl)-2-[3-(4-chlorophenyl)ureido]-N'-[((S)-1-hydroxypropan-2-yl)oxy]propanimidamide | $^1$H-NMR (400 MHz, DMSO-$d_6$) δ 1.02 (3H, d, J = 6.7 Hz), 2.86 (1H, dd, J = 13.4, 7.3 Hz), 3.00 (1H, dd, J = 13.4, 6.1 Hz), 3.23-3.30 (1H, m), 3.36-3.43 (1H, m), 3.77-3.86 (1H, m), 4.41 (2H, t, J = 6.1 Hz), 5.77 (2H, s), 6.23 (1H, d, J = 8.6 Hz), 7.20 (2H, d, J = 8.6 Hz), 7.23 (2H, d, J = 8.6 Hz), 7.30 (2H, d, J = 8.6 Hz), 7.36 (2H, d, J = 8.6 Hz), 8.79 (1H, s). ESIMS (+) 425 [M + H]$^+$ |

TABLE 99

| Ex. No | Str. | Chemical name | P.D. |
|---|---|---|---|
| 22-5 | 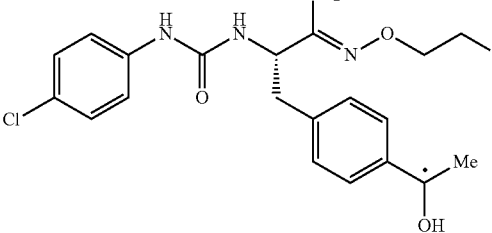<br>From 1st peak | (2S,Z)-2-[3-(4-chlorophenyl)ureido]-N'-(2-hydroxyethoxy)-3-[4-(1-hydroxyethyl)phenyl]-propanimidamide | $^1$H NMR (400 MHz, DMSO-$d_6$) δ 1.28 (3H, d, J = 6.1 Hz), 2.84 (1H, dd, J = 14.6, 7.9 Hz), 3.00 (1H, dd, J = 14.1, 6.1 Hz), 3.77 (2H, t, J = 5.2 Hz), 4.37-4.52 (2H, m), 4.60-4.71 (1H, m), 5.05 (2H, d, J = 4.3 Hz), 5.83 (2H, s), 6.23 (1H, d, J = 8.6 Hz), 7.15 (2H, d, J = 7.9 Hz), 7.20-7.28 (4H, m), 7.37 (2H, d, J = 8.6 Hz), 8.77 (1H, s). |
| 22-6 | 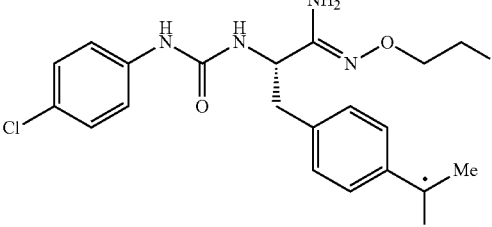<br>From 2nd peak | (2S,Z)-2-[3-(4-chlorophenyl)ureido]-N'-(2-hydroxyethoxy)-3-[4-(1-hydroxyethyl)phenyl]-propanimidamide | $^1$H NMR (400 MHz, DMSO-$d_6$) δ 1.27 (3H, d, J = 6.1 Hz), 2.82 (1H, dd, J = 13.4, 7.9 Hz), 2.99 (1H, dd, J = 13.4, 5.5 Hz), 3.76 (2H, t, J = 5.5 Hz), 4.36-4.50 (2H, m), 4.60-4.69 (1H, m), 5.04 (2H, d, J = 4.3 Hz), 5.79 (2H, s), 6.23 (1H, d, J = 8.6 Hz), 7.14 (2H, d, J = 7.9 Hz), 7.18-7.25 (4H, m), 7.36 (2H, d, J = 8.6 Hz), 8.76 (1H, s). |
| 22-7 | 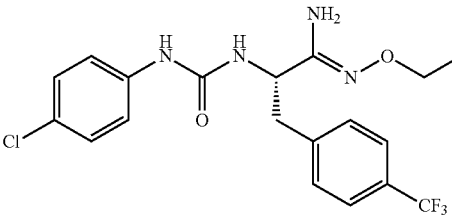 | (2S,Z)-2-[3-(4-chlorophenyl)ureido]-N'-(2-hydroxyethoxy)-3-[4-(trifluoromethyl)phenyl]-propanimidamide | $^1$H NMR (400 MHz, DMSO-$d_6$) δ 2.96 (1H, dd, J = 13.3, 3.5 Hz), 3.11 (1H, dd, J = 13.3, 5.4 Hz), 3.47 (2H, q, J = 5.4 Hz), 3.75 (2H, t, J = 5.4 Hz), 4.44 (1H, t, J = 5.4 Hz), 4.46-4.53 (1H, m), 5.88 (2H, s), 6.27 (1H, d, J = 8.5 Hz), 7.23 (2H, d, J = 9.1 Hz), 7.35 (2H, d, J = 9.1 Hz), 7.41 (2H, d, J = 7.9 Hz), 7.62 (2H, d, J = 7.9 Hz), 8.78 (1H, s). HRESIMS (+): 445.12539 (445.12543 calculated for C19H21ClF3N4O3). |

Example 23

(−)-(S,Z)-3-(4-Acetylphenyl)-2-[3-(4-chlorophenyl)ureido]-N'-(2-hydroxyethoxy)propanimidamide

[Chem. 181]

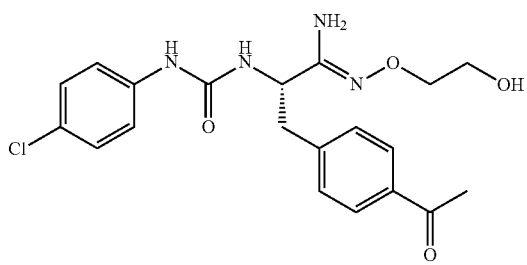 [SMILES: CN(C)C(=O)c1ccc(C[C@H](NC(=O)Nc2ccc(Cl)cc2)/C(N)=N/OCCO)cc1]

To a solution of (S,Z)-4-{3-amino-2-[3-(4-chlorophenyl)ureido]-3-[(2-hydroxyethoxy)imino]propyl}phenyl trifluoromethanesulfonate (347 mg) in toluene (6.6 mL) were added butyl vinyl ether (0.42 mL), triethylamine (0.46 mL), palladium acetate (59.4 mg), and (diphenylphosphino)ferrocene (218 mg) to produce a reaction solution. The reaction solution was stirred under an argon atmosphere at 80° C. for 20 hours. To the reaction solution under ice-cooling was added 1N hydrochloric acid (3 mL), and the mixture was stirred for 1 hour. The reaction solution was adjusted pH 9 by addition of a saturated aqueous sodium hydrogen carbonate, and the mixture was extracted with ethyl acetate. The organic layer was washed with water and then a brine, and dried over anhydrous sodium sulfate. The solvent was removed under reduced pressure, and the obtained residue was then purified by silica gel column chromatography (dichloromethane:acetonitrile=1:1) to obtain the title compound as a white solid (64 mg).

$^1$H-NMR (400 MHz, DMSO-$d_6$) δ 2.49 (3H, s), 2.90 (1H, dd, J=13.5, 8.0 Hz), 3.06 (1H, dd, J=13.5, 6.1 Hz), 3.45 (2H, q, J=5.4 Hz), 3.72 (2H, t, J=5.4 Hz), 4.39-4.48 (2H, m), 5.83 (2H, brs), 6.24 (1H, d, J=9.1 Hz), 7.19 (2H, d, J=9.1 Hz), 7.29-7.32 (4H, m), 7.81 (2H, d, J=7.9 Hz), 8.73 (1H, brs).

ESIMS (+) 419[M+H]$^+$ $[α]_D^{25.8}$ −5.4 (c 0.101, DMSO)

Example 24

(S,Z)-2-(({1-Amino-3-(4-chlorophenyl)-2-[3-(4-chlorophenyl)ureido]propylidene}amino)oxy)acetic Acid

[Chem. 182]

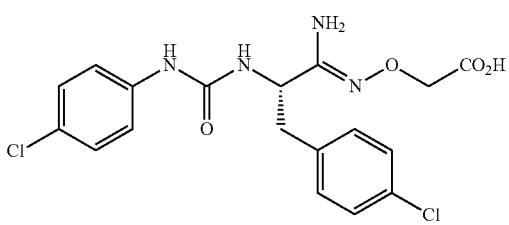

To a solution of ethyl (S,Z)-2-({[1,2-diamino-3-(4-chlorophenyl)propylidene]amino}oxy)acetate (381 mg) in methanol (4 mL) under ice-cooling was added lithium hydroxide monohydrate (35 mg), and the reaction mixture was stirred at the same temperature for 1 hour. To the reaction solution was added 1 mol/L hydrochloric acid to neutralize the solution, and the solvent was removed under reduced pressure. To the obtained residue were added ethyl acetate (3.5 mL), a saturated aqueous sodium hydrogen carbonate (1 mL), and 4-chlorophenyl isocyanate (53.6 mg), and the mixture was stirred at ambient temperature for 1 hour. The reaction solution was extracted with ethyl acetate, and the organic layer was washed with water and a brine, dried over anhydrous sodium sulfate, and filtrated. The solvent of the filtrate was removed under reduced pressure, and the obtained residue was then purified by silica gel column chromatography (ethyl acetate:methanol=4:1) to obtain the title compound as a white solid (40 mg).

$^1$H-NMR (400 MHz, DMSO-$d_6$) δ 1.20 (1H, s), 2.85 (1H, dd, J=13.9, 7.9 Hz), 2.97 (1H, dd, J=13.9, 6.7 Hz), 3.91-4.04 (2H, m), 4.43 (1H, td, J=7.9, 6.1 Hz), 6.11 (2H, br s), 7.18 (2H, d, J=8.5 Hz), 7.22 (2H, d, J=8.5 Hz), 7.27 (2H, d, J=8.5 Hz), 7.39 (2H, d, J=8.5 Hz), 9.67 (1H, s).

ESIMS (+) 425[M+H]$^+$

Example 25

(S)-1-(4-Chlorophenyl)-3-(2-(4-chlorophenyl)-1-(5-oxo-5,6-dihydro-4H-1,2,4-oxadiazin-3-yl)ethyl)urea

[Chem. 183]

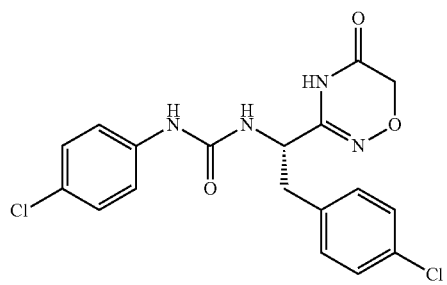

To a solution of (S,Z)-2-(({1-amino-3-(4-chlorophenyl)-2-[3-(4-chlorophenyl)ureido]propylidene}amino)oxy)acetic acid (30 mg) in dichloromethane (3.5 mL) were added 1-ethyl-3-(3-dimethylaminopropyl)carbodiimide hydrochloride (15 mg) and 1-hydroxybenzotriazole (12 mg), and the reaction mixture was stirred at ambient temperature for 16 hours. Water was added to the reaction solution, and the mixture was extracted with ethyl acetate. The organic layer was washed with water and a brine, dried over anhydrous sodium sulfate, and filtrated. The solvent was removed under reduced pressure, and the obtained residue was then purified by silica gel column chromatography (ethyl acetate) to obtain the title compound as a white solid (18 mg).

$^1$H-NMR (400 MHz, DMSO-$d_6$) δ 2.89 (1H, dd, J=13.9, 7.9 Hz), 3.05 (1H, dd, J=13.9, 5.5 Hz), 4.11 (1H, d, J=14.7 Hz), 4.22 (1H, d, J=14.7 Hz), 4.63 (1H, td, J=7.9, 5.5 Hz), 6.43 (1H, d, J=8.5 Hz), 7.21 (2H, d, J=8.5 Hz), 7.23 (2H, d, J=8.5 Hz), 7.34 (4H, d, J=8.5 Hz), 8.82 (1H, s), 11.13 (1H, s).

HRESIMS (+): 405.05142 (405.05212 calculated for $C_{18}H_{15}Cl_2N_4O_3$).

Example 26-1

(S)-1-(4-Fluorophenyl)-3-{1-[5-(2-hydroxyethyl)-1,2,4-oxadiazol-3-yl]-2-(4-methoxyphenyl)ethyl}urea
(A)

(S)—N-{2-[3-(4-Fluorophenyl)ureido]-1-imino-3-(4-methoxyphenyl)propyl}-3-hydroxypropanamide
(B)

[Chem. 184]

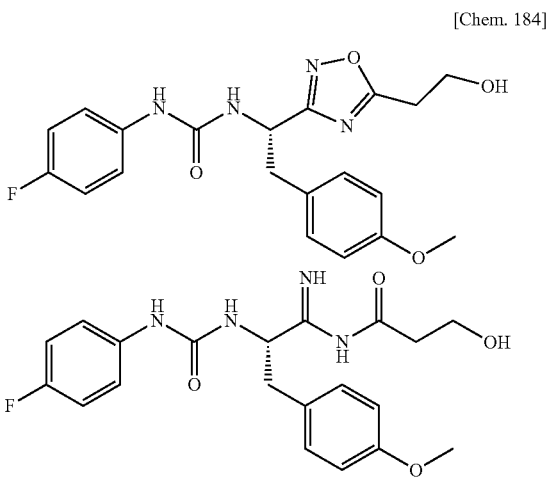

To a solution of ethyl (S)-2-(3-{1-[3-(4-fluorophenyl)ureido]-2-(4-methoxyphenyl)ethyl}-1,2,4-oxadiazol-5-yl)acetate (100 mg) in a mixed solvent of methanol/tetrahydrofuran 1:1 (1 mL) was added sodium borohydride (130 mg) in several times to produce a reaction solution. The reaction solution was heated to reflux for 3 hours. A saturated aqueous sodium hydrogen carbonate was added to the reaction solution, and the mixture was extracted with ethyl acetate. The organic layer was washed with water and then a brine, and dried over anhydrous sodium sulfate. The solvent was removed under reduced pressure, and the obtained residue was then purified by silica gel column chromatography (hexane:ethyl acetate=20:1-1:20) to obtain the title compounds (S)-1-(4-fluorophenyl)-3-{1-[5-(2-hydroxyethyl)-1,2,4-oxadiazol-3-yl]-2-(4-methoxyphenyl)ethyl}urea (A) (12.7 mg) and (S)—N-{2-[3-(4-fluorophenyl)ureido]-1-imino-3-(4-methoxyphenyl)propyl}-3-hydroxypropanamide (B) (9.9 mg) as each white solid.

(S)-1-(4-fluorophenyl)-3-{1-[5-(2-hydroxyethyl)-1,2,4-oxadiazol-3-yl]-2-(4-methoxyphenyl)ethyl}urea
(A)

$^1$H-NMR (400 MHz, DMSO-$d_6$) δ 2.96-3.09 (4H, m), 3.69 (3H, s), 3.80 (2H, q, J=6.1 Hz), 4.96 (1H, t, J=5.1 Hz), 5.06-5.14 (1H, m), 6.64 (1H, d, J=9.1 Hz), 6.81 (2H, d, J=8.5 Hz), 7.01-7.06 (4H, m), 7.30-7.36 (2H, m), 8.60 (1H, s).
ESIMS (+) 401[M+H]$^+$ (S)—N-{2-[3-(4-fluorophenyl)ureido]-1-imino-3-(4-methoxyphenyl)propyl}-3-hydroxypropanamide (B)

$^1$H-NMR (400 MHz, DMSO-$d_6$) δ 1.61-1.77 (2H, m), 2.79-2.89 (1H, m), 2.91-3.01 (1H, m), 3.49 (2H, q, J=6.1 Hz), 3.70 (3H, s), 4.48-4.54 (1H, m), 4.60-4.69 (1H, m), 5.49 (1H, t, J=5.1 Hz), 6.30 (1H, d, J=7.9 Hz), 6.84 (2H, d, J=7.9 Hz), 6.95-7.06 (3H, m), 7.13 (2H, d, J=8.5 Hz), 7.30-7.36 (2H, m), 8.62 (1H, s).
ESIMS (+) 403[M+H]$^+$.

Examples 26-2 to 26-19

The following Examples 26-2 to 26-19 were obtained using each corresponding starting material and reactant in the same method as in Example 26-1.

The structures and spectral data thereof are shown in Tables 100-107.

TABLE 100

| Ex. No | Str. | Chemical name | P.D. |
|---|---|---|---|
| 26-2 | | (S)-N-{2-[3-(4-chlorophenyl)ureido]-1-imino-3-(4-methoxyphenyl)propyl}-3-hydroxypropanamide | $^1$H-NMR (400 MHz, DMSO-$d_6$) δ 1.62-1.78 (2H, m), 2.84 (1H, m), 2.97 (1H, m), 3.49 (2H, m), 3.70 (3H, s), 4.51 (1H, m), 4.65 (1H, m), 5.49 (1H, m), 6.36 (1H, m), 6.84 (2H, m), 6.97-7.03 (1H, m), 7.13 (2H, d, J = 8.5 Hz), 7.24 (2H, m), 7.37 (2H, d, J = 8.5 Hz), 8.81 (1H, br s). ESIMS (+) 419 [M + H]$^+$. |
| 26-3 (A) | | (S)-1-(4-cyanophenyl)-3-{1-[5-(2-hydroxyethyl)-1,2,4-oxadiazol-3-yl]-2-(4-methoxyphenyl)ethyl}urea | $^1$H-NMR (400 MHz, DMSO-$d_6$) δ 2.98-3.09 (4H, m), 3.69 (3H, s), 3.80 (2H, q, J = 5.9 Hz), 4.96 (1H, t, J = 5.4 Hz), 5.07-5.16 (1H, m), 6.81 (2H, d, J = 8.5 H), 6.90 (1H, d, J = 8.5 Hz), 7.06 (2H, d, J = 8.5 Hz), 7.51 |

TABLE 100-continued

| Ex. No | Str. | Chemical name | P.D. |
|---|---|---|---|
| | | | (2H, d, J = 8.5 Hz), 7.65 (2H, d, J = 8.5 Hz), 9.10 (1H, s). ESIMS (+) 408 [M + H]+. |
| 26-3 (B) | | (S)-N-{2-[3-(4-cyanophenyl)-ureido]-1-imino-3-(4-methoxy-phenyl)propyl}-3-hydroxypropanamide | 1H-NMR (400 MHz, DMSO-d6) δ 1.62-1.77 (2H, m), 2.80-2.91 (1H, m), 2.93-3.07 (1H, m), 3.50 (2H, q, J = 5.9 Hz), 3.70 (3H, s), 4.50-4.55 (1H, m), 4.66 (1H, q, J = 7.3 Hz), 5.47-5.52 (1H, m), 6.51-6.57 (1H, m), 6.84 (2H, dd, J = 8.5, 1.2 Hz), 7.01 (1/2H, d, J = 1.2 Hz), 7.05 (1/2H, d, J = 1.2 Hz), 7.13 (2H, d, J = 8.5 Hz), 7.51 (2H, d, J = 9.1 Hz), 7.65 (2H, d, J = 9.1 Hz), 9.12 (1H, s). ESIMS (+) 410 [M + H]+. |

TABLE 101

| Ex. No | Str. | Chemical name | P.D. |
|---|---|---|---|
| 26-4 (A) | | (S)-1-(2-(4-chlorophenyl)-1-(5-(2-hydroxy-ethyl)-1,2,4-oxadiazol-3-yl)ethyl)-3-(4-cyanophenyl)urea | 1H-NMR (400 MHz, DMSO-d6) δ 3.06 (2H, t, J = 6.4 Hz), 3.09-3.18 (2H, m), 3.80 (2H, q, J = 5.4 Hz), 4.96 (1H, t, J = 5.4 Hz), 5.14-5.22 (1H, m), 6.98 (1H, d, J = 9.1 Hz), 7.19 (2H, d, J = 8.5 Hz), 7.31 (2H, d, J = 8.5 Hz), 7.51 (2H, d, J = 8.5 Hz), 7.65 (2H, d, J = 8.5 Hz), 9.10 (1H, s). ESIMS (+) 412 [M + H]+. |
| 26-4 (B) | | (S)-N-(3-(4-chlorophenyl)-2-(3-(4-cyano-phenyl)ureido)-1-iminopropyl)-3-hydroxypropan-amide | 1H-NMR (400 MHz, DMSO-d6) δ 1.65-1.76 (2H, m), 2.89-2.96 (1H, m), 3.03-3.08 (1H, m), 3.50 (2H, q, J = 5.9 Hz), 4.50-4.55 (1H, m), 4.68-4.75 (1H, m), 5.47-5.53 (1H, m), 6.60 (1H, dd, J = 8.5, 6.1 Hz), 7.02-7.08 (1H, m), 7.24 (2H, d, J = 8.5 Hz), 7.34 (2H, dd, J = 8.5, 1.2 Hz), 7.51 (2H, d, J = 9.1 Hz), 7.65 (2H, d, J = 9.1 Hz), 9.10 (1H, s). ESIMS (+) 414 [M + H]+. |
| 26-5 (A) | | (S)-1-(4-chloro-phenyl)-3-{2-(4-chlorophenyl)-1-[5-(2-hydroxy-ethyl)-1,2,4-oxadiazol-3-yl]ethyl}urea | 1H-NMR (400 MHz, DMSO-d6) δ 3.06 (2H, t, J = 6.1 Hz), 3.10 (2H, t, J = 6.4 Hz), 3.77-3.83 (2H, m), 4.97 (1H, t, J = 4.8 Hz), 5.13-5.20 (1H, m), 6.77 (1H, d, J = 9.1 Hz), 7.18 (2H, d, J = 8.5 Hz), 7.24 (2H, d, J = 8.5 Hz), 7.31 (2H, d, J = 8.5 Hz), 7.35 (2H, d, J = 8.5 Hz), 8.70 |

TABLE 101-continued

| Ex. No | Str. | Chemical name | P.D. |
|---|---|---|---|
| | | | (1H, s). ESIMS (+) 421 [M + H]⁺. |
| 26-5 (B) | | (S)-N-{3-(4-chlorophenyl)-2-[3-(4-chlorophenyl)ureido]-1-iminopropyl}-3-hydroxypropanamide | ¹H-NMR (400 MHz, DMSO-d₆) δ 1.62-1.77 (2H, m), 2.87-2.96 (1H, m), 2.99-3.08 (1H, m), 3.49 (2H, q, J = 6.1 Hz), 4.50-4.55 (1H, m), 4.66-4.74 (1H, m), 5.46-5.52 (1H, m), 6.42 (1H, q, J = 4.4 Hz), 7.00-7.06 (1H, m), 7.22-7.26 (4H, m), 7.33-7.37 (4H, m), 8.71 (1H, s). ESIMS (+) 423 [M + H]⁺. |

TABLE 102

| Ex. No | Str. | Chemical name | P.D. |
|---|---|---|---|
| 26-6 (A) | | (S)-1-{2-(4-chlorophenyl)-1-{5-(2-hydroxyethyl)-1,2,4-oxadiazol-3-yl]ethyl}-3-(4-fluorophenyl)urea | ¹H-NMR (400 MHz, DMSO-₆) δ 3.05-3.13 (4H, m), 3.78-3.84 (2H, m), 4.98 (1H, t, J = 5.1 Hz), 5.13-5.21 (1H, m), 6.71 (1H, d, J = 8.5 Hz), 7.01-7.07 (2H, m), 7.19 (2H, d, J = 8.5 Hz), 7.30-7.36 (4H, m), 8.60 (1H, s). ESIMS (+) 405 [M + H]⁺. |
| 26-6 (B) | | (S)-N-{3-(4-chlorophenyl)-2-[3-(4-fluorophenyl)ureido]-1-iminopropyl}-3-hydroxypropanamide | ¹H-NMR (400 MHz, DMSO-d₆) δ 1.62-1.77 (2H, m), 2.87-2.95 (1H, m), 2.99-3.07 (1H, m), 3.49 (2H, q, J = 6.1 Hz), 4.53 (1H, q, J = 4.6 Hz), 4.66-4.73 (1H, m), 5.46-5.52 (1H, m), 6.36 (1H, dd, J = 8.8, 3.3 Hz), 6.99-7.06 (3H, m), 7.24 (2H, d, J = 7.9 Hz), 7.30-7.36 (4H, m), 8.60 (1H, s). ESIMS (+) 407 [M + H]⁺. |
| 26-7 (A) | | (S)-1-(4-chlorophenyl)-3-{2-(4-chlorophenyl)-1-[5-(1-hydroxy-2-methylpropan-2-yl)-1,2,4-oxadiazol-3-yl]ethyl}urea | ¹H-NMR (400 MHz, DMSO-₆) δ 1.309 (3H, s), 1.314 (3H, s), 3.09 (2H, d, J = 7.3 Hz), 3.56 (2H, d, J = 5.5 Hz), 5.08-5.20 (2H, m), 6.87 (1H, m), 7.15 (2H, d, J = 8.5 Hz), 7.24 (2H, d, J = 8.5 Hz), 7.29 (2H, d, J = 8.5 Hz), 7.36 (2H, d, J = 8.5 Hz), 8.84 (1H, m). ESIMS (+) 449 [M + H]⁺. |

TABLE 102-continued

| Ex. No | Str. | Chemical name | P.D. |
|---|---|---|---|
| 26-7 (B) | | (S,Z)-N-(1-amino-3-(4-chlorophenyl)-2-[3-{4-chlorophenyl)-ureido]-propylidene}-3-hydroxy-2,2-dimethylpropanamide | $^1$H-NMR (400 MHz, DMSO-d$_6$) δ 0.74-0.78 (6H, m), 2.84-3.10 (2H, m), 3.20 (2H, m), 4.56 (1H, m), 4.70 (1H, m), 5.25 (1H, m), 6.47 (1H, m), 6.97 (1H, m), 7.21-7.27 (4H, m), 7.30-7.38 (4H, m), 8.79 (1H, m). ESIMS (+) 451 [M + H]$^+$. |

15

TABLE 103

| Ex. No | Str. | Chemical name | P.D. |
|---|---|---|---|
| 26-8 (A) | | (S)-1-{2-(4-chlorophenyl)-1-[5-(1-hydroxy-2-methylpropan-2-yl)-1,2,4-oxadiazol-3-yl]ethyl}-3-(4-fluorophenyl)urea | $^1$H-NMR (400 MHz, DMSO-d$_6$) δ 1.309 (3H, s), 1.315 (3H, s), 3.09 (2H, d, J = 7.9 Hz), 3.56 (2H, d, J = 5.5 Hz), 5.11 (1H, t, J = 5.5 Hz), 5.17 (1H, m), 6.71 (1H, d, J = 9.1 Hz), 7.04 (2H, m), 7.15 (2H, d, J = 8.5 Hz), 7.30 (2H, d, J = 8.5 Hz), 7.33 (2H, m), 8.60 (1H, s). ESIMS (+) 433 [M + H]$^+$. |
| 26-8 (B) | | (S,Z)-N-{1-amino-3-(4-chlorophenyl)-2-[3-(4-fluorophenyl)-ureido]-propylidene}-3-hydroxy-2,2-dimethyl-propanamide | $^1$H-NMR (400 MHz, DMSO-d$_6$) δ 0.74-0.78 (6H, m), 2.84-3.10 (2H, m), 3.20 (2H, m), 4.56 (1H, m), 4.70 (1H, m), 5.25 (1H, m), 6.36-6.50 (1H, m), 6.96 (1H, m), 7.04 (2H, m), 7.20-7.27 (2H, m), 7.30-7.36 (4H, m), 8.65 (1H, m). ESIMS (+) 435 [M + H]$^+$. |
| 26-9 (A) | | (S)-1-(4-chlorophenyl)-3-{2-(4-chlorophenyl)-1-{5-[1-(hydroxymethyl)cyclopropyl]-1,2,4-oxadiazol-3-yl}ethyl)urea | $^1$H-NMR (400 MHz, DMSO-d$_6$) δ 1.21 (2H, m), 1.23 (2H, m), 3.02-3.14 (2H, m), 3.75 (2H, m), 5.01 (1H, m), 5.12 (1H, m), 6.86 (1H, m), 7.18 (2H, d, J = 8.5 Hz), 7.24 (2H, d, J = 8.5 Hz), 7.31 (2H, d, J = 8.5 Hz), 7.35 (2H, d, J = 8.5 Hz), 8.78 (1H, m). ESIMS (−) 445 [M − H]$^-$. |
| 26-9 (B) | | (S,Z)-N-{1-amino-3-(4-chlorophenyl)-2-[3-(4-chlorophenyl)-ureido]-propylidene}-1-(hydroxymethyl)-cyclopropane-carboxamide | $^1$H-NMR (400 MHz, DMSO-d$_6$, 80° C.) δ 0.38-0.44 (2H, m), 0.45-0.52 (2H, m), 2.88-2.99 (2H, m), 3.40-3.54 (2H, m), 4.19 (1H, m), 4.72 (1H, m), 5.41-5.46 (1H, m), 6.28-6.36 (1H, m), 6.79 (1H, m), 7.23 (2H, d, J = 9.1 Hz), 7.26 (2H, m), 7.32 (2H, d, J = 9.1 Hz), 7.36 (2H, d, J = 9.1 Hz), 8.57 (1H, m). ESIMS (+) 449 [M + H]$^+$. |

TABLE 104

| Ex. No | Str. | Chemical name | P.D. |
|---|---|---|---|
| 26-10 (A) | 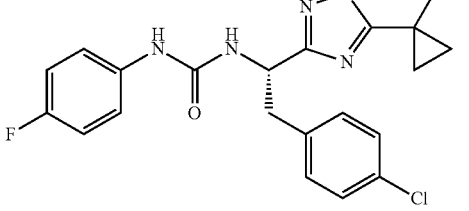 | (S)-1-(2-(4-chlorophenyl)-1-{5-[1-(hydroxymethyl)cyclopropyl]-1,2,4-oxadiazol-3-yl}ethyl)-3-(4-fluorophenyl)urea | $^1$H-NMR (400 MHz, DMSO-$d_6$) δ 1.21 (2H, m), 1.23 (2H, m), 3.01-3.13 (2H, m), 3.75 (2H, m), 5.01 (1H, m), 5.12 (1H, m), 6.74 (1H, m), 7.03 (2H, m), 7.18 (2H, d, J = 7.9 Hz), 7.28-7.36 (4H, m), 8.60 (1H, m). ESIMS (+) 431 [M + H]$^+$. |
| 26-10 (B) | 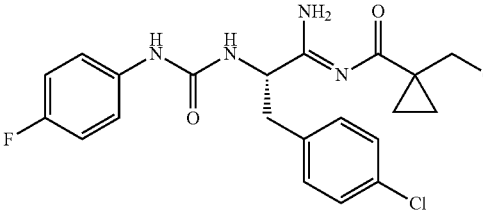 | (S,Z)-N-{1-amino-3-(4-chlorophenyl)-2-[3-(4-fluorophenyl)-ureido]-propylidene}-1-(hydroxymethyl)-cylcopropane-carboxamide | $^1$H-NMR (400 MHz, DMSO-$d_6$) δ 0.41 (4H, m), 2.84-3.10 (2H, m), 3.36-3.44 (1H, m), 3.45-3.52 (1H, m), 4.50 (1H, m), 4.67 (1H, m), 5.41-5.46 (1H, m), 6.56-6.68 (1H, m), 7.00-7.07 (3H, m), 7.17-7.27 (2H, m), 7.30-7.36 (4H, m), 8.80 (1H, m). ESIMS (+) 433 [M + H]$^+$. |
| 26-11 | 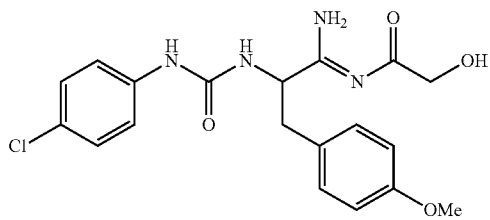 [SMILES: COc1ccc(CC(NC(=O)Nc2ccc(Cl)cc2)/C(N)=N/C(=O)CO)cc1] | N-{2-[3-(4-chlorophenyl)-ureido]-1-imino-3-(4-methoxyphenyl)propyl}-2-hydroxyacetamide | $^1$H-NMR (400 MHz, DMSO-$d_6$) δ 2.84 (1H, m), 2.97 (1H, m), 3.35 (2H, m), 3.70 (3H, s), 4.66 (1H, m), 4.97 (1H, m), 5.37 (1H, m), 6.35 (1H, m), 6.84 (2H, d, J = 8.5 Hz), 7.10-7.16 (3H, m), 7.24 (2H, d, J = 9.1 Hz), 7.36 (2H, d, J = 9.1 Hz), 8.75 (1H, br s). ESIMS (+) 405 [M + H]$^+$. |
| 26-12 | 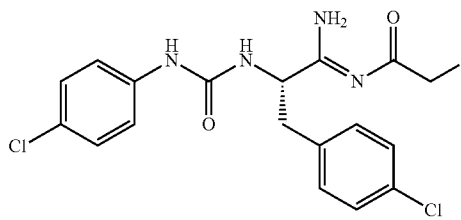 | (S)-N-{3-(4-chlorophenyl)-2-[3-(4-chlorophenyl)ureido]-1-iminopropyl}-2-hydroxyacetamide | $^1$H-NMR (400 MHz, DMSO-$d_6$) δ 2.87-2.96 (1H, m), 3.00-3.08 (1H, m), 3.28-3.39 (2H, m), 4.71 (1H, q, J = 7.3 Hz), 4.98 (1H, q, J = 5.2 Hz), 5.35-5.40 (1H, m), 6.38 (1H, dd, J = 8.8, 3.0 Hz), 7.15 (1H, dd, J = 6.7, 1.8 Hz), 7.22-7.27 (4H, m), 7.32-7.38 (4H, m), 8.72 (1H, d, J = 3.0 Hz). ESIMS (+) 409 [M + H]$^+$. |

TABLE 105

| Ex. No | Str. | Chemical name | P.D. |
|---|---|---|---|
| 26-13 | | (S)-N-{3-(4-chlorophenyl)-2-[3-(4-fluorophenyl)ureido]-1-iminopropyl}-2-hydroxyacetamide | $^1$H-NMR (400 MHz, DMSO-d$_6$) δ 2.87-2.95 (1H, m), 2.99-3.07 (1H, m), 3.30-3.40 (2H, m), 4.71 (1H, q, J = 7.1 Hz), 4.94-5.02 (1H, m), 5.35-5.40 (1H, m), 6.32 (1H, dd, J = 8.5, 3.6 Hz), 7.00-7.07 (2H, m), 7.14 (1H, d, J = 4.8 Hz), 7.25 (2H, dd, J = 8.5, 2.4 Hz), 7.30-7.36 (4H, m), 8.61 (1H, d, J = 3.6 Hz). ESIMS (+) 393 [M + H]$^+$. |
| 26-14 | | (S)-N-{3-(4-chlorophenyl)-2-[3-(4-cyanophenyl)ureido]-1-iminopropyl}-2-hydroxyacetamide | $^1$H-NMR (400 MHz, DMSO-d$_6$) δ 2.88-2.98 (1H, m), 3.01-3.10 (1H, m), 3.30-3.40 (2H, m), 4.68-4.78 (1H, m), 4.95-5.02 (1H, m), 5.35-5.40 (1H, m), 6.59 (1H, d, J = 7.9 Hz), 7.17 (1H, dd, J = 6.4, 1.5 Hz), 7.25 (2H, dd, J = 8.5, 2.4 Hz), 7.34 (2H, d, J = 8.5 Hz), 7.51 (1H, d, J = 8.5 Hz), 7.65 (2H, d, J = 8.5 Hz), 9.12 (1H, d, J = 3.6 Hz). ESIMS (+) 400 [M + H]$^+$. |
| 26-15 | | (S)-N-{3-(4-chlorophenyl)-2-[3-(4-chlorophenyl)ureido]-1-iminopropyl}-acetamide | $^1$H-NMR (400 MHz, DMSO-d$_6$) δ 1.21-1.26 (3H, m), 2.87-2.95 (1H, m), 2.99-3.07 (1H, m), 4.65-4.73 (1H, m), 5.50-5.57 (1H, m), 6.42 (1H, dd, J = 8.5, 3.0 Hz), 7.04 (1H, dd, J = 11.54, 1.8 Hz), 7.22-7.27 (4H, m), 7.32-7.38 (4H, m), 8.72 (1H, s). ESIMS (+) 393 [M + H]$^+$. |
| 26-16 | | (S)-N-{3-(4-chlorophenyl)-2-[3-(4-chlorophenyl)ureido]-1-iminopropyl}-2-(methylsulfonyl)-acetamide | $^1$H-NMR (400 MHz, DMSO-d$_6$) δ 2.88-2.99 (1H, m), 3.03 (3H, s), 3.04-3.10 (1H, m), 3.23-3.31 (1H, m), 3.50-3.56 (1H, m), 4.71-4.78 (1H, m), 5.85-5.91 (1H, m), 6.48 (1H, d, J = 9.1 Hz), 7.23-7.27 (4H, m), 7.34-7.40 (5H, m), 8.73 (1H, d, J = 4.8 Hz). FIMS (+) 470 [M]$^+$. |

TABLE 106

| Ex. No | Str. | Chemical name | P.D. |
|---|---|---|---|
| 26-17 | | (S)-N-{3-(4-chlorophenyl)-2-[3-(4-fluorophenyl)ureido]-1-iminopropyl}-2-(methylsulfonyl)-acetamide | $^1$H-NMR (400 MHz, DMSO-d$_6$) δ 2.89-2.97 (1H, m), 3.03 (3H, s), 3.04-3.09 (1H, m), 3.23-3.30 (1H, m), 3.53 (1H, dd, J = 14.5, 6.1 Hz), 4.70-4.78 (1H, m), 5.85-5.91 (1H, m), 6.41 (1H, d, J = 8.5 Hz), 7.00-7.07 (2H, m), 7.26 (2H, dd, J = 8.5, 3.0 Hz), 7.30-7.39 (5H, m), |

TABLE 106-continued

| Ex. No | Str. | Chemical name | P.D. |
|---|---|---|---|
| | | | 8.61 (1H, d, J = 4.2 Hz). FIMS (+) 455 [M]+. |
| 26-18 (A) | | (S)-1-(4-chlorophenyl)-3-{1-(4-chlorophenyl)-3-[5-(hydroxymethyl)-1,2,4-oxadiazol-3-yl]propan-2-yl}urea | 1H-NMR (400 MHz, DMSO-$d_6$) δ 2.81 (1H, d, J = 3.1 Hz), 2.83 (1H, s), 2.88 (2H, d, J = 6.7 Hz), 4.23 (1H, q, J = 7.1 Hz), 4.68 (2H, d, J = 6.1 Hz), 5.96 (1H, t, J = 6.4 Hz), 6.21 (1H, d, J = 8.5 Hz), 7.23 (4H, t, J = 9.2 Hz), 7.34 (4H, dd, J = 8.6, 5.5 Hz), 8.56 (1H, s). ESIMS (+) 421 [M + H]+. |
| 26-18 (B) | | (S)-N-{4-(4-chlorophenyl)-3-[3-(4-chlorophenyl)ureido]-1-iminobutyl}-2-hydroxyacetamide | 1H-NMR (400 MHz, DMSO-$d_6$) δ 2.34 (2H, q, J = 3.2 Hz), 2.71-2.86 (2H, m), 3.30-3.40 (2H, m), 4.14 (1H, brs), 4.88 (1H, dt, J = 30.9, 6.1 Hz), 5.31 (1H, s), 6.10 (1H, t, J = 7.3 Hz), 7.01 (1H, brs), 7.23 (4H, dd, J = 8.8, 2.7 Hz), 7.35 (4H, t, J = 7.9 Hz), 8.61 (1H, d, J = 3.6 Hz). ESIMS (+) 423 [M + H]+. |

TABLE 107

| Ex. No | Str. | Chemical name | P.D. |
|---|---|---|---|
| 26-19 (A) | | (S)-1-(4-chlorophenyl)-3-(5-(hydroxymethyl)-1,2,4-oxadiazol-3-yl)propan-2-yl)-3-(4-fluorophenyl)urea | 1H-NMR (400 MHz, DMSO-$d_6$) δ 2.81 (1H, d, J = 2.4 Hz), 2.82 (1H, s), 2.87 (2H, d, J = 6.7 Hz), 4.23 (1H, q, J = 7.9 Hz), 4.68 (2H, d, J = 6.7 Hz), 5.96 (1H, t, J = 6.4 Hz), 6.14 (1H, d, J = 8.5 Hz), 7.02 (2H, t, J = 8.8 Hz), 7.24 (2H, d, J = 8.5 Hz), 7.31 (2H, dd, J = 9.2, 4.9 Hz), 7.35 (2H, d, J = 8.5 Hz), 8.44 (1H, s). ESIMS (+) 405 [M + H]+. |

TABLE 107-continued

| Ex. No | Str. | Chemical name | P.D. |
|---|---|---|---|
| 26-19 (B) | | (S)-N-{4-(4-chlorophenyl)-3-[3-(4-fluoro-phenyl)ureido]-1-iminobutyl}-2-hydroxyacetamide | $^1$H-NMR (400 MHz, DMSO-d$_6$) δ 2.33 (2H, dd, J = 6.4, 3.2 Hz), 2.70-2.86 (2H, m), 3.30-3.40 (2H, m), 4.12-4.16 (1H, m), 4.88 (1H, dt, J = 30.9, 6.1 Hz), 5.30-5.32 (1H, m), 6.03 (1H, dd, J = 8.5, 6.1 Hz), 7.02 (3H, t, J = 8.8 Hz), 7.24 (2H, d, J = 8.5 Hz), 7.31-7.35 (4H, m), 8.48 (1H, d, J = 3.6 Hz). ESIMS (+) 407 [M + H]$^+$. |

Example 27-1

2-(3-(4-Chlorophenyl)ureido)-N-(4-hydroxybutyl)-3-(4-methoxyphenyl)propanamide

[Chem. 185]

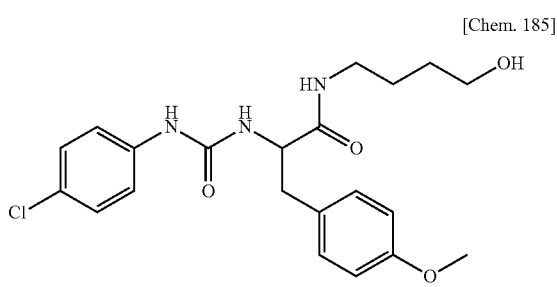 [SMILES: COc1ccc(CC(NC(=O)Nc2ccc(Cl)cc2)C(=O)NCCCCO)cc1]

To 2-[3-(4-chlorophenyl)ureido]-3-(4-methoxyphenyl) propionic acid (50 mg) under ice-cooling was added thionyl chloride (0.14 mL), and the reaction mixture was stirred at ambient temperature for 10 minutes. The thionyl chloride was removed under reduced pressure to obtain a pale yellow liquid.

To a solution of 4-amino-1-butanol (0.13 mL) in dichloromethane (0.10 mL) under ice-cooling was added the above obtained dichloromethane solution (0.20 mL) that was a pale yellow liquid, and the reaction mixture was stirred at ambient temperature for 100 minutes. Water was added to the reaction solution, and the mixture was extracted with dichloromethane. The organic layer was dried over anhydrous sodium sulfate, the solvent was removed under reduced pressure, and the obtained residue was purified by preparative thin-layer chromatography (ethyl acetate:methanol=10:1) to obtain the title compound as a colorless liquid (5.1 mg).

$^1$H NMR (400 MHz, DMSO-d$_6$) δ 1.35 (4H, s), 2.74 (1H, dd, J=13.9, 7.9 Hz), 2.87 (1H, dd, J=13.9, 6.1 Hz), 2.94-3.11 (2H, m), 3.28-3.45 (2H, m), 3.70 (3H, s), 4.29-4.41 (2H, m), 6.31 (1H, d, J=8.5 Hz), 6.82 (2H, d, J=8.5 Hz), 7.08 (2H, d, J=8.5 Hz), 7.23 (2H, d, J=8.5 Hz), 7.35 (2H, d, J=8.5 Hz), 8.02 (1H, t, J=5.4 Hz), 8.79 (1H, s).

ESIMS (+) 420[M+H]$^+$.

Examples 27-2 to 27-4

The following Examples 27-2 to 27-4 were obtained using each corresponding starting material and reactant in the same method as in Example 27-1.

The structures and spectral data thereof are shown in Table 108.

TABLE 108

| Ex. No | Str. | Chemical name | P.D. |
|---|---|---|---|
| 27-2 | | 2-(3-(4-chloro-phenyl)ureido)-N-(3-hydroxy-propyl)-3-(4-methoxyphenyl)-propanamide | $^1$H NMR (400 MHz, DMSO-d$_6$) δ 1.46-1.54 (2H, m), 2.74 (1H, dd, J = 13.9, 7.3 Hz), 2.87 (1H, dd, J = 13.9, 5.4 Hz), 3.02-3.14 (2H, m), 3.32-3.38 (2H, m), 3.70 (3H, s), 4.32-4.41 (2H, m), 6.31 (1H, d, J = 8.5 Hz), 6.82 (2H, d, J = 8.5 Hz), 7.07 (2H, d, J = 8.5 Hz), 7.23 (2H, d, J = 9.1 Hz), 7.35 (2H, d, J = 9.1 Hz), 8.03 (1H, t, J = 5.4 Hz), 8.79 (1H, s). ESIMS (+) 406 [M + H]$^+$. |

TABLE 108-continued

| Ex. No | Str. | Chemical name | P.D. |
|---|---|---|---|
| 27-3 | | 2-(3-(4-chloro-phenyl)ureido)-N-(2-hydroxyethyl)-3-(4-methoxyphenyl)-propanamide | $^1$H NMR (400 MHz, DMSO-$d_6$) δ 2.74 (1H, dd, J = 13.9, 7.3 Hz), 2.89 (1H, dd, J = 13.9, 4.8 Hz), 3.04-3.18 (2H, m), 3.32-3.40 (2H, m), 3.69 (3H, s), 4.40 (1H, dd, J = 12.7, 7.3 Hz), 4.64 (1H, t, J = 5.4 Hz), 6.28 (1H, d, J = 7.9 Hz), 6.81 (2H, d, J = 7.9 Hz), 7.08 (2H, d, J = 7.9 Hz), 7.23 (2H, d, J = 8.5 Hz), 7.35 (2H, d, J = 8.5 Hz), 8.07 (1H, t, J = 5.4 Hz), 8.79 (1H, s). ESIMS (+) 392 [M + H]$^+$. |
| 27-4 | | Ethyl 2-(2-(3-(4-chlorophenyl)-ureido)-3-(4-methoxyphenyl)-propanamido)-propanoate | $^1$H NMR (400 MHz, DMSO-$d_6$) δ 1.16 (3H, t, J = 7.3 Hz), 2.37-2.42 (2H, m), 2.72 (1H, dd, J = 13.9, 7.9 Hz), 2.86 (1H, dd, J = 13.9, 5.4 Hz), 3.19-3.34 (2H, m), 3.70 (3H, s), 4.04 (2H, q, J = 7.3 Hz), 4.32-4.39 (1H, m), 6.29 (1H, d, J = 8.5 Hz), 6.81 (2H, d, J = 9.1 Hz), 7.07 (2H, d, J = 9.1 Hz), 7.23 (2H, d, J = 8.5 Hz), 7.35 (2H, d, J = 8.5 Hz), 8.17 (1H, t, J = 5.4 Hz), 8.79 (1H, s). ESIMS (+) 448 [M + H]$^+$. |

Example 28

3-(2-(3-(4-Chlorophenyl) ureido)-3-(4-methoxyphenyl)propanamide)propionic Acid

[Chem. 186]

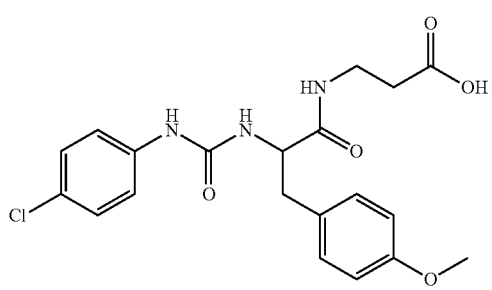

To a solution of ethyl 3-(2-(3-(4-chlorophenyl)ureido)-3-(4-methoxyphenyl)propanamide)propionate (50.0 mg) in tetrahydrofuran-ethanol (each 0.14 mL) was added 2 mol/L aqueous sodium hydroxide (0.14 mL), and the reaction mixture was stirred at ambient temperature for 30 minutes. Water was added to the reaction solution, and the mixture was washed with ethyl acetate. The organic layer was extracted with 1 mol/L aqueous sodium hydroxide. The combined aqueous layer was adjusted pH 4 by addition of a saturated aqueous citric acid solution, and the mixture was extracted with ethyl acetate. The organic layer was washed with a brine, and dried over anhydrous sodium sulfate. The solvent was removed under reduced pressure to obtain the title compound as a pale yellow solid (34.2 mg).

$^1$H NMR (400 MHz, DMSO-$d_6$) δ 2.34 (2H, t, J=6.7 Hz), 2.73 (1H, dd, J=13.9, 7.3 Hz), 2.87 (1H, dd, J=13.9, 5.4 Hz), 3.15-3.33 (2H, m), 3.69 (3H, s), 4.33-4.40 (1H, m), 6.29 (1H, d, J=7.9 Hz), 6.81 (2H, d, J=8.5 Hz), 7.07 (2H, d, J=8.5 Hz), 7.23 (2H, d, J=9.1 Hz), 7.35 (2H, d, J=9.1 Hz), 8.16 (1H, t, J=5.4 Hz), 8.79 (1H, s), 12.24 (1H, brs).
ESIMS (+) 420[M+H]$^+$.

Example 29

(−)-(S)-1-(4-Chlorophenyl)-3-(1-(4-(2-hydroxyethyl)-5-oxo-4,5-dihydro-1,3,4-oxadiazol-2-yl)-2-(4-methoxyphenyl)ethyl)urea

[Chem. 187]

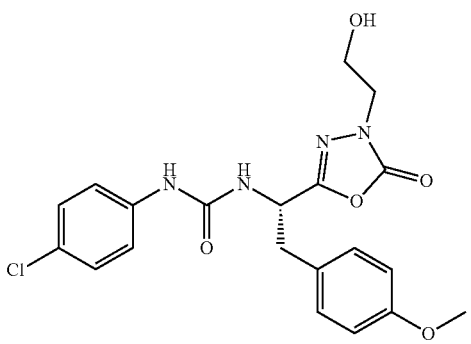

A solution of lithium chloride (107 mg) and sodium borohydride (95.7 mg) in a mixed solvent of methanol (0.42 mL)-THF (0.84 mL) was ice-cooled, and then a solution of ethyl (S)-2-(5-(1-(3-(4-chlorophenyl)ureido)-2-(4-methoxyphenyl)ethyl)-2-oxo-1,3,4-oxadiazol-3(2H)-yl)acetate (300 mg) in tetrahydrofuran was added dropwise to the above ice-cooled solution over 40 minutes. The reaction mixture was stirred for 23 hours. The reaction mixture was adjusted pH 3 by addition of hydrochloric acid (1%), and the mixture was extracted with ethyl acetate. The organic layer was washed with a brine, and dried over anhydrous sodium sulfate. The solvent was removed under reduced pressure, and the obtained residue was then purified by silica gel column chromatography (hexane:ethyl acetate=1:2-1:5) to obtain the title compound as a white solid (70 mg).

$^1$H-NMR (400 MHz, DMSO-$d_6$) δ 2.94-3.09 (2H, m), 3.57 (2H, q, J=5.7 Hz), 3.63-3.66 (2H, m), 3.70 (3H, s), 4.85-4.94 (2H, m), 6.71 (1H, d, J=8.5 Hz), 6.85 (2H, d, J=8.5 Hz), 7.13 (2H, d, J=9.1 Hz), 7.23-7.26 (2H, m), 7.34-7.37 (2H, m), 8.71 (1H, s).

ESIMS (+) 433[M+H]$^+$.

$[α]_D^{27}$ −49.9 (c 0.353, EtOH)

Example 30

(S)-3-(4-Chlorophenyl)-2-(3-(4-chlorophenyl)ureido)-N-(dimethylcarbamoyl)propanimidamide

[Chem. 188]

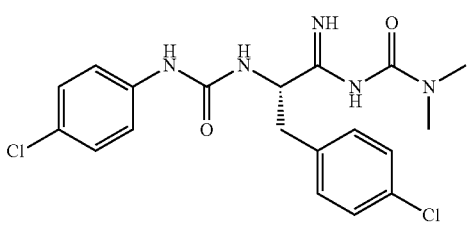

To a solution of (S)-1-(4-chlorophenyl)-3-(2-(4-chlorophenyl)-1-(5-(dimethylamino)-1,2,4-oxadiazol-3-yl)ethyl)urea (60 mg) in ethanol (1 mL) was added platinum oxide (6 mg), and the reaction mixture was stirred under hydrogen atmosphere at ambient temperature for 3 hours. The reaction solution was filtered over Celite, the solvent of the filtrate was removed under reduced pressure, and the obtained residue was then purified by silica gel column chromatography (hexane:ethyl acetate=4:1) to obtain the title compound as a colorless oil (23 mg).

$^1$H-NMR (400 MHz, DMSO-$d_6$) δ 2.78 (3H, s), 2.82 (2H, dd, J=13.9, 7.9 Hz), 2.96 (3H, s), 3.02 (2H, dd, J=13.9, 5.4 Hz), 4.43-4.52 (1H, m), 6.31 (1H, d, J=8.5 Hz), 7.19-7.24 (4H, m), 7.29-7.36 (4H, m), 8.95 (1H, s).

HRESIMS (+): 422.11449 (422.11505 calculated for $C_{19}H_{22}Cl_2N_5O_2$).

Example 31-1

1-(4-Chlorophenyl)-3-(1-hydroxy-3-(4-methoxyphenyl)propan-2-yl)urea

[Chem. 189]

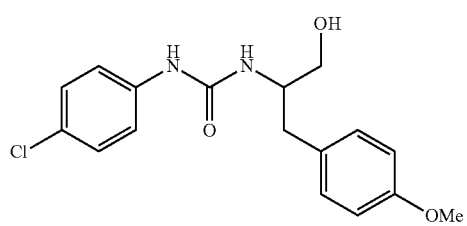

To a solution of 2-amino-3-(4-methoxyphenyl)propan-1-ol (69 mg) in tetrahydrofuran (2 mL) was added 4-chlorophenyl isocyanate (58 mg), and the reaction mixture was stirred at ambient temperature for 1 hour. The solvent was removed under reduced pressure, and the obtained residue was then purified by silica gel column chromatography (hexane:ethyl acetate=1:2) to obtain the title compound as a white solid (93 mg).

$^1$H NMR (400 MHz, CDCl$_3$) δ 2.73-2.89 (3H, m), 3.59-3.65 (1H, m), 3.71-3.78 (1H, m), 3.80 (3H, s), 4.02-4.06 (1H, m), 4.76 (1H, d, J=7.3 Hz), 6.28 (1H, s), 6.85 (2H, d, J=9.1 Hz), 7.10-7.12 (4H, m), 7.23 (2H, d, J=8.5 Hz).

ESIMS (+) 335[M+H]$^+$.

Examples 31-2 to 31-30

The following Examples 31-2 to 31-30 were obtained using each corresponding starting material and reactant in the same method as in Example 31-1.

The structures and spectral data thereof are shown in Tables 109-116.

TABLE 109

| Ex. No | Str. | Chemical name | P.D. |
|---|---|---|---|
| 31-2 | | 1-(4-chloro-phenyl)-3-[1-(4-ethoxyphenyl)-3-hydroxypropan-2-yl]urea | ¹H-NMR (400 MHz, CDCl₃) δ 1.29 (3H, t, J = 6.9 Hz), 2.61 (1H, dd, J = 13.5, 7.1 Hz), 2.74 (1H, dd, J = 13.5, 6.9 Hz), 3.26-3.40 (2H, m), 3.70-3.80 (1H, m), 3.96 (2H, q, J = 6.9 Hz), 4.84 (1H, t, J = 5.1 Hz), 6.06 (1H, d, J = 7.9 Hz), 6.82 (2H, d, J = 8.5 Hz), 7.11 (2H, d, J = 8.5 Hz), 7.23 (2H, d, J = 9.1 Hz), 7.36 (2H, d, J = 9.1 Hz), 8.61 (1H, s). ESIMS (+) 349 [M + H]⁺. |
| 31-3 | | 1-(4-chloro-phenyl)-3-[1-hydroxy-3-(4-methoxy-2-methyphenyl)-propan-2-yl]urea | ¹H-NMR (400 MHz, CDCl₃) δ 2.32 (3H, s), 2.74 (1H, brs), 2.73-2.86 (2H, m), 3.60-3.68 (1H, m), 3.72-3.79 (1H, m), 3.78 (3H, s), 3.97-4.07 (1H, m), 4.79 (1H, d, J = 7.3 Hz), 6.21 (1H, brs), 6.67 (1H, dd, J = 8.5, 2.4 Hz), 6.73 (1H, d, J = 2.4 Hz), 7.01 (1H, d, J = 8.5 Hz), 7.12 (2H, d, J = 8.5 Hz), 7.24 (2H, d, J = 8.5 Hz). ESIMS (+) 349 [M + H]⁺. |
| 31-4 | | 1-(4-chloro-phenyl)-3-[1-(2,3-dihydro-benzofuran-5-yl)-3-hydroxypropan-2-yl]urea | ¹H-NMR (400 MHz, CDCl₃) δ 2.59 (1H, dd, J = 13.6, 6.9 Hz), 2.72 (1H, dd, J = 13.6, 6.7 Hz), 3.12 (2H, t, J = 8.8 Hz), 3.27-3.40 (2H, m), 3.68-3.77 (1H, m), 4.46 (2H, t, J = 8.8 Hz), 4.84 (1H, t, J = 5.1 Hz), 6.06 (1H, d, J = 8.5 Hz), 6.65 (1H, d, J = 7.9 Hz), 6.91 (1H, d, J = 7.9 Hz), 7.07 (1H, s), 7.23 (2H, d, J = 9.0 Hz), 7.37 (2H, d, J = 9.0 Hz), 8.63 (1H, s). ESIMS (+) 347 [M + H]⁺. |
| 31-5 | | 1-(4-chloro-phenyl)-3-[1-(chroman-6-yl)-3-hydroxypropan-2-yl]urea | ¹H-NMR (400 MHz, DMSO-d₆) δ 1.84-1.92 (2H, m), 2.57 (1H, dd, J = 13.9, 6.9 Hz), 2.66-2.73 (3H, m), 3.28-3.40 (2H, m), 3.69-3.78 (1H, m), 4.08 (2H, t, J = 5.1 Hz), 4.84 (1H, t, J = 5.1 Hz), 6.06 (1H, d, J = 8.5 Hz), 6.63 (1H, d, J = 9.1 Hz), 6.88-6.92 (2H, m), 7.24 (2H, d, J = 8.5 Hz), 7.38 (2H, d, J = 8.5 Hz), 8.63 (1H, s). ESIMS (+) 361 [M + H]⁺. |

TABLE 110

| Ex. No | Str. | Chemical name | P.D. |
|---|---|---|---|
| 31-6 | | 1-(4-chlorophenyl)-3-[1-(4-cyanophenyl)-3-hydroxypropan-2-yl]urea | $^1$H-NMR (400 MHz, DMSO-$d_6$) δ 2.77 (1H, dd, J = 13.6, 8.2 Hz), 2.93 (1H, dd, J = 13.6, 6.5 Hz), 3.30-3.42 (2H, m), 3.82-3.92 (1H, m), 4.94 (1H, t, J = 5.1 Hz), 6.16 (1H, d, J = 8.5 Hz), 7.22 (2H, d, J = 9.1 Hz), 7.34 (2H, d, J = 9.1 Hz), 7.43 (2H, d, J = 8.5 Hz), 7.74 (2H, d, J = 8.5 Hz), 8.58 (1H, s). ESIMS (+) 330 [M + H]$^+$. |
| 31-7 | | ethyl 4-[2-[3-(4-chlorophenyl)-ureido]-3-hydroxypropyl]-benzoate | $^1$H-NMR (400 MHz, DMSO-$d_6$) δ 1.29 (3H, t, J = 7.3 Hz), 2.76 (1H, dd, J = 13.3, 7.9 Hz), 2.91 (1H, dd, J = 13.3, 6.1 Hz), 3.27-3.42 (2H, m), 3.80-3.90 (1H, m), 4.27 (2H, q, J = 7.3 Hz), 4.93 (1H, t, J = 5.5 Hz), 6.21 (1H, d, J = 7.9 Hz), 7.21 (2H, d, J = 9.1 Hz), 7.34 (2H, d, J = 9.1 Hz), 7.36 (2H, d, J = 8.5 Hz), 7.86 (2H, d, J = 8.5 Hz), 8.65 (1H, s). ESIMS (+) 377 [M + H]$^+$. |
| 31-8 | | ethyl 3-[2-[3-(4-chlorophenyl)ureido]-3-hydroxypropyl]benzoate | $^1$H-NMR (400 MHz, DMSO-$d_6$) δ 1.29 (3H, t, J = 7.3 Hz), 2.74 (1H, dd, J = 13.3, 7.9 Hz), 2.91 (1H, dd, J = 13.3, 6.1 Hz), 3.26-3.42 (2H, m), 3.77-3.88 (1H, m), 4.28 (2H, q, J = 7.3 Hz), 4.93 (1H, t, J = 5.5 Hz), 6.16 (1H, d, J = 8.5 Hz), 7.22 (2H, d, J = 9.1 Hz), 7.34 (2H, d, J = 9.1 Hz), 7.43 (1H, t, J = 7.9 Hz), 7.50 (1H, d, J = 7.9 Hz), 7.77 (1H, d, J = 7.9 Hz), 7.83 (1H, s), 8.60 (1H, s). ESIMS (+) 377 [M + H]$^+$. |

TABLE 111

| Ex. No | Str. | Chemical name | P.D. |
|---|---|---|---|
| 31-9 | | 1-(4-chlorophenyl)-3-[1-(2-fluoro-4-methoxyphenyl)-3-hydroxypropan-2-yl]urea | $^1$H-NMR (400 MHz, CDCl$_3$) δ 2.62 (1H, dd, J = 13.9, 8.5 Hz), 2.79 (1H, dd, J = 13.9, 6.7 Hz), 3.30-3.40 (2H, m), 3.71 (3H, s), 3.78-3.88 (1H, m), 4.88 (1H, t, J = 5.1 Hz), 6.06 (1H, d, J = 8.5 Hz), 6.67-6.78 (2H, m), 7.15-7.22 (1H, m), 7.22 (2H, d, J = 9.1 |

TABLE 111-continued

| Ex. No | Str. | Chemical name | P.D. |
|---|---|---|---|
| | | | Hz), 7.34 (2H, d, J = 9.1 Hz), 8.60 (1H, s). ESIMS (+) 353 [M + H]+. |
| 31-10 | | 1-(4-chloro-phenyl)-3-[1-(3-fluoro-4-methoxyphenyl)-3-hydroxypropan-2-yl]urea | $^1$H-NMR (400 MHz, DMSO-$d_6$) δ 2.58-2.67 (1H, m), 2.68-2.80 (1H, m), 3.25-3.40 (2H, m), 3.78 (3H, s), 3.73-3.82 (1H, m), 4.87 (1H, t, J = 5.5 Hz), 6.08 (1H, d, J = 8.5 Hz), 6.94-7.18 (3H, m), 7.22 (2H, d, J = 8.5 Hz), 7.35 (2H, d, J = 8.5 Hz), 8.59 (1H, s). ESIMS (+) 353 [M + H]+. |
| 31-11 | | 1-(4-chloro-phenyl)-3-[1-hydroxy-3-[4-(trifluoro-methoxy)phenyl]-propan-2-yl]urea | $^1$H-NMR (400 MHz, DMSO-$d_6$) δ 2.71 (1H, dd, J = 13.9, 7.9 Hz), 2.86 (1H, dd, J = 13.9, 6.7 Hz), 3.30-3.46 (2H, m), 3.76-3.87 (1H, m), 4.91 (1H, t, J = 5.5 Hz), 6.17 (1H, d, J = 8.5 Hz), 7.20-7.29 (4H, m), 7.31-7.38 (4H, m), 8.62 (1H, s). ESIMS (+) 389 [M + H]+. |
| 31-12 | | 1-(4-chloro-phenyl)-3-[1-hydroxy-3-(5-methoxythiophen-2-yl)propan-2-yl]urea | $^1$H-NMR (400 MHz, CDCl$_3$) δ 2.74 (1H, brs), 2.86-2.98 (2H, m), 3.63-3.80 (2H, m), 3.85 (3H, s), 3.94-4.04 (1H, m), 4.96 (1H, d, J = 7.3 Hz), 6.00 (1H, d, J = 3.6 Hz), 6.43 (1H, d, J = 3.6 Hz), 6.45 (1H, brs), 7.17 (2H, d, J = 8.8 Hz), 7.25 (2H, d, J = 8.8 Hz). ESIMS (+) 341 [M + H]+. |

TABLE 112

| Ex. No | Str. | Chemical name | P.D. |
|---|---|---|---|
| 31-13 | | 1-(4-chlorophenyl)-3-(1-(4-(difluoromethoxy)phenyl)-3-hydroxypropan-2-yl]urea | $^1$H-NMR (400 MHz, DMSO-$d_6$) δ 2.68 (1H, dd, J = 13.9, 7.3 Hz), 2.82 (1H, dd, J = 13.9, 6.1 Hz), 3.28-3.40 (2H, m), 3.78-3.80 (1H, m), 4.90 (1H, t, J = 5.1 Hz), 6.16 (1H, d, J = 8.5 Hz), 7.16 (1H, t, J = 74.6 Hz), 7.08 (2H, d, J = 8.5 Hz), 7.22 (2H, d, J = 9.1 Hz), 7.27 (2H, d, J = 8.5 Hz), 7.36 (2H, d, J = 9.1 Hz), 8.64 (1H, s). ESIMS (+) 371 [M + H]+. |

TABLE 112-continued

| Ex. No | Str. | Chemical name | P.D. |
|---|---|---|---|
| 31-14 | | 1-(4-chlorophenyl)-3-(1-(4-chlorophenyl)-3-hydroxypropan-2-yl)urea | $^1$H-NMR (400 MHz, DMSO-$d_6$) δ 2.67 (1H, dd, J = 13.3, 7.3 Hz), 2.82 (1H, dd, J = 13.3, 6.1 Hz), 3.28-3.39 (2H, m), 3.75-3.85 (1H, m), 4.90 (1H, t, J = 5.1 Hz), 6.15 (1H, d, J = 8.5 Hz), 7.21-7.25 (4H, m), 7.31-7.38 (4H, m), 8.62 (1H, s). ESIMS (+) 339 [M + H]$^+$. |
| 31-15 | | 1-(4-chlorophenyl)-3-(1-(4-fluorophenyl)-3-hydroxypropan-2-yl)urea | $^1$H-NMR (400 MHz, DMSO-$d_6$) δ 2.67 (1H, dd, J = 13.3, 7.3 Hz), 2.81 (1H, dd, J = 13.3, 6.7 Hz), 3.31-3.38 (2H, m), 3.73-3.84 (1H, m), 4.89 (1H, t, J = 5.1 Hz), 6.15 (1H, d, J = 8.5 Hz), 7.09 (2H, t, J = 8.8 Hz), 7.20-7.27 (4H, m), 7.36 (2H, dt, J = 9.5, 2.4 Hz), 8.64 (1H, s). ESIMS (+) 323 [M + H]$^+$. |
| 31-16 | | 1-(4-chlorophenyl)-3-(1-hydroxy-3-(4-(trifluoromethyl)phenyl)propan-2-yl)urea | $^1$H-NMR (400 MHz, DMSO-$d_6$) δ 2.78 (1H, dd, J = 13.3, 7.3 Hz), 2.93 (1H, dd, J = 13.3, 6.1 Hz), 3.33-3.39 (2H, m), 3.80-3.91 (1H, m), 4.94 (1H, t, J = 5.1 Hz), 6.17 (1H, d, J = 8.5 Hz), 7.22 (2H, dt, J = 8.5, 1.8 Hz), 7.35 (2H, dt, J = 8.5, 1.8 Hz), 7.45 (2H, d, J = 7.9 Hz), 7.64 (2H, d, J = 7.9 Hz), 8.60 (1H, s). ESIMS (+) 373 [M + H]$^+$. |

TABLE 113

| Ex. No | Str. | Chemical name | P.D. |
|---|---|---|---|
| 31-17 | | 1-(4-chlorophenyl)-3-(1-hydroxy-3-(3-(methoxyphenyl)-propan-2-yl)urea | $^1$H-NMR (400 MHz, DMSO-$d_6$) δ 2.66 (1H, dd, J = 13.3, 7.3 Hz), 2.79 (1H, dd, J = 13.3, 6.7 Hz), 3.28-3.40 (2H, m), 3.71 (3H, s), 3.76-3.86 (1H, m), 4.87 (1H, t, J = 5.1 Hz), 6.15 (1H, d, J = 8.5 Hz), 6.74 (1H, dd, J = 7.3, 1.8 Hz), 6.77-6.81 (2H, m), 7.18 (1H, t, J = 7.3 Hz), 7.23 (2H, d, J = 9.1 Hz), 7.37 (2H, d, J = 9.1 Hz), 8.66 (1H, s). ESIMS (+) 335 [M + H]$^+$. |

TABLE 113-continued

| Ex. No | Str. | Chemical name | P.D. |
|---|---|---|---|
| 31-18 | | 1-[1-hydroxy-3-(4-methoxyphenyl)propan-2-yl]-3-phenylurea | $^1$H-NMR (400 MHz, DMSO-d$_6$) δ 2.61 (1H, q, J = 7.1 Hz), 2.75 (1H, q, J = 6.9 Hz), 3.70 (3H, s), 3.73-3.76 (3H, m), 4.84 (1H, t, J = 5.1 Hz), 6.03 (1H, d, J = 8.5 Hz), 6.83-6.87 (3H, m), 7.12-7.20 (4H, m), 7.33 (2H, d, J = 7.3 Hz), 8.46 (1H, bs). ESIMS (+) 301 [M + H]$^+$. |
| 31-19 | | 1-(3-chlorophenyl)-3-[1-hydroxy-3-(4-methoxyphenyl)-propan-2-yl]urea | $^1$H-NMR (400 MHz, CDCl$_3$) δ 2.64 (1H, bs), 2.82 (2H, ddd, J = 25.4, 13.3, 6.7 Hz), 3.61-3.64 (1H, m), 3.74-3.77 (1H, m), 3.80 (3H, s), 4.02-4.08 (1H, m), 4.83 (1H, d, J = 7.3 Hz), 6.38 (1H, bs), 6.85 (2H, d, J = 8.5 Hz), 6.99-7.31 (6H, m). ESIMS (+) 335 [M − H]$^+$. |
| 31-20 | | 1-(2-chlorophenyl)-3-[1-hydroxy-3-(4-methoxyphenyl)-propan-2-yl]urea | $^1$H-NMR (400 MHz, CDCl$_3$) δ 2.48 (1H, bs), 2.86 (2H, d, J = 7.3 Hz), 3.61-3.67 (1H, m), 3.74-4.78 (1H, m), 3.80 (3H, s), 4.05-4.09 (1H, m), 4.89 (1H, bs), 6.65 (1H, bs), 6.85 (2H, d, J = 7.9 Hz), 6.96-7.01 (1H, m), 7.14 (2H, d, J = 7.9 Hz), 7.20-7.24 (1H, m), 7.33-7.35 (1H, m), 7.91 (1H, dd, J = 7.9, 1.2 Hz). ESIMS (+) 335 [M + H]$^+$. |

TABLE 114

| Ex. No | Str. | Chemical name | P.D. |
|---|---|---|---|
| 31-21 | | 1-(4-fluorophenyl)-3-[1-hydroxy-3-(4-methoxyphenyl)-propan-2-yl]urea | $^1$H-NMR (400 MHz, CDCl$_3$) δ 2.72 (1H, dd, J = 13.9, 7.9 Hz), 2.85 (2H, dd, J = 13.9, 6.7 Hz), 3.85-3.63 (1H, m), 3.72-3.77 (1H, m), 3.80 (3H, s), 3.98-4.07 (1H, m), 4.69 (1H, d, J = 6.1 Hz), 6.16 (1H, bs), 6.83 (2H, d, J = 7.9 Hz), 6.95-6.99 (2H, m), 7.06-7.10 (4H, m). ESIMS (+) 319 [M + H]$^+$. |
| 31-22 | | 1-(4-cyanophenyl)-3-[1-hydroxy-3-(4-methoxyphenyl)-propan-2-yl]urea | $^1$H-NMR (400 MHz, CDCl$_3$) δ 2.23 (1H, bs), 2.85 (2H, d, J = 7.9 Hz), 3.60-3.69 (1H, m), 3.76-3.79 (4H, m), 4.00-4.11 (1H, m), 4.87 (1H, d, J = 6.1 Hz), 6.66 (1H, bs), 6.86 (2H, d, J = 9.1 Hz), 7.15 (2H, d, J = 8.5 Hz), 7.40 (2H, d, J = 8.5 Hz), 7.55 (2H, d, J = 9.1 Hz). ESIMS (+) 326 [M + H]$^+$. |

TABLE 114-continued

| Ex. No | Str. | Chemical name | P.D. |
| --- | --- | --- | --- |
| 31-23 | | 4-{3-[1-hydroxy-3-(4-methoxyphenyl)propan-2-yl]ureido}-N-methylbenzamide | $^1$H NMR (400 MHz, DMSO-d$_6$) δ 2.62 (1H, dd, J = 13.3, 6.7 Hz), 2.73-2.78 (3H, m), 3.09-3.16 (1H, m), 3.31-3.39 (2H, m), 3.70 (3H, s), 3.75-3.77 (1H, m), 4.86 (1H, t, J = 5.5 Hz), 6.15 (1H, d, J = 8.5 Hz), 6.84 (2H, d, J = 8.5 Hz), 7.13 (2H, d, J = 8.5 Hz), 7.39 (2H, d, J = 8.5 Hz), 7.69 (2H, d, J = 8.5 Hz), 8.19 (1H, d, J = 4.9 Hz), 8.73 (1H, bs). ESIMS (+) 358 [M + H]$^+$. |
| 31-24 | | 1-[1-hydroxy-3-(4-methoxyphenyl)propan-2-yl]-3-[4-(methylsulfonyl)phenyl]urea | $^1$H NMR (400 MHz, DMSO-d$_6$) δ 2.63 (1H, dd, J = 13.9, 7.2 Hz), 2.76 (2H, dd, J = 14.5, 7.2 Hz), 3.10 (3H, s), 3.34-3.39 (1H, m), 3.70 (3H, s), 3.77-3.79 (1H, m), 4.88 (1H, t, J = 5.4 Hz), 6.25 (1H, d, J = 8.5 Hz), 6.84 (2H, d, J = 8.5 Hz), 7.14 (2H, d, J = 8.5 Hz), 7.56 (2H, d, J = 8.5 Hz), 7.73 (2H, d, J = 8.5 Hz), 9.02 (1H, bs). ESIMS (−) 379 [M + H]$^+$. |

TABLE 115

| Ex. No | Str. | Chemical name | P.D. |
| --- | --- | --- | --- |
| 31-25 | | 1-(4-bromophenyl)-3-(1-hydroxy-3-(4-methoxyphenyl)-propan-2-yl)urea | $^1$H NMR (400 MHz, CDCl$_3$) δ 2.70-2.79 (2H, m), 2.85 (1H, d, J = 13.9, 6.7 Hz), 3.59-3.65 (1H, m), 3.73-3.78 (1H, m), 3.80 (3H, s), 4.00-4.08 (1H, m), 4.74 (1H, d, J = 6.7 Hz), 6.24 (1H, bs), 6.85 (2H, d, J = 8.5 Hz), 7.07 (2H, d, J = 8.5 Hz), 7.11 (2H, d, J = 8.5 Hz), 7.38 (2H, d, J = 8.5 Hz). ESIMS (+) 380 [M + H]$^+$. |
| 31-26 | | 1-[1-hydroxy-3-(4-methoxy-pehnyl)propan-2-yl]-3-(4-methoxyphenyl)-urea | $^1$H-NMR (400 MHz, CDCl$_3$) δ 2.65 (1H, dd, J = 14.6, 9.1 Hz), 2.83 (1H, dd, J = 13.3, 6.1 Hz), 3.34 (1H, t, J = 4.2 Hz), 3.56-3.61 (1H, m), 3.70-3.75 (1H, m), 3.98 (6H, s), 3.99-4.03 (1H, m), 4.64 (1H, d, J = 4.8 Hz), 5.96 (1H, d, J = 4.8 Hz), 6.81 (4H, d, J = 9.1 Hz), 6.97 (2H, d, J = 9.1 Hz), 7.03 (2H, d, J = 8.5 Hz). ESIMS (+) 331 [M + H]$^+$. |

TABLE 115-continued

| Ex. No | Str. | Chemical name | P.D. |
|---|---|---|---|
| 31-27 | | 1-(6-chloro-pyridine-3-yl)-3-[1-hydroxy-3-(4-methoxy-phenyl)propan-2-yl]urea | ¹H NMR (400 MHz, DMSO-d₆) δ 2.62 (1H, dd, J = 13.9, 7.2 Hz), 2.75 (1H, dd, J = 13.9, 6.7 Hz), 3.31-3.35 (2H, m), 3.70 (3H, s), 3.75-3.77 (1H, m), 4.86 (1H, bs), 6.26 (1H, bs), 6.84 (2H, d, J = 9.1 Hz), 7.13 (2H, d, J = 9.1 Hz), 7.33 (1H, d, J = 7.9 Hz), 7.89 (1H, dd, J = 10.3, 3.6 Hz), 8.33 (1H, d, J = 2.4 Hz), 8.84 (1H, bs). ESIMS (+) 336 [M + H]⁺. |
| 31-28 | | 1-(5-chloro-thiophen-2-yl)-3-[1-hydroxy-3-(4-methoxy-phenyl)propan-2-yl]urea | ¹H-NMR (400 MHz, CDCl₃) δ 2.61 (1H, bs), 2.74 (2H, dd, J = 13.3, 7.2 Hz), 3.71-3.74 (1H, m), 3.80 (3H, s), 3.98-4.02 (2H, m), 4.85 (1H, d, J = 7.2 Hz), 6.32 (1H, d, J = 3.6 Hz), 6.38 (1H, bs), 6.65 (1H, d, J = 4.2 Hz), 6.84 (2H, d, J = 8.5 Hz), 7.07 (2H, d, J = 8.5 Hz). ESIMS (+) 341 [M + H]⁺. |

TABLE 116

| Ex. No | Str. | Chemical name | P.D. |
|---|---|---|---|
| 31-29 | | (+)-(R)-(1-(4-chlorophenyl)-3-[1-hydroxy-3-(4-methoxyphenyl)-propan-2-yl]urea | ¹H-NMR (400 MHz, CDCl₃) δ 2.73-2.79 (2H, m), 2.85 (1H, dd, J = 13.9, 6.7 Hz), 3.62 (1H, dd, J = 11.5, 6.1 Hz), 3.73-3.76 (1H, m), 3.80 (3H, s), 4.02-4.06 (1H, m), 4.76 (1H, d, J = 7.3 Hz), 6.28 (1H, s), 6.85 (2H, d, J = 9.1 Hz), 7.10-7.12 (4H, m), 7.23 (2H, d, J = 8.5 Hz). ESIMS (+) 335 [M + H]⁺. $[\alpha]_D^{29.2}$ + 50 (c 0.20, DMSO). |
| 31-30 | | (−)-(S)-1-(4-chlorophenyl)-3-[1-hydroxy-3-(4-methoxyphenyl)-propan-2-yl]urea | ¹H-NMR (400 MHz, CDCl₃) δ 2.73-2.79 (2H, m), 2.85 (1H, dd, J = 13.9, 6.7 Hz), 3.62 (1H, dd, J = 11.5, 6.1 Hz), 3.73-3.76 (1H, m), 3.80 (3H, s), 4.02-4.06 (1H, m), 4.76 (1H, d, J = 7.3 Hz), 6.28 (1H, s), 6.85 (2H, d, J = 9.1 Hz), 7.10-7.12 (4H, m), 7.23 (2H, d, J = 8.5 Hz). ESIMS (+) 335 [M + H]⁺. $[\alpha]_D^{28.6}$ − 55 (c 0.20, DMSO). |

Example 32

1-(4-Chlorophenyl)-3-[1-hydroxy-(5-methoxypyridin-2-yl)propan-2-yl]urea

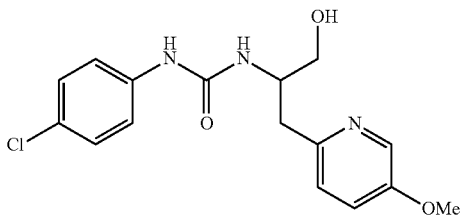

[Chem. 190]

To methyl 2-amino-3-(5-methoxypyridin-2-yl)propionate hydrochloride (337 mg) were added a saturated aqueous sodium hydrogen carbonate (10.0 mL) and ethyl acetate (30.0 mL), and the reaction mixture was stirred at ambient temperature for 5 minutes. The organic layer was washed with water (3.0 mL) and then a brine (3.0 mL), and dried over anhydrous sodium sulfate. The solvent was removed under reduced pressure, and the obtained residue was dissolved in THF (10.0 mL). To the solution under ice-cooling was added lithium aluminium hydride (156 mg), and the reaction mixture was stirred for 15 minutes. To the reaction solution was added 1 mol/L aqueous sodium hydroxide (156 μL) and water (156 μL), and the mixture was stirred for 5 minutes. The mixture was filtered over Celite, and the solvent of the filtrate was removed under reduced pressure. The obtained residue was dissolved in THF (5.00 mL), 4-chlorophenyl isocyanate (178 mg) was added to the solution under ice-cooling, and the mixture was stirred at ambient temperature for 30 minutes. The solvent of the reaction solution was removed under reduced pressure, and the obtained residue was then purified by silica gel column chromatography (chloroform:methanol=10:1) to obtain the title compound as a brown solid (110 mg).

$^1$H-NMR (400 MHz, DMSO-$d_6$) δ 2.77 (1H, dd, J=13.9, 7.9 Hz), 2.92 (1H, dd, J=14.5, 6.7 Hz), 3.27-3.42 (2H, m), 3.78 (3H, s), 3.96-4.01 (1H, m), 4.84 (1H, t, J=5.5 Hz), 6.14 (1H, d, J=7.9 Hz), 7.18-7.23 (3H, m), 7.30 (1H, dd, J=3.0, 8.5 Hz), 7.35 (2H, d, J=8.5 Hz), 8.18 (1H, d, J=3.0 Hz), 8.66 (1H, bs).

ESIMS (+) 336[M+H]$^+$.

Example 33

4-[2-[3-(4-Chlorophenyl)ureido]-3-hydroxypropyl]benzoic Acid

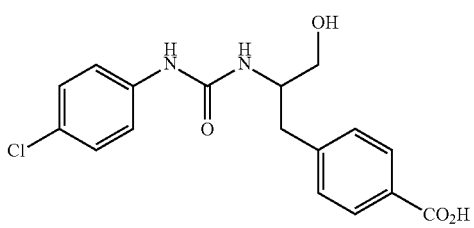 [SMILES: CCOC(=O)c1ccc(CC(CO)NC(=O)Nc2ccc(Cl)cc2)cc1]

[Chem. 191]

To a solution of ethyl 4-[2-[3-(4-chlorophenyl)ureido]-3-hydroxypropyl]benzoate (362 mg) in a mixed solvent of tetrahydrofuran (1 mL) and ethanol (4 mL) at room temperature was added 2 mol/L aqueous potassium hydroxide (2.5 mL), and the reaction mixture was stirred at 50° C. for 1 hour. The reaction solution was adjusted pH 1 by addition of 1 mol/L hydrochloric acid. The precipitated crystal was collected on a filter to obtain the title compound as a colorless crystal (272 mg).

$^1$H-NMR (400 MHz, DMSO-$d_6$) δ 2.75 (1H, dd, J=13.3, 7.9 Hz), 2.90 (1H, dd, J=13.3, 6.7 Hz), 3.25-3.45 (2H, m), 3.80-3.90 (1H, m), 4.87-5.00 (1H, m), 6.19 (1H, d, J=8.5 Hz), 7.2$^2$ (2H, d, J=9.1 Hz), 7.33 (2H, d, J=9.1 Hz), 7.35 (2H, d, J=8.5 Hz), 7.84 (2H, d, J=8.5 Hz), 8.66 (1H, s), 12.80 (1H, brs).

ESIMS (+) 349[M+H]$^+$.

Example 34-1

4-[2-[3-(4-Chlorophenyl)ureido]-3-hydroxypropyl]-N-methylbenzamide

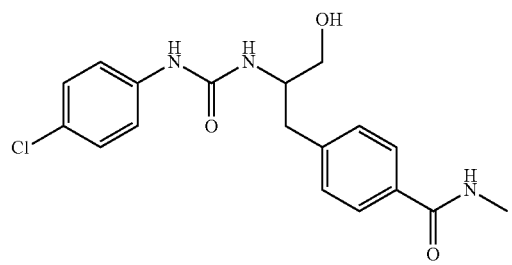 [SMILES: CN(C)C(=O)c1ccc(CC(CO)NC(=O)Nc2ccc(Cl)cc2)cc1]

[Chem. 192]

To a solution of 4-{2-[3-(4-chlorophenyl)ureido]-3-hydroxypropyl}benzoic acid (40.0 mg) in N,N-dimethylformamide (0.6 mL) at room temperature were added 0-(benzotriazol-1-yl)-N,N,N',N'-tetramethyluronium tetrafluoroborate (TBTU)(44.5 mg) and diisopropylethylamine (50 μL), and the reaction mixture was stirred at room temperature for 1 hour. To the reaction solution was added 2 mol/L methylamine/tetrahydrofuran (1 mL), and the mixture was stirred at room temperature for 1 hour. The reaction solution was diluted with ethyl acetate. The organic layer was washed with water, 0.5 mol/L hydrochloric acid, and a brine, and dried over anhydrous sodium sulfate. The solvent was removed and the obtained residue was triturated with ethyl acetate (1 mL) and hexane (0.5 mL) to obtain the title compound as a colorless crystal (23.3 mg).

$^1$H-NMR (400 MHz, DMSO-$d_6$) δ 2.73 (1H, dd, J=13.9, 7.3 Hz), 2.75 (3H, d, J=4.9 Hz), 2.87 (1H, dd, J=13.9, 6.1 Hz), 3.25-3.42 (2H, m), 3.78-3.90 (1H, m)), 4.91 (1H, t, J=5.5 Hz), 6.12 (1H, d, J=8.5 Hz), 7.22 (2H, d, J=9.1 Hz), 7.29 (2H, d, J=7.9 Hz), 7.35 (2H, d, J=9.1 Hz), 7.73 (2H, d, J=7.9 Hz), 8.28-8.37 (1H, m), 8.60 (1H, s).

ESIMS (+) 362[M+H]$^+$.

Example 34-2

The following Example 34-2 was obtained using the corresponding starting material and reactant in the same method as in Example 34-1.

The structure and spectral data thereof are shown in Table 117.

TABLE 117

| Ex. No | Str. | Chemical name | P.D. |
|---|---|---|---|
| 34-2 | (structure: 4-chlorophenyl-NH-C(=O)-NH-CH(CH2OH)-CH2-C6H4-C(=O)N(CH3)2) | 4-[2-[3-(4-chlorophenyl)-ureido]-3-hydroxypropyl]-N,N-dimethyl-benzamide | $^1$H-NMR (400 MHz, DMSO-$d_6$) δ 2.72 (1H, dd, J = 13.9, 7.9 Hz), 2.80-3.00 (7H, m), 3.26-3.43 (2H, m), 3.78-3.89 (1H, m), 4.91 (1H, t, J = 4.9 Hz), 6.13 (1H, d, J = 8.5 Hz), 7.22 (2H, d, J = 9.1 Hz), 7.26 (2H, d, J = 7.9 Hz), 7.30 (2H, d, J = 7.9 Hz), 7.35 (2H, d, J = 9.1 Hz), 8.61 (1H, s). ESIMS (+) 376 [M + H]$^+$. |

Next, results in support of availability of the compound of the present invention will be shown with reference to Test Examples.

Test Example 1

Measurement Test of Agonist Activity on Human FPRL1

(1-1) Construction of Human FPRL1 Expression Vector

Human FPRL (SEQ ID NO: 3) was amplified in a PCR reaction from cDNA derived from a monocytic leukemia cell line THP-1 (TIB-202, ATCC) as a template using a forward primer shown in SEQ ID NO: 1, a reverse primer shown in SEQ ID NO: 2, and KOD-plus-ver. 2 (KOD-211, TOYOBO CO., LTD.). The amplified PCR product and pCMV-script vector (212220, STRATAGENE) were digested with Hind III (1060A, Takara Bio Inc.) and XhoI (1094A, Takara Bio Inc.), and the resultant digest was ligated with Ligation high ver. 2 (LGK-201, TOYOBO CO., LTD.). The ligation product was transformed into DH5α (DNA-901, TOYOBO CO., LTD.), cultured on a 100 μg/mL kanamycin-containing LB medium, and purified with HiSpeed Plasmid Maxi Kit (12662, QIAGEN).

(1-2) Construction of Human Gα15 Expression Vector

Human Gα15 (SEQ ID NO: 6) was amplified in a PCR reaction from cDNA derived from a myeloid leukemia cell line HL-60 (CCL-240, ATCC) as a template using a forward primer shown in SEQ ID NO: 4, a reverse primer shown in SEQ ID NO: 5, and KOD-plus-ver. 2. The amplified PCR product and pCMV-script vector were digested with Hind III and XhoI, and the resultant digest was ligated with Ligation high ver. 2. The ligation product was transformed into DH5α, cultured on a 100 μg/mL kanamycin-containing LB medium, and purified with HiSpeed Plasmid Maxi Kit.

(2-1) Method for Culturing and Subculturing HEK293

HEK293 (JCRB9068, NIBIO) was cultured in an incubator at 5% $CO_2$ and 37° C. using DMEM (11885-092, GIBCO) containing 10% FBS and 1× Penicillin-Streptomycin (15140-122, GIBCO). Subculture was carried out as followings: The cells that reached 80 to 90t confluency were washed with PBS(−), separated using 0.25% Trypsin-EDTA (25200-072, GIBCO), centrifuged, re-suspended in a fresh medium, and then seeded in Collagen Type 1 Coated dish (4020-010, IWAKI) at a split ratio of 1:8 (cultured for 3 days).

(2-2) Introduction of Human FPRL1 and Gα15 Expression Vectors

HEK293 that reached 80 to 90 confluency was washed with PBS(−), separated using 0.25% Trypsin-EDTA, centrifuged, and re-suspended in a fresh medium excluding 1× Penicillin-Streptomycin. The cells were inoculated in a Collagen Type 1 coated 6-well plate (4810-010, IWAKI) to $5×10^5$ cells/2.5 mL/well and cultured overnight. On the next day, human FPRL1 and Gα15 expression vectors were introduced using Lipofectamine 2000 transfection reagent (11668-019, Life technologies). First, the human FPRL1 and Gα15 expression vectors were diluted with Opti-MEM I Reduced Serum Medium (31985-070, GIBCO) to 2 μg/250 μL/well and Lipofectamine 2000 transfection reagent was diluted with Opti-MEM I Reduced Serum Medium to be 4 μL/250 μL/well. The vectors and reagent were softly diffused, and incubated at room temperature for 5 minutes. The vector solution was mixed with Lipofectamine 2000 transfection reagent in equal amounts. In order to form a complex of the vectors and Lipofectamine 2000 transfection reagent, the mixture was incubated at room temperature for 20 minutes, and added at 500 μL/well to the medium of inoculated cells. The treated cells were cultured for 24 hours, inoculated in Poly-D-Lysine coated 96-well plate (356640, BD Biosciences) at a cell density of $7×10^4$ cells/100 μL/well, and cultured for another 24 hours. The resultant cells were used in a measurement test of calcium mobilization in the cells.

(3) Evaluation of Agonist Activity on Human FPRL1 (Test of Calcium Mobilization in Cell)

An appropriate amount of each test compound was first weighed, and dissolved to $10^{-2}$ M by addition of dimethyl sulfoxide (DMSO). For calculation of an $EC_{50}$ value for agonist activity, each compound solution was serially diluted with DMSO by 10-fold increments to make eight solutions having a concentration of $10^{-2}$ M to $10^{-9}$ M. The formed compound solution having each concentration was diluted 100 times with an assay buffer that was contained in Fluo-4 NW Calcium Assay Kit (F36206, Life technologies), and dispensed in an amount of 100 μL into a 96-well plate with a V-bottom shape. The plate dispensed with compound solutions was set in Flexstation (Molecular Devices, LLC.) until measurement.

Subsequently, 10 mL of assay buffer and 100 μL of probenecid solution (dissolved by addition of 1 mL of assay buffer to a 250 mM stock) were sufficiently mixed and dissolved in Fluo-4 NW dye mix. The medium of cells inoculated on the previous day was removed, the dissolved Fluo-4 NW dye mix was added in an amount of 90 μL/well, and a reaction was caused in the dark at 37° C. for 45 minutes. The cells after the reaction and chips for addition of the compound were set in Flexstation, and variation in fluorescence intensity over time after addition of the compound was measured [amount of added compound=10 μL (final concentration $10^{-5}$ M to $10^{-12}$ M), excitation wavelength: 485 nm, measured wavelength: 525 nm, 1.5 sec×54 read]. A value was calculated by subtracting a base value during addition of DMSO from the maximum value of relative fluorescence unit, and analyzed. All the measurement data were analyzed with Prism 4 that was a data analysis tool. As an $EC_{50}$ value, a molar concentration that resulted in 50% maximum activation was calculated. The $EC_{50}$ values of the resultant test compounds are shown in Table I.

TABLE I

| Compound to be tested | Efficacy $EC_{50}$ (nM) |
| --- | --- |
| Example 1-1 | 0.25 |
| Example 1-5 | 0.57 |
| Example 1-7 | 2.70 |
| Example 1-8 | 1.37 |
| Example 1-11 | 0.22 |
| Example 1-15 | 0.63 |
| Example 1-20 | 0.17 |
| Example 1-73 | 0.73 |
| Example 1-75 | 1.41 |
| Example 4 | 0.34 |
| Example 14-3 | 0.22 |
| Example 14-4 | 0.30 |
| Example 18-11 | 0.30 |
| Example 19-1 | 0.56 |
| Example 22-2 | 0.20 |
| Example 26-2 | 0.15 |
| Example 26-5 (B) | 0.66 |
| Example 26-11 | 0.41 |
| Example 31-25 | 8.45 |
| Example 31-29 | 4.12 |

As seen from Table I, the compounds (I) of the present invention or pharmacologically acceptable salts thereof show a superior FPRL1 agonist effect.

Test Example 2

Effect of Lipopolysaccharide Induction on Neutrophilic Infiltration in Mouse Lung A compound to be tested was orally administered to a mouse (BALB/c, male), and after 30 minutes, the mouse was placed in a plastic container. Lipopolysaccharide (0.3 mg/mL) dissolved in physiological saline was aerosolized with an ultrasonic wave nebulizer (NE-U17, OMRON Corporation), and exposed to the mouse for 10 minutes. After 5 hours, the anesthetized mouse was sacrificed by exsanguination. A cannula was inserted in the respiratory tract and bronchoalveolar lavage (BAL) with 1 mL of 0.855 NaCl liquid containing 0.4% sodium citrate was carried out. This operation was repeated 3 times, to obtain a BAL fluid. The BAL fluid was centrifuged at 4° C. and ×200 g for 5 minutes, and the pellet was suspended in a physiological saline containing 0.1% BSA. The number of white blood cells was counted using Turks solution with a microscope, and the total white blood cell count was calculated. The white blood cells were fixed on a glass slide using Cytospin 3 (Thermo BioAnalysis Japan K. K.). The cells were stained with Diff-Quik (SYSMEX INTERNATIONAL REAGENTS CO., LTD.), and the number thereof was counted with a microscope, and the neutrophil ratio was calculated. The neutrophil ratio was multiplied by the total white blood cell count to calculate the total neutrophil count. An effect of the compound to be tested represents a percentage (%) of suppression ratio relative to the neutrophil count in a control. The suppression ratios of the resultant test compounds are shown in Table II.

TABLE II

| Compound to be tested | Suppression Ratio (%) | Dose (mg/kg) |
| --- | --- | --- |
| Example 1-1 | 95.7 | 1 |
| Example 1-15 | 95.7 | 3 |
| Example 1-20 | 94 | 3 |
| Example 19-1 | 96.9 | 3 |
| Example 26-5 (B) | 86 | 3 |
| Example 31-29 | 95.5 | 10 |

As seen from Table II, the compounds (I) of the present invention or pharmacologically acceptable salts thereof had a superior action of suppressing neutrophil infiltration.

INDUSTRIAL APPLICABILITY

The compound of the present invention has a superior action of suppressing neutrophil infiltration due to a superior FPRL1 agonist effect, and therefore is useful as a therapeutic or prophylactic agent for inflammatory disease, chronic airway diseases, cancers, septicemia, allergic symptoms, HIV retrovirus infection, circulatory disorders, neuroinflammation, nervous disorders, pains, prion diseases, amyloidosis, immune disorders and the like.

[Sequence Listing Free Text]

<Sequence Listing 1>

SEQ ID NO: 1 is a sequence of a forward primer used for amplification of DNA of human FPRL1 (SEQ ID NO: 3), and is supplemented with a Hind III recognition site.

<Sequence Listing 2>

SEQ ID NO: 2 is a sequence of a reverse primer used for amplification of DNA of human FPRL1 (SEQ ID NO: 3), and is supplemented with an XhoI recognition site.

<Sequence Listing 3>

SEQ ID NO: 3 is an open reading frame (ORF) of human FPRL1, and is a DNA sequence of a site translated into an amino acid.

<Sequence Listing 4>

SEQ ID NO: 4 is a sequence of a forward primer used for amplification of DNA of human Gα15 (SEQ ID NO: 6), and is supplemented with a Hind III recognition site.

<Sequence Listing 5>

SEQ ID NO: 5 is a sequence of a reverse primer used for amplification of DNA of human Gα15 (SEQ ID NO: 6), and is supplemented with an XhoI recognition site.

<Sequence Listing 6>

SEQ ID NO: 6 is an open reading frame (ORF) of human Gα15, and is a DNA sequence of a site translated into an amino acid.

The invention claimed is:
1. A compound represented by the formula (I) or a pharmacologically acceptable salt thereof:

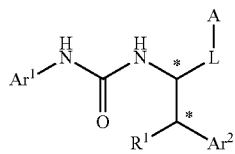
(I)

wherein
in the formula (I), Ar$^1$ is a phenyl group optionally having substituent(s), a monocyclic aromatic heterocyclyl group optionally having substituent(s), or a bicyclic aromatic heterocyclyl group having 9 or 10 atoms and optionally having substituent(s);
Ar$^2$ is a group selected from the group consisting of B1a) and B4a):

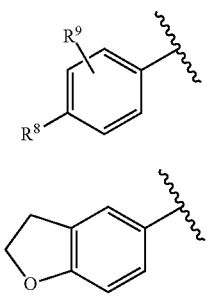
B1a)

B4a);

wherein when Ar$^2$ is B1a), R$^8$ is a fluorine atom, a chlorine atom, a cyano group, a C$_1$ to C$_3$ alkyl group, a C$_1$ to C$_3$ alkyloxy group, a C$_1$ to C$_3$ acyl group, or a hydroxy C$_1$ to C$_4$ alkyl group; and
R$^9$ is a hydrogen atom, a halogen atom, a hydroxy group, a cyano group, or a C$_1$ to C$_3$ alkyl group;
R$^1$ is a hydrogen atom, a C$_1$ to C$_3$ alkyl group, or —CONXY;
X and Y are independently a hydrogen atom or a C$_1$ to C$_3$ alkyl group;
A is a group selected from the group consisting of a cyano group, a hydroxy group, or the following A1), A2), A3), A4), A5), A6), A7), A8), A9), and A10):

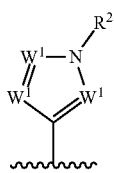
A1)

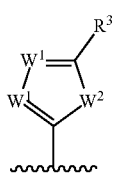
A2)

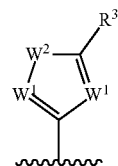
A3)

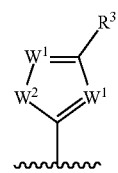
A4)

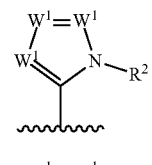
A5)

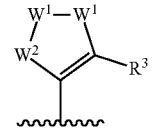
A6)

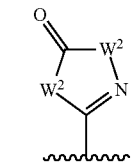
A7)

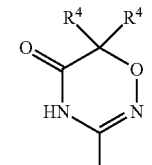
A8)

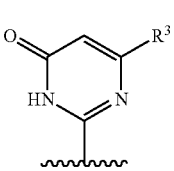
A9)

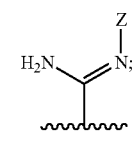
A10)

wherein R$^2$ is a hydrogen atom or a C$_1$ to C$_6$ alkyl group optionally having substituent(s);
R$^3$ is a hydrogen atom, a halogen atom, a hydroxy group, a cyano group, a carboxyl group, a C$_1$ to C$_6$ alkyl group optionally having substituent(s), a C$_1$ to C$_6$ alkyloxy group optionally having substituent(s), a C$_1$ to C$_6$ alkyloxycarbonyl group, a C$_1$ to C$_6$ acyl group optionally having substituent(s), a C$_1$ to C$_6$ alkylsulfanyl group optionally having substituent(s), a C$_1$ to C$_6$ alkylsulfinyl group optionally having substituent(s), a C$_1$ to C$_6$ alkylsulfonyl group optionally having substituent(s), a heterocyclyl group optionally having substituent(s), —CONR$^5$R$^6$, or —NR$^5$R$^6$, wherein when $R^3$ is $-CONR^5R^6$ or $-NR^5R^6$, then $R^5$ is a hydrogen atom, a $C_1$ to $C_6$ alkyl group optionally having substituent(s), a $C_1$ to $C_6$ acyl group optionally having substituent(s), or a $C_1$ to $C_6$ alkylsulfonyl group optionally having substituent(s), and $R^6$ is a hydrogen atom or a $C_1$ to $C_6$ alkyl group optionally having substituent(s), or $R^5$ and $R^6$ may together form a 3- to 10-membered heterocycloalkyl group;

Z is a hydrogen atom, hydroxy group, a $C_1$ to $C_6$ alkyl group optionally having substituent(s), a $C_1$ to $C_6$ acyl group optionally having substituent(s), a $C_1$ to $C_6$ alkyloxy group optionally having substituent(s), a carboxy $C_1$ to $C_6$ alkyl group optionally having substituent(s), or a $C_1$ to $C_6$ alkylsulfonyl group optionally having substituent(s);

$R^4$ is a $C_1$ to $C_3$ alkyl group optionally having substituent(s);

$W^1$ is $C-R^7$ or a nitrogen atom;

$R^7$ is a hydrogen atom or a $C_1$ to $C_6$ alkyl group optionally having substituent(s); and $W^2$ is an oxygen atom, a sulfur atom, or $N-R^2$;

wherein said optional substituents are halogen atoms, an amino group, a hydroxy group, a cyano group, a nitro group, a carboxy group, $C_1$ to $C_6$ alkyloxycarbonyl groups, a formyl group, $C_1$ to $C_6$ acyl groups, $C_1$ to $C_6$ alkyl groups, $C_1$ to $C_6$ alkylamino groups, $C_1$ to $C_6$ alkyloxy groups, $C_1$ to $C_6$ alkylsulfanyl groups, $C_3$ to $C_6$ cycloalkyl groups, 3- to 10-membered heterocycloalkyl groups, aromatic hydrocarbon cyclic groups optionally having a halogen atom, heterocyclyl groups, $C_1$ to $C_6$ acylamino groups, $C_3$ to $C_6$ cycloalkylcarbonylamino groups, 3- to 10-membered heterocycloalkylcarbonylamino groups, aromatic hydrocarbon cyclic carbonylamino groups, or heterocyclyl carbonylamino groups;

L is a single bond or a $C_1$ to $C_3$ alkylene; and each carbon atom marked with an asterisk is an asymmetric carbon atom when the carbon is a tertiary carbon atom.

2. The compound according to claim 1 or a pharmacologically acceptable salt thereof, wherein in the formula (I), A is a hydroxy group, or a group selected from the group consisting of the following A1a), A1b), A1c), A1d), A1e), A1f), A2a), A2b), A2aa), A3a), A3b), A3ba), A3bb), A4a), A4b), A4c), A5a), A6a), A7a), A7b), A7c), A8a), A9a), and A10a):

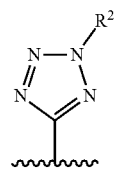

A1a)

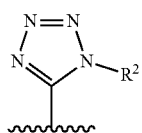

A5a)

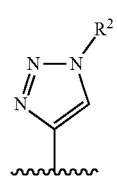

A1b)

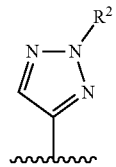

A1c)

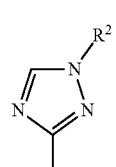

A1d)

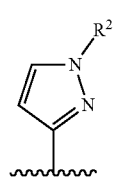

A1e)

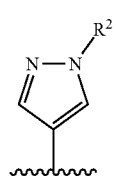

A1f)

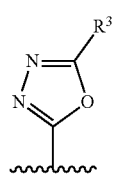

A2a)

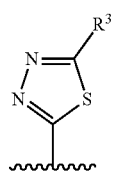

A2b)

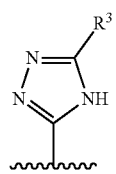

A2c)

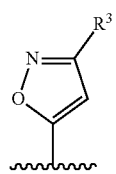

A4a)

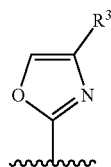

A4b)

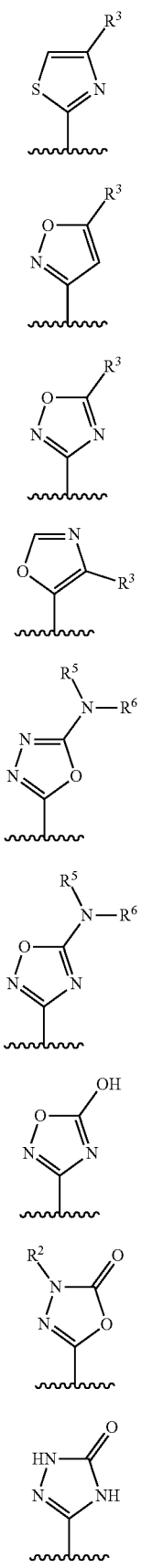
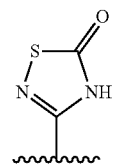
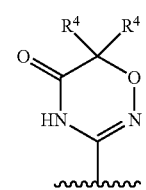
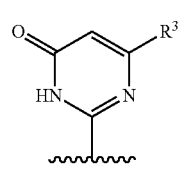

wherein when A is A1a), A1b), A1c), A1d), A1e), A1f), A5a) or A7a), $R^2$ is a hydrogen atom, or a $C_1$ to $C_6$ alkyl group optionally substituted with a group selected from the group consisting of a halogen atom, a hydroxy group, a $C_1$ to $C_3$ alkyloxy group, a carboxyl group, a $C_1$ to $C_3$ alkyloxycarbonyl group, a $C_1$ to $C_3$ alkylsulfinyl group, a $C_1$ to $C_3$ alkylsulfonyl group, an amino group, a $C_1$ to $C_3$ alkylamino group, a $C_1$ to $C_3$ alkylsulfonylamino group, a $C_1$ to $C_3$ acylamino group, a $C_1$ to $C_3$ alkylaminocarbonyl group, and a heterocyclyl group;

when A is A2a), A2b), A2c), A4a), A4b), A4c), A3a), A3b), A6a) or A9a), $R^3$ is a group selected from the group consisting of the following i) to ix):

i) a hydrogen atom,
ii) a halogen atom,
iii) a cyano group,
iv) a carboxyl group,
v) a $C_1$ to $C_6$ alkyloxycarbonyl group,
vi) a carbamoyl group optionally substituted with a $C_1$ to $C_3$ alkyl group,
vii) a $C_1$ to $C_6$ alkyl group optionally substituted with a group selected from the group consisting of a halogen atom, a hydroxy group, a $C_1$ to $C_3$ alkyloxy group, a $C_1$ to $C_3$ acyloxy group, a carboxyl group, a $C_1$ to $C_3$ alkyloxycarbonyl group, a $C_1$ to $C_3$ alkylsulfonyl group, an amino group, a $C_1$ to $C_3$ alkylamino group, a $C_1$ to $C_3$ alkylsulfonylamino group, a $C_1$ to $C_3$ acylamino group, a $C_1$ to $C_3$ alkylaminocarbonyl group, and a heterocyclyl group,
viii) —$CONR^5R^6$ wherein $R^5$ is a hydrogen atom, a $C_1$ to $C_6$ alkyl group, a $C_1$ to $C_6$ acyl group, or a $C_1$ to $C_6$ alkylsulfonyl group, and $R^6$ is a hydrogen atom or a $C_1$ to $C_6$ alkyl group, or $R^5$ and $R^6$ may together form a 3- to 10-membered heterocycloalkyl group,
ix) a heterocyclyl group optionally having substituent(s) selected from halogen atoms, an amino group, a hydroxy group, a cyano group, a nitro group, a carboxy group, $C_1$ to $C_6$ alkyloxycarbonyl groups, a formyl group, $C_1$ to $C_6$ acyl groups, $C_1$ to $C_6$ alkyl groups, $C_1$ to $C_6$ alkylamino groups, $C_1$ to $C_6$ alkyloxy groups, $C_1$ to $C_6$ alkylsulfanyl groups, $C_3$ to $C_6$ cycloalkyl groups, 3- to 10-membered heterocycloalkyl groups, aromatic hydrocarbon cyclic groups optionally having a halogen atom, heterocyclyl groups, $C_1$ to $C_6$ acylamino groups, $C_3$ to $C_6$ cycloalkylcarbonylamino groups, 3- to 10-membered heterocycloalkylcarbonylamino groups, aromatic hydrocarbon cyclic carbonylamino groups, and heterocyclyl carbonylamino groups;

when A is A2aa) or A3ba), $R^5$ is a hydrogen atom, a $C_1$ to $C_6$ alkyl group, a $C_3$ to $C_6$ cycloalkyl group, a halo-$C_1$ to $C_6$ alkyl group, a $C_1$ to $C_6$ acyl group, a hydroxy $C_1$ to $C_6$ acyl group, or a $C_1$ to $C_6$ alkylsulfonyl group, and $R^6$ is a hydrogen atom or a $C_1$ to $C_6$ alkyl group, or $R^5$ and $R^6$ may together form 3- to 10-membered heterocycloalkyl group;

when A is Aa), $R^4$ is a $C_1$ to $C_3$ alkyl group; and when A is A10a), Z is a hydroxy $C_1$ to $C_6$ alkyloxy group, a hydroxy $C_1$ to $C_6$ acyl group, a carboxy $C_1$ to $C_6$ alkyloxy group, a $C_1$ to $C_3$ alkylaminocarbonyl group, a $C_1$ to $C_6$ alkylsulfonyl $C_1$ to $C_6$ acyl group, or a $C_1$ to $C_6$ alkylsulfonyl group.

3. The compound according to claim 1 or a pharmacologically acceptable salt thereof, wherein in the formula (I), $Ar^1$ is a group selected from the group consisting of the following C1), C2), and C3):

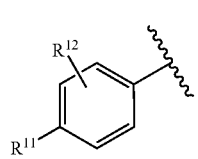

C1)

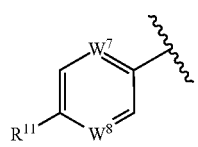

C2)

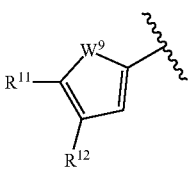

C3)

one of $W^7$ and We is a nitrogen atom, and the other one is CH or a nitrogen atom;

$W^9$ is an oxygen atom, a sulfur atom, or N—$R^2$;

when $W^9$ is N—$R^2$, $R^2$ is a hydrogen atom or a $C_1$ to $C_6$ alkyl group;

$R^{11}$ is a hydrogen atom, a halogen atom, a cyano group, a $C_1$ to $C_3$ alkyl group, a halo-$C_1$ to $C_3$ alkyl group, a hydroxy $C_1$ to $C_4$ alkyl group, a $C_2$ to $C_3$ alkenyl group, a $C_2$ to $C_3$ alkynyl group, a $C_3$ to $C_6$ cycloalkyl group, a $C_1$ to $C_3$ alkyloxy group, a halo-$C_1$ to $C_3$ alkyloxy group, a $C_3$ to $C_6$ cycloalkoxy group, a $C_1$ to $C_6$ acyl group, a $C_1$ to $C_3$ alkyloxycarbonyl group, a $C_1$ to $C_3$ alkylsulfanyl group, a $C_1$ to $C_3$ alkylsulfinyl group, a $C_1$ to $C_3$ alkylsulfonyl group, an aryl group, an aryloxy group, a heterocyclyl group substituted with a $C_1$ to $C_3$ alkyl group, —CONR$^5$R$^6$, or —NR$^5$R$^6$, wherein when $R^{11}$ is —CONR$^5$R$^6$ or —NR$^5$R$^6$, $R^5$ is a hydrogen atom, a $C_1$ to $C_3$ alkyl group, a $C_1$ to $C_3$ acyl group, or a $C_1$ to $C_3$ alkylsulfonyl group, and $R^6$ is a hydrogen atom or a $C_1$ to $C_3$ alkyl group, or $R^5$ and $R^6$ may together form 3- to 10-membered heterocycloalkyl group; and $R^{12}$ is a hydrogen atom, a halogen atom, a hydroxy group, or a $C_1$ to $C_3$ alkyl group.

4. The compound according to claim 1 or a pharmacologically acceptable salt thereof, wherein in the formula (I), A is a group selected from the group consisting of the following A1a), A2a), A3b), A2e) and A10ab):

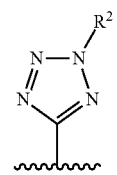

A1a)

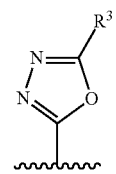

A2a)

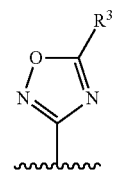

A3b)

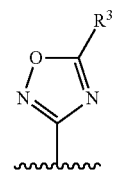

A2e)

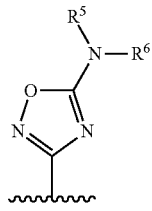

A10ab)

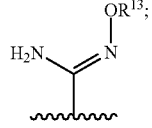

when A is A1a), $R^2$ is a hydrogen atom, a $C_1$ to $C_3$ alkyl group, or a hydroxy $C_1$ to $C_4$ alkyl group;

when A is A2a) or A3b), $R^3$ is a hydrogen atom, a hydroxy group, a $C_1$ to $C_3$ alkyl group, or a hydroxy $C_1$ to $C_4$ alkyl group;

when A is A2e), $R^5$ is a hydrogen atom, a $C_1$ to $C_3$ alkyl group, or a hydroxy $C_1$ to $C_4$ alkyl group, and $R^6$ is a hydrogen atom or a $C_1$ to $C_6$ alkyl group optionally having substituent(s), or $R^5$ and $R^6$ may together form 3- to 10-membered heterocycloalkyl group; and when A is A10ab), $R^{13}$ is a hydrogen atom, a $C_1$ to $C_3$ alkyl group, or a hydroxy $C_1$ to $C_4$ alkyl group; and wherein said optional substituents are halogen atoms, an amino group, a hydroxy group, a cyano group, a nitro group, a carboxy group, $C_1$ to $C_6$ alkyloxycarbonyl groups, $C_1$ to $C_6$ acyl groups, $C_1$ to $C_6$ alkyl groups, $C_1$ to $C_6$ alkylamino groups, $C_1$ to $C_6$ alkyloxy groups, $C_1$ to $C_6$ alkylsulfanyl groups, $C_3$ to $C_6$ cycloalkyl groups, 3- to 10-membered heterocycloalkyl groups, aromatic hydrocarbon cyclic groups optionally having a halogen atom, heterocyclyl groups, $C_1$ to $C_6$ acylamino groups, $C_3$ to $C_6$ cycloalkylcarbonylamino groups, 3- to 10-membered heterocycloalkylcarbonylamino groups, aromatic hydrocarbon cyclic carbonylamino groups, or heterocyclyl carbonylamino groups.

5. The compound according to claim 1 or a pharmacologically acceptable salt thereof, wherein in the formula (I), $Ar^1$ is C1a):

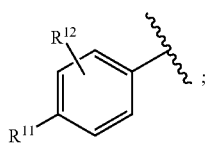

C1a)

$R^{11}$ is a hydrogen atom, a halogen atom, a cyano group, a trifluoromethyl group, or a $C_1$ to $C_3$ alkyl group; and $R^{12}$ is a hydrogen atom or a halogen atom.

6. The urea compound according to claim 5 or a pharmacologically acceptable salt thereof, wherein in the formula (I), $Ar^2$ is B1aa):

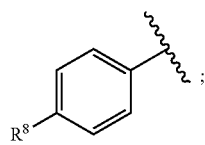

B1aa)

and
$R^8$ is a cyano group, an ethyl group, an acetyl group, or a $C_1$ to $C_3$ alkyloxy group.

7. A compound or a pharmacologically acceptable salt thereof, wherein the compound is
- (−)-(S)-1-(4-chlorophenyl)-3-{1-[2-(2-hydroxyethyl)-2H-tetrazol-5-yl]-2-(4-methoxyphenyl)ethyl}urea,
- (S)-1-(4-fluorophenyl)-3-{1-[2-(2-hydroxyethyl)-2H-tetrazol-5-yl]-2-(4-methoxyphenyl)ethyl}urea,
- (S)-1-(4-cyanophenyl)-3-{1-[2-(2-hydroxyethyl)-2H-tetrazol-5-yl]-2-(4-methoxyphenyl)ethyl}urea,
- (S)-1-(4-chlorophenyl)-3-{2-(4-cyanophenyl)-1-[2-(2-hydroxyethyl)-2H-tetrazol-5-yl]ethyl}urea,
- (S)-1-(4-chlorophenyl)-3-{2-(2,3-dihydrobenzofuran-5-yl)-1-[2-(2-hydroxyethyl)-2H-tetrazol-5-yl]ethyl}urea,
- (S)-1-(4-chlorophenyl)-3-{2-(4-ethylphenyl)-1-[2-(2-hydroxyethyl)-2H-tetrazol-5-yl]ethyl}urea,
- (−)-(S)-1-(4-cyanophenyl)-3-{2-(2,3-dihydrobenzofuran-5-yl)-1-[2-(2-hydroxyethyl)-2H-tetrazol-5-yl]ethyl}urea,
- 1-(4-chlorophenyl)-3-{(1S,2R)-1-[2-(2-hydroxyethyl)-2H-tetrazol-5-yl]-2-(4-methoxyphenyl)propyl}urea,
- 1-(4-chlorophenyl)-3-{(1S,2S)-1-[2-(2-hydroxyethyl)-2H-tetrazol-5-yl]-2-(4-methoxyphenyl)propyl}urea,
- (S)-1-(4-chlorophenyl)-3-(2-(4-ethylphenyl)-1-{5-[(2-hydroxyethylmethyl)amino]-1,2,4-oxadiazol-3-yl}ethyl)urea,
- (+)-(S)-1-(4-chlorophenyl)-3-{1-[2-(3-hydroxypropyl)-2H-tetrazol-5-yl]-2-(4-methoxyphenyl)ethyl}urea,
- (+)-(S)-1-(4-chlorophenyl)-3-(1-(2-(3-hydroxybutyl)-2H-tetrazol-5-yl]-2-(4-methoxyphenyl)ethyl)urea,
- (S)-1-(4-fluorophenyl)-3-{1-[5-(2-hydroxyethyl)-1,3,4-thiadiazol-2-yl]-2-(4-methoxyphenyl)ethyl}urea,
- (S)-1-(4-chlorophenyl)-3-{1-[5-(2-hydroxyethyl)-1,3,4-oxadiazol-2-yl]-2-(4-methoxyphenyl)ethyl}urea,
- (S)-1-(4-fluorophenyl)-3-{1-[5-(2-hydroxyethyl)-1,3,4-oxadiazol-2-yl]-2-(4-methoxyphenyl)ethyl}urea,
- (S)-1-(4-cyanophenyl)-3-{1-[5-(2-hydroxyethyl)-1,3,4-oxadiazol-2-yl]-2-(4-methoxyphenyl)ethyl}urea,
- (S)-2-(5-{1-[3-(4-chlorophenyl)ureido]-2-(4-methoxyphenyl)ethyl}-1,3,4-oxadiazol-2-yl)-N-methylacetamide,
- (S)-2-(5-{1-[3-(4-fluorophenyl)ureido]-2-(4-methoxyphenyl)ethyl}-1,3,4-oxadiazol-2-yl)-N-methylacetamide,
- (S)-1-(4-chlorophenyl)-3-{1-[4-(2-hydroxypropan-2-yl)oxazol-5-yl]-2-(4-methoxyphenyl)ethyl}urea,
- (S)—N-(5-{1-[3-(4-chlorophenyl)ureido]-2-(4-ethylphenyl)ethyl}-1,3,4-oxadiazol-2-yl)acetamide,
- (S)-1-(2-(4-chlorophenyl)-1-{5-[(methylsulfonyl)methyl]-1,2,4-oxadiazol-3-yl}ethyl)-3-(4-fluorophenyl)urea,
- 1-(4-chlorophenyl)-3-{2-(4-methoxyphenyl)-1-[5-(1-methylpiperazin-4-yl)-1,2,4-oxadiazol-3-yl]ethyl}urea,
- (S)-1-(1-(5-amino-1,2,4-oxadiazol-3-yl)-2-(4-methoxyphenyl)ethyl)-3-(4-fluorophenyl)urea,
- (S)-1-(1-(5-amino-1,2,4-oxadiazol-3-yl)-2-(4-methoxyphenyl)ethyl)-3-(4-cyanophenyl)urea,
- (S)-1-(4-chlorophenyl)-3-(2-(4-methoxyphenyl)-1-(5-(methylamino)-1,2,4-oxadiazol-3-yl)ethyl)urea,
- (S)-1-(4-chlorophenyl)-3-(1-(5-(dimethylamino)-1,2,4-oxadiazol-3-yl)-2-(4-methoxyphenyl)ethyl)urea,
- (S)-1-(4-chlorophenyl)-3-(1-(5-(3-hydroxyazetidin-1-yl)-1,2,4-oxadiazol-3-yl)-2-(4-methoxyphenyl)ethyl)urea,
- (S)-1-(4-chlorophenyl)-3-(1-(1-(2-hydroxyethyl)-1H-pyrazol-3-yl)-2-(4-methoxyphenyl)ethyl)urea,
- (S)-1-(4-chlorophenyl)-3-(1-(3-(2-hydroxyethyl)isoxazol-5-yl)-2-(4-methoxyphenyl)ethyl)urea,
- (S)-1-(4-chlorophenyl)-3-(1-(5-(2-hydroxyethyl)isoxazol-3-yl)-2-(4-methoxyphenyl)ethyl)urea,
- (S)-1-(4-chlorophenyl)-3-(1-(2-(2-hydroxyethyl)-2H-1,2,4-triazol-4-yl)-2-(4-methoxyphenyl)ethyl)urea,
- (S)-1-(4-chlorophenyl)-3-(1-(1-(2-hydroxyethyl)-1H-1,2,3-triazol-4-yl)-2-(4-methoxyphenyl)ethyl)urea,
- (S)-1-(4-chlorophenyl)-3-(1-(1-(2-hydroxyethyl)-1H-pyrazol-4-yl)-2-(4-methoxyphenyl)ethyl)urea,
- (−)-(S)-1-(4-chlorophenyl)-3-(2-(4-methoxyphenyl)-1-(2-((methylsulfonyl)methyl)-2H-tetrazol-5-yl)ethyl)urea,
- (−)-(S)-1-(4-chlorophenyl)-3-(2-(4-methoxyphenyl)-1-(2-(2-(methylsulfonyl)methyl)-2H-tetrazol-5-yl)ethyl)urea,
- (−)-(S)—N-(2-(5-(2-(4-chlorophenyl)-1-(3-(4-chlorophenyl)ureido)ethyl)-2H-tetrazol-2-yl)ethyl)methanesulfonamide,
- (−)-(S)—N-(2-(5-(2-(4-chlorophenyl)-1-(3-(4-fluorophenyl)ureido)ethyl)-2H-tetrazol-2-yl)ethyl)methanesulfonamide,
- (−)-1-(4-chlorophenyl)-3-((1S)-2-(4-methoxyphenyl)-1-(2-((methylsulfinyl)methyl)-2H-tetrazol-5-yl)ethyl)urea, (−)-(S)—N-((5-(2-(4-chlorophenyl)-1-(3-(4-chlorophenyl)ureido)ethyl)-1,3,4-oxadiazol-2-yl)methyl)acetamide,
(S)-1-(4-chlorophenyl)-3-(2-(4-chlorophenyl)-1-(5-(2-hydroxypropan-2-yl)-1,3,4-oxadiazol-2-yl)ethyl)urea,
(S)—N-((5-(3-(4-chlorophenyl)ureido)-2-(4-ethylphenyl)ethyl)-1,3,4-oxadiazol-2-yl)methyl)acetamide,
(−)-(S)-1-(4-chlorophenyl)-3-(2-(4-ethylphenyl)-1-(5-(3-hydroxyethyl)-1,3,4-oxadiazol-2-yl)ethyl)urea,
(S)-1-[1-(5-amino-1,3,4-thiadiazol-2-yl)-2-(4-methoxyphenyl)ethyl]-3-(4-chlorophenyl)urea,
5-(1-(3-(4-chlorophenyl)ureido)-2-(4-methoxyphenyl)ethyl)oxazole-4-carboxylic acid,
(S)-5-(1-(3-(4-chlorophenyl)ureido)-2-(4-methoxyphenyl)ethyl)oxazole-4-carboxylic acid,
(−)-(S)-2-(5-(1-(3-(4-chlorophenyl)ureido)-2-(4-methoxyphenyl)ethyl)-2-oxo-1,3,4-oxadiazol-3(2H)-yl)acetic acid,
1-(4-chlorophenyl)-3-(1-(5-(hydroxymethyl)-1,3,4-oxadiazol-2-yl)-2-(4-methoxyphenyl)ethyl)urea,
1-(4-chlorophenyl)-3-(1-(5-(hydroxymethyl)-1,2,4-oxadiazol-3-yl)-2-(4-methoxyphenyl)ethyl)urea,
(S)-1-(4-chlorophenyl)-3-(1-(5-(2-hydroxyethyl)-1,3,4-thiadiazol-2-yl)-2-(4-methoxyphenyl)ethyl)urea,
(S)-1-(4-chlorophenyl)-3-(1-(5-(2-hydroxyethyl)-4H-1,2,4-triazol-3-yl)-2-(4-methoxyphenyl)ethyl)urea,
(+)-(S)-2-(5-{1-[3-(4-chlorophenyl)ureido]-2-(4-methoxyphenyl)ethyl}-2H-tetrazol-2-yl)acetamide,
(S)-5-(1-(3-(4-chlorophenyl)ureido)-2-(4-methoxyphenyl)ethyl)oxazole-4-carboxamide,
(S)-5-(1-(3-(4-chlorophenyl)ureido)-2-(4-methoxyphenyl)ethyl)-N-methyloxazole-4-carboxamide,
(S)-5-(1-(3-(4-chlorophenyl)ureido)-2-(4-methoxyphenyl)ethyl)-N,N-dimethyloxazole-4-carboxamide,
(S)-2-(5-(1-(3-(4-chlorophenyl)ureido)-2-(4-methoxyphenyl)ethyl)-2H-tetrazol-2-yl)-N-methylacetamide,
(S)-1-(4-chlorophenyl)-3-(2-(4-methoxyphenyl)-1-(2-(2-morpholino-2-oxoethyl)-2H-tetrazol-5-yl)ethyl)urea,
(−)-(S)-1-(1-(2-(azetidin-3-yl)-2H-tetrazol-5-yl)-2-(4-methoxyphenyl)ethyl)-3-(4-chlorophenyl)urea,
(−)-(S)—N-(2-(5-(1-(3-(4-chlorophenyl)ureido)-2-(4-methoxyphenyl)ethyl)-2H-tetrazol-2-yl)ethyl)acetamide,
(−)-(S)—N-(2-(5-(1-(3-(4-chlorophenyl)ureido)-2-(4-methoxyphenyl)ethyl)-2H-tetrazol-2-yl)ethyl)methanesulfonamide,
1-(1-(5-amino-1,2,4-oxadiazol-3-yl)-2-(4-methoxyphenyl)ethyl)-3-(4-chlorophenyl)urea,
(S)-1-(1-(5-amino-1,2,4-oxadiazol-3-yl)-2-(4-chlorophenyl)ethyl)-3-(4-chlorophenyl)urea,
(+)-(S)-1-(4-chlorophenyl)-3-(2-(4-chlorophenyl)-1-(5-(methylamino)-1,2,4-oxadiazol-3-yl)ethyl)urea,
(S)-1-(4-chlorophenyl)-3-(2-(4-chlorophenyl)-1-(5-((2-hydroxyethylmethyl)amino)-1,2,4-oxadiazol-3-yl)ethyl)urea,
(S)-1-(4-chlorophenyl)-3-(2-(4-chlorophenyl)-1-(5-(3-hydroxyazetidin-1-yl)-1,2,4-oxadiazol-3-yl)ethyl)urea,
(S)-1-(4-chlorophenyl)-3-(2-(4-chlorophenyl)-1-(5-((1-hydroxy-2-methylpropan-2-yl)amino)-1,2,4-oxadiazol-3-yl)ethyl)urea,
(−)-(S)-1-(2-(4-chlorophenyl)-1-(5-((2-hydroxyethyl)amino)-1,2,4-oxadiazol-3-yl)ethyl)-3-(4-fluorophenyl)urea,
(−)-(S)-1-(4-chlorophenyl)-3-(2-(4-chlorophenyl)-1-(5-((1,3-dihydroxypropan-2-yl)amino)-1,2,4-oxadiazol-3-yl)ethyl)urea,
(−)-(S)-1-(4-chlorophenyl)-3-(1-(5-((1,3-dihydroxypropan-2-yl)amino)-1,2,4-oxadiazol-3-yl)-2-(4-methoxyphenyl)ethyl)urea,
(+)-(S,Z)-2-[3-(4-chlorophenyl)ureido]-3-(4-ethylphenyl)-N'-(2-hydroxyethoxy)propanimidamide,
(+)-(S,Z)-2-[3-(4-chlorophenyl)ureido]-N'-(2-hydroxyethoxy)-3-(4-methoxyphenyl)propanimidamide,
(S,Z)—N-{1-amino-3-(4-chlorophenyl)-2-[3-(4-chlorophenyl)ureido]propylidene}-3-hydroxy-2,2-dimethylpropanamide,
(S)-1-{2-(4-chlorophenyl)-1-[5-(1-hydroxy-2-methylpropan-2-yl)-1,2,4-oxadiazol-3-yl]ethyl}-3-(4-fluorophenyl)urea,
(S)-1-(4-chlorophenyl)-3-(2-(4-chlorophenyl)-1-{5-[1-(hydroxymethyl)cyclopropyl]-1,2,4-oxadiazol-3-yl}ethyl)urea,
(S)-1-(2-(4-chlorophenyl)-1-{5-[1-(hydroxymethyl)cyclopropyl]-1,2,4-oxadiazol-3-yl}ethyl)-3-(4-fluorophenyl)urea,
(−)-(S)-1-(4-chlorophenyl)-3-(1-(4-(2-hydroxyethyl)-5-oxo-4,5-dihydro-1,3,4-oxadiazol-2-yl)-2-(4-methoxyphenyl)ethyl)urea.

8. A method of treating chronic airway diseases, septicemia, allergic symptoms, HIV retrovirus infection, circulatory disorders, neuroinflammation, pains, prion diseases and amyloidosis, in a patient in need thereof, comprising administering the compound according to claim 1 or a pharmacologically acceptable salt thereof to the patient.

9. A pharmaceutical composition containing the compound according to claim 1 or a pharmacologically acceptable salt thereof and a pharmaceutically acceptable carrier.

10. A compound or a pharmacologically acceptable salt thereof, wherein the compound is
2-(3-(4-chlorophenyl)ureido-N'-hydroxy-3-(4-methoxyphenyl)propanimidamide,
(S)—N-{2-[3-(4-fluorophenyl)ureido]-1-imino-3-(4-methoxyphenyl)propyl}-3-hydroxypropanamide,
(S)—N-{2-[3-(4-chlorophenyl)ureido]-1-imino-3-(4-methoxyphenyl)propyl}-3-hydroxypropanamide,
(S)—N-{3-(4-chlorophenyl)-2-[3-(4-fluorophenyl)ureido]-1-iminopropyl}-2-(methanesulfonyl)acetamide,
(S)—N-{4-(4-chlorophenyl)-3-[3-(4-chlorophenyl)ureido]-1-iminobutyl}-2-hydroxyacetamide, or
(+)—(R)-1-(4-chlorophenyl)-3-[1-hydroxy-3-(4-methoxyphenyl)propan-2-yl]urea.

* * * * *